US012661394B2

(12) United States Patent
Shattock et al.

(10) Patent No.: US 12,661,394 B2
(45) Date of Patent: Jun. 23, 2026

(54) CORONAVIRUS VACCINE

(71) Applicant: Imperial College Innovations Limited, London (GB)

(72) Inventors: Robin Shattock, London (GB); Paul McKay, London (GB); Anna Blakney, London (GB)

(73) Assignee: IMPERIAL COLLEGE INNOVATIONS LIMITED, London (GB)

(*) Notice: Subject to any disclaimer, the term of this patent is extended or adjusted under 35 U.S.C. 154(b) by 944 days.

(21) Appl. No.: 17/914,174

(22) PCT Filed: Mar. 26, 2021

(86) PCT No.: PCT/GB2021/050747
§ 371 (c)(1),
(2) Date: Sep. 23, 2022

(87) PCT Pub. No.: WO2021/191630
PCT Pub. Date: Sep. 30, 2021

(65) Prior Publication Data

US 2023/0270841 A1 Aug. 31, 2023

(30) Foreign Application Priority Data

Mar. 27, 2020 (GB) ..................................... 2004493

(51) Int. Cl.

| | |
|---|---|
| ***C07K 14/005*** | (2006.01) |
| ***A61K 39/12*** | (2006.01) |
| ***A61K 39/215*** | (2006.01) |
| ***A61K 48/00*** | (2006.01) |
| ***A61P 31/14*** | (2006.01) |

(52) U.S. Cl.
CPC ............ *A61K 39/215* (2013.01); *A61P 31/14* (2018.01); *C07K 14/005* (2013.01); *C12N 2770/20022* (2013.01); *C12N 2770/20034* (2013.01); *C12N 2770/20071* (2013.01)

(58) Field of Classification Search
CPC .............. C07K 14/005; C07K 14/4703; C12N 2770/20022; C12N 15/86; C12N 2760/20134
See application file for complete search history.

(56) References Cited

U.S. PATENT DOCUMENTS

2006/0240515 A1 10/2006 Dimitrov et al.

FOREIGN PATENT DOCUMENTS

WO 2018081318 5/2018

OTHER PUBLICATIONS

PCT International Search Report & Written Opinion dated Jul. 9, 2021 for PCT Application No. PCT/GB2021/050747.
Wu, F., et al., "A new coronavirus associated with human respiratory disease in China", Nature, Mar. 2020, pp. 265-269, vol. 579, No. 7798.
Vogel, A.B., et al., "Self-Amplifying RNA Vaccines Give Equivalent Protection against Influenza to mRNA Vaccines but at Much Lower Doses", Molecular Therapy, Feb. 2018, pp. 446-455, vol. 26, No. 2.
Kirchdoerfer, R.N., et al., "Stabilized coronavirus spikes are resistant to conformational changes induced by receptor recognition or proteolysis", Scientific Reports, Oct. 2018, pp. 1-11, vol. 8, No. 1.
GB Search and Examination Report dated Dec. 2, 2019 for GB Application No. GB2004493.9.

*Primary Examiner* — Barry A Chestnut
(74) *Attorney, Agent, or Firm* — GATES & COOPER LLP

(57) ABSTRACT

The invention relates to vaccines, and in particular, to vaccines for preventing, treating or ameliorating coronavirus infections, such as severe acute respiratory syndrome coronavirus (SARS), SARS-CoV-2 and Middle East respiratory syndrome-related coronavirus (MERS). The invention is especially concerned with self-amplifying RNA replicons and genetic constructs or vectors encoding such RNA replicons, and their use in vaccine delivery for preventing infections of coronavirus. The invention extends to pharmaceutical compositions comprising such RNA constructs, and methods and uses thereof.

32 Claims, 11 Drawing Sheets

Specification includes a Sequence Listing.

1 - saRNA nCoV 10 ug

2 - saRNA nCoV 10 ug + MPLA 10 ug

3 - plasmid nCoV 10 ug

4 - saRNA Rabies 10 ug (+/- MPLA 10 ug)

CORONAVIRUS VACCINE

CROSS-REFERENCE TO RELATED APPLICATIONS

This application is the National Stage of International Application No. PCT/GB2021/050747 (International Publication No. WO2021/191630), filed Mar. 26, 2021, which claims priority to UK Patent Application Serial No. 2004493.9, filed Mar. 27, 2020, the contents of which are incorporated herein by reference.

The present invention relates to vaccines, and in particular, to vaccines for preventing, treating or ameliorating coronavirus infections, such as severe acute respiratory syndrome coronavirus (SARS), SARS-CoV-2 and Middle East respiratory syndrome-related coronavirus (MERS). The invention is especially concerned with self-amplifying RNA replicons and genetic constructs or vectors encoding such RNA replicons, and their use in vaccine delivery for preventing infections of coronavirus. The invention extends to pharmaceutical compositions comprising such RNA constructs, and methods and uses thereof.

The severe acute respiratory syndrome coronavirus (SARS-CoV-2), causing 2019-nCoV or COVID-19 disease, is a virus belonging in the coronavirus (CoV) group of disease-causing pathogens that includes severe acute respiratory syndrome coronavirus (SARS) and Middle East respiratory syndrome-related coronavirus (MERS). Coronaviruses are usually restricted to their wild hosts (e.g. bats). However, both SARS and MERS, and more recently SARS-CoV-2, have all been transferred to humans, and this caused the SARS and MERS outbreaks of 2003, 2012, and 2019, respectively.

The coronavirus family has been identified recently in a number of emerging pathogen priority lists, i.e. UKVN, WHO blueprint and CEPI, highlighting the urgent need to improve our understanding of immune responses to coronaviruses, both to control current problems and also to be prepared for emerging threats. The large number of genetically distinct coronaviruses and increasing interface between human populations and animal reservoirs of CoV suggests that there is a significant risk of new CoV zoonotic infections. Indeed, the outbreak of SARS-CoV-2 in China has proved this to be the case. Coronaviruses tend to target the respiratory systems and so, due to these periodic outbreaks, a vaccine effectively targeting coronaviruses, and immunising against their infection, is urgently needed.

Recently, self-amplifying (or self-replicating) naked RNA vectors (saRNA replicons) have come into focus as a promising new vaccine technology platform. RNA replicons answer some of the problems associated with conventional DNA plasmid vaccines that have struggled to demonstrate their full potential in large animals and humans despite significant advances including the use of electroporation. RNA replicons are strictly confined to the cytosol, do not require a cDNA intermediary or penetration into the nucleus, and can generate high expression of a gene product with a relatively low initial dose. Their fully synthetic manufacture and ease of production offers the potential to produce hundreds of thousands of doses within a matter of weeks for any emerging virus. As a consequence, saRNA has been shown to induce immune responses with lower doses of saRNA than mRNA (10- to 100-fold lower) and results in prolonged protein expression for up to 60 days in mice.

Therefore, the development of CoV-saRNA-based immunotherapies for the highly pathogenic CoVs will address an immediate unmet medical need and could provide a robust vaccine, not only for current SARS-CoV-2, but also for future emerging pandemic CoVs.

As shown in FIGS. 1A and 1B, the inventors have based their work on a self-amplifying RNA replicon based on a non-infectious Venezuelan Equine Encephalitis (VEE) alphavirus RNA backbone encoding non-structural proteins required for replication (RNA-dependent RNA polymerase complex). As shown, a vaccine "antigen of interest" is inserted in place of structural genes downstream of the subgenomic promoter (SGP). The "antigen of interest" used by the inventors is the full-length sequence of the native coronavirus surface S glycoprotein, which is responsible for viral attachment to, and fusion with, a host cell. The S glycoprotein is a trimer of homodimers made up of S1 and S2 subunits. On entry into host cells, the non-structural proteins are immediately translated to generate the polymerase machinery that synthesises large amounts of genomic and subgenomic RNA leading to very high expression levels of the S glycoprotein. This in turn triggers strong immune-stimulatory potency against the S glycoprotein due to the intrinsic adjuvant activity of RNA replication.

This saRNA replicon, therefore, is a candidate vaccine expressing a pre-fusion trimeric stabilised conformation of the native surface glycoprotein (S). The design of the replicon maximises the potential for induction of neutralising antibodies while simultaneously minimising the induction for off-target responses to post-fusion conformations. As described in the examples, the inventors have confirmed appropriate expression by Western Blot and Flow Cytometry. The vaccine can be rapidly manufactured at low cost and elicit protective immunity across all at risk populations within only four weeks of administration.

Although the saRNA platform described herein, which is based on the backbone of VEEV, has the structural proteins being replaced by the SARS-CoV-2 S protein, it will be appreciated that the same platform could equally be used to express the native surface glycoprotein of SARS-CoV or MERS-CoV.

Accordingly, in a first aspect of the invention, there is provided a self-amplifying RNA (saRNA) construct comprising a nucleic acid sequence encoding a coronavirus surface glycoprotein, or a fragment or variant thereof.

saRNA offers significant advantages over other nucleic acid vaccine platforms yielding exponentially higher levels of protein expression than messenger RNA (mRNA) or DNA. The self-amplifying properties of saRNA mean that much lower doses are required to induce protective immunity, providing a significant advantage to manufacturing costs and speed. Additionally, saRNA is not limited by anti-vector immunity and is safe to administer to individuals unable to receive live attenuated vaccines (e.g. children and the immunocompromised). Advantageously, the vaccine can be rapidly manufactured at low cost and elicit protective immunity across all at risk populations within a few weeks of administration, with the potential for repeat boosting as required.

The skilled person would understand that a self-amplifying RNA construct can also be referred to as a self-replicating RNA virus vector, or an RNA replicon. The RNA construct may be double-stranded or single-stranded.

Preferably, the RNA construct comprises or is derived from a positive stranded RNA virus selected from the group of genus consisting of: alphavirus; picornavirus; flavivirus; rubivirus; pestivirus; hepacivirus; calicivirus and coronavirus.

Suitable wild-type alphavirus sequences are well-known. Representative examples of suitable alphaviruses include Aura, Bebaru virus, Cabassou, Chikungunya virus, Eastern equine encephalomyelitis virus, Fort Morgan, Getah virus, Kyzylagach, Mayaro, Mayaro virus, Middleburg, Mucambo virus, Ndumu, Pixuna virus, Ross River virus, Semliki Forest, Sindbis virus, Tonate, Triniti, Una, Venezuelan equine encephalomyelitis, Western equine encephalomyelitis, Whataroa, and Y-62-33.

Preferably, the RNA construct comprises or is derived from a virus selected from the group of species consisting of: Venezuelan Equine Encephalitis Virus (VEEV); enterovirus 71; Encephalomyocarditis virus; Kunjin virus; and Middle East respiratory syndrome virus. Preferably, the RNA construct comprises or is derived from VEEV. Preferably, the virus from which the RNA construct is derived provides a vector backbone into which the nucleic acid sequence encoding the coronavirus surface glycoprotein is inserted. Preferably, the coronavirus surface glycoprotein or a fragment or variant thereof is an antigen against which antibodies are raised. The saRNA may comprise a nucleic acid sequence encoding a coronavirus surface glycoprotein or a fragment or variant thereof selected from a group consisting of SARS-CoV-2 surface glycoprotein or a fragment or variant thereof; SARS-CoV surface glycoprotein or a fragment or variant thereof; and MERS-CoV surface glycoprotein or a fragment or variant thereof.

In one preferred embodiment, the saRNA comprises a nucleic acid sequence encoding MERS-CoV surface glycoprotein or a fragment or variant thereof. In one embodiment, the wild-type MERS-CoV surface glycoprotein may be represented by Genbank ID No: AFY13307.1, which is provided herein as SEQ ID No: 1, as follows:

[SEQ ID No: 1]

```
MIHSVFLLMFLLTPTESYVDVGPDSVKSACIEVDIQQTFFDKTWPRPIDV
SKADGIIYPQGRTYSNITITYQGLFPYQGDHGDMYVYSAGHATGTTPQKL
FVANYSQDVKQFANGFVVRIGAAANSTGTVIISPSTSATIRKIYPAFMLG
SSVGNFSDGKMGRFFNHTLVLLPDGCGTLLRAFYCILEPRSGNHCPAGNS
YTSFATYHTPATDCSDGNYNRNASLNSFKEYFNLRNCTFMYTYNITEDEI
LEWFGITQTAQGVHLFSSRYVDLYGGNMFQFATLPVYDTIKYYSIIPHSI
RSIQSDRKAWAAFYVYKLQPLTFLLDFSVDGYIRRAIDCGFNDLSQLHCS
YESFDVESGVYSVSSFEAKPSGSVVEQAEGVECDFSPLLSGTPPQVYNFK
RLVFTNCNYNLTKLLSLFSVNDFTCSQISPAAIASNCYSSLILDYFSYPL
SMKSDLSVSSAGPISQFNYKQSFSNPTCLILATVPHNLTTITKPLKYSYI
NKCSRFLSDDRTEVPQLVNANQYSPCVSIVPSTVWEDGDYYRKQLSPLEG
GGWLVASGSTVAMTEQLQMGFGITVQYGTDTNSVCPKLEFANDTKIASQL
GNCVEYSLYGVSGRGVFQNCTAVGVRQQRFVYDAYQNLVGYYSDDGNYYC
LRACVSVPVSVIYDKETKTHATLFGSVACEHISSTMSQYSRSTRSMLKRR
DSTYGPLQTPVGCVLGLVNSSLFVEDCKLPLGQSLCALPDTPSTLTPRSV
RSVPGEMRLASIAFNHPIQVDQLNSSYFKLSIPTNFSFGVTQEYIQTTIQ
KVTVDCKQYVCNGFQKCEQLLREYGQFCSKINQALHGANLRQDDSVRNLF
ASVKSSQSSPIIPGFGGDFNLTLLEPVSISTGSRSARSAIEDLLFDKVTI
ADPGYMQGYDDCMQQGPASARDLICAQYVAGYKVLPPLMDVNMEAAYTSS
LLGSIAGVGWTAGLSSFAAIPFAQSIFYRLNGVGITQQVLSENQKLIANK
```

-continued

```
FNQALGAMQTGFTTTNEAFHKVQDAVNNNAQALSKLASELSNTFGAISAS
IGDIIQRLDVLEQDAQIDRLINGRLTTLNAFVAQQLVRSESAALSAQLAK
DKVNECVKAQSKRSGFCGQGTHIVSFVVNAPNGLYFMHVGYYPSNHIEVV
SAYGLCDAANPTNCIAPVNGYFIKTNNTRIVDEWSYTGSSFYAPEPITSL
NTKYVAPQVTYQNISTNLPPPLLGNSTGIDFQDELDEFFKNVSTSIPNFG
SLTQINTTLLDLTYEMLSLQQVVKALNESYIDLKELGNYTYYNKWPWYIW
LGFIAGLVALALCVFFILCCTGCGTNCMGKLKCNRCCDRYEEYDLEPHKV
HVH
```

Accordingly, preferably the saRNA comprises a nucleic acid sequence encoding MERS-CoV surface glycoprotein having an amino acid sequence substantially as set out in SEQ ID No: 1, or a fragment or variant thereof.

In another preferred embodiment, the saRNA comprises a nucleic acid sequence encoding SARS-CoV surface glycoprotein or a fragment or variant thereof. In one embodiment, the wild-type SARS-CoV surface glycoprotein may be represented by Genbank ID No: AAP13441.1, which is provided herein as SEQ ID No: 2, as follows:

[SEQ ID No: 2]

```
MFIFLLFLTLTSGSDLDRCTTFDDVQAPNYTQHTSSMRGVYYPDEIFRSD
TLYLTQDLFLPFYSNVTGFHTINHTFGNPVIPFKDGIYFAATEKSNVVRG
WVFGSTMNNKSQSVIIINNSTNVVIRACNFELCDNPFFAVSKPMGTQTHT
MIFDNAFNCTFEYISDAFSLDVSEKSGNFKHLREFVFKNKDGFLYVYKGY
QPIDVVRDLPSGFNTLKPIFKLPLGINITNFRAILTAFSPAQDIWGTSAA
AYFVGYLKPTTFMLKYDENGTITDAVDCSQNPLAELKCSVKSFEIDKGIY
QTSNFRVVPSGDVVRFPNITNLCPFGEVFNATKFPSVYAWERKKISNCVA
DYSVLYNSTFFSTFKCYGVSATKLNDLCFSNVYADSFVVKGDDVRQIAPG
QTGVIADYNYKLPDDFMGCVLAWNTRNIDATSTGNYNYKYRYLRHGKLRP
FERDISNVPFSPDGKPCTPPALNCYWPLNDYGFYTTTGIGYQPYRVVVLS
FELLNAPATVCGPKLSTDLIKNQCVNFNFNGLTGTGVLTPSSKRFQPFQQ
FGRDVSDFTDSVRDPKTSEILDISPCSFGGVSVITPGTNASSEVAVLYQD
VNCTDVSTAIHADQLTPAWRIYSTGNNVFQTQAGCLIGAEHVDTSYECDI
PIGAGICASYHTVSLLRSTSQKSIVAYTMSLGADSSIAYSNNTIAIPTNF
SISITTEVMPVSMAKTSVDCNMYICGDSTECANLLLQYGSFCTQLNRALS
GIAAEQDRNTREVFAQVKQMYKTPTLKYFGGFNFSQILPDPLKPTKRSFI
EDLLFNKVTLADAGFMKQYGECLGDINARDLICAQKFNGLTVLPPLLTDD
MIAAYTAALVSGTATAGWTFGAGAALQIPFAMQMAYRFNGIGVTQNVLYE
NQKQIANQFNKAISQIQESLTTTSTALGKLQDVVNQNAQALNTLVKQLSS
NFGAISSVLNDILSRLDKVEAEVQIDRLITGRLQSLQTYVTQQLIRAAEI
RASANLAATKMSECVLGQSKRVDFCGKGYHLMSFPQAAPHGVVFLHVTYV
PSQERNFTTAPAICHEGKAYFPREGVFVFNGTSWFITQRNFFSPQIITTD
NTFVSGNCDVVIGIINNTVYDPLQPELDSFKEELDKYFKNHTSPDVDLGD
```

-continued

ISGINASVVNIQKEIDRLNEVAKNLNESLIDLQELGKYEQYIKWPWYVWL

GFIAGLIAIVMVTILLCCMTSCCSCLKGACSCGSCCKFDEDDSEPVLKGV

KLHYT

Accordingly, preferably the saRNA comprises a nucleic acid sequence encoding SARS-CoV surface glycoprotein having an amino acid sequence substantially as set out in SEQ ID No: 2, or a fragment or variant thereof.

However, in a most preferred embodiment, the saRNA comprises a nucleic acid sequence encoding SARS-CoV-2 surface glycoprotein or a fragment or variant thereof. The skilled person would understand that SARS CoV2 may also be referred to as 2019 novel coronavirus (2019-nCoV) or COVID-19. In one embodiment, the amino acid sequence of the wild-type SARS-CoV-2 surface glycoprotein may be represented by Genbank ID No: QHD43416.1, which is provided herein as SEQ ID No: 3, as follows:

[SEQ ID No: 3]

MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPRRARSVASQSIIAYTMSLG

AENSVAYSNNSIAIPTNFTISVTTEILPVSMTKTSVDCTMYICGDSTECS

NLLLQYGSFCTQLNRALTGIAVEQDKNTQEVFAQVKQIYKTPPIKDFGGF

NFSQILPDPSKPSKRSFIEDLLFNKVTLADAGFIKQYGDCLGDIAARDLI

CAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQD

VVNQNAQALNTLVKQLSSNFGAISSVLNDILSRLDKVEAEVQIDRLITGR

LQSLQTYVTQQLIRAAEIRASANLAATKMSECVLGQSKRVDFCGKGYHLM

SFPQSAPHGVVFLHVTYVPAQEKNFTTAPAICHDGKAHFPREGVFVSNGT

HWFVTQRNFYEPQIITTDNTFVSGNCDVVIGIVNNTVYDPLQPELDSFKE

ELDKYFKNHTSPDVDLGDISGINASVVNIQKEIDRLNEVAKNLNESLIDL

QELGKYEQYIKWPWYIWLGFIAGLIAIVMVTIMLCCMTSCCSCLKGCCSC

GSCCKFDEDDSEPVLKGVKLHYT

Accordingly, preferably the saRNA comprises a nucleic acid sequence encoding SARS-CoV-2 surface glycoprotein having an amino acid sequence substantially as set out in SEQ ID No: 3, or a fragment or variant thereof.

Variants of the SARS-CoV-2 surface glycoprotein may be selected from a group of variants consisting of the B.1.1.7 UK variant; the B.1.1.7 UK variant+E484K variant; the B.1.351 South African variant; and the B.1.1.28 (P.1) Brazilian variant.

In one embodiment, the amino acid sequence of the B.1.1.7 UK variant surface glycoprotein is provided herein as SE ID No: 47, as follows:

[SEQ ID No: 47]

MFVFLVLLPLVSSQCVNLTTRTQLPPAYTNSFTRGVYYPDKVFRSSVLHS

TQDLFLPFFSNVTWFHAISGTNGTKRFDNPVLPFNDGVYFASTEKSNIIR

GWIFGTTLDSKTQSLLIVNNATNVVIKVCEFQFCNDPFLGVYHKNNKSWM

ESEFRVYSSANNCTFEYVSQPFLMDLEGKQGNFKNLREFVFKNIDGYFKI

YSKHTPINLVRDLPQGFSALEPLVDLPIGINITRFQTLLALHRSYLTPGD

SSSGWTAGAAAYYVGYLQPRTFLLKYNENGTITDAVDCALDPLSETKCTL

KSFTVEKGIYQTSNFRVQPTESIVRFPNITNLCPFGEVFNATRFASVYAW

NRKRISNCVADYSVLYNSASFSTFKCYGVSPTKLNDLCFTNVYADSFVIR

GDEVRQIAPGQTGKIADYNYKLPDDFTGCVIAWNSNNLDSKVGGNYNYLY

RLFRKSNLKPFERDISTEIYQAGSTPCNGVEGFNCYFPLQSYGFQPTYGV

GYQPYRVVVLSFELLHAPATVCGPKKSTNLVKNKCVNFNFNGLTGTGVLT

ESNKKFLPFQQFGRDIDDTTDAVRDPQTLEILDITPCSFGGVSVITPGTN

TSNQVAVLYQGVNCTEVPVAIHADQLTPTWRVYSTGSNVFQTRAGCLIGA

EHVNNSYECDIPIGAGICASYQTQTNSHSLASSVASQSIIAYTMSLGAEN

SVAYSNNSIAIPINFTISVTTEILPVSMTKTSVDCTMYICGDSTECSNLL

LQYGSFCTQLNRALTGIAVEQDKNTQEVFAQVKQIYKTPPIKDFGGFNFS

QILPDPSKPSKRSPIEDLLFNKVTLADAGFIKQYGDCLGDIAARDLICAQ

KFNGLTVLPPLLTDEMIAQYTSALLAGTITSGWTFGAGPALQIPFPMQMA

YRFNGIGVTQNVLYENQKLIANQFNSAIGKIQDSLSSTPSALGKLQDVVN

QNAQALNTLVKQLSSNFGAISSVLNDILARLDPPEAEVQIDRLITGRLQS

LQTYVTQQLIRAAEIRASANLAATKMSECVLGQSKRVDFCGKGYHLMSFP

QSAPHGVVFLHVTYVPAQEKNFTTAPAICHDGKAHFPREGVFVSNGTHWF

VTQRNFYEPQIITTHNTFVSGNCDVVIGIVNNTVYDPLQPELDSFKEELD

KYFKNHTSPDVDLGDISGINASVVNIQKEIDRLNEVAKNLNESLIDLQEL

GKYEQYIKWPWYIWLGFIAGLIAIVMVTIMLCCMTSCCSCLKGCCSCGSC

CKFDEDDSEPVLKGVKLHYT*

Accordingly, preferably the saRNA comprises a nucleic acid sequence encoding SARS-CoV-2 surface glycoprotein having an amino acid sequence substantially as set out in SEQ ID No: 47, or a fragment or variant thereof.

In one embodiment, the DNA sequence of the B.1.1.7 UK variant surface glycoprotein is provided herein as SEQ ID No: 48, as follows:

[SEQ ID No: 48]

ATGTTCGTGTTTCTGGTGCTGCTGCCTCTGGTGTCCAGCCAGTGTGTGAA

CCTGACCACCAGAACACAGCTGCCTCCAGCCTACACCAACAGCTTTACCA

GAGGCGTGTACTACCCCGACAAGGTGTTCAGATCCAGCGTGCTGCACTCT

-continued

ACCCAGGACCTGTTCCTGCCTTTCTTCAGCAACGTGACCTGGTTCCACGC

CATCTCCGGCACCAATGGCACCAAGAGATTCGACAACCCCGTGCTGCCCT

TCAACGACGGGGTGTACTTTGCCAGCACCGAGAAGTCCAACATCATCAGA

GGCTGGATCTTCGGCACCACACTGGACAGCAAGACCCAGAGCCTGCTGAT

CGTGAACAACGCCACCAACGTGGTCATCAAAGTGTGCGAGTTCCAGTTCT

GCAACGACCCCTTCCTGGGCGTCTACCACAAGAACAACAAGAGCTGGATG

GAAAGCGAGTTCCGGGTGTACAGCAGCGCCAACAACTGCACCTTCGAGTA

CGTGTCCCAGCCTTTCCTGATGGACCTGGAAGGCAAGCAGGGCAACTTCA

AGAACCTGCGCGAGTTCGTGTTCAAGAACATCGACGGCTACTTCAAGATC

TACAGCAAGCACACCCCTATCAACCTCGTGCGGGATCTGCCTCAGGGCTT

CTCTGCTCTGGAACCCCTGGTGGATCTGCCCATCGGCATCAACATCACCC

GGTTTCAGACACTGCTGGCCCTGCACAGAAGCTACCTGACACCTGGCGAT

AGCAGCAGCGGATGGACAGCTGGTGCCGCCGCTTACTATGTGGGCTACCT

GCAGCCTAGAACCTTCCTGCTGAAGTACAACGAGAACGGCACCATCACCG

ACGCCGTGGATTGTGCCCTTGATCCTCTGAGCGAGACAAAGTGCACCCTG

AAGTCCTTCACCGTGGAAAAGGGCATCTACCAGACCAGCAACTTCCGGGT

GCAGCCCACCGAATCCATCGTGCGGTTCCCCAATATCACCAATCTGTGCC

CCTTCGGCGAGGTGTTCAATGCCACCAGATTCGCCTCTGTGTACGCCTGG

AACCGGAAGCGGATCAGCAATTGCGTGGCCGACTACTCCGTGCTGTACAA

CTCCGCCAGCTTCAGCACCTTCAAGTGCTACGGCGTGTCCCCTACCAAGC

TGAACGACCTGTGCTTCACAAACGTGTACGCCGACAGCTTCGTGATCCGG

GGAGATGAAGTGCGGCAGATTGCCCCTGGACAGACAGGCAAGATCGCCGA

CTACAACTACAAGCTGCCCGACGACTTCACCGGCTGTGTGATTGCCTGGA

ACAGCAACAACCTGGACTCCAAAGTCGGCGGCAACTACAATTACCTGTAC

CGGCTGTTCCGGAAGTCCAATCTGAAGCCCTTCGAGCGGGACATCTCCAC

CGAGATCTATCAGGCCGGCAGCACCCCTTGTAACGGCGTGGAAGGCTTCA

ACTGCTACTTCCCACTGCAGTCCTACGGCTTTCAGCCCACATATGGCGTG

GGCTATCAGCCCTACAGAGTGGTGGTGCTGAGCTTCGAACTGCTGCATGC

CCCTGCCACAGTGTGCGGCCCTAAGAAAAGCACCAATCTCGTGAAGAACA

AATGCGTGAACTTCAACTTCAACGGCCTGACCGGCACAGGCGTGCTGACA

GAGAGCAACAAGAAGTTCCTGCCATTCCAGCAGTTTGGCCGGGATATCGA

CGATACCACAGACGCCGTTAGAGATCCCCAGACACTGGAAATCCTGGACA

TCACCCCTTGCAGCTTCGGCGGAGTGTCTGTGATCACCCCTGGCACCAAC

ACCAGCAATCAGGTGGCAGTGCTGTACCAGGGCGTGAACTGTACCGAAGT

GCCCGTGGCCATTCACGCCGATCAGCTGACACCTACATGGCGGGTGTACT

CCACCGGCAGCAATGTGTTTCAGACCAGAGCCGGCTGTCTGATCGGAGCC

GAGCACGTGAACAATAGCTACGAGTGCGACATCCCCATCGGCGCTGGCAT

CTGTGCCAGCTACCAGACACAGACAAACAGCCACTCTCTGGCCAGCTCTG

TGGCCAGCCAGAGCATCATTGCCTACACAATGTCTCTGGGCGCCGAGAAC

AGCGTGGCCTACTCCAACAACTCTATCGCTATCCCCATCAACTTCACCAT

-continued

CAGCGTGACCACAGAGATCCTGCCTGTGTCCATGACCAAGACCAGCGTGG

ACTGCACCATGTACATCTGCGGCGATTCCACCGAGTGCTCCAACCTGCTG

CTGCAGTACGGCAGCTTCTGCACCCAGCTGAATAGAGCCCTGACAGGGAT

CGCCGTGGAACAGGACAAGAACACCCAAGAGGTGTTCGCCCAAGTGAAGC

AGATCTACAAGACCCCTCCTATCAAGGACTTCGGCGGCTTCAATTTCAGC

CAGATTCTGCCCGATCCTAGCAAGCCCAGCAAGCGGAGCCCCATCGAGGA

CCTGCTGTTCAACAAAGTGACACTGGCCGACGCCGGCTTCATCAAGCAGT

ATGGCGATTGTCTGGGCGACATTGCCGCCAGGGATCTGATTTGCGCCCAG

AAGTTTAACGGACTGACAGTGCTGCCTCCTCTGCTGACCGATGAGATGAT

CGCCCAGTACACATCTGCCCTGCTGGCCGGCACAATCACAAGCGGCTGGA

CATTTGGAGCTGGCCCCGCTCTGCAGATCCCCTTTCCTATGCAGATGGCC

TACAGATTCAACGGCATCGGAGTGACCCAGAATGTGCTGTACGAGAACCA

GAAGCTGATCGCCAACCAGTTCAACAGCGCCATCGGCAAGATCCAGGACA

GCCTGAGCAGCACACCAAGCGCCCTGGGAAAGCTGCAGGACGTGGTCAAC

CAGAATGCCCAGGCACTGAACACCCTGGTCAAGCAGCTGTCCTCCAACTT

CGGCGCCATCAGCTCTGTGCTGAACGATATCCTGGCCAGACTGGACCCTC

CTGAGGCCGAGGTGCAGATCGACAGACTGATCACAGGCAGACTGCAGAGC

CTCCAGACATACGTGACCCAGCAGCTGATCAGAGCCGCCGAGATTAGAGC

CTCTGCCAATCTGGCCGCCACCAAGATGTCTGAGTGTGTGCTGGGCCAGA

GCAAGAGAGTGGACTTTTGCGGCAAGGGCTACCACCTGATGAGCTTCCCT

CAGTCTGCCCCTCACGGCGTGGTGTTTCTGCACGTGACATACGTTCCCGC

TCAAGAGAAGAATTTCACCACCGCTCCAGCCATCTGCCACGACGGCAAAG

CCCACTTTCCTAGAGAAGGCGTGTTCGTGTCCAACGGCACCCATTGGTTC

GTGACACAGCGGAACTTCTACGAGCCCCAGATCATCACCACCCACAACAC

CTTCGTGTCTGGCAACTGCGACGTCGTGATCGGCATTGTGAACAATACCG

TGTACGACCCTCTGCAGCCCGAGCTGGACAGCTTCAAAGAGGAACTGGAC

AAGTACTTTAAGAACCACACAAGCCCCGACGTGGACCTGGGCGATATCAG

CGGAATCAATGCCAGCGTCGTGAACATCCAGAAAGAGATCGACCGGCTGA

ACGAGGTGGCCAAGAATCTGAACGAGAGCCTGATCGACCTGCAAGAACTG

GGGAAGTACGAGCAGTACATCAAGTGGCCCTGGTACATCTGGCTGGGCTT

TATCGCCGGACTGATTGCCATCGTGATGGTCACAATCATGCTGTGTTGCA

TGACCAGCTGCTGTAGCTGCCTGAAGGGCTGTTGTAGCTGTGGCAGCTGC

TGCAAGTTCGACGAGGACGATTCTGAGCCCGTGCTGAAGGGCGTGAAACT

GCACTACACATGA

Hence, preferably the saRNA is encoded by a DNA sequence substantially as set out in SEQ ID No: 48, or a fragment or variant thereof.

In one embodiment, the RNA sequence of the B.1.1.7 UK variant surface glycoprotein is provided herein as SEQ ID No: 49, as follows:

[SEQ ID No: 49]
AUGUUCGUGUUUCUGGUGCUGCUGCCUCUGGUGUCCAGCCAGUGUGUGAA
CCUGACCACCAGAACACAGCUGCCUCCAGCCUACACCAACAGCUUUACCA
GAGGCGUGUACUACCCCGACAAGGUGUUCAGAUCCAGCGUGCUGCACUCU
ACCCAGGACCUGUUCCUGCCUUUCUUCAGCAACGUGACCUGGUUCCACGC
CAUCUCCGGCACCAAUGGCACCAAGAGAUUCGACAACCCCGUGCUGCCCU
UCAACGACGGGGUGUACUUUGCCAGCACCGAGAAGUCCAACAUCAUCAGA
GGCUGGAUCUUCGGCACCACACUGGACAGCAAGACCCAGAGCCUGCUGAU
CGUGAACAACGCCACCAACGUGGUCAUCAAAGUGUGCGAGUUCCAGUUCU
GCAACGACCCCUUCCUGGGCGUCUACCACAAGAACAACAAGAGCUGGAUG
GAAAGCGAGUUCCGGGUGUACAGCAGCGCCAACAACUGCACCUUCGAGUA
CGUGUCCCAGCCUUUCCUGAUGGACCUGGAAGGCAAGCAGGGCAACUUCA
AGAACCUGCGCGAGUUCGUGUUCAAGAACAUCGACGGCUACUUCAAGAUC
UACAGCAAGCACACCCCUAUCAACCUCGUGCGGGAUCUGCCUCAGGGCUU
CUCUGCUCUGGAACCCCUGGUGGAUCUGCCCAUCGGCAUCAACAUCACCC
GGUUUCAGACACUGCUGGCCCUGCACAGAAGCUACCUGACACCUGGCGAU
AGCAGCAGCGGAUGGACAGCUGGUGCCGCCGCUUACUAUGUGGGCUACCU
GCAGCCUAGAACCUUCCUGCUGAAGUACAACGAGAACGGCACCAUCACCG
ACGCCGUGGAUUGUGCCCUUGAUCCUCUGAGCGAGACAAAGUGCACCCUG
AAGUCCUUCACCGUGGAAAAGGGCAUCUACCAGACCAGCAACUUCCGGGU
GCAGCCCACCGAAUCCAUCGUGCGGUUCCCCAAUAUCACCAAUCUGUGCC
CCUUCGGCGAGGUGUUCAAUGCCACCAGAUUCGCCUCUGUGUACGCCUGG
AACCGGAAGCGGAUCAGCAAUUGCGUGGCCGACUACUCCGUGCUGUACAA
CUCCGCCAGCUUCAGCACCUUCAAGUGCUACGGCGUGUCCCCUACCAAGC
UGAACGACCUGUGCUUCACAAACGUGUACGCCGACAGCUUCGUGAUCCGG
GGAGAUGAAGUGCGGCAGAUUGCCCCUGGACAGACAGGCAAGAUCGCCGA
CUACAACUACAAGCUGCCCGACGACUUCACCGGCUGUGUGAUUGCCUGGA
ACAGCAACAACCUGGACUCCAAAGUCGGCGGCAACUACAAUUACCUGUAC
CGGCUGUUCCGGAAGUCCAAUCUGAAGCCCUUCGAGCGGGACAUCUCCAC
CGAGAUCUAUCAGGCCGGCAGCACCCCUUGUAACGGCGUGGAAGGCUUCA
ACUGCUACUUCCCACUGCAGUCCUACGGCUUUCAGCCCACAUAUGGCGUG
GGCUAUCAGCCCUACAGAGUGGUGGUGCUGAGCUUCGAACUGCUGCAUGC
CCCUGCCACAGUGUGCGGCCCUAAGAAAAGCACCAAUCUCGUGAAGAACA
AAUGCGUGAACUUCAACUUCAACGGCCUGACCGGCACAGGCGUGCUGACA
GAGAGCAACAAGAAGUUCCUGCCAUUCCAGCAGUUUGGCCGGGAUAUCGA
CGAUACCACAGACGCCGUUAGAGAUCCCCAGACACUGGAAAUCCUGGACA
UCACCCCUUGCAGCUUCGGCGGAGUGUCUGUGAUCACCCCUGGCACCAAC
ACCAGCAAUCAGGUGGCAGUGCUGUACCAGGGCGUGAACUGUACCGAAGU
GCCCGUGGCCAUUCACGCCGAUCAGCUGACACCUACAUGGCGGGUGUACU

-continued

CCACCGGCAGCAAUGUGUUUCAGACCAGAGCCGGCUGUCUGAUCGGAGCC
GAGCACGUGAACAAUAGCUACGAGUGCGACAUCCCCAUCGGCGCUGGCAU
CUGUGCCAGCUACCAGACACAGACAAACAGCCACUCUCUGGCCAGCUCUG
UGGCCAGCCAGAGCAUCAUUGCCUACACAAUGUCUCUGGGCGCCGAGAAC
AGCGUGGCCUACUCCAACAACUCUAUCGCUAUCCCCAUCAACUUCACCAU
CAGCGUGACCACAGAGAUCCUGCCUGUGUCCAUGACCAAGACCAGCGUGG
ACUGCACCAUGUACAUCUGCGGCGAUUCCACCGAGUGCUCCAACCUGCUG
CUGCAGUACGGCAGCUUCUGCACCCAGCUGAAUAGAGCCCUGACAGGGAU
CGCCGUGGAACAGGACAAGAACACCCAAGAGGUGUUCGCCCAAGUGAAGC
AGAUCUACAAGACCCCUCCUAUCAAGGACUUCGGCGGCUUCAAUUUCAGC
CAGAUUCUGCCCGAUCCUAGCAAGCCCAGCAAGCGGAGCCCCAUCGAGGA
CCUGCUGUUCAACAAAGUGACACUGGCCGACGCCGGCUUCAUCAAGCAGU
AUGGCGAUUGUCUGGGCGACAUUGCCGCCAGGGAUCUGAUUUGCGCCCAG
AAGUUUAACGGACUGACAGUGCUGCCUCCUCUGCUGACCGAUGAGAUGAU
CGCCCAGUACACAUCUGCCCUGCUGGCCGGCACAAUCACAAGCGGCUGGA
CAUUUGGAGCUGGCCCCGCUCUGCAGAUCCCCUUUCCUAUGCAGAUGGCC
UACAGAUUCAACGGCAUCGGAGUGACCCAGAAUGUGCUGUACGAGAACCA
GAAGCUGAUCGCCAACCAGUUCAACAGCGCCAUCGGCAAGAUCCAGGACA
GCCUGAGCAGCACACCAAGCGCCCUGGGAAAGCUGCAGGACGUGGUCAAC
CAGAAUGCCCAGGCACUGAACACCCUGGUCAAGCAGCUGUCCUCCAACUU
CGGCGCCAUCAGCUCUGUGCUGAACGAUAUCCUGGCCAGACUGGACCCUC
CUGAGGCCGAGGUGCAGAUCGACAGACUGAUCACAGGCAGACUGCAGAGC
CUCCAGACAUACGUGACCCAGCAGCUGAUCAGAGCCGCCGAGAUUAGAGC
CUCUGCCAAUCUGGCCGCCACCAAGAUGUCUGAGUGUGUGCUGGGCCAGA
GCAAGAGAGUGGACUUUUGCGGCAAGGGCUACCACCUGAUGAGCUUCCCU
CAGUCUGCCCCUCACGGCGUGGUGUUUCUGCACGUGACAUACGUUCCCGC
UCAAGAGAAGAAUUUCACCACCGCUCCAGCCAUCUGCCACGACGGCAAAG
CCCACUUUCCUAGAGAAGGCGUGUUCGUGUCCAACGGCACCCAUUGGUUC
GUGACACAGCGGAACUUCUACGAGCCCCAGAUCAUCACCACCCACAACAC
CUUCGUGUCUGGCAACUGCGACGUCGUGAUCGGCAUUGUGAACAAUACCG
UGUACGACCCUCUGCAGCCCGAGCUGGACAGCUUCAAAGAGGAACUGGAC
AAGUACUUUAAGAACCACACAAGCCCCGACGUGGACCUGGGCGAUAUCAG
CGGAAUCAAUGCCAGCGUCGUGAACAUCCAGAAAGAGAUCGACCGGCUGA
ACGAGGUGGCCAAGAAUCUGAACGAGAGCCUGAUCGACCUGCAAGAACUG
GGGAAGUACGAGCAGUACAUCAAGUGGCCCUGGUACAUCUGGCUGGGCUU
UAUCGCCGGACUGAUUGCCAUCGUGAUGGUCACAAUCAUGCUGUGUUGCA
UGACCAGCUGCUGUAGCUGCCUGAAGGGCUGUUGUAGCUGUGGCAGCUGC
UGCAAGUUCGACGAGGACGAUUCUGAGCCCGUGCUGAAGGGCGUGAAACU
GCACUACACAUGA

Hence, preferably the saRNA comprises a sequence substantially as set out in SEQ ID No: 49, or a fragment or variant thereof.

In one embodiment, the amino acid sequence of the B.1.1.7 UK+E484K variant surface glycoprotein is provided herein as SEQ ID No: 50, as follows:

[SEQ ID No: 50]

```
MFVFLVLLPLVSSQCVNLTTRTQLPPAYTNSFTRGVYYPD
KVFRSSVLHSTQDLFLPFFSNVTWFHAISGTNGTKRFDNP
VLPFNDGVYFASTEKSNIIRGWIFGTTLDSKTQSLLIVNN
ATNVVIKVCEFQFCNDPFLGVYHKNNKSWMESEFRVYSSA
NNCTFEYVSQPFLMDLEGKQGNFKNLREFVFKNIDGYFKI
YSKHTPINLVRDLPQGFSALEPLVDLPIGINITRFQTLLA
LHRSYLTPGDSSSGWTAGAAAYYVGYLQPRTFLLKYNENG
TITDAVDCALDPLSETKCTLKSFTVEKGIYQTSNFRVQPT
ESIVRFPNITNLCPFGEVFNATRFASVYAWNRKRISNCVA
DYSVLYNSASFSTFKCYGVSPTKLNDLCFTNVYADSFVIR
GDEVRQIAPGQTGKIADYNYKLPDDFTGCVIAWNSNNLDS
KVGGNYNYLYRLFRKSNLKPFERDISTEIYQAGSTPCNGV
KGFNCYFPLQSYGFQPTYGVGYQPYRVVVLSFELLHAPAT
VCGPKKSTNLVKNKCVNFNFNGLTGTGVLTESNKKFLPFQ
QFGRDIDDTTDAVRDPQTLEILDITPCSFGGVSVITPGTN
TSNQVAVLYQGVNCTEVPVAIHADQLTPTWRVYSTGSNVF
QTRAGCLIGAEHVNNSYECDIPIGAGICASYQTQTNSHSL
ASSVASQSIIAYTMSLGAENSVAYSNNSIAIPINFTISVT
TEILPVSMTKTSVDCTMYICGDSTECSNLLLQYGSFCTQL
NRALTGIAVEQDKNTQEVFAPPLLTDEMIAQYTSALLAGT
ITSGWTFGAGPALQIPFPMQMAYRFNGIGVTQNVLYENQK
LIANQFNSAIGKIQDSLSSTPSALGKLQDVVNQNAQALNT
LVKQLSSNFGAISSVLNDILARLDPPEAEVQIDRLITGRL
QSLQTYVTQQLIRAAEIRASANLAATKMSECVLGQSKRVD
FCGKGYHLMSFPQSAPHGVVFLHVTYVPAQEKNFTTAPAI
CHDGKAHFPREGVFVSNGTHWFVTQRNFYEPQIITTHNTF
VSGNCDVVIGIVNNTVYDPLQPELDSFKEELDKYFKNHTS
PDVDLGDISGINASVVNIQKEIDRLNEVAKNLNESLIDLQ
ELGKYEQYIKWPWYIWLGFIAGLIAIVMVTIMLCCMTSCC
SCLKGCCSCGSCCKFDEDDSEPVLKGVKLHYT*
```

Accordingly, preferably the saRNA comprises a nucleic acid sequence encoding SARS-CoV-2 surface glycoprotein having an amino acid sequence substantially as set out in SEQ ID No: 50, or a fragment or variant thereof.

In one embodiment, the DNA sequence of the B.1.1.7 UK+E484K variant surface glycoprotein is provided herein as SEQ ID No: 51, as follows:

[SEQ ID No: 51]

```
ATGTTCGTGTTTCTGGTGCTGCTGCCTCTGGTGTCCAGCC
AGTGTGTGAACCTGACCACCAGAACACAGCTGCCTCCAGC
```

-continued

```
CTACACCAACAGCTTTACCAGAGGCGTGTACTACCCCGAC
AAGGTGTTCAGATCCAGCGTGCTGCACTCTACCCAGGACC
TGTTCCTGCCTTTCTTCAGCAACGTGACCTGGTTCCACGC
CATCTCCGGCACCAATGGCACCAAGAGATTCGACAACCCC
GTGCTGCCCTTCAACGACGGGGTGTACTTTGCCAGCACCG
AGAAGTCCAACATCATCAGAGGCTGGATCTTCGGCACCAC
ACTGGACAGCAAGACCCAGAGCCTGCTGATCGTGAACAAC
GCCACCAACGTGGTCATCAAAGTGTGCGAGTTCCAGTTCT
GCAACGACCCCTTCCTGGGCGTCTACCACAAGAACAACAA
GAGCTGGATGGAAAGCGAGTTCCGGGTGTACAGCAGCGCC
AACAACTGCACCTTCGAGTACGTGTCCCAGCCTTTCCTGA
TGGACCTGGAAGGCAAGCAGGGCAACTTCAAGAACCTGCG
CGAGTTCGTGTTCAAGAACATCGACGGCTACTTCAAGATC
TACAGCAAGCACACCCCTATCAACCTCGTGCGGGATCTGC
CTCAGGGCTTCTCTGCTCTGGAACCCCTGGTGGATCTGCC
CATCGGCATCAACATCACCCGGTTTCAGACACTGCTGGCC
CTGCACAGAAGCTACCTGACACCTGGCGATAGCAGCAGCG
GATGGACAGCTGGTGCCGCCGCTTACTATGTGGGCTACCT
GCAGCCTAGAACCTTCCTGCTGAAGTACAACGAGAACGGC
ACCATCACCGACGCCGTGGATTGTGCCCTTGATCCTCTGA
GCGAGACAAAGTGCACCCTGAAGTCCTTCACCGTGGAAAA
GGGCATCTACCAGACCAGCAACTTCCGGGTGCAGCCCACC
GAATCCATCGTGCGGTTCCCCAATATCACCAATCTGTGCC
CCTTCGGCGAGGTGTTCAATGCCACCAGATTCGCCTCTGT
GTACGCCTGGAACCGGAAGCGGATCAGCAATTGCGTGGCC
GACTACTCCGTGCTGTACAACTCCGCCAGCTTCAGCACCT
TCAAGTGCTACGGCGTGTCCCCTACCAAGCTGAACGACCT
GTGCTTCACAAACGTGTACGCCGACAGCTTCGTGATCCGG
GGAGATGAAGTGCGGCAGATTGCCCCTGGACAGACAGGCA
AGATCGCCGACTACAACTACAAGCTGCCCGACGACTTCAC
CGGCTGTGTGATTGCCTGGAACAGCAACAACCTGGACTCC
AAAGTCGGCGGCAACTACAATTACCTGTACCGGCTGTTCC
GGAAGTCCAATCTGAAGCCCTTCGAGCGGGACATCTCCAC
CGAGATCTATCAGGCCGGCAGCACCCCTTGTAACGGCGTG
AAAGGCTTCAACTGCTACTTCCCACTGCAGTCCTACGGCT
TTCAGCCCACATATGGCGTGGGCTATCAGCCCTACAGAGT
GGTGGTGCTGAGCTTCGAACTGCTGCATGCCCCTGCCACA
GTGTGCGGCCCTAAGAAAAGCACCAATCTCGTGAAGAACA
AATGCGTGAACTTCAACTTCAACGGCCTGACCGGCACAGG
CGTGCTGACAGAGAGCAACAAGAAGTTCCTGCCATTCCAG
```

-continued

CAGTTTGGCCGGGATATCGACGATACCACAGACGCCGTTA

GAGATCCCCAGACACTGGAAATCCTGGACATCACCCCTTG

CAGCTTCGGCGGAGTGTCTGTGATCACCCCTGGCACCAAC

ACCAGCAATCAGGTGGCAGTGCTGTACCAGGGCGTGAACT

GTACCGAAGTGCCCGTGGCCATTCACGCCGATCAGCTGAC

ACCTACATGGCGGGTGTACTCCACCGGCAGCAATGTGTTT

CAGACCAGAGCCGGCTGTCTGATCGGAGCCGAGCACGTGA

ACAATAGCTACGAGTGCGACATCCCCATCGGCGCTGGCAT

CTGTGCCAGCTACCAGACACAGACAAACAGCCACTCTCTG

GCCAGCTCTGTGGCCAGCCAGAGCATCATTGCCTACACAA

TGTCTCTGGGCGCCGAGAACAGCGTGGCCTACTCCAACAA

CTCTATCGCTATCCCCATCAACTTCACCATCAGCGTGACC

ACAGAGATCCTGCCTGTGTCCATGACCAAGACCAGCGTGG

ACTGCACCATGTACATCTGCGGCGATTCCACCGAGTGCTC

CAACCTGCTGCTGCAGTACGGCAGCTTCTGCACCCAGCTG

AATAGAGCCCTGACAGGGATCGCCGTGGAACAGGACAAGA

ACACCCAAGAGGTGTTCGCCCAAGTGAAGCAGATCTACAA

GACCCCTCCTATCAAGGACTTCGGCGGCTTCAATTTCAGC

CAGATTCTGCCCGATCCTAGCAAGCCCAGCAAGCGGAGCC

CCATCGAGGACCTGCTGTTCAACAAAGTGACACTGGCCGA

CGCCGGCTTCATCAAGCAGTATGGCGATTGTCTGGGCGAC

ATTGCCGCCAGGGATCTGATTTGCGCCCAGAAGTTTAACG

GACTGACAGTGCTGCCTCCTCTGCTGACCGATGAGATGAT

CGCCCAGTACACATCTGCCCTGCTGGCCGGCACAATCACA

AGCGGCTGGACATTTGGAGCTGGCCCCGCTCTGCAGATCC

CCTTTCCTATGCAGATGGCCTACAGATTCAACGGCATCGG

AGTGACCCAGAATGTGCTGTACGAGAACCAGAAGCTGATC

GCCAACCAGTTCAACAGCGCCATCGGCAAGATCCAGGACA

GCCTGAGCAGCACACCAAGCGCCCTGGGAAAGCTGCAGGA

CGTGGTCAACCAGAATGCCCAGGCACTGAACACCCTGGTC

AAGCAGCTGTCCTCCAACTTCGGCGCCATCAGCTCTGTGC

TGAACGATATCCTGGCCAGACTGGACCCTCCTGAGGCCGA

GGTGCAGATCGACAGACTGATCACAGGCAGACTGCAGAGC

CTCCAGACATACGTGACCCAGCAGCTGATCAGAGCCGCCG

AGATTAGAGCCTCTGCCAATCTGGCCGCCACCAAGATGTC

TGAGTGTGTGCTGGGCCAGAGCAAGAGAGTGGACTTTTGC

GGCAAGGGCTACCACCTGATGAGCTTCCCTCAGTCTGCCC

CTCACGGCGTGGTGTTTCTGCACGTGACATACGTTCCCGC

TCAAGAGAAGAATTTCACCACCGCTCCAGCCATCTGCCAC

GACGGCAAAGCCCACTTTCCTAGAGAAGGCGTGTTCGTGT

CCAACGGCACCCATTGGTTCGTGACACAGCGGAACTTCTA

-continued

CGAGCCCCAGATCATCACCACCCACAACACCTTCGTGTCT

GGCAACTGCGACGTCGTGATCGGCATTGTGAACAATACCG

TGTACGACCCTCTGCAGCCCGAGCTGGACAGCTTCAAAGA

GGAACTGGACAAGTACTTTAAGAACCACACAAGCCCCGAC

GTGGACCTGGGCGATATCAGCGGAATCAATGCCAGCGTCG

TGAACATCCAGAAAGAGATCGACCGGCTGAACGAGGTGGC

CAAGAATCTGAACGAGAGCCTGATCGACCTGCAAGAACTG

GGGAAGTACGAGCAGTACATCAAGTGGCCCTGGTACATCT

GGCTGGGCTTTATCGCCGGACTGATTGCCATCGTGATGGT

CACAATCATGCTGTGTTGCATGACCAGCTGCTGTAGCTGC

CTGAAGGGCTGTTGTAGCTGTGGCAGCTGCTGCAAGTTCG

ACGAGGACGATTCTGAGCCCGTGCTGAAGGGCGTGAAACT

GCACTACACATGA

Hence, preferably the saRNA is encoded by a DNA sequence substantially as set out in SEQ ID No: 51, or a fragment or variant thereof.

In one embodiment, the RNA sequence of the B.1.1.7 UK+E484K variant surface glycoprotein is provided herein as SE ID No: 52, as follows:

[SEQ ID No: 52]

AUGUUCGUGUUUCUGGUGCUGCUGCCUCUGGUGUCCAGCC

AGUGUGUGAACCUGACCACCAGAACACAGCUGCCUCCAGC

CUACACCAACAGCUUUACCAGAGGCGUGUACUACCCCGAC

AAGGUGUUCAGAUCCAGCGUGCUGCACUCUACCCAGGACC

UGUUCCUGCCUUUCUUCAGCAACGUGACCUGGUUCCACGC

CAUCUCCGGCACCAAUGGCACCAAGAGAUUCGACAACCCC

GUGCUGCCCUUCAACGACGGGGUGUACUUUGCCAGCACCG

AGAAGUCCAACAUCAUCAGAGGCUGGAUCUUCGGCACCAC

ACUGGACAGCAAGACCCAGAGCCUGCUGAUCGUGAACAAC

GCCACCAACGUGGUCAUCAAAGUGUGCGAGUUCCAGUUCU

GCAACGACCCCUUCCUGGGCGUCUACCACAAGAACAACAA

GAGCUGGAUGGAAAGCGAGUUCCGGGUGUACAGCAGCGCC

AACAACUGCACCUUCGAGUACGUGUCCCAGCCUUUCCUGA

UGGACCUGGAAGGCAAGCAGGGCAACUUCAAGAACCUGCG

CGAGUUCGUGUUCAAGAACAUCGACGGCUACUUCAAGAUC

UACAGCAAGCACACCCCUAUCAACCUCGUGCGGGAUCUGC

CUCAGGGCUUCUCUGCUCUGGAACCCCUGGUGGAUCUGCC

CAUCGGCAUCAACAUCACCCGGUUUCAGACACUGCUGGCC

CUGCACAGAAGCUACCUGACACCUGGCGAUAGCAGCAGCG

GAUGGACAGCUGGUGCCGCCGCUUACUAUGUGGGCUACCU

GCAGCCUAGAACCUUCCUGCUGAAGUACAACGAGAACGGC

ACCAUCACCGACGCCGUGGAUUGUGCCCUUGAUCCUCUGA

-continued

GCGAGACAAAGUGCACCCUGAAGUCCUUCACCGUGGAAAA

GGGCAUCUACCAGACCAGCAACUUCCGGGUGCAGCCCACC

GAAUCCAUCGUGCGGUUCCCCAAUAUCACCAAUCUGUGCC

CCUUCGGCGAGGUGUUCAAUGCCACCAGAUUCGCCUCUGU

GUACGCCUGGAACCGGAAGCGGAUCAGCAAUUGCGUGGCC

GACUACUCCGUGCUGUACAACUCCGCCAGCUUCAGCACCU

UCAAGUGCUACGGCGUGUCCCCUACCAAGCUGAACGACCU

GUGCUUCACAAACGUGUACGCCGACAGCUUCGUGAUCCGG

GGAGAUGAAGUGCGGCAGAUUGCCCCUGGACAGACAGGCA

AGAUCGCCGACUACAACUACAAGCUGCCCGACGACUUCAC

CGGCUGUGUGAUUGCCUGGAACAGCAACAACCUGGACUCC

AAAGUCGGCGGCAACUACAAUUACCUGUACCGGCUGUUCC

GGAAGUCCAAUCUGAAGCCCUUCGAGCGGGACAUCUCCAC

CGAGAUCUAUCAGGCCGGCAGCACCCCUUGUAACGGCGUG

AAAGGCUUCAACUGCUACUUCCCACUGCAGUCCUACGGCU

UUCAGCCCACAUAUGGCGUGGGCUAUCAGCCCUACAGAGU

GGUGGUGCUGAGCUUCGAACUGCUGCAUGCCCCUGCCACA

GUGUGCGGCCCUAAGAAAAGCACCAAUCUCGUGAAGAACA

AAUGCGUGAACUUCAACUUCAACGGCCUGACCGGCACAGG

CGUGCUGACAGAGAGCAACAAGAAGUUCCUGCCAUUCCAG

CAGUUUGGCCGGGAUAUCGACGAUACCACAGACGCCGUUA

GAGAUCCCCAGACACUGGAAAUCCUGGACAUCACCCCUUG

CAGCUUCGGCGGAGUGUCUGUGAUCACCCCUGGCACCAAC

ACCAGCAAUCAGGUGGCAGUGCUGUACCAGGGCGUGAACU

GUACCGAAGUGCCCGUGGCCAUUCACGCCGAUCAGCUGAC

ACCUACAUGGCGGGUGUACUCCACCGGCAGCAAUGUGUUU

CAGACCAGAGCCGGCUGUCUGAUCGGAGCCGAGCACGUGA

ACAAUAGCUACGAGUGCGACAUCCCCAUCGGCGCUGGCAU

CUGUGCCAGCUACCAGACACAGACAAACAGCCACUCUCUG

GCCAGCUCUGUGGCCAGCCAGAGCAUCAUUGCCUACACAA

UGUCUCUGGGCGCCGAGAACAGCGUGGCCUACUCCAACAA

CUCUAUCGCUAUCCCCAUCAACUUCACCAUCAGCGUGACC

ACAGAGAUCCUGCCUGUGUCCAUGACCAAGACCAGCGUGG

ACUGCACCAUGUACAUCUGCGGCGAUUCCACCGAGUGCUC

CAACCUGCUGCUGCAGUACGGCAGCUUCUGCACCCAGCUG

AAUAGAGCCCUGACAGGGAUCGCCGUGGAACAGGACAAGA

ACACCCAAGAGGUGUUCGCCCAAGUGAAGCAGAUCUACAA

GACCCCUCCUAUCAAGGACUUCGGCGGCUUCAAUUUCAGC

CAGAUUCUGCCCGAUCCUAGCAAGCCCAGCAAGCGGAGCC

CCAUCGAGGACCUGCUGUUCAACAAAGUGACACUGGCCGA

-continued

CGCCGGCUUCAUCAAGCAGUAUGGCGAUUGUCUGGGCGAC

AUUGCCGCCAGGGAUCUGAUUUGCGCCCAGAAGUUUAACG

GACUGACAGUGCUGCCUCCUCUGCUGACCGAUGAGAUGAU

CGCCCAGUACACAUCUGCCCUGCUGGCCGGCACAAUCACA

AGCGGCUGGACAUUUGGAGCUGGCCCCGCUCUGCAGAUCC

CCUUUCCUAUGCAGAUGGCCUACAGAUUCAACGGCAUCGG

AGUGACCCAGAAUGUGCUGUACGAGAACCAGAAGCUGAUC

GCCAACCAGUUCAACAGCGCCAUCGGCAAGAUCCAGGACA

GCCUGAGCAGCACACCAAGCGCCCUGGGAAAGCUGCAGGA

CGUGGUCAACCAGAAUGCCCAGGCACUGAACACCCUGGUC

AAGCAGCUGUCCUCCAACUUCGGCGCCAUCAGCUCUGUGC

UGAACGAUAUCCUGGCCAGACUGGACCCUCCUGAGGCCGA

GGUGCAGAUCGACAGACUGAUCACAGGCAGACUGCAGAGC

CUCCAGACAUACGUGACCCAGCAGCUGAUCAGAGCCGCCG

AGAUUAGAGCCUCUGCCAAUCUGGCCGCCACCAAGAUGUC

UGAGUGUGUGCUGGGCCAGAGCAAGAGAGUGGACUUUUGC

GGCAAGGGCUACCACCUGAUGAGCUUCCCUCAGUCUGCCC

CUCACGGCGUGGUGUUUCUGCACGUGACAUACGUUCCCGC

UCAAGAGAAGAAUUUCACCACCGCUCCAGCCAUCUGCCAC

GACGGCAAAGCCCACUUUCCUAGAGAAGGCGUGUUCGUGU

CCAACGGCACCCAUUGGUUCGUGACACAGCGGAACUUCUA

CGAGCCCCAGAUCAUCACCACCCACAACACCUUCGUGUCU

GGCAACUGCGACGUCGUGAUCGGCAUUGUGAACAAUACCG

UGUACGACCCUCUGCAGCCCGAGCUGGACAGCUUCAAAGA

GGAACUGGACAAGUACUUUAAGAACCACACAAGCCCCGAC

GUGGACCUGGGCGAUAUCAGCGGAAUCAAUGCCAGCGUCG

UGAACAUCCAGAAAGAGAUCGACCGGCUGAACGAGGUGGC

CAAGAAUCUGAACGAGAGCCUGAUCGACCUGCAAGAACUG

GGGAAGUACGAGCAGUACAUCAAGUGGCCCUGGUACAUCU

GGCUGGGCUUUAUCGCCGGACUGAUUGCCAUCGUGAUGGU

CACAAUCAUGCUGUGUUGCAUGACCAGCUGCUGUAGCUGC

CUGAAGGGCUGUUGUAGCUGUGGCAGCUGCUGCAAGUUCG

ACGAGGACGAUUCUGAGCCCGUGCUGAAGGGCGUGAAACU

GCACUACACAUGA

Hence, preferably the saRNA comprises a sequence substantially as set out in SEQ ID No: 52, or a fragment or variant thereof.

In one embodiment, the amino acid sequence of the B.1.351 South African variant surface glycoprotein is provided herein as SEQ ID No: 53, as follows:

[SEQ ID No: 53]

MFVFLVLLPLVSSQCVNFTTRTQLPPAYTNSFTRGVYYPD

KVFRSSVLHSTQDLFLPFFSNVTWFHAIHVSGTNGTKRFA

NPVLPFNDGVYFASTEKSNIIRGWIFGTTLDSKTQSLLIV

NNATNVVIKVCEFQFCNDPFLGVYYHKNNKSWMESEFRVY

SSANNCTFEYVSQPFLMDLEGKQGNFKNLREFVFKNIDGY

FKIYSKHTPINLVRGLPQGFSALEPLVDLPIGINITRFQT

LHISYLTPGDSSSGWTAGAAAYYVGYLQPRTFLLKYNENG

TITDAVDCALDPLSETKCTLKSFTVEKGIYQTSNFRVQPT

ESIVRFPNITNLCPFGEVFNATRFASVYAWNRKRISNCVA

DYSVLYNSASFSTFKCYGVSPTKLNDLCFTNVYADSFVIR

GDEVRQIAPGQTGNIADYNYKLPDDFTGCVIAWNSNNLDS

KVGGNYNYLYRLFRKSNLKPFERDISTEIYQAGSTPCNGV

KGFNCYFPLQSYGFQPTYGVGYQPYRVVVLSFELLHAPAT

VCGPKKSTNLVKNKCVNFNFNGLTGTGVLTESNKKFLPFQ

QFGRDIADTTDAVRDPQTLEILDITPCSFGGVSVITPGTN

TSNQVAVLYQDVNCTEVPVAIHADQLTPTWRVYSTGSNVF

QTRAGCLIGAEHVNNSYECDIPIGAGICASYQTQTNSPSL

ASSVASQSIIAYTMSLGVENSVAYSNNSIAIPTNFTISVT

TEILPVSMTKTSVDCTMYICGDSTECSNLLLQYGSFCTQL

NRALTGIAVEQDKNTQEVFAQVKQTYKTPPIKDFGGFNFS

QILPDPSKPSKRSPIEDLLFNKVTLADAGFIKQYGDCLGD

IAARDLICAQKFNGLTVLPPLLTDEMIAQYTSALLAGTIT

SGWTFGAGPALQIPFPMQMAYRFNGIGVTQNVLYENQKLI

ANQFNSAIGKIQDSLSSTPSALGKLQDVVNQNAQALNTLV

KQLSSNFGAISSVLNDILSRLDPPEAEVQIDRLITGRLQS

LQTYVTQQLIRAAEIRASANLAATKMSECVLGQSKRVDFC

GKGYHLMSFPQSAPHGVVFLHVTYVPAQEKNFTTAPAICH

DGKAHFPREGVFVSNGTHWFVTQRNFYEPQIITTDNTFVS

GNCDVVIGIVNNTVYDPLQPELDSFKEELDKYFKNHTSPD

VDLGDISGINASVVNIQKEIDRLNEVAKNLNESLIDLQEL

GKYEQYIKWPWYIWLGFIAGLIAIVMVTIMLCCMTSCCSC

LKGCCSCGSCCKFDEDDSEPVLKGVKLHYT*

Accordingly, preferably the saRNA comprises a nucleic acid sequence encoding SARS-CoV-2 surface glycoprotein having an amino acid sequence substantially as set out in SEQ ID No: 53, or a fragment or variant thereof.

In one embodiment, the DNA sequence of the B.1.351 South African variant surface glycoprotein is provided herein as SEQ ID No: 54, as follows:

[SEQ ID No: 54]

ATGTTCGTGTTTCTGGTGCTGCTGCCTCTGGTGTCCAGCC

AGTGTGTGAACTTCACCACCAGAACACAGCTGCCTCCAGC

CTACACCAACAGCTTTACCAGAGGCGTGTACTACCCCGAC

AAGGTGTTCAGATCCAGCGTGCTGCACTCTACCCAGGACC

TGTTCCTGCCTTTCTTCAGCAACGTGACCTGGTTCCACGC

CATCCACGTGTCCGGCACCAATGGCACCAAGAGATTCGCC

AACCCCGTGCTGCCCTTCAACGACGGGGTGTACTTTGCCA

GCACCGAGAAGTCCAACATCATCAGAGGCTGGATCTTCGG

CACCACACTGGACAGCAAGACCCAGAGCCTGCTGATCGTG

AACAACGCCACCAACGTGGTCATCAAAGTGTGCGAGTTCC

AGTTCTGCAACGACCCCTTCCTGGGCGTCTACTACCACAA

GAACAACAAGAGCTGGATGGAAAGCGAGTTCCGGGTGTAC

AGCAGCGCCAACAACTGCACCTTCGAGTACGTGTCCCAGC

CTTTCCTGATGGACCTGGAAGGCAAGCAGGGCAACTTCAA

GAACCTGCGCGAGTTCGTGTTCAAGAACATCGACGGCTAC

TTCAAGATCTACAGCAAGCACACCCCTATCAACCTCGTGC

GGGGTCTGCCTCAGGGCTTCTCTGCTCTGGAACCCCTGGT

GGATCTGCCCATCGGCATCAACATCACCCGGTTTCAGACA

CTGCACATAAGCTACCTGACACCTGGCGATAGCAGCAGCG

GATGGACAGCTGGTGCCGCCGCTTACTATGTGGGCTACCT

GCAGCCTAGAACCTTCCTGCTGAAGTACAACGAGAACGGC

ACCATCACCGACGCCGTGGATTGTGCCCTTGATCCTCTGA

GCGAGACAAAGTGCACCCTGAAGTCCTTCACCGTGGAAAA

GGGCATCTACCAGACCAGCAACTTCCGGGTGCAGCCCACC

GAATCCATCGTGCGGTTCCCCAATATCACCAATCTGTGCC

CCTTCGGCGAGGTGTTCAATGCCACCAGATTCGCCTCTGT

GTACGCCTGGAACCGGAAGCGGATCAGCAATTGCGTGGCC

GACTACTCCGTGCTGTACAACTCCGCCAGCTTCAGCACCT

TCAAGTGCTACGGCGTGTCCCCTACCAAGCTGAACGACCT

GTGCTTCACAAACGTGTACGCCGACAGCTTCGTGATCCGG

GGAGATGAAGTGCGGCAGATTGCCCCTGGACAGACAGGCA

ATATCGCCGACTACAACTACAAGCTGCCCGACGACTTCAC

CGGCTGTGTGATTGCCTGGAACAGCAACAACCTGGACTCC

AAAGTCGGCGGCAACTACAATTACCTGTACCGGCTGTTCC

GGAAGTCCAATCTGAAGCCCTTCGAGCGGGACATCTCCAC

CGAGATCTATCAGGCCGGCAGCACCCCTTGTAACGGCGTG

AAAGGCTTCAACTGCTACTTCCCACTGCAGTCCTACGGCT

TTCAGCCCACATATGGCGTGGGCTATCAGCCCTACAGAGT

-continued

GGTGGTGCTGAGCTTCGAACTGCTGCATGCCCCTGCCACA

GTGTGCGGCCCTAAGAAAAGCACCAATCTCGTGAAGAACA

AATGCGTGAACTTCAACTTCAACGGCCTGACCGGCACAGG

CGTGCTGACAGAGAGCAACAAGAAGTTCCTGCCATTCCAG

CAGTTTGGCCGGGATATCGCCGATACCACAGACGCCGTTA

GAGATCCCCAGACACTGGAAATCCTGGACATCACCCCTTG

CAGCTTCGGCGGAGTGTCTGTGATCACCCCTGGCACCAAC

ACCAGCAATCAGGTGGCAGTGCTGTACCAGGACGTGAACT

GTACCGAAGTGCCCGTGGCCATTCACGCCGATCAGCTGAC

ACCTACATGGCGGGTGTACTCCACCGGCAGCAATGTGTTT

CAGACCAGAGCCGGCTGTCTGATCGGAGCCGAGCACGTGA

ACAATAGCTACGAGTGCGACATCCCCATCGGCGCTGGCAT

CTGTGCCAGCTACCAGACACAGACAAACAGCCCCTCTCTG

GCCAGCTCTGTGGCCAGCCAGAGCATCATTGCCTACACAA

TGTCTCTGGGCGTCGAGAACAGCGTGGCCTACTCCAACAA

CTCTATCGCTATCCCCACCAACTTCACCATCAGCGTGACC

ACAGAGATCCTGCCTGTGTCCATGACCAAGACCAGCGTGG

ACTGCACCATGTACATCTGCGGCGATTCCACCGAGTGCTC

CAACCTGCTGCTGCAGTACGGCAGCTTCTGCACCCAGCTG

AATAGAGCCCTGACAGGGATCGCCGTGGAACAGGACAAGA

ACACCCAAGAGGTGTTCGCCCAAGTGAAGCAGATCTACAA

GACCCCTCCTATCAAGGACTTCGGCGGCTTCAATTTCAGC

CAGATTCTGCCCGATCCTAGCAAGCCCAGCAAGCGGAGCC

CCATCGAGGACCTGCTGTTCAACAAAGTGACACTGGCCGA

CGCCGGCTTCATCAAGCAGTATGGCGATTGTCTGGGCGAC

ATTGCCGCCAGGGATCTGATTTGCGCCCAGAAGTTTAACG

GACTGACAGTGCTGCCTCCTCTGCTGACCGATGAGATGAT

CGCCCAGTACACATCTGCCCTGCTGGCCGGCACAATCACA

AGCGGCTGGACATTTGGAGCTGGCCCCGCTCTGCAGATCC

CCTTTCCTATGCAGATGGCCTACAGATTCAACGGCATCGG

AGTGACCCAGAATGTGCTGTACGAGAACCAGAAGCTGATC

GCCAACCAGTTCAACAGCGCCATCGGCAAGATCCAGGACA

GCCTGAGCAGCACACCAAGCGCCCTGGGAAAGCTGCAGGA

CGTGGTCAACCAGAATGCCCAGGCACTGAACACCCTGGTC

AAGCAGCTGTCCTCCAACTTCGGCGCCATCAGCTCTGTGC

TGAACGATATCCTGAGCAGACTGGACCCTCCTGAGGCCGA

GGTGCAGATCGACAGACTGATCACAGGCAGACTGCAGAGC

CTCCAGACATACGTGACCCAGCAGCTGATCAGAGCCGCCG

AGATTAGAGCCTCTGCCAATCTGGCCGCCACCAAGATGTC

TGAGTGTGTGCTGGGCCAGAGCAAGAGAGTGGACTTTTGC

-continued

GGCAAGGGCTACCACCTGATGAGCTTCCCTCAGTCTGCCC

CTCACGGCGTGGTGTTTCTGCACGTGACATACGTTCCCGC

TCAAGAGAAGAATTTCACCACCGCTCCAGCCATCTGCCAC

GACGGCAAAGCCCACTTTCCTAGAGAAGGCGTGTTCGTGT

CCAACGGCACCCATTGGTTCGTGACACAGCGGAACTTCTA

CGAGCCCCAGATCATCACCACCGACAACACCTTCGTGTCT

GGCAACTGCGACGTCGTGATCGGCATTGTGAACAATACCG

TGTACGACCCTCTGCAGCCCGAGCTGGACAGCTTCAAAGA

GGAACTGGACAAGTACTTTAAGAACCACACAAGCCCCGAC

GTGGACCTGGGCGATATCAGCGGAATCAATGCCAGCGTCG

TGAACATCCAGAAAGAGATCGACCGGCTGAACGAGGTGGC

CAAGAATCTGAACGAGAGCCTGATCGACCTGCAAGAACTG

GGGAAGTACGAGCAGTACATCAAGTGGCCCTGGTACATCT

GGCTGGGCTTTATCGCCGGACTGATTGCCATCGTGATGGT

CACAATCATGCTGTGTTGCATGACCAGCTGCTGTAGCTGC

CTGAAGGGCTGTTGTAGCTGTGGCAGCTGCTGCAAGTTCG

ACGAGGACGATTCTGAGCCCGTGCTGAAGGGCGTGAAACT

GCACTACACATGA

Hence, preferably the saRNA is encoded by a DNA sequence substantially as set out in SEQ ID No: 54, or a fragment or variant thereof.

In one embodiment, the RNA sequence of the B.1.351 South African variant surface glycoprotein is provided herein as SEQ ID No: 55, as follows:

[SEQ ID No: 55]

AUGUUCGUGUUUCUGGUGCUGCUGCCUCUGGUGUCCAGCC

AGUGUGUGAACUUCACCACCAGAACACAGCUGCCUCCAGC

CUACACCAACAGCUUUACCAGAGGCGUGUACUACCCCGAC

AAGGUGUUCAGAUCCAGCGUGCUGCACUCUACCCAGGACC

UGUUCCUGCCUUUCUUCAGCAACGUGACCUGGUUCCACGC

CAUCCACGUGUCCGGCACCAAUGGCACCAAGAGAUUCGCC

AACCCCGUGCUGCCCUUCAACGACGGGGUGUACUUUGCCA

GCACCGAGAAGUCCAACAUCAUCAGAGGCUGGAUCUUCGG

CACCACACUGGACAGCAAGACCCAGAGCCUGCUGAUCGUG

AACAACGCCACCAACGUGGUCAUCAAAGUGUGCGAGUUCC

AGUUCUGCAACGACCCCUUCCUGGGCGUCUACUACCACAA

GAACAACAAGAGCUGGAUGGAAAGCGAGUUCCGGGUGUAC

AGCAGCGCCAACAACUGCACCUUCGAGUACGUGUCCCAGC

CUUUCCUGAUGGACCUGGAAGGCAAGCAGGGCAACUUCAA

GAACCUGCGCGAGUUCGUGUUCAAGAACAUCGACGGCUAC

UUCAAGAUCUACAGCAAGCACACCCCUAUCAACCUCGUGC

GGGGUCUGCCUCAGGGCUUCUCUGCUCUGGAACCCCUGGU

-continued

GGAUCUGCCCAUCGGCAUCAACAUCACCCGGUUUCAGACA

CUGCACAUAAGCUACCUGACACCUGGCGAUAGCAGCAGCG

GAUGGACAGCUGGUGCCGCCGCUUACUAUGUGGGCUACCU

GCAGCCUAGAACCUUCCUGCUGAAGUACAACGAGAACGGC

ACCAUCACCGACGCCGUGGAUUGUGCCCUUGAUCCUCUGA

GCGAGACAAAGUGCACCCUGAAGUCCUUCACCGUGGAAAA

GGGCAUCUACCAGACCAGCAACUUCCGGGUGCAGCCCACC

GAAUCCAUCGUGCGGUUCCCCAAUAUCACCAAUCUGUGCC

CCUUCGGCGAGGUGUUCAAUGCCACCAGAUUCGCCUCUGU

GUACGCCUGGAACCGGAAGCGGAUCAGCAAUUGCGUGGCC

GACUACUCCGUGCUGUACAACUCCGCCAGCUUCAGCACCU

UCAAGUGCUACGGCGUGUCCCCUACCAAGCUGAACGACCU

GUGCUUCACAAACGUGUACGCCGACAGCUUCGUGAUCCGG

GGAGAUGAAGUGCGGCAGAUUGCCCCUGGACAGACAGGCA

AUAUCGCCGACUACAACUACAAGCUGCCCGACGACUUCAC

CGGCUGUGUGAUUGCCUGGAACAGCAACAACCUGGACUCC

AAAGUCGGCGGCAACUACAAUUACCUGUACCGGCUGUUCC

GGAAGUCCAAUCUGAAGCCCUUCGAGCGGGACAUCUCCAC

CGAGAUCUAUCAGGCCGGCAGCACCCCUUGUAACGGCGUG

AAAGGCUUCAACUGCUACUUCCCACUGCAGUCCUACGGCU

UUCAGCCCACAUAUGGCGUGGGCUAUCAGCCCUACAGAGU

GGUGGUGCUGAGCUUCGAACUGCUGCAUGCCCCUGCCACA

GUGUGCGGCCCUAAGAAAAGCACCAAUCUCGUGAAGAACA

AAUGCGUGAACUUCAACUUCAACGGCCUGACCGGCACAGG

CGUGCUGACAGAGAGCAACAAGAAGUUCCUGCCAUUCCAG

CAGUUUGGCCGGGAUAUCGCCGAUACCACAGACGCCGUUA

GAGAUCCCCAGACACUGGAAAUCCUGGACAUCACCCCUUG

CAGCUUCGGCGGAGUGUCUGUGAUCACCCCUGGCACCAAC

ACCAGCAAUCAGGUGGCAGUGCUGUACCAGGACGUGAACU

GUACCGAAGUGCCCGUGGCCAUUCACGCCGAUCAGCUGAC

ACCUACAUGGCGGGUGUACUCCACCGGCAGCAAUGUGUUU

CAGACCAGAGCCGGCUGUCUGAUCGGAGCCGAGCACGUGA

ACAAUAGCUACGAGUGCGACAUCCCCAUCGGCGCUGGCAU

CUGUGCCAGCUACCAGACACAGACAAACAGCCCCUCUCUG

GCCAGCUCUGUGGCCAGCCAGAGCAUCAUUGCCUACACAA

UGUCUCUGGGCGUCGAGAACAGCGUGGCCUACUCCAACAA

CUCUAUCGCUAUCCCCACCAACUUCACCAUCAGCGUGACC

ACAGAGAUCCUGCCUGUGUCCAUGACCAAGACCAGCGUGG

ACUGCACCAUGUACAUCUGCGGCGAUUCCACCGAGUGCUC

CAACCUGCUGCUGCAGUACGGCAGCUUCUGCACCCAGCUG

AAUAGAGCCCUGACAGGGAUCGCCGUGGAACAGGACAAGA

ACACCCAAGAGGUGUUCGCCCAAGUGAAGCAGAUCUACAA

GACCCCUCCUAUCAAGGACUUCGGCGGCUUCAAUUUCAGC

CAGAUUCUGCCCGAUCCUAGCAAGCCCAGCAAGCGGAGCC

CCAUCGAGGACCUGCUGUUCAACAAAGUGACACUGGCCGA

CGCCGGCUUCAUCAAGCAGUAUGGCGAUUGUCUGGGCGAC

AUUGCCGCCAGGGAUCUGAUUUGCGCCCAGAAGUUUAACG

GACUGACAGUGCUGCCUCCUCUGCUGACCGAUGAGAUGAU

CGCCCAGUACACAUCUGCCCUGCUGGCCGGCACAAUCACA

AGCGGCUGGACAUUUGGAGCUGGCCCCGCUCUGCAGAUCC

CCUUUCCUAUGCAGAUGGCCUACAGAUUCAACGGCAUCGG

AGUGACCCAGAAUGUGCUGUACGAGAACCAGAAGCUGAUC

GCCAACCAGUUCAACAGCGCCAUCGGCAAGAUCCAGGACA

GCCUGAGCAGCACACCAAGCGCCCUGGGAAAGCUGCAGGA

CGUGGUCAACCAGAAUGCCCAGGCACUGAACACCCUGGUC

AAGCAGCUGUCCUCCAACUUCGGCGCCAUCAGCUCUGUGC

UGAACGAUAUCCUGAGCAGACUGGACCCUCCUGAGGCCGA

GGUGCAGAUCGACAGACUGAUCACAGGCAGACUGCAGAGC

CUCCAGACAUACGUGACCCAGCAGCUGAUCAGAGCCGCCG

AGAUUAGAGCCUCUGCCAAUCUGGCCGCCACCAAGAUGUC

UGAGUGUGUGCUGGGCCAGAGCAAGAGAGUGGACUUUUGC

GGCAAGGGCUACCACCUGAUGAGCUUCCCUCAGUCUGCCC

CUCACGGCGUGGUGUUUCUGCACGUGACAUACGUUCCCGC

UCAAGAGAAGAAUUUCACCACCGCUCCAGCCAUCUGCCAC

GACGGCAAAGCCCACUUUCCUAGAGAAGGCGUGUUCGUGU

CCAACGGCACCCAUUGGUUCGUGACACAGCGGAACUUCUA

CGAGCCCCAGAUCAUCACCACCGACAACACCUUCGUGUCU

GGCAACUGCGACGUCGUGAUCGGCAUUGUGAACAAUACCG

UGUACGACCCUCUGCAGCCCGAGCUGGACAGCUUCAAAGA

GGAACUGGACAAGUACUUUAAGAACCACACAAGCCCCGAC

GUGGACCUGGGCGAUAUCAGCGGAAUCAAUGCCAGCGUCG

UGAACAUCCAGAAAGAGAUCGACCGGCUGAACGAGGUGGC

CAAGAAUCUGAACGAGAGCCUGAUCGACCUGCAAGAACUG

GGGAAGUACGAGCAGUACAUCAAGUGGCCCUGGUACAUCU

GGCUGGGCUUUAUCGCCGGACUGAUUGCCAUCGUGAUGGU

CACAAUCAUGCUGUGUUGCAUGACCAGCUGCUGUAGCUGC

CUGAAGGGCUGUUGUAGCUGUGGCAGCUGCUGCAAGUUCG

ACGAGGACGAUUCUGAGCCCGUGCUGAAGGGCGUGAAACU

GCACUACACAUGA

Hence, preferably the saRNA comprises a sequence substantially as set out in SEQ ID No: 55, or a fragment or variant thereof.

In one embodiment, the amino acid sequence of the B.1.1.28 (P.1) Brazilian variant surface glycoprotein is provided herein as SEQ ID No: 56, as follows:

[SEQ ID No: 56]

```
MFVFLVLLPLVSSQCVNFTNRTQLPFAYTNSFTRGVYYPD
KVFRSSVLHSTQDLFLPFFSNVTWFHAIHVSGTNGTKRFD
NPVLPFNDGVYFASTEKSNIIRGWIFGTTLDSKTQSLLIV
NNATNVVIKVCEFQFCNYPFLGVYYHKNNKSWMESEFRVY
SSANNCTFEYVSQPFLMDLEGKQGNFKNLSEFVFKNIDGY
FKIYSKHTPINLVRDLPQGFSALEPLVDLPIGINITRFQT
LLALHRSYLTPGDSSSGWTAGAAAYYVGYLQPRTFLLKYN
ENGTITDAVDCALDPLSETKCTLKSFTVEKGIYQTSNFRV
QPTESIVRFPNITNLCPFGEVFNATRFASVYAWNRKRISN
CVADYSVLYNSASFSTFKCYGVSPTKLNDLCFTNVYADSF
VIRGDEVRQIAPGQTGTIADYNYKLPDDFTGCVIAWNSNN
LDSKVGGNYNYLYRLFRKSNLKPFERDISTEIYQAGSTPC
NGVKGFNCYFPLQSYGFQPTYGVGYQPYRVVVLSFELLHA
PATVCGPKKSTNLVKNKCVNFNFNGLTGTGVLTESNKKFL
PFQQFGRDIADTTDAVRDPQTLEILDITPCSFGGVSVITP
GTNTSNQVAVLYQGVNCTEVPVAIHADQLTPTWRVYSTGS
NVFQTRAGCLIGAEYVNNSYECDIPIGAGICASYQTQTNS
PSLASSVASQSIIAYTMSLGAENSVAYSNNSIAIPTNFTI
SVTTEILPVSMTKTSVDCTMYICGDSTECSNLLLQYGSFC
TQLNRALTGIAVEQDKNTQEVFAQVKQIYKTPPIKDFGGF
NFSQILPDPSKPSKRSPIEDLLFNKVTLADAGFIKQYGDC
LGDIAARDLICAQKFNGLTVLPPLLTDEMIAQYTSALLAG
TITSGWTFGAGPALQIPFPMQMAYRFNGIGVTQNVLYENQ
KLIANQFNSAIGKIQDSLSSTPSALGKLQDVVNQNAQALN
TLVKQLSSNFGAISSVLNDILSRLDPPEAEVQIDRLITGR
LQSLQTYVTQQLIRAAEIRASANLAAIKMSECVLGQSKRV
DFCGKGYHLMSFPQSAPHGVVFLHVTYVPAQEKNFTTAPA
ICHDGKAHFPREGVFVSNGTHWFVTQRNFYEPQIITTDNT
FVSGNCDVVIGIVNNTVYDPLQPELDSFKEELDKYFKNHT
SPDVDLGDISGINASFVNIQKEIDRLNEVAKNLNESLIDL
QELGKYEQYIKWPWYIWLGFIAGLIAIVMVTIMLCCMTSC
CSCLKGCCSCGSCCKFDEDDSEPVLKGVKLHYT*
```

Accordingly, preferably the saRNA comprises a nucleic acid sequence encoding SARS-CoV-2 surface glycoprotein having an amino acid sequence substantially as set out in SEQ ID No: 56, or a fragment or variant thereof.

In one embodiment, the DNA sequence of the B.1.1.28 (P.1) Brazilian variant surface glycoprotein is provided herein as SEQ ID No: 57, as follows:

[SEQ ID No: 57]

```
ATGTTCGTGTTTCTGGTGCTGCTGCCTCTGGTGTCCAGCC
AGTGTGTGAACTTCACCAACAGAACACAGCTGCCTTTCGC
CTACACCAACAGCTTTACCAGAGGCGTGTACTACCCCGAC
AAGGTGTTCAGATCCAGCGTGCTGCACTCTACCCAGGACC
TGTTCCTGCCTTTCTTCAGCAACGTGACCTGGTTCCACGC
CATCCACGTGTCCGGCACCAATGGCACCAAGAGATTCGAC
AACCCCGTGCTGCCCTTCAACGACGGGGTGTACTTTGCCA
GCACCGAGAAGTCCAACATCATCAGAGGCTGGATCTTCGG
CACCACACTGGACAGCAAGACCCAGAGCCTGCTGATCGTG
AACAACGCCACCAACGTGGTCATCAAAGTGTGCGAGTTCC
AGTTCTGCAACTACCCCTTCCTGGGCGTCTACTACCACAA
GAACAACAAGAGCTGGATGGAAAGCGAGTTCCGGGTGTAC
AGCAGCGCCAACAACTGCACCTTCGAGTACGTGTCCCAGC
CTTTCCTGATGGACCTGGAAGGCAAGCAGGGCAACTTCAA
GAACCTGAGCGAGTTCGTGTTCAAGAACATCGACGGCTAC
TTCAAGATCTACAGCAAGCACACCCCTATCAACCTCGTGC
GGGATCTGCCTCAGGGCTTCTCTGCTCTGGAACCCCTGGT
GGATCTGCCCATCGGCATCAACATCACCCGGTTTCAGACA
CTGCTGGCCCTGCACAGAAGCTACCTGACACCTGGCGATA
GCAGCAGCGGATGGACAGCTGGTGCCGCCGCTTACTATGT
GGGCTACCTGCAGCCTAGAACCTTCCTGCTGAAGTACAAC
GAGAACGGCACCATCACCGACGCCGTGGATTGTGCCCTTG
ATCCTCTGAGCGAGACAAAGTGCACCCTGAAGTCCTTCAC
CGTGGAAAAGGGCATCTACCAGACCAGCAACTTCCGGGTG
CAGCCCACCGAATCCATCGTGCGGTTCCCCAATATCACCA
ATCTGTGCCCCTTCGGCGAGGTGTTCAATGCCACCAGATT
CGCCTCTGTGTACGCCTGGAACCGGAAGCGGATCAGCAAT
TGCGTGGCCGACTACTCCGTGCTGTACAACTCCGCCAGCT
TCAGCACCTTCAAGTGCTACGGCGTGTCCCCTACCAAGCT
GAACGACCTGTGCTTCACAAACGTGTACGCCGACAGCTTC
GTGATCCGGGGAGATGAAGTGCGGCAGATTGCCCCTGGAC
AGACAGGCACGATCGCCGACTACAACTACAAGCTGCCCGA
CGACTTCACCGGCTGTGTGATTGCCTGGAACAGCAACAAC
CTGGACTCCAAAGTCGGCGGCAACTACAATTACCTGTACC
GGCTGTTCCGGAAGTCCAATCTGAAGCCCTTCGAGCGGGA
CATCTCCACCGAGATCTATCAGGCCGGCAGCACCCCTTGT
AACGGCGTGAAAGGCTTCAACTGCTACTTCCCACTGCAGT
CCTACGGCTTTCAGCCCACATATGGCGTGGGCTATCAGCC
```

-continued

CTACAGAGTGGTGGTGCTGAGCTTCGAACTGCTGCATGCC

CCTGCCACAGTGTGCGGCCCTAAGAAAAGCACCAATCTCG

TGAAGAACAAATGCGTGAACTTCAACTTCAACGGCCTGAC

CGGCACAGGCGTGCTGACAGAGAGCAACAAGAAGTTCCTG

CCATTCCAGCAGTTTGGCCGGGATATCGCCGATACCACAG

ACGCCGTTAGAGATCCCCAGACACTGGAAATCCTGGACAT

CACCCCTTGCAGCTTCGGCGGAGTGTCTGTGATCACCCCT

GGCACCAACACCAGCAATCAGGTGGCAGTGCTGTACCAGG

GCGTGAACTGTACCGAAGTGCCCGTGGCCATTCACGCCGA

TCAGCTGACACCTACATGGCGGGTGTACTCCACCGGCAGC

AATGTGTTTCAGACCAGAGCCGGCTGTCTGATCGGAGCCG

AGTACGTGAACAATAGCTACGAGTGCGACATCCCCATCGG

CGCTGGCATCTGTGCCAGCTACCAGACACAGACAAACAGC

CCCTCTCTGGCCAGCTCTGTGGCCAGCCAGAGCATCATTG

CCTACACAATGTCTCTGGGCGCCGAGAACAGCGTGGCCTA

CTCCAACAACTCTATCGCTATCCCCACCAACTTCACCATC

AGCGTGACCACAGAGATCCTGCCTGTGTCCATGACCAAGA

CCAGCGTGGACTGCACCATGTACATCTGCGGCGATTCCAC

CGAGTGCTCCAACCTGCTGCTGCAGTACGGCAGCTTCTGC

ACCCAGCTGAATAGAGCCCTGACAGGGATCGCCGTGGAAC

AGGACAAGAACACCCAAGAGGTGTTCGCCCAAGTGAAGCA

GATCTACAAGACCCCTCCTATCAAGGACTTCGGCGGCTTC

AATTTCAGCCAGATTCTGCCCGATCCTAGCAAGCCCAGCA

AGCGGAGCCCCATCGAGGACCTGCTGTTCAACAAAGTGAC

ACTGGCCGACGCCGGCTTCATCAAGCAGTATGGCGATTGT

CTGGGCGACATTGCCGCCAGGGATCTGATTTGCGCCCAGA

AGTTTAACGGACTGACAGTGCTGCCTCCTCTGCTGACCGA

TGAGATGATCGCCCAGTACACATCTGCCCTGCTGGCCGGC

ACAATCACAAGCGGCTGGACATTTGGAGCTGGCCCCGCTC

TGCAGATCCCCTTTCCTATGCAGATGGCCTACAGATTCAA

CGGCATCGGAGTGACCCAGAATGTGCTGTACGAGAACCAG

AAGCTGATCGCCAACCAGTTCAACAGCGCCATCGGCAAGA

TCCAGGACAGCCTGAGCAGCACACCAAGCGCCCTGGGAAA

GCTGCAGGACGTGGTCAACCAGAATGCCCAGGCACTGAAC

ACCCTGGTCAAGCAGCTGTCCTCCAACTTCGGCGCCATCA

GCTCTGTGCTGAACGATATCCTGAGCAGACTGGACCCTCC

TGAGGCCGAGGTGCAGATCGACAGACTGATCACAGGCAGA

CTGCAGAGCCTCCAGACATACGTGACCCAGCAGCTGATCA

GAGCCGCCGAGATTAGAGCCTCTGCCAATCTGGCCGCCAT

CAAGATGTCTGAGTGTGTGCTGGGCCAGAGCAAGAGAGTG

-continued

GACTTTTGCGGCAAGGGCTACCACCTGATGAGCTTCCCTC

AGTCTGCCCCTCACGGCGTGGTGTTTCTGCACGTGACATA

CGTTCCCGCTCAAGAGAAGAATTTCACCACCGCTCCAGCC

ATCTGCCACGACGGCAAAGCCCACTTTCCTAGAGAAGGCG

TGTTCGTGTCCAACGGCACCCATTGGTTCGTGACACAGCG

GAACTTCTACGAGCCCCAGATCATCACCACCGACAACACC

TTCGTGTCTGGCAACTGCGACGTCGTGATCGGCATTGTGA

ACAATACCGTGTACGACCCTCTGCAGCCCGAGCTGGACAG

CTTCAAAGAGGAACTGGACAAGTACTTTAAGAACCACACA

AGCCCCGACGTGGACCTGGGCGATATCAGCGGAATCAATG

CCAGCTTCGTGAACATCCAGAAAGAGATCGACCGGCTGAA

CGAGGTGGCCAAGAATCTGAACGAGAGCCTGATCGACCTG

CAAGAACTGGGGAAGTACGAGCAGTACATCAAGTGGCCCT

GGTACATCTGGCTGGGCTTTATCGCCGGACTGATTGCCAT

CGTGATGGTCACAATCATGCTGTGTTGCATGACCAGCTGC

TGTAGCTGCCTGAAGGGCTGTTGTAGCTGTGGCAGCTGCT

GCAAGTTCGACGAGGACGATTCTGAGCCCGTGCTGAAGGG

CGTGAAACTGCACTACACATGA

Hence, preferably the saRNA is encoded by a DNA sequence substantially as set out in SEQ ID No: 57, or a fragment or variant thereof.

In one embodiment, the RNA sequence of the B.1.1.28 (P.1) Brazilian variant surface glycoprotein is provided herein as SEQ ID No: 58, as follows:

[SEQ ID No: 58]

AUGUUCGUGUUUCUGGUGCUGCUGCCUCUGGUGUCCAGCC

AGUGUGUGAACUUCACCAACAGAACACAGCUGCCUUUCGC

CUACACCAACAGCUUUACCAGAGGCGUGUACUACCCCGAC

AAGGUGUUCAGAUCCAGCGUGCUGCACUCUACCCAGGACC

UGUUCCUGCCUUUCUUCAGCAACGUGACCUGGUUCCACGC

CAUCCACGUGUCCGGCACCAAUGGCACCAAGAGAUUCGAC

AACCCCGUGCUGCCCUUCAACGACGGGGUGUACUUUGCCA

GCACCGAGAAGUCCAACAUCAUCAGAGGCUGGAUCUUCGG

CACCACACUGGACAGCAAGACCCAGAGCCUGCUGAUCGUG

AACAACGCCACCAACGUGGUCAUCAAAGUGUGCGAGUUCC

AGUUCUGCAACUACCCCUUCCUGGGCGUCUACUACCACAA

GAACAACAAGAGCUGGAUGGAAAGCGAGUUCCGGGUGUAC

AGCAGCGCCAACAACUGCACCUUCGAGUACGUGUCCCAGC

CUUUCCUGAUGGACCUGGAAGGCAAGCAGGGCAACUUCAA

GAACCUGAGCGAGUUCGUGUUCAAGAACAUCGACGGCUAC

UUCAAGAUCUACAGCAAGCACACCCCUAUCAACCUCGUGC

GGGAUCUGCCUCAGGGCUUCUCUGCUCUGGAACCCCUGGU

-continued

```
GGAUCUGCCCAUCGGCAUCAACAUCACCCGGUUUCAGACA
CUGCUGGCCCUGCACAGAAGCUACCUGACACCUGGCGAUA
GCAGCAGCGGAUGGACAGCUGGUGCCGCCGCUUACUAUGU
GGGCUACCUGCAGCCUAGAACCUUCCUGCUGAAGUACAAC
GAGAACGGCACCAUCACCGACGCCGUGGAUUGUGCCCUUG
AUCCUCUGAGCGAGACAAAGUGCACCCUGAAGUCCUUCAC
CGUGGAAAAGGGCAUCUACCAGACCAGCAACUUCCGGGUG
CAGCCCACCGAAUCCAUCGUGCGGUUCCCCAAUAUCACCA
AUCUGUGCCCCUUCGGCGAGGUGUUCAAUGCCACCAGAUU
CGCCUCUGUGUACGCCUGGAACCGGAAGCGGAUCAGCAAU
UGCGUGGCCGACUACUCCGUGCUGUACAACUCCGCCAGCU
UCAGCACCUUCAAGUGCUACGGCGUGUCCCCUACCAAGCU
GAACGACCUGUGCUUCACAAACGUGUACGCCGACAGCUUC
GUGAUCCGGGGAGAUGAAGUGCGGCAGAUUGCCCCUGGAC
AGACAGGCACGAUCGCCGACUACAACUACAAGCUGCCCGA
CGACUUCACCGGCUGUGUGAUUGCCUGGAACAGCAACAAC
CUGGACUCCAAAGUCGGCGGCAACUACAAUUACCUGUACC
GGCUGUUCCGGAAGUCCAAUCUGAAGCCCUUCGAGCGGGA
CAUCUCCACCGAGAUCUAUCAGGCCGGCAGCACCCCUUGU
AACGGCGUGAAAGGCUUCAACUGCUACUUCCCACUGCAGU
CCUACGGCUUUCAGCCCACAUAUGGCGUGGGCUAUCAGCC
CUACAGAGUGGUGGUGCUGAGCUUCGAACUGCUGCAUGCC
CCUGCCACAGUGUGCGGCCCUAAGAAAAGCACCAAUCUCG
UGAAGAACAAAUGCGUGAACUUCAACUUCAACGGCCUGAC
CGGCACAGGCGUGCUGACAGAGAGCAACAAGAAGUUCCUG
CCAUUCCAGCAGUUUGGCCGGGAUAUCGCCGAUACCACAG
ACGCCGUUAGAGAUCCCCAGACACUGGAAAUCCUGGACAU
CACCCCUUGCAGCUUCGGCGGAGUGUCUGUGAUCACCCCU
GGCACCAACACCAGCAAUCAGGUGGCAGUGCUGUACCAGG
GCGUGAACUGUACCGAAGUGCCCGUGGCCAUUCACGCCGA
UCAGCUGACACCUACAUGGCGGGUGUACUCCACCGGCAGC
AAUGUGUUUCAGACCAGAGCCGGCUGUCUGAUCGGAGCCG
AGUACGUGAACAAUAGCUACGAGUGCGACAUCCCCAUCGG
CGCUGGCAUCUGUGCCAGCUACCAGACACAGACAAACAGC
CCCUCUCUGGCCAGCUCUGUGGCCAGCCAGAGCAUCAUUG
CCUACACAAUGUCUCUGGGCGCCGAGAACAGCGUGGCCUA
CUCCAACAACUCUAUCGCUAUCCCCACCAACUUCACCAUC
AGCGUGACCACAGAGAUCCUGCCUGUGUCCAUGACCAAGA
CCAGCGUGGACUGCACCAUGUACAUCUGCGGCGAUUCCAC
CGAGUGCUCCAACCUGCUGCUGCAGUACGGCAGCUUCUGC
ACCCAGCUGAAUAGAGCCCUGACAGGGAUCGCCGUGGAAC
```

-continued

```
AGGACAAGAACACCCAAGAGGUGUUCGCCCAAGUGAAGCA
GAUCUACAAGACCCCUCCUAUCAAGGACUUCGGCGGCUUC
AAUUUCAGCCAGAUUCUGCCCGAUCCUAGCAAGCCCAGCA
AGCGGAGCCCCAUCGAGGACCUGCUGUUCAACAAAGUGAC
ACUGGCCGACGCCGGCUUCAUCAAGCAGUAUGGCGAUUGU
CUGGGCGACAUUGCCGCCAGGGAUCUGAUUUGCGCCCAGA
AGUUUAACGGACUGACAGUGCUGCCUCCUCUGCUGACCGA
UGAGAUGAUCGCCCAGUACACAUCUGCCCUGCUGGCCGGC
ACAAUCACAAGCGGCUGGACAUUUGGAGCUGGCCCCGCUC
UGCAGAUCCCCUUUCCUAUGCAGAUGGCCUACAGAUUCAA
CGGCAUCGGAGUGACCCAGAAUGUGCUGUACGAGAACCAG
AAGCUGAUCGCCAACCAGUUCAACAGCGCCAUCGGCAAGA
UCCAGGACAGCCUGAGCAGCACACCAAGCGCCCUGGGAAA
GCUGCAGGACGUGGUCAACCAGAAUGCCCAGGCACUGAAC
ACCCUGGUCAAGCAGCUGUCCUCCAACUUCGGCGCCAUCA
GCUCUGUGCUGAACGAUAUCCUGAGCAGACUGGACCCUCC
UGAGGCCGAGGUGCAGAUCGACAGACUGAUCACAGGCAGA
CUGCAGAGCCUCCAGACAUACGUGACCCAGCAGCUGAUCA
GAGCCGCCGAGAUUAGAGCCUCUGCCAAUCUGGCCGCCAU
CAAGAUGUCUGAGUGUGUGCUGGGCCAGAGCAAGAGAGUG
GACUUUUGCGGCAAGGGCUACCACCUGAUGAGCUUCCCUC
AGUCUGCCCCUCACGGCGUGGUGUUUCUGCACGUGACAUA
CGUUCCCGCUCAAGAGAAGAAUUUCACCACCGCUCCAGCC
AUCUGCCACGACGGCAAAGCCCACUUUCCUAGAGAAGGCG
UGUUCGUGUCCAACGGCACCCAUUGGUUCGUGACACAGCG
GAACUUCUACGAGCCCCAGAUCAUCACCACCGACAACACC
UUCGUGUCUGGCAACUGCGACGUCGUGAUCGGCAUUGUGA
ACAAUACCGUGUACGACCCUCUGCAGCCCGAGCUGGACAG
CUUCAAAGAGGAACUGGACAAGUACUUUAAGAACCACACA
AGCCCCGACGUGGACCUGGGCGAUAUCAGCGGAAUCAAUG
CCAGCUUCGUGAACAUCCAGAAAGAGAUCGACCGGCUGAA
CGAGGUGGCCAAGAAUCUGAACGAGAGCCUGAUCGACCUG
CAAGAACUGGGGAAGUACGAGCAGUACAUCAAGUGGCCCU
GGUACAUCUGGCUGGGCUUUAUCGCCGGACUGAUUGCCAU
CGUGAUGGUCACAAUCAUGCUGUGUUGCAUGACCAGCUGC
UGUAGCUGCCUGAAGGGCUGUUGUAGCUGUGGCAGCUGCU
GCAAGUUCGACGAGGACGAUUCUGAGCCCGUGCUGAAGGG
CGUGAAACUGCACUACACAUGA
```

Hence, preferably the saRNA comprises a sequence substantially as set out in SEQ ID No: 58, or a fragment or variant thereof.

The inventors have realised that the optimum immune response elicited by a vaccine would be one triggered by exposure to an antigen which resembles the coronavirus before it attaches to, and fuses with, a host cell, rather than after attachment and fusion with a host cell. This is so that the modification at amino acid V987 comprises a substitution with a proline, i.e. V987P.

Hence, in one embodiment, the modified SARS-CoV-2 surface glycoprotein having the K986P and V987P modifications (highlighted in bold and underline), is provided herein as SEQ ID No: 4, as follows:

[SEQ ID No: 4]

```
MFVFLVLLPLVSSQCVNLTTRTQLPPAYTNSFTRGVYYPDKVFRSSVLHSTQDLFLPFFSNVTWFHAIHVSGTNGTKR
FDNPVLPFNDGVYFASTEKSNIIRGWIFGTTLDSKTQSLLIVNNATNVVIKVCEFQFCNDPFLGVYYHKNNKSWMESE
FRVYSSANNCTFEYVSQPFLMDLEGKQGNFKNLREFVFKNIDGYFKIYSKHTPINLVRDLPQGFSALEPLVDLPIGIN
ITRFQTLLALHRSYLTPGDSSSGWTAGAAAYYVGYLQPRTFLLKYNENGTITDAVDCALDPLSETKCTLKSFTVEKGI
YQTSNFRVQPTESIVRFPNITNLCPFGEVFNATRFASVYAWNRKRISNCVADYSVLYNSASFSTFKCYGVSPTKLNDL
CFTNVYADSFVIRGDEVRQIAPGQTGKIADYNYKLPDDFTGCVIAWNSNNLDSKVGGNYNYLYRLFRKSNLKPFERDI
STEIYQAGSTPCNGVEGFNCYFPLQSYGFQPTNGVGYQPYRVVVLSFELLHAPATVCGPKKSTNLVKNKCVNFNFNGL
TGTGVLTESNKKFLPFQQFGRDIADTTDAVRDPQTLEILDITPCSFGGVSVITPGTNTSNQVAVLYQDVNCTEVPVAI
HADQLTPTWRVYSTGSNVFQTRAGCLIGAEHVNNSYECDIPIGAGICASYQTQTNSPRRARSVASQSIIAYTMSLGAE
NSVAYSNNSIAIPTNFTISVTTEILPVSMTKTSVDCTMYICGDSTECSNLLLQYGSFCTQLNRALTGIAVEQDKNTQE
VFAQVKQIYKTPPIKDFGGFNFSQILPDPSKPSKRSFIEDLLFNKVTLADAGFIKQYGDCLGDIAARDLICAQKFNGL
TVLPPLLTDEMIAQYTSALLAGTITSGWTFGAGAALQIPFAMQMAYRFNGIGVTQNVLYENQKLIANQFNSAIGKIQD
SLSSTASALGKLQDVVNQNAQALNTLVKQLSSNFGAISSVLNDILSRLDPPEAEVQIDRLITGRLQSLQTYVTQQLIR
AAEIRASANLAATKMSECVLGQSKRVDFCGKGYHLMSFPQSAPHGVVFLHVTYVPAQEKNFTTAPAICHDGKAHFPRE
GVFVSNGTHWFVTQRNFYEPQIITTDNTFVSGNCDVVIGIVNNTVYDPLQPELDSFKEELDKYFKNHTSPDVDLGDIS
GINASVVNIQKEIDRLNEVAKNLNESLIDLQELGKYEQYIKWPWYIWLGFIAGLIAIVMVTIMLCCMTSCCSCLKGCC
SCGSCCKFDEDDSEPVLKGVKLHYT
```

antibodies would be produced exhibiting immuno-specificity to the pre-fused conformation of the glycoprotein, and not the fused or post fusion conformations. The trimeric pre-fusion glycoprotein is "meta-unstable" and can undergo conformation change spontaneously even in the absence of receptor binding. Preferably, therefore, the saRNA comprises a nucleic acid sequence encoding coronavirus surface glycoprotein or a fragment or variant thereof in its pre-fusion (i.e. native-like) conformation. As mentioned above, native coronavirus glycoprotein is trimeric, and so it is preferred that the saRNA comprises a nucleic acid sequence encoding coronavirus surface glycoprotein trimer.

The inventors have made two amino acid mutations to the wild-type sequence SARS-CoV-2 surface glycoprotein (K986P and V987P), which have been identified as being required for the stabilisation of the glycoprotein trimer in its native-like pre-fusion conformation, rather than its fused or post-fusion configuration.

Hence, preferably the saRNA comprises a nucleic acid sequence encoding modified SARS-CoV-2 surface glycoprotein comprising an amino acid sequence which has at least one modification in amino acid 986 or amino acid 987 of SEQ ID No: 3, 47, 50, 53 or 56. Preferably, the modified SARS-CoV-2 surface glycoprotein comprises a modification in amino acid 986 and amino acid 987 of SEQ ID No: 3, 47, 50, 53 or 56. Preferably, the modified SARS-CoV-2 surface glycoprotein is formed by a modification of amino acid residue K986 and/or V987 of SEQ ID No: 3, 47, 50, 53 or 56. Preferably, the modification at amino acid K986 comprises a substitution with a proline, i.e. K986P. Preferably, Hence, preferably the saRNA comprises a nucleic acid sequence encoding SARS-CoV-2 surface glycoprotein having an amino acid sequence substantially as set out in SEQ ID No: 4, or a fragment or variant thereof. SEQ ID No:4 is based on SEQ ID No:3, and it will be appreciated that any of SEQ ID No: 47, 50, 53 or 56 may be modified with the K986P and V987P modifications.

In addition to, or as an alternative to the above stabilising modifications (K986P and V987P) that may be made to the SARS-CoV-2 surface glycoprotein, the inventors also believe that mutating the furin cleavage site between the S1 and S2 sub-units of the homodimers that form the trimer will also stabilise the glycoprotein trimer in its native-like pre-fusion conformation, rather than its fused or post-fusion configuration. The furin cleavage site is located at amino acid positions 681-684 (or 682-685), and has the amino acid sequence PRRA [SEQ ID No: 5]. Hence, preferably the saRNA comprises a nucleic acid sequence encoding modified SARS-CoV-2 surface glycoprotein comprising a mutated furin cleavage site, preferably having the sequence represented by SEQ ID No: 5. Preferably, the saRNA comprises a nucleic acid sequence encoding modified SARS-CoV-2 surface glycoprotein comprising an amino acid sequence which has at least one, two, three or four modifications in amino acids 681, 682, 683 and 684 of SEQ ID No: 3, 47, 50, 53 or 56.

Preferably, the modified SARS-CoV-2 surface glycoprotein is formed by a modification of amino acid residue P681 and/or R682 and/or R683 and/or A684 of SEQ ID No: 3, 47, 50, 53 or 56. Any of these amino acids may be mutated to any other of the 20 common amino acids, which will be known the skilled person. Preferably, the modification at amino acid P681 comprises a substitution with a leucine, i.e. P681L. Preferably, the modification at amino acid R682 comprises a substitution with a proline, i.e. R682P. Preferably, the modification at amino acid R683 comprises a substitution with a proline, i.e. R683P. Preferably, the modification at amino acid A684 comprises a substitution with a proline, i.e. A684P.

It will be appreciated that certain stabilising modifications can also be made to SARS-CoV and MERS-CoV surface glycoproteins, which correspond to the stabilising modifications (K986P and V987P) that may be made to the SARS-CoV-2 surface glycoprotein.

It will be appreciated that the amino acid sequence of SARS-CoV-2 surface glycoprotein is very similar to that of SARS-CoV. Accordingly, for SARS-CoV, preferably the saRNA comprises a nucleic acid sequence encoding modified SARS-CoV surface glycoprotein comprising an amino acid sequence which has at least one modification in amino acid 968 or amino acid 969 of SEQ ID No: 2. Preferably, the modified SARS-CoV surface glycoprotein comprises a modification in amino acid 968 and amino acid 969 of SEQ ID No: 2. Preferably, the modified SARS-CoV surface glycoprotein is formed by a modification of amino acid residue K968 and/or V969 of SEQ ID No: 2. Preferably, the modification at amino acid K968 comprises a substitution with a proline, i.e. K968P. Preferably, the modification at amino acid V969 comprises a substitution with a proline, i.e. V969P.

However, for MERS-CoV, preferably the saRNA comprises a nucleic acid sequence encoding modified MERS-CoV surface glycoprotein comprising an amino acid sequence which has at least one modification in amino acid 1060 or amino acid 1061 of SEQ ID No: 1. Preferably, the modified MERS-CoV surface glycoprotein comprises a modification in amino acid 1060 and amino acid 1061 of SEQ ID No: 1. Preferably, the modified MERS-CoV surface glycoprotein is formed by a modification of amino acid residue V1060 and/or L1061 of SEQ ID No: 1. Preferably, the modification at amino acid V1060 comprises a substitution with a proline, i.e. V1060P. Preferably, the modification at amino acid L1061 comprises a substitution with a proline, i.e. L1061P.

As described in the Examples, the inventors focused their attention on a SARS-CoV-2 vaccine based on the saRNA construct of the first aspect, and so they worked with the modified SARS-CoV-2 surface glycoprotein having the K986P and V987P modifications, as shown in SEQ ID No: 4.

The inventors then subjected the modified protein sequence of SEQ ID No: 4 to codon optimisation for human expression, and one embodiment of the codon optimised nucleic acid (DNA) sequence is provided herein as SEQ ID No: 6, as follows:

[SEQ ID No: 6]

ATGTTCGTGTTTCTGGTGCTGCTGCCTCTGGTGTCCAGCC

AGTGTGTGAACCTGACCACCAGAACACAGCTGCCTCCAGC

CTACACCAACAGCTTTACCAGAGGCGTGTACTACCCCGAC

AAGGTGTTCAGATCCAGCGTGCTGCACTCTACCCAGGACC

TGTTCCTGCCTTTCTTCAGCAACGTGACCTGGTTCCACGC

-continued

CATCCACGTGTCCGGCACCAATGGCACCAAGAGATTCGAC

AACCCCGTGCTGCCCTTCAACGACGGGGTGTACTTTGCCA

GCACCGAGAAGTCCAACATCATCAGAGGCTGGATCTTCGG

CACCACACTGGACAGCAAGACCCAGAGCCTGCTGATCGTG

AACAACGCCACCAACGTGGTCATCAAAGTGTGCGAGTTCC

AGTTCTGCAACGACCCCTTCCTGGGCGTCTACTACCACAA

GAACAACAAGAGCTGGATGGAAAGCGAGTTCCGGGTGTAC

AGCAGCGCCAACAACTGCACCTTCGAGTACGTGTCCCAGC

CTTTCCTGATGGACCTGGAAGGCAAGCAGGGCAACTTCAA

GAACCTGCGCGAGTTCGTGTTCAAGAACATCGACGGCTAC

TTCAAGATCTACAGCAAGCACACCCCTATCAACCTCGTGC

GGGATCTGCCTCAGGGCTTCTCTGCTCTGGAACCCCTGGT

GGATCTGCCCATCGGCATCAACATCACCCGGTTTCAGACA

CTGCTGGCCCTGCACAGAAGCTACCTGACACCTGGCGATA

GCAGCAGCGGATGGACAGCTGGTGCCGCCGCTTACTATGT

GGGCTACCTGCAGCCTAGAACCTTCCTGCTGAAGTACAAC

GAGAACGGCACCATCACCGACGCCGTGGATTGTGCCCTTG

ATCCTCTGAGCGAGACAAAGTGCACCCTGAAGTCCTTCAC

CGTGGAAAAGGGCATCTACCAGACCAGCAACTTCCGGGTG

CAGCCCACCGAATCCATCGTGCGGTTCCCCAATATCACCA

ATCTGTGCCCCTTCGGCGAGGTGTTCAATGCCACCAGATT

CGCCTCTGTGTACGCCTGGAACCGGAAGCGGATCAGCAAT

TGCGTGGCCGACTACTCCGTGCTGTACAACTCCGCCAGCT

TCAGCACCTTCAAGTGCTACGGCGTGTCCCCTACCAAGCT

GAACGACCTGTGCTTCACAAACGTGTACGCCGACAGCTTC

GTGATCCGGGGAGATGAAGTGCGGCAGATTGCCCCTGGAC

AGACAGGCAAGATCGCCGACTACAACTACAAGCTGCCCGA

CGACTTCACCGGCTGTGTGATTGCCTGGAACAGCAACAAC

CTGGACTCCAAAGTCGGCGGCAACTACAATTACCTGTACC

GGCTGTTCCGGAAGTCCAATCTGAAGCCCTTCGAGCGGGA

CATCTCCACCGAGATCTATCAGGCCGGCAGCACCCCTTGT

AACGGCGTGGAAGGCTTCAACTGCTACTTCCCACTGCAGT

CCTACGGCTTTCAGCCCACAAATGGCGTGGGCTATCAGCC

CTACAGAGTGGTGGTGCTGAGCTTCGAACTGCTGCATGCC

CCTGCCACAGTGTGCGGCCCTAAGAAAAGCACCAATCTCG

TGAAGAACAAATGCGTGAACTTCAACTTCAACGGCCTGAC

CGGCACAGGCGTGCTGACAGAGAGCAACAAGAAGTTCCTG

CCATTCCAGCAGTTTGGCCGGGATATCGCCGATACCACAG

ACGCCGTTAGAGATCCCCAGACACTGGAAATCCTGGACAT

CACCCCTTGCAGCTTCGGCGGAGTGTCTGTGATCACCCCT

GGCACCAACACCAGCAATCAGGTGGCAGTGCTGTACCAGG

-continued

ACGTGAACTGTACCGAAGTGCCCGTGGCCATTCACGCCGA

TCAGCTGACACCTACATGGCGGGTGTACTCCACCGGCAGC

AATGTGTTTCAGACCAGAGCCGGCTGTCTGATCGGAGCCG

AGCACGTGAACAATAGCTACGAGTGCGACATCCCCATCGG

CGCTGGCATCTGTGCCAGCTACCAGACACAGACAAACAGC

CCCAGACGGGCCAGATCTGTGGCCAGCCAGAGCATCATTG

CCTACACAATGTCTCTGGGCGCCGAGAACAGCGTGGCCTA

CTCCAACAACTCTATCGCTATCCCCACCAACTTCACCATC

AGCGTGACCACAGAGATCCTGCCTGTGTCCATGACCAAGA

CCAGCGTGGACTGCACCATGTACATCTGCGGCGATTCCAC

CGAGTGCTCCAACCTGCTGCTGCAGTACGGCAGCTTCTGC

ACCCAGCTGAATAGAGCCCTGACAGGGATCGCCGTGGAAC

AGGACAAGAACACCCAAGAGGTGTTCGCCCAAGTGAAGCA

GATCTACAAGACCCCTCCTATCAAGGACTTCGGCGGCTTC

AATTTCAGCCAGATTCTGCCCGATCCTAGCAAGCCCAGCA

AGCGGAGCTTCATCGAGGACCTGCTGTTCAACAAAGTGAC

ACTGGCCGACGCCGGCTTCATCAAGCAGTATGGCGATTGT

CTGGGCGACATTGCCGCCAGGGATCTGATTTGCGCCCAGA

AGTTTAACGGACTGACAGTGCTGCCTCCTCTGCTGACCGA

TGAGATGATCGCCCAGTACACATCTGCCCTGCTGGCCGGC

ACAATCACAAGCGGCTGGACATTTGGAGCTGGCGCCGCTC

TGCAGATCCCCTTTGCTATGCAGATGGCCTACAGATTCAA

CGGCATCGGAGTGACCCAGAATGTGCTGTACGAGAACCAG

AAGCTGATCGCCAACCAGTTCAACAGCGCCATCGGCAAGA

TCCAGGACAGCCTGAGCAGCACAGCAAGCGCCCTGGGAAA

GCTGCAGGACGTGGTCAACCAGAATGCCCAGGCACTGAAC

ACCCTGGTCAAGCAGCTGTCCTCCAACTTCGGCGCCATCA

GCTCTGTGCTGAACGATATCCTGAGCAGACTGGACCCTCC

TGAGGCCGAGGTGCAGATCGACAGACTGATCACAGGCAGA

CTGCAGAGCCTCCAGACATACGTGACCCAGCAGCTGATCA

GAGCCGCCGAGATTAGAGCCTCTGCCAATCTGGCCGCCAC

CAAGATGTCTGAGTGTGTGCTGGGCCAGAGCAAGAGAGTG

GACTTTTGCGGCAAGGGCTACCACCTGATGAGCTTCCCTC

AGTCTGCCCCTCACGGCGTGGTGTTTCTGCACGTGACATA

CGTTCCCGCTCAAGAGAAGAATTTCACCACCGCTCCAGCC

ATCTGCCACGACGGCAAAGCCCACTTTCCTAGAGAAGGCG

TGTTCGTGTCCAACGGCACCCATTGGTTCGTGACACAGCG

GAACTTCTACGAGCCCCAGATCATCACCACCGACAACACC

TTCGTGTCTGGCAACTGCGACGTCGTGATCGGCATTGTGA

ACAATACCGTGTACGACCCTCTGCAGCCCGAGCTGGACAG

-continued

CTTCAAAGAGGAACTGGACAAGTACTTTAAGAACCACACA

AGCCCCGACGTGGACCTGGGCGATATCAGCGGAATCAATG

CCAGCGTCGTGAACATCCAGAAAGAGATCGACCGGCTGAA

CGAGGTGGCCAAGAATCTGAACGAGAGCCTGATCGACCTG

CAAGAACTGGGGAAGTACGAGCAGTACATCAAGTGGCCCT

GGTACATCTGGCTGGGCTTTATCGCCGGACTGATTGCCAT

CGTGATGGTCACAATCATGCTGTGTTGCATGACCAGCTGC

TGTAGCTGCCTGAAGGGCTGTTGTAGCTGTGGCAGCTGCT

GCAAGTTCGACGAGGACGATTCTGAGCCCGTGCTGAAGGG

CGTGAAACTGCACTACACATGA

Hence, preferably the saRNA is encoded by a DNA sequence substantially as set out in 55 SEQ ID No: 6, or a fragment or variant thereof.

In an embodiment, the RNA sequence corresponding to the codon optimised DNA sequence of SEQ ID No: 6 is provided herein as SEQ ID No: 36, as follows:

[SEQ ID No: 36]

AUGUUCGUGUUUCUGGUGCUGCUGCCUCUGGUGUCCAGCC

AGUGUGUGAACCUGACCACCAGAACACAGCUGCCUCCAGC

CUACACCAACAGCUUUACCAGAGGCGUGUACUACCCCGAC

AAGGUGUUCAGAUCCAGCGUGCUGCACUCUACCCAGGACC

UGUUCCUGCCUUUCUUCAGCAACGUGACCUGGUUCCACGC

CAUCCACGUGUCCGGCACCAAUGGCACCAAGAGAUUCGAC

AACCCCGUGCUGCCCUUCAACGACGGGGUGUACUUUGCCA

GCACCGAGAAGUCCAACAUCAUCAGAGGCUGGAUCUUCGG

CACCACACUGGACAGCAAGACCCAGAGCCUGCUGAUCGUG

AACAACGCCACCAACGUGGUCAUCAAAGUGUGCGAGUUCC

AGUUCUGCAACGACCCCUUCCUGGGCGUCUACUACCACAA

GAACAACAAGAGCUGGAUGGAAAGCGAGUUCCGGGUGUAC

AGCAGCGCCAACAACUGCACCUUCGAGUACGUGUCCCAGC

CUUUCCUGAUGGACCUGGAAGGCAAGCAGGGCAACUUCAA

GAACCUGCGCGAGUUCGUGUUCAAGAACAUCGACGGCUAC

UUCAAGAUCUACAGCAAGCACACCCCUAUCAACCUCGUGC

GGGAUCUGCCUCAGGGCUUCUCUGCUCUGGAACCCCUGGU

GGAUCUGCCCAUCGGCAUCAACAUCACCCGGUUUCAGACA

CUGCUGGCCCUGCACAGAAGCUACCUGACACCUGGCGAUA

GCAGCAGCGGAUGGACAGCUGGUGCCGCCGCUUACUAUGU

GGGCUACCUGCAGCCUAGAACCUUCCUGCUGAAGUACAAC

GAGAACGGCACCAUCACCGACGCCGUGGAUUGUGCCCUUG

AUCCUCUGAGCGAGACAAAGUGCACCCUGAAGUCCUUCAC

CGUGGAAAAGGGCAUCUACCAGACCAGCAACUUCCGGGUG

CAGCCCACCGAAUCCAUCGUGCGGUUCCCCAAUAUCACCA

-continued

```
AUCUGUGCCCCUUCGGCGAGGUGUUCAAUGCCACCAGAUU
CGCCUCUGUGUACGCCUGGAACCGGAAGCGGAUCAGCAAU
UGCGUGGCCGACUACUCCGUGCUGUACAACUCCGCCAGCU
UCAGCACCUUCAAGUGCUACGGCGUGUCCCCUACCAAGCU
GAACGACCUGUGCUUCACAAACGUGUACGCCGACAGCUUC
GUGAUCCGGGGAGAUGAAGUGCGGCAGAUUGCCCCUGGAC
AGACAGGCAAGAUCGCCGACUACAACUACAAGCUGCCCGA
CGACUUCACCGGCUGUGUGAUUGCCUGGAACAGCAACAAC
CUGGACUCCAAAGUCGGCGGCAACUACAAUUACCUGUACC
GGCUGUUCCGGAAGUCCAAUCUGAAGCCCUUCGAGCGGGA
CAUCUCCACCGAGAUCUAUCAGGCCGGCAGCACCCCUUGU
AACGGCGUGGAAGGCUUCAACUGCUACUUCCCACUGCAGU
CCUACGGCUUUCAGCCCACAAAUGGCGUGGGCUAUCAGCC
CUACAGAGUGGUGGUGCUGAGCUUCGAACUGCUGCAUGCC
CCUGCCACAGUGUGCGGCCCUAAGAAAAGCACCAAUCUCG
UGAAGAACAAAUGCGUGAACUUCAACUUCAACGGCCUGAC
CGGCACAGGCGUGCUGACAGAGAGCAACAAGAAGUUCCUG
CCAUUCCAGCAGUUUGGCCGGGAUAUCGCCGAUACCACAG
ACGCCGUUAGAGAUCCCCAGACACUGGAAAUCCUGGACAU
CACCCCUUGCAGCUUCGGCGGAGUGUCUGUGAUCACCCCU
GGCACCAACACCAGCAAUCAGGUGGCAGUGCUGUACCAGG
ACGUGAACUGUACCGAAGUGCCCGUGGCCAUUCACGCCGA
UCAGCUGACACCUACAUGGCGGGUGUACUCCACCGGCAGC
AAUGUGUUUCAGACCAGAGCCGGCUGUCUGAUCGGAGCCG
AGCACGUGAACAAUAGCUACGAGUGCGACAUCCCCAUCGG
CGCUGGCAUCUGUGCCAGCUACCAGACACAGACAAACAGC
CCCAGACGGGCCAGAUCUGUGGCCAGCCAGAGCAUCAUUG
CCUACACAAUGUCUCUGGGCGCCGAGAACAGCGUGGCCUA
CUCCAACAACUCUAUCGCUAUCCCCACCAACUUCACCAUC
AGCGUGACCACAGAGAUCCUGCCUGUGUCCAUGACCAAGA
CCAGCGUGGACUGCACCAUGUACAUCUGCGGCGAUUCCAC
CGAGUGCUCCAACCUGCUGCUGCAGUACGGCAGCUUCUGC
ACCCAGCUGAAUAGAGCCCUGACAGGGAUCGCCGUGGAAC
AGGACAAGAACACCCAAGAGGUGUUCGCCCAAGUGAAGCA
GAUCUACAAGACCCCUCCUAUCAAGGACUUCGGCGGCUUC
AAUUUCAGCCAGAUUCUGCCCGAUCCUAGCAAGCCCAGCA
AGCGGAGCUUCAUCGAGGACCUGCUGUUCAACAAAGUGAC
ACUGGCCGACGCCGGCUUCAUCAAGCAGUAUGGCGAUUGU
CUGGGCGACAUUGCCGCCAGGGAUCUGAUUUGCGCCCAGA
AGUUUAACGGACUGACAGUGCUGCCUCCUCUGCUGACCGA
UGAGAUGAUCGCCCAGUACACAUCUGCCCUGCUGGCCGGC
```

-continued

```
ACAAUCACAAGCGGCUGGACAUUUGGAGCUGGCGCCGCUC
UGCAGAUCCCCUUUGCUAUGCAGAUGGCCUACAGAUUCAA
CGGCAUCGGAGUGACCCAGAAUGUGCUGUACGAGAACCAG
AAGCUGAUCGCCAACCAGUUCAACAGCGCCAUCGGCAAGA
UCCAGGACAGCCUGAGCAGCACAGCAAGCGCCCUGGGAAA
GCUGCAGGACGUGGUCAACCAGAAUGCCCAGGCACUGAAC
ACCCUGGUCAAGCAGCUGUCCUCCAACUUCGGCGCCAUCA
GCUCUGUGCUGAACGAUAUCCUGAGCAGACUGGACCCUCC
UGAGGCCGAGGUGCAGAUCGACAGACUGAUCACAGGCAGA
CUGCAGAGCCUCCAGACAUACGUGACCCAGCAGCUGAUCA
GAGCCGCCGAGAUUAGAGCCUCUGCCAAUCUGGCCGCCAC
CAAGAUGUCUGAGUGUGUGCUGGGCCAGAGCAAGAGAGUG
GACUUUUGCGGCAAGGGCUACCACCUGAUGAGCUUCCCUC
AGUCUGCCCCUCACGGCGUGGUGUUUCUGCACGUGACAUA
CGUUCCCGCUCAAGAGAAGAAUUUCACCACCGCUCCAGCC
AUCUGCCACGACGGCAAAGCCCACUUUCCUAGAGAAGGCG
UGUUCGUGUCCAACGGCACCCAUUGGUUCGUGACACAGCG
GAACUUCUACGAGCCCCAGAUCAUCACCACCGACAACACC
UUCGUGUCUGGCAACUGCGACGUCGUGAUCGGCAUUGUGA
ACAAUACCGUGUACGACCCUCUGCAGCCCGAGCUGGACAG
CUUCAAAGAGGAACUGGACAAGUACUUUAAGAACCACACA
AGCCCCGACGUGGACCUGGGCGAUAUCAGCGGAAUCAAUG
CCAGCGUCGUGAACAUCCAGAAAGAGAUCGACCGGCUGAA
CGAGGUGGCCAAGAAUCUGAACGAGAGCCUGAUCGACCUG
CAAGAACUGGGGAAGUACGAGCAGUACAUCAAGUGGCCCU
GGUACAUCUGGCUGGGCUUUAUCGCCGGACUGAUUGCCAU
CGUGAUGGUCACAAUCAUGCUGUGUUGCAUGACCAGCUGC
UGUAGCUGCCUGAAGGGCUGUUGUAGCUGUGGCAGCUGCU
GCAAGUUCGACGAGGACGAUUCUGAGCCCGUGCUGAAGGG
CGUGAAACUGCACUACACAUGA
```

Hence, preferably the saRNA comprises a sequence substantially as set out in SEQ ID No: 36, or a fragment or variant thereof.

Accordingly, it will be appreciated that SEQ ID No: 6 is the codon optimised DNA sequence encoding the RNA sequence of SEQ ID No: 36, which is translated into the modified SARS-CoV-2 coronavirus surface glycoprotein (K986P and V987P) sequence of SEQ ID No: 4.

It should be noted that SEQ ID No: 4 is the full length S protein. However, the inventors have also designed and synthesised, truncated versions of the SARS-CoV-2 surface glycoprotein in which the transmembrane domain (TMD) and/or the cytoplasmic domain (CT) have been deleted, and these truncated versions are soluble so and therefore useful for eliciting an immune response. As such, these truncated proteins could also be used as antigen in the vaccines described herein. For the SARS-CoV-2 surface glycoprotein, the extracellular amino acids are residues 1-1213, the transmembrane domain corresponds to residues 1214-1234 and the cytoplasmic domain corresponds to residues 1235-1273. It will be appreciated that similar soluble, truncated versions of the MERS-CoV and SARS-CoV glycoproteins can also be made in the same way deleting the same domains. Preferably, therefore, the saRNA comprises a nucleotide sequence encoding SARS-CoV-2, MERS-CoV or SARS-CoV surface glycoprotein which lacks the transmembrane domain and/or the cytoplasmic domain, or a truncation thereof, most preferably lacking both the transmembrane and cytoplasmic domains, or truncations thereof.

The amino acid sequence of the transmembrane domain (shown as bold residues at the N-terminus) and cytoplasmic domain (shown as non-bold residues at the C-terminus) for SARS-CoV-2 surface glycoprotein is provided herein as SEQ ID No: 37, as follows:

[SEQ ID No: 37]

WYIWLGFIAGLIAIVMVTIMLCCMTSCCSCLKGCCSCGSC

CKFDEDDSEPVLKGVKLHYT

Therefore, preferably the saRNA construct comprises a nucleic acid sequence encoding truncated SARS-CoV-2 (or SARS-CoV) surface glycoprotein having an amino acid sequence which lacks the amino acid sequence substantially as set out in SEQ ID No: 37, or a fragment or variant thereof.

Thus, one embodiment of the pre-fusion stabilised SARS-CoV-2 surface glycoprotein lacking the transmembrane domain and the cytoplasmic domain is provided herein as SEQ ID No: 38, as follows:

[SEQ ID No: 38]

MFVFLVLLPLVSSQCVNLTTRTQLPPAYTNSFTRGVYYPD

KVFRSSVLHSTQDLFLPFFSNVTWFHAIHVSGTNGTKRFD

NPVLPFNDGVYFASTEKSNIIRGWIFGTTLDSKTQSLLIV

NNATNVVIKVCEFQFCNDPFLGVYYHKNNKSWMESEFRVY

SSANNCTFEYVSQPFLMDLEGKQGNFKNLREFVFKNIDGY

FKIYSKHTPINLVRDLPQGFSALEPLVDLPIGINITRFQT

LLALHRSYLTPGDSSSGWTAGAAAYYVGYLQPRTFLLKYN

ENGTITDAVDCALDPLSETKCTLKSFTVEKGIYQTSNFRV

QPTESIVRFPNITNLCPFGEVFNATRFASVYAWNRKRISN

CVADYSVLYNSASFSTFKCYGVSPTKLNDLCFTNVYADSF

VIRGDEVRQIAPGQTGKIADYNYKLPDDFTGCVIAWNSNN

LDSKVGGNYNYLYRLFRKSNLKPFERDISTEIYQAGSTPC

NGVEGFNCYFPLQSYGFQPTNGVGYQPYRVVVLSFELLHA

PATVCGPKKSTNLVKNKCVNFNFNGLTGTGVLTESNKKFL

PFQQFGRDIADTTDAVRDPQTLEILDITPCSFGGVSVITP

GTNTSNQVAVLYQDVNCTEVPVAIHADQLTPTWRVYSTGS

NVFQTRAGCLIGAEHVNNSYECDIPIGAGICASYQTQTNS

PRRARSVASQSIIAYTMSLGAENSVAYSNNSIAIPTNFTI

SVTTEILPVSMTKTSVDCTMYICGDSTECSNLLLQYGSFC

TQLNRALTGIAVEQDKNTQEVFAQVKQIYKTPPIKDFGGF

-continued

NFSQILPDPSKPSKRSFIEDLLFNKVTLADAGFIKQYGDC

LGDIAARDLICAQKFNGLTVLPPLLTDEMIAQYTSALLAG

TITSGWTFGAGAALQIPFAMQMAYRFNGIGVTQNVLYENQ

KLIANQFNSAIGKIQDSLSSTASALGKLQDVVNQNAQALN

TLVKQLSSNFGAISSVLNDILSRLDKVEAEVQIDRLITGR

LQSLQTYVTQQLIRAAEIRASANLAATKMSECVLGQSKRV

DFCGKGYHLMSFPQSAPHGVVFLHVTYVPAQEKNFTTAPA

ICHDGKAHFPREGVFVSNGTHWFVTQRNFYEPQIITTDNT

FVSGNCDVVIGIVNNTVYDPLQPELDSFKEELDKYFKNHT

SPDVDLGDISGINASVVNIQKEIDRLNEVAKNLNESLIDL

QELGKYEQYIKWP

Hence, preferably the saRNA construct comprises a nucleic acid sequence encoding truncated SARS-CoV-2 surface glycoprotein having an amino acid sequence substantially as set out in SEQ ID No: 38, or a fragment or variant thereof.

Therefore, one embodiment of the nucleic acid (DNA) sequence encoding the pre-fusion stabilised S glycoprotein (DNA sequence) with deletion of the transmembrane and cytoplasmic domains is provided herein as SEQ ID No: 39, as follows:

[SEQ ID No: 39]

ATGTTCGTGTTTCTGGTGCTGCTGCCTCTGGTGTCCAGCC

AGTGTGTGAACCTGACCACCAGAACACAGCTGCCTCCAGC

CTACACCAACAGCTTTACCAGAGGCGTGTACTACCCCGAC

AAGGTGTTCAGATCCAGCGTGCTGCACTCTACCCAGGACC

TGTTCCTGCCTTTCTTCAGCAACGTGACCTGGTTCCACGC

CATCCACGTGTCCGGCACCAATGGCACCAAGAGATTCGAC

AACCCCGTGCTGCCCTTCAACGACGGGGTGTACTTTGCCA

GCACCGAGAAGTCCAACATCATCAGAGGCTGGATCTTCGG

CACCACACTGGACAGCAAGACCCAGAGCCTGCTGATCGTG

AACAACGCCACCAACGTGGTCATCAAAGTGTGCGAGTTCC

AGTTCTGCAACGACCCCTTCCTGGGCGTCTACTACCACAA

GAACAACAAGAGCTGGATGGAAAGCGAGTTCCGGGTGTAC

AGCAGCGCCAACAACTGCACCTTCGAGTACGTGTCCCAGC

CTTTCCTGATGGACCTGGAAGGCAAGCAGGGCAACTTCAA

GAACCTGCGCGAGTTCGTGTTCAAGAACATCGACGGCTAC

TTCAAGATCTACAGCAAGCACACCCCTATCAACCTCGTGC

GGGATCTGCCTCAGGGCTTCTCTGCTCTGGAACCCCTGGT

GGATCTGCCCATCGGCATCAACATCACCCGGTTTCAGACA

CTGCTGGCCCTGCACAGAAGCTACCTGACACCTGGCGATA

GCAGCAGCGGATGGACAGCTGGTGCCGCCGCTTACTATGT

GGGCTACCTGCAGCCTAGAACCTTCCTGCTGAAGTACAAC

-continued

GAGAACGGCACCATCACCGACGCCGTGGATTGTGCCCTTG
ATCCTCTGAGCGAGACAAAGTGCACCCTGAAGTCCTTCAC
CGTGGAAAAGGGCATCTACCAGACCAGCAACTTCCGGGTG
CAGCCCACCGAATCCATCGTGCGGTTCCCCAATATCACCA
ATCTGTGCCCCTTCGGCGAGGTGTTCAATGCCACCAGATT
CGCCTCTGTGTACGCCTGGAACCGGAAGCGGATCAGCAAT
TGCGTGGCCGACTACTCCGTGCTGTACAACTCCGCCAGCT
TCAGCACCTTCAAGTGCTACGGCGTGTCCCCTACCAAGCT
GAACGACCTGTGCTTCACAAACGTGTACGCCGACAGCTTC
GTGATCCGGGGAGATGAAGTGCGGCAGATTGCCCCTGGAC
AGACAGGCAAGATCGCCGACTACAACTACAAGCTGCCCGA
CGACTTCACCGGCTGTGTGATTGCCTGGAACAGCAACAAC
CTGGACTCCAAAGTCGGCGGCAACTACAATTACCTGTACC
GGCTGTTCCGGAAGTCCAATCTGAAGCCCTTCGAGCGGGA
CATCTCCACCGAGATCTATCAGGCCGGCAGCACCCCTTGT
AACGGCGTGGAAGGCTTCAACTGCTACTTCCCACTGCAGT
CCTACGGCTTTCAGCCCACAAATGGCGTGGGCTATCAGCC
CTACAGAGTGGTGGTGCTGAGCTTCGAACTGCTGCATGCC
CCTGCCACAGTGTGCGGCCCTAAGAAAAGCACCAATCTCG
TGAAGAACAAATGCGTGAACTTCAACTTCAACGGCCTGAC
CGGCACAGGCGTGCTGACAGAGAGCAACAAGAAGTTCCTG
CCATTCCAGCAGTTTGGCCGGGATATCGCCGATACCACAG
ACGCCGTTAGAGATCCCCAGACACTGGAAATCCTGGACAT
CACCCCTTGCAGCTTCGGCGGAGTGTCTGTGATCACCCCT
GGCACCAACACCAGCAATCAGGTGGCAGTGCTGTACCAGG
ACGTGAACTGTACCGAAGTGCCCGTGGCCATTCACGCCGA
TCAGCTGACACCTACATGGCGGGTGTACTCCACCGGCAGC
AATGTGTTTCAGACCAGAGCCGGCTGTCTGATCGGAGCCG
AGCACGTGAACAATAGCTACGAGTGCGACATCCCCATCGG
CGCTGGCATCTGTGCCAGCTACCAGACACAGACAAACAGC
CCCAGACGGGCCAGATCTGTGGCCAGCCAGAGCATCATTG
CCTACACAATGTCTCTGGGCGCCGAGAACAGCGTGGCCTA
CTCCAACAACTCTATCGCTATCCCCACCAACTTCACCATC
AGCGTGACCACAGAGATCCTGCCTGTGTCCATGACCAAGA
CCAGCGTGGACTGCACCATGTACATCTGCGGCGATTCCAC
CGAGTGCTCCAACCTGCTGCTGCAGTACGGCAGCTTCTGC
ACCCAGCTGAATAGAGCCCTGACAGGGATCGCCGTGGAAC
AGGACAAGAACACCCAAGAGGTGTTCGCCCAAGTGAAGCA
GATCTACAAGACCCCTCCTATCAAGGACTTCGGCGGCTTC
AATTTCAGCCAGATTCTGCCCGATCCTAGCAAGCCCAGCA
AGCGGAGCTTCATCGAGGACCTGCTGTTCAACAAAGTGAC

-continued

ACTGGCCGACGCCGGCTTCATCAAGCAGTATGGCGATTGT
CTGGGCGACATTGCCGCCAGGGATCTGATTTGCGCCCAGA
AGTTTAACGGACTGACAGTGCTGCCTCCTCTGCTGACCGA
TGAGATGATCGCCCAGTACACATCTGCCCTGCTGGCCGGC
ACAATCACAAGCGGCTGGACATTTGGAGCTGGCGCCGCTC
TGCAGATCCCCTTTGCTATGCAGATGGCCTACAGATTCAA
CGGCATCGGAGTGACCCAGAATGTGCTGTACGAGAACCAG
AAGCTGATCGCCAACCAGTTCAACAGCGCCATCGGCAAGA
TCCAGGACAGCCTGAGCAGCACAGCAAGCGCCCTGGGAAA
GCTGCAGGACGTGGTCAACCAGAATGCCCAGGCACTGAAC
ACCCTGGTCAAGCAGCTGTCCTCCAACTTCGGCGCCATCA
GCTCTGTGCTGAACGATATCCTGAGCAGACTGGACcctcc
tGAGGCCGAGGTGCAGATCGACAGACTGATCACAGGCAGAC
TGCAGAGCCTCCAGACATACGTGACCCAGCAGCTGATCAG
AGCCGCCGAGATTAGAGCCTCTGCCAATCTGGCCGCCACC
AAGATGTCTGAGTGTGTGCTGGGCCAGAGCAAGAGAGTGG
ACTTTTGCGGCAAGGGCTACCACCTGATGAGCTTCCCTCA
GTCTGCCCCTCACGGCGTGGTGTTTCTGCACGTGACATAC
GTTCCCGCTCAAGAGAAGAATTTCACCACCGCTCCAGCCA
TCTGCCACGACGGCAAAGCCCACTTTCCTAGAGAAGGCGT
GTTCGTGTCCAACGGCACCCATTGGTTCGTGACACAGCGG
AACTTCTACGAGCCCCAGATCATCACCACCGACAACACCT
TCGTGTCTGGCAACTGCGACGTCGTGATCGGCATTGTGAA
CAATACCGTGTACGACCCTCTGCAGCCCGAGCTGGACAGC
TTCAAAGAGGAACTGGACAAGTACTTTAAGAACCACACAA
GCCCCGACGTGGACCTGGGCGATATCAGCGGAATCAATGC
CAGCGTCGTGAACATCCAGAAAGAGATCGACCGGCTGAAC
GAGGTGGCCAAGAATCTGAACGAGAGCCTGATCGACCTGC
AAGAACTGGGGAAGTACGAGCAG Hence, preferably the saRNA is encoded by a DNA sequence substantially as set out in SEQ ID No: 39, or a fragment or variant thereof.

The corresponding nucleic acid (RNA) sequence of the pre-fusion stabilised S glycoprotein (DNA sequence) with deletion of the transmembrane and cytoplasmic domains is provided herein as SEQ ID No: 40, as follows:

[SEQ ID No: 40]

AUGUUCGUGUUUCUGGUGCUGCUGCCUCUGGUGUCCAGCC
AGUGUGUGAACCUGACCACCAGAACACAGCUGCCUCCAGC
CUACACCAACAGCUUUACCAGAGGCGUGUACUACCCCGAC
AAGGUGUUCAGAUCCAGCGUGCUGCACUCUACCCAGGACC
UGUUCCUGCCUUUCUUCAGCAACGUGACCUGGUUCCACGC

-continued

CAUCCACGUGUCCGGCACCAAUGGCACCAAGAGAUUCGAC
AACCCCGUGCUGCCCUUCAACGACGGGGUGUACUUUGCCA
GCACCGAGAAGUCCAACAUCAUCAGAGGCUGGAUCUUCGG
CACCACACUGGACAGCAAGACCCAGAGCCUGCUGAUCGUG
AACAACGCCACCAACGUGGUCAUCAAAGUGUGCGAGUUCC
AGUUCUGCAACGACCCCUUCCUGGGCGUCUACUACCACAA
GAACAACAAGAGCUGGAUGGAAAGCGAGUUCCGGGUGUAC
AGCAGCGCCAACAACUGCACCUUCGAGUACGUGUCCCAGC
CUUUCCUGAUGGACCUGGAAGGCAAGCAGGGCAACUUCAA
GAACCUGCGCGAGUUCGUGUUCAAGAACAUCGACGGCUAC
UUCAAGAUCUACAGCAAGCACACCCCUAUCAACCUCGUGC
GGGAUCUGCCUCAGGGCUUCUCUGCUCUGGAACCCCUGGU
GGAUCUGCCCAUCGGCAUCAACAUCACCCGGUUUCAGACA
CUGCUGGCCCUGCACAGAAGCUACCUGACACCUGGCGAUA
GCAGCAGCGGAUGGACAGCUGGUGCCGCCGCUUACUAUGU
GGGCUACCUGCAGCCUAGAACCUUCCUGCUGAAGUACAAC
GAGAACGGCACCAUCACCGACGCCGUGGAUUGUGCCCUUG
AUCCUCUGAGCGAGACAAAGUGCACCCUGAAGUCCUUCAC
CGUGGAAAAGGGCAUCUACCAGACCAGCAACUUCCGGGUG
CAGCCCACCGAAUCCAUCGUGCGGUUCCCCAAUAUCACCA
AUCUGUGCCCCUUCGGCGAGGUGUUCAAUGCCACCAGAUU
CGCCUCUGUGUACGCCUGGAACCGGAAGCGGAUCAGCAAU
UGCGUGGCCGACUACUCCGUGCUGUACAACUCCGCCAGCU
UCAGCACCUUCAAGUGCUACGGCGUGUCCCCUACCAAGCU
GAACGACCUGUGCUUCACAAACGUGUACGCCGACAGCUUC
GUGAUCCGGGGAGAUGAAGUGCGGCAGAUUGCCCCUGGAC
AGACAGGCAAGAUCGCCGACUACAACUACAAGCUGCCCGA
CGACUUCACCGGCUGUGUGAUUGCCUGGAACAGCAACAAC
CUGGACUCCAAAGUCGGCGGCAACUACAAUUACCUGUACC
GGCUGUUCCGGAAGUCCAAUCUGAAGCCCUUCGAGCGGGA
CAUCUCCACCGAGAUCUAUCAGGCCGGCAGCACCCCUUGU
AACGGCGUGGAAGGCUUCAACUGCUACUUCCCACUGCAGU
CCUACGGCUUUCAGCCCACAAAUGGCGUGGGCUAUCAGCC
CUACAGAGUGGUGGUGCUGAGCUUCGAACUGCUGCAUGCC
CCUGCCACAGUGUGCGGCCCUAAGAAAAGCACCAAUCUCG
UGAAGAACAAAUGCGUGAACUUCAACUUCAACGGCCUGAC
CGGCACAGGCGUGCUGACAGAGAGCAACAAGAAGUUCCUG
CCAUUCCAGCAGUUUGGCCGGGAUAUCGCCGAUACCACAG
ACGCCGUUAGAGAUCCCCAGACACUGGAAAUCCUGGACAU
CACCCCUUGCAGCUUCGGCGGAGUGUCUGUGAUCACCCCU
GGCACCAACACCAGCAAUCAGGUGGCAGUGCUGUACCAGG

-continued

ACGUGAACUGUACCGAAGUGCCCGUGGCCAUUCACGCCGA
UCAGCUGACACCUACAUGGCGGGUGUACUCCACCGGCAGC
AAUGUGUUUCAGACCAGAGCCGGCUGUCUGAUCGGAGCCG
AGCACGUGAACAAUAGCUACGAGUGCGACAUCCCCAUCGG
CGCUGGCAUCUGUGCCAGCUACCAGACACAGACAAACAGC
CCCAGACGGGCCAGAUCUGUGGCCAGCCAGAGCAUCAUUG
CCUACACAAUGUCUCUGGGCGCCGAGAACAGCGUGGCCUA
CUCCAACAACUCUAUCGCUAUCCCCACCAACUUCACCAUC
AGCGUGACCACAGAGAUCCUGCCUGUGUCCAUGACCAAGA
CCAGCGUGGACUGCACCAUGUACAUCUGCGGCGAUUCCAC
CGAGUGCUCCAACCUGCUGCUGCAGUACGGCAGCUUCUGC
ACCCAGCUGAAUAGAGCCCUGACAGGGAUCGCCGUGGAAC
AGGACAAGAACACCCAAGAGGUGUUCGCCCAAGUGAAGCA
GAUCUACAAGACCCCUCCUAUCAAGGACUUCGGCGGCUUC
AAUUUCAGCCAGAUUCUGCCCGAUCCUAGCAAGCCCAGCA
AGCGGAGCUUCAUCGAGGACCUGCUGUUCAACAAAGUGAC
ACUGGCCGACGCCGGCUUCAUCAAGCAGUAUGGCGAUUGU
CUGGGCGACAUUGCCGCCAGGGAUCUGAUUUGCGCCCAGA
AGUUUAACGGACUGACAGUGCUGCCUCCUCUGCUGACCGA
UGAGAUGAUCGCCCAGUACACAUCUGCCCUGCUGGCCGGC
ACAAUCACAAGCGGCUGGACAUUUGGAGCUGGCGCCGCUC
UGCAGAUCCCCUUUGCUAUGCAGAUGGCCUACAGAUUCAA
CGGCAUCGGAGUGACCCAGAAUGUGCUGUACGAGAACCAG
AAGCUGAUCGCCAACCAGUUCAACAGCGCCAUCGGCAAGA
UCCAGGACAGCCUGAGCAGCACAGCAAGCGCCCUGGGAAA
GCUGCAGGACGUGGUCAACCAGAAUGCCCAGGCACUGAAC
ACCCUGGUCAAGCAGCUGUCCUCCAACUUCGGCGCCAUCA
GCUCUGUGCUGAACGAUAUCCUGAGCAGACUGGACccUcc
UGAGGCCGAGGUGCAGAUCGACAGACUGAUCACAGGCAGA
CUGCAGAGCCUCCAGACAUACGUGACCCAGCAGCUGAUCA
GAGCCGCCGAGAUUAGAGCCUCUGCCAAUCUGGCCGCCAC
CAAGAUGUCUGAGUGUGUGCUGGGCCAGAGCAAGAGAGUG
GACUUUUGCGGCAAGGGCUACCACCUGAUGAGCUUCCCUC
AGUCUGCCCCUCACGGCGUGGUGUUUCUGCACGUGACAUA
CGUUCCCGCUCAAGAGAAGAAUUUCACCACCGCUCCAGCC
AUCUGCCACGACGGCAAAGCCCACUUUCCUAGAGAAGGCG
UGUUCGUGUCCAACGGCACCCAUUGGUUCGUGACACAGCG
GAACUUCUACGAGCCCCAGAUCAUCACCACCGACAACACC
UUCGUGUCUGGCAACUGCGACGUCGUGAUCGGCAUUGUGA
ACAAUACCGUGUACGACCCUCUGCAGCCCGAGCUGGACAG

-continued

```
CUUCAAAGAGGAACUGGACAAGUACUUUAAGAACCACACA

AGCCCCGACGUGGACCUGGGCGAUAUCAGCGGAAUCAAUG

CCAGCGUCGUGAACAUCCAGAAAGAGAUCGACCGGCUGAA

CGAGGUGGCCAAGAAUCUGAACGAGAGCCUGAUCGACCUG

CAAGAACUGGGGAAGUACGAGCAG
```

Hence, preferably the saRNA comprises a sequence substantially as set out in SEQ ID No: 40, or a fragment or variant thereof.

The inventors believe that, in at least some embodiments, deletion of just the cytoplasmic tail (CT) of the spike glycoprotein may not lead to a soluble protein, because it is the transmembrane domain (TMD) that determines membrane tethering. However, the inventors are of the view that deletion of just the cytoplasmic tail, or only truncations of the cytoplasmic tail, will significantly increase surface expression for the glycoprotein, thereby increasing immunogenicity. This is because of a putative endoplasmic reticulum (ER) retrieval motif (KxHxx—a dibasic motif) that is present at the C-terminus of the cytoplasmic tail that has been shown to bind to COPI (coatomer complex I) in vitro and which would be a potent ER retention and retrieval signal.

Therefore, deletion of at least the endoplasmic reticulum (ER) retrieval motif (KxHxx—a dibasic motif) from the CT of the spike glycoprotein is preferred, as it will avoid ER retention/retrieval and will be expressed more than if this motif were present. Preferably, therefore, the saRNA comprises a nucleotide sequence encoding SARS-CoV-2, MERS-CoV or SARS-CoV surface glycoprotein which lacks an endoplasmic reticulum (ER) retrieval motif (KxHxx) from the cytoplasmic tail of the glycoprotein.

The cytoplasmic tail has a total of eight cysteine residues, which could enhance the stability of the S2' part of the spike protein. These cysteines are located towards the N-terminus of the CT. Thus, the inventors believe that preserving this multi-cysteine region is important for retaining the 3D configuration of the spike protein, and thereby eliciting a robust antibody response to the protein. Accordingly, in some embodiments, it is preferred that at least one, two, three of four of these cysteines in the CT remain present. More preferably, at least five, six, seven or eight of these cysteines in the CT remain present.

In some embodiments, therefore, the saRNA comprises a nucleotide sequence encoding SARS-CoV-2, MERS-CoV or SARS-CoV surface glycoprotein which lacks up to −19, −20 or −21 amino acid deletions from the C-terminus of the cytoplasmic tail of the glycoprotein. Preferably, no more than 5, 6, 7, 8 or 9 amino acids are deleted from the C-terminus of the cytoplasmic tail of the glycoprotein. More preferably, no more than 10, 11, 12, 13, 14 so or 15 amino acids are deleted from the C-terminus of the cytoplasmic tail of the glycoprotein. More preferably, no more than 16, 17, 18, or 19 amino acids are deleted from the C-terminus of the cytoplasmic tail of the glycoprotein. Accordingly, such deletions preserve the cysteines towards the N-terminus of the CT, while removing the (ER) retrieval motif (KxHxx).

The amino acid sequence of the cytoplasmic tail for SARS-CoV-2 surface glycoprotein is provided herein as SEQ ID No: 77, as follows:

```
                                        [SEQ ID No: 77]
CCMTSCCSCLKGCCSCGSCCKFDEDDSEPVLKGVKLHYT
```

Therefore, preferably the saRNA construct comprises a nucleic acid sequence encoding truncated surface glycoprotein having an amino acid sequence which lacks the amino acid sequence substantially as set out in SEQ ID No: 77, or a fragment or variant thereof.

The skilled person would know the sequence of the CT for SARS-CoV and for MERS surface glycoprotein, and could delete it (or truncations thereof) accordingly. The following sequences are illustrative CT deletions, or CT truncations, based on SARS-CoV-2 glycoprotein, but it will be appreciated can equally apply to SARS-CoV and for MERS surface glycoprotein, In one embodiment, the pre-fusion stabilised SARS-CoV-2 surface glycoprotein may lack the complete cytoplasmic domain. One embodiment of the amino acid sequence is provided herein as SEQ ID No: 78, as follows:

```
                                        [SEQ ID No: 78]
MFVFLVLLPLVSSQCVNLTTRTQLPPAYTNSFTRGVYYPDKVFRSSVLH

STQDLFLPFFSNVTWFHAIHVSGTNGTKRFDNPVLPFNDGVYFASTEKS

NIIRGWIFGTTLDSKTQSLLIVNNATNVVIKVCEFQFCNDPFLGVYYHK

NNKSWMESEFRVYSSANNCTFEYVSQPFLMDLEGKQGNFKNLREFVFKN

IDGYFKIYSKHTPINLVRDLPQGFSALEPLVDLPIGINITRFQTLLALH

RSYLTPGDSSSGWTAGAAAYYVGYLQPRTFLLKYNENGTITDAVDCALD

PLSETKCTLKSFTVEKGIYQTSNFRVQPTESIVRFPNITNLCPFGEVFN

ATRFASVYAWNRKRISNCVADYSVLYNSASFSTFKCYGVSPTKLNDLCF

TNVYADSFVIRGDEVRQIAPGQTGKIADYNYKLPDDFTGCVIAWNSNNL

DSKVGGNYNYLYRLFRKSNLKPFERDISTEIYQAGSTPCNGVEGFNCYF

PLQSYGFQPTNGVGYQPYRVVVLSFELLHAPATVCGPKKSTNLVKNKCV

NFNFNGLTGTGVLTESNKKFLPFQQFGRDIADTTDAVRDPQTLEILDIT

PCSFGGVSVITPGTNTSNQVAVLYQDVNCTEVPVAIHADQLTPTWRVYS

TGSNVFQTRAGCLIGAEHVNNSYECDIPIGAGICASYQTQTNSPRRARS

VASQSIIAYTMSLGAENSVAYSNNSIAIPTNFTISVTTEILPVSMTKTS

VDCTMYICGDSTECSNLLLQYGSFCTQLNRALTGIAVEQDKNTQEVFAQ

VKQIYKTPPIKDFGGFNFSQILPDPSKPSKRSFIEDLLFNKVTLADAGF

IKQYGDCLGDIAARDLICAQKFNGLTVLPPLLTDEMIAQYTSALLAGTI

TSGWTFGAGAALQIPFAMQMAYRFNGIGVTQNVLYENQKLIANQFNSAI

GKIQDSLSSTASALGKLQDVVNQNAQALNTLVKQLSSNFGAISSVLNDI

LSRLDPPEAEVQIDRLITGRLQSLQTYVTQQLIRAAEIRASANLAATKM

SECVLGQSKRVDFCGKGYHLMSFPQSAPHGVVFLHVTYVPAQEKNFTTA

PAICHDGKAHFPREGVFVSNGTHWFVTQRNFYEPQIITTDNTFVSGNCD

VVIGIVNNTVYDPLQPELDSFKEELDKYFKNHTSPDVDLGDISGINASV

VNIQKEIDRLNEVAKNLNESLIDLQELGKYEQYIKWPWYIWLGFIAGLI

AIVMVTIML
```

Therefore, preferably the saRNA construct comprises a nucleic acid sequence encoding truncated SARS-CoV-2 surface glycoprotein having an amino acid sequence substantially as set out in SEQ ID No: 78, or a fragment or variant thereof.

Therefore, one embodiment of the nucleic acid (DNA) sequence encoding the pre-fusion stabilised SARS-CoV-2 surface glycoprotein lacking the complete cytoplasmic domain is provided herein as SEQ ID No: 79, as follows:

[SEQ ID No: 79]

ATGTTCGTGTTTCTGGTGCTGCTGCCTCTGGTGTCCAGCCAGTGTGTGA

ACCTGACCACCAGAACACAGCTGCCTCCAGCCTACACCAACAGCTTTAC

CAGAGGCGTGTACTACCCCGACAAGGTGTTCAGATCCAGCGTGCTGCAC

TCTACCCAGGACCTGTTCCTGCCTTTCTTCAGCAACGTGACCTGGTTCC

ACGCCATCCACGTGTCCGGCACCAATGGCACCAAGAGATTCGACAACCC

CGTGCTGCCCTTCAACGACGGGGTGTACTTTGCCAGCACCGAGAAGTCC

AACATCATCAGAGGCTGGATCTTCGGCACCACACTGGACAGCAAGACCC

AGAGCCTGCTGATCGTGAACAACGCCACCAACGTGGTCATCAAAGTGTG

CGAGTTCCAGTTCTGCAACGACCCCTTCCTGGGCGTCTACTACCACAAG

AACAACAAGAGCTGGATGGAAAGCGAGTTCCGGGTGTACAGCAGCGCCA

ACAACTGCACCTTCGAGTACGTGTCCCAGCCTTTCCTGATGGACCTGGA

AGGCAAGCAGGGCAACTTCAAGAACCTGCGCGAGTTCGTGTTCAAGAAC

ATCGACGGCTACTTCAAGATCTACAGCAAGCACACCCCTATCAACCTCG

TGCGGGATCTGCCTCAGGGCTTCTCTGCTCTGGAACCCCTGGTGGATCT

GCCCATCGGCATCAACATCACCCGGTTTCAGACACTGCTGGCCCTGCAC

AGAAGCTACCTGACACCTGGCGATAGCAGCAGCGGATGGACAGCTGGTG

CCGCCGCTTACTATGTGGGCTACCTGCAGCCTAGAACCTTCCTGCTGAA

GTACAACGAGAACGGCACCATCACCGACGCCGTGGATTGTGCCCTTGAT

CCTCTGAGCGAGACAAAGTGCACCCTGAAGTCCTTCACCGTGGAAAAGG

GCATCTACCAGACCAGCAACTTCCGGGTGCAGCCCACCGAATCCATCGT

GCGGTTCCCCAATATCACCAATCTGTGCCCCTTCGGCGAGGTGTTCAAT

GCCACCAGATTCGCCTCTGTGTACGCCTGGAACCGGAAGCGGATCAGCA

ATTGCGTGGCCGACTACTCCGTGCTGTACAACTCCGCCAGCTTCAGCAC

CTTCAAGTGCTACGGCGTGTCCCCTACCAAGCTGAACGACCTGTGCTTC

ACAAACGTGTACGCCGACAGCTTCGTGATCCGGGGAGATGAAGTGCGGC

AGATTGCCCCTGGACAGACAGGCAAGATCGCCGACTACAACTACAAGCT

GCCCGACGACTTCACCGGCTGTGTGATTGCCTGGAACAGCAACAACCTG

GACTCCAAAGTCGGCGGCAACTACAATTACCTGTACCGGCTGTTCCGGA

AGTCCAATCTGAAGCCCTTCGAGCGGGACATCTCCACCGAGATCTATCA

GGCCGGCAGCACCCCTTGTAACGGCGTGGAAGGCTTCAACTGCTACTTC

CCACTGCAGTCCTACGGCTTTCAGCCCACAAATGGCGTGGGCTATCAGC

CCTACAGAGTGGTGGTGCTGAGCTTCGAACTGCTGCATGCCCCTGCCAC

AGTGTGCGGCCCTAAGAAAAGCACCAATCTCGTGAAGAACAAATGCGTG

AACTTCAACTTCAACGGCCTGACCGGCACAGGCGTGCTGACAGAGAGCA

-continued

ACAAGAAGTTCCTGCCATTCCAGCAGTTTGGCCGGGATATCGCCGATAC

CACAGACGCCGTTAGAGATCCCCAGACACTGGAAATCCTGGACATCACC

CCTTGCAGCTTCGGCGGAGTGTCTGTGATCACCCCTGGCACCAACACCA

GCAATCAGGTGGCAGTGCTGTACCAGGACGTGAACTGTACCGAAGTGCC

CGTGGCCATTCACGCCGATCAGCTGACACCIACATGGCGGGTGTACTCC

ACCGGCAGCAATGTGTTTCAGACCAGAGCCGGCTGTCTGATCGGAGCCG

AGCACGTGAACAATAGCTACGAGTGCGACATCCCCATCGGCGCTGGCAT

CTGTGCCAGCTACCAGACACAGACAAACAGCCCCAGACGGGCCAGATCT

GTGGCCAGCCAGAGCATCATTGCCTACACAATGTCTCTGGGCGCCGAGA

ACAGCGTGGCCTACTCCAACAACTCTATCGCTATCCCCACCAACTTCAC

CATCAGCGTGACCACAGAGATCCTGCCTGTGTCCATGACCAAGACCAGC

GTGGACTGCACCATGTACATCTGCGGCGATTCCACCGAGTGCTCCAACC

TGCTGCTGCAGTACGGCAGCTTCTGCACCCAGCTGAATAGAGCCCTGAC

AGGGATCGCCGTGGAACAGGACAAGAACACCCAAGAGGTGTTCGCCCAA

GTGAAGCAGATCTACAAGACCCCTCCTATCAAGGACTTCGGCGGCTTCA

ATTTCAGCCAGATTCTGCCCGATCCTAGCAAGCCCAGCAAGCGGAGCTT

CATCGAGGACCTGCTGTTCAACAAAGTGACACTGGCCGACGCCGGCTTC

ATCAAGCAGTATGGCGATTGTCTGGGCGACATTGCCGCCAGGGATCTGA

TTTGCGCCCAGAAGTTTAACGGACTGACAGTGCTGCCTCCTCTGCTGAC

CGATGAGATGATCGCCCAGTACACATCTGCCCTGCTGGCCGGCACAATC

ACAAGCGGCTGGACATTTGGAGCTGGCGCCGCTCTGCAGATCCCCTTTG

CTATGCAGATGGCCTACAGATTCAACGGCATCGGAGTGACCCAGAATGT

GCTGTACGAGAACCAGAAGCTGATCGCCAACCAGTTCAACAGCGCCATC

GGCAAGATCCAGGACAGCCTGAGCAGCACAGCAAGCGCCCTGGGAAAGC

TGCAGGACGTGGTCAACCAGAATGCCCAGGCACTGAACACCCTGGTCAA

GCAGCTGTCCTCCAACTTCGGCGCCATCAGCTCTGTGCTGAACGATATC

CTGAGCAGACTGGACCCTCCTGAGGCCGAGGTGCAGATCGACAGACTGA

TCACAGGCAGACTGCAGAGCCTCCAGACATACGTGACCCAGCAGCTGAT

CAGAGCCGCCGAGATTAGAGCCTCTGCCAATCTGGCCGCCACCAAGATG

TCTGAGTGTGTGCTGGGCCAGAGCAAGAGAGTGGACTTTTGCGGCAAGG

GCTACCACCTGATGAGCTTCCCTCAGTCTGCCCCTCACGGCGTGGTGTT

TCTGCACGTGACATACGTTCCCGCTCAAGAGAAGAATTTCACCACCGCT

CCAGCCATCTGCCACGACGGCAAAGCCCACTTTCCTAGAGAAGGCGTGT

TCGTGTCCAACGGCACCCATTGGTTCGTGACACAGCGGAACTTCTACGA

GCCCCAGATCATCACCACCGACAACACCTTCGTGTCTGGCAACTGCGAC

GTCGTGATCGGCATTGTGAACAATACCGTGTACGACCCTCTGCAGCCCG

AGCTGGACAGCTTCAAAGAGGAACTGGACAAGTACTTTAAGAACCACAC

AAGCCCCGACGTGGACCTGGGCGATATCAGCGGAATCAATGCCAGCGTC

GTGAACATCCAGAAAGAGATCGACCGGCTGAACGAGGTGGCCAAGAATC

TGAACGAGAGCCTGATCGACCTGCAAGAACTGGGGAAGTACGAGCAGTA

CATCAAGTGGCCCTGGTACATCTGGCTGGGCTTTATCGCCGGACTGATT

GCCATCGTGATGGTCACAATCATGCTG

Hence, preferably the saRNA is encoded by a DNA sequence substantially as set out in SEQ ID No: 79, or a fragment or variant thereof.

The corresponding nucleic acid (RNA) sequence of the pre-fusion stabilised SARS-CoV-2 surface glycoprotein lacking the complete cytoplasmic domain is provided herein as SEQ ID No: 80, as follows:

[SEQ ID No: 80]

AUGUUCGUGUUUCUGGUGCUGCUGCCUCUGGUGUCCAGCCAGUGUGUGA

ACCUGACCACCAGAACACAGCUGCCUCCAGCCUACACCAACAGCUUUAC

CAGAGGCGUGUACUACCCCGACAAGGUGUUCAGAUCCAGCGUGCUGCAC

UCUACCCAGGACCUGUUCCUGCCUUUCUUCAGCAACGUGACCUGGUUCC

ACGCCAUCCACGUGUCCGGCACCAAUGGCACCAAGAGAUUCGACAACCC

CGUGCUGCCCUUCAACGACGGGGUGUACUUUGCCAGCACCGAGAAGUCC

AACAUCAUCAGAGGCUGGAUCUUCGGCACCACACUGGACAGCAAGACCC

AGAGCCUGCUGAUCGUGAACAACGCCACCAACGUGGUCAUCAAAGUGUG

CGAGUUCCAGUUCUGCAACGACCCCUUCCUGGGCGUCUACUACCACAAG

AACAACAAGAGCUGGAUGGAAAGCGAGUUCCGGGUGUACAGCAGCGCCA

ACAACUGCACCUUCGAGUACGUGUCCCAGCCUUUCCUGAUGGACCUGGA

AGGCAAGCAGGGCAACUUCAAGAACCUGCGCGAGUUCGUGUUCAAGAAC

AUCGACGGCUACUUCAAGAUCUACAGCAAGCACACCCCUAUCAACCUCG

UGCGGGAUCUGCCUCAGGGCUUCUCUGCUCUGGAACCCCUGGUGGAUCU

GCCCAUCGGCAUCAACAUCACCCGGUUUCAGACACUGCUGGCCCUGCAC

AGAAGCUACCUGACACCUGGCGAUAGCAGCAGCGGAUGGACAGCUGGUG

CCGCCGCUUACUAUGUGGGCUACCUGCAGCCUAGAACCUUCCUGCUGAA

GUACAACGAGAACGGCACCAUCACCGACGCCGUGGAUUGUGCCCUUGAU

CCUCUGAGCGAGACAAAGUGCACCCUGAAGUCCUUCACCGUGGAAAAGG

GCAUCUACCAGACCAGCAACUUCCGGGUGCAGCCCACCGAAUCCAUCGU

GCGGUUCCCCAAUAUCACCAAUCUGUGCCCCUUCGGCGAGGUGUUCAAU

GCCACCAGAUUCGCCUCUGUGUACGCCUGGAACCGGAAGCGGAUCAGCA

AUUGCGUGGCCGACUACUCCGUGCUGUACAACUCCGCCAGCUUCAGCAC

CUUCAAGUGCUACGGCGUGUCCCCUACCAAGCUGAACGACCUGUGCUUC

ACAAACGUGUACGCCGACAGCUUCGUGAUCCGGGGAGAUGAAGUGCGGC

AGAUUGCCCCUGGACAGACAGGCAAGAUCGCCGACUACAACUACAAGCU

GCCCGACGACUUCACCGGCUGUGUGAUUGCCUGGAACAGCAACAACCUG

GACUCCAAAGUCGGCGGCAACUACAAUUACCUGUACCGGCUGUUCCGGA

AGUCCAAUCUGAAGCCCUUCGAGCGGGACAUCUCCACCGAGAUCUAUCA

GGCCGGCAGCACCCCUUGUAACGGCGUGGAAGGCUUCAACUGCUACUUC

CCACUGCAGUCCUACGGCUUUCAGCCCACAAAUGGCGUGGGCUAUCAGC

CCUACAGAGUGGUGGUGCUGAGCUUCGAACUGCUGCAUGCCCCUGCCAC

AGUGUGCGGCCCUAAGAAAAGCACCAAUCUCGUGAAGAACAAAUGCGUG

AACUUCAACUUCAACGGCCUGACCGGCACAGGCGUGCUGACAGAGAGCA

ACAAGAAGUUCCUGCCAUUCCAGCAGUUUGGCCGGGAUAUCGCCGAUAC

CACAGACGCCGUUAGAGAUCCCCAGACACUGGAAAUCCUGGACAUCACC

CCUUGCAGCUUCGGCGGAGUGUCUGUGAUCACCCCUGGCACCAACACCA

GCAAUCAGGUGGCAGUGCUGUACCAGGACGUGAACUGUACCGAAGUGCC

CGUGGCCAUUCACGCCGAUCAGCUGACACCUACAUGGCGGGUGUACUCC

ACCGGCAGCAAUGUGUUUCAGACCAGAGCCGGCUGUCUGAUCGGAGCCG

AGCACGUGAACAAUAGCUACGAGUGCGACAUCCCCAUCGGCGCUGGCAU

CUGUGCCAGCUACCAGACACAGACAAACAGCCCCAGACGGGCCAGAUCU

GUGGCCAGCCAGAGCAUCAUUGCCUACACAAUGUCUCUGGGCGCCGAGA

ACAGCGUGGCCUACUCCAACAACUCUAUCGCUAUCCCCACCAACUUCAC

CAUCAGCGUGACCACAGAGAUCCUGCCUGUGUCCAUGACCAAGACCAGC

GUGGACUGCACCAUGUACAUCUGCGGCGAUUCCACCGAGUGCUCCAACC

UGCUGCUGCAGUACGGCAGCUUCUGCACCCAGCUGAAUAGAGCCCUGAC

AGGGAUCGCCGUGGAACAGGACAAGAACACCCAAGAGGUGUUCGCCCAA

GUGAAGCAGAUCUACAAGACCCCUCCUAUCAAGGACUUCGGCGGCUUCA

AUUUCAGCCAGAUUCUGCCCGAUCCUAGCAAGCCCAGCAAGCGGAGCUU

CAUCGAGGACCUGCUGUUCAACAAAGUGACACUGGCCGACGCCGGCUUC

AUCAAGCAGUAUGGCGAUUGUCUGGGCGACAUUGCCGCCAGGGAUCUGA

UUUGCGCCCAGAAGUUUAACGGACUGACAGUGCUGCCUCCUCUGCUGAC

CGAUGAGAUGAUCGCCCAGUACACAUCUGCCCUGCUGGCCGGCACAAUC

ACAAGCGGCUGGACAUUUGGAGCUGGCGCCGCUCUGCAGAUCCCCUUUG

CUAUGCAGAUGGCCUACAGAUUCAACGGCAUCGGAGUGACCCAGAAUGU

GCUGUACGAGAACCAGAAGCUGAUCGCCAACCAGUUCAACAGCGCCAUC

GGCAAGAUCCAGGACAGCCUGAGCAGCACAGCAAGCGCCCUGGGAAAGC

UGCAGGACGUGGUCAACCAGAAUGCCCAGGCACUGAACACCCUGGUCAA

GCAGCUGUCCUCCAACUUCGGCGCCAUCAGCUCUGUGCUGAACGAUAUC

CUGAGCAGACUGGACCCUCCUGAGGCCGAGGUGCAGAUCGACAGACUGA

UCACAGGCAGACUGCAGAGCCUCCAGACAUACGUGACCCAGCAGCUGAU

CAGAGCCGCCGAGAUUAGAGCCUCUGCCAAUCUGGCCGCCACCAAGAUG

UCUGAGUGUGUGCUGGGCCAGAGCAAGAGAGUGGACUUUUGCGGCAAGG

GCUACCACCUGAUGAGCUUCCCUCAGUCUGCCCCUCACGGCGUGGUGUU

UCUGCACGUGACAUACGUUCCCGCUCAAGAGAAGAAUUUCACCACCGCU

CCAGCCAUCUGCCACGACGGCAAAGCCCACUUUCCUAGAGAAGGCGUGU

UCGUGUCCAACGGCACCCAUUGGUUCGUGACACAGCGGAACUUCUACGA

GCCCCAGAUCAUCACCACCGACAACACCUUCGUGUCUGGCAACUGCGAC

GUCGUGAUCGGCAUUGUGAACAAUACCGUGUACGACCCUCUGCAGCCCG

AGCUGGACAGCUUCAAAGAGGAACUGGACAAGUACUUUAAGAACCACAC

AAGCCCCGACGUGGACCUGGGCGAUAUCAGCGGAAUCAAUGCCAGCGUC

-continued

```
GUGAACAUCCAGAAAGAGAUCGACCGGCUGAACGAGGUGGCCAAGAAUC

UGAACGAGAGCCUGAUCGACCUGCAAGAACUGGGGAAGUACGAGCAGUA

CAUCAAGUGGCCCUGGUACAUCUGGCUGGGCUUUAUCGCCGGACUGAUU

GCCAUCGUGAUGGUCACAAUCAUGCUG
```

Hence, preferably the saRNA comprises a sequence substantially as set out in SEQ ID No: 80, or a fragment or variant thereof.

In one embodiment, the pre-fusion stabilised SARS-CoV-2 surface glycoprotein may lack part (19 amino acid deletion from C-terminus) of the cytoplasmic domain. One embodiment of the amino acid sequence is provided herein as SEQ ID No: 81, as follows:

```
                                          [SEQ ID No: 81]
MFVFLVLLPLVSSQCVNLTTRTQLPPAYTNSFTRGVYYPDKVFRSSVLH

STQDLFLPFFSNVTWFHAIHVSGTNGTKRFDNPVLPFNDGVYFASTEKS

NIIRGWIFGTTLDSKTQSLLIVNNATNVVIKVCEFQFCNDPFLGVYYHK

NNKSWMESEFRVYSSANNCTFEYVSQPFLMDLEGKQGNFKNLREFVFKN

IDGYFKIYSKHTPINLVRDLPQGFSALEPLVDLPIGINITRFQTLLALH

RSYLTPGDSSSGWTAGAAAYYVGYLQPRTFLLKYNENGTITDAVDCALD

PLSETKCTLKSFTVEKGIYQTSNFRVQPTESIVRFPNITNLCPFGEVFN

ATRFASVYAWNRKRISNCVADYSVLYNSASFSTFKCYGVSPTKLNDLCF

TNVYADSFVIRGDEVRQIAPGQTGKIADYNYKLPDDFTGCVIAWNSNNL

DSKVGGNYNYLYRLFRKSNLKPFERDISTEIYQAGSTPCNGVEGFNCYF

PLQSYGFQPTNGVGYQPYRVVVLSFELLHAPATVCGPKKSTNLVKNKCV

NFNFNGLTGTGVLTESNKKFLPFQQFGRDIADTTDAVRDPQTLEILDIT

PCSFGGVSVITPGTNTSNQVAVLYQDVNCTEVPVAIHADQLTPTWRVYS

TGSNVFQTRAGCLIGAEHVNNSYECDIPIGAGICASYQTQTNSPRRARS

VASQSIIAYTMSLGAENSVAYSNNSIAIPTNFTISVTTEILPVSMTKTS

VDCTMYICGDSTECSNLLLQYGSFCTQLNRALTGIAVEQDKNTQEVFAQ

VKQIYKTPPIKDFGGFNFSQILPDPSKPSKRSFIEDLLFNKVTLADAGF

IKQYGDCLGDIAARDLICAQKFNGLTVLPPLLTDEMIAQYTSALLAGTI

TSGWTFGAGAALQIPFAMQMAYRFNGIGVTQNVLYENQKLIANQFNSAI

GKIQDSLSSTASALGKLQDVVNQNAQALNTLVKQLSSNFGAISSVLNDI

LSRLDPPEAEVQIDRLITGRLQSLQTYVTQQLIRAAEIRASANLAATKM

SECVLGQSKRVDFCGKGYHLMSFPQSAPHGVVFLHVTYVPAQEKNFTTA

PAICHDGKAHFPREGVFVSNGTHWFVTQRNFYEPQIITTDNTFVSGNCD

VVIGIVNNTVYDPLQPELDSFKEELDKYFKNHTSPDVDLGDISGINASV

VNIQKEIDRLNEVAKNLNESLIDLQELGKYEQYIKWPWYIWLGFIAGLI

AIVMVTIMLCCMTSCCSCLKGCCSCGSCC
```

Therefore, preferably the saRNA construct comprises a nucleic acid sequence encoding truncated SARS-CoV-2 surface glycoprotein having an amino acid sequence substantially as set out in SEQ ID No: 81, or a fragment or variant thereof.

Therefore, one embodiment of the nucleic acid (DNA) sequence encoding the pre-fusion stabilised SARS-CoV-2 surface glycoprotein lacking part (19 amino acid deletion from C-terminus) of the CT, is provided herein as SEQ ID No: 82, as follows:

```
                                          [SEQ ID No: 82]
ATGTTCGTGTTTCTGGTGCTGCTGCCTCTGGTGTCCAGCCAGTGTGTGA

ACCTGACCACCAGAACACAGCTGCCTCCAGCCTACACCAACAGCTTTAC

CAGAGGCGTGTACTACCCCGACAAGGTGTTCAGATCCAGCGTGCTGCAC

TCTACCCAGGACCTGTTCCTGCCTTTCTTCAGCAACGTGACCTGGTTCC

ACGCCATCCACGTGTCCGGCACCAATGGCACCAAGAGATTCGACAACCC

CGTGCTGCCCTTCAACGACGGGGTGTACTTTGCCAGCACCGAGAAGTCC

AACATCATCAGAGGCTGGATCTTCGGCACCACACTGGACAGCAAGACCC

AGAGCCTGCTGATCGTGAACAACGCCACCAACGTGGTCATCAAAGTGTG

CGAGTTCCAGTTCTGCAACGACCCCTTCCTGGGCGTCTACTACCACAAG

AACAACAAGAGCTGGATGGAAAGCGAGTTCCGGGTGTACAGCAGCGCCA

ACAACTGCACCTTCGAGTACGTGTCCCAGCCTTTCCTGATGGACCTGGA

AGGCAAGCAGGGCAACTTCAAGAACCTGCGCGAGTTCGTGTTCAAGAAC

ATCGACGGCTACTTCAAGATCTACAGCAAGCACACCCCTATCAACCTCG

TGCGGGATCTGCCTCAGGGCTTCTCTGCTCTGGAACCCCTGGTGGATCT

GCCCATCGGCATCAACATCACCCGGTTTCAGACACTGCTGGCCCTGCAC

AGAAGCTACCTGACACCTGGCGATAGCAGCAGCGGATGGACAGCTGGTG

CCGCCGCTTACTATGTGGGCTACCTGCAGCCTAGAACCTTCCTGCTGAA

GTACAACGAGAACGGCACCATCACCGACGCCGTGGATTGTGCCCTTGAT

CCTCTGAGCGAGACAAAGTGCACCCTGAAGTCCTTCACCGTGGAAAAGG

GCATCTACCAGACCAGCAACTTCCGGGTGCAGCCCACCGAATCCATCGT

GCGGTTCCCCAATATCACCAATCTGTGCCCCTTCGGCGAGGTGTTCAAT

GCCACCAGATTCGCCTCTGTGTACGCCTGGAACCGGAAGCGGATCAGCA

ATTGCGTGGCCGACTACTCCGTGCTGTACAACTCCGCCAGCTTCAGCAC

CTTCAAGTGCTACGGCGTGTCCCCTACCAAGCTGAACGACCTGTGCTTC

ACAAACGTGTACGCCGACAGCTTCGTGATCCGGGGAGATGAAGTGCGGC

AGATTGCCCCTGGACAGACAGGCAAGATCGCCGACTACAACTACAAGCT

GCCCGACGACTTCACCGGCTGTGTGATTGCCTGGAACAGCAACAACCTG

GACTCCAAAGTCGGCGGCAACTACAATTACCTGTACCGGCTGTTCCGGA

AGTCCAATCTGAAGCCCTTCGAGCGGGACATCTCCACCGAGATCTATCA

GGCCGGCAGCACCCCTTGTAACGGCGTGGAAGGCTTCAACTGCTACTTC

CCACTGCAGTCCTACGGCTTTCAGCCCACAAATGGCGTGGGCTATCAGC

CCTACAGAGTGGTGGTGCTGAGCTTCGAACTGCTGCATGCCCCTGCCAC

AGTGTGCGGCCCTAAGAAAAGCACCAATCTCGTGAAGAACAAATGCGTG

AACTTCAACTTCAACGGCCTGACCGGCACAGGCGTGCTGACAGAGAGCA

ACAAGAAGTTCCTGCCATTCCAGCAGTTTGGCCGGGATATCGCCGATAC

CACAGACGCCGTTAGAGATCCCCAGACACTGGAAATCCTGGACATCACC

CCTTGCAGCTTCGGCGGAGTGTCTGTGATCACCCCTGGCACCAACACCA

GCAATCAGGTGGCAGTGCTGTACCAGGACGTGAACTGTACCGAAGTGCC
```

-continued

```
CGTGGCCATTCACGCCGATCAGCTGACACCTACATGGCGGGTGTACTCC
ACCGGCAGCAATGTGTTTCAGACCAGAGCCGGCTGTCTGATCGGAGCCG
AGCACGTGAACAATAGCTACGAGTGCGACATCCCCATCGGCGCTGGCAT
CTGTGCCAGCTACCAGACACAGACAAACAGCCCCAGACGGGCCAGATCT
GTGGCCAGCCAGAGCATCATTGCCTACACAATGTCTCTGGGCGCCGAGA
ACAGCGTGGCCTACTCCAACAACTCTATCGCTATCCCCACCAACTTCAC
CATCAGCGTGACCACAGAGATCCTGCCTGTGTCCATGACCAAGACCAGC
GTGGACTGCACCATGTACATCTGCGGCGATTCCACCGAGTGCTCCAACC
TGCTGCTGCAGTACGGCAGCTTCTGCACCCAGCTGAATAGAGCCCTGAC
AGGGATCGCCGTGGAACAGGACAAGAACACCCAAGAGGTGTTCGCCCAA
GTGAAGCAGATCTACAAGACCCCTCCTATCAAGGACTTCGGCGGCTTCA
ATTTCAGCCAGATTCTGCCCGATCCTAGCAAGCCCAGCAAGCGGAGCTT
CATCGAGGACCTGCTGTTCAACAAAGTGACACTGGCCGACGCCGGCTTC
ATCAAGCAGTATGGCGATTGTCTGGGCGACATTGCCGCCAGGGATCTGA
TTTGCGCCCAGAAGTTTAACGGACTGACAGTGCTGCCTCCTCTGCTGAC
CGATGAGATGATCGCCCAGTACACATCTGCCCTGCTGGCCGGCACAATC
ACAAGCGGCTGGACATTTGGAGCTGGCGCCGCTCTGCAGATCCCCTTTG
CTATGCAGATGGCCTACAGATTCAACGGCATCGGAGTGACCCAGAATGT
GCTGTACGAGAACCAGAAGCTGATCGCCAACCAGTTCAACAGCGCCATC
GGCAAGATCCAGGACAGCCTGAGCAGCACAGCAAGCGCCCTGGGAAAGC
TGCAGGACGTGGTCAACCAGAATGCCCAGGCACTGAACACCCTGGTCAA
GCAGCTGTCCTCCAACTTCGGCGCCATCAGCTCTGTGCTGAACGATATC
CTGAGCAGACTGGACCCTCCTGAGGCCGAGGTGCAGATCGACAGACTGA
TCACAGGCAGACTGCAGAGCCTCCAGACATACGTGACCCAGCAGCTGAT
CAGAGCCGCCGAGATTAGAGCCTCTGCCAATCTGGCCGCCACCAAGATG
TCTGAGTGTGTGCTGGGCCAGAGCAAGAGAGTGGACTTTTGCGGCAAGG
GCTACCACCTGATGAGCTTCCCTCAGTCTGCCCCTCACGGCGTGGTGTT
TCTGCACGTGACATACGTTCCCGCTCAAGAGAAGAATTTCACCACCGCT
CCAGCCATCTGCCACGACGGCAAAGCCCACTTTCCTAGAGAAGGCGTGT
TCGTGTCCAACGGCACCCATTGGTTCGTGACACAGCGGAACTTCTACGA
GCCCCAGATCATCACCACCGACAACACCTTCGTGTCTGGCAACTGCGAC
GTCGTGATCGGCATTGTGAACAATACCGTGTACGACCCTCTGCAGCCCG
AGCTGGACAGCTTCAAAGAGGAACTGGACAAGTACTTTAAGAACCACAC
AAGCCCCGACGTGGACCTGGGCGATATCAGCGGAATCAATGCCAGCGTC
GTGAACATCCAGAAAGAGATCGACCGGCTGAACGAGGTGGCCAAGAATC
TGAACGAGAGCCTGATCGACCTGCAAGAACTGGGGAAGTACGAGCAGTA
CATCAAGTGGCCCTGGTACATCTGGCTGGGCTTTATCGCCGGACTGATT
GCCATCGTGATGGTCACAATCATGCTGTGTTGCATGACCAGCTGCTGTA
GCTGCCTGAAGGGCTGTTGTAGCTGTGGCAGCTGCTGC
```

Hence, preferably the saRNA is encoded by a DNA sequence substantially as set out in SEQ ID No: 82, or a fragment or variant thereof.

The corresponding nucleic acid (RNA) sequence of the pre-fusion stabilised SARS-CoV-2 surface glycoprotein lacking part (19 amino acid deletion from C-terminus) of the CT, 55 is provided herein as SEQ ID No: 83, as follows:

```
                                              [SEQ ID No: 83]
AUGUUCGUGUUUCUGGUGCUGCUGCCUCUGGUGUCCAGCCAGUGUGUGA
ACCUGACCACCAGAACACAGCUGCCUCCAGCCUACACCAACAGCUUUAC
CAGAGGCGUGUACUACCCCGACAAGGUGUUCAGAUCCAGCGUGCUGCAC
UCUACCCAGGACCUGUUCCUGCCUUUCUUCAGCAACGUGACCUGGUUCC
ACGCCAUCCACGUGUCCGGCACCAAUGGCACCAAGAGAUUCGACAACCC
CGUGCUGCCCUUCAACGACGGGGUGUACUUUGCCAGCACCGAGAAGUCC
AACAUCAUCAGAGGCUGGAUCUUCGGCACCACACUGGACAGCAAGACCC
AGAGCCUGCUGAUCGUGAACAACGCCACCAACGUGGUCAUCAAAGUGUG
CGAGUUCCAGUUCUGCAACGACCCCUUCCUGGGCGUCUACUACCACAAG
AACAACAAGAGCUGGAUGGAAAGCGAGUUCCGGGUGUACAGCAGCGCCA
ACAACUGCACCUUCGAGUACGUGUCCCAGCCUUUCCUGAUGGACCUGGA
AGGCAAGCAGGGCAACUUCAAGAACCUGCGCGAGUUCGUGUUCAAGAAC
AUCGACGGCUACUUCAAGAUCUACAGCAAGCACACCCCUAUCAACCUCG
UGCGGGAUCUGCCUCAGGGCUUCUCUGCUCUGGAACCCCUGGUGGAUCU
GCCCAUCGGCAUCAACAUCACCCGGUUUCAGACACUGCUGGCCCUGCAC
AGAAGCUACCUGACACCUGGCGAUAGCAGCAGCGGAUGGACAGCUGGUG
CCGCCGCUUACUAUGUGGGCUACCUGCAGCCUAGAACCUUCCUGCUGAA
GUACAACGAGAACGGCACCAUCACCGACGCCGUGGAUUGUGCCCUUGAU
CCUCUGAGCGAGACAAAGUGCACCCUGAAGUCCUUCACCGUGGAAAAGG
GCAUCUACCAGACCAGCAACUUCCGGGUGCAGCCCACCGAAUCCAUCGU
GCGGUUCCCCAAUAUCACCAAUCUGUGCCCCUUCGGCGAGGUGUUCAAU
GCCACCAGAUUCGCCUCUGUGUACGCCUGGAACCGGAAGCGGAUCAGCA
AUUGCGUGGCCGACUACUCCGUGCUGUACAACUCCGCCAGCUUCAGCAC
CUUCAAGUGCUACGGCGUGUCCCCUACCAAGCUGAACGACCUGUGCUUC
ACAAACGUGUACGCCGACAGCUUCGUGAUCCGGGGAGAUGAAGUGCGGC
AGAUUGCCCCUGGACAGACAGGCAAGAUCGCCGACUACAACUACAAGCU
GCCCGACGACUUCACCGGCUGUGUGAUUGCCUGGAACAGCAACAACCUG
GACUCCAAAGUCGGCGGCAACUACAAUUACCUGUACCGGCUGUUCCGGA
AGUCCAAUCUGAAGCCCUUCGAGCGGGACAUCUCCACCGAGAUCUAUCA
GGCCGGCAGCACCCCUUGUAACGGCGUGGAAGGCUUCAACUGCUACUUC
CCACUGCAGUCCUACGGCUUUCAGCCCACAAAUGGCGUGGGCUAUCAGC
CCUACAGAGUGGUGGUGCUGAGCUUCGAACUGCUGCAUGCCCCUGCCAC
AGUGUGCGGCCCUAAGAAAAGCACCAAUCUCGUGAAGAACAAAUGCGUG
AACUUCAACUUCAACGGCCUGACCGGCACAGGCGUGCUGACAGAGAGCA
ACAAGAAGUUCCUGCCAUUCCAGCAGUUUGGCCGGGAUAUCGCCGAUAC
CACAGACGCCGUUAGAGAUCCCCAGACACUGGAAAUCCUGGACAUCACC
CCUUGCAGCUUCGGCGGAGUGUCUGUGAUCACCCCUGGCACCAACACCA
```

-continued

GCAAUCAGGUGGCAGUGCUGUACCAGGACGUGAACUGUACCGAAGUGCC

CGUGGCCAUUCACGCCGAUCAGCUGACACCUACAUGGCGGGUGUACUCC

ACCGGCAGCAAUGUGUUUCAGACCAGAGCCGGCUGUCUGAUCGGAGCCG

AGCACGUGAACAAUAGCUACGAGUGCGACAUCCCCAUCGGCGCUGGCAU

CUGUGCCAGCUACCAGACACAGACAAACAGCCCCAGACGGGCCAGAUCU

GUGGCCAGCCAGAGCAUCAUUGCCUACACAAUGUCUCUGGGCGCCGAGA

ACAGCGUGGCCUACUCCAACAACUCUAUCGCUAUCCCCACCAACUUCAC

CAUCAGCGUGACCACAGAGAUCCUGCCUGUGUCCAUGACCAAGACCAGC

GUGGACUGCACCAUGUACAUCUGCGGCGAUUCCACCGAGUGCUCCAACC

UGCUGCUGCAGUACGGCAGCUUCUGCACCCAGCUGAAUAGAGCCCUGAC

AGGGAUCGCCGUGGAACAGGACAAGAACACCCAAGAGGUGUUCGCCCAA

GUGAAGCAGAUCUACAAGACCCCUCCUAUCAAGGACUUCGGCGGCUUCA

AUUUCAGCCAGAUUCUGCCCGAUCCUAGCAAGCCCAGCAAGCGGAGCUU

CAUCGAGGACCUGCUGUUCAACAAAGUGACACUGGCCGACGCCGGCUUC

AUCAAGCAGUAUGGCGAUUGUCUGGGCGACAUUGCCGCCAGGGAUCUGA

UUUGCGCCCAGAAGUUUAACGGACUGACAGUGCUGCCUCCUCUGCUGAC

CGAUGAGAUGAUCGCCCAGUACACAUCUGCCCUGCUGGCCGGCACAAUC

ACAAGCGGCUGGACAUUUGGAGCUGGCGCCGCUCUGCAGAUCCCCUUUG

CUAUGCAGAUGGCCUACAGAUUCAACGGCAUCGGAGUGACCCAGAAUGU

GCUGUACGAGAACCAGAAGCUGAUCGCCAACCAGUUCAACAGCGCCAUC

GGCAAGAUCCAGGACAGCCUGAGCAGCACAGCAAGCGCCCUGGGAAAGC

UGCAGGACGUGGUCAACCAGAAUGCCCAGGCACUGAACACCCUGGUCAA

GCAGCUGUCCUCCAACUUCGGCGCCAUCAGCUCUGUGCUGAACGAUAUC

CUGAGCAGACUGGACCCUCCUGAGGCCGAGGUGCAGAUCGACAGACUGA

UCACAGGCAGACUGCAGAGCCUCCAGACAUACGUGACCCAGCAGCUGAU

CAGAGCCGCCGAGAUUAGAGCCUCUGCCAAUCUGGCCGCCACCAAGAUG

UCUGAGUGUGUGCUGGGCCAGAGCAAGAGAGUGGACUUUUGCGGCAAGG

GCUACCACCUGAUGAGCUUCCCUCAGUCUGCCCCUCACGGCGUGGUGUU

UCUGCACGUGACAUACGUUCCCGCUCAAGAGAAGAAUUUCACCACCGCU

CCAGCCAUCUGCCACGACGGCAAAGCCCACUUUCCUAGAGAAGGCGUGU

UCGUGUCCAACGGCACCCAUUGGUUCGUGACACAGCGGAACUUCUACGA

GCCCCAGAUCAUCACCACCGACAACACCUUCGUGUCUGGCAACUGCGAC

GUCGUGAUCGGCAUUGUGAACAAUACCGUGUACGACCCUCUGCAGCCCG

AGCUGGACAGCUUCAAAGAGGAACUGGACAAGUACUUUAAGAACCACAC

AAGCCCCGACGUGGACCUGGGCGAUAUCAGCGGAAUCAAUGCCAGCGUC

GUGAACAUCCAGAAAGAGAUCGACCGGCUGAACGAGGUGGCCAAGAAUC

UGAACGAGAGCCUGAUCGACCUGCAAGAACUGGGGAAGUACGAGCAGUA

CAUCAAGUGGCCCUGGUACAUCUGGCUGGGCUUUAUCGCCGGACUGAUU

GCCAUCGUGAUGGUCACAAUCAUGCUGUGUUGCAUGACCAGCUGCUGUA

GCUGCCUGAAGGGCUGUUGUAGCUGUGGCAGCUGCUGC

Hence, preferably the saRNA comprises a sequence substantially as set out in SEQ ID No: 83, or a fragment or variant thereof.

In one embodiment, the pre-fusion stabilised SARS-CoV-2 surface glycoprotein may lack part (21 amino acid deletion from C-terminus) of the cytoplasmic domain. One embodiment of the amino acid sequence is provided herein as SEQ ID No: 84, as follows:

[SEQ ID No: 84]

MFVFLVLLPLVSSQCVNLTTRTQLPPAYTNSFTRGVYYPDKVFRSSVLH

STQDLFLPFFSNVTWFHAIHVSGTNGTKRFDNPVLPFNDGVYFASTEKS

NIIRGWIFGTTLDSKTQSLLIVNNATNVVIKVCEFQFCNDPFLGVYYHK

NNKSWMESEFRVYSSANNCTFEYVSQPFLMDLEGKQGNFKNLREFVFKN

IDGYFKIYSKHTPINLVRDLPQGFSALEPLVDLPIGINITRFQTLLALH

RSYLTPGDSSSGWTAGAAAYYVGYLQPRTFLLKYNENGTITDAVDCALD

PLSETKCTLKSFTVEKGIYQTSNFRVQPTESIVRFPNITNLCPFGEVFN

ATRFASVYAWNRKRISNCVADYSVLYNSASFSTFKCYGVSPTKLNDLCF

TNVYADSFVIRGDEVRQIAPGQTGKIADYNYKLPDDFTGCVIAWNSNNL

DSKVGGNYNYLYRLFRKSNLKPFERDISTEIYQAGSTPCNGVEGFNCYF

PLQSYGFQPTNGVGYQPYRVVVLSFELLHAPATVCGPKKSTNLVKNKCV

NFNFNGLTGTGVLTESNKKFLPFQQFGRDIADTTDAVRDPQTLEILDIT

PCSFGGVSVITPGTNTSNQVAVLYQDVNCTEVPVAIHADQLTPTWRVYS

TGSNVFQTRAGCLIGAEHVNNSYECDIPIGAGICASYQTQTNSPRRARS

VASQSIIAYTMSLGAENSVAYSNNSIAIPTNFTISVTTEILPVSMTKTS

VDCTMYICGDSTECSNLLLQYGSFCTQLNRALTGIAVEQDKNTQEVFAQ

VKQIYKTPPIKDFGGFNFSQILPDPSKPSKRSFIEDLLFNKVTLADAGF

IKQYGDCLGDIAARDLICAQKFNGLTVLPPLLTDEMIAQYTSALLAGTI

TSGWTFGAGAALQIPFAMQMAYRFNGIGVTQNVLYENQKLIANQFNSAI

GKIQDSLSSTASALGKLQDVVNQNAQALNTLVKQLSSNFGAISSVLNDI

LSRLDPPEAEVQIDRLITGRLQSLQTYVTQQLIRAAEIRASANLAATKM

SECVLGQSKRVDFCGKGYHLMSFPQSAPHGVVFLHVTYVPAQEKNFTTA

PAICHDGKAHFPREGVFVSNGTHWFVTQRNFYEPQIITTDNTFVSGNCD

VVIGIVNNTVYDPLQPELDSFKEELDKYFKNHTSPDVDLGDISGINASV

VNIQKEIDRLNEVAKNLNESLIDLQELGKYEQYIKWPWYIWLGFIAGLI

AIVMVTIMLCCMTSCCSCLKGCCSCGS

Therefore, preferably the saRNA construct comprises a nucleic acid sequence encoding truncated SARS-CoV-2 surface glycoprotein having an amino acid sequence substantially as set out in SEQ ID No: 84, or a fragment or variant thereof.

Therefore, one embodiment of the nucleic acid (DNA) sequence encoding the pre-fusion stabilised SARS-CoV-2 surface glycoprotein lacking part (21 amino acid deletion from C-terminus) of the CT, is provided herein as SEQ ID No: 85, as follows:

[SEQ ID No: 85]

ATGTTCGTGTTTCTGGTGCTGCTGCCTCTGGTGTCCAGCCAGTGTGTGA
ACCTGACCACCAGAACACAGCTGCCTCCAGCCTACACCAACAGCTTTAC
CAGAGGCGTGTACTACCCCGACAAGGTGTTCAGATCCAGCGTGCTGCAC
TCTACCCAGGACCTGTTCCTGCCTTTCTTCAGCAACGTGACCTGGTTCC
ACGCCATCCACGTGTCCGGCACCAATGGCACCAAGAGATTCGACAACCC
CGTGCTGCCCTTCAACGACGGGGTGTACTTTGCCAGCACCGAGAAGTCC
AACATCATCAGAGGCTGGATCTTCGGCACCACACTGGACAGCAAGACCC
AGAGCCTGCTGATCGTGAACAACGCCACCAACGTGGTCATCAAAGTGTG
CGAGTTCCAGTTCTGCAACGACCCCTTCCTGGGCGTCTACTACCACAAG
AACAACAAGAGCTGGATGGAAAGCGAGTTCCGGGTGTACAGCAGCGCCA
ACAACTGCACCTTCGAGTACGTGTCCCAGCCTTTCCTGATGGACCTGGA
AGGCAAGCAGGGCAACTTCAAGAACCTGCGCGAGTTCGTGTTCAAGAAC
ATCGACGGCTACTTCAAGATCTACAGCAAGCACACCCCTATCAACCTCG
TGCGGGATCTGCCTCAGGGCTTCTCTGCTCTGGAACCCCTGGTGGATCT
GCCCATCGGCATCAACATCACCCGGTTTCAGACACTGCTGGCCCTGCAC
AGAAGCTACCTGACACCTGGCGATAGCAGCAGCGGATGGACAGCTGGTG
CCGCCGCTTACTATGTGGGCTACCTGCAGCCTAGAACCTTCCTGCTGAA
GTACAACGAGAACGGCACCATCACCGACGCCGTGGATTGTGCCCTTGAT
CCTCTGAGCGAGACAAAGTGCACCCTGAAGTCCTTCACCGTGGAAAAGG
GCATCTACCAGACCAGCAACTTCCGGGTGCAGCCCACCGAATCCATCGT
GCGGTTCCCCAATATCACCAATCTGTGCCCCTTCGGCGAGGTGTTCAAT
GCCACCAGATTCGCCTCTGTGTACGCCTGGAACCGGAAGCGGATCAGCA
ATTGCGTGGCCGACTACTCCGTGCTGTACAACTCCGCCAGCTTCAGCAC
CTTCAAGTGCTACGGCGTGTCCCCTACCAAGCTGAACGACCTGTGCTTC
ACAAACGTGTACGCCGACAGCTTCGTGATCCGGGGAGATGAAGTGCGGC
AGATTGCCCCTGGACAGACAGGCAAGATCGCCGACTACAACTACAAGCT
GCCCGACGACTTCACCGGCTGTGTGATTGCCTGGAACAGCAACAACCTG
GACTCCAAAGTCGGCGGCAACTACAATTACCTGTACCGGCTGTTCCGGA
AGTCCAATCTGAAGCCCTTCGAGCGGGACATCTCCACCGAGATCTATCA
GGCCGGCAGCACCCCTTGTAACGGCGTGGAAGGCTTCAACTGCTACTTC
CCACTGCAGTCCTACGGCTTTCAGCCCACAAATGGCGTGGGCTATCAGC
CCTACAGAGTGGTGGTGCTGAGCTTCGAACTGCTGCATGCCCCTGCCAC
AGTGTGCGGCCCTAAGAAAAGCACCAATCTCGTGAAGAACAAATGCGTG
AACTTCAACTTCAACGGCCTGACCGGCACAGGCGTGCTGACAGAGAGCA
ACAAGAAGTTCCTGCCATTCCAGCAGTTTGGCCGGGATATCGCCGATAC
CACAGACGCCGTTAGAGATCCCCAGACACTGGAAATCCTGGACATCACC
CCTTGCAGCTTCGGCGGAGTGTCTGTGATCACCCCTGGCACCAACACCA
GCAATCAGGTGGCAGTGCTGTACCAGGACGTGAACTGTACCGAAGTGCC
CGTGGCCATTCACGCCGATCAGCTGACACCTACATGGCGGGTGTACTCC
ACCGGCAGCAATGTGTTTCAGACCAGAGCCGGCTGTCTGATCGGAGCCG

-continued

AGCACGTGAACAATAGCTACGAGTGCGACATCCCCATCGGCGCTGGCAT
CTGTGCCAGCTACCAGACACAGACAAACAGCCCCAGACGGGCCAGATCT
GTGGCCAGCCAGAGCATCATTGCCTACACAATGTCTCTGGGCGCCGAGA
ACAGCGTGGCCTACTCCAACAACTCTATCGCTATCCCCACCAACTTCAC
CATCAGCGTGACCACAGAGATCCTGCCTGTGTCCATGACCAAGACCAGC
GTGGACTGCACCATGTACATCTGCGGCGATTCCACCGAGTGCTCCAACC
TGCTGCTGCAGTACGGCAGCTTCTGCACCCAGCTGAATAGAGCCCTGAC
AGGGATCGCCGTGGAACAGGACAAGAACACCCAAGAGGTGTTCGCCCAA
GTGAAGCAGATCTACAAGACCCCTCCTATCAAGGACTTCGGCGGCTTCA
ATTTCAGCCAGATTCTGCCCGATCCTAGCAAGCCCAGCAAGCGGAGCTT
CATCGAGGACCTGCTGTTCAACAAAGTGACACTGGCCGACGCCGGCTTC
ATCAAGCAGTATGGCGATTGTCTGGGCGACATTGCCGCCAGGGATCTGA
TTTGCGCCCAGAAGTTTAACGGACTGACAGTGCTGCCTCCTCTGCTGAC
CGATGAGATGATCGCCCAGTACACATCTGCCCTGCTGGCCGGCACAATC
ACAAGCGGCTGGACATTTGGAGCTGGCGCCGCTCTGCAGATCCCCTTTG
CTATGCAGATGGCCTACAGATTCAACGGCATCGGAGTGACCCAGAATGT
GCTGTACGAGAACCAGAAGCTGATCGCCAACCAGTTCAACAGCGCCATC
GGCAAGATCCAGGACAGCCTGAGCAGCACAGCAAGCGCCCTGGGAAAGC
TGCAGGACGTGGTCAACCAGAATGCCCAGGCACTGAACACCCTGGTCAA
GCAGCTGTCCTCCAACTTCGGCGCCATCAGCTCTGTGCTGAACGATATC
CTGAGCAGACTGGACCCTCCTGAGGCCGAGGTGCAGATCGACAGACTGA
TCACAGGCAGACTGCAGAGCCTCCAGACATACGTGACCCAGCAGCTGAT
CAGAGCCGCCGAGATTAGAGCCTCTGCCAATCTGGCCGCCACCAAGATG
TCTGAGTGTGTGCTGGGCCAGAGCAAGAGAGTGGACTTTTGCGGCAAGG
GCTACCACCTGATGAGCTTCCCTCAGTCTGCCCCTCACGGCGTGGTGTT
TCTGCACGTGACATACGTTCCCGCTCAAGAGAAGAATTTCACCACCGCT
CCAGCCATCTGCCACGACGGCAAAGCCCACTTTCCTAGAGAAGGCGTGT
TCGTGTCCAACGGCACCCATTGGTTCGTGACACAGCGGAACTTCTACGA
GCCCCAGATCATCACCACCGACAACACCTTCGTGTCTGGCAACTGCGAC
GTCGTGATCGGCATTGTGAACAATACCGTGTACGACCCTCTGCAGCCCG
AGCTGGACAGCTTCAAAGAGGAACTGGACAAGTACTTTAAGAACCACAC
AAGCCCCGACGTGGACCTGGGCGATATCAGCGGAATCAATGCCAGCGTC
GTGAACATCCAGAAAGAGATCGACCGGCTGAACGAGGTGGCCAAGAATC
TGAACGAGAGCCTGATCGACCTGCAAGAACTGGGGAAGTACGAGCAGTA
CATCAAGTGGCCCTGGTACATCTGGCTGGGCTTTATCGCCGGACTGATT
GCCATCGTGATGGTCACAATCATGCTGTGTTGCATGACCAGCTGCTGTA
GCTGCCTGAAGGGCTGTTGTAGCTGTGGCAGC

Hence, preferably the saRNA is encoded by a DNA sequence substantially as set out in SEQ ID No: 85, or a fragment or variant thereof.

The corresponding nucleic acid (RNA) sequence of the pre-fusion stabilised SARS-CoV-2 surface glycoprotein lacking part (21 amino acid deletion from C-terminus) of the CT, is provided herein as SEQ ID No: 86, as follows:

[SEQ ID No: 86]

AUGUUCGUGUUUCUGGUGCUGCUGCCUCUGGUGUCCAGCCAGUGUGUG

AACCUGACCACCAGAACACAGCUGCCUCCAGCCUACACCAACAGCUUU

ACCAGAGGCGUGUACUACCCCGACAAGGUGUUCAGAUCCAGCGUGCUG

CACUCUACCCAGGACCUGUUCCUGCCUUUCUUCAGCAACGUGACCUGG

UUCCACGCCAUCCACGUGUCCGGCACCAAUGGCACCAAGAGAUUCGAC

AACCCCGUGCUGCCCUUCAACGACGGGGUGUACUUUGCCAGCACCGAG

AAGUCCAACAUCAUCAGAGGCUGGAUCUUCGGCACCACACUGGACAGC

AAGACCCAGAGCCUGCUGAUCGUGAACAACGCCACCAACGUGGUCAUC

AAAGUGUGCGAGUUCCAGUUCUGCAACGACCCCUUCCUGGGCGUCUAC

UACCACAAGAACAACAAGAGCUGGAUGGAAAGCGAGUUCCGGGUGUAC

AGCAGCGCCAACAACUGCACCUUCGAGUACGUGUCCCAGCCUUUCCUG

AUGGACCUGGAAGGCAAGCAGGGCAACUUCAAGAACCUGCGCGAGUUC

GUGUUCAAGAACAUCGACGGCUACUUCAAGAUCUACAGCAAGCACACC

CCUAUCAACCUCGUGCGGGAUCUGCCUCAGGGCUUCUCUGCUCUGGAA

CCCCUGGUGGAUCUGCCCAUCGGCAUCAACAUCACCCGGUUUCAGACA

CUGCUGGCCCUGCACAGAAGCUACCUGACACCUGGCGAUAGCAGCAGC

GGAUGGACAGCUGGUGCCGCCGCUUACUAUGUGGGCUACCUGCAGCCU

AGAACCUUCCUGCUGAAGUACAACGAGAACGGCACCAUCACCGACGCC

GUGGAUUGUGCCCUUGAUCCUCUGAGCGAGACAAAGUGCACCCUGAAG

UCCUUCACCGUGGAAAAGGGCAUCUACCAGACCAGCAACUUCCGGGUG

CAGCCCACCGAAUCCAUCGUGCGGUUCCCCAAUAUCACCAAUCUGUGC

CCCUUCGGCGAGGUGUUCAAUGCCACCAGAUUCGCCUCUGUGUACGCC

UGGAACCGGAAGCGGAUCAGCAAUUGCGUGGCCGACUACUCCGUGCUG

UACAACUCCGCCAGCUUCAGCACCUUCAAGUGCUACGGCGUGUCCCCU

ACCAAGCUGAACGACCUGUGCUUCACAAACGUGUACGCCGACAGCUUC

GUGAUCCGGGGAGAUGAAGUGCGGCAGAUUGCCCCUGGACAGACAGGC

AAGAUCGCCGACUACAACUACAAGCUGCCCGACGACUUCACCGGCUGU

GUGAUUGCCUGGAACAGCAACAACCUGGACUCCAAAGUCGGCGGCAAC

UACAAUUACCUGUACCGGCUGUUCCGGAAGUCCAAUCUGAAGCCCUUC

GAGCGGGACAUCUCCACCGAGAUCUAUCAGGCCGGCAGCACCCCUUGU

AACGGCGUGGAAGGCUUCAACUGCUACUUCCCACUGCAGUCCUACGGC

UUUCAGCCCACAAAUGGCGUGGGCUAUCAGCCCUACAGAGUGGUGGUG

CUGAGCUUCGAACUGCUGCAUGCCCCUGCCACAGUGUGCGGCCCUAAG

AAAAGCACCAAUCUCGUGAAGAACAAAUGCGUGAACUUCAACUUCAAC

GGCCUGACCGGCACAGGCGUGCUGACAGAGAGCAACAAGAAGUUCCUG

CCAUUCCAGCAGUUUGGCCGGGAUAUCGCCGAUACCACAGACGCCGUU

AGAGAUCCCCAGACACUGGAAAUCCUGGACAUCACCCCUUGCAGCUUC

-continued

GGCGGAGUGUCUGUGAUCACCCCUGGCACCAACACCAGCAAUCAGGUG

GCAGUGCUGUACCAGGACGUGAACUGUACCGAAGUGCCCGUGGCCAUU

CACGCCGAUCAGCUGACACCUACAUGGCGGGUGUACUCCACCGGCAGC

AAUGUGUUUCAGACCAGAGCCGGCUGUCUGAUCGGAGCCGAGCACGUG

AACAAUAGCUACGAGUGCGACAUCCCCAUCGGCGCUGGCAUCUGUGCC

AGCUACCAGACACAGACAAACAGCCCCAGACGGGCCAGAUCUGUGGCC

AGCCAGAGCAUCAUUGCCUACACAAUGUCUCUGGGCGCCGAGAACAGC

GUGGCCUACUCCAACAACUCUAUCGCUAUCCCCACCAACUUCACCAUC

AGCGUGACCACAGAGAUCCUGCCUGUGUCCAUGACCAAGACCAGCGUG

GACUGCACCAUGUACAUCUGCGGCGAUUCCACCGAGUGCUCCAACCUG

CUGCUGCAGUACGGCAGCUUCUGCACCCAGCUGAAUAGAGCCCUGACA

GGGAUCGCCGUGGAACAGGACAAGAACACCCAAGAGGUGUUCGCCCAA

GUGAAGCAGAUCUACAAGACCCCUCCUAUCAAGGACUUCGGCGGCUUC

AAUUUCAGCCAGAUUCUGCCCGAUCCUAGCAAGCCCAGCAAGCGGAGC

UUCAUCGAGGACCUGCUGUUCAACAAAGUGACACUGGCCGACGCCGGC

UUCAUCAAGCAGUAUGGCGAUUGUCUGGGCGACAUUGCCGCCAGGGAU

CUGAUUUGCGCCCAGAAGUUUAACGGACUGACAGUGCUGCCUCCUCUG

CUGACCGAUGAGAUGAUCGCCCAGUACACAUCUGCCCUGCUGGCCGGC

ACAAUCACAAGCGGCUGGACAUUUGGAGCUGGCGCCGCUCUGCAGAUC

CCCUUUGCUAUGCAGAUGGCCUACAGAUUCAACGGCAUCGGAGUGACC

CAGAAUGUGCUGUACGAGAACCAGAAGCUGAUCGCCAACCAGUUCAAC

AGCGCCAUCGGCAAGAUCCAGGACAGCCUGAGCAGCACAGCAAGCGCC

CUGGGAAAGCUGCAGGACGUGGUCAACCAGAAUGCCCAGGCACUGAAC

ACCCUGGUCAAGCAGCUGUCCUCCAACUUCGGCGCCAUCAGCUCUGUG

CUGAACGAUAUCCUGAGCAGACUGGACCCUCCUGAGGCCGAGGUGCAG

AUCGACAGACUGAUCACAGGCAGACUGCAGAGCCUCCAGACAUACGUG

ACCCAGCAGCUGAUCAGAGCCGCCGAGAUUAGAGCCUCUGCCAAUCUG

GCCGCCACCAAGAUGUCUGAGUGUGUGCUGGGCCAGAGCAAGAGAGUG

GACUUUUGCGGCAAGGGCUACCACCUGAUGAGCUUCCCUCAGUCUGCC

CCUCACGGCGUGGUGUUUCUGCACGUGACAUACGUUCCCGCUCAAGAG

AAGAAUUUCACCACCGCUCCAGCCAUCUGCCACGACGGCAAAGCCCAC

UUUCCUAGAGAAGGCGUGUUCGUGUCCAACGGCACCCAUUGGUUCGUG

ACACAGCGGAACUUCUACGAGCCCCAGAUCAUCACCACCGACAACACC

UUCGUGUCUGGCAACUGCGACGUCGUGAUCGGCAUUGUGAACAAUACC

GUGUACGACCCUCUGCAGCCCGAGCUGGACAGCUUCAAAGAGGAACUG

GACAAGUACUUUAAGAACCACACAAGCCCCGACGUGGACCUGGGCGAU

AUCAGCGGAAUCAAUGCCAGCGUCGUGAACAUCCAGAAAGAGAUCGAC

CGGCUGAACGAGGUGGCCAAGAAUCUGAACGAGAGCCUGAUCGACCUG

-continued

CAAGAACUGGGGAAGUACGAGCAGUACAUCAAGUGGCCCUGGUACAUC

UGGCUGGGCUUUAUCGCCGGACUGAUUGCCAUCGUGAUGGUCACAAUC

AUGCUGUGUUGCAUGACCAGCUGCUGUAGCUGCCUGAAGGGCUGUUGU

AGCUGUGGCAGC

Hence, preferably the saRNA comprises a sequence substantially as set out in SEQ ID No: 86, or a fragment or variant thereof.

In addition to the above modifications in which the glycoprotein lacks the transmembrane domain and/or the cytoplasmic domain, the inventors have also formed a soluble glycoprotein which comprises a trimerization motif which promotes the formation of trimers of the glycoprotein. Thus, preferably the saRNA comprises a nucleotide sequence which encodes a glycoprotein which comprises a trimerization motif.

For example, in one embodiment, the trimerisation motif may Foldon motif and an optional linker for enhancing trimerization. Hence, the nucleic acid (DNA) sequence encoding the trimerization motif (Bold bases correspond to the optional linker region; italicized bases correspond to Foldon motif) is provided herein as SEQ ID No: 41, as follows:

[SEQ ID No: 41]

GGAGGCGGAGGATCTGGCGGAGGCGGAAGT*GGATCTGGCTATATCCCTGAGGCTCCCAGAGATGGCCAGG*

*CCTATGTTCGGAAGGATGGCGAATGGGTGCTGCTGAGCACATTCCTCGGT*

Hence, preferably the saRNA is encoded by a DNA sequence substantially as set out in SEQ ID No: 41, or a fragment or variant thereof. Preferably, the trimerization motif is disposed 3' of the sequence represented by SEQ ID No: 39.

The corresponding nucleic acid (RNA) sequence encoding the trimerization motif (Bold bases correspond to the optional linker region; italicized bases correspond to Foldon motif) is provided herein as SEQ ID No: 42, as follows:

[SEQ ID No: 42]

GGAGGCGGAGGAUCUGGCGGAGGCGGAAGU*GGAUCUGGCUAUAUCCCUG*

*AGGCUCCCAGAGAUGGCCAGGCCUAUGUUCGGAAGGAUGGCGAAUGGGU*

*GCUGCUGAGCACAUUCCUCGGU*

Hence, preferably the saRNA comprises a sequence substantially as set out in SEQ ID No: 42, or a fragment or variant thereof. Preferably, the trimerization motif is disposed 3' of the sequence represented by SEQ ID No: 40.

Furthermore, the amino acid sequence for the linker (amino acids shown in bold) and the so Foldon motif is provided herein as SEQ ID No:43, as follows:

[SEQ ID No: 43]

GGGGSGGGGSGSGYIPEAPRDGQAYVRKDEWVLLSTFLG

Preferably, the saRNA construct comprises a nucleic acid sequence encoding a trimerization sequence having an amino acid sequence substantially as set out in SEQ ID No: 43, or a fragment or variant thereof. It should appreciated that the linker sequence shown in bold may be omitted entirely, or be substituted with alternative sequences of different length and/or sequence.

However, in another embodiment, the trimerization motif may instead comprise a GCN4 motif and an optional linker for enhancing trimerization. Therefore, the nucleic acid (DNA) sequence encoding the trimerization motif (Bold bases correspond to the optional linker region; italicized bases correspond to GCN4 motif) is provided herein as SEQ ID No: 44, as follows:

[SEQ ID No: 44]

GGCTCTGGCTCTGGCAATGGAACC*GGCAGAATGAAGCAGATCGAGGACA*

*AGATCGAGAACATCACCAGCAAGATCTACAATATCACCAACGAGATCGC*

*CCGGATCAAGAAGCTGATCGGCAACAGAACA*

Hence, preferably the saRNA is encoded by a DNA sequence substantially as set out in SEQ ID No: 44, or a fragment or variant thereof. Preferably, the trimerization motif is disposed 3' of the sequence represented by SEQ ID No: 39.

The corresponding RNA sequence encoding the trimerization motif is provided herein as SEQ ID No: 45, as follows:

[SEQ ID No: 45]

GGCUCUGGCUCUGGCAAUGGAACC*GGCAGAAUGAAGCAGAUCGAGGACA*

*AGAUCGAGAACAUCACCAGCAAGAUCUACAAUAUCACCAACGAGAUCGC*

*CCGGAUCAAGAAGCUGAUCGGCAACAGAACA*

Hence, preferably the saRNA comprises a sequence substantially as set out in SEQ ID No: 45, or a fragment or variant thereof. Preferably, the trimerization motif is disposed 3' of the sequence represented by SEQ ID No: 40.

Furthermore, the amino acid sequence for the optional linker (amino acids shown in bold) and the GCN4 motif is provided herein as SEQ ID No:46, as follows:

[SEQ ID No: 46]

GSGSGNGTGRMKQIEDKIENITSKIYNITNEIARIKKLIGNRT

Preferably, the saRNA construct comprises a nucleic acid sequence encoding a trimerization sequence having an amino acid sequence substantially as set out in SEQ ID No: 46, or a fragment or variant thereof. It should appreciated that the linker sequence shown in bold may be omitted entirely, or be substituted with alternative sequences of different length and/or sequence.

In some embodiments, the RNA construct comprises a sequence, which encodes an innate inhibitor protein (IIP), which is capable of reducing or blocking the innate immune response to the saRNA according to the invention. Preferably, this is achieved by reducing or blocking recognition of the saRNA.

The innate inhibitor protein may be capable of either: (i) reducing or blocking the action of Melanoma Differentiation-Associated protein 5 (MDA5), for example by preventing oligomerization of MDA5 and binding of MDA5 to RNA, and/or (ii) blocking or reducing the binding of PACT to RNA, which may also be referred to as PKR activating protein, to RNA. In some embodiments, both types of IIP are present in the saRNA construct.

Preferably, the at least one innate inhibitor protein blocking the action of MDA5 is a paramyxovirus V protein. Most preferably, the at least one innate inhibitor protein blocking the action of MDA5 is Parainfluenza virus type 5 V protein (PIV5 V).

In one embodiment, the PIV5 V polypeptide is provided herein as SEQ ID No: 7, as follows:

```
                                            [SEQ ID No: 7]
MDPTDLSFSPDEINKLIETGLNTVEYFTSQQVTGTSSLGKNTIPPGVTGL
LTNAAEAKIQESTNHQKGSVGGGAKPKKPRPKIAIVPADDKTVPGKPIPN
PLLGLDSTPSTQTVLDLSGKTLPSGSYKGVKLAKFGKENLMTRFIEEPRE
NPIATSSPIDFKRGRDTGGFHRREYSIGWVGDEVKVTEWCNPSCSPITAA
ARRFECTCHQCPVTCSECERDT
```

Accordingly, preferably the PIV5 V polypeptide comprises an amino acid sequence substantially as set out in SEQ ID NO: 7, or a biologically active variant or fragment thereof. Hence, the RNA construct of the first aspect preferably comprises a RNA nucleotide sequence which encodes SEQ ID No: 7, or a biologically active variant or fragment thereof.

In one embodiment, the PIV5 V polypeptide is encoded by the nucleotide sequence of SEQ ID No: 8, as follows:

```
                                            [SEQ ID No: 8]
ATGGACCCTACCGACCTGAGCTTCAGCCCCGACGAGATCAACAAGCTGAT
CGAGACAGGCCTGAACACCGTGGAATACTTCACCAGCCAGCAAGTGACCG
GCACAAGCAGCCTGGGCAAGAACACAATTCCTCCAGGCGTGACCGGCCTG
CTGACAAATGCTGCCGAGGCCAAGATCCAAGAGAGCACCAACCACCAGAA
GGGCTCTGTTGGAGGCGGAGCCAAGCCTAAGAAGCCCAGACCTAAGATCG
CCATCGTGCCCGCCGACGATAAGACAGTGCCTGGCAAGCCCATTCCTAAT
CCTCTGCTGGGCCTCGACAGCACCCCTAGCACACAGACAGTGCTGGATCT
GAGCGGCAAGACACTGCCTAGCGGCAGCTATAAGGGCGTGAAGCTGGCCA
AGTTCGGCAAAGAAAACCTGATGACCCGGTTCATCGAGGAACCCAGAGAG
AACCCTATCGCCACCAGCTCTCCCATCGACTTCAAGAGAGGCAGAGACAC
CGGCGGCTTCCACAGAAGAGAGTACAGCATTGGCTGGGTCGGAGATGAAG
TGAAAGTGACCGAGTGGTGCAACCCCAGCTGCAGCCCTATTACAGCCGCC
GCTAGAAGATTCGAGTGCACCTGTCACCAGTGTCCTGTGACCTGTAGCGA
GTGCGAGCGGGACACA
```

Accordingly, preferably the PIV5 V polypeptide is encoded by the nucleotide sequence substantially as set out in SEQ ID NO: 8, or a variant or fragment thereof.

Thus, the RNA construct may comprise an RNA nucleotide sequence of SEQ ID No: 9, as follows:

```
                                            [SEQ ID No: 9]
AUGGACCCUACCGACCUGAGCUUCAGCCCCGACGAGAUCAACAAGCUGAU
CGAGACAGGCCUGAACACCGUGGAAUACUUCACCAGCCAGCAAGUGACCG
```

-continued

```
GCACAAGCAGCCUGGGCAAGAACACAAUUCCUCCAGGCGUGACCGGCCUG
CUGACAAAUGCUGCCGAGGCCAAGAUCCAAGAGAGCACCAACCACCAGAA
GGGCUCUGUUGGAGGCGGAGCCAAGCCUAAGAAGCCCAGACCUAAGAUCG
CCAUCGUGCCCGCCGACGAUAAGACAGUGCCUGGCAAGCCCAUUCCUAAU
CCUCUGCUGGGCCUCGACAGCACCCCUAGCACACAGACAGUGCUGGAUCU
GAGCGGCAAGACACUGCCUAGCGGCAGCUAUAAGGGCGUGAAGCUGGCCA
AGUUCGGCAAAGAAAACCUGAUGACCCGGUUCAUCGAGGAACCCAGAGAG
AACCCUAUCGCCACCAGCUCUCCCAUCGACUUCAAGAGAGGCAGAGACAC
CGGCGGCUUCCACAGAAGAGAGUACAGCAUUGGCUGGGUCGGAGAUGAAG
UGAAAGUGACCGAGUGGUGCAACCCCAGCUGCAGCCCUAUUACAGCCGCC
GCUAGAAGAUUCGAGUGCACCUGUCACCAGUGUCCUGUGACCUGUAGCGA
GUGCGAGCGGGACACA
```

Accordingly, therefore, preferably the RNA construct comprises an RNA nucleotide sequence substantially as set out as SEQ ID No: 9, or a variant or fragment thereof.

Preferably, however, the innate inhibitor protein blocks or reduces the binding of PACT to RNA, and may be selected from the group consisting of: ORF4a (NS4a) of any coronaviruses, or the nucleocapsid proteins of mouse hepatitis virus and SARS (coronavirus); and orthologues thereof.

In one embodiment, the RNA construct comprises a sequence, which encodes an innate inhibitor protein (IIP), which is a coronavirus ORF4a (NS4a).

Preferably, the ORF4a (NS4a) is Middle East Respiratory Syndrome (MERS) coronavirus (ORF4a). The MERS-CoV ORF4a polypeptide is provided herein as SEQ ID No: 10, as follows:

```
                                           [SEQ ID No: 10]
MDYVSLLNQIWQKYLNSPYTTCLYIPKPTAKYTPLVGTSLHPVLWNCQLS
FAGYTESAVNSTKALAKQDAAQRIAWLLHKDGGIPDGCSLYLRHSSLFAQ
SEEEESFSN
```

Accordingly, preferably the MERS-CoV ORF4a polypeptide comprises an amino acid sequence substantially as set out in SEQ ID NO: 10, or a biologically active variant or fragment thereof. Hence, the RNA construct of the first aspect preferably comprises an RNA nucleotide sequence which encodes SEQ ID No: 10, or a variant or fragment thereof.

In one embodiment, the MERS-CoV ORF4a polypeptide is encoded by the nucleotide sequence of SEQ ID No: 11, as follows:

```
                                           [SEQ ID No: 11]
ATGGACTACGTGTCCCTGCTGAACCAGATTTGGCAGAAGTACCTGAACAG
CCCCTACACCACCTGTCTGTACATCCCCAAGCCTACCGCCAAGTACACAC
CTCTCGTGGGCACATCTCTGCACCCCGTGCTGTGGAATTGCCAGCTGAGC
TTTGCCGGCTACACCGAGTCTGCCGTGAACAGCACAAAGGCCCTGGCCAA
ACAGGACGCCGCTCAGAGAATTGCCTGGCTGCTGCACAAGGATGGCGGCA
```

-continued

TCCCTGATGGCTGTAGCCTGTACCTGAGACACAGCAGCCTGTTCGCCCAG

AGCGAGGAAGAGGAATCCTTCAGCAAC

Accordingly, preferably the MERS-CoV ORF4a polypeptide is encoded by the nucleotide sequence substantially as set out in SEQ ID NO: 11, or a variant or fragment thereof.

Thus, the RNA construct may comprise an RNA nucleotide sequence of SEQ ID No: 12, as follows:

[SEQ ID No: 12]

AUGGACUACGUGUCCCUGCUGAACCAGAUUUGGCAGAAGUACCUGAACAG

CCCCUACACCACCUGUCUGUACAUCCCCAAGCCUACCGCCAAGUACACAC

CUCUCGUGGGCACAUCUCUGCACCCCGUGCUGUGGAAUUGCCAGCUGAGC

UUUGCCGGCUACACCGAGUCUGCCGUGAACAGCACAAAGGCCCUGGCCAA

ACAGGACGCCGCUCAGAGAAUUGCCUGGCUGCUGCACAAGGAUGGCGGCA

UCCCUGAUGGCUGUAGCCUGUACCUGAGACACAGCAGCCUGUUCGCCCAG

AGCGAGGAAGAGGAAUCCUUCAGCAAC

Accordingly, therefore, preferably the RNA construct comprises an RNA nucleotide sequence substantially as set out as SEQ ID No: 12, or a variant or fragment thereof.

In one embodiment, the RNA construct may encode SARS-CoV-2 surface glycoprotein and ORF4a, which has an amino acid sequence is provided herein as SEQ ID No: 59, as follows:

[SEQ ID No: 59]

MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPRRARSVASQSIIAYTMSLG

AENSVAYSNNSIAIPTNFTISVTTEILPVSMTKTSVDCTMYICGDSTECS

NLLLQYGSFCTQLNRALTGIAVEQDKNTQEVFAQVKQIYKTPPIKDFGGF

NFSQILPDPSKPSKRSFIEDLLFNKVTLADAGFIKQYGDCLGDIAARDLI

CAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQD

VVNQNAQALNTLVKQLSSNFGAISSVLNDILSRLDPPEAEVQIDRLITGR

LQSLQTYVTQQLIRAAEIRASANLAATKMSECVLGQSKRVDFCGKGYHLM

-continued

SFPQSAPHGVVFLHVTYVPAQEKNFTTAPAICHDGKAHFPREGVFVSNGT

HWFVTQRNFYEPQIITTDNTFVSGNCDVVIGIVNNTVYDPLQPELDSFKE

ELDKYFKNHTSPDVDLGDISGINASVVNIQKEIDRLNEVAKNLNESLIDL

QELGKYEQYIKWPWYIWLGFIAGLIAIVMVTIMLCCMTSCCSCLKGCCSC

GSCCKFDEDDSEPVLKGVKLHYTDRRKRGSGEGRGSLLTCGDVEENPGPM

DYVSLLNQIWQKYLNSPYTTCLYIPKPTAKYTPLVGTSLHPVLWNCQLSF

AGYTESAVNSTKALAKQDAAQRIAWLLHKDGGIPDGCSLYLRHSSLFAQS

EEEESFSN*

Accordingly, preferably the saRNA comprises a nucleic acid sequence encoding SARS-CoV-2 surface glycoprotein and ORF4a having an amino acid sequence substantially as set out in SEQ ID No: 59, or a fragment or variant thereof.

In an embodiment, the SARS-CoV-2 surface glycoprotein and ORF4a polypeptide sequence may be encoded by the nucleotide sequence provided herein as SEQ ID No: 60, as follows:

[SEQ ID No: 60]

ATGTTCGTGTTTCTGGTGCTGCTGCCTCTGGTGTCCAGCCAGTGTGTGAA

CCTGACCACCAGAACACAGCTGCCTCCAGCCTACACCAACAGCTTTACCA

GAGGCGTGTACTACCCCGACAAGGTGTTCAGATCCAGCGTGCTGCACTCT

ACCCAGGACCTGTTCCTGCCTTTCTTCAGCAACGTGACCTGGTTCCACGC

CATCCACGTGTCCGGCACCAATGGCACCAAGAGATTCGACAACCCCGTGC

TGCCCTTCAACGACGGGGTGTACTTTGCCAGCACCGAGAAGTCCAACATC

ATCAGAGGCTGGATCTTCGGCACCACACTGGACAGCAAGACCCAGAGCCT

GCTGATCGTGAACAACGCCACCAACGTGGTCATCAAAGTGTGCGAGTTCC

AGTTCTGCAACGACCCCTTCCTGGGCGTCTACTACCACAAGAACAACAAG

AGCTGGATGGAAAGCGAGTTCCGGGTGTACAGCAGCGCCAACAACTGCAC

CTTCGAGTACGTGTCCCAGCCTTTCCTGATGGACCTGGAAGGCAAGCAGG

GCAACTTCAAGAACCTGCGCGAGTTCGTGTTCAAGAACATCGACGGCTAC

TTCAAGATCTACAGCAAGCACACCCCTATCAACCTCGTGCGGGATCTGCC

TCAGGGCTTCTCTGCTCTGGAACCCCTGGTGGATCTGCCCATCGGCATCA

ACATCACCCGGTTTCAGACACTGCTGGCCCTGCACAGAAGCTACCTGACA

CCTGGCGATAGCAGCAGCGGATGGACAGCTGGTGCCGCCGCTTACTATGT

GGGCTACCTGCAGCCTAGAACCTTCCTGCTGAAGTACAACGAGAACGGCA

CCATCACCGACGCCGTGGATTGTGCCCTTGATCCTCTGAGCGAGACAAAG

TGCACCCTGAAGTCCTTCACCGTGGAAAAGGGCATCTACCAGACCAGCAA

CTTCCGGGTGCAGCCCACCGAATCCATCGTGCGGTTCCCCAATATCACCA

ATCTGTGCCCCTTCGGCGAGGTGTTCAATGCCACCAGATTCGCCTCTGTG

TACGCCTGGAACCGGAAGCGGATCAGCAATTGCGTGGCCGACTACTCCGT

GCTGTACAACTCCGCCAGCTTCAGCACCTTCAAGTGCTACGGCGTGTCCC

CTACCAAGCTGAACGACCTGTGCTTCACAAACGTGTACGCCGACAGCTTC

GTGATCCGGGGAGATGAAGTGCGGCAGATTGCCCCTGGACAGACAGGCAA

GATCGCCGACTACAACTACAAGCTGCCCGACGACTTCACCGGCTGTGTGA

-continued

TTGCCTGGAACAGCAACAACCTGGACTCCAAAGTCGGCGGCAACTACAAT

TACCTGTACCGGCTGTTCCGGAAGTCCAATCTGAAGCCCTTCGAGCGGGA

CATCTCCACCGAGATCTATCAGGCCGGCAGCACCCCTTGTAACGGCGTGG

AAGGCTTCAACTGCTACTTCCCACTGCAGTCCTACGGCTTTCAGCCCACA

AATGGCGTGGGCTATCAGCCCTACAGAGTGGTGGTGCTGAGCTTCGAACT

GCTGCATGCCCCTGCCACAGTGTGCGGCCCTAAGAAAAGCACCAATCTCG

TGAAGAACAAATGCGTGAACTTCAACTTCAACGGCCTGACCGGCACAGGC

GTGCTGACAGAGAGCAACAAGAAGTTCCTGCCATTCCAGCAGTTTGGCCG

GGATATCGCCGATACCACAGACGCCGTTAGAGATCCCCAGACACTGGAAA

TCCTGGACATCACCCCTTGCAGCTTCGGCGGAGTGTCTGTGATCACCCCT

GGCACCAACACCAGCAATCAGGTGGCAGTGCTGTACCAGGACGTGAACTG

TACCGAAGTGCCCGTGGCCATTCACGCCGATCAGCTGACACCTACATGGC

GGGTGTACTCCACCGGCAGCAATGTGTTTCAGACCAGAGCCGGCTGTCTG

ATCGGAGCCGAGCACGTGAACAATAGCTACGAGTGCGACATCCCCATCGG

CGCTGGCATCTGTGCCAGCTACCAGACACAGACAAACAGCCCCAGACGGG

CCAGATCTGTGGCCAGCCAGAGCATCATTGCCTACACAATGTCTCTGGGC

GCCGAGAACAGCGTGGCCTACTCCAACAACTCTATCGCTATCCCCACCAA

CTTCACCATCAGCGTGACCACAGAGATCCTGCCTGTGTCCATGACCAAGA

CCAGCGTGGACTGCACCATGTACATCTGCGGCGATTCCACCGAGTGCTCC

AACCTGCTGCTGCAGTACGGCAGCTTCTGCACCCAGCTGAATAGAGCCCT

GACAGGGATCGCCGTGGAACAGGACAAGAACACCCAAGAGGTGTTCGCCC

AAGTGAAGCAGATCTACAAGACCCCTCCTATCAAGGACTTCGGCGGCTTC

AATTTCAGCCAGATTCTGCCCGATCCTAGCAAGCCCAGCAAGCGGAGCTT

CATCGAGGACCTGCTGTTCAACAAAGTGACACTGGCCGACGCCGGCTTCA

TCAAGCAGTATGGCGATTGTCTGGGCGACATTGCCGCCAGGGATCTGATT

TGCGCCCAGAAGTTTAACGGACTGACAGTGCTGCCTCCTCTGCTGACCGA

TGAGATGATCGCCCAGTACACATCTGCCCTGCTGGCCGGCACAATCACAA

GCGGCTGGACATTTGGAGCTGGCGCCGCTCTGCAGATCCCCTTTGCTATG

CAGATGGCCTACAGATTCAACGGCATCGGAGTGACCCAGAATGTGCTGTA

CGAGAACCAGAAGCTGATCGCCAACCAGTTCAACAGCGCCATCGGCAAGA

TCCAGGACAGCCTGAGCAGCACAGCAAGCGCCCTGGGAAAGCTGCAGGAC

GTGGTCAACCAGAATGCCCAGGCACTGAACACCCTGGTCAAGCAGCTGTC

CTCCAACTTCGGCGCCATCAGCTCTGTGCTGAACGATATCCTGAGCAGAC

TGGACCCTCCTGAGGCCGAGGTGCAGATCGACAGACTGATCACAGGCAGA

CTGCAGAGCCTCCAGACATACGTGACCCAGCAGCTGATCAGAGCCGCCGA

GATTAGAGCCTCTGCCAATCTGGCCGCCACCAAGATGTCTGAGTGTGTGC

TGGGCCAGAGCAAGAGAGTGGACTTTTGCGGCAAGGGCTACCACCTGATG

AGCTTCCCTCAGTCTGCCCCTCACGGCGTGGTGTTTCTGCACGTGACATA

CGTTCCCGCTCAAGAGAAGAATTTCACCACCGCTCCAGCCATCTGCCACG

ACGGCAAAGCCCACTTTCCTAGAGAAGGCGTGTTCGTGTCCAACGGCACC

-continued

CATTGGTTCGTGACACAGCGGAACTTCTACGAGCCCCAGATCATCACCAC

CGACAACACCTTCGTGTCTGGCAACTGCGACGTCGTGATCGGCATTGTGA

ACAATACCGTGTACGACCCTCTGCAGCCCGAGCTGGACAGCTTCAAAGAG

GAACTGGACAAGTACTTTAAGAACCACACAAGCCCCGACGTGGACCTGGG

CGATATCAGCGGAATCAATGCCAGCGTCGTGAACATCCAGAAAGAGATCG

ACCGGCTGAACGAGGTGGCCAAGAATCTGAACGAGAGCCTGATCGACCTG

CAAGAACTGGGGAAGTACGAGCAGTACATCAAGTGGCCCTGGTACATCTG

GCTGGGCTTTATCGCCGGACTGATTGCCATCGTGATGGTCACAATCATGC

TGTGTTGCATGACCAGCTGCTGTAGCTGCCTGAAGGGCTGTTGTAGCTGT

GGCAGCTGCTGCAAGTTCGACGAGGACGATTCTGAGCCCGTGCTGAAGGG

CGTGAAACTGCACTACACAGATCGGAGAAAGAGAGGCTCTGGCGAAGGCA

GAGGCAGCCTGCTTACATGTGGCGACGTGGAAGAGAACCCCGGACCTATG

GATTATGTGTCCCTGCTGAACCAGATTTGGCAGAAGTACCTGAACAGCCC

CTACACCACCTGTCTGTACATCCCCAAGCCTACCGCCAAGTACACACCTC

TCGTGGGCACATCTCTGCACCCCGTGCTGTGGAATTGCCAGCTGAGCTTT

GCCGGCTACACCGAGTCTGCCGTGAACAGCACAAAGGCCCTGGCCAAACA

GGACGCCGCTCAGAGAATTGCCTGGCTGCTGCACAAGGATGGCGGCATCC

CTGATGGCTGTAGCCTGTACCTGAGACACAGCAGCCTGTTCGCCCAGAGC

GAGGAAGAGGAATCCTTCAGCAACTGA

Accordingly, preferably the SARS-CoV-2 surface glycoprotein and ORF4a polypeptide sequence is encoded by the nucleotide sequence substantially as set out in SEQ ID NO: 60, or a variant or fragment thereof.

In an embodiment, the RNA sequence of the SARS-CoV-2 surface glycoprotein and ORF4a polypeptide may be provided herein as SEQ ID No: 61, as follows:

[SEQ ID No: 61]

AUGUUCGUGUUUCUGGUGCUGCUGCCUCUGGUGUCCAGCCAGUGUGUGAA

CCUGACCACCAGAACACAGCUGCCUCCAGCCUACACCAACAGCUUUACCA

GAGGCGUGUACUACCCCGACAAGGUGUUCAGAUCCAGCGUGCUGCACUCU

ACCCAGGACCUGUUCCUGCCUUUCUUCAGCAACGUGACCUGGUUCCACGC

CAUCCACGUGUCCGGCACCAAUGGCACCAAGAGAUUCGACAACCCCGUGC

UGCCCUUCAACGACGGGGUGUACUUUGCCAGCACCGAGAAGUCCAACAUC

AUCAGAGGCUGGAUCUUCGGCACCACACUGGACAGCAAGACCCAGAGCCU

GCUGAUCGUGAACAACGCCACCAACGUGGUCAUCAAAGUGUGCGAGUUCC

AGUUCUGCAACGACCCCUUCCUGGGCGUCUACUACCACAAGAACAACAAG

AGCUGGAUGGAAAGCGAGUUCCGGGUGUACAGCAGCGCCAACAACUGCAC

CUUCGAGUACGUGUCCCAGCCUUUCCUGAUGGACCUGGAAGGCAAGCAGG

GCAACUUCAAGAACCUGCGCGAGUUCGUGUUCAAGAACAUCGACGGCUAC

UUCAAGAUCUACAGCAAGCACACCCCUAUCAACCUCGUGCGGGAUCUGCC

UCAGGGCUUCUCUGCUCUGGAACCCCUGGUGGAUCUGCCCAUCGGCAUCA

ACAUCACCCGGUUUCAGACACUGCUGGCCCUGCACAGAAGCUACCUGACA

CCUGGCGAUAGCAGCAGCGGAUGGACAGCUGGUGCCGCCGCUUACUAUGU

-continued

GGGCUACCUGCAGCCUAGAACCUUCCUGCUGAAGUACAACGAGAACGGCA
CCAUCACCGACGCCGUGGAUUGUGCCCUUGAUCCUCUGAGCGAGACAAAG
UGCACCCUGAAGUCCUUCACCGUGGAAAAGGGCAUCUACCAGACCAGCAA
CUUCCGGGUGCAGCCCACCGAAUCCAUCGUGCGGUUCCCCAAUAUCACCA
AUCUGUGCCCCUUCGGCGAGGUGUUCAAUGCCACCAGAUUCGCCUCUGUG
UACGCCUGGAACCGGAAGCGGAUCAGCAAUUGCGUGGCCGACUACUCCGU
GCUGUACAACUCCGCCAGCUUCAGCACCUUCAAGUGCUACGGCGUGUCCC
CUACCAAGCUGAACGACCUGUGCUUCACAAACGUGUACGCCGACAGCUUC
GUGAUCCGGGGAGAUGAAGUGCGGCAGAUUGCCCCUGGACAGACAGGCAA
GAUCGCCGACUACAACUACAAGCUGCCCGACGACUUCACCGGCUGUGUGA
UUGCCUGGAACAGCAACAACCUGGACUCCAAAGUCGGCGGCAACUACAAU
UACCUGUACCGGCUGUUCCGGAAGUCCAAUCUGAAGCCCUUCGAGCGGGA
CAUCUCCACCGAGAUCUAUCAGGCCGGCAGCACCCCUUGUAACGGCGUGG
AAGGCUUCAACUGCUACUUCCCACUGCAGUCCUACGGCUUUCAGCCCACA
AAUGGCGUGGGCUAUCAGCCCUACAGAGUGGUGGUGCUGAGCUUCGAACU
GCUGCAUGCCCCUGCCACAGUGUGCGGCCCUAAGAAAAGCACCAAUCUCG
UGAAGAACAAAUGCGUGAACUUCAACUUCAACGGCCUGACCGGCACAGGC
GUGCUGACAGAGAGCAACAAGAAGUUCCUGCCAUUCCAGCAGUUUGGCCG
GGAUAUCGCCGAUACCACAGACGCCGUUAGAGAUCCCCAGACACUGGAAA
UCCUGGACAUCACCCCUUGCAGCUUCGGCGGAGUGUCUGUGAUCACCCCU
GGCACCAACACCAGCAAUCAGGUGGCAGUGCUGUACCAGGACGUGAACUG
UACCGAAGUGCCCGUGGCCAUUCACGCCGAUCAGCUGACACCUACAUGGC
GGGUGUACUCCACCGGCAGCAAUGUGUUUCAGACCAGAGCCGGCUGUCUG
AUCGGAGCCGAGCACGUGAACAAUAGCUACGAGUGCGACAUCCCCAUCGG
CGCUGGCAUCUGUGCCAGCUACCAGACACAGACAAACAGCCCCAGACGGG
CCAGAUCUGUGGCCAGCCAGAGCAUCAUUGCCUACACAAUGUCUCUGGGC
GCCGAGAACAGCGUGGCCUACUCCAACAACUCUAUCGCUAUCCCCACCAA
CUUCACCAUCAGCGUGACCACAGAGAUCCUGCCUGUGUCCAUGACCAAGA
CCAGCGUGGACUGCACCAUGUACAUCUGCGGCGAUUCCACCGAGUGCUCC
AACCUGCUGCUGCAGUACGGCAGCUUCUGCACCCAGCUGAAUAGAGCCCU
GACAGGGAUCGCCGUGGAACAGGACAAGAACACCCAAGAGGUGUUCGCCC
AAGUGAAGCAGAUCUACAAGACCCCUCCUAUCAAGGACUUCGGCGGCUUC
AAUUUCAGCCAGAUUCUGCCCGAUCCUAGCAAGCCCAGCAAGCGGAGCUU
CAUCGAGGACCUGCUGUUCAACAAAGUGACACUGGCCGACGCCGGCUUCA
UCAAGCAGUAUGGCGAUUGUCUGGGCGACAUUGCCGCCAGGGAUCUGAUU
UGCGCCCAGAAGUUUAACGGACUGACAGUGCUGCCUCCUCUGCUGACCGA
UGAGAUGAUCGCCCAGUACACAUCUGCCCUGCUGGCCGGCACAAUCACAA
GCGGCUGGACAUUUGGAGCUGGCGCCGCUCUGCAGAUCCCCUUUGCUAUG
CAGAUGGCCUACAGAUUCAACGGCAUCGGAGUGACCCAGAAUGUGCUGUA
CGAGAACCAGAAGCUGAUCGCCAACCAGUUCAACAGCGCCAUCGGCAAGA
UCCAGGACAGCCUGAGCAGCACAGCAAGCGCCCUGGGAAAGCUGCAGGAC

-continued

GUGGUCAACCAGAAUGCCCAGGCACUGAACACCCUGGUCAAGCAGCUGUC
CUCCAACUUCGGCGCCAUCAGCUCUGUGCUGAACGAUAUCCUGAGCAGAC
UGGACCCUCCUGAGGCCGAGGUGCAGAUCGACAGACUGAUCACAGGCAGA
CUGCAGAGCCUCCAGACAUACGUGACCCAGCAGCUGAUCAGAGCCGCCGA
GAUUAGAGCCUCUGCCAAUCUGGCCGCCACCAAGAUGUCUGAGUGUGUGC
UGGGCCAGAGCAAGAGAGUGGACUUUUGCGGCAAGGGCUACCACCUGAUG
AGCUUCCCUCAGUCUGCCCCUCACGGCGUGGUGUUUCUGCACGUGACAUA
CGUUCCCGCUCAAGAGAAGAAUUUCACCACCGCUCCAGCCAUCUGCCACG
ACGGCAAAGCCCACUUUCCUAGAGAAGGCGUGUUCGUGUCCAACGGCACC
CAUUGGUUCGUGACACAGCGGAACUUCUACGAGCCCCAGAUCAUCACCAC
CGACAACACCUUCGUGUCUGGCAACUGCGACGUCGUGAUCGGCAUUGUGA
ACAAUACCGUGUACGACCCUCUGCAGCCCGAGCUGGACAGCUUCAAAGAG
GAACUGGACAAGUACUUUAAGAACCACACAAGCCCCGACGUGGACCUGGG
CGAUAUCAGCGGAAUCAAUGCCAGCGUCGUGAACAUCCAGAAAGAGAUCG
ACCGGCUGAACGAGGUGGCCAAGAAUCUGAACGAGAGCCUGAUCGACCUG
CAAGAACUGGGGAAGUACGAGCAGUACAUCAAGUGGCCCUGGUACAUCUG
GCUGGGCUUUAUCGCCGGACUGAUUGCCAUCGUGAUGGUCACAAUCAUGC
UGUGUUGCAUGACCAGCUGCUGUAGCUGCCUGAAGGGCUGUUGUAGCUGU
GGCAGCUGCUGCAAGUUCGACGAGGACGAUUCUGAGCCCGUGCUGAAGGG
CGUGAAACUGCACUACACAGAUCGGAGAAAGAGAGGCUCUGGCGAAGGCA
GAGGCAGCCUGCUUACAUGUGGCGACGUGGAAGAGAACCCCGGACCUAUG
GAUUAUGUGUCCCUGCUGAACCAGAUUUGGCAGAAGUACCUGAACAGCCC
CUACACCACCUGUCUGUACAUCCCCAAGCCUACCGCCAAGUACACACCUC
UCGUGGGCACAUCUCUGCACCCCGUGCUGUGGAAUUGCCAGCUGAGCUUU
GCCGGCUACACCGAGUCUGCCGUGAACAGCACAAAGGCCCUGGCCAAACA
GGACGCCGCUCAGAGAAUUGCCUGGCUGCUGCACAAGGAUGGCGGCAUCC
CUGAUGGCUGUAGCCUGUACCUGAGACACAGCAGCCUGUUCGCCCAGAGC
GAGGAAGAGGAAUCCUUCAGCAACUGA

Accordingly, preferably the RNA construct comprises an RNA nucleotide sequence substantially as set out as SEQ ID No: 61, or a variant or fragment thereof.

The sequence encoding the at least one innate inhibitor protein may be disposed anywhere within the saRNA construct or replicon sequence, such that the sequence encoding the coronavirus glycoprotein may be disposed 5' or 3' to the sequence encoding the innate inhibitor protein. The sequence encoding the innate inhibitor protein may be disposed 3' of the sequence encoding the coronavirus glycoprotein. However, preferably the sequence encoding the innate inhibitor protein is disposed 5' of the sequence encoding the coronavirus glycoprotein.

Preferably, the RNA construct according to the first aspect comprises at least one promotor, either genomic or sub-genomic. Preferably, the promoter is a sub-genomic promoter. The skilled person would understand that the sub-genomic promotor relates to a promoter that is operably linked to the sequence encoding the coronavirus surface glycoprotein, such that it enables the transcription of the nucleotide sequence encoding glycoprotein.

Preferably, the sub genomic promoter is 26S, which is provided herein as SEQ ID No: 13, as follows:

[SEQ ID No: 13]
GGGCCCCTATAACTCTCTACGGCTAACCTGAATGGACTACGACAT

Accordingly, preferably the promoter (preferably, a sub genomic promoter) is as substantially as set out in SEQ ID NO: 13, or a variant or fragment thereof.

In one embodiment, the promoter is disposed 5' of the sequence encoding the coronavirus glycoprotein. The inventor's design in which the NSP1-4 and coronavirus glycoprotein antigen are encoded in a single strand, advantageously enables the use of much smaller doses of RNA because it ensures that the proteins are being expressed in the same cell.

In embodiments in which the saRNA construct encodes an innate inhibitor protein, the construct may further comprise a linker sequence disposed between the sequence encoding the coronavirus glycoprotein and the sequence encoding the innate inhibitor protein. The linker sequence may comprise a sequence that encodes a peptide spacer that is configured to be digested or cleaved to thereby separate the coronavirus glycoprotein and the innate inhibitor protein. Therefore, preferably the spacer sequence so is disposed between the sequence encoding the coronavirus glycoprotein and the sequence encoding the innate inhibitor protein.

As such, the spacer sequence is preferably a cleavable peptide, for example a 2A peptide. Suitable 2A peptides include the porcine teschovirus-12A (P2A)—ATNFSLLKQAGDVEENPGP (SEQ ID No: 14), thosea asigna virus 2A (T2A)—QCTNYALLKLAGDVESNPGP (SEQ ID No: 15), equine rhinitis A virus 2A (E2A), and Foot and mouth disease virus 2A (F2A) VKQTLNFDLLKLAGDVESNPGP (SEQ ID No: 16). Preferably, the 2A peptide is thosea asigna virus 2A (T2A).

In another embodiment, the cleavable peptide is a self-cleaving peptide. Preferably, the self-cleaving peptide is a furin/2A peptide. The furin sequence may be disposed 3' or 5' of the 2A sequence. Preferably, however, the furin sequence is disposed 5' of the 2A sequence, and preferably with a GSG spacer disposed between the furin and 2A sequence.

The skilled person would appreciate that furin is a ubiquitous calcium-dependent proprotein convertase located in the secretory pathway (mainly in the golgi and trans-golgi network) that cleaves precursor proteins at a specific recognition sequence—canonically R-X-R/K/X-R (SEQ ID No: 17), and cleaving the proprotein after the final R. Thus, in one embodiment the furin sequence is R-X-R/K/X-R. However, preferably, the furin sequence is the optimised sequence RRRRRR (SEQ ID No: 18) a GSG sequence. Preferably, the GSG spacer is disposed 3' of the furin sequence and 5' of the 2A sequence.

Thus, preferably, the spacer sequence is the furin/T2A, as provided by NCBI Reference Sequence: GenBank: AAC97195.1, and provided herein as SEQ ID No: 19, as follows:

[SEQ ID No: 19]
RRRRRRGSGEGRGSLLTCGDVEENPGP

Hence, preferably the spacer sequence comprises an amino acid sequence substantially as set out in SEQ ID NO: 19, or a variant or fragment thereof.

In one embodiment, the sequence encoding the coronavirus glycoprotein and the innate inhibitor protein may be separated by a stop codon followed by an internal ribosome entry site (IRES) sequence capable of initiating translation of the downstream sequence. Typical IRES sequences include those such as the IRES sequence of encephalomyocarditis virus or vascular endothelial growth factor and type 1 collagen-inducible protein (VCIP), and would be known to those skilled in the art. Therefore, preferably the IRES sequence is disposed between the sequence encoding the coronavirus glycoprotein and the sequence encoding the innate inhibitor protein.

In another embodiment, the sequence encoding the coronavirus glycoprotein and the innate inhibitor protein may be separated by a stop codon followed by a second subgenomic promotor sequence capable of initiating transcription of the downstream sequence.

The RNA construct may encode at least one non-structural protein (NSP), disposed 5' or 3' of the sequence encoding the coronavirus glycoprotein. Preferably, the sequence encoding the at least one NSP is disposed 5' of the sequence encoding the coronavirus glycoprotein. Thus, preferably the sequence encoding the at least one NSP is disposed at the 5' end of the RNA construct.

The at least one non-structural protein, which is encoded by the RNA construct, may be the RNA polymerase nsP4. Preferably, the construct encodes nsP1, nsP2, nsP3 and nsP4. The skilled person would understand that nsP1 is the viral capping enzyme and membrane anchor of the replication complex (RC), while nsP2 is an RNA helicase and the protease responsible for the ns polyprotein processing. nsP3 interacts with several host proteins and may modulate protein poly- and mono-ADP-ribosylation, and nsP4 is the core viral RNA-dependent RNA polymerase.

In one embodiment, nsP1 is provided herein as SEQ ID No: 20, as follows:

[SEQ ID No: 20]
MEKVHVDIEEDSPFLRALQRSFPQFEVEAKQVTDNDHANARAFSHLASKL
IETEVDPSDTILDIGSAPARRMYSKHKYHCICPMRCAEDPDRLYKYATKL
KKNCKEITDKELDKKMKELAAVMSDPDLETETMCLHDDESCRYEGQVAVY
QDVYAVDGPTSLYHQANKGVRVAYWIGFDTTPFMFKNLAGAYPSYSTNWA
DETVLTARNIGLCSSDVMERSRRGMSILRKKYLKPSNNVLFSVGSTIYHE
KRDLLRSWHLPSVFHLRGKQNYTCRCETIVSCDGYVVKRIAISPGLYGKP
SGYAATMHREGFLCCKVTDTLNGERVSFPVCTYVPATLCDQMTGILATDV
SADDAQKLLVGLNQRIVVNGRTQRNTNTMKNYLLPVVAQAFARWAKEYKE
DQEDERPLGLRDRQLVMGCCWAFRRHKITSIYKRPDTQTIIKVNSDFHSF
VLPRIGSNTLEIGLRTRIRKMLEEHKEPSPLITAEDVQEAKCAADEAKEV
REAEELRAALPPLAADVEEPTLEADVDLMLQEAGA

Accordingly, nsP1 preferably comprises an amino acid sequence as substantially as set out in SEQ ID No: 20, or a biologically active variant or fragment thereof.

In one embodiment, nsP1 is encoded by a nucleotide sequence a defined in SEQ ID No: 21, as follows:

[SEQ ID No: 21]
ATGGAGAAAGTTCACGTTGACATCGAGGAAGACAGCCCATTCCTCAGAGC
TTTGCAGCGGAGCTTCCCGCAGTTTGAGGTAGAAGCCAAGCAGGTCACTG
ATAATGACCATGCTAATGCCAGAGCGTTTTCGCATCTGGCTTCAAAACTG
ATCGAAACGGAGGTGGACCCATCCGACACGATCCTTGACATTGGAAGTGC

-continued

GCCCGCCCGCAGAATGTATTCTAAGCACAAGTATCATTGTATCTGTCCGA

TGAGATGTGCGGAAGATCCGGACAGATTGTATAAGTATGCAACTAAGCTG

AAGAAAAACTGTAAGGAAATAACTGATAAGGAATTGGACAAGAAAATGAA

GGAGCTGGCCGCCGTCATGAGCGACCCTGACCTGGAAACTGAGACTATGT

GCCTCCACGACGACGAGTCGTGTCGCTACGAAGGGCAAGTCGCTGTTTAC

CAGGATGTATACGCGGTTGACGGACCGACAAGTCTCTATCACCAAGCCAA

TAAGGGAGTTAGAGTCGCCTACTGGATAGGCTTTGACACCACCCCTTTTA

TGTTTAAGAACTTGGCTGGAGCATATCCATCATACTCTACCAACTGGGCC

GACGAAACCGTGTTAACGGCTCGTAACATAGGCCTATGCAGCTCTGACGT

TATGGAGCGGTCACGTAGAGGGATGTCCATTCTTAGAAAGAAGTATTTGA

AACCATCCAACAATGTTCTATTCTCTGTTGGCTCGACCATCTACCACGAG

AAGAGGGACTTACTGAGGAGCTGGCACCTGCCGTCTGTATTTCACTTACG

TGGCAAGCAAAATTACACATGTCGGTGTGAGACTATAGTTAGTTGCGACG

GGTACGTCGTTAAAAGAATAGCTATCAGTCCAGGCCTGTATGGGAAGCCT

TCAGGCTATGCTGCTACGATGCACCGCGAGGGATTCTTGTGCTGCAAAGT

GACAGACACATTGAACGGGGAGAGGGTCTCTTTTCCCGTGTGCACGTATG

TGCCAGCTACATTGTGTGACCAAATGACTGGCATACTGGCAACAGATGTC

AGTGCGGACGACGCGCAAAAACTGCTGGTTGGGCTCAACCAGCGTATAGT

CGTCAACGGTCGCACCCAGAGAAACACCAATACCATGAAAAATTACCTTT

TGCCCGTAGTGGCCCAGGCATTTGCTAGGTGGGCAAAGGAATATAAGGAA

GATCAAGAAGATGAAAGGCCACTAGGACTACGAGATAGACAGTTAGTCAT

GGGGTGTTGTTGGGCTTTTAGAAGGCACAAGATAACATCTATTTATAAGC

GCCCGGATACCCAAACCATCATCAAAGTGAACAGCGATTTCCACTCATTC

GTGCTGCCCAGGATAGGCAGTAACACATTGGAGATCGGGCTGAGAACAAG

AATCAGGAAAATGTTAGAGGAGCACAAGGAGCCGTCACCTCTCATTACCG

CCGAGGACGTACAAGAAGCTAAGTGCGCAGCCGATGAGGCTAAGGAGGTG

CGTGAAGCCGAGGAGTTGCGCGCAGCTCTACCACCTTTGGCAGCTGATGT

TGAGGAGCCCACTCTGGAAGCCGATGTCGACTTGATGTTACAAGAGGCTG

GGGCC

Accordingly, nsP1 is preferably encoded by a nucleotide sequence as substantially as set out in SEQ ID No: 21, or a variant or fragment thereof.

In one embodiment, the RNA construct may comprise SEQ ID No 22, as follows:

[SEQ ID No: 22]

AUGGAGAAAGUUCACGUUGACAUCGAGGAAGACAGCCCAUUCCUCAGAGC

UUUGCAGCGGAGCUUCCCGCAGUUUGAGGUAGAAGCCAAGCAGGUCACUG

AUAAUGACCAUGCUAAUGCCAGAGCGUUUUCGCAUCUGGCUUCAAAACUG

AUCGAAACGGAGGUGGACCCAUCCGACACGAUCCUUGACAUUGGAAGUGC

GCCCGCCCGCAGAAUGUAUUCUAAGCACAAGUAUCAUUGUAUCUGUCCGA

UGAGAUGUGCGGAAGAUCCGGACAGAUUGUAUAAGUAUGCAACUAAGCUG

AAGAAAAACUGUAAGGAAAUAACUGAUAAGGAAUUGGACAAGAAAAUGAA

-continued

GGAGCUGGCCGCCGUCAUGAGCGACCCUGACCUGGAAACUGAGACUAUGU

GCCUCCACGACGACGAGUCGUGUCGCUACGAAGGGCAAGUCGCUGUUUAC

CAGGAUGUAUACGCGGUUGACGGACCGACAAGUCUCUAUCACCAAGCCAA

UAAGGGAGUUAGAGUCGCCUACUGGAUAGGCUUUGACACCACCCCUUUUA

UGUUUAAGAACUUGGCUGGAGCAUAUCCAUCAUACUCUACCAACUGGGCC

GACGAAACCGUGUUAACGGCUCGUAACAUAGGCCUAUGCAGCUCUGACGU

UAUGGAGCGGUCACGUAGAGGGAUGUCCAUUCUUAGAAAGAAGUAUUUGA

AACCAUCCAACAAUGUUCUAUUCUCUGUUGGCUCGACCAUCUACCACGAG

AAGAGGGACUUACUGAGGAGCUGGCACCUGCCGUCUGUAUUUCACUUACG

UGGCAAGCAAAAUUACACAUGUCGGUGUGAGACUAUAGUUAGUUGCGACG

GGUACGUCGUUAAAAGAAUAGCUAUCAGUCCAGGCCUGUAUGGGAAGCCU

UCAGGCUAUGCUGCUACGAUGCACCGCGAGGGAUUCUUGUGCUGCAAAGU

GACAGACACAUUGAACGGGGAGAGGGUCUCUUUUCCCGUGUGCACGUAUG

UGCCAGCUACAUUGUGUGACCAAAUGACUGGCAUACUGGCAACAGAUGUC

AGUGCGGACGACGCGCAAAAACUGCUGGUUGGGCUCAACCAGCGUAUAGU

CGUCAACGGUCGCACCCAGAGAAACACCAAUACCAUGAAAAAUUACCUUU

UGCCCGUAGUGGCCCAGGCAUUUGCUAGGUGGGCAAAGGAAUAUAAGGAA

GAUCAAGAAGAUGAAAGGCCACUAGGACUACGAGAUAGACAGUUAGUCAU

GGGGUGUUGUUGGGCUUUUAGAAGGCACAAGAUAACAUCUAUUUAUAAGC

GCCCGGAUACCCAAACCAUCAUCAAAGUGAACAGCGAUUUCCACUCAUUC

GUGCUGCCCAGGAUAGGCAGUAACACAUUGGAGAUCGGGCUGAGAACAAG

AAUCAGGAAAAUGUUAGAGGAGCACAAGGAGCCGUCACCUCUCAUUACCG

CCGAGGACGUACAAGAAGCUAAGUGCGCAGCCGAUGAGGCUAAGGAGGUG

CGUGAAGCCGAGGAGUUGCGCGCAGCUCUACCACCUUUGGCAGCUGAUGU

UGAGGAGCCCACUCUGGAAGCCGAUGUCGACUUGAUGUUACAAGAGGCUG

GGGCC

Accordingly, therefore, preferably the RNA construct comprises an RNA nucleotide sequence substantially as set out as SEQ ID No: 22, or a variant or fragment thereof.

In one embodiment, nsP2 is provided herein as SEQ ID No: 23, as follows:

[SEQ ID No: 23]

GSVETPRGLIKVTSYDGEDKIGSYAVLSPQAVLKSEKLSCIHPLAEQVIV

ITHSGRKGRYAVEPYHGKVVVPEGHAIPVQDFQALSESATIVYNEREFVN

RYLHHIATHGGALNTDEEYYKTVKPSEHDGEYLYDIDRKQCVKKELVTGL

GLTGELVDPPFHEFAYESLRTRPAAPYQVPTIGVYGVPGSGKSGIIKSAV

TKKDLVVSAKKENCAEIIRDVKKMKGLDVNARTVDSVLLNGCKHPVETLY

IDEAFACHAGTLRALIAIIRPKKAVLCGDPKQCGFFNMMCLKVHFNHEIC

TQVFHKSISRRCTKSVTSVVSTLFYDKKMRTTNPKETKIVIDTTGSTKPK

QDDLILTCFRGWVKQLQIDYKGNEIMTAAASQGLTRKGVYVFQNKANVCW

AKALVPVLKTAGIDMTTEQWNTVDYFETDKAHSAEIVLNQLCVRFFGLDL

-continued

DSGLFSAPTVPLSIRNNHWDNSPSPNMYGLNKEVVRQLSRRYPQLPRAVA

TGRVYDMNTGTLRNYDPRINLVPVNRRLPHALVLHHNEHPQSDFSSFVSK

LKGRTVLVVGEKLSVPGKMVDWLSDRPEATFRARLDLGIPGDVPKYDIIF

VNVRTPYKYHHYQQCEDHAIKLSMLTKKACLHLNPGGTCVSIGYGYADRA

-continued

SESIIGAIARQFKFSRVCKPKSSLEETEVLFVFIGYDRKARTHNSYKLSS

TLTNIYTGSRLHEAGC

Accordingly, nsP2 preferably comprises an amino acid sequence as substantially as set out in SEQ ID No: 23, or a biologically active variant or fragment thereof.

In one embodiment, nsP2 is encoded by a nucleotide sequence as defined in SEQ ID No: 24, as follows:

[SEQ ID No: 24]

GGCTCAGTGGAGACACCTCGTGGCTTGATAAAGGTTACCAGCTACGATGGCGAGGACAAGATCGGCTCTTACGCTGTG

CTTTCTCCGCAGGCTGTACTCAAGAGTGAAAAATTATCTTGCATCCACCCTCTCGCTGAACAAGTCATAGTGATAACA

CACTCTGGCCGAAAAGGGCGTTATGCCGTGGAACCATACCATGGTAAAGTAGTGGTGCCAGAGGGACATGCAATACCC

GTCCAGGACTTTCAAGCTCTGAGTGAAAGTGCCACCATTGTGTACAACGAACGTGAGTTCGTAAACAGGTACCTGCAC

CATATTGCCACACATGGAGGAGCGCTGAACACTGATGAAGAATATTACAAAACTGTCAAGCCCAGCGAGCACGACGGC

GAATACCTGTACGACATCGACAGGAAACAGTGCGTCAAGAAAGAACTAGTCACTGGGCTAGGGCTCACAGGCGAGCTG

GTGGATCCTCCCTTCCATGAATTCGCCTACGAGAGTCTGAGAACACGACCAGCCGCTCCTTACCAAGTACCAACCATA

GGGGTGTATGGCGTGCCAGGATCAGGCAAGTCTGGCATCATTAAAAGCGCAGTCACCAAAAAAGATCTAGTGGTGAGC

GCCAAGAAAGAAAACTGTGCAGAAATTATAAGGGACGTCAAGAAAATGAAAGGGCTGGACGTCAATGCCAGAACTGTG

GACTCAGTGCTCTTGAATGGATGCAAACACCCCGTAGAGACCCTGTATATTGACGAAGCTTTTGCTTGTCATGCAGGT

ACTCTCAGAGCGCTCATAGCCATTATAAGACCTAAAAAGGCAGTGCTCTGCGGGGATCCCAAACAGTGCGGTTTTTTT

AACATGATGTGCCTGAAAGTGCATTTTAACCACGAGATTTGCACACAAGTCTTCCACAAAAGCATCTCTCGCCGTTGC

ACTAAATCTGTGACTTCGGTCGTCTCAACCTTGTTTTACGACAAAAAAATGAGAACGACGAATCCGAAAGAGACTAAG

ATTGTGATTGACACTACCGGCAGTACCAAACCTAAGCAGGACGATCTCATTCTCACTTGTTTCAGAGGGTGGGTGAAG

CAGTTGCAAATAGATTACAAAGGCAACGAAATAATGACGGCAGCTGCCTCTCAAGGGCTGACCCGTAAAGGTGTGTAT

GCCGTTCGGTACAAGGTGAATGAAAATCCTCTGTACGCACCCACCTCAGAACATGTGAACGTCCTACTGACCCGCACG

GAGGACCGCATCGTGTGGAAAACACTAGCCGGCGACCCATGGATAAAAACACTGACTGCCAAGTACCCTGGGAATTTC

ACTGCCACGATAGAGGAGTGGCAAGCAGAGCATGATGCCATCATGAGGCACATCTTGGAGAGACCGGACCCTACCGAC

GTCTTCCAGAATAAGGCAAACGTGTGTTGGGCCAAGGCTTTAGTGCCGGTGCTGAAGACCGCTGGCATAGACATGACC

ACTGAACAATGGAACACTGTGGATTATTTTGAAACGGACAAAGCTCACTCAGCAGAGATAGTATTGAACCAACTATGC

GTGAGGTTCTTTGGACTCGATCTGGACTCCGGTCTATTTTCTGCACCCACTGTTCCGTTATCCATTAGGAATAATCAC

TGGGATAACTCCCCGTCGCCTAACATGTACGGGCTGAATAAAGAAGTGGTCCGTCAGCTCTCTCGCAGGTACCCACAA

CTGCCTCGGGCAGTTGCCACTGGAAGAGTCTATGACATGAACACTGGTACACTGCGCAATTATGATCCGCGCATAAAC

CTAGTACCTGTAAACAGAAGACTGCCTCATGCTTTAGTCCTCCACCATAATGAACACCCACAGAGTGACTTTTCTTCA

TTCGTCAGCAAATTGAAGGGCAGAACTGTCCTGGTGGTCGGGGAAAAGTTGTCCGTCCCAGGCAAAATGGTTGACTGG

TTGTCAGACCGGCCTGAGGCTACCTTCAGAGCTCGGCTGGATTTAGGCATCCCAGGTGATGTGCCCAAATATGACATA

ATATTTGTTAATGTGAGGACCCCATATAAATACCATCACTATCAGCAGTGTGAAGACCATGCCATTAAGCTTAGCATG

TTGACCAAGAAAGCTTGTCTGCATCTGAATCCCGGCGGAACCTGTGTCAGCATAGGTTATGGTTACGCTGACAGGGCC

AGCGAAAGCATCATTGGTGCTATAGCGCGGCAGTTCAAGTTTTCCCGGGTATGCAAACCGAAATCCTCACTTGAAGAG

ACGGAAGTTCTGTTTGTATTCATTGGGTACGATCGCAAGGCCCGTACGCACAATTCTTACAAGCTTTCATCAACCTTG

ACCAACATTTATACAGGTTCCAGACTCCACGAAGCCGGATGT

Accordingly, preferably nsP2 is encoded by a nucleotide sequence as substantially as set out in SEQ ID No: 24, or a variant or fragment thereof.

In one embodiment, the RNA construct may comprise SEQ ID No 25, as follows:

[SEQ ID No: 25]

GGCUCAGUGGAGACACCUCGUGGCUUGAUAAAGGUUACCAGCUACGAUGGCGAGGACAAGAUCGGCUCUUACGCUGUG

CUUUCUCCGCAGGCUGUACUCAAGAGUGAAAAAUUAUCUUGCAUCCACCCUCUCGCUGAACAAGUCAUAGUGAUAACA

CACUCUGGCCGAAAAGGGCGUUAUGCCGUGGAACCAUACCAUGGUAAAGUAGUGGUGCCAGAGGGACAUGCAAUACCC

GUCCAGGACUUUCAAGCUCUGAGUGAAAGUGCCACCAUUGUGUACAACGAACGUGAGUUCGUAAACAGGUACCUGCAC

CAUAUUGCCACACAUGGAGGAGCGCUGAACACUGAUGAAGAAUAUUACAAAACUGUCAAGCCCAGCGAGCACGACGGC

GAAUACCUGUACGACAUCGACAGGAAACAGUGCGUCAAGAAAGAACUAGUCACUGGGCUAGGGCUCACAGGCGAGCUG

GUGGAUCCUCCCUUCCAUGAAUUCGCCUACGAGAGUCUGAGAACACGACCAGCCGCUCCUUACCAAGUACCAACCAUA

GGGGUGUAUGGCGUGCCAGGAUCAGGCAAGUCUGGCAUCAUUAAAAGCGCAGUCACCAAAAAAGAUCUAGUGGUGAGC

GCCAAGAAAGAAAACUGUGCAGAAAUUAUAAGGGACGUCAAGAAAAUGAAAGGGCUGGACGUCAAUGCCAGAACUGUG

GACUCAGUGCUCUUGAAUGGAUGCAAACACCCCGUAGAGACCCUGUAUAUUGACGAAGCUUUUGCUUGUCAUGCAGGU

ACUCUCAGAGCGCUCAUAGCCAUUAUAAGACCUAAAAAGGCAGUGCUCUGCGGGGAUCCCAAACAGUGCGGUUUUUUU

AACAUGAUGUGCCUGAAAGUGCAUUUUAACCACGAGAUUUGCACACAAGUCUUCCACAAAAGCAUCUCUCGCCGUUGC

ACUAAAUCUGUGACUUCGGUCGUCUCAACCUUGUUUUACGACAAAAAAAUGAGAACGACGAAUCCGAAAGAGACUAAG

AUUGUGAUUGACACUACCGGCAGUACCAAACCUAAGCAGGACGAUCUCAUUCUCACUUGUUUCAGAGGGUGGGUGAAG

CAGUUGCAAAUAGAUUACAAAGGCAACGAAAUAAUGACGGCAGCUGCCUCUCAAGGGCUGACCCGUAAAGGUGUGUAU

GCCGUUCGGUACAAGGUGAAUGAAAAUCCUCUGUACGCACCCACCUCAGAACAUGUGAACGUCCUACUGACCCGCACG

GAGGACCGCAUCGUGUGGAAAACACUAGCCGGCGACCCAUGGAUAAAAACACUGACUGCCAAGUACCCUGGGAAUUUC

ACUGCCACGAUAGAGGAGUGGCAAGCAGAGCAUGAUGCCAUCAUGAGGCACAUCUUGGAGAGACCGGACCCUACCGAC

GUCUUCCAGAAUAAGGCAAACGUGUGUUGGGCCAAGGCUUUAGUGCCGGUGCUGAAGACCGCUGGCAUAGACAUGACC

ACUGAACAAUGGAACACUGUGGAUUAUUUUGAAACGGACAAAGCUCACUCAGCAGAGAUAGUAUUGAACCAACUAUGC

GUGAGGUUCUUUGGACUCGAUCUGGACUCCGGUCUAUUUUCUGCACCCACUGUUCCGUUAUCCAUUAGGAAUAAUCAC

UGGGAUAACUCCCCGUCGCCUAACAUGUACGGGCUGAAUAAAGAAGUGGUCCGUCAGCUCUCUCGCAGGUACCCACAA

CUGCCUCGGGCAGUUGCCACUGGAAGAGUCUAUGACAUGAACACUGGUACACUGCGCAAUUAUGAUCCGCGCAUAAAC

CUAGUACCUGUAAACAGAAGACUGCCUCAUGCUUUAGUCCUCCACCAUAAUGAACACCCACAGAGUGACUUUUCUUCA

UUCGUCAGCAAAUUGAAGGGCAGAACUGUCCUGGUGGUCGGGGAAAAGUUGUCCGUCCCAGGCAAAAUGGUUGACUGG

UUGUCAGACCGGCCUGAGGCUACCUUCAGAGCUCGGCUGGAUUUAGGCAUCCCAGGUGAUGUGCCCAAAUAUGACAUA

AUAUUUGUUAAUGUGAGGACCCCAUAUAAAUACCAUCACUAUCAGCAGUGUGAAGACCAUGCCAUUAAGCUUAGCAUG

UUGACCAAGAAAGCUUGUCUGCAUCUGAAUCCCGGCGGAACCUGUGUCAGCAUAGGUUAUGGUUACGCUGACAGGGCC

AGCGAAAGCAUCAUUGGUGCUAUAGCGCGGCAGUUCAAGUUUUCCCGGGUAUGCAAACCGAAAUCCUCACUUGAAGAG

ACGGAAGUUCUGUUUGUAUUCAUUGGGUACGAUCGCAAGGCCCGUACGCACAAUUCUUACAAGCUUUCAUCAACCUUG

ACCAACAUUUAUACAGGUUCCAGACUCCACGAAGCCGGAUGU

Accordingly, therefore, preferably the RNA construct comprises an RNA nucleotide sequence substantially as set out as SEQ ID No: 25, or a variant or fragment thereof.

In one embodiment, nsP3 is provided herein as SEQ ID No: 26, as follows:

[SEQ ID No: 26]

APSYHVVRGDIATATEGVIINAANSKGQPGGGVCGALYKKFPESFDLQPI

EVGKARLVKGAAKHIIHAVGPNFNKVSEVEGDKQLAEAYESIAKIVNDNN

YKSVAIPLLSTGIFSGNKDRLTQSLNHLLTALDTTDADVAIYCRDKKWEM

TLKEAVARREAVEEICISDDSSVTEPDAELVRVHPKSSLAGRKGYSTSDG

KTFSYLEGTKFHQAAKDIAEINAMWPVATEANEQVCMYILGESMSSIRSK

CPVEESEASTPPSTLPCLCIHAMTPERVQRLKASRPEQITVCSSFPLPKY

RITGVQKIQCSQPILFSPKVPAYIHPRKYLVETPPVDETPEPSAENQSTE

GTPEQPPLITEDETRTRTPEPIIIEEEEEDSISLLSDGPTHQVLQVEADI

HGPPSVSSSSWSIPHASDFDVDSLSILDTLEGASVTSGATSAETNSYFAK

SMEFLARPVPAPRTVFRNPPHPAPRTRTPSLAPSRACSRTSLVSTPPGVN

RVITREELEALTPSRTPSRSVSRTSLVSNPPGVNRVITREEFEAFVAQQQ

RFDAGA

Accordingly, preferably nsP3 comprises an amino acid sequence as substantially as set out in SEQ ID No: 26, or a biologically active variant or fragment thereof.

In one embodiment, nsP3 is encoded by a nucleotide sequence a defined in SEQ ID No: 27, as follows:

[SEQ ID No: 27]

GCACCCTCATATCATGTGGTGCGAGGGGATATTGCCACGGCCACCGAAGG

AGTGATTATAAATGCTGCTAACAGCAAAGGACAACCTGGCGGAGGGGTGT

GCGGAGCGCTGTATAAGAAATTCCCGGAAAGCTTCGATTTACAGCCGATC

GAAGTAGGAAAAGCGCGACTGGTCAAAGGTGCAGCTAAACATATCATTCA

TGCCGTAGGACCAAACTTCAACAAAGTTTCGGAGGTTGAAGGTGACAAAC

AGTTGGCAGAGGCTTATGAGTCCATCGCTAAGATTGTCAACGATAACAAT

TACAAGTCAGTAGCGATTCCACTGTTGTCCACCGGCATCTTTTCCGGGAA

CAAAGATCGACTAACCCAATCATTGAACCATTTGCTGACAGCTTTAGACA

CCACTGATGCAGATGTAGCCATATACTGCAGGGACAAGAAATGGGAAATG

ACTCTCAAGGAAGCAGTGGCTAGGAGAGAAGCAGTGGAGGAGATATGCAT

ATCCGACGACTCTTCAGTGACAGAACCTGATGCAGAGCTGGTGAGGGTGC

ATCCGAAGAGTTCTTTGGCTGGAAGGAAGGGCTACAGCACAAGCGATGGC

AAAACTTTCTCATATTTGGAAGGGACCAAGTTTCACCAGGCGGCCAAGGA

TATAGCAGAAATTAATGCCATGTGGCCCGTTGCAACGGAGGCCAATGAGC

AGGTATGCATGTATATCCTCGGAGAAAGCATGAGCAGTATTAGGTCGAAA

TGCCCCGTCGAAGAGTCGGAAGCCTCCACACCACCTAGCACGCTGCCTTG

CTTGTGCATCCATGCCATGACTCCAGAAAGAGTACAGCGCCTAAAAGCCT

CACGTCCAGAACAAATTACTGTGTGCTCATCCTTTCCATTGCCGAAGTAT

AGAATCACTGGTGTGCAGAAGATCCAATGCTCCCAGCCTATATTGTTCTC

ACCGAAAGTGCCTGCGTATATTCATCCAAGGAAGTATCTCGTGGAAACAC

-continued

CACCGGTAGACGAGACTCCGGAGCCATCGGCAGAGAACCAATCCACAGAG

GGGACACCTGAACAACCACCACTTATAACCGAGGATGAGACCAGGACTAG

AACGCCTGAGCCGATCATCATCGAAGAGGAAGAAGAGGATAGCATAAGTT

TGCTGTCAGATGGCCCGACCCACCAGGTGCTGCAAGTCGAGGCAGACATT

CACGGGCCGCCCTCTGTATCTAGCTCATCCTGGTCCATTCCTCATGCATC

CGACTTTGATGTGGACAGTTTATCCATACTTGACACCCTGGAGGGAGCTA

GCGTGACCAGCGGGGCAACGTCAGCCGAGACTAACTCTTACTTCGCAAAG

AGTATGGAGTTTCTGGCGCGACCGGTGCCTGCGCCTCGAACAGTATTCAG

GAACCCTCCACATCCCGCTCCGCGCACAAGAACACCGTCACTTGCACCCA

GCAGGGCCTGCTCGAGAACCAGCCTAGTTTCCACCCCGCCAGGCGTGAAT

AGGGTGATCACTAGAGAGGAGCTCGAGGCGCTTACCCCGTCACGCACTCC

TAGCAGGTCGGTCTCGAGAACCAGCCTGGTCTCCAACCCGCCAGGCGTAA

ATAGGGTGATTACAAGAGAGGAGTTTGAGGCGTTCGTAGCACAACAACAA

TGACGGTTTGATGCGGGTGCA

Accordingly, preferably nsP3 is encoded by a nucleotide sequence as substantially as set out in SEQ ID No: 27, or a variant or fragment thereof.

Thus, the RNA construct may comprise SEQ ID No: 28, as follows:

[SEQ ID No: 28]

GCACCCUCAUAUCAUGUGGUGCGAGGGGAUAUUGCCACGGCCACCGAAGG

AGUGAUUAUAAAUGCUGCUAACAGCAAAGGACAACCUGGCGGAGGGGUGU

GCGGAGCGCUGUAUAAGAAAUUCCCGGAAAGCUUCGAUUUACAGCCGAUC

GAAGUAGGAAAAGCGCGACUGGUCAAAGGUGCAGCUAAACAUAUCAUUCA

UGCCGUAGGACCAAACUUCAACAAAGUUUCGGAGGUUGAAGGUGACAAAC

AGUUGGCAGAGGCUUAUGAGUCCAUCGCUAAGAUUGUCAACGAUAACAAU

UACAAGUCAGUAGCGAUUCCACUGUUGUCCACCGGCAUCUUUUCCGGGAA

CAAAGAUCGACUAACCCAAUCAUUGAACCAUUUGCUGACAGCUUUAGACA

CCACUGAUGCAGAUGUAGCCAUAUACUGCAGGGACAAGAAAUGGGAAAUG

ACUCUCAAGGAAGCAGUGGCUAGGAGAGAAGCAGUGGAGGAGAUAUGCAU

AUCCGACGACUCUUCAGUGACAGAACCUGAUGCAGAGCUGGUGAGGGUGC

AUCCGAAGAGUUCUUUGGCUGGAAGGAAGGGCUACAGCACAAGCGAUGGC

AAAACUUUCUCAUAUUUGGAAGGGACCAAGUUUCACCAGGCGGCCAAGGA

UAUAGCAGAAAUUAAUGCCAUGUGGCCCGUUGCAACGGAGGCCAAUGAGC

AGGUAUGCAUGUAUAUCCUCGGAGAAAGCAUGAGCAGUAUUAGGUCGAAA

UGCCCCGUCGAAGAGUCGGAAGCCUCCACACCACCUAGCACGCUGCCUUG

CUUGUGCAUCCAUGCCAUGACUCCAGAAAGAGUACAGCGCCUAAAAGCCU

CACGUCCAGAACAAAUUACUGUGUGCUCAUCCUUUCCAUUGCCGAAGUAU

AGAAUCACUGGUGUGCAGAAGAUCCAAUGCUCCCAGCCUAUAUUGUUCUC

ACCGAAAGUGCCUGCGUAUAUUCAUCCAAGGAAGUAUCUCGUGGAAACAC

CACCGGUAGACGAGACUCCGGAGCCAUCGGCAGAGAACCAAUCCACAGAG

-continued

GGGACACCUGAACAACCACCACUUAUAACCGAGGAUGAGACCAGGACUAG

AACGCCUGAGCCGAUCAUCAUCGAAGAGGAAGAAGAGGAUAGCAUAAGUU

UGCUGUCAGAUGGCCCGACCCACCAGGUGCUGCAAGUCGAGGCAGACAUU

CACGGGCCGCCCUCUGUAUCUAGCUCAUCCUGGUCCAUUCCUCAUGCAUC

CGACUUUGAUGUGGACAGUUUAUCCAUACUUGACACCCUGGAGGGAGCUA

GCGUGACCAGCGGGGCAACGUCAGCCGAGACUAACUCUUACUUCGCAAAG

AGUAUGGAGUUUCUGGCGCGACCGGUGCCUGCGCCUCGAACAGUAUUCAG

GAACCCUCCACAUCCCGCUCCGCGCACAAGAACACCGUCACUUGCACCCA

GCAGGGCCUGCUCGAGAACCAGCCUAGUUUCCACCCCGCCAGGCGUGAAU

AGGGUGAUCACUAGAGAGGAGCUCGAGGCGCUUACCCCGUCACGCACUCC

UAGCAGGUCGGUCUCGAGAACCAGCCUGGUCUCCAACCCGCCAGGCGUAA

AUAGGGUGAUUACAAGAGAGGAGUUUGAGGCGUUCGUAGCACAACAACAA

UGACGGUUUGAUGCGGGUGCA

Accordingly, therefore, preferably the RNA construct comprises an RNA nucleotide sequence substantially as set out as SEQ ID No: 28, or a variant or fragment thereof.

In one embodiment, nsP4 is provided herein as SEQ ID No: 29, as follows:

[SEQ ID No: 29]

YIFSSDTGQGHLQQKSVRQTVLSEVVLERTELEISYAPRLDQEKEELLRK

KLQLNPTPANRSRYQSRKVENMKAITARRILQGLGHYLKAEGKVECYRTL

HPVPLYSSSVNRAFSSPKVAVEACNAMLKENFPTVASYCIIPEYDAYLDM

VDGASCCLDTASFCPAKLRSFPKKHSYLEPTIRSAVPSAIQNTLQNVLAA

ATKRNCNVTQMRELPVLDSAAFNVECFKKYACNNEYWETFKENPIRLTEE

NVVNYITKLKGPKAAALFAKTHNLNMLQDIPMDRFVMDLKRDVKVTPGTK

HTEERPKVQVIQAADPLATAYLCGIHRELVRRLNAVLLPNIHTLFDMSAE

DFDAIIAEHFQPGDCVLETDIASFDKSEDDAMALTALMILEDLGVDAELL

TLIEAAFGEISSIHLPTKTKFKFGAMMKSGMFLTLFVNTVINIVIASRVL

RERLTGSPCAAFIGDDNIVKGVKSDKLMADRCATWLNMEVKIIDAVVGEK

APYFCGGFILCDSVTGTACRVADPLKRLFKLGKPLAADDEHDDDRRRALH

EESTRWNRVGILSELCKAVESRYETVGTSIIVMAMTTLASSVKSFSYLRG

APITLYG

Accordingly, preferably nsP4 comprises an amino acid sequence as substantially as set out in SEQ ID No: 29, or a biologically active variant or fragment thereof.

In one embodiment, nsP4 is encoded by a nucleotide sequence as defined in SEQ ID No: 30, as follows:

[SEQ ID No: 30]

TACATCTTTTCCTCCGACACCGGTCAAGGGCATTTACAACAAAAATCAGT

AAGGCAAACGGTGCTATCCGAAGTGGTGTTGGAGAGGACCGAATTGGAGA

TTTCGTATGCCCCGCGCCTCGACCAAGAAAAAGAAGAATTACTACGCAAG

AAATTACAGTTAAATCCCACACCTGCTAACAGAAGCAGATACCAGTCCAG

GAAGGTGGAGAACATGAAAGCCATAACAGCTAGACGTATTCTGCAAGGCC

-continued

TAGGGCATTATTTGAAGGCAGAAGGAAAAGTGGAGTGCTACCGAACCCTG

CATCCTGTTCCTTTGTATTCATCTAGTGTGAACCGTGCCTTTTCAAGCCC

CAAGGTCGCAGTGGAAGCCTGTAACGCCATGTTGAAAGAGAACTTTCCGA

CTGTGGCTTCTTACTGTATTATTCCAGAGTACGATGCCTATTTGGACATG

GTTGACGGAGCTTCATGCTGCTTAGACACTGCCAGTTTTTGCCCTGCAAA

GCTGCGCAGCTTTCCAAAGAAACACTCCTATTTGGAACCCACAATACGAT

CGGCAGTGCCTTCAGCGATCCAGAACACGCTCCAGAACGTCCTGGCAGCT

GCCACAAAAAGAAATTGCAATGTCACGCAAATGAGAGAATTGCCCGTATT

GGATTCGGCGGCCTTTAATGTGGAATGCTTCAAGAAATATGCGTGTAATA

ATGAATATTGGGAAACGTTTAAAGAAAACCCCATCAGGCTTACTGAAGAA

AACGTGGTAAATTACATTACCAAATTAAAAGGACCAAAAGCTGCTGCTCT

TTTTGCGAAGACACATAATTTGAATATGTTGCAGGACATACCAATGGACA

GGTTTGTAATGGACTTAAAGAGAGACGTGAAAGTGACTCCAGGAACAAAA

CATACTGAAGAACGGCCCAAGGTACAGGTGATCCAGGCTGCCGATCCGCT

AGCAACAGCGTATCTGTGCGGAATCCACCGAGAGCTGGTTAGGAGATTAA

ATGCGGTCCTGCTTCCGAACATTCATACACTGTTTGATATGTCGGCTGAA

GACTTTGACGCTATTATAGCCGAGCACTTCCAGCCTGGGGATTGTGTTCT

GGAAACTGACATCGCGTCGTTTGATAAAAGTGAGGACGACGCCATGGCTC

TGACCGCGTTAATGATTCTGGAAGACTTAGGTGTGGACGCAGAGCTGTTG

ACGCTGATTGAGGCGGCTTTCGGCGAAATTTCATCAATACATTTGCCCAC

TAAAACTAAATTTAAATTCGGAGCCATGATGAAATCTGGAATGTTCCTCA

CACTGTTTGTGAACACAGTCATTAACATTGTAATCGCAAGCAGAGTGTTG

AGAGAACGGCTAACCGGATCACCATGTGCAGCATTCATTGGAGATGACAA

TATCGTGAAAGGAGTCAAATCGGACAAATTAATGGCAGACAGGTGCGCCA

CCTGGTTGAATATGGAAGTCAAGATTATAGATGCTGTGGTGGGCGAGAAA

GCGCCTTATTTCTGTGGAGGGTTTATTTTGTGTGACTCCGTGACCGGCAC

AGCGTGCCGTGTGGCAGACCCCCTAAAAAGGCTGTTTAAGCTTGGCAAAC

CTCTGGCAGCAGACGATGAACATGATGATGACAGGAGAAGGGCATTGCAT

GAAGAGTCAACACGCTGGAACCGAGTGGGTATTCTTTCAGAGCTGTGCAA

GGCAGTAGAATCAAGGTATGAAACCGTAGGAACTTCCATCATAGTTATGG

CCATGACTACTCTAGCTAGCAGTGTTAAATCATTCAGCTACCTGAGAGGG

GCCCCTATAACTCTCTACGGC

Accordingly, preferably nsP4 is encoded by a nucleotide sequence as substantially as set out in SEQ ID No: 30, or a variant or fragment thereof.

Thus, in one embodiment, the RNA construct may comprise SEQ ID No: 31, as follows:

[SEQ ID No: 31]

UACAUCUUUUCCUCCGACACCGGUCAAGGGCAUUUACAACAAAAAUCAGU

AAGGCAAACGGUGCUAUCCGAAGUGGUGUUGGAGAGGACCGAAUUGGAGA

UUUCGUAUGCCCCGCGCCUCGACCAAGAAAAAGAAGAAUUACUACGCAAG

AAAUUACAGUUAAAUCCCACACCUGCUAACAGAAGCAGAUACCAGUCCAG

-continued

```
GAAGGUGGAGAACAUGAAAGCCAUAACAGCUAGACGUAUUCUGCAAGGCC

UAGGGCAUUAUUUGAAGGCAGAAGGAAAAGUGGAGUGCUACCGAACCCUG

CAUCCUGUUCCUUUGUAUUCAUCUAGUGUGAACCGUGCCUUUUCAAGCCC

CAAGGUCGCAGUGGAAGCCUGUAACGCCAUGUUGAAAGAGAACUUUCCGA

CUGUGGCUUCUUACUGUAUUAUUCCAGAGUACGAUGCCUAUUUGGACAUG

GUUGACGGAGCUUCAUGCUGCUUAGACACUGCCAGUUUUUGCCCUGCAAA

GCUGCGCAGCUUUCCAAAGAAACACUCCUAUUUGGAACCCACAAUACGAU

CGGCAGUGCCUUCAGCGAUCCAGAACACGCUCCAGAACGUCCUGGCAGCU

GCCACAAAAAGAAAUUGCAAUGUCACGCAAAUGAGAGAAUUGCCCGUAUU

GGAUUCGGCGGCCUUUAAUGUGGAAUGCUUCAAGAAAUAUGCGUGUAAUA

AUGAAUAUUGGGAAACGUUUAAAGAAAACCCCAUCAGGCUUACUGAAGAA

AACGUGGUAAAUUACAUUACCAAAUUAAAAGGACCAAAAGCUGCUGCUCU

UUUUGCGAAGACACAUAAUUUGAAUAUGUUGCAGGACAUACCAAUGGACA

GGUUUGUAAUGGACUUAAAGAGAGACGUGAAAGUGACUCCAGGAACAAAA

CAUACUGAAGAACGGCCCAAGGUACAGGUGAUCCAGGCUGCCGAUCCGCU

AGCAACAGCGUAUCUGUGCGGAAUCCACCGAGAGCUGGUUAGGAGAUUAA

AUGCGGUCCUGCUUCCGAACAUUCAUACACUGUUUGAUAUGUCGGCUGAA

GACUUUGACGCUAUUAUAGCCGAGCACUUCCAGCCUGGGGAUUGUGUUCU

GGAAACUGACAUCGCGUCGUUUGAUAAAAGUGAGGACGACGCCAUGGCUC

UGACCGCGUUAAUGAUUCUGGAAGACUUAGGUGUGGACGCAGAGCUGUUG

ACGCUGAUUGAGGCGGCUUUCGGCGAAAUUUCAUCAAUACAUUUGCCCAC

UAAAACUAAAUUUAAAUUCGGAGCCAUGAUGAAAUCUGGAAUGUUCCUCA

CACUGUUUGUGAACACAGUCAUUAACAUUGUAAUCGCAAGCAGAGUGUUG

AGAGAACGGCUAACCGGAUCACCAUGUGCAGCAUUCAUUGGAGAUGACAA

UAUCGUGAAAGGAGUCAAAUCGGACAAAUUAAUGGCAGACAGGUGCGCCA

CCUGGUUGAAUAUGGAAGUCAAGAUUAUAGAUGCUGUGGUGGGCGAGAAA

GCGCCUUAUUUCUGUGGAGGGUUUAUUUUGUGUGACUCCGUGACCGGCAC

AGCGUGCCGUGUGGCAGACCCCCUAAAAAGGCUGUUUAAGCUUGGCAAAC

CUCUGGCAGCAGACGAUGAACAUGAUGAUGACAGGAGAAGGGCAUUGCAU

GAAGAGUCAACACGCUGGAACCGAGUGGGUAUUCUUUCAGAGCUGUGCAA

GGCAGUAGAAUCAAGGUAUGAAACCGUAGGAACUUCCAUCAUAGUUAUGG

CCAUGACUACUCUAGCUAGCAGUGUUAAAUCAUUCAGCUACCUGAGAGGG

GCCCCUAUAACUCUCUACGGC
```

Accordingly, therefore, preferably the RNA construct comprises an RNA nucleotide sequence substantially as set out as SEQ ID No: 31, or a variant or fragment thereof.

Preferably, together with proteins present in a host cell, the non-structural proteins encoded by the RNA construct of the invention form an enzyme complex that is required for genome replication and transcription of the sequences encoding the coronavirus glycoprotein. For example, the one or more non-structural protein may encode a polymerase to enable the construct to amplify the nucleotide sequence encoding the coronavirus glycoprotein, as shown in FIG. 1B.

The host cell may be a eukaryotic or prokaryotic host cell. Preferably, the host cell is a eukaryotic host cell. More preferably, the host cell is a mammalian host cell.

The RNA construct may further comprise a promoter disposed 5' of the at least one non-structural protein, such that the promoter is operably linked to sequence encoding the at least one non-structural protein and enables expression of the at least one non-structural protein in a host cell.

Preferably, the promoter comprises a 5' UTR conserved sequence element, which may be referred to herein as SEQ ID No: 32, as follows:

```
                                        [SEQ ID No: 32]
AUGGGCGGCGCAUGAGAGAAGCCCAGACCAAUUACCUACCCAAA
```

Accordingly, preferably the UTR is disposed 5' of the at least one non-structural protein and comprises a nucleotide sequence substantially as set out in SEQ ID No: 32, or a fragment or variant thereof.

Preferably, the replicon comprises a polyA tail. Preferably, the polyA tail is disposed at the 3' end of the replicon. The replicon may further comprise a 5' cap. In the context of the present invention, the term "5'-cap" includes a 5'-cap analogue that resembles the RNA cap structure and is modified to possess the ability to stabilize RNA and/or enhance translation of RNA if attached thereto, preferably in vivo and/or in a cell.

An RNA with a 5-cap may be achieved by in vitro transcription of a DNA template in presence of said 5'-cap, wherein said 5'-cap is co-transcriptionally incorporated into the generated RNA strand, or the RNA may be generated, for example, by in vitro transcription, and the 5-cap may be attached to the RNA post-transcriptionally using capping enzymes, for example, capping enzymes of vaccinia virus. In capped RNA, the 3' position of the first base of a (capped) RNA molecule is linked to the 5' position of the subsequent base of the RNA molecule ("second base") via a phosphodiester bond.

In one embodiment, the RNA construct of the invention comprises, preferably 5' to 3', a promoter and a sequence encoding a coronavirus glycoprotein.

In another embodiment, the RNA construct comprises, preferably 5' to 3', a first promoter, a sequence encoding at least one non-structural protein, a second promoter, and a sequence encoding a coronavirus glycoprotein.

In another embodiment, the RNA construct comprises, preferably 5' to 3', a first promoter, a sequence encoding at least one non-structural protein, a second promoter, a sequence encoding a coronavirus glycoprotein, and a polyA tail.

In another embodiment, the RNA construct comprises, preferably 5' to 3', a promoter, a sequence encoding at least one non-structural protein, a sub-genomic promoter, a sequence encoding a coronavirus glycoprotein, and a polyA tail.

In another embodiment, the RNA construct comprises, preferably 5' to 3', a 5' cap, a promoter, a sequence encoding at least one non-structural protein, a sub genomic promoter, a sequence encoding a coronavirus glycoprotein, and a polyA tail.

In a preferred embodiment, the RNA construct comprises, 5' to 3', a 5' cap, a promoter, nsP1, nsP2, nsP3, nsP4, the sub genomic promoter 26S, a sequence encoding the modified coronavirus glycoprotein, a spacer sequence, a sequence encoding MERS-CoV ORF4a, and a polyA tail.

The saRNA constructs of the invention may be made using the DNA plasmid, which is shown in FIG. 3, 7-11, as a template. RNA copies may be made by in vitro transcription using a polymerase, such as T7 polymerase, and the T7 promoter is shown upstream of the saRNA in the plasmid map in FIG. 3, 7-11.

In one embodiment (SARS-CoV-2 coronavirus surface glycoprotein), therefore, the RNA construct may comprise or consist of SEQ ID No: 33, as follows:

[SEQ ID No: 33]

AUGGAGAAAGUUCACGUUGACAUCGAGGAAGACAGCCCAUUCCUCAGAGCUUUGCAGCGGAGCUUCCCGCAGUUUGAG

GUAGAAGCCAAGCAGGUCACUGAUAAUGACCAUGCUAAUGCCAGAGCGUUUUCGCAUCUGGCUUCAAAACUGAUCGAA

ACGGAGGUGGACCCAUCCGACACGAUCCUUGACAUUGGAAGUGCGCCCGCCCGCAGAAUGUAUUCUAAGCACAAGUAU

CAUUGUAUCUGUCCGAUGAGAUGUGCGGAAGAUCCGGACAGAUUGUAUAAGUAUGCAACUAAGCUGAAGAAAAACUGU

AAGGAAAUAACUGAUAAGGAAUUGGACAAGAAAAUGAAGGAGCUGGCCGCCGUCAUGAGCGACCCUGACCUGGAAACU

GAGACUAUGUGCCUCCACGACGACGAGUCGUGUCGCUACGAAGGGCAAGUCGCUGUUUACCAGGAUGUAUACGCGGUU

GACGGACCGACAAGUCUCUAUCACCAAGCCAAUAAGGGAGUUAGAGUCGCCUACUGGAUAGGCUUUGACACCACCCCU

UUUAUGUUUAAGAACUUGGCUGGAGCAUAUCCAUCAUACUCUACCAACUGGGCCGACGAAACCGUGUUAACGGCUCGU

AACAUAGGCCUAUGCAGCUCUGACGUUAUGGAGCGGUCACGUAGAGGGAUGUCCAUUCUUAGAAAGAAGUAUUUGAAA

CCAUCCAACAAUGUUCUAUUCUCUGUUGGCUCGACCAUCUACCACGAGAAGAGGGACUUACUGAGGAGCUGGCACCUG

CCGUCUGUAUUUCACUUACGUGGCAAGCAAAAUUACACAUGUCGGUGUGAGACUAUAGUUAGUUGCGACGGGUACGUC

GUUAAAAGAAUAGCUAUCAGUCCAGGCCUGUAUGGGAAGCCUUCAGGCUAUGCUGCUACGAUGCACCGCGAGGGAUUC

UUGUGCUGCAAAGUGACAGACACAUUGAACGGGGAGAGGGUCUCUUUUCCCGUGUGCACGUAUGUGCCAGCUACAUUG

UGUGACCAAAUGACUGGCAUACUGGCAACAGAUGUCAGUGCGGACGACGCGCAAAAACUGCUGGUUGGGCUCAACCAG

CGUAUAGUCGUCAACGGUCGCACCCAGAGAAACACCAAUACCAUGAAAAAUUACCUUUUGCCCGUAGUGGCCCAGGCA

UUUGCUAGGUGGGCAAAGGAAUAUAAGGAAGAUCAAGAAGAUGAAAGGCCACUAGGACUACGAGAUAGACAGUUAGUC

AUGGGGUGUUGUUGGGCUUUUAGAAGGCACAAGAUAACAUCUAUUUAUAAGCGCCCGGAUACCCAAACCAUCAUCAAA

GUGAACAGCGAUUUCCACUCAUUCGUGCUGCCCAGGAUAGGCAGUAACACAUUGGAGAUCGGGCUGAGAACAAGAAUC

AGGAAAAUGUUAGAGGAGCACAAGGAGCCGUCACCUCUCAUUACCGCCGAGGACGUACAAGAAGCUAAGUGCGCAGCC

GAUGAGGCUAAGGAGGUGCGUGAAGCCGAGGAGUUGCGCGCAGCUCUACCACCUUUGGCAGCUGAUGUUGAGGAGCCC

ACUCUGGAAGCCGAUGUCGACUUGAUGUUACAAGAGGCUGGGGCCGGCUCAGUGGAGACACCUCGUGGCUUGAUAAAG

GUUACCAGCUACGAUGGCGAGGACAAGAUCGGCUCUUACGCUGUGCUUUCUCCGCAGGCUGUACUCAAGAGUGAAAAA

UUAUCUUGCAUCCACCCUCUCGCUGAACAAGUCAUAGUGAUAACACACUCUGGCCGAAAAGGGCGUUAUGCCGUGGAA

CCAUACCAUGGUAAAGUAGUGGUGCCAGAGGGACAUGCAAUACCCGUCCAGGACUUUCAAGCUCUGAGUGAAAGUGCC

ACCAUUGUGUACAACGAACGUGAGUUCGUAAACAGGUACCUGCACCAUAUUGCCACACAUGGAGGAGCGCUGAACACU

GAUGAAGAAUAUUACAAAACUGUCAAGCCCAGCGAGCACGACGGCGAAUACCUGUACGACAUCGACAGGAAACAGUGC

GUCAAGAAAGAACUAGUCACUGGGCUAGGGCUCACAGGCGAGCUGGUGGAUCCUCCCUUCCAUGAAUUCGCCUACGAG

AGUCUGAGAACACGACCAGCCGCUCCUUACCAAGUACCAACCAUAGGGGUGUAUGGCGUGCCAGGAUCAGGCAAGUCU

GGCAUCAUUAAAAGCGCAGUCACCAAAAAAGAUCUAGUGGUGAGCGCCAAGAAAGAAAACUGUGCAGAAAUUAUAAGG

GACGUCAAGAAAAUGAAAGGGCUGGACGUCAAUGCCAGAACUGUGGACUCAGUGCUCUUGAAUGGAUGCAAACACCCC

GUAGAGACCCUGUAUAUUGACGAAGCUUUUGCUUGUCAUGCAGGUACUCUCAGAGCGCUCAUAGCCAUUAUAAGACCU

AAAAAGGCAGUGCUCUGCGGGGAUCCCAAACAGUGCGGUUUUUUUAACAUGAUGUGCCUGAAAGUGCAUUUUAACCAC

GAGAUUUGCACACAAGUCUUCCACAAAAGCAUCUCUCGCCGUUGCACUAAAUCUGUGACUUCGGUCGUCUCAACCUUG

UUUUACGACAAAAAAAUGAGAACGACGAAUCCGAAAGAGACUAAGAUUGUGAUUGACACUACCGGCAGUACCAAACCU

AAGCAGGACGAUCUCAUUCUCACUUGUUUCAGAGGGUGGGUGAAGCAGUUGCAAAUAGAUUACAAAGGCAACGAAAUA

AUGACGGCAGCUGCCUCUCAAGGGCUGACCCGUAAAGGUGUGUAUGCCGUUCGGUACAAGGUGAAUGAAAAUCCUCUG

UACGCACCCACCUCAGAACAUGUGAACGUCCUACUGACCCGCACGGAGGACCGCAUCGUGUGGAAAACACUAGCCGGC

-continued

GACCCAUGGAUAAAAACACUGACUGCCAAGUACCCUGGGAAUUUCACUGCCACGAUAGAGGAGUGGCAAGCAGAGCAU

GAUGCCAUCAUGAGGCACAUCUUGGAGAGACCGGACCCUACCGACGUCUUCCAGAAUAAGGCAAACGUGUGUUGGGCC

AAGGCUUUAGUGCCGGUGCUGAAGACCGCUGGCAUAGACAUGACCACUGAACAAUGGAACACUGUGGAUUAUUUUGAA

ACGGACAAAGCUCACUCAGCAGAGAUAGUAUUGAACCAACUAUGCGUGAGGUUCUUUGGACUCGAUCUGGACUCCGGU

CUAUUUUCUGCACCCACUGUUCCGUUAUCCAUUAGGAAUAAUCACUGGGAUAACUCCCCGUCGCCUAACAUGUACGGG

CUGAAUAAAGAAGUGGUCCGUCAGCUCUCUCGCAGGUACCCACAACUGCCUCGGGCAGUUGCCACUGGAAGAGUCUAU

GACAUGAACACUGGUACACUGCGCAAUUAUGAUCCGCGCAUAAACCUAGUACCUGUAAACAGAAGACUGCCUCAUGCU

UUAGUCCUCCACCAUAAUGAACACCCACAGAGUGACUUUUCUUCAUUCGUCAGCAAAUUGAAGGGCAGAACUGUCCUG

GUGGUCGGGGAAAAGUUGUCCGUCCCAGGCAAAAUGGUUGACUGGUUGUCAGACCGGCCUGAGGCUACCUUCAGAGCU

CGGCUGGAUUUAGGCAUCCCAGGUGAUGUGCCCAAAUAUGACAUAAUAUUUGUUAAUGUGAGGACCCCAUAUAAAUAC

CAUCACUAUCAGCAGUGUGAAGACCAUGCCAUUAAGCUUAGCAUGUUGACCAAGAAAGCUUGUCUGCAUCUGAAUCCC

GGCGGAACCUGUGUCAGCAUAGGUUAUGGUUACGCUGACAGGGCCAGCGAAAGCAUCAUUGGUGCUAUAGCGCGGCAG

UUCAAGUUUUCCCGGGUAUGCAAACCGAAAUCCUCACUUGAAGAGACGGAAGUUCUGUUUGUAUUCAUUGGGUACGAU

CGCAAGGCCCGUACGCACAAUUCUUACAAGCUUUCAUCAACCUUGACCAACAUUUAUACAGGUUCCAGACUCCACGAA

GCCGGAUGUGCACCCUCAUAUCAUGUGGUGCGAGGGGAUAUUGCCACGGCCACCGAAGGAGUGAUUAUAAAUGCUGCU

AACAGCAAAGGACAACCUGGCGGAGGGGUGUGCGGAGCGCUGUAUAAGAAAUUCCCGGAAAGCUUCGAUUUACAGCCG

AUCGAAGUAGGAAAAGCGCGACUGGUCAAAGGUGCAGCUAAACAUAUCAUUCAUGCCGUAGGACCAAACUUCAACAAA

GUUUCGGAGGUUGAAGGUGACAAACAGUUGGCAGAGGCUUAUGAGUCCAUCGCUAAGAUUGUCAACGAUAACAAUUAC

AAGUCAGUAGCGAUUCCACUGUUGUCCACCGGCAUCUUUUCCGGGAACAAAGAUCGACUAACCCAAUCAUUGAACCAU

UUGCUGACAGCUUUAGACACCACUGAUGCAGAUGUAGCCAUAUACUGCAGGGACAAGAAAUGGGAAAUGACUCUCAAG

GAAGCAGUGGCUAGGAGAGAAGCAGUGGAGGAGAUAUGCAUAUCCGACGACUCUUCAGUGACAGAACCUGAUGCAGAG

CUGGUGAGGGUGCAUCCGAAGAGUUCUUUGGCUGGAAGGAAGGGCUACAGCACAAGCGAUGGCAAAACUUUCUCAUAU

UUGGAAGGGACCAAGUUUCACCAGGCGGCCAAGGAUAUAGCAGAAAUUAAUGCCAUGUGGCCCGUUGCAACGGAGGCC

AAUGAGCAGGUAUGCAUGUAUAUCCUCGGAGAAAGCAUGAGCAGUAUUAGGUCGAAAUGCCCCGUCGAAGAGUCGGAA

GCCUCCACACCACCUAGCACGCUGCCUUGCUUGUGCAUCCAUGCCAUGACUCCAGAAAGAGUACAGCGCCUAAAAGCC

UCACGUCCAGAACAAAUUACUGUGUGCUCAUCCUUUCCAUUGCCGAAGUAUAGAAUCACUGGUGUGCAGAAGAUCCAA

UGCUCCCAGCCUAUAUUGUUCUCACCGAAAGUGCCUGCGUAUAUUCAUCCAAGGAAGUAUCUCGUGGAAACACCACCG

GUAGACGAGACUCCGGAGCCAUCGGCAGAGAACCAAUCCACAGAGGGGACACCUGAACAACCACCACUUAUAACCGAG

GAUGAGACCAGGACUAGAACGCCUGAGCCGAUCAUCAUCGAAGAGGAAGAAGAGGAUAGCAUAAGUUUGCUGUCAGAU

GGCCCGACCCACCAGGUGCUGCAAGUCGAGGCAGACAUUCACGGGCCGCCCUCUGUAUCUAGCUCAUCCUGGUCCAUU

CCUCAUGCAUCCGACUUUGAUGUGGACAGUUUAUCCAUACUUGACACCCUGGAGGGAGCUAGCGUGACCAGCGGGGCA

ACGUCAGCCGAGACUAACUCUUACUUCGCAAAGAGUAUGGAGUUUCUGGCGCGACCGGUGCCUGCGCCUCGAACAGUA

UUCAGGAACCCUCCACAUCCCGCUCCGCGCACAAGAACACCGUCACUUGCACCCAGCAGGGCCUGCUCGAGAACCAGC

CUAGUUUCCACCCCGCCAGGCGUGAAUAGGGUGAUCACUAGAGAGGAGCUCGAGGCGCUUACCCCGUCACGCACUCCU

AGCAGGUCGGUCUCGAGAACCAGCCUGGUCUCCAACCCGCCAGGCGUAAAUAGGGUGAUUACAAGAGAGGAGUUUGAG

GCGUUCGUAGCACAACAACAAUGACGGUUUGAUGCGGGUGCAUACAUCUUUUCCUCCGACACCGGUCAAGGGCAUUUA

CAACAAAAAUCAGUAAGGCAAACGGUGCUAUCCGAAGUGGUGUUGGAGAGGACCGAAUUGGAGAUUUCGUAUGCCCCG

CGCCUCGACCAAGAAAAAGAAGAAUUACUACGCAAGAAAUUACAGUUAAAUCCCACACCUGCUAACAGAAGCAGAUAC

CAGUCCAGGAAGGUGGAGAACAUGAAAGCCAUAACAGCUAGACGUAUUCUGCAAGGCCUAGGGCAUUAUUUGAAGGCA

GAAGGAAAAGUGGAGUGCUACCGAACCCUGCAUCCUGUUCCUUUGUAUUCAUCUAGUGUGAACCGUGCCUUUUCAAGC

-continued

CCCAAGGUCGCAGUGGAAGCCUGUAACGCCAUGUUGAAAGAGAACUUUCCGACUGUGGCUUCUUACUGUAUUAUUCCA

GAGUACGAUGCCUAUUUGGACAUGGUUGACGGAGCUUCAUGCUGCUUAGACACUGCCAGUUUUUGCCCUGCAAAGCUG

CGCAGCUUUCCAAAGAAACACUCCUAUUUGGAACCCACAAUACGAUCGGCAGUGCCUUCAGCGAUCCAGAACACGCUC

CAGAACGUCCUGGCAGCUGCCACAAAAAGAAAUUGCAAUGUCACGCAAAUGAGAGAAUUGCCCGUAUUGGAUUCGGCG

GCCUUUAAUGUGGAAUGCUUCAAGAAAUAUGCGUGUAAUAAUGAAUAUUGGGAAACGUUUAAAGAAAACCCCAUCAGG

CUUACUGAAGAAAACGUGGUAAAUUACAUUACCAAAUUAAAAGGACCAAAAGCUGCUGCUCUUUUUGCGAAGACACAU

AAUUUGAAUAUGUUGCAGGACAUACCAAUGGACAGGUUUGUAAUGGACUUAAAGAGAGACGUGAAAGUGACUCCAGGA

ACAAAACAUACUGAAGAACGGCCCAAGGUACAGGUGAUCCAGGCUGCCGAUCCGCUAGCAACAGCGUAUCUGUGCGGA

AUCCACCGAGAGCUGGUUAGGAGAUUAAAUGCGGUCCUGCUUCCGAACAUUCAUACACUGUUUGAUAUGUCGGCUGAA

GACUUUGACGCUAUUAUAGCCGAGCACUUCCAGCCUGGGGAUUGUGUUCUGGAAACUGACAUCGCGUCGUUUGAUAAA

AGUGAGGACGACGCCAUGGCUCUGACCGCGUUAAUGAUUCUGGAAGACUUAGGUGUGGACGCAGAGCUGUUGACGCUG

AUUGAGGCGGCUUUCGGCGAAAUUUCAUCAAUACAUUUGCCCACUAAAACUAAAUUUAAAUUCGGAGCCAUGAUGAAA

UCUGGAAUGUUCCUCACACUGUUUGUGAACACAGUCAUUAACAUUGUAAUCGCAAGCAGAGUGUUGAGAGAACGGCUA

ACCGGAUCACCAUGUGCAGCAUUCAUUGGAGAUGACAAUAUCGUGAAAGGAGUCAAAUCGGACAAAUUAAUGGCAGAC

AGGUGCGCCACCUGGUUGAAUAUGGAAGUCAAGAUUAUAGAUGCUGUGGUGGGCGAGAAAGCGCCUUAUUUCUGUGGA

GGGUUUAUUUUGUGUGACUCCGUGACCGGCACAGCGUGCCGUGUGGCAGACCCCCUAAAAAGGCUGUUUAAGCUUGGC

AAACCUCUGGCAGCAGACGAUGAACAUGAUGAUGACAGGAGAAGGGCAUUGCAUGAAGAGUCAACACGCUGGAACCGA

GUGGGUAUUCUUUCAGAGCUGUGCAAGGCAGUAGAAUCAAGGUAUGAAACCGUAGGAACUUCCAUCAUAGUUAUGGCC

AUGACUACUCUAGCUAGCAGUGUUAAAUCAUUCAGCUACCUGAGAGGGGCCCCUAUAACUCUCUACGGCUAACCUGAA

UGGACUACGACAUAGUCUAGUCCGCCAAGUCUAGCAUAUGGCCACCAUGUUCGUGUUUCUGGUGCUGCUGCCUCUGGU

GUCCAGCCAGUGUGUGAACCUGACCACCAGAACACAGCUGCCUCCAGCCUACACCAACAGCUUUACCAGAGGCGUGUA

CUACCCCGACAAGGUGUUCAGAUCCAGCGUGCUGCACUCUACCCAGGACCUGUUCCUGCCUUUCUUCAGCAACGUGAC

CUGGUUCCACGCCAUCCACGUGUCCGGCACCAAUGGCACCAAGAGAUUCGACAACCCCGUGCUGCCCUUCAACGACGG

GGUGUACUUUGCCAGCACCGAGAAGUCCAACAUCAUCAGAGGCUGGAUCUUCGGCACCACACUGGACAGCAAGACCCA

GAGCCUGCUGAUCGUGAACAACGCCACCAACGUGGUCAUCAAAGUGUGCGAGUUCCAGUUCUGCAACGACCCCUUCCU

GGGCGUCUACUACCACAAGAACAACAAGAGCUGGAUGGAAAGCGAGUUCCGGGUGUACAGCAGCGCCAACAACUGCAC

CUUCGAGUACGUGUCCCAGCCUUUCCUGAUGGACCUGGAAGGCAAGCAGGGCAACUUCAAGAACCUGCGCGAGUUCGU

GUUCAAGAACAUCGACGGCUACUUCAAGAUCUACAGCAAGCACACCCCUAUCAACCUCGUGCGGGAUCUGCCUCAGGG

CUUCUCUGCUCUGGAACCCCUGGUGGAUCUGCCCAUCGGCAUCAACAUCACCCGGUUUCAGACACUGCUGGCCCUGCA

CAGAAGCUACCUGACACCUGGCGAUAGCAGCAGCGGAUGGACAGCUGGUGCCGCCGCUUACUAUGUGGGCUACCUGCA

GCCUAGAACCUUCCUGCUGAAGUACAACGAGAACGGCACCAUCACCGACGCCGUGGAUUGUGCCCUUGAUCCUCUGAG

CGAGACAAAGUGCACCCUGAAGUCCUUCACCGUGGAAAAGGGCAUCUACCAGACCAGCAACUUCCGGGUGCAGCCCAC

CGAAUCCAUCGUGCGGUUCCCCAAUAUCACCAAUCUGUGCCCCUUCGGCGAGGUGUUCAAUGCCACCAGAUUCGCCUC

UGUGUACGCCUGGAACCGGAAGCGGAUCAGCAAUUGCGUGGCCGACUACUCCGUGCUGUACAACUCCGCCAGCUUCAG

CACCUUCAAGUGCUACGGCGUGUCCCCUACCAAGCUGAACGACCUGUGCUUCACAAACGUGUACGCCGACAGCUUCGU

GAUCCGGGGAGAUGAAGUGCGGCAGAUUGCCCCUGGACAGACAGGCAAGAUCGCCGACUACAACUACAAGCUGCCCGA

CGACUUCACCGGCUGUGUGAUUGCCUGGAACAGCAACAACCUGGACUCCAAAGUCGGCGGCAACUACAAUUACCUGUA

CCGGCUGUUCCGGAAGUCCAAUCUGAAGCCCUUCGAGCGGGACAUCUCCACCGAGAUCUAUCAGGCCGGCAGCACCCC

UUGUAACGGCGUGGAAGGCUUCAACUGCUACUUCCCACUGCAGUCCUACGGCUUUCAGCCCACAAAUGGCGUGGGCUA

UCAGCCCUACAGAGUGGUGGUGCUGAGCUUCGAACUGCUGCAUGCCCCUGCCACAGUGUGCGGCCCUAAGAAAAGCAC

CAAUCUCGUGAAGAACAAAUGCGUGAACUUCAACUUCAACGGCCUGACCGGCACAGGCGUGCUGACAGAGAGCAACAA

-continued

GAAGUUCCUGCCAUUCCAGCAGUUUGGCCGGGAUAUCGCCGAUACCACAGACGCCGUUAGAGAUCCCCAGACACUGGA

AAUCCUGGACAUCACCCCUUGCAGCUUCGGCGGAGUGUCUGUGAUCACCCCUGGCACCAACACCAGCAAUCAGGUGGC

AGUGCUGUACCAGGACGUGAACUGUACCGAAGUGCCCGUGGCCAUUCACGCCGAUCAGCUGACACCUACAUGGCGGGU

GUACUCCACCGGCAGCAAUGUGUUUCAGACCAGAGCCGGCUGUCUGAUCGGAGCCGAGCACGUGAACAAUAGCUACGA

GUGCGACAUCCCCAUCGGCGCUGGCAUCUGUGCCAGCUACCAGACACAGACAAACAGCCCCAGACGGGCCAGAUCUGU

GGCCAGCCAGAGCAUCAUUGCCUACACAAUGUCUCUGGGCGCCGAGAACAGCGUGGCCUACUCCAACAACUCUAUCGC

UAUCCCCACCAACUUCACCAUCAGCGUGACCACAGAGAUCCUGCCUGUGUCCAUGACCAAGACCAGCGUGGACUGCAC

CAUGUACAUCUGCGGCGAUUCCACCGAGUGCUCCAACCUGCUGCUGCAGUACGGCAGCUUCUGCACCCAGCUGAAUAG

AGCCCUGACAGGGAUCGCCGUGGAACAGGACAAGAACACCCAAGAGGUGUUCGCCCAAGUGAAGCAGAUCUACAAGAC

CCCUCCUAUCAAGGACUUCGGCGGCUUCAAUUUCAGCCAGAUUCUGCCCGAUCCUAGCAAGCCCAGCAAGCGGAGCUU

CAUCGAGGACCUGCUGUUCAACAAAGUGACACUGGCCGACGCCGGCUUCAUCAAGCAGUAUGGCGAUUGUCUGGGCGA

CAUUGCCGCCAGGGAUCUGAUUUGCGCCCAGAAGUUUAACGGACUGACAGUGCUGCCUCCUCUGCUGACCGAUGAGAU

GAUCGCCCAGUACACAUCUGCCCUGCUGGCCGGCACAAUCACAAGCGGCUGGACAUUUGGAGCUGGCGCCGCUCUGCA

GAUCCCCUUUGCUAUGCAGAUGGCCUACAGAUUCAACGGCAUCGGAGUGACCCAGAAUGUGCUGUACGAGAACCAGAA

GCUGAUCGCCAACCAGUUCAACAGCGCCAUCGGCAAGAUCCAGGACAGCCUGAGCAGCACAGCAAGCGCCCUGGGAAA

GCUGCAGGACGUGGUCAACCAGAAUGCCCAGGCACUGAACACCCUGGUCAAGCAGCUGUCCUCCAACUUCGGCGCCAU

CAGCUCUGUGCUGAACGAUAUCCUGAGCAGACUGGACCCUCCUGAGGCCGAGGUGCAGAUCGACAGACUGAUCACAGG

CAGACUGCAGAGCCUCCAGACAUACGUGACCCAGCAGCUGAUCAGAGCCGCCGAGAUUAGAGCCUCUGCCAAUCUGGC

CGCCACCAAGAUGUCUGAGUGUGUGCUGGGCCAGAGCAAGAGAGUGGACUUUUGCGGCAAGGGCUACCACCUGAUGAG

CUUCCCUCAGUCUGCCCCUCACGGCGUGGUGUUUCUGCACGUGACAUACGUUCCCGCUCAAGAGAAGAAUUUCACCAC

CGCUCCAGCCAUCUGCCACGACGGCAAAGCCCACUUUCCUAGAGAAGGCGUGUUCGUGUCCAACGGCACCCAUUGGUU

CGUGACACAGCGGAACUUCUACGAGCCCCAGAUCAUCACCACCGACAACACCUUCGUGUCUGGCAACUGCGACGUCGU

GAUCGGCAUUGUGAACAAUACCGUGUACGACCCUCUGCAGCCCGAGCUGGACAGCUUCAAAGAGGAACUGGACAAGUA

CUUUAAGAACCACACAAGCCCCGACGUGGACCUGGGCGAUAUCAGCGGAAUCAAUGCCAGCGUCGUGAACAUCCAGAA

AGAGAUCGACCGGCUGAACGAGGUGGCCAAGAAUCUGAACGAGAGCCUGAUCGACCUGCAAGAACUGGGGAAGUACGA

GCAGUACAUCAAGUGGCCCUGGUACAUCUGGCUGGGCUUUAUCGCCGGACUGAUUGCCAUCGUGAUGGUCACAAUCAU

GCUGUGUUGCAUGACCAGCUGCUGUAGCUGCCUGAAGGGCUGUUGUAGCUGUGGCAGCUGCUGCAAGUUCGACGAGGA

CGAUUCUGAGCCCGUGCUGAAGGGCGUGAAACUGCACUACACAUGAGCGGCCGCGAAUUGGCAAGCUGCUUACAUAGA

ACUCGCGGCGAUUGGCAUGCCGCCUUAAAAUUUUUAUUUUAUUUUUCUUUUCUUUUCCGAAUCGGAUUUUGUUUUUAA

UAUUUCAAAAAAAAAAAAAAAAAAAAAAAAAAAAAAAAAAAA

Accordingly, preferably the RNA construct comprises a nucleotide sequence substantially as set out in SEQ ID No: 33, or a fragment or variant thereof.

In another embodiment (the B.1.1.7 UK variant of SARS-CoV-2 glycoprotein), the RNA construct may comprise or consist of SEQ ID No: 62, as follows:

[SEQ ID No: 62]

AUGGGCGGCGCAUGAGAGAAGCCCAGACCAAUUACCUACCCAAAAUGGAGAAAGUUCACGUUGACAUCGAGGAAGACA

GCCCAUUCCUCAGAGCUUUGCAGCGGAGCUUCCCGCAGUUUGAGGUAGAAGCCAAGCAGGUCACUGAUAAUGACCAUG

CUAAUGCCAGAGCGUUUUCGCAUCUGGCUUCAAAACUGAUCGAAACGGAGGUGGACCCAUCCGACACGAUCCUUGACA

UUGGAAGUGCGCCCGCCCGCAGAAUGUAUUCUAAGCACAAGUAUCAUUGUAUCUGUCCGAUGAGAUGUGCGGAAGAUC

CGGACAGAUUGUAUAAGUAUGCAACUAAGCUGAAGAAAAACUGUAAGGAAAUAACUGAUAAGGAAUUGGACAAGAAAA

UGAAGGAGCUGGCCGCCGUCAUGAGCGACCCUGACCUGGAAACUGAGACUAUGUGCCUCCACGACGACGAGUCGUGUC

-continued

GCUACGAAGGGCAAGUCGCUGUUUACCAGGAUGUAUACGCGGUUGACGGACCGACAAGUCUCUAUCACCAAGCCAAUA

AGGGAGUUAGAGUCGCCUACUGGAUAGGCUUUGACACCACCCCUUUUAUGUUUAAGAACUUGGCUGGAGCAUAUCCAU

CAUACUCUACCAACUGGGCCGACGAAACCGUGUUAACGGCUCGUAACAUAGGCCUAUGCAGCUCUGACGUUAUGGAGC

GGUCACGUAGAGGGAUGUCCAUUCUUAGAAAGAAGUAUUUGAAACCAUCCAACAAUGUUCUAUUCUCUGUUGGCUCGA

CCAUCUACCACGAGAAGAGGGACUUACUGAGGAGCUGGCACCUGCCGUCUGUAUUUCACUUACGUGGCAAGCAAAAUU

ACACAUGUCGGUGUGAGACUAUAGUUAGUUGCGACGGGUACGUCGUUAAAAGAAUAGCUAUCAGUCCAGGCCUGUAUG

GGAAGCCUUCAGGCUAUGCUGCUACGAUGCACCGCGAGGGAUUCUUGUGCUGCAAAGUGACAGACACAUUGAACGGGG

AGAGGGUCUCUUUUCCCGUGUGCACGUAUGUGCCAGCUACAUUGUGUGACCAAAUGACUGGCAUACUGGCAACAGAUG

UCAGUGCGGACGACGCGCAAAAACUGCUGGUUGGGCUCAACCAGCGUAUAGUCGUCAACGGUCGCACCCAGAGAAACA

CCAAUACCAUGAAAAAUUACCUUUUGCCCGUAGUGGCCCAGGCAUUUGCUAGGUGGGCAAAGGAAUAUAAGGAAGAUC

AAGAAGAUGAAAGGCCACUAGGACUACGAGAUAGACAGUUAGUCAUGGGGUGUUGUUGGGCUUUUAGAAGGCACAAGA

UAACAUCUAUUUAUAAGCGCCCGGAUACCCAAACCAUCAUCAAAGUGAACAGCGAUUUCCACUCAUUCGUGCUGCCCA

GGAUAGGCAGUAACACAUUGGAGAUCGGGCUGAGAACAAGAAUCAGGAAAAUGUUAGAGGAGCACAAGGAGCCGUCAC

CUCUCAUUACCGCCGAGGACGUACAAGAAGCUAAGUGCGCAGCCGAUGAGGCUAAGGAGGUGCGUGAAGCCGAGGAGU

UGCGCGCAGCUCUACCACCUUUGGCAGCUGAUGUUGAGGAGCCCACUCUGGAGGCAGACGUCGACUUGAUGUUACAAG

AGGCUGGGGCCGGCUCAGUGGAGACACCUCGUGGCUUGAUAAAGGUUACCAGCUACGAUGGCGAGGACAAGAUCGGCU

CUUACGCUGUGCUUUCUCCGCAGGCUGUACUCAAGAGUGAAAAAUUAUCUUGCAUCCACCCUCUCGCUGAACAAGUCA

UAGUGAUAACACACUCUGGCCGAAAAGGGCGUUAUGCCGUGGAACCAUACCAUGGUAAAGUAGUGGUGCCAGAGGGAC

AUGCAAUACCCGUCCAGGACUUUCAAGCUCUGAGUGAAAGUGCCACCAUUGUGUACAACGAACGUGAGUUCGUAAACA

GGUACCUGCACCAUAUUGCCACACAUGGAGGAGCGCUGAACACUGAUGAAGAAUAUUACAAAACUGUCAAGCCCAGCG

AGCACGACGGCGAAUACCUGUACGACAUCGACAGGAAACAGUGCGUCAAGAAAGAACUAGUCACUGGGCUAGGGCUCA

CAGGCGAGCUGGUGGAUCCUCCCUUCCAUGAAUUCGCCUACGAGAGUCUGAGAACACGACCAGCCGCUCCUUACCAAG

UACCAACCAUAGGGGUGUAUGGCGUGCCAGGAUCAGGCAAGUCUGGCAUCAUUAAAAGCGCAGUCACCAAAAAAGAUC

UAGUGGUGAGCGCCAAGAAAGAAAACUGUGCAGAAAUUAUAAGGGACGUCAAGAAAAUGAAAGGGCUGGACGUCAAUG

CCAGAACUGUGGACUCAGUGCUCUUGAAUGGAUGCAAACACCCCGUAGAGACCCUGUAUAUUGACGAAGCUUUUGCUU

GUCAUGCAGGUACUCUCAGAGCGCUCAUAGCCAUUAUAAGACCUAAAAAGGCAGUGCUCUGCGGGGAUCCCAAACAGU

GCGGUUUUUUAACAUGAUGUGCCUGAAAGUGCAUUUUAACCACGAGAUUUGCACACAAGUCUUCCACAAAAGCAUCU

CUCGCCGUUGCACUAAAUCUGUGACUUCGGUCGUCUCAACCUUGUUUUACGACAAAAAAAUGAGAACGACGAAUCCGA

AAGAGACUAAGAUUGUGAUUGACACUACCGGCAGUACCAAACCUAAGCAGGACGAUCUCAUUCUCACUUGUUUCAGAG

GGUGGGUGAAGCAGUUGCAAAUAGAUUACAAAGGCAACGAAAUAAUGACGGCAGCUGCCUCUCAAGGGCUGACCCGUA

AAGGUGUGUAUGCCGUUCGGUACAAGGUGAAUGAAAAUCCUCUGUACGCACCCACCUCAGAACAUGUGAACGUCCUAC

UGACCCGCACGGAGGACCGCAUCGUGUGGAAAACACUAGCCGGCGACCCAUGGAUAAAAACACUGACUGCCAAGUACC

CUGGGAAUUUCACUGCCACGAUAGAGGAGUGGCAAGCAGAGCAUGAUGCCAUCAUGAGGCACAUCUUGGAGAGACCGG

ACCCUACCGACGUCUUCCAGAAUAAGGCAAACGUGUGUUGGGCCAAGGCUUUAGUGCCGGUGCUGAAGACCGCUGGCA

UAGACAUGACCACUGAACAAUGGAACACUGUGGAUUAUUUUGAAACGGACAAAGCUCACUCAGCAGAGAUAGUAUUGA

ACCAACUAUGCGUGAGGUUCUUUGGACUCGAUCUGGACUCCGGUCUAUUUUCUGCACCCACUGUUCCGUUAUCCAUUA

GGAAUAAUCACUGGGAUAACUCCCCGUCGCCUAACAUGUACGGGCUGAAUAAAGAAGUGGUCCGUCAGCUCUCUCGCA

GGUACCCACAACUGCCUCGGGCAGUUGCCACUGGAAGAGUCUAUGACAUGAACACUGGUACACUGCGCAAUUAUGAUC

CGCGCAUAAACCUAGUACCUGUAAACAGAAGACUGCCUCAUGCUUUAGUCCUCCACCAUAAUGAACACCCACAGAGUG

ACUUUUCUUCAUUCGUCAGCAAAUUGAAGGGCAGAACUGUCCUGGUGGUCGGGGAAAAGUUGUCCGUCCCAGGCAAAA

UGGUUGACUGGUUGUCAGACCGGCCUGAGGCUACCUUCAGAGCUCGGCUGGAUUUAGGCAUCCCAGGUGAUGUGCCCA

-continued

AAUAUGACAUAAUAUUUGUUAAUGUGAGGACCCCAUAUAAAUACCAUCACUAUCAGCAGUGUGAAGACCAUGCCAUUA

AGCUUAGCAUGUUGACCAAGAAAGCUUGUCUGCAUCUGAAUCCCGGCGGAACCUGUGUCAGCAUAGGUUAUGGUUACG

CUGACAGGGCCAGCGAAAGCAUCAUUGGUGCUAUAGCGCGGCAGUUCAAGUUUUCCCGGGUAUGCAAACCGAAAUCCU

CACUUGAAGAGACGGAAGUUCUGUUUGUAUUCAUUGGGUACGAUCGCAAGGCCCGUACGCACAAUUCUUACAAGCUUU

CAUCAACCUUGACCAACAUUUAUACAGGUUCCAGACUCCACGAAGCCGGAUGUGCACCCUCAUAUCAUGUGGUGCGAG

GGGAUAUUGCCACGGCCACCGAAGGAGUGAUUAUAAAUGCUGCUAACAGCAAAGGACAACCUGGCGGAGGGGUGUGCG

GAGCGCUGUAUAAGAAAUUCCCGGAAAGCUUCGAUUUACAGCCGAUCGAAGUAGGAAAAGCGCGACUGGUCAAAGGUG

CAGCUAAACAUAUCAUUCAUGCCGUAGGACCAAACUUCAACAAAGUUUCGGAGGUUGAAGGUGACAAACAGUUGGCAG

AGGCUUAUGAGUCCAUCGCUAAGAUUGUCAACGAUAACAAUUACAAGUCAGUAGCGAUUCCACUGUUGUCCACCGGCA

UCUUUUCCGGGAACAAAGAUCGACUAACCCAAUCAUUGAACCAUUUGCUGACAGCUUUAGACACCACUGAUGCAGAUG

UAGCCAUAUACUGCAGGGACAAGAAAUGGGAAAUGACUCUCAAGGAAGCAGUGGCUAGGAGAGAAGCAGUGGAGGAGA

UAUGCAUAUCCGACGACUCUUCAGUGACAGAACCUGAUGCAGAGCUGGUGAGGGUGCAUCCGAAGAGUUCUUUGGCUG

GAAGGAAGGGCUACAGCACAAGCGAUGGCAAAACUUUCUCAUAUUUGGAAGGGACCAAGUUUCACCAGGCGGCCAAGG

AUAUAGCAGAAAUUAAUGCCAUGUGGCCCGUUGCAACGGAGGCCAAUGAGCAGGUAUGCAUGUAUAUCCUCGGAGAAA

GCAUGAGCAGUAUUAGGUCGAAAUGCCCCGUCGAAGAGUCGGAAGCCUCCACACCACCUAGCACGCUGCCUUGCUUGU

GCAUCCAUGCCAUGACUCCAGAAAGAGUACAGCGCCUAAAAGCCUCACGUCCAGAACAAAUUACUGUGUGCUCAUCCU

UUCCAUUGCCGAAGUAUAGAAUCACUGGUGUGCAGAAGAUCCAAUGCUCCCAGCCUAUAUUGUUCUCACCGAAAGUGC

CUGCGUAUAUUCAUCCAAGGAAGUAUCUCGUGGAAACACCACCGGUAGACGAGACUCCGGAGCCAUCGGCAGAGAACC

AAUCCACAGAGGGGACACCUGAACAACCACCACUUAUAACCGAGGAUGAGACCAGGACUAGAACGCCUGAGCCGAUCA

UCAUCGAAGAGGAAGAAGAGGAUAGCAUAAGUUUGCUGUCAGAUGGCCCGACCCACCAGGUGCUGCAAGUCGAGGCAG

ACAUUCACGGGCCGCCCUCUGUAUCUAGCUCAUCCUGGUCCAUUCCUCAUGCAUCCGACUUUGAUGUGGACAGUUUAU

CCAUACUUGACACCCUGGAGGGAGCUAGCGUGACCAGCGGGGCAACGUCAGCCGAGACUAACUCUUACUUCGCAAAGA

GUAUGGAGUUUCUGGCGCGACCGGUGCCUGCGCCUCGAACAGUAUUCAGGAACCCUCCACAUCCCGCUCCGCGCACAA

GAACACCGUCACUUGCACCCAGCAGGGCCUGCUCGAGAACCAGCCUAGUUUCCACCCCGCCAGGCGUGAAUAGGGUGA

UCACUAGAGAGGAGCUCGAGGCGCUUACCCCGUCACGCACUCCUAGCAGGUCGGUCUCGAGAACCAGCCUGGUCUCCA

ACCCGCCAGGCGUAAAUAGGGUGAUUACAAGAGAGGAGUUUGAGGCGUUCGUAGCACAACAACAAUGACGGUUUGAUG

CGGGUGCAUACAUCUUUUCCUCCGACACCGGUCAAGGGCAUUUACAACAAAAAUCAGUAAGGCAAACGGUGCUAUCCG

AAGUGGUGUUGGAGAGGACCGAAUUGGAGAUUUCGUAUGCCCCGCGCCUCGACCAAGAAAAAGAAGAAUUACUACGCA

AGAAAUUACAGUUAAAUCCCACACCUGCUAACAGAAGCAGAUACCAGUCCAGGAAGGUGGAGAACAUGAAAGCCAUAA

CAGCUAGACGUAUUCUGCAAGGCCUAGGGCAUUAUUUGAAGGCAGAAGGAAAAGUGGAGUGCUACCGAACCCUGCAUC

CUGUUCCUUUGUAUUCAUCUAGUGUGAACCGUGCCUUUUCAAGCCCCAAGGUCGCAGUGGAAGCCUGUAACGCCAUGU

UGAAAGAGAACUUUCCGACUGUGGCUUCUUACUGUAUUAUUCCAGAGUACGAUGCCUAUUUGGACAUGGUUGACGGAG

CUUCAUGCUGCUUAGACACUGCCAGUUUUUGCCCUGCAAAGCUGCGCAGCUUUCCAAAGAAACACUCCUAUUUGGAAC

CCACAAUACGAUCGGCAGUGCCUUCAGCGAUCCAGAACACGCUCCAGAACGUCCUGGCAGCUGCCACAAAAAGAAAUU

GCAAUGUCACGCAAAUGAGAGAAUUGCCCGUAUUGGAUUCGGCGGCCUUUAAUGUGGAAUGCUUCAAGAAAUAUGCGU

GUAAUAAUGAAUAUUGGGAAACGUUUAAAGAAAACCCCAUCAGGCUUACUGAAGAAAACGUGGUAAAUUACAUUACCA

AAUUAAAAGGACCAAAAGCUGCUGCUCUUUUUGCGAAGACACAUAAUUUGAAUAUGUUGCAGGACAUACCAAUGGACA

GGUUUGUAAUGGACUUAAAGAGAGACGUGAAAGUGACUCCAGGAACAAAACAUACUGAAGAACGGCCCAAGGUACAGG

UGAUCCAGGCUGCCGAUCCGCUAGCAACAGCGUAUCUGUGCGGAAUCCACCGAGAGCUGGUUAGGAGAUUAAAUGCGG

UCCUGCUUCCGAACAUUCAUACACUGUUUGAUAUGUCGGCUGAAGACUUUGACGCUAUUAUAGCCGAGCACUUCCAGC

-continued

CUGGGGAUUGUGUUCUGGAAACUGACAUCGCGUCGUUUGAUAAAAGUGAGGACGACGCCAUGGCUCUGACCGCGUUAA

UGAUUCUGGAAGACUUAGGUGUGGACGCAGAGCUGUUGACGCUGAUUGAGGCGGCUUUCGGCGAAAUUUCAUCAAUAC

AUUUGCCCACUAAAACUAAAUUUAAAUUCGGAGCCAUGAUGAAAUCUGGAAUGUUCCUCACACUGUUUGUGAACACAG

UCAUUAACAUUGUAAUCGCAAGCAGAGUGUUGAGAGAACGGCUAACCGGAUCACCAUGUGCAGCAUUCAUUGGAGAUG

ACAAUAUCGUGAAAGGAGUCAAAUCGGACAAAUUAAUGGCAGACAGGUGCGCCACCUGGUUGAAUAUGGAAGUCAAGA

UUAUAGAUGCUGUGGUGGGCGAGAAAGCGCCUUAUUUCUGUGGAGGGUUUAUUUUGUGUGACUCCGUGACCGGCACAG

CGUGCCGUGUGGCAGACCCCCUAAAAAGGCUGUUUAAGCUUGGCAAACCUCUGGCAGCAGACGAUGAACAUGAUGAUG

ACAGGAGAAGGGCAUUGCAUGAAGAGUCAACACGCUGGAACCGAGUGGGUAUUCUUUCAGAGCUGUGCAAGGCAGUAG

AAUCAAGGUAUGAAACCGUAGGAACUUCCAUCAUAGUUAUGGCCAUGACUACUCUAGCUAGCAGUGUUAAAUCAUUCA

GCUACCUGAGAGGGGCCCCUAUAACUCUCUACGGCUAACCUGAAUGGACUACGACAUAGUCUAGUCCGCCAAGUCUAG

CAUAUGGCCACCAUGUUCGUGUUUCUGGUGCUGCUGCCUCUGGUGUCCAGCCAGUGUGUGAACCUGACCACCAGAACA

CAGCUGCCUCCAGCCUACACCAACAGCUUUACCAGAGGCGUGUACUACCCCGACAAGGUGUUCAGAUCCAGCGUGCUG

CACUCUACCCAGGACCUGUUCCUGCCUUUCUUCAGCAACGUGACCUGGUUCCACGCCAUCUCCGGCACCAAUGGCACC

AAGAGAUUCGACAACCCCGUGCUGCCCUUCAACGACGGGGUGUACUUUGCCAGCACCGAGAAGUCCAACAUCAUCAGA

GGCUGGAUCUUCGGCACCACACUGGACAGCAAGACCCAGAGCCUGCUGAUCGUGAACAACGCCACCAACGUGGUCAUC

AAAGUGUGCGAGUUCCAGUUCUGCAACGACCCCUUCCUGGGCGUCUACCACAAGAACAACAAGAGCUGGAUGGAAAGC

GAGUUCCGGGUGUACAGCAGCGCCAACAACUGCACCUUCGAGUACGUGUCCCAGCCUUUCCUGAUGGACCUGGAAGGC

AAGCAGGGCAACUUCAAGAACCUGCGCGAGUUCGUGUUCAAGAACAUCGACGGCUACUUCAAGAUCUACAGCAAGCAC

ACCCCUAUCAACCUCGUGCGGGAUCUGCCUCAGGGCUUCUCUGCUCUGGAACCCCUGGUGGAUCUGCCCAUCGGCAUC

AACAUCACCCGGUUUCAGACACUGCUGGCCCUGCACAGAAGCUACCUGACACCUGGCGAUAGCAGCAGCGGAUGGACA

GCUGGUGCCGCCGCUUACUAUGUGGGCUACCUGCAGCCUAGAACCUUCCUGCUGAAGUACAACGAGAACGGCACCAUC

ACCGACGCCGUGGAUUGUGCCCUUGAUCCUCUGAGCGAGACAAAGUGCACCCUGAAGUCCUUCACCGUGGAAAAGGGC

AUCUACCAGACCAGCAACUUCCGGGUGCAGCCCACCGAAUCCAUCGUGCGGUUCCCCAAUAUCACCAAUCUGUGCCCC

UUCGGCGAGGUGUUCAAUGCCACCAGAUUCGCCUCUGUGUACGCCUGGAACCGGAAGCGGAUCAGCAAUUGCGUGGCC

GACUACUCCGUGCUGUACAACUCCGCCAGCUUCAGCACCUUCAAGUGCUACGGCGUGUCCCCUACCAAGCUGAACGAC

CUGUGCUUCACAAACGUGUACGCCGACAGCUUCGUGAUCCGGGGAGAUGAAGUGCGGCAGAUUGCCCCUGGACAGACA

GGCAAGAUCGCCGACUACAACUACAAGCUGCCCGACGACUUCACCGGCUGUGUGAUUGCCUGGAACAGCAACAACCUG

GACUCCAAAGUCGGCGGCAACUACAAUUACCUGUACCGGCUGUUCCGGAAGUCCAAUCUGAAGCCCUUCGAGCGGGAC

AUCUCCACCGAGAUCUAUCAGGCCGGCAGCACCCCUUGUAACGGCGUGGAAGGCUUCAACUGCUACUUCCCACUGCAG

UCCUACGGCUUUCAGCCCACAUAUGGCGUGGGCUAUCAGCCCUACAGAGUGGUGGUGCUGAGCUUCGAACUGCUGCAU

GCCCCUGCCACAGUGUGCGGCCCUAAGAAAAGCACCAAUCUCGUGAAGAACAAAUGCGUGAACUUCAACUUCAACGGC

CUGACCGGCACAGGCGUGCUGACAGAGAGCAACAAGAAGUUCCUGCCAUUCCAGCAGUUUGGCCGGGAUAUCGACGAU

ACCACAGACGCCGUUAGAGAUCCCCAGACACUGGAAAUCCUGGACAUCACCCCUUGCAGCUUCGGCGGAGUGUCUGUG

AUCACCCCUGGCACCAACACCAGCAAUCAGGUGGCAGUGCUGUACCAGGGCGUGAACUGUACCGAAGUGCCCGUGGCC

AUUCACGCCGAUCAGCUGACACCUACAUGGCGGGUGUACUCCACCGGCAGCAAUGUGUUUCAGACCAGAGCCGGCUGU

CUGAUCGGAGCCGAGCACGUGAACAAUAGCUACGAGUGCGACAUCCCCAUCGGCGCUGGCAUCUGUGCCAGCUACCAG

ACACAGACAAACAGCCACUCUCUGGCCAGCUCUGUGGCCAGCCAGAGCAUCAUUGCCUACACAAUGUCUCUGGGCGCC

GAGAACAGCGUGGCCUACUCCAACAACUCUAUCGCUAUCCCCAUCAACUUCACCAUCAGCGUGACCACAGAGAUCCUG

CCUGUGUCCAUGACCAAGACCAGCGUGGACUGCACCAUGUACAUCUGCGGCGAUUCCACCGAGUGCUCCAACCUGCUG

CUGCAGUACGGCAGCUUCUGCACCCAGCUGAAUAGAGCCCUGACAGGGAUCGCCGUGGAACAGGACAAGAACACCCAA

GAGGUGUUCGCCCAAGUGAAGCAGAUCUACAAGACCCCUCCUAUCAAGGACUUCGGCGGCUUCAAUUUCAGCCAGAUU

-continued

CUGCCCGAUCCUAGCAAGCCCAGCAAGCGGAGCCCCAUCGAGGACCUGCUGUUCAACAAAGUGACACUGGCCGACGCC

GGCUUCAUCAAGCAGUAUGGCGAUUGUCUGGGCGACAUUGCCGCCAGGGAUCUGAUUUGCGCCCAGAAGUUUAACGGA

CUGACAGUGCUGCCUCCUCUGCUGACCGAUGAGAUGAUCGCCCAGUACACAUCUGCCCUGCUGGCCGGCACAAUCACA

AGCGGCUGGACAUUUGGAGCUGGCCCCGCUCUGCAGAUCCCCUUUCCUAUGCAGAUGGCCUACAGAUUCAACGGCAUC

GGAGUGACCCAGAAUGUGCUGUACGAGAACCAGAAGCUGAUCGCCAACCAGUUCAACAGCGCCAUCGGCAAGAUCCAG

GACAGCCUGAGCAGCACACCAAGCGCCCUGGGAAAGCUGCAGGACGUGGUCAACCAGAAUGCCCAGGCACUGAACACC

CUGGUCAAGCAGCUGUCCUCCAACUUCGGCGCCAUCAGCUCUGUGCUGAACGAUAUCCUGGCCAGACUGGACCCUCCU

GAGGCCGAGGUGCAGAUCGACAGACUGAUCACAGGCAGACUGCAGAGCCUCCAGACAUACGUGACCCAGCAGCUGAUC

AGAGCCGCCGAGAUUAGAGCCUCUGCCAAUCUGGCCGCCACCAAGAUGUCUGAGUGUGUGCUGGGCCAGAGCAAGAGA

GUGGACUUUUGCGGCAAGGGCUACCACCUGAUGAGCUUCCCUCAGUCUGCCCCUCACGGCGUGGUGUUUCUGCACGUG

ACAUACGUUCCCGCUCAAGAGAAGAAUUUCACCACCGCUCCAGCCAUCUGCCACGACGGCAAAGCCCACUUUCCUAGA

GAAGGCGUGUUCGUGUCCAACGGCACCCAUUGGUUCGUGACACAGCGGAACUUCUACGAGCCCCAGAUCAUCACCACC

CACAACACCUUCGUGUCUGGCAACUGCGACGUCGUGAUCGGCAUUGUGAACAAUACCGUGUACGACCCUCUGCAGCCC

GAGCUGGACAGCUUCAAAGAGGAACUGGACAAGUACUUUAAGAACCACACAAGCCCCGACGUGGACCUGGGCGAUAUC

AGCGGAAUCAAUGCCAGCGUCGUGAACAUCCAGAAAGAGAUCGACCGGCUGAACGAGGUGGCCAAGAAUCUGAACGAG

AGCCUGAUCGACCUGCAAGAACUGGGGAAGUACGAGCAGUACAUCAAGUGGCCCUGGUACAUCUGGCUGGGCUUUAUC

GCCGGACUGAUUGCCAUCGUGAUGGUCACAAUCAUGCUGUGUUGCAUGACCAGCUGCUGUAGCUGCCUGAAGGGCUGU

UGUAGCUGUGGCAGCUGCUGCAAGUUCGACGAGGACGAUUCUGAGCCCGUGCUGAAGGGCGUGAAACUGCACUACACA

UGAGCGGCCGCGAAUUGGCAAGCUGCUUACAUAGAACUCGCGGCGAUUGGCAUGCCGCCUUAAAAUUUUUAUUUUAUU

UUUCUUUUCUUUUCCGAAUCGGAUUUUGUUUUUAAUAUUUCAAAAAAAAAAAAAAAAAAAAAAAAAAAAAAAAAA

Accordingly, preferably the RNA construct comprises a nucleotide sequence substantially as set out in SEQ ID No: 62, or a fragment or variant thereof.

In another embodiment (the B.1.1.7 UK+E484K variant of SARS-CoV-2 glycoprotein), the RNA construct may comprise or consist of SEQ ID No: 63, as follows:

[SEQ ID No: 63]

AUGGGCGGCGCAUGAGAGAAGCCCAGACCAAUUACCUACCCAAAAUGGAGAAAGUUCACGUUGACAUCGAGGAAGACA

GCCCAUUCCUCAGAGCUUUGCAGCGGAGCUUCCCGCAGUUUGAGGUAGAAGCCAAGCAGGUCACUGAUAAUGACCAUG

CUAAUGCCAGAGCGUUUUCGCAUCUGGCUUCAAAACUGAUCGAAACGGAGGUGGACCCAUCCGACACGAUCCUUGACA

UUGGAAGUGCGCCCGCCCGCAGAAUGUAUUCUAAGCACAAGUAUCAUUGUAUCUGUCCGAUGAGAUGUGCGGAAGAUC

CGGACAGAUUGUAUAAGUAUGCAACUAAGCUGAAGAAAAACUGUAAGGAAAUAACUGAUAAGGAAUUGGACAAGAAAA

UGAAGGAGCUGGCCGCCGUCAUGAGCGACCCUGACCUGGAAACUGAGACUAUGUGCCUCCACGACGACGAGUCGUGUC

GCUACGAAGGGCAAGUCGCUGUUUACCAGGAUGUAUACGCGGUUGACGGACCGACAAGUCUCUAUCACCAAGCCAAUA

AGGGAGUUAGAGUCGCCUACUGGAUAGGCUUUGACACCACCCCUUUUAUGUUUAAGAACUUGGCUGGAGCAUAUCCAU

CAUACUCUACCAACUGGGCCGACGAAACCGUGUUAACGGCUCGUAACAUAGGCCUAUGCAGCUCUGACGUUAUGGAGC

GGUCACGUAGAGGGAUGUCCAUUCUUAGAAAGAAGUAUUUGAAACCAUCCAACAAUGUUCUAUUCUCUGUUGGCUCGA

CCAUCUACCACGAGAAGAGGGACUUACUGAGGAGCUGGCACCUGCCGUCUGUAUUUCACUUACGUGGCAAGCAAAAUU

ACACAUGUCGGUGUGAGACUAUAGUUAGUUGCGACGGGUACGUCGUUAAAAGAAUAGCUAUCAGUCCAGGCCUGUAUG

GGAAGCCUUCAGGCUAUGCUGCUACGAUGCACCGCGAGGGAUUCUUGUGCUGCAAAGUGACAGACACAUUGAACGGGG

AGAGGGUCUCUUUUCCCGUGUGCACGUAUGUGCCAGCUACAUUGUGUGACCAAAUGACUGGCAUACUGGCAACAGAUG

UCAGUGCGGACGACGCGCAAAAACUGCUGGUUGGGCUCAACCAGCGUAUAGUCGUCAACGGUCGCACCCAGAGAAACA

CCAAUACCAUGAAAAAUUACCUUUUGCCCGUAGUGGCCCAGGCAUUUGCUAGGUGGGCAAAGGAAUAUAAGGAAGAUC

-continued

AAGAAGAUGAAAGGCCACUAGGACUACGAGAUAGACAGUUAGUCAUGGGGUGUUGUUGGGCUUUUAGAAGGCACAAGA

UAACAUCUAUUUAUAAGCGCCCGGAUACCCAAACCAUCAUCAAAGUGAACAGCGAUUUCCACUCAUUCGUGCUGCCCA

GGAUAGGCAGUAACACAUUGGAGAUCGGGCUGAGAACAAGAAUCAGGAAAAUGUUAGAGGAGCACAAGGAGCCGUCAC

CUCUCAUUACCGCCGAGGACGUACAAGAAGCUAAGUGCGCAGCCGAUGAGGCUAAGGAGGUGCGUGAAGCCGAGGAGU

UGCGCGCAGCUCUACCACCUUUGGCAGCUGAUGUUGAGGAGCCCACUCUGGAGGCAGACGUCGACUUGAUGUUACAAG

AGGCUGGGGCCGGCUCAGUGGAGACACCUCGUGGCUUGAUAAAGGUUACCAGCUACGAUGGCGAGGACAAGAUCGGCU

CUUACGCUGUGCUUUCUCCGCAGGCUGUACUCAAGAGUGAAAAAUUAUCUUGCAUCCACCCUCUCGCUGAACAAGUCA

UAGUGAUAACACACUCUGGCCGAAAAGGGCGUUAUGCCGUGGAACCAUACCAUGGUAAAGUAGUGGUGCCAGAGGGAC

AUGCAAUACCCGUCCAGGACUUUCAAGCUCUGAGUGAAAGUGCCACCAUUGUGUACAACGAACGUGAGUUCGUAAACA

GGUACCUGCACCAUAUUGCCACACAUGGAGGAGCGCUGAACACUGAUGAAGAAUAUUACAAAACUGUCAAGCCCAGCG

AGCACGACGGCGAAUACCUGUACGACAUCGACAGGAAACAGUGCGUCAAGAAAGAACUAGUCACUGGGCUAGGGCUCA

CAGGCGAGCUGGUGGAUCCUCCCUUCCAUGAAUUCGCCUACGAGAGUCUGAGAACACGACCAGCCGCUCCUUACCAAG

UACCAACCAUAGGGGUGUAUGGCGUGCCAGGAUCAGGCAAGUCUGGCAUCAUUAAAAGCGCAGUCACCAAAAAAGAUC

UAGUGGUGAGCGCCAAGAAAGAAAACUGUGCAGAAAUUAUAAGGGACGUCAAGAAAAUGAAAGGGCUGGACGUCAAUG

CCAGAACUGUGGACUCAGUGCUCUUGAAUGGAUGCAAACACCCCGUAGAGACCCUGUAUAUUGACGAAGCUUUUGCUU

GUCAUGCAGGUACUCUCAGAGCGCUCAUAGCCAUUAUAAGACCUAAAAAGGCAGUGCUCUGCGGGGAUCCCAAACAGU

GCGGUUUUUUAACAUGAUGUGCCUGAAAGUGCAUUUUAACCACGAGAUUUGCACACAAGUCUUCCACAAAAGCAUCU

CUCGCCGUUGCACUAAAUCUGUGACUUCGGUCGUCUCAACCUUGUUUUACGACAAAAAAAUGAGAACGACGAAUCCGA

AAGAGACUAAGAUUGUGAUUGACACUACCGGCAGUACCAAACCUAAGCAGGACGAUCUCAUUCUCACUUGUUUCAGAG

GGUGGGUGAAGCAGUUGCAAAUAGAUUACAAAGGCAACGAAAUAAUGACGGCAGCUGCCUCUCAAGGGCUGACCCGUA

AAGGUGUGUAUGCCGUUCGGUACAAGGUGAAUGAAAAUCCUCUGUACGCACCCACCUCAGAACAUGUGAACGUCCUAC

UGACCCGCACGGAGGACCGCAUCGUGUGGAAAACACUAGCCGGCGACCCAUGGAUAAAAACACUGACUGCCAAGUACC

CUGGGAAUUUCACUGCCACGAUAGAGGAGUGGCAAGCAGAGCAUGAUGCCAUCAUGAGGCACAUCUUGGAGAGACCGG

ACCCUACCGACGUCUUCCAGAAUAAGGCAAACGUGUGUUGGGCCAAGGCUUUAGUGCCGGUGCUGAAGACCGCUGGCA

UAGACAUGACCACUGAACAAUGGAACACUGUGGAUUAUUUUGAAACGGACAAAGCUCACUCAGCAGAGAUAGUAUUGA

ACCAACUAUGCGUGAGGUUCUUUGGACUCGAUCUGGACUCCGGUCUAUUUUCUGCACCCACUGUUCCGUUAUCCAUUA

GGAAUAAUCACUGGGAUAACUCCCCGUCGCCUAACAUGUACGGGCUGAAUAAAGAAGUGGUCCGUCAGCUCUCUCGCA

GGUACCCACAACUGCCUCGGGCAGUUGCCACUGGAAGAGUCUAUGACAUGAACACUGGUACACUGCGCAAUUAUGAUC

CGCGCAUAAACCUAGUACCUGUAAACAGAAGACUGCCUCAUGCUUUAGUCCUCCACCAUAAUGAACACCCACAGAGUG

ACUUUUCUUCAUUCGUCAGCAAAUUGAAGGGCAGAACUGUCCUGGUGGUCGGGGAAAAGUUGUCCGUCCCAGGCAAAA

UGGUUGACUGGUUGUCAGACCGGCCUGAGGCUACCUUCAGAGCUCGGCUGGAUUUAGGCAUCCCAGGUGAUGUGCCCA

AAUAUGACAUAAUAUUUGUUAAUGUGAGGACCCCAUAUAAAUACCAUCACUAUCAGCAGUGUGAAGACCAUGCCAUUA

AGCUUAGCAUGUUGACCAAGAAAGCUUGUCUGCAUCUGAAUCCCGGCGGAACCUGUGUCAGCAUAGGUUAUGGUUACG

CUGACAGGGCCAGCGAAAGCAUCAUUGGUGCUAUAGCGCGGCAGUUCAAGUUUUCCCGGGUAUGCAAACCGAAAUCCU

CACUUGAAGAGACGGAAGUUCUGUUUGUAUUCAUUGGGUACGAUCGCAAGGCCCGUACGCACAAUUCUUACAAGCUUU

CAUCAACCUUGACCAACAUUUAUACAGGUUCCAGACUCCACGAAGCCGGAUGUGCACCCUCAUAUCAUGUGGUGCGAG

GGGAUAUUGCCACGGCCACCGAAGGAGUGAUUAUAAAUGCUGCUAACAGCAAAGGACAACCUGGCGGAGGGGUGUGCG

GAGCGCUGUAUAAGAAAUUCCCGGAAAGCUUCGAUUUACAGCCGAUCGAAGUAGGAAAAGCGCGACUGGUCAAAGGUG

CAGCUAAACAUAUCAUUCAUGCCGUAGGACCAAACUUCAACAAAGUUUCGGAGGUUGAAGGUGACAAACAGUUGGCAG

AGGCUUAUGAGUCCAUCGCUAAGAUUGUCAACGAUAACAAUUACAAGUCAGUAGCGAUUCCACUGUUGUCCACCGGCA

UCUUUUCCGGGAACAAAGAUCGACUAACCCAAUCAUUGAACCAUUUGCUGACAGCUUUAGACACCACUGAUGCAGAUG

-continued

UAGCCAUAUACUGCAGGGACAAGAAAUGGGAAAUGACUCUCAAGGAAGCAGUGGCUAGGAGAGAAGCAGUGGAGGAGA

UAUGCAUAUCCGACGACUCUUCAGUGACAGAACCUGAUGCAGAGCUGGUGAGGGUGCAUCCGAAGAGUUCUUUGGCUG

GAAGGAAGGGCUACAGCACAAGCGAUGGCAAAACUUUCUCAUAUUUGGAAGGGACCAAGUUUCACCAGGCGGCCAAGG

AUAUAGCAGAAAUUAAUGCCAUGUGGCCCGUUGCAACGGAGGCCAAUGAGCAGGUAUGCAUGUAUAUCCUCGGAGAAA

GCAUGAGCAGUAUUAGGUCGAAAUGCCCCGUCGAAGAGUCGGAAGCCUCCACACCACCUAGCACGCUGCCUUGCUUGU

GCAUCCAUGCCAUGACUCCAGAAAGAGUACAGCGCCUAAAAGCCUCACGUCCAGAACAAAUUACUGUGUGCUCAUCCU

UUCCAUUGCCGAAGUAUAGAAUCACUGGUGUGCAGAAGAUCCAAUGCUCCCAGCCUAUAUUGUUCUCACCGAAAGUGC

CUGCGUAUAUUCAUCCAAGGAAGUAUCUCGUGGAAACACCACCGGUAGACGAGACUCCGGAGCCAUCGGCAGAGAACC

AAUCCACAGAGGGGACACCUGAACAACCACCACUUAUAACCGAGGAUGAGACCAGGACUAGAACGCCUGAGCCGAUCA

UCAUCGAAGAGGAAGAAGAGGAUAGCAUAAGUUUGCUGUCAGAUGGCCCGACCCACCAGGUGCUGCAAGUCGAGGCAG

ACAUUCACGGGCCGCCCUCUGUAUCUAGCUCAUCCUGGUCCAUUCCUCAUGCAUCCGACUUUGAUGUGGACAGUUUAU

CCAUACUUGACACCCUGGAGGGAGCUAGCGUGACCAGCGGGGCAACGUCAGCCGAGACUAACUCUUACUUCGCAAAGA

GUAUGGAGUUUCUGGCGCGACCGGUGCCUGCGCCUCGAACAGUAUUCAGGAACCCUCCACAUCCCGCUCCGCGCACAA

GAACACCGUCACUUGCACCCAGCAGGGCCUGCUCGAGAACCAGCCUAGUUUCCACCCCGCCAGGCGUGAAUAGGGUGA

UCACUAGAGAGGAGCUCGAGGCGCUUACCCCGUCACGCACUCCUAGCAGGUCGGUCUCGAGAACCAGCCUGGUCUCCA

ACCCGCCAGGCGUAAAUAGGGUGAUUACAAGAGAGGAGUUUGAGGCGUUCGUAGCACAACAACAAUGACGGUUUGAUG

CGGGUGCAUACAUCUUUUCCUCCGACACCGGUCAAGGGCAUUUACAACAAAAAUCAGUAAGGCAAACGGUGCUAUCCG

AAGUGGUGUUGGAGAGGACCGAAUUGGAGAUUUCGUAUGCCCCGCGCCUCGACCAAGAAAAAGAAGAAUUACUACGCA

AGAAAUUACAGUUAAAUCCCACACCUGCUAACAGAAGCAGAUACCAGUCCAGGAAGGUGGAGAACAUGAAAGCCAUAA

CAGCUAGACGUAUUCUGCAAGGCCUAGGGCAUUAUUUGAAGGCAGAAGGAAAAGUGGAGUGCUACCGAACCCUGCAUC

CUGUUCCUUUGUAUUCAUCUAGUGUGAACCGUGCCUUUUCAAGCCCCAAGGUCGCAGUGGAAGCCUGUAACGCCAUGU

UGAAAGAGAACUUUCCGACUGUGGCUUCUUACUGUAUUAUUCCAGAGUACGAUGCCUAUUUGGACAUGGUUGACGGAG

CUUCAUGCUGCUUAGACACUGCCAGUUUUUGCCCUGCAAAGCUGCGCAGCUUUCCAAAGAAACACUCCUAUUUGGAAC

CCACAAUACGAUCGGCAGUGCCUUCAGCGAUCCAGAACACGCUCCAGAACGUCCUGGCAGCUGCCACAAAAAGAAAUU

GCAAUGUCACGCAAAUGAGAGAAUUGCCCGUAUUGGAUUCGGCGGCCUUUAAUGUGGAAUGCUUCAAGAAAUAUGCGU

GUAAUAAUGAAUAUUGGGAAACGUUUAAAGAAAACCCCAUCAGGCUUACUGAAGAAAACGUGGUAAAUUACAUUACCA

AAUUAAAAGGACCAAAAGCUGCUGCUCUUUUUGCGAAGACACAUAAUUUGAAUAUGUUGCAGGACAUACCAAUGGACA

GGUUUGUAAUGGACUUAAAGAGAGACGUGAAAGUGACUCCAGGAACAAAACAUACUGAAGAACGGCCCAAGGUACAGG

UGAUCCAGGCUGCCGAUCCGCUAGCAACAGCGUAUCUGUGCGGAAUCCACCGAGAGCUGGUUAGGAGAUUAAAUGCGG

UCCUGCUUCCGAACAUUCAUACACUGUUUGAUAUGUCGGCUGAAGACUUUGACGCUAUUAUAGCCGAGCACUUCCAGC

CUGGGGAUUGUGUUCUGGAAACUGACAUCGCGUCGUUUGAUAAAAGUGAGGACGACGCCAUGGCUCUGACCGCGUUAA

UGAUUCUGGAAGACUUAGGUGUGGACGCAGAGCUGUUGACGCUGAUUGAGGCGGCUUUCGGCGAAAUUUCAUCAAUAC

AUUUGCCCACUAAAACUAAAUUUAAAUUCGGAGCCAUGAUGAAAUCUGGAAUGUUCCUCACACUGUUUGUGAACACAG

UCAUUAACAUUGUAAUCGCAAGCAGAGUGUUGAGAGAACGGCUAACCGGAUCACCAUGUGCAGCAUUCAUUGGAGAUG

ACAAUAUCGUGAAAGGAGUCAAAUCGGACAAAUUAAUGGCAGACAGGUGCGCCACCUGGUUGAAUAUGGAAGUCAAGA

UUAUAGAUGCUGUGGUGGGCGAGAAAGCGCCUUAUUUCUGUGGAGGGUUUAUUUUGUGUGACUCCGUGACCGGCACAG

CGUGCCGUGUGGCAGACCCCCUAAAAAGGCUGUUUAAGCUUGGCAAACCUCUGGCAGCAGACGAUGAACAUGAUGAUG

ACAGGAGAAGGGCAUUGCAUGAAGAGUCAACACGCUGGAACCGAGUGGGUAUUCUUUCAGAGCUGUGCAAGGCAGUAG

AAUCAAGGUAUGAAACCGUAGGAACUUCCAUCAUAGUUAUGGCCAUGACUACUCUAGCUAGCAGUGUUAAAUCAUUCA

GCUACCUGAGAGGGGCCCCUAUAACUCUCUACGGCUAACCUGAAUGGACUACGACAUAGUCUAGUCCGCCAAGUCUAG

-continued

CAUAUGGCCACCAUGUUCGUGUUUCUGGUGCUGCUGCCUCUGGUGUCCAGCCAGUGUGUGAACCUGACCACCAGAACA

CAGCUGCCUCCAGCCUACACCAACAGCUUUACCAGAGGCGUGUACUACCCCGACAAGGUGUUCAGAUCCAGCGUGCUG

CACUCUACCCAGGACCUGUUCCUGCCUUUCUUCAGCAACGUGACCUGGUUCCACGCCAUCUCCGGCACCAAUGGCACC

AAGAGAUUCGACAACCCCGUGCUGCCCUUCAACGACGGGGUGUACUUUGCCAGCACCGAGAAGUCCAACAUCAUCAGA

GGCUGGAUCUUCGGCACCACACUGGACAGCAAGACCCAGAGCCUGCUGAUCGUGAACAACGCCACCAACGUGGUCAUC

AAAGUGUGCGAGUUCCAGUUCUGCAACGACCCCUUCCUGGGCGUCUACCACAAGAACAACAAGAGCUGGAUGGAAAGC

GAGUUCCGGGUGUACAGCAGCGCCAACAACUGCACCUUCGAGUACGUGUCCCAGCCUUUCCUGAUGGACCUGGAAGGC

AAGCAGGGCAACUUCAAGAACCUGCGCGAGUUCGUGUUCAAGAACAUCGACGGCUACUUCAAGAUCUACAGCAAGCAC

ACCCCUAUCAACCUCGUGCGGGAUCUGCCUCAGGGCUUCUCUGCUCUGGAACCCCUGGUGGAUCUGCCCAUCGGCAUC

AACAUCACCCGGUUUCAGACACUGCUGGCCCUGCACAGAAGCUACCUGACACCUGGCGAUAGCAGCAGCGGAUGGACA

GCUGGUGCCGCCGCUUACUAUGUGGGCUACCUGCAGCCUAGAACCUUCCUGCUGAAGUACAACGAGAACGGCACCAUC

ACCGACGCCGUGGAUUGUGCCCUUGAUCCUCUGAGCGAGACAAAGUGCACCCUGAAGUCCUUCACCGUGGAAAAGGGC

AUCUACCAGACCAGCAACUUCCGGGUGCAGCCCACCGAAUCCAUCGUGCGGUUCCCCAAUAUCACCAAUCUGUGCCCC

UUCGGCGAGGUGUUCAAUGCCACCAGAUUCGCCUCUGUGUACGCCUGGAACCGGAAGCGGAUCAGCAAUUGCGUGGCC

GACUACUCCGUGCUGUACAACUCCGCCAGCUUCAGCACCUUCAAGUGCUACGGCGUGUCCCCUACCAAGCUGAACGAC

CUGUGCUUCACAAACGUGUACGCCGACAGCUUCGUGAUCCGGGGAGAUGAAGUGCGGCAGAUUGCCCCUGGACAGACA

GGCAAGAUCGCCGACUACAACUACAAGCUGCCCGACGACUUCACCGGCUGUGUGAUUGCCUGGAACAGCAACAACCUG

GACUCCAAAGUCGGCGGCAACUACAAUUACCUGUACCGGCUGUUCCGGAAGUCCAAUCUGAAGCCCUUCGAGCGGGAC

AUCUCCACCGAGAUCUAUCAGGCCGGCAGCACCCCUUGUAACGGCGUGAAAGGCUUCAACUGCUACUUCCCACUGCAG

UCCUACGGCUUUCAGCCCACAUAUGGCGUGGGCUAUCAGCCCUACAGAGUGGUGGUGCUGAGCUUCGAACUGCUGCAU

GCCCCUGCCACAGUGUGCGGCCCUAAGAAAAGCACCAAUCUCGUGAAGAACAAAUGCGUGAACUUCAACUUCAACGGC

CUGACCGGCACAGGCGUGCUGACAGAGAGCAACAAGAAGUUCCUGCCAUUCCAGCAGUUUGGCCGGGAUAUCGACGAU

ACCACAGACGCCGUUAGAGAUCCCCAGACACUGGAAAUCCUGGACAUCACCCCUUGCAGCUUCGGCGGAGUGUCUGUG

AUCACCCCUGGCACCAACACCAGCAAUCAGGUGGCAGUGCUGUACCAGGGCGUGAACUGUACCGAAGUGCCCGUGGCC

AUUCACGCCGAUCAGCUGACACCUACAUGGCGGGUGUACUCCACCGGCAGCAAUGUGUUUCAGACCAGAGCCGGCUGU

CUGAUCGGAGCCGAGCACGUGAACAAUAGCUACGAGUGCGACAUCCCCAUCGGCGCUGGCAUCUGUGCCAGCUACCAG

ACACAGACAAACAGCCACUCUCUGGCCAGCUCUGUGGCCAGCCAGAGCAUCAUUGCCUACACAAUGUCUCUGGGCGCC

GAGAACAGCGUGGCCUACUCCAACAACUCUAUCGCUAUCCCCAUCAACUUCACCAUCAGCGUGACCACAGAGAUCCUG

CCUGUGUCCAUGACCAAGACCAGCGUGGACUGCACCAUGUACAUCUGCGGCGAUUCCACCGAGUGCUCCAACCUGCUG

CUGCAGUACGGCAGCUUCUGCACCCAGCUGAAUAGAGCCCUGACAGGGAUCGCCGUGGAACAGGACAAGAACACCCAA

GAGGUGUUCGCCCAAGUGAAGCAGAUCUACAAGACCCCUCCUAUCAAGGACUUCGGCGGCUUCAAUUUCAGCCAGAUU

CUGCCCGAUCCUAGCAAGCCCAGCAAGCGGAGCCCCAUCGAGGACCUGCUGUUCAACAAAGUGACACUGGCCGACGCC

GGCUUCAUCAAGCAGUAUGGCGAUUGUCUGGGCGACAUUGCCGCCAGGGAUCUGAUUUGCGCCCAGAAGUUUAACGGA

CUGACAGUGCUGCCUCCUCUGCUGACCGAUGAGAUGAUCGCCCAGUACACAUCUGCCCUGCUGGCCGGCACAAUCACA

AGCGGCUGGACAUUUGGAGCUGGCCCCGCUCUGCAGAUCCCCUUUCCUAUGCAGAUGGCCUACAGAUUCAACGGCAUC

GGAGUGACCCAGAAUGUGCUGUACGAGAACCAGAAGCUGAUCGCCAACCAGUUCAACAGCGCCAUCGGCAAGAUCCAG

GACAGCCUGAGCAGCACACCAAGCGCCCUGGGAAAGCUGCAGGACGUGGUCAACCAGAAUGCCCAGGCACUGAACACC

CUGGUCAAGCAGCUGUCCUCCAACUUCGGCGCCAUCAGCUCUGUGCUGAACGAUAUCCUGGCCAGACUGGACCCUCCU

GAGGCCGAGGUGCAGAUCGACAGACUGAUCACAGGCAGACUGCAGAGCCUCCAGACAUACGUGACCCAGCAGCUGAUC

AGAGCCGCCGAGAUUAGAGCCUCUGCCAAUCUGGCCGCCACCAAGAUGUCUGAGUGUGUGCUGGGCCAGAGCAAGAGA

GUGGACUUUUGCGGCAAGGGCUACCACCUGAUGAGCUUCCCUCAGUCUGCCCCUCACGGCGUGGUGUUUCUGCACGUG

-continued

ACAUACGUUCCCGCUCAAGAGAAGAAUUUCACCACCGCUCCAGCCAUCUGCCACGACGGCAAAGCCCACUUUCCUAGA

GAAGGCGUGUUCGUGUCCAACGGCACCCAUUGGUUCGUGACACAGCGGAACUUCUACGAGCCCCAGAUCAUCACCACC

CACAACACCUUCGUGUCUGGCAACUGCGACGUCGUGAUCGGCAUUGUGAACAAUACCGUGUACGACCCUCUGCAGCCC

GAGCUGGACAGCUUCAAAGAGGAACUGGACAAGUACUUUAAGAACCACACAAGCCCCGACGUGGACCUGGGCGAUAUC

AGCGGAAUCAAUGCCAGCGUCGUGAACAUCCAGAAAGAGAUCGACCGGCUGAACGAGGUGGCCAAGAAUCUGAACGAG

AGCCUGAUCGACCUGCAAGAACUGGGGAAGUACGAGCAGUACAUCAAGUGGCCCUGGUACAUCUGGCUGGGCUUUAUC

GCCGGACUGAUUGCCAUCGUGAUGGUCACAAUCAUGCUGUGUUGCAUGACCAGCUGCUGUAGCUGCCUGAAGGGCUGU

UGUAGCUGUGGCAGCUGCUGCAAGUUCGACGAGGACGAUUCUGAGCCCGUGCUGAAGGGCGUGAAACUGCACUACACA

UGAGCGGCCGCGAAUUGGCAAGCUGCUUACAUAGAACUCGCGGCGAUUGGCAUGCCGCCUUAAAAUUUUUAUUUUAUU

UUUCUUUUCUUUUCCGAAUCGGAUUUUGUUUUUAAUAUUUCAAAAAAAAAAAAAAAAAAAAAAAAAAAAAAAAAAA

Accordingly, preferably the RNA construct comprises a nucleotide sequence substantially as set out in SEQ ID No: 63, or a fragment or variant thereof.

In another embodiment (the B.1.351 South African variant of SARS-CoV-2 glycoprotein), the RNA construct may comprise or consist of SEQ ID No: 64, as follows:

[SEQ ID No: 64]

AUGGGCGGCGCAUGAGAGAAGCCCAGACCAAUUACCUACCCAAAAUGGAGAAAGUUCACGUUGACAUCGAGGAAGACA

GCCCAUUCCUCAGAGCUUUGCAGCGGAGCUUCCCGCAGUUUGAGGUAGAAGCCAAGCAGGUCACUGAUAAUGACCAUG

CUAAUGCCAGAGCGUUUUCGCAUCUGGCUUCAAAACUGAUCGAAACGGAGGUGGACCCAUCCGACACGAUCCUUGACA

UUGGAAGUGCGCCCGCCCGCAGAAUGUAUUCUAAGCACAAGUAUCAUUGUAUCUGUCCGAUGAGAUGUGCGGAAGAUC

CGGACAGAUUGUAUAAGUAUGCAACUAAGCUGAAGAAAAACUGUAAGGAAAUAACUGAUAAGGAAUUGGACAAGAAAA

UGAAGGAGCUGGCCGCCGUCAUGAGCGACCCUGACCUGGAAACUGAGACUAUGUGCCUCCACGACGACGAGUCGUGUC

GCUACGAAGGGCAAGUCGCUGUUUACCAGGAUGUAUACGCGGUUGACGGACCGACAAGUCUCUAUCACCAAGCCAAUA

AGGGAGUUAGAGUCGCCUACUGGAUAGGCUUUGACACCACCCCUUUUAUGUUUAAGAACUUGGCUGGAGCAUAUCCAU

CAUACUCUACCAACUGGGCCGACGAAACCGUGUUAACGGCUCGUAACAUAGGCCUAUGCAGCUCUGACGUUAUGGAGC

GGUCACGUAGAGGGAUGUCCAUUCUUAGAAAGAAGUAUUUGAAACCAUCCAACAAUGUUCUAUUCUCUGUUGGCUCGA

CCAUCUACCACGAGAAGAGGGACUUACUGAGGAGCUGGCACCUGCCGUCUGUAUUUCACUUACGUGGCAAGCAAAAUU

ACACAUGUCGGUGUGAGACUAUAGUUAGUUGCGACGGGUACGUCGUUAAAAGAAUAGCUAUCAGUCCAGGCCUGUAUG

GGAAGCCUUCAGGCUAUGCUGCUACGAUGCACCGCGAGGGAUUCUUGUGCUGCAAAGUGACAGACACAUUGAACGGGG

AGAGGGUCUCUUUUCCCGUGUGCACGUAUGUGCCAGCUACAUUGUGUGACCAAAUGACUGGCAUACUGGCAACAGAUG

UCAGUGCGGACGACGCGCAAAAACUGCUGGUUGGGCUCAACCAGCGUAUAGUCGUCAACGGUCGCACCCAGAGAAACA

CCAAUACCAUGAAAAAUUACCUUUUGCCCGUAGUGGCCCAGGCAUUUGCUAGGUGGGCAAAGGAAUAUAAGGAAGAUC

AAGAAGAUGAAAGGCCACUAGGACUACGAGAUAGACAGUUAGUCAUGGGGUGUUGUUGGGCUUUUAGAAGGCACAAGA

UAACAUCUAUUUAUAAGCGCCCGGAUACCCAAACCAUCAUCAAAGUGAACAGCGAUUUCCACUCAUUCGUGCUGCCCA

GGAUAGGCAGUAACACAUUGGAGAUCGGGCUGAGAACAAGAAUCAGGAAAAUGUUAGAGGAGCACAAGGAGCCGUCAC

CUCUCAUUACCGCCGAGGACGUACAAGAAGCUAAGUGCGCAGCCGAUGAGGCUAAGGAGGUGCGUGAAGCCGAGGAGU

UGCGCGCAGCUCUACCACCUUUGGCAGCUGAUGUUGAGGAGCCCACUCUGGAGGCAGACGUCGACUUGAUGUUACAAG

AGGCUGGGGCCGGCUCAGUGGAGACACCUCGUGGCUUGAUAAAGGUUACCAGCUACGAUGGCGAGGACAAGAUCGGCU

CUUACGCUGUGCUUUCUCCGCAGGCUGUACUCAAGAGUGAAAAAUUAUCUUGCAUCCACCCUCUCGCUGAACAAGUCA

UAGUGAUAACACACUCUGGCCGAAAAGGGCGUUAUGCCGUGGAACCAUACCAUGGUAAAGUAGUGGUGCCAGAGGGAC

AUGCAAUACCCGUCCAGGACUUUCAAGCUCUGAGUGAAAGUGCCACCAUUGUGUACAACGAACGUGAGUUCGUAAACA

GGUACCUGCACCAUAUUGCCACACAUGGAGGAGCGCUGAACACUGAUGAAGAAUAUUACAAAACUGUCAAGCCCAGCG

-continued

AGCACGACGGCGAAUACCUGUACGACAUCGACAGGAAACAGUGCGUCAAGAAAGAACUAGUCACUGGGCUAGGGCUCA

CAGGCGAGCUGGUGGAUCCUCCCUUCCAUGAAUUCGCCUACGAGAGUCUGAGAACACGACCAGCCGCUCCUUACCAAG

UACCAACCAUAGGGGUGUAUGGCGUGCCAGGAUCAGGCAAGUCUGGCAUCAUUAAAAGCGCAGUCACCAAAAAAGAUC

UAGUGGUGAGCGCCAAGAAAGAAAACUGUGCAGAAAUUAUAAGGGACGUCAAGAAAAUGAAAGGGCUGGACGUCAAUG

CCAGAACUGUGGACUCAGUGCUCUUGAAUGGAUGCAAACACCCCGUAGAGACCCUGUAUAUUGACGAAGCUUUUGCUU

GUCAUGCAGGUACUCUCAGAGCGCUCAUAGCCAUUAUAAGACCUAAAAAGGCAGUGCUCUGCGGGGAUCCCAAACAGU

GCGGUUUUUUUAACAUGAUGUGCCUGAAAGUGCAUUUUAACCACGAGAUUUGCACACAAGUCUUCCACAAAAGCAUCU

CUCGCCGUUGCACUAAAUCUGUGACUUCGGUCGUCUCAACCUUGUUUUACGACAAAAAAAUGAGAACGACGAAUCCGA

AAGAGACUAAGAUUGUGAUUGACACUACCGGCAGUACCAAACCUAAGCAGGACGAUCUCAUUCUCACUUGUUUCAGAG

GGUGGGUGAAGCAGUUGCAAAUAGAUUACAAAGGCAACGAAAUAAUGACGGCAGCUGCCUCUCAAGGGCUGACCCGUA

AAGGUGUGUAUGCCGUUCGGUACAAGGUGAAUGAAAAUCCUCUGUACGCACCCACCUCAGAACAUGUGAACGUCCUAC

UGACCCGCACGGAGGACCGCAUCGUGUGGAAAACACUAGCCGGCGACCCAUGGAUAAAAACACUGACUGCCAAGUACC

CUGGGAAUUUCACUGCCACGAUAGAGGAGUGGCAAGCAGAGCAUGAUGCCAUCAUGAGGCACAUCUUGGAGAGACCGG

ACCCUACCGACGUCUUCCAGAAUAAGGCAAACGUGUGUUGGGCCAAGGCUUUAGUGCCGGUGCUGAAGACCGCUGGCA

UAGACAUGACCACUGAACAAUGGAACACUGUGGAUUAUUUUGAAACGGACAAAGCUCACUCAGCAGAGAUAGUAUUGA

ACCAACUAUGCGUGAGGUUCUUUGGACUCGAUCUGGACUCCGGUCUAUUUUCUGCACCCACUGUUCCGUUAUCCAUUA

GGAAUAAUCACUGGGAUAACUCCCCGUCGCCUAACAUGUACGGGCUGAAUAAAGAAGUGGUCCGUCAGCUCUCUCGCA

GGUACCCACAACUGCCUCGGGCAGUUGCCACUGGAAGAGUCUAUGACAUGAACACUGGUACACUGCGCAAUUAUGAUC

CGCGCAUAAACCUAGUACCUGUAAACAGAAGACUGCCUCAUGCUUUAGUCCUCCACCAUAAUGAACACCCACAGAGUG

ACUUUUCUUCAUUCGUCAGCAAAUUGAAGGGCAGAACUGUCCUGGUGGUCGGGGAAAAGUUGUCCGUCCCAGGCAAAA

UGGUUGACUGGUUGUCAGACCGGCCUGAGGCUACCUUCAGAGCUCGGCUGGAUUUAGGCAUCCCAGGUGAUGUGCCCA

AAUAUGACAUAAUAUUUGUUAAUGUGAGGACCCCAUAUAAAUACCAUCACUAUCAGCAGUGUGAAGACCAUGCCAUUA

AGCUUAGCAUGUUGACCAAGAAAGCUUGUCUGCAUCUGAAUCCCGGCGGAACCUGUGUCAGCAUAGGUUAUGGUUACG

CUGACAGGGCCAGCGAAAGCAUCAUUGGUGCUAUAGCGCGGCAGUUCAAGUUUUCCCGGGUAUGCAAACCGAAAUCCU

CACUUGAAGAGACGGAAGUUCUGUUUGUAUUCAUUGGGUACGAUCGCAAGGCCCGUACGCACAAUUCUUACAAGCUUU

CAUCAACCUUGACCAACAUUUAUACAGGUUCCAGACUCCACGAAGCCGGAUGUGCACCCUCAUAUCAUGUGGUGCGAG

GGGAUAUUGCCACGGCCACCGAAGGAGUGAUUAUAAAUGCUGCUAACAGCAAAGGACAACCUGGCGGAGGGGUGUGCG

GAGCGCUGUAUAAGAAAUUCCCGGAAAGCUUCGAUUUACAGCCGAUCGAAGUAGGAAAAGCGCGACUGGUCAAAGGUG

CAGCUAAACAUAUCAUUCAUGCCGUAGGACCAAACUUCAACAAAGUUUCGGAGGUUGAAGGUGACAAACAGUUGGCAG

AGGCUUAUGAGUCCAUCGCUAAGAUUGUCAACGAUAACAAUUACAAGUCAGUAGCGAUUCCACUGUUGUCCACCGGCA

UCUUUUCCGGGAACAAAGAUCGACUAACCCAAUCAUUGAACCAUUUGCUGACAGCUUUAGACACCACUGAUGCAGAUG

UAGCCAUAUACUGCAGGGACAAGAAAUGGGAAAUGACUCUCAAGGAAGCAGUGGCUAGGAGAGAAGCAGUGGAGGAGA

UAUGCAUAUCCGACGACUCUUCAGUGACAGAACCUGAUGCAGAGCUGGUGAGGGUGCAUCCGAAGAGUUCUUUGGCUG

GAAGGAAGGGCUACAGCACAAGCGAUGGCAAAACUUUCUCAUAUUUGGAAGGGACCAAGUUUCACCAGGCGGCCAAGG

AUAUAGCAGAAAUUAAUGCCAUGUGGCCCGUUGCAACGGAGGCCAAUGAGCAGGUAUGCAUGUAUAUCCUCGGAGAAA

GCAUGAGCAGUAUUAGGUCGAAAUGCCCCGUCGAAGAGUCGGAAGCCUCCACACCACCUAGCACGCUGCCUUGCUUGU

GCAUCCAUGCCAUGACUCCAGAAAGAGUACAGCGCCUAAAAGCCUCACGUCCAGAACAAAUUACUGUGUGCUCAUCCU

UUCCAUUGCCGAAGUAUAGAAUCACUGGUGUGCAGAAGAUCCAAUGCUCCCAGCCUAUAUUGUUCUCACCGAAAGUGC

CUGCGUAUAUUCAUCCAAGGAAGUAUCUCGUGGAAACACCACCGGUAGACGAGACUCCGGAGCCAUCGGCAGAGAACC

AAUCCACAGAGGGGACACCUGAACAACCACCACUUAUAACCGAGGAUGAGACCAGGACUAGAACGCCUGAGCCGAUCA

UCAUCGAAGAGGAAGAAGAGGAUAGCAUAAGUUUGCUGUCAGAUGGCCCGACCCACCAGGUGCUGCAAGUCGAGGCAG

-continued

ACAUUCACGGGCCGCCCUCUGUAUCUAGCUCAUCCUGGUCCAUUCCUCAUGCAUCCGACUUUGAUGUGGACAGUUUAU

CCAUACUUGACACCCUGGAGGGAGCUAGCGUGACCAGCGGGGCAACGUCAGCCGAGACUAACUCUUACUUCGCAAAGA

GUAUGGAGUUUCUGGCGCGACCGGUGCCUGCGCCUCGAACAGUAUUCAGGAACCCUCCACAUCCCGCUCCGCGCACAA

GAACACCGUCACUUGCACCCAGCAGGGCCUGCUCGAGAACCAGCCUAGUUUCCACCCCGCCAGGCGUGAAUAGGGUGA

UCACUAGAGAGGAGCUCGAGGCGCUUACCCCGUCACGCACUCCUAGCAGGUCGGUCUCGAGAACCAGCCUGGUCUCCA

ACCCGCCAGGCGUAAAUAGGGUGAUUACAAGAGAGGAGUUUGAGGCGUUCGUAGCACAACAACAAUGACGGUUUGAUG

CGGGUGCAUACAUCUUUUCCUCCGACACCGGUCAAGGGCAUUUACAACAAAAAUCAGUAAGGCAAACGGUGCUAUCCG

AAGUGGUGUUGGAGAGGACCGAAUUGGAGAUUUCGUAUGCCCCGCGCCUCGACCAAGAAAAAGAAGAAUUACUACGCA

AGAAAUUACAGUUAAAUCCCACACCUGCUAACAGAAGCAGAUACCAGUCCAGGAAGGUGGAGAACAUGAAAGCCAUAA

CAGCUAGACGUAUUCUGCAAGGCCUAGGGCAUUAUUUGAAGGCAGAAGGAAAAGUGGAGUGCUACCGAACCCUGCAUC

CUGUUCCUUUGUAUUCAUCUAGUGUGAACCGUGCCUUUUCAAGCCCCAAGGUCGCAGUGGAAGCCUGUAACGCCAUGU

UGAAAGAGAACUUUCCGACUGUGGCUUCUUACUGUAUUAUUCCAGAGUACGAUGCCUAUUUGGACAUGGUUGACGGAG

CUUCAUGCUGCUUAGACACUGCCAGUUUUUGCCCUGCAAAGCUGCGCAGCUUUCCAAAGAAACACUCCUAUUUGGAAC

CCACAAUACGAUCGGCAGUGCCUUCAGCGAUCCAGAACACGCUCCAGAACGUCCUGGCAGCUGCCACAAAAAGAAAUU

GCAAUGUCACGCAAAUGAGAGAAUUGCCCGUAUUGGAUUCGGCGGCCUUUAAUGUGGAAUGCUUCAAGAAAUAUGCGU

GUAAUAAUGAAUAUUGGGAAACGUUUAAAGAAAACCCCAUCAGGCUUACUGAAGAAAACGUGGUAAAUUACAUUACCA

AAUUAAAAGGACCAAAAGCUGCUGCUCUUUUUGCGAAGACACAUAAUUUGAAUAUGUUGCAGGACAUACCAAUGGACA

GGUUUGUAAUGGACUUAAAGAGAGACGUGAAAGUGACUCCAGGAACAAAACAUACUGAAGAACGGCCCAAGGUACAGG

UGAUCCAGGCUGCCGAUCCGCUAGCAACAGCGUAUCUGUGCGGAAUCCACCGAGAGCUGGUUAGGAGAUUAAAUGCGG

UCCUGCUUCCGAACAUUCAUACACUGUUUGAUAUGUCGGCUGAAGACUUUGACGCUAUUAUAGCCGAGCACUUCCAGC

CUGGGGAUUGUGUUCUGGAAACUGACAUCGCGUCGUUUGAUAAAAGUGAGGACGACGCCAUGGCUCUGACCGCGUUAA

UGAUUCUGGAAGACUUAGGUGUGGACGCAGAGCUGUUGACGCUGAUUGAGGCGGCUUUCGGCGAAAUUUCAUCAAUAC

AUUUGCCCACUAAAACUAAAUUUAAAUUCGGAGCCAUGAUGAAAUCUGGAAUGUUCCUCACACUGUUUGUGAACACAG

UCAUUAACAUUGUAAUCGCAAGCAGAGUGUUGAGAGAACGGCUAACCGGAUCACCAUGUGCAGCAUUCAUUGGAGAUG

ACAAUAUCGUGAAAGGAGUCAAAUCGGACAAAUUAAUGGCAGACAGGUGCGCCACCUGGUUGAAUAUGGAAGUCAAGA

UUAUAGAUGCUGUGGUGGGCGAGAAAGCGCCUUAUUUCUGUGGAGGGUUUAUUUUGUGUGACUCCGUGACCGGCACAG

CGUGCCGUGUGGCAGACCCCCUAAAAAGGCUGUUUAAGCUUGGCAAACCUCUGGCAGCAGACGAUGAACAUGAUGAUG

ACAGGAGAAGGGCAUUGCAUGAAGAGUCAACACGCUGGAACCGAGUGGGUAUUCUUUCAGAGCUGUGCAAGGCAGUAG

AAUCAAGGUAUGAAACCGUAGGAACUUCCAUCAUAGUUAUGGCCAUGACUACUCUAGCUAGCAGUGUUAAAUCAUUCA

GCUACCUGAGAGGGGCCCCUAUAACUCUCUACGGCUAACCUGAAUGGACUACGACAUAGUCUAGUCCGCCAAGUCUAG

CAUAUGGCCACCAUGUUCGUGUUUCUGGUGCUGCUGCCUCUGGUGUCCAGCCAGUGUGUGAACUUCACCACCAGAACA

CAGCUGCCUCCAGCCUACACCAACAGCUUUACCAGAGGCGUGUACUACCCCGACAAGGUGUUCAGAUCCAGCGUGCUG

CACUCUACCCAGGACCUGUUCCUGCCUUUCUUCAGCAACGUGACCUGGUUCCACGCCAUCCACGUGUCCGGCACCAAU

GGCACCAAGAGAUUCGCCAACCCCGUGCUGCCCUUCAACGACGGGGUGUACUUUGCCAGCACCGAGAAGUCCAACAUC

AUCAGAGGCUGGAUCUUCGGCACCACACUGGACAGCAAGACCCAGAGCCUGCUGAUCGUGAACAACGCCACCAACGUG

GUCAUCAAAGUGUGCGAGUUCCAGUUCUGCAACGACCCCUUCCUGGGCGUCUACUACCACAAGAACAACAAGAGCUGG

AUGGAAAGCGAGUUCCGGGUGUACAGCAGCGCCAACAACUGCACCUUCGAGUACGUGUCCCAGCCUUUCCUGAUGGAC

CUGGAAGGCAAGCAGGGCAACUUCAAGAACCUGCGCGAGUUCGUGUUCAAGAACAUCGACGGCUACUUCAAGAUCUAC

AGCAAGCACACCCCUAUCAACCUCGUGCGGGGUCUGCCUCAGGGCUUCUCUGCUCUGGAACCCCUGGUGGAUCUGCCC

AUCGGCAUCAACAUCACCCGGUUUCAGACACUGCACAUAAGCUACCUGACACCUGGCGAUAGCAGCAGCGGAUGGACA

-continued

GCUGGUGCCGCCGCUUACUAUGUGGGCUACCUGCAGCCUAGAACCUUCCUGCUGAAGUACAACGAGAACGGCACCAUC

ACCGACGCCGUGGAUUGUGCCCUUGAUCCUCUGAGCGAGACAAAGUGCACCCUGAAGUCCUUCACCGUGGAAAAGGGC

AUCUACCAGACCAGCAACUUCCGGGUGCAGCCCACCGAAUCCAUCGUGCGGUUCCCCAAUAUCACCAAUCUGUGCCCC

UUCGGCGAGGUGUUCAAUGCCACCAGAUUCGCCUCUGUGUACGCCUGGAACCGGAAGCGGAUCAGCAAUUGCGUGGCC

GACUACUCCGUGCUGUACAACUCCGCCAGCUUCAGCACCUUCAAGUGCUACGGCGUGUCCCCUACCAAGCUGAACGAC

CUGUGCUUCACAAACGUGUACGCCGACAGCUUCGUGAUCCGGGGAGAUGAAGUGCGGCAGAUUGCCCCUGGACAGACA

GGCAAUAUCGCCGACUACAACUACAAGCUGCCCGACGACUUCACCGGCUGUGUGAUUGCCUGGAACAGCAACAACCUG

GACUCCAAAGUCGGCGGCAACUACAAUUACCUGUACCGGCUGUUCCGGAAGUCCAAUCUGAAGCCCUUCGAGCGGGAC

AUCUCCACCGAGAUCUAUCAGGCCGGCAGCACCCCUUGUAACGGCGUGAAAGGCUUCAACUGCUACUUCCCACUGCAG

UCCUACGGCUUUCAGCCCACAUAUGGCGUGGGCUAUCAGCCCUACAGAGUGGUGGUGCUGAGCUUCGAACUGCUGCAU

GCCCCUGCCACAGUGUGCGGCCCUAAGAAAAGCACCAAUCUCGUGAAGAACAAAUGCGUGAACUUCAACUUCAACGGC

CUGACCGGCACAGGCGUGCUGACAGAGAGCAACAAGAAGUUCCUGCCAUUCCAGCAGUUUGGCCGGGAUAUCGCCGAU

ACCACAGACGCCGUUAGAGAUCCCCAGACACUGGAAAUCCUGGACAUCACCCCUUGCAGCUUCGGCGGAGUGUCUGUG

AUCACCCCUGGCACCAACACCAGCAAUCAGGUGGCAGUGCUGUACCAGGACGUGAACUGUACCGAAGUGCCCGUGGCC

AUUCACGCCGAUCAGCUGACACCUACAUGGCGGGUGUACUCCACCGGCAGCAAUGUGUUUCAGACCAGAGCCGGCUGU

CUGAUCGGAGCCGAGCACGUGAACAAUAGCUACGAGUGCGACAUCCCCAUCGGCGCUGGCAUCUGUGCCAGCUACCAG

ACACAGACAAACAGCCCCUCUCUGGCCAGCUCUGUGGCCAGCCAGAGCAUCAUUGCCUACACAAUGUCUCUGGGCGUC

GAGAACAGCGUGGCCUACUCCAACAACUCUAUCGCUAUCCCCACCAACUUCACCAUCAGCGUGACCACAGAGAUCCUG

CCUGUGUCCAUGACCAAGACCAGCGUGGACUGCACCAUGUACAUCUGCGGCGAUUCCACCGAGUGCUCCAACCUGCUG

CUGCAGUACGGCAGCUUCUGCACCCAGCUGAAUAGAGCCCUGACAGGGAUCGCCGUGGAACAGGACAAGAACACCCAA

GAGGUGUUCGCCCAAGUGAAGCAGAUCUACAAGACCCCUCCUAUCAAGGACUUCGGCGGCUUCAAUUUCAGCCAGAUU

CUGCCCGAUCCUAGCAAGCCCAGCAAGCGGAGCCCCAUCGAGGACCUGCUGUUCAACAAAGUGACACUGGCCGACGCC

GGCUUCAUCAAGCAGUAUGGCGAUUGUCUGGGCGACAUUGCCGCCAGGGAUCUGAUUUGCGCCCAGAAGUUUAACGGA

CUGACAGUGCUGCCUCCUCUGCUGACCGAUGAGAUGAUCGCCCAGUACACAUCUGCCCUGCUGGCCGGCACAAUCACA

AGCGGCUGGACAUUUGGAGCUGGCCCCGCUCUGCAGAUCCCCUUUCCUAUGCAGAUGGCCUACAGAUUCAACGGCAUC

GGAGUGACCCAGAAUGUGCUGUACGAGAACCAGAAGCUGAUCGCCAACCAGUUCAACAGCGCCAUCGGCAAGAUCCAG

GACAGCCUGAGCAGCACACCAAGCGCCCUGGGAAAGCUGCAGGACGUGGUCAACCAGAAUGCCCAGGCACUGAACACC

CUGGUCAAGCAGCUGUCCUCCAACUUCGGCGCCAUCAGCUCUGUGCUGAACGAUAUCCUGAGCAGACUGGACCCUCCU

GAGGCCGAGGUGCAGAUCGACAGACUGAUCACAGGCAGACUGCAGAGCCUCCAGACAUACGUGACCCAGCAGCUGAUC

AGAGCCGCCGAGAUUAGAGCCUCUGCCAAUCUGGCCGCCACCAAGAUGUCUGAGUGUGUGCUGGGCCAGAGCAAGAGA

GUGGACUUUUGCGGCAAGGGCUACCACCUGAUGAGCUUCCCUCAGUCUGCCCCUCACGGCGUGGUGUUUCUGCACGUG

ACAUACGUUCCCGCUCAAGAGAAGAAUUUCACCACCGCUCCAGCCAUCUGCCACGACGGCAAAGCCCACUUUCCUAGA

GAAGGCGUGUUCGUGUCCAACGGCACCCAUUGGUUCGUGACACAGCGGAACUUCUACGAGCCCCAGAUCAUCACCACC

GACAACACCUUCGUGUCUGGCAACUGCGACGUCGUGAUCGGCAUUGUGAACAAUACCGUGUACGACCCUCUGCAGCCC

GAGCUGGACAGCUUCAAAGAGGAACUGGACAAGUACUUUAAGAACCACACAAGCCCCGACGUGGACCUGGGCGAUAUC

AGCGGAAUCAAUGCCAGCGUCGUGAACAUCCAGAAAGAGAUCGACCGGCUGAACGAGGUGGCCAAGAAUCUGAACGAG

AGCCUGAUCGACCUGCAAGAACUGGGGAAGUACGAGCAGUACAUCAAGUGGCCCUGGUACAUCUGGCUGGGCUUUAUC

GCCGGACUGAUUGCCAUCGUGAUGGUCACAAUCAUGCUGUGUUGCAUGACCAGCUGCUGUAGCUGCCUGAAGGGCUGU

UGUAGCUGUGGCAGCUGCUGCAAGUUCGACGAGGACGAUUCUGAGCCCGUGCUGAAGGGCGUGAAACUGCACUACACA

UGAGCGGCCGCGAAUUGGCAAGCUGCUUACAUAGAACUCGCGGCGAUUGGCAUGCCGCCUUAAAAUUUUUAUUUUAUU

UUUCUUUUCUUUUCCGAAUCGGAUUUUGUUUUUAAUAUUUCAAAAAAAAAAAAAAAAAAAAAAAAAAAAAAAAAAA

Accordingly, preferably the RNA construct comprises a nucleotide sequence substantially as set out in SEQ ID No: 64, or a fragment or variant thereof.

In another embodiment (the B.1.1.28 (P.1) Brazilian variant of SARS-CoV-2 glycoprotein), the RNA construct may comprise or consist of SEQ ID No: 65, as follows:

[SEQ ID No: 65]

AUGGGCGGCGCAUGAGAGAAGCCCAGACCAAUUACCUACCCAAAAUGGAGAAAGUUCACGUUGACAUCGAGGAAGACA

GCCCAUUCCUCAGAGCUUUGCAGCGGAGCUUCCCGCAGUUUGAGGUAGAAGCCAAGCAGGUCACUGAUAAUGACCAUG

CUAAUGCCAGAGCGUUUUCGCAUCUGGCUUCAAAACUGAUCGAAACGGAGGUGGACCCAUCCGACACGAUCCUUGACA

UUGGAAGUGCGCCCGCCCGCAGAAUGUAUUCUAAGCACAAGUAUCAUUGUAUCUGUCCGAUGAGAUGUGCGGAAGAUC

CGGACAGAUUGUAUAAGUAUGCAACUAAGCUGAAGAAAAACUGUAAGGAAAUAACUGAUAAGGAAUUGGACAAGAAAA

UGAAGGAGCUGGCCGCCGUCAUGAGCGACCCUGACCUGGAAACUGAGACUAUGUGCCUCCACGACGACGAGUCGUGUC

GCUACGAAGGGCAAGUCGCUGUUUACCAGGAUGUAUACGCGGUUGACGGACCGACAAGUCUCUAUCACCAAGCCAAUA

AGGGAGUUAGAGUCGCCUACUGGAUAGGCUUUGACACCACCCCUUUUAUGUUUAAGAACUUGGCUGGAGCAUAUCCAU

CAUACUCUACCAACUGGGCCGACGAAACCGUGUUAACGGCUCGUAACAUAGGCCUAUGCAGCUCUGACGUUAUGGAGC

GGUCACGUAGAGGGAUGUCCAUUCUUAGAAAGAAGUAUUUGAAACCAUCCAACAAUGUUCUAUUCUCUGUUGGCUCGA

CCAUCUACCACGAGAAGAGGGACUUACUGAGGAGCUGGCACCUGCCGUCUGUAUUUCACUUACGUGGCAAGCAAAAUU

ACACAUGUCGGUGUGAGACUAUAGUUAGUUGCGACGGGUACGUCGUUAAAAGAAUAGCUAUCAGUCCAGGCCUGUAUG

GGAAGCCUUCAGGCUAUGCUGCUACGAUGCACCGCGAGGGAUUCUUGUGCUGCAAAGUGACAGACACAUUGAACGGGG

AGAGGGUCUCUUUUCCCGUGUGCACGUAUGUGCCAGCUACAUUGUGUGACCAAAUGACUGGCAUACUGGCAACAGAUG

UCAGUGCGGACGACGCGCAAAAACUGCUGGUUGGGCUCAACCAGCGUAUAGUCGUCAACGGUCGCACCCAGAGAAACA

CCAAUACCAUGAAAAAUUACCUUUUGCCCGUAGUGGCCCAGGCAUUUGCUAGGUGGGCAAAGGAAUAUAAGGAAGAUC

AAGAAGAUGAAAGGCCACUAGGACUACGAGAUAGACAGUUAGUCAUGGGGUGUUGUUGGGCUUUUAGAAGGCACAAGA

UAACAUCUAUUUAUAAGCGCCCGGAUACCCAAACCAUCAUCAAAGUGAACAGCGAUUUCCACUCAUUCGUGCUGCCCA

GGAUAGGCAGUAACACAUUGGAGAUCGGGCUGAGAACAAGAAUCAGGAAAAUGUUAGAGGAGCACAAGGAGCCGUCAC

CUCUCAUUACCGCCGAGGACGUACAAGAAGCUAAGUGCGCAGCCGAUGAGGCUAAGGAGGUGCGUGAAGCCGAGGAGU

UGCGCGCAGCUCUACCACCUUUGGCAGCUGAUGUUGAGGAGCCCACUCUGGAGGCAGACGUCGACUUGAUGUUACAAG

AGGCUGGGGCCGGCUCAGUGGAGACACCUCGUGGCUUGAUAAAGGUUACCAGCUACGAUGGCGAGGACAAGAUCGGCU

CUUACGCUGUGCUUUCUCCGCAGGCUGUACUCAAGAGUGAAAAAUUAUCUUGCAUCCACCCUCUCGCUGAACAAGUCA

UAGUGAUAACACACUCUGGCCGAAAAGGGCGUUAUGCCGUGGAACCAUACCAUGGUAAAGUAGUGGUGCCAGAGGGAC

AUGCAAUACCCGUCCAGGACUUUCAAGCUCUGAGUGAAAGUGCCACCAUUGUGUACAACGAACGUGAGUUCGUAAACA

GGUACCUGCACCAUAUUGCCACACAUGGAGGAGCGCUGAACACUGAUGAAGAAUAUUACAAAACUGUCAAGCCCAGCG

AGCACGACGGCGAAUACCUGUACGACAUCGACAGGAAACAGUGCGUCAAGAAAGAACUAGUCACUGGGCUAGGGCUCA

CAGGCGAGCUGGUGGAUCCUCCCUUCCAUGAAUUCGCCUACGAGAGUCUGAGAACACGACCAGCCGCUCCUUACCAAG

UACCAACCAUAGGGGUGUAUGGCGUGCCAGGAUCAGGCAAGUCUGGCAUCAUUAAAAGCGCAGUCACCAAAAAAGAUC

UAGUGGUGAGCGCCAAGAAAGAAAACUGUGCAGAAAUUAUAAGGGACGUCAAGAAAAUGAAAGGGCUGGACGUCAAUG

CCAGAACUGUGGACUCAGUGCUCUUGAAUGGAUGCAAACACCCCGUAGAGACCCUGUAUAUUGACGAAGCUUUUGCUU

GUCAUGCAGGUACUCUCAGAGCGCUCAUAGCCAUUAUAAGACCUAAAAAGGCAGUGCUCUGCGGGGAUCCCAAACAGU

GCGGUUUUUUUAACAUGAUGUGCCUGAAAGUGCAUUUUAACCACGAGAUUUGCACACAAGUCUUCCACAAAAGCAUCU

CUCGCCGUUGCACUAAAUCUGUGACUUCGGUCGUCUCAACCUUGUUUUACGACAAAAAAAUGAGAACGACGAAUCCGA

AAGAGACUAAGAUUGUGAUUGACACUACCGGCAGUACCAAACCUAAGCAGGACGAUCUCAUUCUCACUUGUUUCAGAG

GGUGGGUGAAGCAGUUGCAAAUAGAUUACAAAGGCAACGAAAUAAUGACGGCAGCUGCCUCUCAAGGGCUGACCCGUA

AAGGUGUGUAUGCCGUUCGGUACAAGGUGAAUGAAAAUCCUCUGUACGCACCCACCUCAGAACAUGUGAACGUCCUAC

UGACCCGCACGGAGGACCGCAUCGUGUGGAAAACACUAGCCGGCGACCCAUGGAUAAAAACACUGACUGCCAAGUACC

-continued

CUGGGAAUUUCACUGCCACGAUAGAGGAGUGGCAAGCAGAGCAUGAUGCCAUCAUGAGGCACAUCUUGGAGAGACCGG

ACCCUACCGACGUCUUCCAGAAUAAGGCAAACGUGUGUUGGGCCAAGGCUUUAGUGCCGGUGCUGAAGACCGCUGGCA

UAGACAUGACCACUGAACAAUGGAACACUGUGGAUUAUUUUGAAACGGACAAAGCUCACUCAGCAGAGAUAGUAUUGA

ACCAACUAUGCGUGAGGUUCUUUGGACUCGAUCUGGACUCCGGUCUAUUUUCUGCACCCACUGUUCCGUUAUCCAUUA

GGAAUAAUCACUGGGAUAACUCCCCGUCGCCUAACAUGUACGGGCUGAAUAAAGAAGUGGUCCGUCAGCUCUCUCGCA

GGUACCCACAACUGCCUCGGGCAGUUGCCACUGGAAGAGUCUAUGACAUGAACACUGGUACACUGCGCAAUUAUGAUC

CGCGCAUAAACCUAGUACCUGUAAACAGAAGACUGCCUCAUGCUUUAGUCCUCCACCAUAAUGAACACCCACAGAGUG

ACUUUUCUUCAUUCGUCAGCAAAUUGAAGGGCAGAACUGUCCUGGUGGUCGGGGAAAAGUUGUCCGUCCCAGGCAAAA

UGGUUGACUGGUUGUCAGACCGGCCUGAGGCUACCUUCAGAGCUCGGCUGGAUUUAGGCAUCCCAGGUGAUGUGCCCA

AAUAUGACAUAAUAUUUGUUAAUGUGAGGACCCCAUAUAAAUACCAUCACUAUCAGCAGUGUGAAGACCAUGCCAUUA

AGCUUAGCAUGUUGACCAAGAAAGCUUGUCUGCAUCUGAAUCCCGGCGGAACCUGUGUCAGCAUAGGUUAUGGUUACG

CUGACAGGGCCAGCGAAAGCAUCAUUGGUGCUAUAGCGCGGCAGUUCAAGUUUUCCCGGGUAUGCAAACCGAAAUCCU

CACUUGAAGAGACGGAAGUUCUGUUUGUAUUCAUUGGGUACGAUCGCAAGGCCCGUACGCACAAUUCUUACAAGCUUU

CAUCAACCUUGACCAACAUUUAUACAGGUUCCAGACUCCACGAAGCCGGAUGUGCACCCUCAUAUCAUGUGGUGCGAG

GGGAUAUUGCCACGGCCACCGAAGGAGUGAUUAUAAAUGCUGCUAACAGCAAAGGACAACCUGGCGGAGGGGUGUGCG

GAGCGCUGUAUAAGAAAUUCCCGGAAAGCUUCGAUUUACAGCCGAUCGAAGUAGGAAAAGCGCGACUGGUCAAAGGUG

CAGCUAAACAUAUCAUUCAUGCCGUAGGACCAAACUUCAACAAAGUUUCGGAGGUUGAAGGUGACAAACAGUUGGCAG

AGGCUUAUGAGUCCAUCGCUAAGAUUGUCAACGAUAACAAUUACAAGUCAGUAGCGAUUCCACUGUUGUCCACCGGCA

UCUUUUCCGGGAACAAAGAUCGACUAACCCAAUCAUUGAACCAUUUGCUGACAGCUUUAGACACCACUGAUGCAGAUG

UAGCCAUAUACUGCAGGGACAAGAAAUGGGAAAUGACUCUCAAGGAAGCAGUGGCUAGGAGAGAAGCAGUGGAGGAGA

UAUGCAUAUCCGACGACUCUUCAGUGACAGAACCUGAUGCAGAGCUGGUGAGGGUGCAUCCGAAGAGUUCUUUGGCUG

GAAGGAAGGGCUACAGCACAAGCGAUGGCAAAACUUUCUCAUAUUUGGAAGGGACCAAGUUUCACCAGGCGGCCAAGG

AUAUAGCAGAAAUUAAUGCCAUGUGGCCCGUUGCAACGGAGGCCAAUGAGCAGGUAUGCAUGUAUAUCCUCGGAGAAA

GCAUGAGCAGUAUUAGGUCGAAAUGCCCCGUCGAAGAGUCGGAAGCCUCCACACCACCUAGCACGCUGCCUUGCUUGU

GCAUCCAUGCCAUGACUCCAGAAAGAGUACAGCGCCUAAAAGCCUCACGUCCAGAACAAAUUACUGUGUGCUCAUCCU

UUCCAUUGCCGAAGUAUAGAAUCACUGGUGUGCAGAAGAUCCAAUGCUCCCAGCCUAUAUUGUUCUCACCGAAAGUGC

CUGCGUAUAUUCAUCCAAGGAAGUAUCUCGUGGAAACACCACCGGUAGACGAGACUCCGGAGCCAUCGGCAGAGAACC

AAUCCACAGAGGGGACACCUGAACAACCACCACUUAUAACCGAGGAUGAGACCAGGACUAGAACGCCUGAGCCGAUCA

UCAUCGAAGAGGAAGAAGAGGAUAGCAUAAGUUUGCUGUCAGAUGGCCCGACCCACCAGGUGCUGCAAGUCGAGGCAG

ACAUUCACGGGCCGCCCUCUGUAUCUAGCUCAUCCUGGUCCAUUCCUCAUGCAUCCGACUUUGAUGUGGACAGUUUAU

CCAUACUUGACACCCUGGAGGGAGCUAGCGUGACCAGCGGGGCAACGUCAGCCGAGACUAACUCUUACUUCGCAAAGA

GUAUGGAGUUUCUGGCGCGACCGGUGCCUGCGCCUCGAACAGUAUUCAGGAACCCUCCACAUCCCGCUCCGCGCACAA

GAACACCGUCACUUGCACCCAGCAGGGCCUGCUCGAGAACCAGCCUAGUUUCCACCCCGCCAGGCGUGAAUAGGGUGA

UCACUAGAGAGGAGCUCGAGGCGCUUACCCCGUCACGCACUCCUAGCAGGUCGGUCUCGAGAACCAGCCUGGUCUCCA

ACCCGCCAGGCGUAAAUAGGGUGAUUACAAGAGAGGAGUUUGAGGCGUUCGUAGCACAACAACAAUGACGGUUUGAUG

CGGGUGCAUACAUCUUUUCCUCCGACACCGGUCAAGGGCAUUUACAACAAAAAUCAGUAAGGCAAACGGUGCUAUCCG

AAGUGGUGUUGGAGAGGACCGAAUUGGAGAUUUCGUAUGCCCCGCGCCUCGACCAAGAAAAAGAAGAAUUACUACGCA

AGAAAUUACAGUUAAAUCCCACACCUGCUAACAGAAGCAGAUACCAGUCCAGGAAGGUGGAGAACAUGAAAGCCAUAA

CAGCUAGACGUAUUCUGCAAGGCCUAGGGCAUUAUUUGAAGGCAGAAGGAAAAGUGGAGUGCUACCGAACCCUGCAUC

CUGUUCCUUUGUAUUCAUCUAGUGUGAACCGUGCCUUUUCAAGCCCCAAGGUCGCAGUGGAAGCCUGUAACGCCAUGU

-continued

UGAAAGAGAACUUUCCGACUGUGGCUUCUUACUGUAUUAUUCCAGAGUACGAUGCCUAUUUGGACAUGGUUGACGGAG

CUUCAUGCUGCUUAGACACUGCCAGUUUUUGCCCUGCAAAGCUGCGCAGCUUUCCAAAGAAACACUCCUAUUUGGAAC

CCACAAUACGAUCGGCAGUGCCUUCAGCGAUCCAGAACACGCUCCAGAACGUCCUGGCAGCUGCCACAAAAAGAAAUU

GCAAUGUCACGCAAAUGAGAGAAUUGCCCGUAUUGGAUUCGGCGGCCUUUAAUGUGGAAUGCUUCAAGAAAUAUGCGU

GUAAUAAUGAAUAUUGGGAAACGUUUAAAGAAAACCCCAUCAGGCUUACUGAAGAAAACGUGGUAAAUUACAUUACCA

AAUUAAAAGGACCAAAAGCUGCUGCUCUUUUUGCGAAGACACAUAAUUUGAAUAUGUUGCAGGACAUACCAAUGGACA

GGUUUGUAAUGGACUUAAAGAGAGACGUGAAAGUGACUCCAGGAACAAAACAUACUGAAGAACGGCCCAAGGUACAGG

UGAUCCAGGCUGCCGAUCCGCUAGCAACAGCGUAUCUGUGCGGAAUCCACCGAGAGCUGGUUAGGAGAUUAAAUGCGG

UCCUGCUUCCGAACAUUCAUACACUGUUUGAUAUGUCGGCUGAAGACUUUGACGCUAUUAUAGCCGAGCACUUCCAGC

CUGGGGAUUGUGUUCUGGAAACUGACAUCGCGUCGUUUGAUAAAAGUGAGGACGACGCCAUGGCUCUGACCGCGUUAA

UGAUUCUGGAAGACUUAGGUGUGGACGCAGAGCUGUUGACGCUGAUUGAGGCGGCUUUCGGCGAAAUUUCAUCAAUAC

AUUUGCCCACUAAAACUAAAUUUAAAUUCGGAGCCAUGAUGAAAUCUGGAAUGUUCCUCACACUGUUUGUGAACACAG

UCAUUAACAUUGUAAUCGCAAGCAGAGUGUUGAGAGAACGGCUAACCGGAUCACCAUGUGCAGCAUUCAUUGGAGAUG

ACAAUAUCGUGAAAGGAGUCAAAUCGGACAAAUUAAUGGCAGACAGGUGCGCCACCUGGUUGAAUAUGGAAGUCAAGA

UUAUAGAUGCUGUGGUGGGCGAGAAAGCGCCUUAUUUCUGUGGAGGGUUUAUUUUGUGUGACUCCGUGACCGGCACAG

CGUGCCGUGUGGCAGACCCCCUAAAAAGGCUGUUUAAGCUUGGCAAACCUCUGGCAGCAGACGAUGAACAUGAUGAUG

ACAGGAGAAGGGCAUUGCAUGAAGAGUCAACACGCUGGAACCGAGUGGGUAUUCUUUCAGAGCUGUGCAAGGCAGUAG

AAUCAAGGUAUGAAACCGUAGGAACUUCCAUCAUAGUUAUGGCCAUGACUACUCUAGCUAGCAGUGUUAAAUCAUUCA

GCUACCUGAGAGGGGCCCCUAUAACUCUCUACGGCUAACCUGAAUGGACUACGACAUAGUCUAGUCCGCCAAGUCUAG

CAUAUGGCCACCAUGUUCGUGUUUCUGGUGCUGCUGCCUCUGGUGUCCAGCCAGUGUGUGAACUUCACCAACAGAACA

CAGCUGCCUUUCGCCUACACCAACAGCUUUACCAGAGGCGUGUACUACCCCGACAAGGUGUUCAGAUCCAGCGUGCUG

CACUCUACCCAGGACCUGUUCCUGCCUUUCUUCAGCAACGUGACCUGGUUCCACGCCAUCCACGUGUCCGGCACCAAU

GGCACCAAGAGAUUCGACAACCCCGUGCUGCCCUUCAACGACGGGGUGUACUUUGCCAGCACCGAGAAGUCCAACAUC

AUCAGAGGCUGGAUCUUCGGCACCACACUGGACAGCAAGACCCAGAGCCUGCUGAUCGUGAACAACGCCACCAACGUG

GUCAUCAAAGUGUGCGAGUUCCAGUUCUGCAACUACCCCUUCCUGGGCGUCUACUACCACAAGAACAACAAGAGCUGG

AUGGAAAGCGAGUUCCGGGUGUACAGCAGCGCCAACAACUGCACCUUCGAGUACGUGUCCCAGCCUUUCCUGAUGGAC

CUGGAAGGCAAGCAGGGCAACUUCAAGAACCUGAGCGAGUUCGUGUUCAAGAACAUCGACGGCUACUUCAAGAUCUAC

AGCAAGCACACCCCUAUCAACCUCGUGCGGGAUCUGCCUCAGGGCUUCUCUGCUCUGGAACCCCUGGUGGAUCUGCCC

AUCGGCAUCAACAUCACCCGGUUUCAGACACUGCUGGCCCUGCACAGAAGCUACCUGACACCUGGCGAUAGCAGCAGC

GGAUGGACAGCUGGUGCCGCCGCUUACUAUGUGGGCUACCUGCAGCCUAGAACCUUCCUGCUGAAGUACAACGAGAAC

GGCACCAUCACCGACGCCGUGGAUUGUGCCCUUGAUCCUCUGAGCGAGACAAAGUGCACCCUGAAGUCCUUCACCGUG

GAAAAGGGCAUCUACCAGACCAGCAACUUCCGGGUGCAGCCCACCGAAUCCAUCGUGCGGUUCCCCAAUAUCACCAAU

CUGUGCCCCUUCGGCGAGGUGUUCAAUGCCACCAGAUUCGCCUCUGUGUACGCCUGGAACCGGAAGCGGAUCAGCAAU

UGCGUGGCCGACUACUCCGUGCUGUACAACUCCGCCAGCUUCAGCACCUUCAAGUGCUACGGCGUGUCCCCUACCAAG

CUGAACGACCUGUGCUUCACAAACGUGUACGCCGACAGCUUCGUGAUCCGGGGAGAUGAAGUGCGGCAGAUUGCCCCU

GGACAGACAGGCACGAUCGCCGACUACAACUACAAGCUGCCCGACGACUUCACCGGCUGUGUGAUUGCCUGGAACAGC

AACAACCUGGACUCCAAAGUCGGCGGCAACUACAAUUACCUGUACCGGCUGUUCCGGAAGUCCAAUCUGAAGCCCUUC

GAGCGGGACAUCUCCACCGAGAUCUAUCAGGCCGGCAGCACCCCUUGUAACGGCGUGAAAGGCUUCAACUGCUACUUC

CCACUGCAGUCCUACGGCUUUCAGCCCACAUAUGGCGUGGGCUAUCAGCCCUACAGAGUGGUGGUGCUGAGCUUCGAA

CUGCUGCAUGCCCCUGCCACAGUGUGCGGCCCUAAGAAAAGCACCAAUCUCGUGAAGAACAAAUGCGUGAACUUCAAC

UUCAACGGCCUGACCGGCACAGGCGUGCUGACAGAGAGCAACAAGAAGUUCCUGCCAUUCCAGCAGUUUGGCCGGGAU

-continued

AUCGCCGAUACCACAGACGCCGUUAGAGAUCCCCAGACACUGGAAAUCCUGGACAUCACCCCUUGCAGCUUCGGCGGA

GUGUCUGUGAUCACCCCUGGCACCAACACCAGCAAUCAGGUGGCAGUGCUGUACCAGGGCGUGAACUGUACCGAAGUG

CCCGUGGCCAUUCACGCCGAUCAGCUGACACCUACAUGGCGGGUGUACUCCACCGGCAGCAAUGUGUUUCAGACCAGA

GCCGGCUGUCUGAUCGGAGCCGAGUACGUGAACAAUAGCUACGAGUGCGACAUCCCCAUCGGCGCUGGCAUCUGUGCC

AGCUACCAGACACAGACAAACAGCCCCUCUCUGGCCAGCUCUGUGGCCAGCCAGAGCAUCAUUGCCUACACAAUGUCU

CUGGGCGCCGAGAACAGCGUGGCCUACUCCAACAACUCUAUCGCUAUCCCCACCAACUUCACCAUCAGCGUGACCACA

GAGAUCCUGCCUGUGUCCAUGACCAAGACCAGCGUGGACUGCACCAUGUACAUCUGCGGCGAUUCCACCGAGUGCUCC

AACCUGCUGCUGCAGUACGGCAGCUUCUGCACCCAGCUGAAUAGAGCCCUGACAGGGAUCGCCGUGGAACAGGACAAG

AACACCCAAGAGGUGUUCGCCCAAGUGAAGCAGAUCUACAAGACCCCUCCUAUCAAGGACUUCGGCGGCUUCAAUUUC

AGCCAGAUUCUGCCCGAUCCUAGCAAGCCCAGCAAGCGGAGCCCCAUCGAGGACCUGCUGUUCAACAAAGUGACACUG

GCCGACGCCGGCUUCAUCAAGCAGUAUGGCGAUUGUCUGGGCGACAUUGCCGCCAGGGAUCUGAUUUGCGCCCAGAAG

UUUAACGGACUGACAGUGCUGCCUCCUCUGCUGACCGAUGAGAUGAUCGCCCAGUACACAUCUGCCCUGCUGGCCGGC

ACAAUCACAAGCGGCUGGACAUUUGGAGCUGGCCCCGCUCUGCAGAUCCCCUUUCCUAUGCAGAUGGCCUACAGAUUC

AACGGCAUCGGAGUGACCCAGAAUGUGCUGUACGAGAACCAGAAGCUGAUCGCCAACCAGUUCAACAGCGCCAUCGGC

AAGAUCCAGGACAGCCUGAGCAGCACACCAAGCGCCCUGGGAAAGCUGCAGGACGUGGUCAACCAGAAUGCCCAGGCA

CUGAACACCCUGGUCAAGCAGCUGUCCUCCAACUUCGGCGCCAUCAGCUCUGUGCUGAACGAUAUCCUGAGCAGACUG

GACCCUCCUGAGGCCGAGGUGCAGAUCGACAGACUGAUCACAGGCAGACUGCAGAGCCUCCAGACAUACGUGACCCAG

CAGCUGAUCAGAGCCGCCGAGAUUAGAGCCUCUGCCAAUCUGGCCGCCAUCAAGAUGUCUGAGUGUGUGCUGGGCCAG

AGCAAGAGAGUGGACUUUUGCGGCAAGGGCUACCACCUGAUGAGCUUCCCUCAGUCUGCCCCUCACGGCGUGGUGUUU

CUGCACGUGACAUACGUUCCCGCUCAAGAGAAGAAUUUCACCACCGCUCCAGCCAUCUGCCACGACGGCAAAGCCCAC

UUUCCUAGAGAAGGCGUGUUCGUGUCCAACGGCACCCAUUGGUUCGUGACACAGCGGAACUUCUACGAGCCCCAGAUC

AUCACCACCGACAACACCUUCGUGUCUGGCAACUGCGACGUCGUGAUCGGCAUUGUGAACAAUACCGUGUACGACCCU

CUGCAGCCCGAGCUGGACAGCUUCAAAGAGGAACUGGACAAGUACUUUAAGAACCACACAAGCCCCGACGUGGACCUG

GGCGAUAUCAGCGGAAUCAAUGCCAGCUUCGUGAACAUCCAGAAAGAGAUCGACCGGCUGAACGAGGUGGCCAAGAAU

CUGAACGAGAGCCUGAUCGACCUGCAAGAACUGGGGAAGUACGAGCAGUACAUCAAGUGGCCCUGGUACAUCUGGCUG

GGCUUUAUCGCCGGACUGAUUGCCAUCGUGAUGGUCACAAUCAUGCUGUGUUGCAUGACCAGCUGCUGUAGCUGCCUG

AAGGGCUGUUGUAGCUGUGGCAGCUGCUGCAAGUUCGACGAGGACGAUUCUGAGCCCGUGCUGAAGGGCGUGAAACUG

CACUACACAUGAGCGGCCGCGAAUUGGCAAGCUGCUUACAUAGAACUCGCGGCGAUUGGCAUGCCGCCUUAAAAUUUU

UAUUUUAUUUUUCUUUUCUUUUCCGAAUCGGAUUUUGUUUUUAAUAUUUCAAAAAAAAAAAAAAAAAAAAAAAAAAA

AAAAAAA

Accordingly, preferably the RNA construct comprises a nucleotide sequence substantially as set out in SEQ ID No: 65, or a fragment or variant thereof.

In another embodiment (the SARS-CoV-2 surface glycoprotein with ORF4a IIP), the RNA construct may comprise or consist of SE ID No: 66, as follows:

[SEQ ID No: 66]

AUGGGCGGCGCAUGAGAGAAGCCCAGACCAAUUACCUACCCAAAAUGGAGAAAGUUCACGUUGACAUCGAGGAAGACA

GCCCAUUCCUCAGAGCUUUGCAGCGGAGCUUCCCGCAGUUUGAGGUAGAAGCCAAGCAGGUCACUGAUAAUGACCAUG

CUAAUGCCAGAGCGUUUUCGCAUCUGGCUUCAAAACUGAUCGAAACGGAGGUGGACCCAUCCGACACGAUCCUUGACA

UUGGAAGUGCGCCCGCCCGCAGAAUGUAUUCUAAGCACAAGUAUCAUUGUAUCUGUCCGAUGAGAUGUGCGGAAGAUC

CGGACAGAUUGUAUAAGUAUGCAACUAAGCUGAAGAAAAACUGUAAGGAAAUAACUGAUAAGGAAUUGGACAAGAAAA

UGAAGGAGCUGGCCGCCGUCAUGAGCGACCCUGACCUGGAAACUGAGACUAUGUGCCUCCACGACGACGAGUCGUGUC

-continued

GCUACGAAGGGCAAGUCGCUGUUUACCAGGAUGUAUACGCGGUUGACGGACCGACAAGUCUCUAUCACCAAGCCAAUA

AGGGAGUUAGAGUCGCCUACUGGAUAGGCUUUGACACCACCCCUUUUAUGUUUAAGAACUUGGCUGGAGCAUAUCCAU

CAUACUCUACCAACUGGGCCGACGAAACCGUGUUAACGGCUCGUAACAUAGGCCUAUGCAGCUCUGACGUUAUGGAGC

GGUCACGUAGAGGGAUGUCCAUUCUUAGAAAGAAGUAUUUGAAACCAUCCAACAAUGUUCUAUUCUCUGUUGGCUCGA

CCAUCUACCACGAGAAGAGGGACUUACUGAGGAGCUGGCACCUGCCGUCUGUAUUUCACUUACGUGGCAAGCAAAAUU

ACACAUGUCGGUGUGAGACUAUAGUUAGUUGCGACGGGUACGUCGUUAAAAGAAUAGCUAUCAGUCCAGGCCUGUAUG

GGAAGCCUUCAGGCUAUGCUGCUACGAUGCACCGCGAGGGAUUCUUGUGCUGCAAAGUGACAGACACAUUGAACGGGG

AGAGGGUCUCUUUUCCCGUGUGCACGUAUGUGCCAGCUACAUUGUGUGACCAAAUGACUGGCAUACUGGCAACAGAUG

UCAGUGCGGACGACGCGCAAAAACUGCUGGUUGGGCUCAACCAGCGUAUAGUCGUCAACGGUCGCACCCAGAGAAACA

CCAAUACCAUGAAAAAUUACCUUUUGCCCGUAGUGGCCCAGGCAUUUGCUAGGUGGGCAAAGGAAUAUAAGGAAGAUC

AAGAAGAUGAAAGGCCACUAGGACUACGAGAUAGACAGUUAGUCAUGGGGUGUUGUUGGGCUUUUAGAAGGCACAAGA

UAACAUCUAUUUAUAAGCGCCCGGAUACCCAAACCAUCAUCAAAGUGAACAGCGAUUUCCACUCAUUCGUGCUGCCCA

GGAUAGGCAGUAACACAUUGGAGAUCGGGCUGAGAACAAGAAUCAGGAAAAUGUUAGAGGAGCACAAGGAGCCGUCAC

CUCUCAUUACCGCCGAGGACGUACAAGAAGCUAAGUGCGCAGCCGAUGAGGCUAAGGAGGUGCGUGAAGCCGAGGAGU

UGCGCGCAGCUCUACCACCUUUGGCAGCUGAUGUUGAGGAGCCCACUCUGGAGGCAGACGUCGACUUGAUGUUACAAG

AGGCUGGGGCCGGCUCAGUGGAGACACCUCGUGGCUUGAUAAAGGUUACCAGCUACGAUGGCGAGGACAAGAUCGGCU

CUUACGCUGUGCUUUCUCCGCAGGCUGUACUCAAGAGUGAAAAAUUAUCUUGCAUCCACCCUCUCGCUGAACAAGUCA

UAGUGAUAACACACUCUGGCCGAAAAGGGCGUUAUGCCGUGGAACCAUACCAUGGUAAAGUAGUGGUGCCAGAGGGAC

AUGCAAUACCCGUCCAGGACUUUCAAGCUCUGAGUGAAAGUGCCACCAUUGUGUACAACGAACGUGAGUUCGUAAACA

GGUACCUGCACCAUAUUGCCACACAUGGAGGAGCGCUGAACACUGAUGAAGAAUAUUACAAAACUGUCAAGCCCAGCG

AGCACGACGGCGAAUACCUGUACGACAUCGACAGGAAACAGUGCGUCAAGAAAGAACUAGUCACUGGGCUAGGGCUCA

CAGGCGAGCUGGUGGAUCCUCCCUUCCAUGAAUUCGCCUACGAGAGUCUGAGAACACGACCAGCCGCUCCUUACCAAG

UACCAACCAUAGGGGUGUAUGGCGUGCCAGGAUCAGGCAAGUCUGGCAUCAUUAAAAGCGCAGUCACCAAAAAAGAUC

UAGUGGUGAGCGCCAAGAAAGAAAACUGUGCAGAAAUUAUAAGGGACGUCAAGAAAAUGAAAGGGCUGGACGUCAAUG

CCAGAACUGUGGACUCAGUGCUCUUGAAUGGAUGCAAACACCCCGUAGAGACCCUGUAUAUUGACGAAGCUUUUGCUU

GUCAUGCAGGUACUCUCAGAGCGCUCAUAGCCAUUAUAAGACCUAAAAAGGCAGUGCUCUGCGGGGAUCCCAAACAGU

GCGGUUUUUUAACAUGAUGUGCCUGAAAGUGCAUUUUAACCACGAGAUUUGCACACAAGUCUUCCACAAAAGCAUCU

CUCGCCGUUGCACUAAAUCUGUGACUUCGGUCGUCUCAACCUUGUUUUACGACAAAAAAAUGAGAACGACGAAUCCGA

AAGAGACUAAGAUUGUGAUUGACACUACCGGCAGUACCAAACCUAAGCAGGACGAUCUCAUUCUCACUUGUUUCAGAG

GGUGGGUGAAGCAGUUGCAAAUAGAUUACAAAGGCAACGAAAUAAUGACGGCAGCUGCCUCUCAAGGGCUGACCCGUA

AAGGUGUGUAUGCCGUUCGGUACAAGGUGAAUGAAAAUCCUCUGUACGCACCCACCUCAGAACAUGUGAACGUCCUAC

UGACCCGCACGGAGGACCGCAUCGUGUGGAAAACACUAGCCGGCGACCCAUGGAUAAAAACACUGACUGCCAAGUACC

CUGGGAAUUUCACUGCCACGAUAGAGGAGUGGCAAGCAGAGCAUGAUGCCAUCAUGAGGCACAUCUUGGAGAGACCGG

ACCCUACCGACGUCUUCCAGAAUAAGGCAAACGUGUGUUGGGCCAAGGCUUUAGUGCCGGUGCUGAAGACCGCUGGCA

UAGACAUGACCACUGAACAAUGGAACACUGUGGAUUAUUUUGAAACGGACAAAGCUCACUCAGCAGAGAUAGUAUUGA

ACCAACUAUGCGUGAGGUUCUUUGGACUCGAUCUGGACUCCGGUCUAUUUUCUGCACCCACUGUUCCGUUAUCCAUUA

GGAAUAAUCACUGGGAUAACUCCCCGUCGCCUAACAUGUACGGGCUGAAUAAAGAAGUGGUCCGUCAGCUCUCUCGCA

GGUACCCACAACUGCCUCGGGCAGUUGCCACUGGAAGAGUCUAUGACAUGAACACUGGUACACUGCGCAAUUAUGAUC

CGCGCAUAAACCUAGUACCUGUAAACAGAAGACUGCCUCAUGCUUUAGUCCUCCACCAUAAUGAACACCCACAGAGUG

ACUUUUCUUCAUUCGUCAGCAAAUUGAAGGGCAGAACUGUCCUGGUGGUCGGGGAAAAGUUGUCCGUCCCAGGCAAAA

UGGUUGACUGGUUGUCAGACCGGCCUGAGGCUACCUUCAGAGCUCGGCUGGAUUUAGGCAUCCCAGGUGAUGUGCCCA

-continued

AAUAUGACAUAAUAUUUGUUAAUGUGAGGACCCCAUAUAAAUACCAUCACUAUCAGCAGUGUGAAGACCAUGCCAUUA

AGCUUAGCAUGUUGACCAAGAAAGCUUGUCUGCAUCUGAAUCCCGGCGGAACCUGUGUCAGCAUAGGUUAUGGUUACG

CUGACAGGGCCAGCGAAAGCAUCAUUGGUGCUAUAGCGCGGCAGUUCAAGUUUUCCCGGGUAUGCAAACCGAAAUCCU

CACUUGAAGAGACGGAAGUUCUGUUUGUAUUCAUUGGGUACGAUCGCAAGGCCCGUACGCACAAUUCUUACAAGCUUU

CAUCAACCUUGACCAACAUUUAUACAGGUUCCAGACUCCACGAAGCCGGAUGUGCACCCUCAUAUCAUGUGGUGCGAG

GGGAUAUUGCCACGGCCACCGAAGGAGUGAUUAUAAAUGCUGCUAACAGCAAAGGACAACCUGGCGGAGGGGUGUGCG

GAGCGCUGUAUAAGAAAUUCCCGGAAAGCUUCGAUUUACAGCCGAUCGAAGUAGGAAAAGCGCGACUGGUCAAAGGUG

CAGCUAAACAUAUCAUUCAUGCCGUAGGACCAAACUUCAACAAAGUUUCGGAGGUUGAAGGUGACAAACAGUUGGCAG

AGGCUUAUGAGUCCAUCGCUAAGAUUGUCAACGAUAACAAUUACAAGUCAGUAGCGAUUCCACUGUUGUCCACCGGCA

UCUUUUCCGGGAACAAAGAUCGACUAACCCAAUCAUUGAACCAUUUGCUGACAGCUUUAGACACCACUGAUGCAGAUG

UAGCCAUAUACUGCAGGGACAAGAAAUGGGAAAUGACUCUCAAGGAAGCAGUGGCUAGGAGAGAAGCAGUGGAGGAGA

UAUGCAUAUCCGACGACUCUUCAGUGACAGAACCUGAUGCAGAGCUGGUGAGGGUGCAUCCGAAGAGUUCUUUGGCUG

GAAGGAAGGGCUACAGCACAAGCGAUGGCAAAACUUUCUCAUAUUUGGAAGGGACCAAGUUUCACCAGGCGGCCAAGG

AUAUAGCAGAAAUUAAUGCCAUGUGGCCCGUUGCAACGGAGGCCAAUGAGCAGGUAUGCAUGUAUAUCCUCGGAGAAA

GCAUGAGCAGUAUUAGGUCGAAAUGCCCCGUCGAAGAGUCGGAAGCCUCCACACCACCUAGCACGCUGCCUUGCUUGU

GCAUCCAUGCCAUGACUCCAGAAAGAGUACAGCGCCUAAAAGCCUCACGUCCAGAACAAAUUACUGUGUGCUCAUCCU

UUCCAUUGCCGAAGUAUAGAAUCACUGGUGUGCAGAAGAUCCAAUGCUCCCAGCCUAUAUUGUUCUCACCGAAAGUGC

CUGCGUAUAUUCAUCCAAGGAAGUAUCUCGUGGAAACACCACCGGUAGACGAGACUCCGGAGCCAUCGGCAGAGAACC

AAUCCACAGAGGGGACACCUGAACAACCACCACUUAUAACCGAGGAUGAGACCAGGACUAGAACGCCUGAGCCGAUCA

UCAUCGAAGAGGAAGAAGAGGAUAGCAUAAGUUUGCUGUCAGAUGGCCCGACCCACCAGGUGCUGCAAGUCGAGGCAG

ACAUUCACGGGCCGCCCUCUGUAUCUAGCUCAUCCUGGUCCAUUCCUCAUGCAUCCGACUUUGAUGUGGACAGUUUAU

CCAUACUUGACACCCUGGAGGGAGCUAGCGUGACCAGCGGGGCAACGUCAGCCGAGACUAACUCUUACUUCGCAAAGA

GUAUGGAGUUUCUGGCGCGACCGGUGCCUGCGCCUCGAACAGUAUUCAGGAACCCUCCACAUCCCGCUCCGCGCACAA

GAACACCGUCACUUGCACCCAGCAGGGCCUGCUCGAGAACCAGCCUAGUUUCCACCCCGCCAGGCGUGAAUAGGGUGA

UCACUAGAGAGGAGCUCGAGGCGCUUACCCCGUCACGCACUCCUAGCAGGUCGGUCUCGAGAACCAGCCUGGUCUCCA

ACCCGCCAGGCGUAAAUAGGGUGAUUACAAGAGAGGAGUUUGAGGCGUUCGUAGCACAACAACAAUGACGGUUUGAUG

CGGGUGCAUACAUCUUUUCCUCCGACACCGGUCAAGGGCAUUUACAACAAAAAUCAGUAAGGCAAACGGUGCUAUCCG

AAGUGGUGUUGGAGAGGACCGAAUUGGAGAUUUCGUAUGCCCCGCGCCUCGACCAAGAAAAAGAAGAAUUACUACGCA

AGAAAUUACAGUUAAAUCCCACACCUGCUAACAGAAGCAGAUACCAGUCCAGGAAGGUGGAGAACAUGAAAGCCAUAA

CAGCUAGACGUAUUCUGCAAGGCCUAGGGCAUUAUUUGAAGGCAGAAGGAAAAGUGGAGUGCUACCGAACCCUGCAUC

CUGUUCCUUUGUAUUCAUCUAGUGUGAACCGUGCCUUUUCAAGCCCCAAGGUCGCAGUGGAAGCCUGUAACGCCAUGU

UGAAAGAGAACUUUCCGACUGUGGCUUCUUACUGUAUUAUUCCAGAGUACGAUGCCUAUUUGGACAUGGUUGACGGAG

CUUCAUGCUGCUUAGACACUGCCAGUUUUUGCCCUGCAAAGCUGCGCAGCUUUCCAAAGAAACACUCCUAUUUGGAAC

CCACAAUACGAUCGGCAGUGCCUUCAGCGAUCCAGAACACGCUCCAGAACGUCCUGGCAGCUGCCACAAAAAGAAAUU

GCAAUGUCACGCAAAUGAGAGAAUUGCCCGUAUUGGAUUCGGCGGCCUUUAAUGUGGAAUGCUUCAAGAAAUAUGCGU

GUAAUAAUGAAUAUUGGGAAACGUUUAAAGAAAACCCCAUCAGGCUUACUGAAGAAAACGUGGUAAAUUACAUUACCA

AAUUAAAAGGACCAAAAGCUGCUGCUCUUUUUGCGAAGACACAUAAUUUGAAUAUGUUGCAGGACAUACCAAUGGACA

GGUUUGUAAUGGACUUAAAGAGAGACGUGAAAGUGACUCCAGGAACAAAACAUACUGAAGAACGGCCCAAGGUACAGG

UGAUCCAGGCUGCCGAUCCGCUAGCAACAGCGUAUCUGUGCGGAAUCCACCGAGAGCUGGUUAGGAGAUUAAAUGCGG

UCCUGCUUCCGAACAUUCAUACACUGUUUGAUAUGUCGGCUGAAGACUUUGACGCUAUUAUAGCCGAGCACUUCCAGC

-continued

CUGGGGAUUGUGUUCUGGAAACUGACAUCGCGUCGUUUGAUAAAAGUGAGGACGACGCCAUGGCUCUGACCGCGUUAA

UGAUUCUGGAAGACUUAGGUGUGGACGCAGAGCUGUUGACGCUGAUUGAGGCGGCUUUCGGCGAAAUUUCAUCAAUAC

AUUUGCCCACUAAAACUAAAUUUAAAUUCGGAGCCAUGAUGAAAUCUGGAAUGUUCCUCACACUGUUUGUGAACACAG

UCAUUAACAUUGUAAUCGCAAGCAGAGUGUUGAGAGAACGGCUAACCGGAUCACCAUGUGCAGCAUUCAUUGGAGAUG

ACAAUAUCGUGAAAGGAGUCAAAUCGGACAAAUUAAUGGCAGACAGGUGCGCCACCUGGUUGAAUAUGGAAGUCAAGA

UUAUAGAUGCUGUGGUGGGCGAGAAAGCGCCUUAUUUCUGUGGAGGGUUUAUUUUGUGUGACUCCGUGACCGGCACAG

CGUGCCGUGUGGCAGACCCCCUAAAAAGGCUGUUUAAGCUUGGCAAACCUCUGGCAGCAGACGAUGAACAUGAUGAUG

ACAGGAGAAGGGCAUUGCAUGAAGAGUCAACACGCUGGAACCGAGUGGGUAUUCUUUCAGAGCUGUGCAAGGCAGUAG

AAUCAAGGUAUGAAACCGUAGGAACUUCCAUCAUAGUUAUGGCCAUGACUACUCUAGCUAGCAGUGUUAAAUCAUUCA

GCUACCUGAGAGGGGCCCCUAUAACUCUCUACGGCUAACCUGAAUGGACUACGACAUAGUCUAGUCCGCCAAGUCUAG

CAUAUGGCCACCAUGUUCGUGUUUCUGGUGCUGCUGCCUCUGGUGUCCAGCCAGUGUGUGAACCUGACCACCAGAACA

CAGCUGCCUCCAGCCUACACCAACAGCUUUACCAGAGGCGUGUACUACCCCGACAAGGUGUUCAGAUCCAGCGUGCUG

CACUCUACCCAGGACCUGUUCCUGCCUUUCUUCAGCAACGUGACCUGGUUCCACGCCAUCCACGUGUCCGGCACCAAU

GGCACCAAGAGAUUCGACAACCCCGUGCUGCCCUUCAACGACGGGGUGUACUUUGCCAGCACCGAGAAGUCCAACAUC

AUCAGAGGCUGGAUCUUCGGCACCACACUGGACAGCAAGACCCAGAGCCUGCUGAUCGUGAACAACGCCACCAACGUG

GUCAUCAAAGUGUGCGAGUUCCAGUUCUGCAACGACCCCUUCCUGGGCGUCUACUACCACAAGAACAACAAGAGCUGG

AUGGAAAGCGAGUUCCGGGUGUACAGCAGCGCCAACAACUGCACCUUCGAGUACGUGUCCCAGCCUUUCCUGAUGGAC

CUGGAAGGCAAGCAGGGCAACUUCAAGAACCUGCGCGAGUUCGUGUUCAAGAACAUCGACGGCUACUUCAAGAUCUAC

AGCAAGCACACCCCUAUCAACCUCGUGCGGGAUCUGCCUCAGGGCUUCUCUGCUCUGGAACCCCUGGUGGAUCUGCCC

AUCGGCAUCAACAUCACCCGGUUUCAGACACUGCUGGCCCUGCACAGAAGCUACCUGACACCUGGCGAUAGCAGCAGC

GGAUGGACAGCUGGUGCCGCCGCUUACUAUGUGGGCUACCUGCAGCCUAGAACCUUCCUGCUGAAGUACAACGAGAAC

GGCACCAUCACCGACGCCGUGGAUUGUGCCCUUGAUCCUCUGAGCGAGACAAAGUGCACCCUGAAGUCCUUCACCGUG

GAAAAGGGCAUCUACCAGACCAGCAACUUCCGGGUGCAGCCCACCGAAUCCAUCGUGCGGUUCCCCAAUAUCACCAAU

CUGUGCCCCUUCGGCGAGGUGUUCAAUGCCACCAGAUUCGCCUCUGUGUACGCCUGGAACCGGAAGCGGAUCAGCAAU

UGCGUGGCCGACUACUCCGUGCUGUACAACUCCGCCAGCUUCAGCACCUUCAAGUGCUACGGCGUGUCCCCUACCAAG

CUGAACGACCUGUGCUUCACAAACGUGUACGCCGACAGCUUCGUGAUCCGGGGAGAUGAAGUGCGGCAGAUUGCCCCU

GGACAGACAGGCAAGAUCGCCGACUACAACUACAAGCUGCCCGACGACUUCACCGGCUGUGUGAUUGCCUGGAACAGC

AACAACCUGGACUCCAAAGUCGGCGGCAACUACAAUUACCUGUACCGGCUGUUCCGGAAGUCCAAUCUGAAGCCCUUC

GAGCGGGACAUCUCCACCGAGAUCUAUCAGGCCGGCAGCACCCCUUGUAACGGCGUGGAAGGCUUCAACUGCUACUUC

CCACUGCAGUCCUACGGCUUUCAGCCCACAAAUGGCGUGGGCUAUCAGCCCUACAGAGUGGUGGUGCUGAGCUUCGAA

CUGCUGCAUGCCCCUGCCACAGUGUGCGGCCCUAAGAAAAGCACCAAUCUCGUGAAGAACAAAUGCGUGAACUUCAAC

UUCAACGGCCUGACCGGCACAGGCGUGCUGACAGAGAGCAACAAGAAGUUCCUGCCAUUCCAGCAGUUUGGCCGGGAU

AUCGCCGAUACCACAGACGCCGUUAGAGAUCCCCAGACACUGGAAAUCCUGGACAUCACCCCUUGCAGCUUCGGCGGA

GUGUCUGUGAUCACCCCUGGCACCAACACCAGCAAUCAGGUGGCAGUGCUGUACCAGGACGUGAACUGUACCGAAGUG

CCCGUGGCCAUUCACGCCGAUCAGCUGACACCUACAUGGCGGGUGUACUCCACCGGCAGCAAUGUGUUUCAGACCAGA

GCCGGCUGUCUGAUCGGAGCCGAGCACGUGAACAAUAGCUACGAGUGCGACAUCCCCAUCGGCGCUGGCAUCUGUGCC

AGCUACCAGACACAGACAAACAGCCCCAGACGGGCCAGAUCUGUGGCCAGCCAGAGCAUCAUUGCCUACACAAUGUCU

CUGGGCGCCGAGAACAGCGUGGCCUACUCCAACAACUCUAUCGCUAUCCCCACCAACUUCACCAUCAGCGUGACCACA

GAGAUCCUGCCUGUGUCCAUGACCAAGACCAGCGUGGACUGCACCAUGUACAUCUGCGGCGAUUCCACCGAGUGCUCC

AACCUGCUGCUGCAGUACGGCAGCUUCUGCACCCAGCUGAAUAGAGCCCUGACAGGGAUCGCCGUGGAACAGGACAAG

AACACCCAAGAGGUGUUCGCCCAAGUGAAGCAGAUCUACAAGACCCCUCCUAUCAAGGACUUCGGCGGCUUCAAUUUC

-continued

AGCCAGAUUCUGCCCGAUCCUAGCAAGCCCAGCAAGCGGAGCUUCAUCGAGGACCUGCUGUUCAACAAAGUGACACUG

GCCGACGCCGGCUUCAUCAAGCAGUAUGGCGAUUGUCUGGGCGACAUUGCCGCCAGGGAUCUGAUUUGCGCCCAGAAG

UUUAACGGACUGACAGUGCUGCCUCCUCUGCUGACCGAUGAGAUGAUCGCCCAGUACACAUCUGCCCUGCUGGCCGGC

ACAAUCACAAGCGGCUGGACAUUUGGAGCUGGCGCCGCUCUGCAGAUCCCCUUUGCUAUGCAGAUGGCCUACAGAUUC

AACGGCAUCGGAGUGACCCAGAAUGUGCUGUACGAGAACCAGAAGCUGAUCGCCAACCAGUUCAACAGCGCCAUCGGC

AAGAUCCAGGACAGCCUGAGCAGCACAGCAAGCGCCCUGGGAAAGCUGCAGGACGUGGUCAACCAGAAUGCCCAGGCA

CUGAACACCCUGGUCAAGCAGCUGUCCUCCAACUUCGGCGCCAUCAGCUCUGUGCUGAACGAUAUCCUGAGCAGACUG

GACCCUCCUGAGGCCGAGGUGCAGAUCGACAGACUGAUCACAGGCAGACUGCAGAGCCUCCAGACAUACGUGACCCAG

CAGCUGAUCAGAGCCGCCGAGAUUAGAGCCUCUGCCAAUCUGGCCGCCACCAAGAUGUCUGAGUGUGUGCUGGGCCAG

AGCAAGAGAGUGGACUUUUGCGGCAAGGGCUACCACCUGAUGAGCUUCCCUCAGUCUGCCCCUCACGGCGUGGUGUUU

CUGCACGUGACAUACGUUCCCGCUCAAGAGAAGAAUUUCACCACCGCUCCAGCCAUCUGCCACGACGGCAAAGCCCAC

UUUCCUAGAGAAGGCGUGUUCGUGUCCAACGGCACCCAUUGGUUCGUGACACAGCGGAACUUCUACGAGCCCCAGAUC

AUCACCACCGACAACACCUUCGUGUCUGGCAACUGCGACGUCGUGAUCGGCAUUGUGAACAAUACCGUGUACGACCCU

CUGCAGCCCGAGCUGGACAGCUUCAAAGAGGAACUGGACAAGUACUUUAAGAACCACACAAGCCCCGACGUGGACCUG

GGCGAUAUCAGCGGAAUCAAUGCCAGCGUCGUGAACAUCCAGAAAGAGAUCGACCGGCUGAACGAGGUGGCCAAGAAU

CUGAACGAGAGCCUGAUCGACCUGCAAGAACUGGGGAAGUACGAGCAGUACAUCAAGUGGCCCUGGUACAUCUGGCUG

GGCUUUAUCGCCGGACUGAUUGCCAUCGUGAUGGUCACAAUCAUGCUGUGUUGCAUGACCAGCUGCUGUAGCUGCCUG

AAGGGCUGUUGUAGCUGUGGCAGCUGCUGCAAGUUCGACGAGGACGAUUCUGAGCCCGUGCUGAAGGGCGUGAAACUG

CACUACACAGAUCGGAGAAAGAGAGGCUCUGGCGAAGGCAGAGGCAGCCUGCUUACAUGUGGCGACGUGGAAGAGAAC

CCCGGACCUAUGGAUUAUGUGUCCCUGCUGAACCAGAUUUGGCAGAAGUACCUGAACAGCCCCUACACCACCUGUCUG

UACAUCCCCAAGCCUACCGCCAAGUACACACCUCUCGUGGGCACAUCUCUGCACCCCGUGCUGUGGAAUUGCCAGCUG

AGCUUUGCCGGCUACACCGAGUCUGCCGUGAACAGCACAAAGGCCCUGGCCAAACAGGACGCCGCUCAGAGAAUUGCC

UGGCUGCUGCACAAGGAUGGCGGCAUCCCUGAUGGCUGUAGCCUGUACCUGAGACACAGCAGCCUGUUCGCCCAGAGC

GAGGAAGAGGAAUCCUUCAGCAACUGAGCGGCCGCGAAUUGGCAAGCUGCUUACAUAGAACUCGCGGCGAUUGGCAUG

CCGCCUUAAAAUUUUUAUUUUAUUUUUCUUUUCUUUUCCGAAUCGGAUUUUGUUUUUAAUAUUUCAAAAAAAAAAAAA

AAAAAAAAAAAAAAAAAAAAAA

Accordingly, preferably the RNA construct comprises a nucleotide sequence substantially as set out in SEQ ID No: 66, or a fragment or variant thereof.

In a second aspect of the invention, there is provided a nucleic acid sequence encoding the RNA construct of the first aspect.

In one embodiment (SARS-CoV-2 coronavirus surface glycoprotein), the nucleic acid sequence is preferably DNA, and may comprise or consist of SEQ ID No: 34, as follows:

[SEQ ID No: 34]

ATGGAGAAAGTTCACGTTGACATCGAGGAAGACAGCCCATTCCTCAGAGCTTTGCAGCGGAGCTTCCCGCAGTTTGAG

GTAGAAGCCAAGCAGGTCACTGATAATGACCATGCTAATGCCAGAGCGTTTTCGCATCTGGCTTCAAAACTGATCGAA

ACGGAGGTGGACCCATCCGACACGATCCTTGACATTGGAAGTGCGCCCGCCCGCAGAATGTATTCTAAGCACAAGTAT

CATTGTATCTGTCCGATGAGATGTGCGGAAGATCCGGACAGATTGTATAAGTATGCAACTAAGCTGAAGAAAAACTGT

AAGGAAATAACTGATAAGGAATTGGACAAGAAAATGAAGGAGCTGGCCGCCGTCATGAGCGACCCTGACCTGGAAACT

GAGACTATGTGCCTCCACGACGACGAGTCGTGTCGCTACGAAGGGCAAGTCGCTGTTTACCAGGATGTATACGCGGTT

GACGGACCGACAAGTCTCTATCACCAAGCCAATAAGGGAGTTAGAGTCGCCTACTGGATAGGCTTTGACACCACCCCT

-continued

TTTATGTTTAAGAACTTGGCTGGAGCATATCCATCATACTCTACCAACTGGGCCGACGAAACCGTGTTAACGGCTCGT

AACATAGGCCTATGCAGCTCTGACGTTATGGAGCGGTCACGTAGAGGGATGTCCATTCTTAGAAAGAAGTATTTGAAA

CCATCCAACAATGTTCTATTCTCTGTTGGCTCGACCATCTACCACGAGAAGAGGGACTTACTGAGGAGCTGGCACCTG

CCGTCTGTATTTCACTTACGTGGCAAGCAAAATTACACATGTCGGTGTGAGACTATAGTTAGTTGCGACGGGTACGTC

GTTAAAAGAATAGCTATCAGTCCAGGCCTGTATGGGAAGCCTTCAGGCTATGCTGCTACGATGCACCGCGAGGGATTC

TTGTGCTGCAAAGTGACAGACACATTGAACGGGGAGAGGGTCTCTTTTCCCGTGTGCACGTATGTGCCAGCTACATTG

TGTGACCAAATGACTGGCATACTGGCAACAGATGTCAGTGCGGACGACGCGCAAAAACTGCTGGTTGGGCTCAACCAG

CGTATAGTCGTCAACGGTCGCACCCAGAGAAACACCAATACCATGAAAAATTACCTTTTGCCCGTAGTGGCCCAGGCA

TTTGCTAGGTGGGCAAAGGAATATAAGGAAGATCAAGAAGATGAAAGGCCACTAGGACTACGAGATAGACAGTTAGTC

ATGGGGTGTTGTTGGGCTTTTAGAAGGCACAAGATAACATCTATTTATAAGCGCCCGGATACCCAAACCATCATCAAA

GTGAACAGCGATTTCCACTCATTCGTGCTGCCCAGGATAGGCAGTAACACATTGGAGATCGGGCTGAGAACAAGAATC

AGGAAAATGTTAGAGGAGCACAAGGAGCCGTCACCTCTCATTACCGCCGAGGACGTACAAGAAGCTAAGTGCGCAGCC

GATGAGGCTAAGGAGGTGCGTGAAGCCGAGGAGTTGCGCGCAGCTCTACCACCTTTGGCAGCTGATGTTGAGGAGCCC

ACTCTGGAAGCCGATGTCGACTTGATGTTACAAGAGGCTGGGGCCGGCTCAGTGGAGACACCTCGTGGCTTGATAAAG

GTTACCAGCTACGATGGCGAGGACAAGATCGGCTCTTACGCTGTGCTTTCTCCGCAGGCTGTACTCAAGAGTGAAAAA

TTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCC

ACCATTGTGTACAACGAACGTGAGTTCGTAAACAGGTACCTGCACCATATTGCCACACATGGAGGAGCGCTGAACACT

GATGAAGAATATTACAAAACTGTCAAGCCCAGCGAGCACGACGGCGAATACCTGTACGACATCGACAGGAAACAGTGC

GTCAAGAAAGAACTAGTCACTGGGCTAGGGCTCACAGGCGAGCTGGTGGATCCTCCCTTCCATGAATTCGCCTACGAG

AGTCTGAGAACACGACCAGCCGCTCCTTACCAAGTACCAACCATAGGGGTGTATGGCGTGCCAGGATCAGGCAAGTCT

GGCATCATTAAAAGCGCAGTCACCAAAAAAGATCTAGTGGTGAGCGCCAAGAAAGAAAACTGTGCAGAAATTATAAGG

GACGTCAAGAAAATGAAAGGGCTGGACGTCAATGCCAGAACTGTGGACTCAGTGCTCTTGAATGGATGCAAACACCCC

GTAGAGACCCTGTATATTGACGAAGCTTTTGCTTGTCATGCAGGTACTCTCAGAGCGCTCATAGCCATTATAAGACCT

AAAAAGGCAGTGCTCTGCGGGGATCCCAAACAGTGCGGTTTTTTTAACATGATGTGCCTGAAAGTGCATTTTAACCAC

GAGATTTGCACACAAGTCTTCCACAAAAGCATCTCTCGCCGTTGCACTAAATCTGTGACTTCGGTCGTCTCAACCTTG

TTTTACGACAAAAAAATGAGAACGACGAATCCGAAAGAGACTAAGATTGTGATTGACACTACCGGCAGTACCAAACCT

AAGCAGGACGATCTCATTCTCACTTGTTTCAGAGGGTGGGTGAAGCAGTTGCAAATAGATTACAAAGGCAACGAAATA

ATGACGGCAGCTGCCTCTCAAGGGCTGACCCGTAAAGGTGTGTATGCCGTTCGGTACAAGGTGAATGAAAATCCTCTG

TACGCACCCACCTCAGAACATGTGAACGTCCTACTGACCCGCACGGAGGACCGCATCGTGTGGAAAACACTAGCCGGC

GACCCATGGATAAAAACACTGACTGCCAAGTACCCTGGGAATTTCACTGCCACGATAGAGGAGTGGCAAGCAGAGCAT

GATGCCATCATGAGGCACATCTTGGAGAGACCGGACCCTACCGACGTCTTCCAGAATAAGGCAAACGTGTGTTGGGCC

AAGGCTTTAGTGCCGGTGCTGAAGACCGCTGGCATAGACATGACCACTGAACAATGGAACACTGTGGATTATTTTGAA

ACGGACAAAGCTCACTCAGCAGAGATAGTATTGAACCAACTATGCGTGAGGTTCTTTGGACTCGATCTGGACTCCGGT

CTATTTTCTGCACCCACTGTTCCGTTATCCATTAGGAATAATCACTGGGATAACTCCCCGTCGCCTAACATGTACGGG

CTGAATAAAGAAGTGGTCCGTCAGCTCTCTCGCAGGTACCCACAACTGCCTCGGGCAGTTGCCACTGGAAGAGTCTAT

GACATGAACACTGGTACACTGCGCAATTATGATCCGCGCATAAACCTAGTACCTGTAAACAGAAGACTGCCTCATGCT

TTAGTCCTCCACCATAATGAACACCCACAGAGTGACTTTTCTTCATTCGTCAGCAAATTGAAGGGCAGAACTGTCCTG

GTGGTCGGGGAAAAGTTGTCCGTCCCAGGCAAAATGGTTGACTGGTTGTCAGACCGGCCTGAGGCTACCTTCAGAGCT

CGGCTGGATTTAGGCATCCCAGGTGATGTGCCCAAATATGACATAATATTTGTTAATGTGAGGACCCCATATAAATAC

-continued

CATCACTATCAGCAGTGTGAAGACCATGCCATTAAGCTTAGCATGTTGACCAAGAAAGCTTGTCTGCATCTGAATCCC

GGCGGAACCTGTGTCAGCATAGGTTATGGTTACGCTGACAGGGCCAGCGAAAGCATCATTGGTGCTATAGCGCGGCAG

TTCAAGTTTTCCCGGGTATGCAAACCGAAATCCTCACTTGAAGAGACGGAAGTTCTGTTTGTATTCATTGGGTACGAT

CGCAAGGCCCGTACGCACAATTCTTACAAGCTTTCATCAACCTTGACCAACATTTATACAGGTTCCAGACTCCACGAA

GCCGGATGTGCACCCTCATATCATGTGGTGCGAGGGGATATTGCCACGGCCACCGAAGGAGTGATTATAAATGCTGCT

AACAGCAAAGGACAACCTGGCGGAGGGGTGTGCGGAGCGCTGTATAAGAAATTCCCGGAAAGCTTCGATTTACAGCCG

ATCGAAGTAGGAAAAGCGCGACTGGTCAAAGGTGCAGCTAAACATATCATTCATGCCGTAGGACCAAACTTCAACAAA

GTTTCGGAGGTTGAAGGTGACAAACAGTTGGCAGAGGCTTATGAGTCCATCGCTAAGATTGTCAACGATAACAATTAC

AAGTCAGTAGCGATTCCACTGTTGTCCACCGGCATCTTTTCCGGGAACAAAGATCGACTAACCCAATCATTGAACCAT

TTGCTGACAGCTTTAGACACCACTGATGCAGATGTAGCCATATACTGCAGGGACAAGAAATGGGAAATGACTCTCAAG

GAAGCAGTGGCTAGGAGAGAAGCAGTGGAGGAGATATGCATATCCGACGACTCTTCAGTGACAGAACCTGATGCAGAG

CTGGTGAGGGTGCATCCGAAGAGTTCTTTGGCTGGAAGGAAGGGCTACAGCACAAGCGATGGCAAAACTTTCTCATAT

TTGGAAGGGACCAAGTTTCACCAGGCGGCCAAGGATATAGCAGAAATTAATGCCATGTGGCCCGTTGCAACGGAGGCC

AATGAGCAGGTATGCATGTATATCCTCGGAGAAAGCATGAGCAGTATTAGGTCGAAATGCCCCGTCGAAGAGTCGGAA

GCCTCCACACCACCTAGCACGCTGCCTTGCTTGTGCATCCATGCCATGACTCCAGAAAGAGTACAGCGCCTAAAAGCC

TCACGTCCAGAACAAATTACTGTGTGCTCATCCTTTCCATTGCCGAAGTATAGAATCACTGGTGTGCAGAAGATCCAA

TGCTCCCAGCCTATATTGTTCTCACCGAAAGTGCCTGCGTATATTCATCCAAGGAAGTATCTCGTGGAAACACCACCG

GTAGACGAGACTCCGGAGCCATCGGCAGAGAACCAATCCACAGAGGGGACACCTGAACAACCACCACTTATAACCGAG

GATGAGACCAGGACTAGAACGCCTGAGCCGATCATCATCGAAGAGGAAGAAGAGGATAGCATAAGTTTGCTGTCAGAT

GGCCCGACCCACCAGGTGCTGCAAGTCGAGGCAGACATTCACGGGCCGCCCTCTGTATCTAGCTCATCCTGGTCCATT

CCTCATGCATCCGACTTTGATGTGGACAGTTTATCCATACTTGACACCCTGGAGGGAGCTAGCGTGACCAGCGGGGCA

ACGTCAGCCGAGACTAACTCTTACTTCGCAAAGAGTATGGAGTTTCTGGCGCGACCGGTGCCTGCGCCTCGAACAGTA

TTCAGGAACCCTCCACATCCCGCTCCGCGCACAAGAACACCGTCACTTGCACCCAGCAGGGCCTGCTCGAGAACCAGC

CTAGTTTCCACCCCGCCAGGCGTGAATAGGGTGATCACTAGAGAGGAGCTCGAGGCGCTTACCCCGTCACGCACTCCT

AGCAGGTCGGTCTCGAGAACCAGCCTGGTCTCCAACCCGCCAGGCGTAAATAGGGTGATTACAAGAGAGGAGTTTGAG

GCGTTCGTAGCACAACAACAATGACGGTTTGATGCGGGTGCATACATCTTTTCCTCCGACACCGGTCAAGGGCATTTA

CAACAAAAATCAGTAAGGCAAACGGTGCTATCCGAAGTGGTGTTGGAGAGGACCGAATTGGAGATTTCGTATGCCCCG

CGCCTCGACCAAGAAAAAGAAGAATTACTACGCAAGAAATTACAGTTAAATCCCACACCTGCTAACAGAAGCAGATAC

CAGTCCAGGAAGGTGGAGAACATGAAAGCCATAACAGCTAGACGTATTCTGCAAGGCCTAGGGCATTATTTGAAGGCA

GAAGGAAAAGTGGAGTGCTACCGAACCCTGCATCCTGTTCCTTTGTATTCATCTAGTGTGAACCGTGCCTTTTCAAGC

CCCAAGGTCGCAGTGGAAGCCTGTAACGCCATGTTGAAAGAGAACTTTCCGACTGTGGCTTCTTACTGTATTATTCCA

GAGTACGATGCCTATTTGGACATGGTTGACGGAGCTTCATGCTGCTTAGACACTGCCAGTTTTTGCCCTGCAAAGCTG

CGCAGCTTTCCAAAGAAACACTCCTATTTGGAACCCACAATACGATCGGCAGTGCCTTCAGCGATCCAGAACACGCTC

CAGAACGTCCTGGCAGCTGCCACAAAAAGAAATTGCAATGTCACGCAAATGAGAGAATTGCCCGTATTGGATTCGGCG

GCCTTTAATGTGGAATGCTTCAAGAAATATGCGTGTAATAATGAATATTGGGAAACGTTTAAAGAAAACCCCATCAGG

CTTACTGAAGAAAACGTGGTAAATTACATTACCAAATTAAAAGGACCAAAAGCTGCTGCTCTTTTTGCGAAGACACAT

AATTTGAATATGTTGCAGGACATACCAATGGACAGGTTTGTAATGGACTTAAAGAGAGACGTGAAAGTGACTCCAGGA

ACAAAACATACTGAAGAACGGCCCAAGGTACAGGTGATCCAGGCTGCCGATCCGCTAGCAACAGCGTATCTGTGCGGA

ATCCACCGAGAGCTGGTTAGGAGATTAAATGCGGTCCTGCTTCCGAACATTCATACACTGTTTGATATGTCGGCTGAA

GACTTTGACGCTATTATAGCCGAGCACTTCCAGCCTGGGGATTGTGTTCTGGAAACTGACATCGCGTCGTTTGATAAA

AGTGAGGACGACGCCATGGCTCTGACCGCGTTAATGATTCTGGAAGACTTAGGTGTGGACGCAGAGCTGTTGACGCTG

-continued

ATTGAGGCGGCTTTCGGCGAAATTTCATCAATACATTTGCCCACTAAAACTAAATTTAAATTCGGAGCCATGATGAAA

TCTGGAATGTTCCTCACACTGTTTGTGAACACAGTCATTAACATTGTAATCGCAAGCAGAGTGTTGAGAGAACGGCTA

ACCGGATCACCATGTGCAGCATTCATTGGAGATGACAATATCGTGAAAGGAGTCAAATCGGACAAATTAATGGCAGAC

AGGTGCGCCACCTGGTTGAATATGGAAGTCAAGATTATAGATGCTGTGGTGGGCGAGAAAGCGCCTTATTTCTGTGGA

GGGTTTATTTTGTGTGACTCCGTGACCGGCACAGCGTGCCGTGTGGCAGACCCCCTAAAAAGGCTGTTTAAGCTTGGC

AAACCTCTGGCAGCAGACGATGAACATGATGATGACAGGAGAAGGGCATTGCATGAAGAGTCAACACGCTGGAACCGA

GTGGGTATTCTTTCAGAGCTGTGCAAGGCAGTAGAATCAAGGTATGAAACCGTAGGAACTTCCATCATAGTTATGGCC

ATGACTACTCTAGCTAGCAGTGTTAAATCATTCAGCTACCTGAGAGGGGCCCCTATAACTCTCTACGGCTAACCTGAA

TGGACTACGACATAGTCTAGTCCGCCAAGTCTAGCATATGGCCACCATGTTCGTGTTTCTGGTGCTGCTGCCTCTGGT

GTCCAGCCAGTGTGTGAACCTGACCACCAGAACACAGCTGCCTCCAGCCTACACCAACAGCTTTACCAGAGGCGTGTA

CTACCCCGACAAGGTGTTCAGATCCAGCGTGCTGCACTCTACCCAGGACCTGTTCCTGCCTTTCTTCAGCAACGTGAC

CTGGTTCCACGCCATCCACGTGTCCGGCACCAATGGCACCAAGAGATTCGACAACCCCGTGCTGCCCTTCAACGACGG

GGTGTACTTTGCCAGCACCGAGAAGTCCAACATCATCAGAGGCTGGATCTTCGGCACCACACTGGACAGCAAGACCCA

GAGCCTGCTGATCGTGAACAACGCCACCAACGTGGTCATCAAAGTGTGCGAGTTCCAGTTCTGCAACGACCCCTTCCT

GGGCGTCTACTACCACAAGAACAACAAGAGCTGGATGGAAAGCGAGTTCCGGGTGTACAGCAGCGCCAACAACTGCAC

CTTCGAGTACGTGTCCCAGCCTTTCCTGATGGACCTGGAAGGCAAGCAGGGCAACTTCAAGAACCTGCGCGAGTTCGT

GTTCAAGAACATCGACGGCTACTTCAAGATCTACAGCAAGCACACCCCTATCAACCTCGTGCGGGATCTGCCTCAGGG

CTTCTCTGCTCTGGAACCCCTGGTGGATCTGCCCATCGGCATCAACATCACCCGGTTTCAGACACTGCTGGCCCTGCA

CAGAAGCTACCTGACACCTGGCGATAGCAGCAGCGGATGGACAGCTGGTGCCGCCGCTTACTATGTGGGCTACCTGCA

GCCTAGAACCTTCCTGCTGAAGTACAACGAGAACGGCACCATCACCGACGCCGTGGATTGTGCCCTTGATCCTCTGAG

CGAGACAAAGTGCACCCTGAAGTCCTTCACCGTGGAAAAGGGCATCTACCAGACCAGCAACTTCCGGGTGCAGCCCAC

CGAATCCATCGTGCGGTTCCCCAATATCACCAATCTGTGCCCCTTCGGCGAGGTGTTCAATGCCACCAGATTCGCCTC

TGTGTACGCCTGGAACCGGAAGCGGATCAGCAATTGCGTGGCCGACTACTCCGTGCTGTACAACTCCGCCAGCTTCAG

CACCTTCAAGTGCTACGGCGTGTCCCCTACCAAGCTGAACGACCTGTGCTTCACAAACGTGTACGCCGACAGCTTCGT

GATCCGGGGAGATGAAGTGCGGCAGATTGCCCCTGGACAGACAGGCAAGATCGCCGACTACAACTACAAGCTGCCCGA

CGACTTCACCGGCTGTGTGATTGCCTGGAACAGCAACAACCTGGACTCCAAAGTCGGCGGCAACTACAATTACCTGTA

CCGGCTGTTCCGGAAGTCCAATCTGAAGCCCTTCGAGCGGGACATCTCCACCGAGATCTATCAGGCCGGCAGCACCCC

TTGTAACGGCGTGGAAGGCTTCAACTGCTACTTCCCACTGCAGTCCTACGGCTTTCAGCCCACAAATGGCGTGGGCTA

TCAGCCCTACAGAGTGGTGGTGCTGAGCTTCGAACTGCTGCATGCCCCTGCCACAGTGTGCGGCCCTAAGAAAAGCAC

CAATCTCGTGAAGAACAAATGCGTGAACTTCAACTTCAACGGCCTGACCGGCACAGGCGTGCTGACAGAGAGCAACAA

GAAGTTCCTGCCATTCCAGCAGTTTGGCCGGGATATCGCCGATACCACAGACGCCGTTAGAGATCCCCAGACACTGGA

AATCCTGGACATCACCCCTTGCAGCTTCGGCGGAGTGTCTGTGATCACCCCTGGCACCAACACCAGCAATCAGGTGGC

AGTGCTGTACCAGGACGTGAACTGTACCGAAGTGCCCGTGGCCATTCACGCCGATCAGCTGACACCTACATGGCGGGT

GTACTCCACCGGCAGCAATGTGTTTCAGACCAGAGCCGGCTGTCTGATCGGAGCCGAGCACGTGAACAATAGCTACGA

GTGCGACATCCCCATCGGCGCTGGCATCTGTGCCAGCTACCAGACACAGACAAACAGCCCCAGACGGGCCAGATCTGT

GGCCAGCCAGAGCATCATTGCCTACACAATGTCTCTGGGCGCCGAGAACAGCGTGGCCTACTCCAACAACTCTATCGC

TATCCCCACCAACTTCACCATCAGCGTGACCACAGAGATCCTGCCTGTGTCCATGACCAAGACCAGCGTGGACTGCAC

CATGTACATCTGCGGCGATTCCACCGAGTGCTCCAACCTGCTGCTGCAGTACGGCAGCTTCTGCACCCAGCTGAATAG

AGCCCTGACAGGGATCGCCGTGGAACAGGACAAGAACACCCAAGAGGTGTTCGCCCAAGTGAAGCAGATCTACAAGAC

CCCTCCTATCAAGGACTTCGGCGGCTTCAATTTCAGCCAGATTCTGCCCGATCCTAGCAAGCCCAGCAAGCGGAGCTT

-continued

CATCGAGGACCTGCTGTTCAACAAAGTGACACTGGCCGACGCCGGCTTCATCAAGCAGTATGGCGATTGTCTGGGCGA

CATTGCCGCCAGGGATCTGATTTGCGCCCAGAAGTTTAACGGACTGACAGTGCTGCCTCCTCTGCTGACCGATGAGAT

GATCGCCCAGTACACATCTGCCCTGCTGGCCGGCACAATCACAAGCGGCTGGACATTTGGAGCTGGCGCCGCTCTGCA

GATCCCCTTTGCTATGCAGATGGCCTACAGATTCAACGGCATCGGAGTGACCCAGAATGTGCTGTACGAGAACCAGAA

GCTGATCGCCAACCAGTTCAACAGCGCCATCGGCAAGATCCAGGACAGCCTGAGCAGCACAGCAAGCGCCCTGGGAAA

GCTGCAGGACGTGGTCAACCAGAATGCCCAGGCACTGAACACCCTGGTCAAGCAGCTGTCCTCCAACTTCGGCGCCAT

CAGCTCTGTGCTGAACGATATCCTGAGCAGACTGGACCCTCCTGAGGCCGAGGTGCAGATCGACAGACTGATCACAGG

CAGACTGCAGAGCCTCCAGACATACGTGACCCAGCAGCTGATCAGAGCCGCCGAGATTAGAGCCTCTGCCAATCTGGC

CGCCACCAAGATGTCTGAGTGTGTGCTGGGCCAGAGCAAGAGAGTGGACTTTTGCGGCAAGGGCTACCACCTGATGAG

CTTCCCTCAGTCTGCCCCTCACGGCGTGGTGTTTCTGCACGTGACATACGTTCCCGCTCAAGAGAAGAATTTCACCAC

CGCTCCAGCCATCTGCCACGACGGCAAAGCCCACTTTCCTAGAGAAGGCGTGTTCGTGTCCAACGGCACCCATTGGTT

CGTGACACAGCGGAACTTCTACGAGCCCCAGATCATCACCACCGACAACACCTTCGTGTCTGGCAACTGCGACGTCGT

GATCGGCATTGTGAACAATACCGTGTACGACCCTCTGCAGCCCGAGCTGGACAGCTTCAAAGAGGAACTGGACAAGTA

CTTTAAGAACCACACAAGCCCCGACGTGGACCTGGGCGATATCAGCGGAATCAATGCCAGCGTCGTGAACATCCAGAA

AGAGATCGACCGGCTGAACGAGGTGGCCAAGAATCTGAACGAGAGCCTGATCGACCTGCAAGAACTGGGGAAGTACGA

GCAGTACATCAAGTGGCCCTGGTACATCTGGCTGGGCTTTATCGCCGGACTGATTGCCATCGTGATGGTCACAATCAT

GCTGTGTTGCATGACCAGCTGCTGTAGCTGCCTGAAGGGCTGTTGTAGCTGTGGCAGCTGCTGCAAGTTCGACGAGGA

CGATTCTGAGCCCGTGCTGAAGGGCGTGAAACTGCACTACACATGAGCGGCCGCGAATTGGCAAGCTGCTTACATAGA

ACTCGCGGCGATTGGCATGCCGCCTTAAAATTTTTATTTTATTTTTCTTTTCTTTTCCGAATCGGATTTTGTTTTTAA

TATTTCAAAAAAAAAAAAAAAAAAAAAAAAAAAAAAAAAAAA

Accordingly, preferably the nucleic acid sequence comprises a nucleotide sequence substantially as set out in SEQ ID No: 34, or a fragment or variant thereof.

In another embodiment (the B.1.1.7 UK variant of SARS-CoV-2 glycoprotein), the nucleic acid sequence is preferably DNA, and comprise or consist of SEQ ID No: 67, as follows:

[SEQ ID No: 67]

ATGGGCGGCGCATGAGAGAAGCCCAGACCAATTACCTACCCAAAATGGAGAAAGTTCACGTTGACATCGAGGAAGACA

GCCCATTCCTCAGAGCTTTGCAGCGGAGCTTCCCGCAGTTTGAGGTAGAAGCCAAGCAGGTCACTGATAATGACCATG

CTAATGCCAGAGCGTTTTCGCATCTGGCTTCAAAACTGATCGAAACGGAGGTGGACCCATCCGACACGATCCTTGACA

TTGGAAGTGCGCCCGCCCGCAGAATGTATTCTAAGCACAAGTATCATTGTATCTGTCCGATGAGATGTGCGGAAGATC

CGGACAGATTGTATAAGTATGCAACTAAGCTGAAGAAAAACTGTAAGGAAATAACTGATAAGGAATTGGACAAGAAAA

TGAAGGAGCTGGCCGCCGTCATGAGCGACCCTGACCTGGAAACTGAGACTATGTGCCTCCACGACGACGAGTCGTGTC

GCTACGAAGGGCAAGTCGCTGTTTACCAGGATGTATACGCGGTTGACGGACCGACAAGTCTCTATCACCAAGCCAATA

AGGGAGTTAGAGTCGCCTACTGGATAGGCTTTGACACCACCCCTTTTATGTTTAAGAACTTGGCTGGAGCATATCCAT

CATACTCTACCAACTGGGCCGACGAAACCGTGTTAACGGCTCGTAACATAGGCCTATGCAGCTCTGACGTTATGGAGC

GGTCACGTAGAGGGATGTCCATTCTTAGAAAGAAGTATTTGAAACCATCCAACAATGTTCTATTCTCTGTTGGCTCGA

CCATCTACCACGAGAAGAGGGACTTACTGAGGAGCTGGCACCTGCCGTCTGTATTTCACTTACGTGGCAAGCAAAATT

ACACATGTCGGTGTGAGACTATAGTTAGTTGCGACGGGTACGTCGTTAAAAGAATAGCTATCAGTCCAGGCCTGTATG

GGAAGCCTTCAGGCTATGCTGCTACGATGCACCGCGAGGGATTCTTGTGCTGCAAAGTGACAGACACATTGAACGGGG

AGAGGGTCTCTTTTCCCGTGTGCACGTATGTGCCAGCTACATTGTGTGACCAAATGACTGGCATACTGGCAACAGATG

TCAGTGCGGACGACGCGCAAAAACTGCTGGTTGGGCTCAACCAGCGTATAGTCGTCAACGGTCGCACCCAGAGAAACA

CCAATACCATGAAAAATTACCTTTTGCCCGTAGTGGCCCAGGCATTTGCTAGGTGGGCAAAGGAATATAAGGAAGATC

AAGAAGATGAAAGGCCACTAGGACTACGAGATAGACAGTTAGTCATGGGGTGTTGTTGGGCTTTTAGAAGGCACAAGA

-continued

TAACATCTATTTATAAGCGCCCGGATACCCAAACCATCATCAAAGTGAACAGCGATTTCCACTCATTCGTGCTGCCCA

GGATAGGCAGTAACACATTGGAGATCGGGCTGAGAACAAGAATCAGGAAAATGTTAGAGGAGCACAAGGAGCCGTCAC

CTCTCATTACCGCCGAGGACGTACAAGAAGCTAAGTGCGCAGCCGATGAGGCTAAGGAGGTGCGTGAAGCCGAGGAGT

TGCGCGCAGCTCTACCACCTTTGGCAGCTGATGTTGAGGAGCCCACTCTGGAGGCAGACGTCGACTTGATGTTACAAG

AGGCTGGGGCCGGCTCAGTGGAGACACCTCGTGGCTTGATAAAGGTTACCAGCTACGATGGCGAGGACAAGATCGGCT

CTTACGCTGTGCTTTCTCCGCAGGCTGTACTCAAGAGTGAAAAATTATCTTGCATCCACCCTCTCGCTGAACAAGTCA

TAGTGATAACACACTCTGGCCGAAAAGGGCGTTATGCCGTGGAACCATACCATGGTAAAGTAGTGGTGCCAGAGGGAC

ATGCAATACCCGTCCAGGACTTTCAAGCTCTGAGTGAAAGTGCCACCATTGTGTACAACGAACGTGAGTTCGTAAACA

GGTACCTGCACCATATTGCCACACATGGAGGAGCGCTGAACACTGATGAAGAATATTACAAAACTGTCAAGCCCAGCG

AGCACGACGGCGAATACCTGTACGACATCGACAGGAAACAGTGCGTCAAGAAAGAACTAGTCACTGGGCTAGGGCTCA

CAGGCGAGCTGGTGGATCCTCCCTTCCATGAATTCGCCTACGAGAGTCTGAGAACACGACCAGCCGCTCCTTACCAAG

TACCAACCATAGGGGTGTATGGCGTGCCAGGATCAGGCAAGTCTGGCATCATTAAAAGCGCAGTCACCAAAAAAGATC

TAGTGGTGAGCGCCAAGAAAGAAAACTGTGCAGAAATTATAAGGGACGTCAAGAAAATGAAAGGGCTGGACGTCAATG

CCAGAACTGTGGACTCAGTGCTCTTGAATGGATGCAAACACCCCGTAGAGACCCTGTATATTGACGAAGCTTTTGCTT

GTCATGCAGGTACTCTCAGAGCGCTCATAGCCATTATAAGACCTAAAAAGGCAGTGCTCTGCGGGGATCCCAAACAGT

GCGGTTTTTTAACATGATGTGCCTGAAAGTGCATTTTAACCACGAGATTTGCACACAAGTCTTCCACAAAAGCATCT

CTCGCCGTTGCACTAAATCTGTGACTTCGGTCGTCTCAACCTTGTTTTACGACAAAAAAATGAGAACGACGAATCCGA

AAGAGACTAAGATTGTGATTGACACTACCGGCAGTACCAAACCTAAGCAGGACGATCTCATTCTCACTTGTTTCAGAG

GGTGGGTGAAGCAGTTGCAAATAGATTACAAAGGCAACGAAATAATGACGGCAGCTGCCTCTCAAGGGCTGACCCGTA

AAGGTGTGTATGCCGTTCGGTACAAGGTGAATGAAAATCCTCTGTACGCACCCACCTCAGAACATGTGAACGTCCTAC

TGACCCGCACGGAGGACCGCATCGTGTGGAAAACACTAGCCGGCGACCCATGGATAAAAACACTGACTGCCAAGTACC

CTGGGAATTTCACTGCCACGATAGAGGAGTGGCAAGCAGAGCATGATGCCATCATGAGGCACATCTTGGAGAGACCGG

ACCCTACCGACGTCTTCCAGAATAAGGCAAACGTGTGTTGGGCCAAGGCTTTAGTGCCGGTGCTGAAGACCGCTGGCA

TAGACATGACCACTGAACAATGGAACACTGTGGATTATTTTGAAACGGACAAAGCTCACTCAGCAGAGATAGTATTGA

ACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCA

GGTACCCACAACTGCCTCGGGCAGTTGCCACTGGAAGAGTCTATGACATGAACACTGGTACACTGCGCAATTATGATC

CGCGCATAAACCTAGTACCTGTAAACAGAAGACTGCCTCATGCTTTAGTCCTCCACCATAATGAACACCCACAGAGTG

ACTTTTCTTCATTCGTCAGCAAATTGAAGGGCAGAACTGTCCTGGTGGTCGGGGAAAAGTTGTCCGTCCCAGGCAAAA

TGGTTGACTGGTTGTCAGACCGGCCTGAGGCTACCTTCAGAGCTCGGCTGGATTTAGGCATCCCAGGTGATGTGCCCA

AATATGACATAATATTTGTTAATGTGAGGACCCCATATAAATACCATCACTATCAGCAGTGTGAAGACCATGCCATTA

AGCTTAGCATGTTGACCAAGAAAGCTTGTCTGCATCTGAATCCCGGCGGAACCTGTGTCAGCATAGGTTATGGTTACG

CTGACAGGGCCAGCGAAAGCATCATTGGTGCTATAGCGCGGCAGTTCAAGTTTTCCCGGGTATGCAAACCGAAATCCT

CACTTGAAGAGACGGAAGTTCTGTTTGTATTCATTGGGTACGATCGCAAGGCCCGTACGCACAATTCTTACAAGCTTT

CATCAACCTTGACCAACATTTATACAGGTTCCAGACTCCACGAAGCCGGATGTGCACCCTCATATCATGTGGTGCGAG

GGGATATTGCCACGGCCACCGAAGGAGTGATTATAAATGCTGCTAACAGCAAAGGACAACCTGGCGGAGGGGTGTGCG

GAGCGCTGTATAAGAAATTCCCGGAAAGCTTCGATTTACAGCCGATCGAAGTAGGAAAAGCGCGACTGGTCAAAGGTG

CAGCTAAACATATCATTCATGCCGTAGGACCAAACTTCAACAAAGTTTCGGAGGTTGAAGGTGACAAACAGTTGGCAG

AGGCTTATGAGTCCATCGCTAAGATTGTCAACGATAACAATTACAAGTCAGTAGCGATTCCACTGTTGTCCACCGGCA

TCTTTTCCGGGAACAAAGATCGACTAACCCAATCATTGAACCATTTGCTGACAGCTTTAGACACCACTGATGCAGATG

-continued

TAGCCATATACTGCAGGGACAAGAAATGGGAAATGACTCTCAAGGAAGCAGTGGCTAGGAGAGAAGCAGTGGAGGAGA

TATGCATATCCGACGACTCTTCAGTGACAGAACCTGATGCAGAGCTGGTGAGGGTGCATCCGAAGAGTTCTTTGGCTG

GAAGGAAGGGCTACAGCACAAGCGATGGCAAAACTTTCTCATATTTGGAAGGGACCAAGTTTCACCAGGCGGCCAAGG

ATATAGCAGAAATTAATGCCATGTGGCCCGTTGCAACGGAGGCCAATGAGCAGGTATGCATGTATATCCTCGGAGAAA

GCATGAGCAGTATTAGGTCGAAATGCCCCGTCGAAGAGTCGGAAGCCTCCACACCACCTAGCACGCTGCCTTGCTTGT

GCATCCATGCCATGACTCCAGAAAGAGTACAGCGCCTAAAAGCCTCACGTCCAGAACAAATTACTGTGTGCTCATCCT

TTCCATTGCCGAAGTATAGAATCACTGGTGTGCAGAAGATCCAATGCTCCCAGCCTATATTGTTCTCACCGAAAGTGC

CTGCGTATATTCATCCAAGGAAGTATCTCGTGGAAACACCACCGGTAGACGAGACTCCGGAGCCATCGGCAGAGAACC

AATCCACAGAGGGGACACCTGAACAACCACCACTTATAACCGAGGATGAGACCAGGACTAGAACGCCTGAGCCGATCA

TCATCGAAGAGGAAGAAGAGGATAGCATAAGTTTGCTGTCAGATGGCCCGACCCACCAGGTGCTGCAAGTCGAGGCAG

ACATTCACGGGCCGCCCTCTGTATCTAGCTCATCCTGGTCCATTCCTCATGCATCCGACTTTGATGTGGACAGTTTAT

CCATACTTGACACCCTGGAGGGAGCTAGCGTGACCAGCGGGGCAACGTCAGCCGAGACTAACTCTTACTTCGCAAAGA

GTATGGAGTTTCTGGCGCGACCGGTGCCTGCGCCTCGAACAGTATTCAGGAACCCTCCACATCCCGCTCCGCGCACAA

GAACACCGTCACTTGCACCCAGCAGGGCCTGCTCGAGAACCAGCCTAGTTTCCACCCCGCCAGGCGTGAATAGGGTGA

TCACTAGAGAGGAGCTCGAGGCGCTTACCCCGTCACGCACTCCTAGCAGGTCGGTCTCGAGAACCAGCCTGGTCTCCA

ACCCGCCAGGCGTAAATAGGGTGATTACAAGAGAGGAGTTTGAGGCGTTCGTAGCACAACAACAATGACGGTTTGATG

CGGGTGCATACATCTTTTCCTCCGACACCGGTCAAGGGCATTTACAACAAAAATCAGTAAGGCAAACGGTGCTATCCG

AAGTGGTGTTGGAGAGGACCGAATTGGAGATTTCGTATGCCCCGCGCCTCGACCAAGAAAAAGAAGAATTACTACGCA

AGAAATTACAGTTAAATCCCACACCTGCTAACAGAAGCAGATACCAGTCCAGGAAGGTGGAGAACATGAAAGCCATAA

CAGCTAGACGTATTCTGCAAGGCCTAGGGCATTATTTGAAGGCAGAAGGAAAAGTGGAGTGCTACCGAACCCTGCATC

CTGTTCCTTTGTATTCATCTAGTGTGAACCGTGCCTTTTCAAGCCCCAAGGTCGCAGTGGAAGCCTGTAACGCCATGT

TGAAAGAGAACTTTCCGACTGTGGCTTCTTACTGTATTATTCCAGAGTACGATGCCTATTTGGACATGGTTGACGGAG

CTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATT

GCAATGTCACGCAAATGAGAGAATTGCCCGTATTGGATTCGGCGGCCTTTAATGTGGAATGCTTCAAGAAATATGCGT

GTAATAATGAATATTGGGAAACGTTTAAAGAAAACCCCATCAGGCTTACTGAAGAAAACGTGGTAAATTACATTACCA

AATTAAAAGGACCAAAAGCTGCTGCTCTTTTTGCGAAGACACATAATTTGAATATGTTGCAGGACATACCAATGGACA

GGTTTGTAATGGACTTAAAGAGAGACGTGAAAGTGACTCCAGGAACAAAACATACTGAAGAACGGCCCAAGGTACAGG

TGATCCAGGCTGCCGATCCGCTAGCAACAGCGTATCTGTGCGGAATCCACCGAGAGCTGGTTAGGAGATTAAATGCGG

TCCTGCTTCCGAACATTCATACACTGTTTGATATGTCGGCTGAAGACTTTGACGCTATTATAGCCGAGCACTTCCAGC

CTGGGGATTGTGTTCTGGAAACTGACATCGCGTCGTTTGATAAAAGTGAGGACGACGCCATGGCTCTGACCGCGTTAA

TGATTCTGGAAGACTTAGGTGTGGACGCAGAGCTGTTGACGCTGATTGAGGCGGCTTTCGGCGAAATTTCATCAATAC

ATTTGCCCACTAAAACTAAATTTAAATTCGGAGCCATGATGAAATCTGGAATGTTCCTCACACTGTTTGTGAACACAG

TCATTAACATTGTAATCGCAAGCAGAGTGTTGAGAGAACGGCTAACCGGATCACCATGTGCAGCATTCATTGGAGATG

ACAATATCGTGAAAGGAGTCAAATCGGACAAATTAATGGCAGACAGGTGCGCCACCTGGTTGAATATGGAAGTCAAGA

TTATAGATGCTGTGGTGGGCGAGAAAGCGCCTTATTTCTGTGGAGGGTTTATTTTGTGTGACTCCGTGACCGGCACAG

CGTGCCGTGTGGCAGACCCCCTAAAAAGGCTGTTTAAGCTTGGCAAACCTCTGGCAGCAGACGATGAACATGATGATG

ACAGGAGAAGGGCATTGCATGAAGAGTCAACACGCTGGAACCGAGTGGGTATTCTTTCAGAGCTGTGCAAGGCAGTAG

AATCAAGGTATGAAACCGTAGGAACTTCCATCATAGTTATGGCCATGACTACTCTAGCTAGCAGTGTTAAATCATTCA

GCTACCTGAGAGGGGCCCCTATAACTCTCTACGGCTAACCTGAATGGACTACGACATAGTCTAGTCCGCCAAGTCTAG

CATATGGCCACCATGTTCGTGTTTCTGGTGCTGCTGCCTCTGGTGTCCAGCCAGTGTGTGAACCTGACCACCAGAACA

-continued

CAGCTGCCTCCAGCCTACACCAACAGCTTTACCAGAGGCGTGTACTACCCCGACAAGGTGTTCAGATCCAGCGTGCTG

CACTCTACCCAGGACCTGTTCCTGCCTTTCTTCAGCAACGTGACCTGGTTCCACGCCATCTCCGGCACCAATGGCACC

AAGAGATTCGACAACCCCGTGCTGCCCTTCAACGACGGGGTGTACTTTGCCAGCACCGAGAAGTCCAACATCATCAGA

GGCTGGATCTTCGGCACCACACTGGACAGCAAGACCCAGAGCCTGCTGATCGTGAACAACGCCACCAACGTGGTCATC

AAAGTGTGCGAGTTCCAGTTCTGCAACGACCCCTTCCTGGGCGTCTACCACAAGAACAACAAGAGCTGGATGGAAAGC

GAGTTCCGGGTGTACAGCAGCGCCAACAACTGCACCTTCGAGTACGTGTCCCAGCCTTTCCTGATGGACCTGGAAGGC

AAGCAGGGCAACTTCAAGAACCTGCGCGAGTTCGTGTTCAAGAACATCGACGGCTACTTCAAGATCTACAGCAAGCAC

ACCCCTATCAACCTCGTGCGGGATCTGCCTCAGGGCTTCTCTGCTCTGGAACCCCTGGTGGATCTGCCCATCGGCATC

AACATCACCCGGTTTCAGACACTGCTGGCCCTGCACAGAAGCTACCTGACACCTGGCGATAGCAGCAGCGGATGGACA

GCTGGTGCCGCCGCTTACTATGTGGGCTACCTGCAGCCTAGAACCTTCCTGCTGAAGTACAACGAGAACGGCACCATC

ACCGACGCCGTGGATTGTGCCCTTGATCCTCTGAGCGAGACAAAGTGCACCCTGAAGTCCTTCACCGTGGAAAAGGGC

ATCTACCAGACCAGCAACTTCCGGGTGCAGCCCACCGAATCCATCGTGCGGTTCCCCAATATCACCAATCTGTGCCCC

TTCGGCGAGGTGTTCAATGCCACCAGATTCGCCTCTGTGTACGCCTGGAACCGGAAGCGGATCAGCAATTGCGTGGCC

GACTACTCCGTGCTGTACAACTCCGCCAGCTTCAGCACCTTCAAGTGCTACGGCGTGTCCCCTACCAAGCTGAACGAC

CTGTGCTTCACAAACGTGTACGCCGACAGCTTCGTGATCCGGGGAGATGAAGTGCGGCAGATTGCCCCTGGACAGACA

GGCAAGATCGCCGACTACAACTACAAGCTGCCCGACGACTTCACCGGCTGTGTGATTGCCTGGAACAGCAACAACCTG

GACTCCAAAGTCGGCGGCAACTACAATTACCTGTACCGGCTGTTCCGGAAGTCCAATCTGAAGCCCTTCGAGCGGGAC

ATCTCCACCGAGATCTATCAGGCCGGCAGCACCCCTTGTAACGGCGTGGAAGGCTTCAACTGCTACTTCCCACTGCAG

TCCTACGGCTTTCAGCCCACATATGGCGTGGGCTATCAGCCCTACAGAGTGGTGGTGCTGAGCTTCGAACTGCTGCAT

GCCCCTGCCACAGTGTGCGGCCCTAAGAAAAGCACCAATCTCGTGAAGAACAAATGCGTGAACTTCAACTTCAACGGC

CTGACCGGCACAGGCGTGCTGACAGAGAGCAACAAGAAGTTCCTGCCATTCCAGCAGTTTGGCCGGGATATCGACGAT

ACCACAGACGCCGTTAGAGATCCCCAGACACTGGAAATCCTGGACATCACCCCTTGCAGCTTCGGCGGAGTGTCTGTG

ATCACCCCTGGCACCAACACCAGCAATCAGGTGGCAGTGCTGTACCAGGGCGTGAACTGTACCGAAGTGCCCGTGGCC

ATTCACGCCGATCAGCTGACACCTACATGGCGGGTGTACTCCACCGGCAGCAATGTGTTTCAGACCAGAGCCGGCTGT

CTGATCGGAGCCGAGCACGTGAACAATAGCTACGAGTGCGACATCCCCATCGGCGCTGGCATCTGTGCCAGCTACCAG

ACACAGACAAACAGCCACTCTCTGGCCAGCTCTGTGGCCAGCCAGAGCATCATTGCCTACACAATGTCTCTGGGCGCC

GAGAACAGCGTGGCCTACTCCAACAACTCTATCGCTATCCCCATCAACTTCACCATCAGCGTGACCACAGAGATCCTG

CCTGTGTCCATGACCAAGACCAGCGTGGACTGCACCATGTACATCTGCGGCGATTCCACCGAGTGCTCCAACCTGCTG

CTGCAGTACGGCAGCTTCTGCACCCAGCTGAATAGAGCCCTGACAGGGATCGCCGTGGAACAGGACAAGAACACCCAA

GAGGTGTTCGCCCAAGTGAAGCAGATCTACAAGACCCCTCCTATCAAGGACTTCGGCGGCTTCAATTTCAGCCAGATT

CTGCCCGATCCTAGCAAGCCCAGCAAGCGGAGCCCCATCGAGGACCTGCTGTTCAACAAAGTGACACTGGCCGACGCC

GGCTTCATCAAGCAGTATGGCGATTGTCTGGGCGACATTGCCGCCAGGGATCTGATTTGCGCCCAGAAGTTTAACGGA

CTGACAGTGCTGCCTCCTCTGCTGACCGATGAGATGATCGCCCAGTACACATCTGCCCTGCTGGCCGGCACAATCACA

AGCGGCTGGACATTTGGAGCTGGCCCCGCTCTGCAGATCCCCTTTCCTATGCAGATGGCCTACAGATTCAACGGCATC

GGAGTGACCCAGAATGTGCTGTACGAGAACCAGAAGCTGATCGCCAACCAGTTCAACAGCGCCATCGGCAAGATCCAG

GACAGCCTGAGCAGCACACCAAGCGCCCTGGGAAAGCTGCAGGACGTGGTCAACCAGAATGCCCAGGCACTGAACACC

CTGGTCAAGCAGCTGTCCTCCAACTTCGGCGCCATCAGCTCTGTGCTGAACGATATCCTGGCCAGACTGGACCCTCCT

GAGGCCGAGGTGCAGATCGACAGACTGATCACAGGCAGACTGCAGAGCCTCCAGACATACGTGACCCAGCAGCTGATC

AGAGCCGCCGAGATTAGAGCCTCTGCCAATCTGGCCGCCACCAAGATGTCTGAGTGTGTGCTGGGCCAGAGCAAGAGA

GTGGACTTTTGCGGCAAGGGCTACCACCTGATGAGCTTCCCTCAGTCTGCCCCTCACGGCGTGGTGTTTCTGCACGTG

-continued

ACATACGTTCCCGCTCAAGAGAAGAATTTCACCACCGCTCCAGCCATCTGCCACGACGGCAAAGCCCACTTTCCTAGA

GAAGGCGTGTTCGTGTCCAACGGCACCCATTGGTTCGTGACACAGCGGAACTTCTACGAGCCCCAGATCATCACCACC

CACAACACCTTCGTGTCTGGCAACTGCGACGTCGTGATCGGCATTGTGAACAATACCGTGTACGACCCTCTGCAGCCC

GAGCTGGACAGCTTCAAAGAGGAACTGGACAAGTACTTTAAGAACCACACAAGCCCCGACGTGGACCTGGGCGATATC

AGCGGAATCAATGCCAGCGTCGTGAACATCCAGAAAGAGATCGACCGGCTGAACGAGGTGGCCAAGAATCTGAACGAG

AGCCTGATCGACCTGCAAGAACTGGGGAAGTACGAGCAGTACATCAAGTGGCCCTGGTACATCTGGCTGGGCTTTATC

GCCGGACTGATTGCCATCGTGATGGTCACAATCATGCTGTGTTGCATGACCAGCTGCTGTAGCTGCCTGAAGGGCTGT

TGTAGCTGTGGCAGCTGCTGCAAGTTCGACGAGGACGATTCTGAGCCCGTGCTGAAGGGCGTGAAACTGCACTACACA

TGAGCGGCCGCGAATTGGCAAGCTGCTTACATAGAACTCGCGGCGATTGGCATGCCGCCTTAAAATTTTTATTTTATT

TTTCTTTTCTTTTCCGAATCGGATTTTGTTTTTAATATTTCAAAAAAAAAAAAAAAAAAAAAAAAAAAAAAAAAAA

Accordingly, preferably the nucleic acid sequence comprises a nucleotide sequence substantially as set out in SEQ ID No: 67, or a fragment or variant thereof.

In another embodiment (the B.1.1.7 UK+E484K variant of SARS-CoV-2 glycoprotein), the nucleic acid sequence is preferably DNA, and comprise or consist of SEQ ID No: 68, as follows:

[SEQ ID No: 68]

ATGGGCGGCGCATGAGAGAAGCCCAGACCAATTACCTACCCAAAATGGAGAAAGTTCACGTTGACATCGAGGAAGACA

GCCCATTCCTCAGAGCTTTGCAGCGGAGCTTCCCGCAGTTTGAGGTAGAAGCCAAGCAGGTCACTGATAATGACCATG

CTAATGCCAGAGCGTTTTCGCATCTGGCTTCAAAACTGATCGAAACGGAGGTGGACCCATCCGACACGATCCTTGACA

TTGGAAGTGCGCCCGCCCGCAGAATGTATTCTAAGCACAAGTATCATTGTATCTGTCCGATGAGATGTGCGGAAGATC

CGGACAGATTGTATAAGTATGCAACTAAGCTGAAGAAAAACTGTAAGGAAATAACTGATAAGGAATTGGACAAGAAAA

TGAAGGAGCTGGCCGCCGTCATGAGCGACCCTGACCTGGAAACTGAGACTATGTGCCTCCACGACGACGAGTCGTGTC

GCTACGAAGGGCAAGTCGCTGTTTACCAGGATGTATACGCGGTTGACGGACCGACAAGTCTCTATCACCAAGCCAATA

AGGGAGTTAGAGTCGCCTACTGGATAGGCTTTGACACCACCCCTTTTATGTTTAAGAACTTGGCTGGAGCATATCCAT

CATACTCTACCAACTGGGCCGACGAAACCGTGTTAACGGCTCGTAACATAGGCCTATGCAGCTCTGACGTTATGGAGC

GGTCACGTAGAGGGATGTCCATTCTTAGAAAGAAGTATTTGAAACCATCCAACAATGTTCTATTCTCTGTTGGCTCGA

CCATCTACCACGAGAAGAGGGACTTACTGAGGAGCTGGCACCTGCCGTCTGTATTTCACTTACGTGGCAAGCAAAATT

ACACATGTCGGTGTGAGACTATAGTTAGTTGCGACGGGTACGTCGTTAAAAGAATAGCTATCAGTCCAGGCCTGTATG

GGAAGCCTTCAGGCTATGCTGCTACGATGCACCGCGAGGGATTCTTGTGCTGCAAAGTGACAGACACATTGAACGGGG

AGAGGGTCTCTTTTCCCGTGTGCACGTATGTGCCAGCTACATTGTGTGACCAAATGACTGGCATACTGGCAACAGATG

TCAGTGCGGACGACGCGCAAAAACTGCTGGTTGGGCTCAACCAGCGTATAGTCGTCAACGGTCGCACCCAGAGAAACA

CCAATACCATGAAAAATTACCTTTTGCCCGTAGTGGCCCAGGCATTTGCTAGGTGGGCAAAGGAATATAAGGAAGATC

AAGAAGATGAAAGGCCACTAGGACTACGAGATAGACAGTTAGTCATGGGGTGTTGTTGGGCTTTTAGAAGGCACAAGA

TAACATCTATTTATAAGCGCCCGGATACCCAAACCATCATCAAAGTGAACAGCGATTTCCACTCATTCGTGCTGCCCA

GGATAGGCAGTAACACATTGGAGATCGGGCTGAGAACAAGAATCAGGAAAATGTTAGAGGAGCACAAGGAGCCGTCAC

CTCTCATTACCGCCGAGGACGTACAAGAAGCTAAGTGCGCAGCCGATGAGGCTAAGGAGGTGCGTGAAGCCGAGGAGT

TGCGCGCAGCTCTACCACCTTTGGCAGCTGATGTTGAGGAGCCCACTCTGGAGGCAGACGTCGACTTGATGTTACAAG

AGGCTGGGGCCGGCTCAGTGGAGACACCTCGTGGCTTGATAAAGGTTACCAGCTACGATGGCGAGGACAAGATCGGCT

CTTACGCTGTGCTTTCTCCGCAGGCTGTACTCAAGAGTGAAAAATTATCTTGCATCCACCCTCTCGCTGAACAAGTCA

TAGTGATAACACACTCTGGCCGAAAAGGGCGTTATGCCGTGGAACCATACCATGGTAAAGTAGTGGTGCCAGAGGGAC

-continued

ATGCAATACCCGTCCAGGACTTTCAAGCTCTGAGTGAAAGTGCCACCATTGTGTACAACGAACGTGAGTTCGTAAACA

GGTACCTGCACCATATTGCCACACATGGAGGAGCGCTGAACACTGATGAAGAATATTACAAAACTGTCAAGCCCAGCG

AGCACGACGGCGAATACCTGTACGACATCGACAGGAAACAGTGCGTCAAGAAAGAACTAGTCACTGGGCTAGGGCTCA

CAGGCGAGCTGGTGGATCCTCCCTTCCATGAATTCGCCTACGAGAGTCTGAGAACACGACCAGCCCGCTCCTTACCAAG

TACCAACCATAGGGGTGTATGGCGTGCCAGGATCAGGCAAGTCTGGCATCATTAAAAGCGCAGTCACCAAAAAAGATC

TAGTGGTGAGCGCCAAGAAAGAAAACTGTGCAGAAATTATAAGGGACGTCAAGAAAATGAAAGGGCTGGACGTCAATG

CCAGAACTGTGGACTCAGTGCTCTTGAATGGATGCAAACACCCCGTAGAGACCCTGTATATTGACGAAGCTTTTGCTT

GTCATGCAGGTACTCTCAGAGCGCTCATAGCCATTATAAGACCTAAAAAGGCAGTGCTCTGCGGGGATCCCAAACAGT

GCGGTTTTTTTAACATGATGTGCCTGAAAGTGCATTTTAACCACGAGATTTGCACACAAGTCTTCCACAAAAGCATCT

CTCGCCGTTGCACTAAATCTGTGACTTCGGTCGTCTCAACCTTGTTTTACGACAAAAAAATGAGAACGACGAATCCGA

AAGAGACTAAGATTGTGATTGACACTACCGGCAGTACCAAACCTAAGCAGGACGATCTCATTCTCACTTGTTTCAGAG

GGTGGGTGAAGCAGTTGCAAATAGATTACAAAGGCAACGAAATAATGACGGCAGCTGCCTCTCAAGGGCTGACCCGTA

AAGGTGTGTATGCCGTTCGGTACAAGGTGAATGAAAATCCTCTGTACGCACCCACCTCAGAACATGTGAACGTCCTAC

TGACCCGCACGGAGGACCGCATCGTGTGGAAAACACTAGCCGGCGACCCATGGATAAAAACACTGACTGCCAAGTACC

CTGGGAATTTCACTGCCACGATAGAGGAGTGGCAAGCAGAGCATGATGCCATCATGAGGCACATCTTGGAGAGACCGG

ACCCTACCGACGTCTTCCAGAATAAGGCAAACGTGTGTTGGGCCAAGGCTTTAGTGCCGGTGCTGAAGACCGCTGGCA

TAGACATGACCACTGAACAATGGAACACTGTGGATTATTTTGAAACGGACAAAGCTCACTCAGCAGAGATAGTATTGA

ACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCA

GGTACCCACAACTGCCTCGGGCAGTTGCCACTGGAAGAGTCTATGACATGAACACTGGTACACTGCGCAATTATGATC

CGCGCATAAACCTAGTACCTGTAAACAGAAGACTGCCTCATGCTTTAGTCCTCCACCATAATGAACACCCACAGAGTG

ACTTTTCTTCATTCGTCAGCAAATTGAAGGGCAGAACTGTCCTGGTGGTCGGGGAAAAGTTGTCCGTCCCAGGCAAAA

TGGTTGACTGGTTGTCAGACCGGCCTGAGGCTACCTTCAGAGCTCGGCTGGATTTAGGCATCCCAGGTGATGTGCCCA

AATATGACATAATATTTGTTAATGTGAGGACCCCATATAAATACCATCACTATCAGCAGTGTGAAGACCATGCCATTA

AGCTTAGCATGTTGACCAAGAAAGCTTGTCTGCATCTGAATCCCGGCGGAACCTGTGTCAGCATAGGTTATGGTTACG

CTGACAGGGCCAGCGAAAGCATCATTGGTGCTATAGCGCGGCAGTTCAAGTTTTCCCGGGTATGCAAACCGAAATCCT

CACTTGAAGAGACGGAAGTTCTGTTTGTATTCATTGGGTACGATCGCAAGGCCCGTACGCACAATTCTTACAAGCTTT

CATCAACCTTGACCAACATTTATACAGGTTCCAGACTCCACGAAGCCGGATGTGCACCCTCATATCATGTGGTGCGAG

GGGATATTGCCACGGCCACCGAAGGAGTGATTATAAATGCTGCTAACAGCAAAGGACAACCTGGCGGAGGGGTGTGCG

GAGCGCTGTATAAGAAATTCCCGGAAAGCTTCGATTTACAGCCGATCGAAGTAGGAAAAGCGCGACTGGTCAAAGGTG

CAGCTAAACATATCATTCATGCCGTAGGACCAAACTTCAACAAAGTTTCGGAGGTTGAAGGTGACAAACAGTTGGCAG

AGGCTTATGAGTCCATCGCTAAGATTGTCAACGATAACAATTACAAGTCAGTAGCGATTCCACTGTTGTCCACCGGCA

TCTTTTCCGGGAACAAAGATCGACTAACCCAATCATTGAACCATTTGCTGACAGCTTTAGACACCACTGATGCAGATG

TAGCCATATACTGCAGGGACAAGAAATGGGAAATGACTCTCAAGGAAGCAGTGGCTAGGAGAGAAGCAGTGGAGGAGA

TATGCATATCCGACGACTCTTCAGTGACAGAACCTGATGCAGAGCTGGTGAGGGTGCATCCGAAGAGTTCTTTGGCTG

GAAGGAAGGGCTACAGCACAAGCGATGGCAAAACTTTCTCATATTTGGAAGGGACCAAGTTTCACCAGGCGGCCAAGG

ATATAGCAGAAATTAATGCCATGTGGCCCGTTGCAACGGAGGCCAATGAGCAGGTATGCATGTATATCCTCGGAGAAA

GCATGAGCAGTATTAGGTCGAAATGCCCCGTCGAAGAGTCGGAAGCCTCCACACCACCTAGCACGCTGCCTTGCTTGT

GCATCCATGCCATGACTCCAGAAAGAGTACAGCGCCTAAAAGCCTCACGTCCAGAACAAATTACTGTGTGCTCATCCT

TTCCATTGCCGAAGTATAGAATCACTGGTGTGCAGAAGATCCAATGCTCCCAGCCTATATTGTTCTCACCGAAAGTGC

CTGCGTATATTCATCCAAGGAAGTATCTCGTGGAAACACCACCGGTAGACGAGACTCCGGAGCCATCGGCAGAGAACC

-continued

AATCCACAGAGGGGACACCTGAACAACCACCACTTATAACCGAGGATGAGACCAGGACTAGAACGCCTGAGCCGATCA

TCATCGAAGAGGAAGAAGAGGATAGCATAAGTTTGCTGTCAGATGGCCCGACCCACCAGGTGCTGCAAGTCGAGGCAG

ACATTCACGGGCCGCCCTCTGTATCTAGCTCATCCTGGTCCATTCCTCATGCATCCGACTTTGATGTGGACAGTTTAT

CCATACTTGACACCCTGGAGGGAGCTAGCGTGACCAGCGGGGCAACGTCAGCCGAGACTAACTCTTACTTCGCAAAGA

GTATGGAGTTTCTGGCGCGACCGGTGCCTGCGCCTCGAACAGTATTCAGGAACCCTCCACATCCCGCTCCGCGCACAA

GAACACCGTCACTTGCACCCAGCAGGGCCTGCTCGAGAACCAGCCTAGTTTCCACCCCGCCAGGCGTGAATAGGGTGA

TCACTAGAGAGGAGCTCGAGGCGCTTACCCCGTCACGCACTCCTAGCAGGTCGGTCTCGAGAACCAGCCTGGTCTCCA

ACCCGCCAGGCGTAAATAGGGTGATTACAAGAGAGGAGTTTGAGGCGTTCGTAGCACAACAACAATGACGGTTTGATG

CGGGTGCATACATCTTTTCCTCCGACACCGGTCAAGGGCATTTACAACAAAAATCAGTAAGGCAAACGGTGCTATCCG

AAGTGGTGTTGGAGAGGACCGAATTGGAGATTTCGTATGCCCCGCGCCTCGACCAAGAAAAAGAAGAATTACTACGCA

AGAAATTACAGTTAAATCCCACACCTGCTAACAGAAGCAGATACCAGTCCAGGAAGGTGGAGAACATGAAAGCCATAA

CAGCTAGACGTATTCTGCAAGGCCTAGGGCATTATTTGAAGGCAGAAGGAAAAGTGGAGTGCTACCGAACCCTGCATC

CTGTTCCTTTGTATTCATCTAGTGTGAACCGTGCCTTTTCAAGCCCCAAGGTCGCAGTGGAAGCCTGTAACGCCATGT

TGAAAGAGAACTTTCCGACTGTGGCTTCTTACTGTATTATTCCAGAGTACGATGCCTATTTGGACATGGTTGACGGAG

CTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATT

GCAATGTCACGCAAATGAGAGAATTGCCCGTATTGGATTCGGCGGCCTTTAATGTGGAATGCTTCAAGAAATATGCGT

GTAATAATGAATATTGGGAAACGTTTAAAGAAAACCCCATCAGGCTTACTGAAGAAAACGTGGTAAATTACATTACCA

AATTAAAAGGACCAAAAGCTGCTGCTCTTTTTGCGAAGACACATAATTTGAATATGTTGCAGGACATACCAATGGACA

GGTTTGTAATGGACTTAAAGAGAGACGTGAAAGTGACTCCAGGAACAAAACATACTGAAGAACGGCCCAAGGTACAGG

TGATCCAGGCTGCCGATCCGCTAGCAACAGCGTATCTGTGCGGAATCCACCGAGAGCTGGTTAGGAGATTAAATGCGG

TCCTGCTTCCGAACATTCATACACTGTTTGATATGTCGGCTGAAGACTTTGACGCTATTATAGCCGAGCACTTCCAGC

CTGGGGATTGTGTTCTGGAAACTGACATCGCGTCGTTTGATAAAAGTGAGGACGACGCCATGGCTCTGACCGCGTTAA

TGATTCTGGAAGACTTAGGIGTGGACGCAGAGCTGTTGACGCTGATTGAGGCGGCTTTCGGCGAAATTTCATCAATAC

ATTTGCCCACTAAAACTAAATTTAAATTCGGAGCCATGATGAAATCTGGAATGTTCCTCACACTGTTTGTGAACACAG

TCATTAACATTGTAATCGCAAGCAGAGTGTTGAGAGAACGGCTAACCGGATCACCATGTGCAGCATTCATTGGAGATG

ACAATATCGTGAAAGGAGTCAAATCGGACAAATTAATGGCAGACAGGTGCGCCACCTGGTTGAATATGGAAGTCAAGA

TTATAGATGCTGTGGTGGGCGAGAAAGCGCCTTATTTCTGTGGAGGGTTTATTTTGTGTGACTCCGTGACCGGCACAG

CGTGCCGTGTGGCAGACCCCCTAAAAAGGCTGTTTAAGCTTGGCAAACCTCTGGCAGCAGACGATGAACATGATGATG

ACAGGAGAAGGGCATTGCATGAAGAGTCAACACGCTGGAACCGAGTGGGTATTCTTTCAGAGCTGTGCAAGGCAGTAG

AATCAAGGTATGAAACCGTAGGAACTTCCATCATAGTTATGGCCATGACTACTCTAGCTAGCAGTGTTAAATCATTCA

GCTACCTGAGAGGGGCCCCTATAACTCTCTACGGCTAACCTGAATGGACTACGACATAGTCTAGTCCGCCAAGTCTAG

CATATGGCCACCATGTTCGTGTTTCTGGTGCTGCTGCCTCTGGTGTCCAGCCAGTGTGTGAACCTGACCACCAGAACA

CAGCTGCCTCCAGCCTACACCAACAGCTTTACCAGAGGCGTGTACTACCCCGACAAGGTGTTCAGATCCAGCGTGCTG

CACTCTACCCAGGACCTGTTCCTGCCTTTCTTCAGCAACGTGACCTGGTTCCACGCCATCTCCGGCACCAATGGCACC

AAGAGATTCGACAACCCCGTGCTGCCCTTCAACGACGGGGTGTACTTTGCCAGCACCGAGAAGTCCAACATCATCAGA

GGCTGGATCTTCGGCACCACACTGGACAGCAAGACCCAGAGCCTGCTGATCGTGAACAACGCCACCAACGTGGTCATC

AAAGTGTGCGAGTTCCAGTTCTGCAACGACCCCTTCCTGGGCGTCTACCACAAGAACAACAAGAGCTGGATGGAAAGC

GAGTTCCGGGTGTACAGCAGCGCCAACAACTGCACCTTCGAGTACGTGTCCCAGCCTTTCCTGATGGACCTGGAAGGC

AAGCAGGGCAACTTCAAGAACCTGCGCGAGTTCGTGTTCAAGAACATCGACGGCTACTTCAAGATCTACAGCAAGCAC

-continued

ACCCCTATCAACCTCGTGCGGGATCTGCCTCAGGGCTTCTCTGCTCTGGAACCCCTGGTGGATCTGCCCATCGGCATC

AACATCACCCGGTTTCAGACACTGCTGGCCCTGCACAGAAGCTACCTGACACCTGGCGATAGCAGCAGCGGATGGACA

GCTGGTGCCGCCGCTTACTATGTGGGCTACCTGCAGCCTAGAACCTTCCTGCTGAAGTACAACGAGAACGGCACCATC

ACCGACGCCGTGGATTGTGCCCTTGATCCTCTGAGCGAGACAAAGTGCACCCTGAAGTCCTTCACCGTGGAAAAGGGC

ATCTACCAGACCAGCAACTTCCGGGTGCAGCCCACCGAATCCATCGTGCGGTTCCCCAATATCACCAATCTGTGCCCC

TTCGGCGAGGTGTTCAATGCCACCAGATTCGCCTCTGTGTACGCCTGGAACCGGAAGCGGATCAGCAATTGCGTGGCC

GACTACTCCGTGCTGTACAACTCCGCCAGCTTCAGCACCTTCAAGTGCTACGGCGTGTCCCCTACCAAGCTGAACGAC

CTGTGCTTCACAAACGTGTACGCCGACAGCTTCGTGATCCGGGGAGATGAAGTGCGGCAGATTGCCCCTGGACAGACA

GGCAAGATCGCCGACTACAACTACAAGCTGCCCGACGACTTCACCGGCTGTGTGATTGCCTGGAACAGCAACAACCTG

GACTCCAAAGTCGGCGGCAACTACAATTACCTGTACCGGCTGTTCCGGAAGTCCAATCTGAAGCCCTTCGAGCGGGAC

ATCTCCACCGAGATCTATCAGGCCGGCAGCACCCCTTGTAACGGCGTGAAAGGCTTCAACTGCTACTTCCCACTGCAG

TCCTACGGCTTTCAGCCCACATATGGCGTGGGCTATCAGCCCTACAGAGTGGTGGTGCTGAGCTTCGAACTGCTGCAT

GCCCCTGCCACAGTGTGCGGCCCTAAGAAAAGCACCAATCTCGTGAAGAACAAATGCGTGAACTTCAACTTCAACGGC

CTGACCGGCACAGGCGTGCTGACAGAGAGCAACAAGAAGTTCCTGCCATTCCAGCAGTTTGGCCGGGATATCGACGAT

ACCACAGACGCCGTTAGAGATCCCCAGACACTGGAAATCCTGGACATCACCCCTTGCAGCTTCGGCGGAGTGTCTGTG

ATCACCCCTGGCACCAACACCAGCAATCAGGTGGCAGTGCTGTACCAGGGCGTGAACTGTACCGAAGTGCCCGTGGCC

ATTCACGCCGATCAGCTGACACCTACATGGCGGGTGTACTCCACCGGCAGCAATGTGTTTCAGACCAGAGCCGGCTGT

CTGATCGGAGCCGAGCACGTGAACAATAGCTACGAGTGCGACATCCCCATCGGCGCTGGCATCTGTGCCAGCTACCAG

ACACAGACAAACAGCCACTCTCTGGCCAGCTCTGTGGCCAGCCAGAGCATCATTGCCTACACAATGTCTCTGGGCGCC

GAGAACAGCGTGGCCTACTCCAACAACTCTATCGCTATCCCCATCAACTTCACCATCAGCGTGACCACAGAGATCCTG

CCTGTGTCCATGACCAAGACCAGCGTGGACTGCACCATGTACATCTGCGGCGATTCCACCGAGTGCTCCAACCTGCTG

CTGCAGTACGGCAGCTTCTGCACCCAGCTGAATAGAGCCCTGACAGGGATCGCCGTGGAACAGGACAAGAACACCCAA

GAGGTGTTCGCCCAAGTGAAGCAGATCTACAAGACCCCTCCTATCAAGGACTTCGGCGGCTTCAATTTCAGCCAGATT

CTGCCCGATCCTAGCAAGCCCAGCAAGCGGAGCCCCATCGAGGACCTGCTGTTCAACAAAGTGACACTGGCCGACGCC

GGCTTCATCAAGCAGTATGGCGATTGTCTGGGCGACATTGCCGCCAGGGATCTGATTTGCGCCCAGAAGTTTAACGGA

CTGACAGTGCTGCCTCCTCTGCTGACCGATGAGATGATCGCCCAGTACACATCTGCCCTGCTGGCCGGCACAATCACA

AGCGGCTGGACATTTGGAGCTGGCCCCGCTCTGCAGATCCCCTTTCCTATGCAGATGGCCTACAGATTCAACGGCATC

GGAGTGACCCAGAATGTGCTGTACGAGAACCAGAAGCTGATCGCCAACCAGTTCAACAGCGCCATCGGCAAGATCCAG

GACAGCCTGAGCAGCACACCAAGCGCCCTGGGAAAGCTGCAGGACGTGGTCAACCAGAATGCCCAGGCACTGAACACC

CTGGTCAAGCAGCTGTCCTCCAACTTCGGCGCCATCAGCTCTGTGCTGAACGATATCCTGGCCAGACTGGACCCTCCT

GAGGCCGAGGTGCAGATCGACAGACTGATCACAGGCAGACTGCAGAGCCTCCAGACATACGTGACCCAGCAGCTGATC

AGAGCCGCCGAGATTAGAGCCTCTGCCAATCTGGCCGCCACCAAGATGTCTGAGTGTGTGCTGGGCCAGAGCAAGAGA

GTGGACTTTTGCGGCAAGGGCTACCACCTGATGAGCTTCCCTCAGTCTGCCCCTCACGGCGTGGTGTTTCTGCACGTG

ACATACGTTCCCGCTCAAGAGAAGAATTTCACCACCGCTCCAGCCATCTGCCACGACGGCAAAGCCCACTTTCCTAGA

GAAGGCGTGTTCGTGTCCAACGGCACCCATTGGTTCGTGACACAGCGGAACTTCTACGAGCCCCAGATCATCACCACC

CACAACACCTTCGTGTCTGGCAACTGCGACGTCGTGATCGGCATTGTGAACAATACCGTGTACGACCCTCTGCAGCCC

GAGCTGGACAGCTTCAAAGAGGAACTGGACAAGTACTTTAAGAACCACACAAGCCCCGACGTGGACCTGGGCGATATC

AGCGGAATCAATGCCAGCGTCGTGAACATCCAGAAAGAGATCGACCGGCTGAACGAGGTGGCCAAGAATCTGAACGAG

AGCCTGATCGACCTGCAAGAACTGGGGAAGTACGAGCAGTACATCAAGTGGCCCTGGTACATCTGGCTGGGCTTTATC

GCCGGACTGATTGCCATCGTGATGGTCACAATCATGCTGTGTTGCATGACCAGCTGCTGTAGCTGCCTGAAGGGCTGT

TGTAGCTGTGGCAGCTGCTGCAAGTTCGACGAGGACGATTCTGAGCCCGTGCTGAAGGGCGTGAAACTGCACTACACA

-continued

TGAGCGGCCGCGAATTGGCAAGCTGCTTACATAGAACTCGCGGCGATTGGCATGCCGCCTTAAAATTTTTATTTTATT

TTTCTTTTCTTTTCCGAATCGGATTTTGTTTTTAATATTTCAAAAAAAAAAAAAAAAAAAAAAAAAAAAAAAAAAAA

Accordingly, preferably the nucleic acid sequence comprises a nucleotide sequence substantially as set out in SEQ ID No: 68, or a fragment or variant thereof.

In another embodiment (the B.1.351 South African variant of SARS-CoV-2 glycoprotein), the nucleic acid sequence is preferably DNA, and comprise or consist of SEQ ID No: 69, as follows:

[SEQ ID No: 69]

ATGGGCGGCGCATGAGAGAAGCCCAGACCAATTACCTACCCAAAATGGAGAAAGTTCACGTTGACATCGAGGAAGACA

GCCCATTCCTCAGAGCTTTGCAGCGGAGCTTCCCGCAGTTTGAGGTAGAAGCCAAGCAGGTCACTGATAATGACCATG

CTAATGCCAGAGCGTTTTCGCATCTGGCTTCAAAACTGATCGAAACGGAGGTGGACCCATCCGACACGATCCTTGACA

TTGGAAGTGCGCCCGCCCGCAGAATGTATTCTAAGCACAAGTATCATTGTATCTGTCCGATGAGATGTGCGGAAGATC

CGGACAGATTGTATAAGTATGCAACTAAGCTGAAGAAAAACTGTAAGGAAATAACTGATAAGGAATTGGACAAGAAAA

TGAAGGAGCTGGCCGCCGTCATGAGCGACCCTGACCTGGAAACTGAGACTATGTGCCTCCACGACGACGAGTCGTGTC

GCTACGAAGGGCAAGTCGCTGTTTACCAGGATGTATACGCGGTTGACGGACCGACAAGTCTCTATCACCAAGCCAATA

AGGGAGTTAGAGTCGCCTACTGGATAGGCTTTGACACCACCCCTTTTATGTTTAAGAACTTGGCTGGAGCATATCCAT

CATACTCTACCAACTGGGCCGACGAAACCGTGTTAACGGCTCGTAACATAGGCCTATGCAGCTCTGACGTTATGGAGC

GGTCACGTAGAGGGATGTCCATTCTTAGAAAGAAGTATTTGAAACCATCCAACAATGTTCTATTCTCTGTTGGCTCGA

CCATCTACCACGAGAAGAGGGACTTACTGAGGAGCTGGCACCTGCCGTCTGTATTTCACTTACGTGGCAAGCAAAATT

ACACATGTCGGTGTGAGACTATAGTTAGTTGCGACGGGTACGTCGTTAAAAGAATAGCTATCAGTCCAGGCCTGTATG

GGAAGCCTTCAGGCTATGCTGCTACGATGCACCGCGAGGGATTCTTGTGCTGCAAAGTGACAGACACATTGAACGGGG

AGAGGGTCTCTTTTCCCGTGTGCACGTATGTGCCAGCTACATTGTGTGACCAAATGACTGGCATACTGGCAACAGATG

TCAGTGCGGACGACGCGCAAAAACTGCTGGTTGGGCTCAACCAGCGTATAGTCGTCAACGGTCGCACCCAGAGAAACA

CCAATACCATGAAAAATTACCTTTTGCCCGTAGTGGCCCAGGCATTTGCTAGGTGGGCAAAGGAATATAAGGAAGATC

AAGAAGATGAAAGGCCACTAGGACTACGAGATAGACAGTTAGTCATGGGGTGTTGTTGGGCTTTTAGAAGGCACAAGA

TAACATCTATTTATAAGCGCCCGGATACCCAAACCATCATCAAAGTGAACAGCGATTTCCACTCATTCGTGCTGCCCA

GGATAGGCAGTAACACATTGGAGATCGGGCTGAGAACAAGAATCAGGAAAATGTTAGAGGAGCACAAGGAGCCGTCAC

CTCTCATTACCGCCGAGGACGTACAAGAAGCTAAGTGCGCAGCCGATGAGGCTAAGGAGGTGCGTGAAGCCGAGGAGT

TGCGCGCAGCTCTACCACCTTTGGCAGCTGATGTTGAGGAGCCCACTCTGGAGGCAGACGTCGACTTGATGTTACAAG

AGGCTGGGGCCGGCTCAGTGGAGACACCTCGTGGCTTGATAAAGGTTACCAGCTACGATGGCGAGGACAAGATCGGCT

CTTACGCTGTGCTTTCTCCGCAGGCTGTACTCAAGAGTGAAAAATTATCTTGCATCCACCCTCTCGCTGAACAAGTCA

TAGTGATAACACACTCTGGCCGAAAAGGGCGTTATGCCGTGGAACCATACCATGGTAAAGTAGTGGTGCCAGAGGGAC

ATGCAATACCCGTCCAGGACTTTCAAGCTCTGAGTGAAAGTGCCACCATTGTGTACAACGAACGTGAGTTCGTAAACA

GGTACCTGCACCATATTGCCACACATGGAGGAGCGCTGAACACTGATGAAGAATATTACAAAACTGTCAAGCCCAGCG

AGCACGACGGCGAATACCTGTACGACATCGACAGGAAACAGTGCGTCAAGAAAGAACTAGTCACTGGGCTAGGGCTCA

CAGGCGAGCTGGTGGATCCTCCCTTCCATGAATTCGCCTACGAGAGTCTGAGAACACGACCAGCCGCTCCTTACCAAG

TACCAACCATAGGGGTGTATGGCGTGCCAGGATCAGGCAAGTCTGGCATCATTAAAAGCGCAGTCACCAAAAAAGATC

TAGTGGTGAGCGCCAAGAAAGAAAACTGTGCAGAAATTATAAGGGACGTCAAGAAAATGAAAGGGCTGGACGTCAATG

CCAGAACTGTGGACTCAGTGCTCTTGAATGGATGCAAACACCCCGTAGAGACCCTGTATATTGACGAAGCTTTTGCTT

GTCATGCAGGTACTCTCAGAGCGCTCATAGCCATTATAAGACCTAAAAAGGCAGTGCTCTGCGGGGATCCCAAACAGT

-continued

GCGGTTTTTTTAACATGATGTGCCTGAAAGTGCATTTTAACCACGAGATTTGCACACAAGTCTTCCACAAAAGCATCT

CTCGCCGTTGCACTAAATCTGTGACTTCGGTCGTCTCAACCTTGTTTTACGACAAAAAAATGAGAACGACGAATCCGA

AAGAGACTAAGATTGTGATTGACACTACCGGCAGTACCAAACCTAAGCAGGACGATCTCATTCTCACTTGTTTCAGAG

GGTGGGTGAAGCAGTTGCAAATAGATTACAAAGGCAACGAAATAATGACGGCAGCTGCCTCTCAAGGGCTGACCCGTA

AAGGTGTGTATGCCGTTCGGTACAAGGTGAATGAAAATCCTCTGTACGCACCCACCTCAGAACATGTGAACGTCCTAC

TGACCCGCACGGAGGACCGCATCGTGTGGAAAACACTAGCCGGCGACCCATGGATAAAAACACTGACTGCCAAGTACC

CTGGGAATTTCACTGCCACGATAGAGGAGTGGCAAGCAGAGCATGATGCCATCATGAGGCACATCTTGGAGAGACCGG

ACCCTACCGACGTCTTCCAGAATAAGGCAAACGTGTGTTGGGCCAAGGCTTTAGTGCCGGTGCTGAAGACCGCTGGCA

TAGACATGACCACTGAACAATGGAACACTGTGGATTATTTTGAAACGGACAAAGCTCACTCAGCAGAGATAGTATTGA

ACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCA

GGTACCCACAACTGCCTCGGGCAGTTGCCACTGGAAGAGTCTATGACATGAACACTGGTACACTGCGCAATTATGATC

CGCGCATAAACCTAGTACCTGTAAACAGAAGACTGCCTCATGCTTTAGTCCTCCACCATAATGAACACCCACAGAGTG

ACTTTTCTTCATTCGTCAGCAAATTGAAGGGCAGAACTGTCCTGGTGGTCGGGGAAAAGTTGTCCGTCCCAGGCAAAA

TGGTTGACTGGTTGTCAGACCGGCCTGAGGCTACCTTCAGAGCTCGGCTGGATTTAGGCATCCCAGGTGATGTGCCCA

AATATGACATAATATTTGTTAATGTGAGGACCCCATATAAATACCATCACTATCAGCAGTGTGAAGACCATGCCATTA

AGCTTAGCATGTTGACCAAGAAAGCTTGTCTGCATCTGAATCCCGGCGGAACCTGTGTCAGCATAGGTTATGGTTACG

CTGACAGGGCCAGCGAAAGCATCATTGGTGCTATAGCGCGGCAGTTCAAGTTTTCCCGGGTATGCAAACCGAAATCCT

CACTTGAAGAGACGGAAGTTCTGTTTGTATTCATTGGGTACGATCGCAAGGCCCGTACGCACAATTCTTACAAGCTTT

CATCAACCTTGACCAACATTTATACAGGTTCCAGACTCCACGAAGCCGGATGTGCACCCTCATATCATGTGGTGCGAG

GGGATATTGCCACGGCCACCGAAGGAGTGATTATAAATGCTGCTAACAGCAAAGGACAACCTGGCGGAGGGGTGTGCG

GAGCGCTGTATAAGAAATTCCCGGAAAGCTTCGATTTACAGCCGATCGAAGTAGGAAAAGCGCGACTGGTCAAAGGTG

CAGCTAAACATATCATTCATGCCGTAGGACCAAACTTCAACAAAGTTTCGGAGGTTGAAGGTGACAAACAGTTGGCAG

AGGCTTATGAGTCCATCGCTAAGATTGTCAACGATAACAATTACAAGTCAGTAGCGATTCCACTGTTGTCCACCGGCA

TCTTTTCCGGGAACAAAGATCGACTAACCCAATCATTGAACCATTTGCTGACAGCTTTAGACACCACTGATGCAGATG

TAGCCATATACTGCAGGGACAAGAAATGGGAAATGACTCTCAAGGAAGCAGTGGCTAGGAGAGAAGCAGTGGAGGAGA

TATGCATATCCGACGACTCTTCAGTGACAGAACCTGATGCAGAGCTGGTGAGGGTGCATCCGAAGAGTTCTTTGGCTG

GAAGGAAGGGCTACAGCACAAGCGATGGCAAAACTTTCTCATATTTGGAAGGGACCAAGTTTCACCAGGCGGCCAAGG

ATATAGCAGAAATTAATGCCATGTGGCCCGTTGCAACGGAGGCCAATGAGCAGGTATGCATGTATATCCTCGGAGAAA

GCATGAGCAGTATTAGGTCGAAATGCCCCGTCGAAGAGTCGGAAGCCTCCACACCACCTAGCACGCTGCCTTGCTTGT

GCATCCATGCCATGACTCCAGAAAGAGTACAGCGCCTAAAAGCCTCACGTCCAGAACAAATTACTGTGTGCTCATCCT

TTCCATTGCCGAAGTATAGAATCACTGGTGTGCAGAAGATCCAATGCTCCCAGCCTATATTGTTCTCACCGAAAGTGC

CTGCGTATATTCATCCAAGGAAGTATCTCGTGGAAACACCACCGGTAGACGAGACTCCGGAGCCATCGGCAGAGAACC

AATCCACAGAGGGGACACCTGAACAACCACCACTTATAACCGAGGATGAGACCAGGACTAGAACGCCTGAGCCGATCA

TCATCGAAGAGGAAGAAGAGGATAGCATAAGTTTGCTGTCAGATGGCCCGACCCACCAGGTGCTGCAAGTCGAGGCAG

ACATTCACGGGCCGCCCTCTGTATCTAGCTCATCCTGGTCCATTCCTCATGCATCCGACTTTGATGTGGACAGTTTAT

CCATACTTGACACCCTGGAGGGAGCTAGCGTGACCAGCGGGGCAACGTCAGCCGAGACTAACTCTTACTTCGCAAAGA

GTATGGAGTTTCTGGCGCGACCGGTGCCTGCGCCTCGAACAGTATTCAGGAACCCTCCACATCCCGCTCCGCGCACAA

GAACACCGTCACTTGCACCCAGCAGGGCCTGCTCGAGAACCAGCCTAGTTTCCACCCCGCCAGGCGTGAATAGGGTGA

TCACTAGAGAGGAGCTCGAGGCGCTTACCCCGTCACGCACTCCTAGCAGGTCGGTCTCGAGAACCAGCCTGGTCTCCA

-continued

ACCCGCCAGGCGTAAATAGGGTGATTACAAGAGAGGAGTTTGAGGCGTTCGTAGCACAACAACAATGACGGTTTGATG

CGGGTGCATACATCTTTTCCTCCGACACCGGTCAAGGGCATTTACAACAAAAATCAGTAAGGCAAACGGTGCTATCCG

AAGTGGTGTTGGAGAGGACCGAATTGGAGATTTCGTATGCCCCGCGCCTCGACCAAGAAAAAGAAGAATTACTACGCA

AGAAATTACAGTTAAATCCCACACCTGCTAACAGAAGCAGATACCAGTCCAGGAAGGTGGAGAACATGAAAGCCATAA

CAGCTAGACGTATTCTGCAAGGCCTAGGGCATTATTTGAAGGCAGAAGGAAAAGTGGAGTGCTACCGAACCCTGCATC

CTGTTCCTTTGTATTCATCTAGTGTGAACCGTGCCTTTTCAAGCCCCAAGGTCGCAGTGGAAGCCTGTAACGCCATGT

TGAAAGAGAACTTTCCGACTGTGGCTTCTTACTGTATTATTCCAGAGTACGATGCCTATTTGGACATGGTTGACGGAG

CTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATT

GCAATGTCACGCAAATGAGAGAATTGCCCGTATTGGATTCGGCGGCCTTTAATGTGGAATGCTTCAAGAAATATGCGT

GTAATAATGAATATTGGGAAACGTTTAAAGAAAACCCCATCAGGCTTACTGAAGAAAACGTGGTAAATTACATTACCA

AATTAAAAGGACCAAAAGCTGCTGCTCTTTTTGCGAAGACACATAATTTGAATATGTTGCAGGACATACCAATGGACA

GGTTTGTAATGGACTTAAAGAGAGACGTGAAAGTGACTCCAGGAACAAAACATACTGAAGAACGGCCCAAGGTACAGG

TGATCCAGGCTGCCGATCCGCTAGCAACAGCGTATCTGTGCGGAATCCACCGAGAGCTGGTTAGGAGATTAAATGCGG

TCCTGCTTCCGAACATTCATACACTGTTTGATATGTCGGCTGAAGACTTTGACGCTATTATAGCCGAGCACTTCCAGC

CTGGGGATTGTGTTCTGGAAACTGACATCGCGTCGTTTGATAAAAGTGAGGACGACGCCATGGCTCTGACCGCGTTAA

TGATTCTGGAAGACTTAGGTGTGGACGCAGAGCTGTTGACGCTGATTGAGGCGGCTTTCGGCGAAATTTCATCAATAC

ATTTGCCCACTAAAACTAAATTTAAATTCGGAGCCATGATGAAATCTGGAATGTTCCTCACACTGTTTGTGAACACAG

TCATTAACATTGTAATCGCAAGCAGAGTGTTGAGAGAACGGCTAACCGGATCACCATGTGCAGCATTCATTGGAGATG

ACAATATCGTGAAAGGAGTCAAATCGGACAAATTAATGGCAGACAGGTGCGCCACCTGGTTGAATATGGAAGTCAAGA

TTATAGATGCTGTGGTGGGCGAGAAAGCGCCTTATTTCTGTGGAGGGTTTATTTTGTGTGACTCCGTGACCGGCACAG

CGTGCCGTGTGGCAGACCCCCTAAAAAGGCTGTTTAAGCTTGGCAAACCTCTGGCAGCAGACGATGAACATGATGATG

ACAGGAGAAGGGCATTGCATGAAGAGTCAACACGCTGGAACCGAGTGGGTATTCTTTCAGAGCTGTGCAAGGCAGTAG

AATCAAGGTATGAAACCGTAGGAACTTCCATCATAGTTATGGCCATGACTACTCTAGCTAGCAGTGTTAAATCATTCA

GCTACCTGAGAGGGGCCCCTATAACTCTCTACGGCTAACCTGAATGGACTACGACATAGTCTAGTCCGCCAAGTCTAG

CATATGGCCACCATGTTCGTGTTTCTGGTGCTGCTGCCTCTGGTGTCCAGCCAGTGTGTGAACTTCACCACCAGAACA

CAGCTGCCTCCAGCCTACACCAACAGCTTTACCAGAGGCGTGTACTACCCCGACAAGGTGTTCAGATCCAGCGTGCTG

CACTCTACCCAGGACCTGTTCCTGCCTTTCTTCAGCAACGTGACCTGGTTCCACGCCATCCACGTGTCCGGCACCAAT

GGCACCAAGAGATTCGCCAACCCCGTGCTGCCCTTCAACGACGGGGTGTACTTTGCCAGCACCGAGAAGTCCAACATC

ATCAGAGGCTGGATCTTCGGCACCACACTGGACAGCAAGACCCAGAGCCTGCTGATCGTGAACAACGCCACCAACGTG

GTCATCAAAGTGTGCGAGTTCCAGTTCTGCAACGACCCCTTCCTGGGCGTCTACTACCACAAGAACAACAAGAGCTGG

ATGGAAAGCGAGTTCCGGGTGTACAGCAGCGCCAACAACTGCACCTTCGAGTACGTGTCCCAGCCTTTCCTGATGGAC

CTGGAAGGCAAGCAGGGCAACTTCAAGAACCTGCGCGAGTTCGTGTTCAAGAACATCGACGGCTACTTCAAGATCTAC

AGCAAGCACACCCCTATCAACCTCGTGCGGGGTCTGCCTCAGGGCTTCTCTGCTCTGGAACCCCTGGTGGATCTGCCC

ATCGGCATCAACATCACCCGGTTTCAGACACTGCACATAAGCTACCTGACACCTGGCGATAGCAGCAGCGGATGGACA

GCTGGTGCCGCCGCTTACTATGTGGGCTACCTGCAGCCTAGAACCTTCCTGCTGAAGTACAACGAGAACGGCACCATC

ACCGACGCCGTGGATTGTGCCCTTGATCCTCTGAGCGAGACAAAGTGCACCCTGAAGTCCTTCACCGTGGAAAAGGGC

ATCTACCAGACCAGCAACTTCCGGGTGCAGCCCACCGAATCCATCGTGCGGTTCCCCAATATCACCAATCTGTGCCCC

TTCGGCGAGGTGTTCAATGCCACCAGATTCGCCTCTGTGTACGCCTGGAACCGGAAGCGGATCAGCAATTGCGTGGCC

GACTACTCCGTGCTGTACAACTCCGCCAGCTTCAGCACCTTCAAGTGCTACGGCGTGTCCCCTACCAAGCTGAACGAC

CTGTGCTTCACAAACGTGTACGCCGACAGCTTCGTGATCCGGGGAGATGAAGTGCGGCAGATTGCCCCTGGACAGACA

-continued

GGCAATATCGCCGACTACAACTACAAGCTGCCCGACGACTTCACCGGCTGTGTGATTGCCTGGAACAGCAACAACCTG

GACTCCAAAGTCGGCGGCAACTACAATTACCTGTACCGGCTGTTCCGGAAGTCCAATCTGAAGCCCTTCGAGCGGGAC

ATCTCCACCGAGATCTATCAGGCCGGCAGCACCCCTTGTAACGGCGTGAAAGGCTTCAACTGCTACTTCCCACTGCAG

TCCTACGGCTTTCAGCCCACATATGGCGTGGGCTATCAGCCCTACAGAGTGGTGGTGCTGAGCTTCGAACTGCTGCAT

GCCCCTGCCACAGTGTGCGGCCCTAAGAAAAGCACCAATCTCGTGAAGAACAAATGCGTGAACTTCAACTTCAACGGC

CTGACCGGCACAGGCGTGCTGACAGAGAGCAACAAGAAGTTCCTGCCATTCCAGCAGTTTGGCCGGGATATCGCCGAT

ACCACAGACGCCGTTAGAGATCCCCAGACACTGGAAATCCTGGACATCACCCCTTGCAGCTTCGGCGGAGTGTCTGTG

ATCACCCCTGGCACCAACACCAGCAATCAGGTGGCAGTGCTGTACCAGGACGTGAACTGTACCGAAGTGCCCGTGGCC

ATTCACGCCGATCAGCTGACACCTACATGGCGGGTGTACTCCACCGGCAGCAATGTGTTTCAGACCAGAGCCGGCTGT

CTGATCGGAGCCGAGCACGTGAACAATAGCTACGAGTGCGACATCCCCATCGGCGCTGGCATCTGTGCCAGCTACCAG

ACACAGACAAACAGCCCCTCTCTGGCCAGCTCTGTGGCCAGCCAGAGCATCATTGCCTACACAATGTCTCTGGGCGTC

GAGAACAGCGTGGCCTACTCCAACAACTCTATCGCTATCCCCACCAACTTCACCATCAGCGTGACCACAGAGATCCTG

CCTGTGTCCATGACCAAGACCAGCGTGGACTGCACCATGTACATCTGCGGCGATTCCACCGAGTGCTCCAACCTGCTG

CTGCAGTACGGCAGCTTCTGCACCCAGCTGAATAGAGCCCTGACAGGGATCGCCGTGGAACAGGACAAGAACACCCAA

GAGGTGTTCGCCCAAGTGAAGCAGATCTACAAGACCCCTCCTATCAAGGACTTCGGCGGCTTCAATTTCAGCCAGATT

CTGCCCGATCCTAGCAAGCCCAGCAAGCGGAGCCCCATCGAGGACCTGCTGTTCAACAAAGTGACACTGGCCGACGCC

GGCTTCATCAAGCAGTATGGCGATTGTCTGGGCGACATTGCCGCCAGGGATCTGATTTGCGCCCAGAAGTTTAACGGA

CTGACAGTGCTGCCTCCTCTGCTGACCGATGAGATGATCGCCCAGTACACATCTGCCCTGCTGGCCGGCACAATCACA

AGCGGCTGGACATTTGGAGCTGGCCCCGCTCTGCAGATCCCCTTTCCTATGCAGATGGCCTACAGATTCAACGGCATC

GGAGTGACCCAGAATGTGCTGTACGAGAACCAGAAGCTGATCGCCAACCAGTTCAACAGCGCCATCGGCAAGATCCAG

GACAGCCTGAGCAGCACACCAAGCGCCCTGGGAAAGCTGCAGGACGTGGTCAACCAGAATGCCCAGGCACTGAACACC

CTGGTCAAGCAGCTGTCCTCCAACTTCGGCGCCATCAGCTCTGTGCTGAACGATATCCTGAGCAGACTGGACCCTCCT

GAGGCCGAGGTGCAGATCGACAGACTGATCACAGGCAGACTGCAGAGCCTCCAGACATACGTGACCCAGCAGCTGATC

AGAGCCGCCGAGATTAGAGCCTCTGCCAATCTGGCCGCCACCAAGATGTCTGAGTGTGTGCTGGGCCAGAGCAAGAGA

GTGGACTTTTGCGGCAAGGGCTACCACCTGATGAGCTTCCCTCAGTCTGCCCCTCACGGCGTGGTGTTTCTGCACGTG

ACATACGTTCCCGCTCAAGAGAAGAATTTCACCACCGCTCCAGCCATCTGCCACGACGGCAAAGCCCACTTTCCTAGA

GAAGGCGTGTTCGTGTCCAACGGCACCCATTGGTTCGTGACACAGCGGAACTTCTACGAGCCCCAGATCATCACCACC

GACAACACCTTCGTGTCTGGCAACTGCGACGTCGTGATCGGCATTGTGAACAATACCGTGTACGACCCTCTGCAGCCC

GAGCTGGACAGCTTCAAAGAGGAACTGGACAAGTACTTTAAGAACCACACAAGCCCCGACGTGGACCTGGGCGATATC

AGCGGAATCAATGCCAGCGTCGTGAACATCCAGAAAGAGATCGACCGGCTGAACGAGGTGGCCAAGAATCTGAACGAG

AGCCTGATCGACCTGCAAGAACTGGGGAAGTACGAGCAGTACATCAAGTGGCCCTGGTACATCTGGCTGGGCTTTATC

GCCGGACTGATTGCCATCGTGATGGTCACAATCATGCTGTGTTGCATGACCAGCTGCTGTAGCTGCCTGAAGGGCTGT

TGTAGCTGTGGCAGCTGCTGCAAGTTCGACGAGGACGATTCTGAGCCCGTGCTGAAGGGCGTGAAACTGCACTACACA

TGAGCGGCCGCGAATTGGCAAGCTGCTTACATAGAACTCGCGGCGATTGGCATGCCGCCTTAAAATTTTTATTTTATT

TTTCTTTTCTTTTCCGAATCGGATTTTGTTTTTAATATTTCAAAAAAAAAAAAAAAAAAAAAAAAAAAAAAAAAAAA

Accordingly, preferably the nucleic acid sequence comprises a nucleotide sequence substantially as set out in SEQ ID No: 69, or a fragment or variant thereof.

In another embodiment (the B.1.1.28 (P.1) Brazilian variant of SARS-CoV-2 glycoprotein), the nucleic acid sequence is preferably DNA, and comprise or consist of SEQ ID No: 70, as follows:

[SEQ ID No: 70]

ATGGGCGGCGCATGAGAGAAGCCCAGACCAATTACCTACCCAAAATGGAGAAAGTTCACGTTGACATCGAGGAAGACA

GCCCATTCCTCAGAGCTTTGCAGCGGAGCTTCCCGCAGTTTGAGGTAGAAGCCAAGCAGGTCACTGATAATGACCATG

CTAATGCCAGAGCGTTTTCGCATCTGGCTTCAAAACTGATCGAAACGGAGGTGGACCCATCCGACACGATCCTTGACA

TTGGAAGTGCGCCCGCCCGCAGAATGTATTCTAAGCACAAGTATCATTGTATCTGTCCGATGAGATGTGCGGAAGATC

CGGACAGATTGTATAAGTATGCAACTAAGCTGAAGAAAAACTGTAAGGAAATAACTGATAAGGAATTGGACAAGAAAA

TGAAGGAGCTGGCCGCCGTCATGAGCGACCCTGACCTGGAAACTGAGACTATGTGCCTCCACGACGACGAGTCGTGTC

GCTACGAAGGGCAAGTCGCTGTTTACCAGGATGTATACGCGGTTGACGGACCGACAAGTCTCTATCACCAAGCCAATA

AGGGAGTTAGAGTCGCCTACTGGATAGGCTTTGACACCACCCCTTTTATGTTTAAGAACTTGGCTGGAGCATATCCAT

CATACTCTACCAACTGGGCCGACGAAACCGTGTTAACGGCTCGTAACATAGGCCTATGCAGCTCTGACGTTATGGAGC

GGTCACGTAGAGGGATGTCCATTCTTAGAAAGAAGTATTTGAAACCATCCAACAATGTTCTATTCTCTGTTGGCTCGA

CCATCTACCACGAGAAGAGGGACTTACTGAGGAGCTGGCACCTGCCGTCTGTATTTCACTTACGTGGCAAGCAAAATT

ACACATGTCGGTGTGAGACTATAGTTAGTTGCGACGGGTACGTCGTTAAAAGAATAGCTATCAGTCCAGGCCTGTATG

GGAAGCCTTCAGGCTATGCTGCTACGATGCACCGCGAGGGATTCTTGTGCTGCAAAGTGACAGACACATTGAACGGGG

AGAGGGTCTCTTTTCCCGTGTGCACGTATGTGCCAGCTACATTGTGTGACCAAATGACTGGCATACTGGCAACAGATG

TCAGTGCGGACGACGCGCAAAAACTGCTGGTTGGGCTCAACCAGCGTATAGTCGTCAACGGTCGCACCCAGAGAAACA

CCAATACCATGAAAAATTACCTTTTGCCCGTAGTGGCCCAGGCATTTGCTAGGTGGGCAAAGGAATATAAGGAAGATC

AAGAAGATGAAAGGCCACTAGGACTACGAGATAGACAGTTAGTCATGGGGTGTTGTTGGGCTTTTAGAAGGCACAAGA

TAACATCTATTTATAAGCGCCCGGATACCCAAACCATCATCAAAGTGAACAGCGATTTCCACTCATTCGTGCTGCCCA

GGATAGGCAGTAACACATTGGAGATCGGGCTGAGAACAAGAATCAGGAAAATGTTAGAGGAGCACAAGGAGCCGTCAC

CTCTCATTACCGCCGAGGACGTACAAGAAGCTAAGTGCGCAGCCGATGAGGCTAAGGAGGTGCGTGAAGCCGAGGAGT

TGCGCGCAGCTCTACCACCTTTGGCAGCTGATGTTGAGGAGCCCACTCTGGAGGCAGACGTCGACTTGATGTTACAAG

AGGCTGGGGCCGGCTCAGTGGAGACACCTCGTGGCTTGATAAAGGTTACCAGCTACGATGGCGAGGACAAGATCGGCT

CTTACGCTGTGCTTTCTCCGCAGGCTGTACTCAAGAGTGAAAAATTATCTTGCATCCACCCTCTCGCTGAACAAGTCA

TAGTGATAACACACTCTGGCCGAAAAGGGCGTTATGCCGTGGAACCATACCATGGTAAAGTAGTGGTGCCAGAGGGAC

ATGCAATACCCGTCCAGGACTTTCAAGCTCTGAGTGAAAGTGCCACCATTGTGTACAACGAACGTGAGTTCGTAAACA

GGTACCTGCACCATATTGCCACACATGGAGGAGCGCTGAACACTGATGAAGAATATTACAAAACTGTCAAGCCCAGCG

AGCACGACGGCGAATACCTGTACGACATCGACAGGAAACAGTGCGTCAAGAAAGAACTAGTCACTGGGCTAGGGCTCA

CAGGCGAGCTGGTGGATCCTCCCTTCCATGAATTCGCCTACGAGAGTCTGAGAACACGACCAGCCGCTCCTTACCAAG

TACCAACCATAGGGGTGTATGGCGTGCCAGGATCAGGCAAGTCTGGCATCATTAAAAGCGCAGTCACCAAAAAAGATC

TAGTGGTGAGCGCCAAGAAAGAAAACTGTGCAGAAATTATAAGGGACGTCAAGAAAATGAAAGGGCTGGACGTCAATG

CCAGAACTGTGGACTCAGTGCTCTTGAATGGATGCAAACACCCCGTAGAGACCCTGTATATTGACGAAGCTTTTGCTT

GTCATGCAGGTACTCTCAGAGCGCTCATAGCCATTATAAGACCTAAAAAGGCAGTGCTCTGCGGGGATCCCAAACAGT

GCGGTTTTTTTAACATGATGTGCCTGAAAGTGCATTTTAACCACGAGATTTGCACACAAGTCTTCCACAAAAGCATCT

CTCGCCGTTGCACTAAATCTGTGACTTCGGTCGTCTCAACCTTGTTTTACGACAAAAAAATGAGAACGACGAATCCGA

AAGAGACTAAGATTGTGATTGACACTACCGGCAGTACCAAACCTAAGCAGGACGATCTCATTCTCACTTGTTTCAGAG

GGTGGGTGAAGCAGTTGCAAATAGATTACAAAGGCAACGAAATAATGACGGCAGCTGCCTCTCAAGGGCTGACCCGTA

-continued

AAGGTGTGTATGCCGTTCGGTACAAGGTGAATGAAAATCCTCTGTACGCACCCACCTCAGAACATGTGAACGTCCTAC

TGACCCGCACGGAGGACCGCATCGTGTGGAAAACACTAGCCGGCGACCCATGGATAAAAACACTGACTGCCAAGTACC

CTGGGAATTTCACTGCCACGATAGAGGAGTGGCAAGCAGAGCATGATGCCATCATGAGGCACATCTTGGAGAGACCGG

ACCCTACCGACGTCTTCCAGAATAAGGCAAACGTGTGTTGGGCCAAGGCTTTAGTGCCGGTGCTGAAGACCGCTGGCA

TAGACATGACCACTGAACAATGGAACACTGTGGATTATTTTGAAACGGACAAAGCTCACTCAGCAGAGATAGTATTGA

ACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCA

GGTACCCACAACTGCCTCGGGCAGTTGCCACTGGAAGAGTCTATGACATGAACACTGGTACACTGCGCAATTATGATC

CGCGCATAAACCTAGTACCTGTAAACAGAAGACTGCCTCATGCTTTAGTCCTCCACCATAATGAACACCCACAGAGTG

ACTTTTCTTCATTCGTCAGCAAATTGAAGGGCAGAACTGTCCTGGTGGTCGGGGAAAAGTTGTCCGTCCCAGGCAAAA

TGGTTGACTGGTTGTCAGACCGGCCTGAGGCTACCTTCAGAGCTCGGCTGGATTTAGGCATCCCAGGTGATGTGCCCA

AATATGACATAATATTTGTTAATGTGAGGACCCCATATAAATACCATCACTATCAGCAGTGTGAAGACCATGCCATTA

AGCTTAGCATGTTGACCAAGAAAGCTTGTCTGCATCTGAATCCCGGCGGAACCTGTGTCAGCATAGGTTATGGTTACG

CTGACAGGGCCAGCGAAAGCATCATTGGTGCTATAGCGCGGCAGTTCAAGTTTTCCCGGGTATGCAAACCGAAATCCT

CACTTGAAGAGACGGAAGTTCTGTTTGTATTCATTGGGTACGATCGCAAGGCCCGTACGCACAATTCTTACAAGCTTT

CATCAACCTTGACCAACATTTATACAGGTTCCAGACTCCACGAAGCCGGATGTGCACCCTCATATCATGTGGTGCGAG

GGGATATTGCCACGGCCACCGAAGGAGTGATTATAAATGCTGCTAACAGCAAAGGACAACCTGGCGGAGGGGTGTGCG

GAGCGCTGTATAAGAAATTCCCGGAAAGCTTCGATTTACAGCCGATCGAAGTAGGAAAAGCGCGACTGGTCAAAGGTG

CAGCTAAACATATCATTCATGCCGTAGGACCAAACTTCAACAAAGTTTCGGAGGTTGAAGGTGACAAACAGTTGGCAG

AGGCTTATGAGTCCATCGCTAAGATTGTCAACGATAACAATTACAAGTCAGTAGCGATTCCACTGTTGTCCACCGGCA

TCTTTTCCGGGAACAAAGATCGACTAACCCAATCATTGAACCATTTGCTGACAGCTTTAGACACCACTGATGCAGATG

TAGCCATATACTGCAGGGACAAGAAATGGGAAATGACTCTCAAGGAAGCAGTGGCTAGGAGAGAAGCAGTGGAGGAGA

TATGCATATCCGACGACTCTTCAGTGACAGAACCTGATGCAGAGCTGGTGAGGGTGCATCCGAAGAGTTCTTTGGCTG

GAAGGAAGGGCTACAGCACAAGCGATGGCAAAACTTTCTCATATTTGGAAGGGACCAAGTTTCACCAGGCGGCCAAGG

ATATAGCAGAAATTAATGCCATGTGGCCCGTTGCAACGGAGGCCAATGAGCAGGTATGCATGTATATCCTCGGAGAAA

GCATGAGCAGTATTAGGTCGAAATGCCCCGTCGAAGAGTCGGAAGCCTCCACACCACCTAGCACGCTGCCTTGCTTGT

GCATCCATGCCATGACTCCAGAAAGAGTACAGCGCCTAAAAGCCTCACGTCCAGAACAAATTACTGTGTGCTCATCCT

TTCCATTGCCGAAGTATAGAATCACTGGTGTGCAGAAGATCCAATGCTCCCAGCCTATATTGTTCTCACCGAAAGTGC

CTGCGTATATTCATCCAAGGAAGTATCTCGTGGAAACACCACCGGTAGACGAGACTCCGGAGCCATCGGCAGAGAACC

AATCCACAGAGGGGACACCTGAACAACCACCACTTATAACCGAGGATGAGACCAGGACTAGAACGCCTGAGCCGATCA

TCATCGAAGAGGAAGAAGAGGATAGCATAAGTTTGCTGTCAGATGGCCCGACCCACCAGGTGCTGCAAGTCGAGGCAG

ACATTCACGGGCCGCCCTCTGTATCTAGCTCATCCTGGTCCATTCCTCATGCATCCGACTTTGATGTGGACAGTTTAT

CCATACTTGACACCCTGGAGGGAGCTAGCGTGACCAGCGGGGCAACGTCAGCCGAGACTAACTCTTACTTCGCAAAGA

GTATGGAGTTTCTGGCGCGACCGGTGCCTGCGCCTCGAACAGTATTCAGGAACCCTCCACATCCCGCTCCGCGCACAA

GAACACCGTCACTTGCACCCAGCAGGGCCTGCTCGAGAACCAGCCTAGTTTCCACCCCGCCAGGCGTGAATAGGGTGA

TCACTAGAGAGGAGCTCGAGGCGCTTACCCCGTCACGCACTCCTAGCAGGTCGGTCTCGAGAACCAGCCTGGTCTCCA

ACCCGCCAGGCGTAAATAGGGTGATTACAAGAGAGGAGTTTGAGGCGTTCGTAGCACAACAACAATGACGGTTTGATG

CGGGTGCATACATCTTTTCCTCCGACACCGGTCAAGGGCATTTACAACAAAAATCAGTAAGGCAAACGGTGCTATCCG

AAGTGGTGTTGGAGAGGACCGAATTGGAGATTTCGTATGCCCCGCGCCTCGACCAAGAAAAAGAAGAATTACTACGCA

AGAAATTACAGTTAAATCCCACACCTGCTAACAGAAGCAGATACCAGTCCAGGAAGGTGGAGAACATGAAAGCCATAA

-continued

CAGCTAGACGTATTCTGCAAGGCCTAGGGCATTATTTGAAGGCAGAAGGAAAAGTGGAGTGCTACCGAACCCTGCATC

CTGTTCCTTTGTATTCATCTAGTGTGAACCGTGCCTTTTCAAGCCCCAAGGTCGCAGTGGAAGCCTGTAACGCCATGT

TGAAAGAGAACTTTCCGACTGTGGCTTCTTACTGTATTATTCCAGAGTACGATGCCTATTTGGACATGGTTGACGGAG

CTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATT

GCAATGTCACGCAAATGAGAGAATTGCCCGTATTGGATTCGGCGGCCTTTAATGTGGAATGCTTCAAGAAATATGCGT

GTAATAATGAATATTGGGAAACGTTTAAAGAAAACCCCATCAGGCTTACTGAAGAAAACGTGGTAAATTACATTACCA

AATTAAAAGGACCAAAAGCTGCTGCTCTTTTTGCGAAGACACATAATTTGAATATGTTGCAGGACATACCAATGGACA

GGTTTGTAATGGACTTAAAGAGAGACGTGAAAGTGACTCCAGGAACAAAACATACTGAAGAACGGCCCAAGGTACAGG

TGATCCAGGCTGCCGATCCGCTAGCAACAGCGTATCTGTGCGGAATCCACCGAGAGCTGGTTAGGAGATTAAATGCGG

TCCTGCTTCCGAACATTCATACACTGTTTGATATGTCGGCTGAAGACTTTGACGCTATTATAGCCGAGCACTTCCAGC

CTGGGGATTGTGTTCTGGAAACTGACATCGCGTCGTTTGATAAAAGTGAGGACGACGCCATGGCTCTGACCGCGTTAA

TGATTCTGGAAGACTTAGGTGTGGACGCAGAGCTGTTGACGCTGATTGAGGCGGCTTTCGGCGAAATTTCATCAATAC

ATTTGCCCACTAAAACTAAATTTAAATTCGGAGCCATGATGAAATCTGGAATGTTCCTCACACTGTTTGTGAACACAG

TCATTAACATTGTAATCGCAAGCAGAGTGTTGAGAGAACGGCTAACCGGATCACCATGTGCAGCATTCATTGGAGATG

ACAATATCGTGAAAGGAGTCAAATCGGACAAATTAATGGCAGACAGGTGCGCCACCTGGTTGAATATGGAAGTCAAGA

TTATAGATGCTGTGGTGGGCGAGAAAGCGCCTTATTTCTGTGGAGGGTTTATTTTGTGTGACTCCGTGACCGGCACAG

CGTGCCGTGTGGCAGACCCCCTAAAAAGGCTGTTTAAGCTTGGCAAACCTCTGGCAGCAGACGATGAACATGATGATG

ACAGGAGAAGGGCATTGCATGAAGAGTCAACACGCTGGAACCGAGTGGGTATTCTTTCAGAGCTGTGCAAGGCAGTAG

AATCAAGGTATGAAACCGTAGGAACTTCCATCATAGTTATGGCCATGACTACTCTAGCTAGCAGTGTTAAATCATTCA

GCTACCTGAGAGGGGCCCCTATAACTCTCTACGGCTAACCTGAATGGACTACGACATAGTCTAGTCCGCCAAGTCTAG

CATATGGCCACCATGTTCGTGTTTCTGGTGCTGCTGCCTCTGGTGTCCAGCCAGTGTGTGAACTTCACCAACAGAACA

CAGCTGCCTTTCGCCTACACCAACAGCTTTACCAGAGGCGTGTACTACCCCGACAAGGTGTTCAGATCCAGCGTGCTG

CACTCTACCCAGGACCTGTTCCTGCCTTTCTTCAGCAACGTGACCTGGTTCCACGCCATCCACGTGTCCGGCACCAAT

GGCACCAAGAGATTCGACAACCCCGTGCTGCCCTTCAACGACGGGGTGTACTTTGCCAGCACCGAGAAGTCCAACATC

ATCAGAGGCTGGATCTTCGGCACCACACTGGACAGCAAGACCCAGAGCCTGCTGATCGTGAACAACGCCACCAACGTG

GTCATCAAAGTGTGCGAGTTCCAGTTCTGCAACTACCCCTTCCTGGGCGTCTACTACCACAAGAACAACAAGAGCTGG

ATGGAAAGCGAGTTCCGGGTGTACAGCAGCGCCAACAACTGCACCTTCGAGTACGTGTCCCAGCCTTTCCTGATGGAC

CTGGAAGGCAAGCAGGGCAACTTCAAGAACCTGAGCGAGTTCGTGTTCAAGAACATCGACGGCTACTTCAAGATCTAC

AGCAAGCACACCCCTATCAACCTCGTGCGGGATCTGCCTCAGGGCTTCTCTGCTCTGGAACCCCTGGTGGATCTGCCC

ATCGGCATCAACATCACCCGGTTTCAGACACTGCTGGCCCTGCACAGAAGCTACCTGACACCTGGCGATAGCAGCAGC

GGATGGACAGCTGGTGCCGCCGCTTACTATGTGGGCTACCTGCAGCCTAGAACCTTCCTGCTGAAGTACAACGAGAAC

GGCACCATCACCGACGCCGTGGATTGTGCCCTTGATCCTCTGAGCGAGACAAAGTGCACCCTGAAGTCCTTCACCGTG

GAAAAGGGCATCTACCAGACCAGCAACTTCCGGGTGCAGCCCACCGAATCCATCGTGCGGTTCCCCAATATCACCAAT

CTGTGCCCCTTCGGCGAGGTGTTCAATGCCACCAGATTCGCCTCTGTGTACGCCTGGAACCGGAAGCGGATCAGCAAT

TGCGTGGCCGACTACTCCGTGCTGTACAACTCCGCCAGCTTCAGCACCTTCAAGTGCTACGGCGTGTCCCCTACCAAG

CTGAACGACCTGTGCTTCACAAACGTGTACGCCGACAGCTTCGTGATCCGGGGAGATGAAGTGCGGCAGATTGCCCCT

GGACAGACAGGCACGATCGCCGACTACAACTACAAGCTGCCCGACGACTTCACCGGCTGTGTGATTGCCTGGAACAGC

AACAACCTGGACTCCAAAGTCGGCGGCAACTACAATTACCTGTACCGGCTGTTCCGGAAGTCCAATCTGAAGCCCTTC

GAGCGGGACATCTCCACCGAGATCTATCAGGCCGGCAGCACCCCTTGTAACGGCGTGAAAGGCTTCAACTGCTACTTC

CCACTGCAGTCCTACGGCTTTCAGCCCACATATGGCGTGGGCTATCAGCCCTACAGAGTGGTGGTGCTGAGCTTCGAA

-continued

CTGCTGCATGCCCCTGCCACAGTGTGCGGCCCTAAGAAAAGCACCAATCTCGTGAAGAACAAATGCGTGAACTTCAAC

TTCAACGGCCTGACCGGCACAGGCGTGCTGACAGAGAGCAACAAGAAGTTCCTGCCATTCCAGCAGTTTGGCCGGGAT

ATCGCCGATACCACAGACGCCGTTAGAGATCCCCAGACACTGGAAATCCTGGACATCACCCCTTGCAGCTTCGGCGGA

GTGTCTGTGATCACCCCTGGCACCAACACCAGCAATCAGGTGGCAGTGCTGTACCAGGGCGTGAACTGTACCGAAGTG

CCCGTGGCCATTCACGCCGATCAGCTGACACCTACATGGCGGGTGTACTCCACCGGCAGCAATGTGTTTCAGACCAGA

GCCGGCTGTCTGATCGGAGCCGAGTACGTGAACAATAGCTACGAGTGCGACATCCCCATCGGCGCTGGCATCTGTGCC

AGCTACCAGACACAGACAAACAGCCCCTCTCTGGCCAGCTCTGTGGCCAGCCAGAGCATCATTGCCTACACAATGTCT

CTGGGCGCCGAGAACAGCGTGGCCTACTCCAACAACTCTATCGCTATCCCCACCAACTTCACCATCAGCGTGACCACA

GAGATCCTGCCTGTGTCCATGACCAAGACCAGCGTGGACTGCACCATGTACATCTGCGGCGATTCCACCGAGTGCTCC

AACCTGCTGCTGCAGTACGGCAGCTTCTGCACCCAGCTGAATAGAGCCCTGACAGGGATCGCCGTGGAACAGGACAAG

AACACCCAAGAGGTGTTCGCCCAAGTGAAGCAGATCTACAAGACCCCTCCTATCAAGGACTTCGGCGGCTTCAATTTC

AGCCAGATTCTGCCCGATCCTAGCAAGCCCAGCAAGCGGAGCCCCATCGAGGACCTGCTGTTCAACAAAGTGACACTG

GCCGACGCCGGCTTCATCAAGCAGTATGGCGATTGTCTGGGCGACATTGCCGCCAGGGATCTGATTTGCGCCCAGAAG

TTTAACGGACTGACAGTGCTGCCTCCTCTGCTGACCGATGAGATGATCGCCCAGTACACATCTGCCCTGCTGGCCGGC

ACAATCACAAGCGGCTGGACATTTGGAGCTGGCCCCGCTCTGCAGATCCCCTTTCCTATGCAGATGGCCTACAGATTC

AACGGCATCGGAGTGACCCAGAATGTGCTGTACGAGAACCAGAAGCTGATCGCCAACCAGTTCAACAGCGCCATCGGC

AAGATCCAGGACAGCCTGAGCAGCACACCAAGCGCCCTGGGAAAGCTGCAGGACGTGGTCAACCAGAATGCCCAGGCA

CTGAACACCCTGGTCAAGCAGCTGTCCTCCAACTTCGGCGCCATCAGCTCTGTGCTGAACGATATCCTGAGCAGACTG

GACCCTCCTGAGGCCGAGGTGCAGATCGACAGACTGATCACAGGCAGACTGCAGAGCCTCCAGACATACGTGACCCAG

CAGCTGATCAGAGCCGCCGAGATTAGAGCCTCTGCCAATCTGGCCGCCATCAAGATGTCTGAGTGTGTGCTGGGCCAG

AGCAAGAGAGTGGACTTTTGCGGCAAGGGCTACCACCTGATGAGCTTCCCTCAGTCTGCCCCTCACGGCGTGGTGTTT

CTGCACGTGACATACGTTCCCGCTCAAGAGAAGAATTTCACCACCGCTCCAGCCATCTGCCACGACGGCAAAGCCCAC

TTTCCTAGAGAAGGCGTGTTCGTGTCCAACGGCACCCATTGGTTCGTGACACAGCGGAACTTCTACGAGCCCCAGATC

ATCACCACCGACAACACCTTCGTGTCTGGCAACTGCGACGTCGTGATCGGCATTGTGAACAATACCGTGTACGACCCT

CTGCAGCCCGAGCTGGACAGCTTCAAAGAGGAACTGGACAAGTACTTTAAGAACCACACAAGCCCCGACGTGGACCTG

GGCGATATCAGCGGAATCAATGCCAGCTTCGTGAACATCCAGAAAGAGATCGACCGGCTGAACGAGGTGGCCAAGAAT

CTGAACGAGAGCCTGATCGACCTGCAAGAACTGGGGAAGTACGAGCAGTACATCAAGTGGCCCTGGTACATCTGGCTG

GGCTTTATCGCCGGACTGATTGCCATCGTGATGGTCACAATCATGCTGTGTTGCATGACCAGCTGCTGTAGCTGCCTG

AAGGGCTGTTGTAGCTGTGGCAGCTGCTGCAAGTTCGACGAGGACGATTCTGAGCCCGTGCTGAAGGGCGTGAAACTG

CACTACACATGAGCGGCCGCGAATTGGCAAGCTGCTTACATAGAACTCGCGGCGATTGGCATGCCGCCTTAAAATTTT

TATTTTATTTTTCTTTTCTTTTCCGAATCGGATTTTGTTTTTAATATTTCAAAAAAAAAAAAAAAAAAAAAAAAAAAA

AAAAAAA

Accordingly, preferably the nucleic acid sequence comprises a nucleotide sequence substantially as set out in SEQ ID No: 70, or a fragment or variant thereof.

In another embodiment (the SARS-CoV-2 surface glycoprotein with ORF4a IIP), the nucleic acid sequence is preferably DNA, and comprise or consist of SEQ ID No: 71, as follows:

[SEQ ID No: 71]

ATGGGCGGCGCATGAGAGAAGCCCAGACCAATTACCTACCCAAAATGGAGAAAGTTCACGTTGACATCGAGGAAGACA

GCCCATTCCTCAGAGCTTTGCAGCGGAGCTTCCCGCAGTTTGAGGTAGAAGCCAAGCAGGTCACTGATAATGACCATG

-continued

CTAATGCCAGAGCGTTTTCGCATCTGGCTTCAAAACTGATCGAAACGGAGGTGGACCCATCCGACACGATCCTTGACA

TTGGAAGTGCGCCCGCCCGCAGAATGTATTCTAAGCACAAGTATCATTGTATCTGTCCGATGAGATGTGCGGAAGATC

CGGACAGATTGTATAAGTATGCAACTAAGCTGAAGAAAAACTGTAAGGAAATAACTGATAAGGAATTGGACAAGAAAA

TGAAGGAGCTGGCCGCCGTCATGAGCGACCCTGACCTGGAAACTGAGACTATGTGCCTCCACGACGACGAGTCGTGTC

GCTACGAAGGGCAAGTCGCTGTTTACCAGGATGTATACGCGGTTGACGGACCGACAAGTCTCTATCACCAAGCCAATA

AGGGAGTTAGAGTCGCCTACTGGATAGGCTTTGACACCACCCCTTTTATGTTTAAGAACTTGGCTGGAGCATATCCAT

CATACTCTACCAACTGGGCCGACGAAACCGTGTTAACGGCTCGTAACATAGGCCTATGCAGCTCTGACGTTATGGAGC

GGTCACGTAGAGGGATGTCCATTCTTAGAAAGAAGTATTTGAAACCATCCAACAATGTTCTATTCTCTGTTGGCTCGA

CCATCTACCACGAGAAGAGGGACTTACTGAGGAGCTGGCACCTGCCGTCTGTATTTCACTTACGTGGCAAGCAAAATT

ACACATGTCGGTGTGAGACTATAGTTAGTTGCGACGGGTACGTCGTTAAAAGAATAGCTATCAGTCCAGGCCTGTATG

GGAAGCCTTCAGGCTATGCTGCTACGATGCACCGCGAGGGATTCTTGTGCTGCAAAGTGACAGACACATTGAACGGGG

AGAGGGTCTCTTTTCCCGTGTGCACGTATGTGCCAGCTACATTGTGTGACCAAATGACTGGCATACTGGCAACAGATG

TCAGTGCGGACGACGCGCAAAAACTGCTGGTTGGGCTCAACCAGCGTATAGTCGTCAACGGTCGCACCCAGAGAAACA

CCAATACCATGAAAAATTACCTTTTGCCCGTAGTGGCCCAGGCATTTGCTAGGTGGGCAAAGGAATATAAGGAAGATC

AAGAAGATGAAAGGCCACTAGGACTACGAGATAGACAGTTAGTCATGGGGTGTTGTTGGGCTTTTAGAAGGCACAAGA

TAACATCTATTTATAAGCGCCCGGATACCCAAACCATCATCAAAGTGAACAGCGATTTCCACTCATTCGTGCTGCCCA

GGATAGGCAGTAACACATTGGAGATCGGGCTGAGAACAAGAATCAGGAAAATGTTAGAGGAGCACAAGGAGCCGTCAC

CTCTCATTACCGCCGAGGACGTACAAGAAGCTAAGTGCGCAGCCGATGAGGCTAAGGAGGTGCGTGAAGCCGAGGAGT

TGCGCGCAGCTCTACCACCTTTGGCAGCTGATGTTGAGGAGCCCACTCTGGAGGCAGACGTCGACTTGATGTTACAAG

AGGCTGGGGCCGGCTCAGTGGAGACACCTCGTGGCTTGATAAAGGTTACCAGCTACGATGGCGAGGACAAGATCGGCT

CTTACGCTGTGCTTTCTCCGCAGGCTGTACTCAAGAGTGAAAAATTATCTTGCATCCACCCTCTCGCTGAACAAGTCA

TAGTGATAACACACTCTGGCCGAAAAGGGCGTTATGCCGTGGAACCATACCATGGTAAAGTAGTGGTGCCAGAGGGAC

ATGCAATACCCGTCCAGGACTTTCAAGCTCTGAGTGAAAGTGCCACCATTGTGTACAACGAACGTGAGTTCGTAAACA

GGTACCTGCACCATATTGCCACACATGGAGGAGCGCTGAACACTGATGAAGAATATTACAAAACTGTCAAGCCCAGCG

AGCACGACGGCGAATACCTGTACGACATCGACAGGAAACAGTGCGTCAAGAAAGAACTAGTCACTGGGCTAGGGCTCA

CAGGCGAGCTGGTGGATCCTCCCTTCCATGAATTCGCCTACGAGAGTCTGAGAACACGACCAGCCGCTCCTTACCAAG

TACCAACCATAGGGGTGTATGGCGTGCCAGGATCAGGCAAGTCTGGCATCATTAAAAGCGCAGTCACCAAAAAAGATC

TAGTGGTGAGCGCCAAGAAAGAAAACTGTGCAGAAATTATAAGGGACGTCAAGAAAATGAAAGGGCTGGACGTCAATG

CCAGAACTGTGGACTCAGTGCTCTTGAATGGATGCAAACACCCCGTAGAGACCCTGTATATTGACGAAGCTTTTGCTT

GTCATGCAGGTACTCTCAGAGCGCTCATAGCCATTATAAGACCTAAAAAGGCAGTGCTCTGCGGGGATCCCAAACAGT

GCGGTTTTTTAACATGATGTGCCTGAAAGTGCATTTTAACCACGAGATTTGCACACAAGTCTTCCACAAAAGCATCT

CTCGCCGTTGCACTAAATCTGTGACTTCGGTCGTCTCAACCTTGTTTTACGACAAAAAAATGAGAACGACGAATCCGA

AAGAGACTAAGATTGTGATTGACACTACCGGCAGTACCAAACCTAAGCAGGACGATCTCATTCTCACTTGTTTCAGAG

GGTGGGTGAAGCAGTTGCAAATAGATTACAAAGGCAACGAAATAATGACGGCAGCTGCCTCTCAAGGGCTGACCCGTA

AAGGTGTGTATGCCGTTCGGTACAAGGTGAATGAAAATCCTCTGTACGCACCCACCTCAGAACATGTGAACGTCCTAC

TGACCCGCACGGAGGACCGCATCGTGTGGAAAACACTAGCCGGCGACCCATGGATAAAAACACTGACTGCCAAGTACC

CTGGGAATTTCACTGCCACGATAGAGGAGTGGCAAGCAGAGCATGATGCCATCATGAGGCACATCTTGGAGAGACCGG

ACCCTACCGACGTCTTCCAGAATAAGGCAAACGTGTGTTGGGCCAAGGCTTTAGTGCCGGTGCTGAAGACCGCTGGCA

TAGACATGACCACTGAACAATGGAACACTGTGGATTATTTTGAAACGGACAAAGCTCACTCAGCAGAGATAGTATTGA

ACCAACTATGCGTGAGGTTCTTTGGACTCGATCTGGACTCCGGTCTATTTTCTGCACCCACTGTTCCGTTATCCATTA

-continued

GGAATAATCACTGGGATAACTCCCCGTCGCCTAACATGTACGGGCTGAATAAAGAAGTGGTCCGTCAGCTCTCTCGCA

GGTACCCACAACTGCCTCGGGCAGTTGCCACTGGAAGAGTCTATGACATGAACACTGGTACACTGCGCAATTATGATC

CGCGCATAAACCTAGTACCTGTAAACAGAAGACTGCCTCATGCTTTAGTCCTCCACCATAATGAACACCCACAGAGTG

ACTTTTCTTCATTCGTCAGCAAATTGAAGGGCAGAACTGTCCTGGTGGTCGGGGAAAAGTTGTCCGTCCCAGGCAAAA

TGGTTGACTGGTTGTCAGACCGGCCTGAGGCTACCTTCAGAGCTCGGCTGGATTTAGGCATCCCAGGTGATGTGCCCA

AATATGACATAATATTTGTTAATGTGAGGACCCCATATAAATACCATCACTATCAGCAGTGTGAAGACCATGCCATTA

AGCTTAGCATGTTGACCAAGAAAGCTTGTCTGCATCTGAATCCCGGCGGAACCTGTGTCAGCATAGGTTATGGTTACG

CTGACAGGGCCAGCGAAAGCATCATTGGTGCTATAGCGCGGCAGTTCAAGTTTTCCCGGGTATGCAAACCGAAATCCT

CACTTGAAGAGACGGAAGTTCTGTTTGTATTCATTGGGTACGATCGCAAGGCCCGTACGCACAATTCTTACAAGCTTT

CATCAACCTTGACCAACATTTATACAGGTTCCAGACTCCACGAAGCCGGATGTGCACCCTCATATCATGTGGTGCGAG

GGGATATTGCCACGGCCACCGAAGGAGTGATTATAAATGCTGCTAACAGCAAAGGACAACCTGGCGGAGGGGTGTGCG

GAGCGCTGTATAAGAAATTCCCGGAAAGCTTCGATTTACAGCCGATCGAAGTAGGAAAAGCGCGACTGGTCAAAGGTG

CAGCTAAACATATCATTCATGCCGTAGGACCAAACTTCAACAAAGTTTCGGAGGTTGAAGGTGACAAACAGTTGGCAG

AGGCTTATGAGTCCATCGCTAAGATTGTCAACGATAACAATTACAAGTCAGTAGCGATTCCACTGTTGTCCACCGGCA

TCTTTTCCGGGAACAAAGATCGACTAACCCAATCATTGAACCATTTGCTGACAGCTTTAGACACCACTGATGCAGATG

TAGCCATATACTGCAGGGACAAGAAATGGGAAATGACTCTCAAGGAAGCAGTGGCTAGGAGAGAAGCAGTGGAGGAGA

TATGCATATCCGACGACTCTTCAGTGACAGAACCTGATGCAGAGCTGGTGAGGGTGCATCCGAAGAGTTCTTTGGCTG

GAAGGAAGGGCTACAGCACAAGCGATGGCAAAACTTTCTCATATTTGGAAGGGACCAAGTTTCACCAGGCGGCCAAGG

ATATAGCAGAAATTAATGCCATGTGGCCCGTTGCAACGGAGGCCAATGAGCAGGTATGCATGTATATCCTCGGAGAAA

GCATGAGCAGTATTAGGTCGAAATGCCCCGTCGAAGAGTCGGAAGCCTCCACACCACCTAGCACGCTGCCTTGCTTGT

GCATCCATGCCATGACTCCAGAAAGAGTACAGCGCCTAAAAGCCTCACGTCCAGAACAAATTACTGTGTGCTCATCCT

TTCCATTGCCGAAGTATAGAATCACTGGTGTGCAGAAGATCCAATGCTCCCAGCCTATATTGTTCTCACCGAAAGTGC

CTGCGTATATTCATCCAAGGAAGTATCTCGTGGAAACACCACCGGTAGACGAGACTCCGGAGCCATCGGCAGAGAACC

AATCCACAGAGGGGACACCTGAACAACCACCACTTATAACCGAGGATGAGACCAGGACTAGAACGCCTGAGCCGATCA

TCATCGAAGAGGAAGAAGAGGATAGCATAAGTTTGCTGTCAGATGGCCCGACCCACCAGGTGCTGCAAGTCGAGGCAG

ACATTCACGGGCCGCCCTCTGTATCTAGCTCATCCTGGTCCATTCCTCATGCATCCGACTTTGATGTGGACAGTTTAT

CCATACTTGACACCCTGGAGGGAGCTAGCGTGACCAGCGGGGCAACGTCAGCCGAGACTAACTCTTACTTCGCAAAGA

GTATGGAGTTTCTGGCGCGACCGGTGCCTGCGCCTCGAACAGTATTCAGGAACCCTCCACATCCCGCTCCGCGCACAA

GAACACCGTCACTTGCACCCAGCAGGGCCTGCTCGAGAACCAGCCTAGTTTCCACCCCGCCAGGCGTGAATAGGGTGA

TCACTAGAGAGGAGCTCGAGGCGCTTACCCCGTCACGCACTCCTAGCAGGTCGGTCTCGAGAACCAGCCTGGTCTCCA

ACCCGCCAGGCGTAAATAGGGTGATTACAAGAGAGGAGTTTGAGGCGTTCGTAGCACAACAACAATGACGGTTTGATG

CGGGTGCATACATCTTTTCCTCCGACACCGGTCAAGGGCATTTACAACAAAAATCAGTAAGGCAAACGGTGCTATCCG

AAGTGGTGTTGGAGAGGACCGAATTGGAGATTTCGTATGCCCCGCGCCTCGACCAAGAAAAAGAAGAATTACTACGCA

AGAAATTACAGTTAAATCCCACACCTGCTAACAGAAGCAGATACCAGTCCAGGAAGGTGGAGAACATGAAAGCCATAA

CAGCTAGACGTATTCTGCAAGGCCTAGGGCATTATTTGAAGGCAGAAGGAAAAGTGGAGTGCTACCGAACCCTGCATC

CTGTTCCTTTGTATTCATCTAGTGTGAACCGTGCCTTTTCAAGCCCCAAGGTCGCAGTGGAAGCCTGTAACGCCATGT

TGAAAGAGAACTTTCCGACTGTGGCTTCTTACTGTATTATTCCAGAGTACGATGCCTATTTGGACATGGTTGACGGAG

CTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATT

GCAATGTCACGCAAATGAGAGAATTGCCCGTATTGGATTCGGCGGCCTTTAATGTGGAATGCTTCAAGAAATATGCGT

GTAATAATGAATATTGGGAAACGTTTAAAGAAAACCCCATCAGGCTTACTGAAGAAAACGTGGTAAATTACATTACCA

-continued

AATTAAAAGGACCAAAAGCTGCTGCTCTTTTTGCGAAGACACATAATTTGAATATGTTGCAGGACATACCAATGGACA

GGTTTGTAATGGACTTAAAGAGAGACGTGAAAGTGACTCCAGGAACAAAACATACTGAAGAACGGCCCAAGGTACAGG

TGATCCAGGCTGCCGATCCGCTAGCAACAGCGTATCTGTGCGGAATCCACCGAGAGCTGGTTAGGAGATTAAATGCGG

TCCTGCTTCCGAACATTCATACACTGTTTGATATGTCGGCTGAAGACTTTGACGCTATTATAGCCGAGCACTTCCAGC

CTGGGGATTGTGTTCTGGAAACTGACATCGCGTCGTTTGATAAAAGTGAGGACGACGCCATGGCTCTGACCGCGTTAA

TGATTCTGGAAGACTTAGGTGTGGACGCAGAGCTGTTGACGCTGATTGAGGCGGCTTTCGGCGAAATTTCATCAATAC

ATTTGCCCACTAAAACTAAATTTAAATTCGGAGCCATGATGAAATCTGGAATGTTCCTCACACTGTTTGTGAACACAG

TCATTAACATTGTAATCGCAAGCAGAGTGTTGAGAGAACGGCTAACCGGATCACCATGTGCAGCATTCATTGGAGATG

ACAATATCGTGAAAGGAGTCAAATCGGACAAATTAATGGCAGACAGGTGCGCCACCTGGTTGAATATGGAAGTCAAGA

TTATAGATGCTGTGGTGGGCGAGAAAGCGCCTTATTTCTGTGGAGGGTTTATTTTGTGTGACTCCGTGACCGGCACAG

CGTGCCGTGTGGCAGACCCCCTAAAAAGGCTGTTTAAGCTTGGCAAACCTCTGGCAGCAGACGATGAACATGATGATG

ACAGGAGAAGGGCATTGCATGAAGAGTCAACACGCTGGAACCGAGTGGGTATTCTTTCAGAGCTGTGCAAGGCAGTAG

AATCAAGGTATGAAACCGTAGGAACTTCCATCATAGTTATGGCCATGACTACTCTAGCTAGCAGTGTTAAATCATTCA

GCTACCTGAGAGGGGCCCCTATAACTCTCTACGGCTAACCTGAATGGACTACGACATAGTCTAGTCCGCCAAGTCTAG

CATATGGCCACCATGTTCGTGTTTCTGGTGCTGCTGCCTCTGGTGTCCAGCCAGTGTGTGAACCTGACCACCAGAACA

CAGCTGCCTCCAGCCTACACCAACAGCTTTACCAGAGGCGTGTACTACCCCGACAAGGTGTTCAGATCCAGCGTGCTG

CACTCTACCCAGGACCTGTTCCTGCCTTTCTTCAGCAACGTGACCTGGTTCCACGCCATCCACGTGTCCGGCACCAAT

GGCACCAAGAGATTCGACAACCCCGTGCTGCCCTTCAACGACGGGGTGTACTTTGCCAGCACCGAGAAGTCCAACATC

ATCAGAGGCTGGATCTTCGGCACCACACTGGACAGCAAGACCCAGAGCCTGCTGATCGTGAACAACGCCACCAACGTG

GTCATCAAAGTGTGCGAGTTCCAGTTCTGCAACGACCCCTTCCTGGGCGTCTACTACCACAAGAACAACAAGAGCTGG

ATGGAAAGCGAGTTCCGGGTGTACAGCAGCGCCAACAACTGCACCTTCGAGTACGTGTCCCAGCCTTTCCTGATGGAC

CTGGAAGGCAAGCAGGGCAACTTCAAGAACCTGCGCGAGTTCGTGTTCAAGAACATCGACGGCTACTTCAAGATCTAC

AGCAAGCACACCCCTATCAACCTCGTGCGGGATCTGCCTCAGGGCTTCTCTGCTCTGGAACCCCTGGTGGATCTGCCC

ATCGGCATCAACATCACCCGGTTTCAGACACTGCTGGCCCTGCACAGAAGCTACCTGACACCTGGCGATAGCAGCAGC

GGATGGACAGCTGGTGCCGCCGCTTACTATGTGGGCTACCTGCAGCCTAGAACCTTCCTGCTGAAGTACAACGAGAAC

GGCACCATCACCGACGCCGTGGATTGTGCCCTTGATCCTCTGAGCGAGACAAAGTGCACCCTGAAGTCCTTCACCGTG

GAAAAGGGCATCTACCAGACCAGCAACTTCCGGGTGCAGCCCACCGAATCCATCGTGCGGTTCCCCAATATCACCAAT

CTGTGCCCCTTCGGCGAGGTGTTCAATGCCACCAGATTCGCCTCTGTGTACGCCTGGAACCGGAAGCGGATCAGCAAT

TGCGTGGCCGACTACTCCGTGCTGTACAACTCCGCCAGCTTCAGCACCTTCAAGTGCTACGGCGTGTCCCCTACCAAG

CTGAACGACCTGTGCTTCACAAACGTGTACGCCGACAGCTTCGTGATCCGGGGAGATGAAGTGCGGCAGATTGCCCCT

GGACAGACAGGCAAGATCGCCGACTACAACTACAAGCTGCCCGACGACTTCACCGGCTGTGTGATTGCCTGGAACAGC

AACAACCTGGACTCCAAAGTCGGCGGCAACTACAATTACCTGTACCGGCTGTTCCGGAAGTCCAATCTGAAGCCCTTC

GAGCGGGACATCTCCACCGAGATCTATCAGGCCGGCAGCACCCCTTGTAACGGCGTGGAAGGCTTCAACTGCTACTTC

CCACTGCAGTCCTACGGCTTTCAGCCCACAAATGGCGTGGGCTATCAGCCCTACAGAGTGGTGGTGCTGAGCTTCGAA

CTGCTGCATGCCCCTGCCACAGTGTGCGGCCCTAAGAAAAGCACCAATCTCGTGAAGAACAAATGCGTGAACTTCAAC

TTCAACGGCCTGACCGGCACAGGCGTGCTGACAGAGAGCAACAAGAAGTTCCTGCCATTCCAGCAGTTTGGCCGGGAT

ATCGCCGATACCACAGACGCCGTTAGAGATCCCCAGACACTGGAAATCCTGGACATCACCCCTTGCAGCTTCGGCGGA

GTGTCTGTGATCACCCCTGGCACCAACACCAGCAATCAGGTGGCAGTGCTGTACCAGGACGTGAACTGTACCGAAGTG

CCCGTGGCCATTCACGCCGATCAGCTGACACCTACATGGCGGGTGTACTCCACCGGCAGCAATGTGTTTCAGACCAGA

GCCGGCTGTCTGATCGGAGCCGAGCACGTGAACAATAGCTACGAGTGCGACATCCCCATCGGCGCTGGCATCTGTGCC

-continued

AGCTACCAGACACAGACAAACAGCCCCAGACGGGCCAGATCTGTGGCCAGCCAGAGCATCATTGCCTACACAATGTCT

CTGGGCGCCGAGAACAGCGTGGCCTACTCCAACAACTCTATCGCTATCCCCACCAACTTCACCATCAGCGTGACCACA

GAGATCCTGCCTGTGTCCATGACCAAGACCAGCGTGGACTGCACCATGTACATCTGCGGCGATTCCACCGAGTGCTCC

AACCTGCTGCTGCAGTACGGCAGCTTCTGCACCCAGCTGAATAGAGCCCTGACAGGGATCGCCGTGGAACAGGACAAG

AACACCCAAGAGGTGTTCGCCCAAGTGAAGCAGATCTACAAGACCCCTCCTATCAAGGACTTCGGCGGCTTCAATTTC

AGCCAGATTCTGCCCGATCCTAGCAAGCCCAGCAAGCGGAGCTTCATCGAGGACCTGCTGTTCAACAAAGTGACACTG

GCCGACGCCGGCTTCATCAAGCAGTATGGCGATTGTCTGGGCGACATTGCCGCCAGGGATCTGATTTGCGCCCAGAAG

TTTAACGGACTGACAGTGCTGCCTCCTCTGCTGACCGATGAGATGATCGCCCAGTACACATCTGCCCTGCTGGCCGGC

ACAATCACAAGCGGCTGGACATTTGGAGCTGGCGCCGCTCTGCAGATCCCCTTTGCTATGCAGATGGCCTACAGATTC

AACGGCATCGGAGTGACCCAGAATGTGCTGTACGAGAACCAGAAGCTGATCGCCAACCAGTTCAACAGCGCCATCGGC

AAGATCCAGGACAGCCTGAGCAGCACAGCAAGCGCCCTGGGAAAGCTGCAGGACGTGGTCAACCAGAATGCCCAGGCA

CTGAACACCCTGGTCAAGCAGCTGTCCTCCAACTTCGGCGCCATCAGCTCTGTGCTGAACGATATCCTGAGCAGACTG

GACCCTCCTGAGGCCGAGGTGCAGATCGACAGACTGATCACAGGCAGACTGCAGAGCCTCCAGACATACGTGACCCAG

CAGCTGATCAGAGCCGCCGAGATTAGAGCCTCTGCCAATCTGGCCGCCACCAAGATGTCTGAGTGTGTGCTGGGCCAG

AGCAAGAGAGTGGACTTTTGCGGCAAGGGCTACCACCTGATGAGCTTCCCTCAGTCTGCCCCTCACGGCGTGGTGTTT

CTGCACGTGACATACGTTCCCGCTCAAGAGAAGAATTTCACCACCGCTCCAGCCATCTGCCACGACGGCAAAGCCCAC

TTTCCTAGAGAAGGCGTGTTCGTGTCCAACGGCACCCATTGGTTCGTGACACAGCGGAACTTCTACGAGCCCCAGATC

ATCACCACCGACAACACCTTCGTGTCTGGCAACTGCGACGTCGTGATCGGCATTGTGAACAATACCGTGTACGACCCT

CTGCAGCCCGAGCTGGACAGCTTCAAAGAGGAACTGGACAAGTACTTTAAGAACCACACAAGCCCCGACGTGGACCTG

GGCGATATCAGCGGAATCAATGCCAGCGTCGTGAACATCCAGAAAGAGATCGACCGGCTGAACGAGGTGGCCAAGAAT

CTGAACGAGAGCCTGATCGACCTGCAAGAACTGGGGAAGTACGAGCAGTACATCAAGTGGCCCTGGTACATCTGGCTG

GGCTTTATCGCCGGACTGATTGCCATCGTGATGGTCACAATCATGCTGTGTTGCATGACCAGCTGCTGTAGCTGCCTG

AAGGGCTGTTGTAGCTGTGGCAGCTGCTGCAAGTTCGACGAGGACGATTCTGAGCCCGTGCTGAAGGGCGTGAAACTG

CACTACACAGATCGGAGAAAGAGAGGCTCTGGCGAAGGCAGAGGCAGCCTGCTTACATGTGGCGACGTGGAAGAGAAC

CCCGGACCTATGGATTATGTGTCCCTGCTGAACCAGATTTGGCAGAAGTACCTGAACAGCCCCTACACCACCTGTCTG

TACATCCCCAAGCCTACCGCCAAGTACACACCTCTCGTGGGCACATCTCTGCACCCCGTGCTGTGGAATTGCCAGCTG

AGCTTTGCCGGCTACACCGAGTCTGCCGTGAACAGCACAAAGGCCCTGGCCAAACAGGACGCCGCTCAGAGAATTGCC

TGGCTGCTGCACAAGGATGGCGGCATCCCTGATGGCTGTAGCCTGTACCTGAGACACAGCAGCCTGTTCGCCCAGAGC

GAGGAAGAGGAATCCTTCAGCAACTGAGCGGCCGCGAATTGGCAAGCTGCTTACATAGAACTCGCGGCGATTGGCATG

CCGCCTTAAAATTTTATTTTATTTTTCTTTTCTTTTCCGAATCGGATTTTGTTTTTAATATTTCAAAAAAAAAAAAAA

AAAAAAAAAAAAAAAAAAAAAA

Accordingly, preferably the nucleic acid sequence comprises a nucleotide sequence substantially as set out in SEQ ID No: 71, or a fragment or variant thereof.

In a third aspect, there is provided an expression cassette comprising a nucleic acid sequence according to the second aspect.

As shown in FIG. 3, the inventors incorporated the codon optimised sequence encoding 55 the coronavirus glycoprotein having the two modifications which stabilise the protein in its pre-fusion conformation into the VEEV backbone plasmid, to create the vector shown in FIG. 3. Hence, the nucleic acid sequences of the invention are preferably harboured in a recombinant vector, for example a recombinant vector for delivery into a host cell of interest to enable production of the RNA construct.

Accordingly, in a fourth aspect, there is provided a recombinant vector comprising the expression cassette according to the third aspect.

In one embodiment (SARS-CoV-2 coronavirus surface glycoprotein), the vector may comprise the nucleic acid sequence of SEQ ID No: 35, as follows:

[SEQ ID No: 35]

CGCCAGCAACGCGAGCTCTAATACGACTCACTATAGATGGGCGGCGCATGAGAGAAGCCCAGACCAATTACCTACCCA

AAATGGAGAAAGTTCACGTTGACATCGAGGAAGACAGCCCATTCCTCAGAGCTTTGCAGCGGAGCTTCCCGCAGTTTG

-continued

AGGTAGAAGCCAAGCAGGTCACTGATAATGACCATGCTAATGCCAGAGCGTTTTCGCATCTGGCTTCAAAACTGATCG

AAACGGAGGTGGACCCATCCGACACGATCCTTGACATTGGAAGTGCGCCCGCCCGCAGAATGTATTCTAAGCACAAGT

ATCATTGTATCTGTCCGATGAGATGTGCGGAAGATCCGGACAGATTGTATAAGTATGCAACTAAGCTGAAGAAAAACT

GTAAGGAAATAACTGATAAGGAATTGGACAAGAAAATGAAGGAGCTGGCCGCCGTCATGAGCGACCCTGACCTGGAAA

CTGAGACTATGTGCCTCCACGACGACGAGTCGTGTCGCTACGAAGGGCAAGTCGCTGTTTACCAGGATGTATACGCGG

TTGACGGACCGACAAGTCTCTATCACCAAGCCAATAAGGGAGTTAGAGTCGCCTACTGGATAGGCTTTGACACCACCC

CTTTTATGTTTAAGAACTTGGCTGGAGCATATCCATCATACTCTACCAACTGGGCCGACGAAACCGTGTTAACGGCTC

GTAACATAGGCCTATGCAGCTCTGACGTTATGGAGCGGTCACGTAGAGGGATGTCCATTCTTAGAAAGAAGTATTTGA

AACCATCCAACAATGTTCTATTCTCTGTTGGCTCGACCATCTACCACGAGAAGAGGGACTTACTGAGGAGCTGGCACC

TGCCGTCTGTATTTCACTTACGTGGCAAGCAAAATTACACATGTCGGTGTGAGACTATAGTTAGTTGCGACGGGTACG

TCGTTAAAAGAATAGCTATCAGTCCAGGCCTGTATGGGAAGCCTTCAGGCTATGCTGCTACGATGCACCGCGAGGGAT

TCTTGTGCTGCAAAGTGACAGACACATTGAACGGGGAGAGGGTCTCTTTTCCCGTGTGCACGTATGTGCCAGCTACAT

TGTGTGACCAAATGACTGGCATACTGGCAACAGATGTCAGTGCGGACGACGCGCAAAAACTGCTGGTTGGGCTCAACC

AGCGTATAGTCGTCAACGGTCGCACCCAGAGAAACACCAATACCATGAAAAATTACCTTTTGCCCGTAGTGGCCCAGG

CATTTGCTAGGTGGGCAAAGGAATATAAGGAAGATCAAGAAGATGAAAGGCCACTAGGACTACGAGATAGACAGTTAG

TCATGGGGTGTTGTTGGGCTTTTAGAAGGCACAAGATAACATCTATTTATAAGCGCCCGGATACCCAAACCATCATCA

AAGTGAACAGCGATTTCCACTCATTCGTGCTGCCCAGGATAGGCAGTAACACATTGGAGATCGGGCTGAGAACAAGAA

TCAGGAAAATGTTAGAGGAGCACAAGGAGCCGTCACCTCTCATTACCGCCGAGGACGTACAAGAAGCTAAGTGCGCAG

CCGATGAGGCTAAGGAGGTGCGTGAAGCCGAGGAGTTGCGCGCAGCTCTACCACCTTTGGCAGCTGATGTTGAGGAGC

CCACTCTGGAAGCCGATGTCGACTTGATGTTACAAGAGGCTGGGGCCGGCTCAGTGGAGACACCTCGTGGCTTGATAA

AGGTTACCAGCTACGATGGCGAGGACAAGATCGGCTCTTACGCTGTGCTTTCTCCGCAGGCTGTACTCAAGAGTGAAA

AATTATCTTGCATCCACCCTCTCGCTGAACAAGTCATAGTGATAACACACTCTGGCCGAAAAGGGCGTTATGCCGTGG

AACCATACCATGGTAAAGTAGTGGTGCCAGAGGGACATGCAATACCCGTCCAGGACTTTCAAGCTCTGAGTGAAAGTG

CCACCATTGTGTACAACGAACGTGAGTTCGTAAACAGGTACCTGCACCATATTGCCACACATGGAGGAGCGCTGAACA

CTGATGAAGAATATTACAAAACTGTCAAGCCCAGCGAGCACGACGGCGAATACCTGTACGACATCGACAGGAAACAGT

GCGTCAAGAAAGAACTAGTCACTGGGCTAGGGCTCACAGGCGAGCTGGTGGATCCTCCCTTCCATGAATTCGCCTACG

AGAGTCTGAGAACACGACCAGCCGCTCCTTACCAAGTACCAACCATAGGGGTGTATGGCGTGCCAGGATCAGGCAAGT

CTGGCATCATTAAAAGCGCAGTCACCAAAAAAGATCTAGTGGTGAGCGCCAAGAAAGAAAACTGTGCAGAAATTATAA

GGGACGTCAAGAAAATGAAAGGGCTGGACGTCAATGCCAGAACTGTGGACTCAGTGCTCTTGAATGGATGCAAACACC

CCGTAGAGACCCTGTATATTGACGAAGCTTTTGCTTGTCATGCAGGTACTCTCAGAGCGCTCATAGCCATTATAAGAC

CTAAAAAGGCAGTGCTCTGCGGGGATCCCAAACAGTGCGGTTTTTTTAACATGATGTGCCTGAAAGTGCATTTTAACC

ACGAGATTTGCACACAAGTCTTCCACAAAAGCATCTCTCGCCGTTGCACTAAATCTGTGACTTCGGTCGTCTCAACCT

TGTTTTACGACAAAAAAATGAGAACGACGAATCCGAAAGAGACTAAGATTGTGATTGACACTACCGGCAGTACCAAAC

CTAAGCAGGACGATCTCATTCTCACTTGTTTCAGAGGGTGGGTGAAGCAGTTGCAAATAGATTACAAAGGCAACGAAA

TAATGACGGCAGCTGCCTCTCAAGGGCTGACCCGTAAAGGTGTGTATGCCGTTCGGTACAAGGTGAATGAAAATCCTC

TGTACGCACCCACCTCAGAACATGTGAACGTCCTACTGACCCGCACGGAGGACCGCATCGTGTGGAAAACACTAGCCG

GCGACCCATGGATAAAAACACTGACTGCCAAGTACCCTGGGAATTTCACTGCCACGATAGAGGAGTGGCAAGCAGAGC

ATGATGCCATCATGAGGCACATCTTGGAGAGACCGGACCCTACCGACGTCTTCCAGAATAAGGCAAACGTGTGTTGGG

CCAAGGCTTTAGTGCCGGTGCTGAAGACCGCTGGCATAGACATGACCACTGAACAATGGAACACTGTGGATTATTTTG

AAACGGACAAAGCTCACTCAGCAGAGATAGTATTGAACCAACTATGCGTGAGGTTCTTTGGACTCGATCTGGACTCCG

-continued

GTCTATTTTCTGCACCCACTGTTCCGTTATCCATTAGGAATAATCACTGGGATAACTCCCCGTCGCCTAACATGTACG

GGCTGAATAAAGAAGTGGTCCGTCAGCTCTCTCGCAGGTACCCACAACTGCCTCGGGCAGTTGCCACTGGAAGAGTCT

ATGACATGAACACTGGTACACTGCGCAATTATGATCCGCGCATAAACCTAGTACCTGTAAACAGAAGACTGCCTCATG

CTTTAGTCCTCCACCATAATGAACACCCACAGAGTGACTTTTCTTCATTCGTCAGCAAATTGAAGGGCAGAACTGTCC

TGGTGGTCGGGGAAAAGTTGTCCGTCCCAGGCAAAATGGTTGACTGGTTGTCAGACCGGCCTGAGGCTACCTTCAGAG

CTCGGCTGGATTTAGGCATCCCAGGTGATGTGCCCAAATATGACATAATATTTGTTAATGTGAGGACCCCATATAAAT

ACCATCACTATCAGCAGTGTGAAGACCATGCCATTAAGCTTAGCATGTTGACCAAGAAAGCTTGTCTGCATCTGAATC

CCGGCGGAACCTGTGTCAGCATAGGTTATGGTTACGCTGACAGGGCCAGCGAAAGCATCATTGGTGCTATAGCGCGGC

AGTTCAAGTTTTCCCGGGTATGCAAACCGAAATCCTCACTTGAAGAGACGGAAGTTCTGTTTGTATTCATTGGGTACG

ATCGCAAGGCCCGTACGCACAATTCTTACAAGCTTTCATCAACCTTGACCAACATTTATACAGGTTCCAGACTCCACG

AAGCCGGATGTGCACCCTCATATCATGTGGTGCGAGGGGATATTGCCACGGCCACCGAAGGAGTGATTATAAATGCTG

CTAACAGCAAAGGACAACCTGGCGGAGGGGTGTGCGGAGCGCTGTATAAGAAATTCCCGGAAAGCTTCGATTTACAGC

CGATCGAAGTAGGAAAAGCGCGACTGGTCAAAGGTGCAGCTAAACATATCATTCATGCCGTAGGACCAAACTTCAACA

AAGTTTCGGAGGTTGAAGGTGACAAACAGTTGGCAGAGGCTTATGAGTCCATCGCTAAGATTGTCAACGATAACAATT

ACAAGTCAGTAGCGATTCCACTGTTGTCCACCGGCATCTTTTCCGGGAACAAAGATCGACTAACCCAATCATTGAACC

ATTTGCTGACAGCTTTAGACACCACTGATGCAGATGTAGCCATATACTGCAGGGACAAGAAATGGGAAATGACTCTCA

AGGAAGCAGTGGCTAGGAGAGAAGCAGTGGAGGAGATATGCATATCCGACGACTCTTCAGTGACAGAACCTGATGCAG

AGCTGGTGAGGGTGCATCCGAAGAGTTCTTTGGCTGGAAGGAAGGGCTACAGCACAAGCGATGGCAAAACTTTCTCAT

ATTTGGAAGGGACCAAGTTTCACCAGGCGGCCAAGGATATAGCAGAAATTAATGCCATGTGGCCCGTTGCAACGGAGG

CCAATGAGCAGGTATGCATGTATATCCTCGGAGAAAGCATGAGCAGTATTAGGTCGAAATGCCCCGTCGAAGAGTCGG

AAGCCTCCACACCACCTAGCACGCTGCCTTGCTTGTGCATCCATGCCATGACTCCAGAAAGAGTACAGCGCCTAAAAG

CCTCACGTCCAGAACAAATTACTGTGTGCTCATCCTTTCCATTGCCGAAGTATAGAATCACTGGTGTGCAGAAGATCC

AATGCTCCCAGCCTATATTGTTCTCACCGAAAGTGCCTGCGTATATTCATCCAAGGAAGTATCTCGTGGAAACACCAC

CGGTAGACGAGACTCCGGAGCCATCGGCAGAGAACCAATCCACAGAGGGGACACCTGAACAACCACCACTTATAACCG

AGGATGAGACCAGGACTAGAACGCCTGAGCCGATCATCATCGAAGAGGAAGAAGAGGATAGCATAAGTTTGCTGTCAG

ATGGCCCGACCCACCAGGTGCTGCAAGTCGAGGCAGACATTCACGGGCCGCCCTCTGTATCTAGCTCATCCTGGTCCA

TTCCTCATGCATCCGACTTTGATGTGGACAGTTTATCCATACTTGACACCCTGGAGGGAGCTAGCGTGACCAGCGGGG

CAACGTCAGCCGAGACTAACTCTTACTTCGCAAAGAGTATGGAGTTTCTGGCGCGACCGGTGCCTGCGCCTCGAACAG

TATTCAGGAACCCTCCACATCCCGCTCCGCGCACAAGAACACCGTCACTTGCACCCAGCAGGGCCTGCTCGAGAACCA

GCCTAGTTTCCACCCCGCCAGGCGTGAATAGGGTGATCACTAGAGAGGAGCTCGAGGCGCTTACCCCGTCACGCACTC

CTAGCAGGTCGGTCTCGAGAACCAGCCTGGTCTCCAACCCGCCAGGCGTAAATAGGGTGATTACAAGAGAGGAGTTTG

AGGCGTTCGTAGCACAACAACAATGACGGTTTGATGCGGGTGCATACATCTTTTCCTCCGACACCGGTCAAGGGCATT

TACAACAAAAATCAGTAAGGCAAACGGTGCTATCCGAAGTGGTGTTGGAGAGGACCGAATTGGAGATTTCGTATGCCC

CGCGCCTCGACCAAGAAAAAGAAGAATTACTACGCAAGAAATTACAGTTAAATCCCACACCTGCTAACAGAAGCAGAT

ACCAGTCCAGGAAGGTGGAGAACATGAAAGCCATAACAGCTAGACGTATTCTGCAAGGCCTAGGGCATTATTTGAAGG

CAGAAGGAAAAGTGGAGTGCTACCGAACCCTGCATCCTGTTCCTTTGTATTCATCTAGTGTGAACCGTGCCTTTTCAA

GCCCCAAGGTCGCAGTGGAAGCCTGTAACGCCATGTTGAAAGAGAACTTTCCGACTGTGGCTTCTTACTGTATTATTC

CAGAGTACGATGCCTATTTGGACATGGTTGACGGAGCTTCATGCTGCTTAGACACTGCCAGTTTTTGCCCTGCAAAGC

TGCGCAGCTTTCCAAAGAAACACTCCTATTTGGAACCCACAATACGATCGGCAGTGCCTTCAGCGATCCAGAACACGC

TCCAGAACGTCCTGGCAGCTGCCACAAAAAGAAATTGCAATGTCACGCAAATGAGAGAATTGCCCGTATTGGATTCGG

CGGCCTTTAATGTGGAATGCTTCAAGAAATATGCGTGTAATAATGAATATTGGGAAACGTTTAAAGAAAACCCCATCA

-continued

GGCTTACTGAAGAAAACGTGGTAAATTACATTACCAAATTAAAAGGACCAAAAGCTGCTGCTCTTTTTGCGAAGACAC

ATAATTTGAATATGTTGCAGGACATACCAATGGACAGGTTTGTAATGGACTTAAAGAGAGACGTGAAAGTGACTCCAG

GAACAAAACATACTGAAGAACGGCCCAAGGTACAGGTGATCCAGGCTGCCGATCCGCTAGCAACAGCGTATCTGTGCG

GAATCCACCGAGAGCTGGTTAGGAGATTAAATGCGGTCCTGCTTCCGAACATTCATACACTGTTTGATATGTCGGCTG

AAGACTTTGACGCTATTATAGCCGAGCACTTCCAGCCTGGGGATTGTGTTCTGGAAACTGACATCGCGTCGTTTGATA

AAAGTGAGGACGACGCCATGGCTCTGACCGCGTTAATGATTCTGGAAGACTTAGGTGTGGACGCAGAGCTGTTGACGC

TGATTGAGGCGGCTTTCGGCGAAATTTCATCAATACATTTGCCCACTAAAACTAAATTTAAATTCGGAGCCATGATGA

AATCTGGAATGTTCCTCACACTGTTTGTGAACACAGTCATTAACATTGTAATCGCAAGCAGAGTGTTGAGAGAACGGC

TAACCGGATCACCATGTGCAGCATTCATTGGAGATGACAATATCGTGAAAGGAGTCAAATCGGACAAATTAATGGCAG

ACAGGTGCGCCACCTGGTTGAATATGGAAGTCAAGATTATAGATGCTGTGGTGGGCGAGAAAGCGCCTTATTTCTGTG

GAGGGTTTATTTTGTGTGACTCCGTGACCGGCACAGCGTGCCGTGTGGCAGACCCCCTAAAAAGGCTGTTTAAGCTTG

GCAAACCTCTGGCAGCAGACGATGAACATGATGATGACAGGAGAAGGGCATTGCATGAAGAGTCAACACGCTGGAACC

GAGTGGGTATTCTTTCAGAGCTGTGCAAGGCAGTAGAATCAAGGTATGAAACCGTAGGAACTTCCATCATAGTTATGG

CCATGACTACTCTAGCTAGCAGTGTTAAATCATTCAGCTACCTGAGAGGGGCCCCTATAACTCTCTACGGCTAACCTG

AATGGACTACGACATAGTCTAGTCCGCCAAGTCTAGCATATGGCCACCATGTTCGTGTTTCTGGTGCTGCTGCCTCTG

GTGTCCAGCCAGTGTGTGAACCTGACCACCAGAACACAGCTGCCTCCAGCCTACACCAACAGCTTTACCAGAGGCGTG

TACTACCCCGACAAGGTGTTCAGATCCAGCGTGCTGCACTCTACCCAGGACCTGTTCCTGCCTTTCTTCAGCAACGTG

ACCTGGTTCCACGCCATCCACGTGTCCGGCACCAATGGCACCAAGAGATTCGACAACCCCGTGCTGCCCTTCAACGAC

GGGGTGTACTTTGCCAGCACCGAGAAGTCCAACATCATCAGAGGCTGGATCTTCGGCACCACACTGGACAGCAAGACC

CAGAGCCTGCTGATCGTGAACAACGCCACCAACGTGGTCATCAAAGTGTGCGAGTTCCAGTTCTGCAACGACCCCTTC

CTGGGCGTCTACTACCACAAGAACAACAAGAGCTGGATGGAAAGCGAGTTCCGGGTGTACAGCAGCGCCAACAACTGC

ACCTTCGAGTACGTGTCCCAGCCTTTCCTGATGGACCTGGAAGGCAAGCAGGGCAACTTCAAGAACCTGCGCGAGTTC

GTGTTCAAGAACATCGACGGCTACTTCAAGATCTACAGCAAGCACACCCCTATCAACCTCGTGCGGGATCTGCCTCAG

GGCTTCTCTGCTCTGGAACCCCTGGTGGATCTGCCCATCGGCATCAACATCACCCGGTTTCAGACACTGCTGGCCCTG

CACAGAAGCTACCTGACACCTGGCGATAGCAGCAGCGGATGGACAGCTGGTGCCGCCGCTTACTATGTGGGCTACCTG

CAGCCTAGAACCTTCCTGCTGAAGTACAACGAGAACGGCACCATCACCGACGCCGTGGATTGTGCCCTTGATCCTCTG

AGCGAGACAAAGTGCACCCTGAAGTCCTTCACCGTGGAAAAGGGCATCTACCAGACCAGCAACTTCCGGGTGCAGCCC

ACCGAATCCATCGTGCGGTTCCCCAATATCACCAATCTGTGCCCCTTCGGCGAGGTGTTCAATGCCACCAGATTCGCC

TCTGTGTACGCCTGGAACCGGAAGCGGATCAGCAATTGCGTGGCCGACTACTCCGTGCTGTACAACTCCGCCAGCTTC

AGCACCTTCAAGTGCTACGGCGTGTCCCCTACCAAGCTGAACGACCTGTGCTTCACAAACGTGTACGCCGACAGCTTC

GTGATCCGGGGAGATGAAGTGCGGCAGATTGCCCCTGGACAGACAGGCAAGATCGCCGACTACAACTACAAGCTGCCC

GACGACTTCACCGGCTGTGTGATTGCCTGGAACAGCAACAACCTGGACTCCAAAGTCGGCGGCAACTACAATTACCTG

TACCGGCTGTTCCGGAAGTCCAATCTGAAGCCCTTCGAGCGGGACATCTCCACCGAGATCTATCAGGCCGGCAGCACC

CCTTGTAACGGCGTGGAAGGCTTCAACTGCTACTTCCCACTGCAGTCCTACGGCTTTCAGCCCACAAATGGCGTGGGC

TATCAGCCCTACAGAGTGGTGGTGCTGAGCTTCGAACTGCTGCATGCCCCTGCCACAGTGTGCGGCCCTAAGAAAAGC

ACCAATCTCGTGAAGAACAAATGCGTGAACTTCAACTTCAACGGCCTGACCGGCACAGGCGTGCTGACAGAGAGCAAC

AAGAAGTTCCTGCCATTCCAGCAGTTTGGCCGGGATATCGCCGATACCACAGACGCCGTTAGAGATCCCCAGACACTG

GAAATCCTGGACATCACCCCTTGCAGCTTCGGCGGAGTGTCTGTGATCACCCCTGGCACCAACACCAGCAATCAGGTG

GCAGTGCTGTACCAGGACGTGAACTGTACCGAAGTGCCCGTGGCCATTCACGCCGATCAGCTGACACCTACATGGCGG

GTGTACTCCACCGGCAGCAATGTGTTTCAGACCAGAGCCGGCTGTCTGATCGGAGCCGAGCACGTGAACAATAGCTAC

-continued

GAGTGCGACATCCCCATCGGCGCTGGCATCTGTGCCAGCTACCAGACACAGACAAACAGCCCCAGACGGGCCAGATCT

GTGGCCAGCCAGAGCATCATTGCCTACACAATGTCTCTGGGCGCCGAGAACAGCGTGGCCTACTCCAACAACTCTATC

GCTATCCCCACCAACTTCACCATCAGCGTGACCACAGAGATCCTGCCTGTGTCCATGACCAAGACCAGCGTGGACTGC

ACCATGTACATCTGCGGCGATTCCACCGAGTGCTCCAACCTGCTGCTGCAGTACGGCAGCTTCTGCACCCAGCTGAAT

AGAGCCCTGACAGGGATCGCCGTGGAACAGGACAAGAACACCCAAGAGGTGTTCGCCCAAGTGAAGCAGATCTACAAG

ACCCCTCCTATCAAGGACTTCGGCGGCTTCAATTTCAGCCAGATTCTGCCCGATCCTAGCAAGCCCAGCAAGCGGAGC

TTCATCGAGGACCTGCTGTTCAACAAAGTGACACTGGCCGACGCCGGCTTCATCAAGCAGTATGGCGATTGTCTGGGC

GACATTGCCGCCAGGGATCTGATTTGCGCCCAGAAGTTTAACGGACTGACAGTGCTGCCTCCTCTGCTGACCGATGAG

ATGATCGCCCAGTACACATCTGCCCTGCTGGCCGGCACAATCACAAGCGGCTGGACATTTGGAGCTGGCGCCGCTCTG

CAGATCCCCTTTGCTATGCAGATGGCCTACAGATTCAACGGCATCGGAGTGACCCAGAATGTGCTGTACGAGAACCAG

AAGCTGATCGCCAACCAGTTCAACAGCGCCATCGGCAAGATCCAGGACAGCCTGAGCAGCACAGCAAGCGCCCTGGGA

AAGCTGCAGGACGTGGTCAACCAGAATGCCCAGGCACTGAACACCCTGGTCAAGCAGCTGTCCTCCAACTTCGGCGCC

ATCAGCTCTGTGCTGAACGATATCCTGAGCAGACTGGACCCTCCTGAGGCCGAGGTGCAGATCGACAGACTGATCACA

GGCAGACTGCAGAGCCTCCAGACATACGTGACCCAGCAGCTGATCAGAGCCGCCGAGATTAGAGCCTCTGCCAATCTG

GCCGCCACCAAGATGTCTGAGTGTGTGCTGGGCCAGAGCAAGAGAGTGGACTTTTGCGGCAAGGGCTACCACCTGATG

AGCTTCCCTCAGTCTGCCCCTCACGGCGTGGTGTTTCTGCACGTGACATACGTTCCCGCTCAAGAGAAGAATTTCACC

ACCGCTCCAGCCATCTGCCACGACGGCAAAGCCCACTTTCCTAGAGAAGGCGTGTTCGTGTCCAACGGCACCCATTGG

TTCGTGACACAGCGGAACTTCTACGAGCCCCAGATCATCACCACCGACAACACCTTCGTGTCTGGCAACTGCGACGTC

GTGATCGGCATTGTGAACAATACCGTGTACGACCCTCTGCAGCCCGAGCTGGACAGCTTCAAAGAGGAACTGGACAAG

TACTTTAAGAACCACACAAGCCCCGACGTGGACCTGGGCGATATCAGCGGAATCAATGCCAGCGTCGTGAACATCCAG

AAAGAGATCGACCGGCTGAACGAGGTGGCCAAGAATCTGAACGAGAGCCTGATCGACCTGCAAGAACTGGGGAAGTAC

GAGCAGTACATCAAGTGGCCCTGGTACATCTGGCTGGGCTTTATCGCCGGACTGATTGCCATCGTGATGGTCACAATC

ATGCTGTGTTGCATGACCAGCTGCTGTAGCTGCCTGAAGGGCTGTTGTAGCTGTGGCAGCTGCTGCAAGTTCGACGAG

GACGATTCTGAGCCCGTGCTGAAGGGCGTGAAACTGCACTACACATGAGCGGCCGCGAATTGGCAAGCTGCTTACATA

GAACTCGCGGCGATTGGCATGCCGCCTTAAAATTTTTATTTTATTTTTCTTTTCTTTTCCGAATCGGATTTTGTTTTT

AATATTTCAAAAAAAAAAAAAAAAAAAAAAAAAAAAAAAAAAAACGCGTCGAGGGGAATTAATTCTTGAAGACGAAAGG

GCCAGGTGGCACTTTTCGGGGAAATGTGCGCGGAACCCCTATTTGTTTATTTTTCTAAATACATTCAAATATGTATCC

GCTCATGAGACAATAACCCTGATAAATGCTTCAATAATATTGAAAAAGGAAGAGTATGAGTATTCAACATTTCCGTGT

CGCCCTTATTCCCTTTTTTGCGGCATTTTGCCTTCCTGTTTTTGCTCACCCAGAAACGCTGGTGAAAGTAAAAGATGC

TGAAGATCAGTTGGGTGCACGAGTGGGTTACATCGAACTGGATCTCAACAGCGGTAAGATCCTTGAGAGTTTTCGCCC

CGAAGAACGTTTTCCAATGATGAGCACTTTTAAAGTTCTGCTATGTGGCGCGGTATTATCCCGTGTTGACGCCGGGCA

AGAGCAACTCGGTCGCCGCATACACTATTCTCAGAATGACTTGGTTGAGTACTCACCAGTCACAGAAAAGCATCTTAC

GGATGGCATGACAGTAAGAGAATTATGCAGTGCTGCCATAACCATGAGTGATAACACTGCGGCCAACTTACTTCTGAC

AACGATCGGAGGACCGAAGGAGCTAACCGCTTTTTTGCACAACATGGGGGATCATGTAACTCGCCTTGATCGTTGGGA

ACCGGAGCTGAATGAAGCCATACCAAACGACGAGCGTGACACCACGATGCCTGTAGCAATGGCAACAACGTTGCGCAA

ACTATTAACTGGCGAACTACTTACTCTAGCTTCCCGGCAACAATTAATAGACTGGATGGAGGCGGATAAAGTTGCAGG

ACCACTTCTGCGCTCGGCCCTTCCGGCTGGCTGGTTTATTGCTGATAAATCTGGAGCCGGTGAGCGTGGGTCTCGCGG

TATCATTGCAGCACTGGGGCCAGATGGTAAGCCCTCCCGTATCGTAGTTATCTACACGACGGGGAGTCAGGCAACTAT

GGATGAACGAAATAGACAGATCGCTGAGATAGGTGCCTCACTGATTAAGCATTGGTAACTGTCAGACCAAGTTTACTC

ATATATACTTTAGATTGATTTAAAACTTCATTTTTAATTTAAAAGGATCTAGGTGAAGATCCTTTTTGATAATCTCAT

GACCAAAATCCCTTAACGTGAGTTTTCGTTCCACTGAGCGTCAGACCCCGTAGAAAAGATCAAAGGATCTTCTTGAGA

-continued

TCCTTTTTTTCTGCGCGTAATCTGCTGCTTGCAAACAAAAAAACCACCGCTACCAGCGGTGGTTTGTTTGCCGGATCA

AGAGCTACCAACTCTTTTTCCGAAGGTAACTGGCTTCAGCAGAGCGCAGATACCAAATACTGTCCTTCTAGTGTAGCC

GTAGTTAGGCCACCACTTCAAGAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGATAAGGCGCAGCGGTCGGGCTG

AACGGGGGGTTCGTGCACACAGCCCAGCTTGGAGCGAACGACCTACACCGAACTGAGATACCTACAGCGTGAGCATTG

AGAAAGCGCCACGCTTCCCGAAGGGAGAAAGGCGGACAGGTATCCGGTAAGCGGCAGGGTCGGAACAGGAGAGCGCAC

GAGGGAGCTTCCAGGGGGAAACGCCTGGTATCTTTATAGTCCTGTCGGGTTTCGCCACCTCTGACTTGAGCGTCGATT

TTTGTGATGCTCGTCAGGGGGGCGGAGCCTATGGAAAAA

Accordingly, preferably the vector comprises the nucleotide sequence substantially as set out in SEQ ID NO: 35, or a variant or fragment thereof.

In one embodiment (the B.1.1.7 UK variant of SARS-CoV-2 glycoprotein), the vector may comprise the nucleic acid sequence of SEQ ID No: 72, as follows:

[SEQ ID No: 72]

ATCCTCTGTACGCACCCACCTCAGAACATGTGAACGTCCTACTGACCCGCACGGAGGACCGCATCGTGTGGAAAACAC

TAGCCGGCGACCCATGGATAAAAACACTGACTGCCAAGTACCCTGGGAATTTCACTGCCACGATAGAGGAGTGGCAAG

CAGAGCATGATGCCATCATGAGGCACATCTTGGAGAGACCGGACCCTACCGACGTCTTCCAGAATAAGGCAAACGTGT

GTTGGGCCAAGGCTTTAGTGCCGGTGCTGAAGACCGCTGGCATAGACATGACCACTGAACAATGGAACACTGTGGATT

ATTTTGAAACGGACAAAGCTCACTCAGCAGAGATAGTATTGAACCAACTATGCGTGAGGTTCTTTGGACTCGATCTGG

ACTCCGGTCTATTTTCTGCACCCACTGTTCCGTTATCCATTAGGAATAATCACTGGGATAACTCCCCGTCGCCTAACA

TGTACGGGCTGAATAAAGAAGTGGTCCGTCAGCTCTCTCGCAGGTACCCACAACTGCCTCGGGCAGTTGCCACTGGAA

GAGTCTATGACATGAACACTGGTACACTGCGCAATTATGATCCGCGCATAAACCTAGTACCTGTAAACAGAAGACTGC

CTCATGCTTTAGTCCTCCACCATAATGAACACCCACAGAGTGACTTTTCTTCATTCGTCAGCAAATTGAAGGGCAGAA

CTGTCCTGGTGGTCGGGGAAAAGTTGTCCGTCCCAGGCAAAATGGTTGACTGGTTGTCAGACCGGCCTGAGGCTACCT

TCAGAGCTCGGCTGGATTTAGGCATCCCAGGTGATGTGCCCAAATATGACATAATATTTGTTAATGTGAGGACCCCAT

ATAAATACCATCACTATCAGCAGTGTGAAGACCATGCCATTAAGCTTAGCATGTTGACCAAGAAAGCTTGTCTGCATC

TGAATCCCGGCGGAACCTGTGTCAGCATAGGTTATGGTTACGCTGACAGGGCCAGCGAAAGCATCATTGGTGCTATAG

CGCGGCAGTTCAAGTTTTCCCGGGTATGCAAACCGAAATCCTCACTTGAAGAGACGGAAGTTCTGTTTGTATTCATTG

GGTACGATCGCAAGGCCCGTACGCACAATTCTTACAAGCTTTCATCAACCTTGACCAACATTTATACAGGTTCCAGAC

TCCACGAAGCCGGATGTGCACCCTCATATCATGTGGTGCGAGGGGATATTGCCACGGCCACCGAAGGAGTGATTATAA

ATGCTGCTAACAGCAAAGGACAACCTGGCGGAGGGGTGTGCGGAGCGCTGTATAAGAAATTCCCGGAAAGCTTCGATT

TACAGCCGATCGAAGTAGGAAAAGCGCGACTGGTCAAAGGTGCAGCTAAACATATCATTCATGCCGTAGGACCAAACT

TCAACAAAGTTTCGGAGGTTGAAGGTGACAAACAGTTGGCAGAGGCTTATGAGTCCATCGCTAAGATTGTCAACGATA

ACAATTACAAGTCAGTAGCGATTCCACTGTTGTCCACCGGCATCTTTTCCGGGAACAAAGATCGACTAACCCAATCAT

TGAACCATTTGCTGACAGCTTTAGACACCACTGATGCAGATGTAGCCATATACTGCAGGGACAAGAAATGGGAAATGA

CTCTCAAGGAAGCAGTGGCTAGGAGAGAAGCAGTGGAGGAGATATGCATATCCGACGACTCTTCAGTGACAGAACCTG

ATGCAGAGCTGGTGAGGGTGCATCCGAAGAGTTCTTTGGCTGGAAGGAAGGGCTACAGCACAAGCGATGGCAAAACTT

TCTCATATTTGGAAGGGACCAAGTTTCACCAGGCGGCCAAGGATATAGCAGAAATTAATGCCATGTGGCCCGTTGCAA

CGGAGGCCAATGAGCAGGTATGCATGTATATCCTCGGAGAAAGCATGAGCAGTATTAGGTCGAAATGCCCCGTCGAAG

AGTCGGAAGCCTCCACACCACCTAGCACGCTGCCTTGCTTGTGCATCCATGCCATGACTCCAGAAAGAGTACAGCGCC

TAAAAGCCTCACGTCCAGAACAAATTACTGTGTGCTCATCCTTTCCATTGCCGAAGTATAGAATCACTGGTGTGCAGA

AGATCCAATGCTCCCAGCCTATATTGTTCTCACCGAAAGTGCCTGCGTATATTCATCCAAGGAAGTATCTCGTGGAAA

-continued

CACCACCGGTAGACGAGACTCCGGAGCCATCGGCAGAGAACCAATCCACAGAGGGGACACCTGAACAACCACCACTTA

TAACCGAGGATGAGACCAGGACTAGAACGCCTGAGCCGATCATCATCGAAGAGGAAGAAGAGGATAGCATAAGTTTGC

TGTCAGATGGCCCGACCCACCAGGTGCTGCAAGTCGAGGCAGACATTCACGGGCCGCCCTCTGTATCTAGCTCATCCT

GGTCCATTCCTCATGCATCCGACTTTGATGTGGACAGTTTATCCATACTTGACACCCTGGAGGGAGCTAGCGTGACCA

GCGGGGCAACGTCAGCCGAGACTAACTCTTACTTCGCAAAGAGTATGGAGTTTCTGGCGCGACCGGTGCCTGCGCCTC

GAACAGTATTCAGGAACCCTCCACATCCCGCTCCGCGCACAAGAACACCGTCACTTGCACCCAGCAGGGCCTGCTCGA

GAACCAGCCTAGTTTCCACCCCGCCAGGCGTGAATAGGGTGATCACTAGAGAGGAGCTCGAGGCGCTTACCCCGTCAC

GCACTCCTAGCAGGTCGGTCTCGAGAACCAGCCTGGTCTCCAACCCGCCAGGCGTAAATAGGGTGATTACAAGAGAGG

AGTTTGAGGCGTTCGTAGCACAACAACAATGACGGTTTGATGCGGGTGCATACATCTTTTCCTCCGACACCGGTCAAG

GGCATTTACAACAAAAATCAGTAAGGCAAACGGTGCTATCCGAAGTGGTGTTGGAGAGGACCGAATTGGAGATTTCGT

ATGCCCCGCGCCTCGACCAAGAAAAAGAAGAATTACTACGCAAGAAATTACAGTTAAATCCCACACCTGCTAACAGAA

GCAGATACCAGTCCAGGAAGGTGGAGAACATGAAAGCCATAACAGCTAGACGTATTCTGCAAGGCCTAGGGCATTATT

TGAAGGCAGAAGGAAAAGTGGAGTGCTACCGAACCCTGCATCCTGTTCCTTTGTATTCATCTAGTGTGAACCGTGCCT

TTTCAAGCCCCAAGGTCGCAGTGGAAGCCTGTAACGCCATGTTGAAAGAGAACTTTCCGACTGTGGCTTCTTACTGTA

TTATTCCAGAGTACGATGCCTATTTGGACATGGTTGACGGAGCTTCATGCTGCTTAGACACTGCCAGTTTTTGCCCTG

CAAAGCTGCGCAGCTTTCCAAAGAAACACTCCTATTTGGAACCCACAATACGATCGGCAGTGCCTTCAGCGATCCAGA

ACACGCTCCAGAACGTCCTGGCAGCTGCCACAAAAAGAAATTGCAATGTCACGCAAATGAGAGAATTGCCCGTATTGG

ATTCGGCGGCCTTTAATGTGGAATGCTTCAAGAAATATGCGTGTAATAATGAATATTGGGAAACGTTTAAAGAAAACC

CCATCAGGCTTACTGAAGAAAACGTGGTAAATTACATTACCAAATTAAAAGGACCAAAAGCTGCTGCTCTTTTTGCGA

AGACACATAATTTGAATATGTTGCAGGACATACCAATGGACAGGTTTGTAATGGACTTAAAGAGAGACGTGAAAGTGA

CTCCAGGAACAAAACATACTGAAGAACGGCCCAAGGTACAGGTGATCCAGGCTGCCGATCCGCTAGCAACAGCGTATC

TGTGCGGAATCCACCGAGAGCTGGTTAGGAGATTAAATGCGGTCCTGCTTCCGAACATTCATACACTGTTTGATATGT

CGGCTGAAGACTTTGACGCTATTATAGCCGAGCACTTCCAGCCTGGGGATTGTGTTCTGGAAACTGACATCGCGTCGT

TTGATAAAAGTGAGGACGACGCCATGGCTCTGACCGCGTTAATGATTCTGGAAGACTTAGGTGTGGACGCAGAGCTGT

TGACGCTGATTGAGGCGGCTTTCGGCGAAATTTCATCAATACATTTGCCCACTAAAACTAAATTTAAATTCGGAGCCA

TGATGAAATCTGGAATGTTCCTCACACTGTTTGTGAACACAGTCATTAACATTGTAATCGCAAGCAGAGTGTTGAGAG

AACGGCTAACCGGATCACCATGTGCAGCATTCATTGGAGATGACAATATCGTGAAAGGAGTCAAATCGGACAAATTAA

TGGCAGACAGGTGCGCCACCTGGTTGAATATGGAAGTCAAGATTATAGATGCTGTGGTGGGCGAGAAAGCGCCTTATT

TCTGTGGAGGGTTTATTTTGTGTGACTCCGTGACCGGCACAGCGTGCCGTGTGGCAGACCCCCTAAAAAGGCTGTTTA

AGCTTGGCAAACCTCTGGCAGCAGACGATGAACATGATGATGACAGGAGAAGGGCATTGCATGAAGAGTCAACACGCT

GGAACCGAGTGGGTATTCTTTCAGAGCTGTGCAAGGCAGTAGAATCAAGGTATGAAACCGTAGGAACTTCCATCATAG

TTATGGCCATGACTACTCTAGCTAGCAGTGTTAAATCATTCAGCTACCTGAGAGGGGCCCCTATAACTCTCTACGGCT

AACCTGAATGGACTACGACATAGTCTAGTCCGCCAAGTCTAGCATATGGCCACCATGTTCGTGTTTCTGGTGCTGCTG

CCTCTGGTGTCCAGCCAGTGTGTGAACCTGACCACCAGAACACAGCTGCCTCCAGCCTACACCAACAGCTTTACCAGA

GGCGTGTACTACCCCGACAAGGTGTTCAGATCCAGCGTGCTGCACTCTACCCAGGACCTGTTCCTGCCTTTCTTCAGC

AACGTGACCTGGTTCCACGCCATCTCCGGCACCAATGGCACCAAGAGATTCGACAACCCCGTGCTGCCCTTCAACGAC

GGGGTGTACTTTGCCAGCACCGAGAAGTCCAACATCATCAGAGGCTGGATCTTCGGCACCACACTGGACAGCAAGACC

CAGAGCCTGCTGATCGTGAACAACGCCACCAACGTGGTCATCAAAGTGTGCGAGTTCCAGTTCTGCAACGACCCCTTC

CTGGGCGTCTACCACAAGAACAACAAGAGCTGGATGGAAAGCGAGTTCCGGGTGTACAGCAGCGCCAACAACTGCACC

TTCGAGTACGTGTCCCAGCCTTTCCTGATGGACCTGGAAGGCAAGCAGGGCAACTTCAAGAACCTGCGCGAGTTCGTG

TTCAAGAACATCGACGGCTACTTCAAGATCTACAGCAAGCACACCCCTATCAACCTCGTGCGGGATCTGCCTCAGGGC

-continued

TTCTCTGCTCTGGAACCCCTGGTGGATCTGCCCATCGGCATCAACATCACCCGGTTTCAGACACTGCTGGCCCTGCAC
AGAAGCTACCTGACACCTGGCGATAGCAGCAGCGGATGGACAGCTGGTGCCGCCGCTTACTATGTGGGCTACCTGCAG
CCTAGAACCTTCCTGCTGAAGTACAACGAGAACGGCACCATCACCGACGCCGTGGATTGTGCCCTTGATCCTCTGAGC
GAGACAAAGTGCACCCTGAAGTCCTTCACCGTGGAAAAGGGCATCTACCAGACCAGCAACTTCCGGGTGCAGCCCACC
GAATCCATCGTGCGGTTCCCCAATATCACCAATCTGTGCCCCTTCGGCGAGGTGTTCAATGCCACCAGATTCGCCTCT
GTGTACGCCTGGAACCGGAAGCGGATCAGCAATTGCGTGGCCGACTACTCCGTGCTGTACAACTCCGCCAGCTTCAGC
ACCTTCAAGTGCTACGGCGTGTCCCCTACCAAGCTGAACGACCTGTGCTTCACAAACGTGTACGCCGACAGCTTCGTG
ATCCGGGGAGATGAAGTGCGGCAGATTGCCCCTGGACAGACAGGCAAGATCGCCGACTACAACTACAAGCTGCCCGAC
GACTTCACCGGCTGTGTGATTGCCTGGAACAGCAACAACCTGGACTCCAAAGTCGGCGGCAACTACAATTACCTGTAC
CGGCTGTTCCGGAAGTCCAATCTGAAGCCCTTCGAGCGGGACATCTCCACCGAGATCTATCAGGCCGGCAGCACCCCT
TGTAACGGCGTGGAAGGCTTCAACTGCTACTTCCCACTGCAGTCCTACGGCTTTCAGCCCACATATGGCGTGGGCTAT
CAGCCCTACAGAGTGGTGGTGCTGAGCTTCGAACTGCTGCATGCCCCTGCCACAGTGTGCGGCCCTAAGAAAAGCACC
AATCTCGTGAAGAACAAATGCGTGAACTTCAACTTCAACGGCCTGACCGGCACAGGCGTGCTGACAGAGAGCAACAAG
AAGTTCCTGCCATTCCAGCAGTTTGGCCGGGATATCGACGATACCACAGACGCCGTTAGAGATCCCCAGACACTGGAA
ATCCTGGACATCACCCCTTGCAGCTTCGGCGGAGTGTCTGTGATCACCCCTGGCACCAACACCAGCAATCAGGTGGCA
GTGCTGTACCAGGGCGTGAACTGTACCGAAGTGCCCGTGGCCATTCACGCCGATCAGCTGACACCTACATGGCGGGTG
TACTCCACCGGCAGCAATGTGTTTCAGACCAGAGCCGGCTGTCTGATCGGAGCCGAGCACGTGAACAATAGCTACGAG
TGCGACATCCCCATCGGCGCTGGCATCTGTGCCAGCTACCAGACACAGACAAACAGCCACTCTCTGGCCAGCTCTGTG
GCCAGCCAGAGCATCATTGCCTACACAATGTCTCTGGGCGCCGAGAACAGCGTGGCCTACTCCAACAACTCTATCGCT
ATCCCCATCAACTTCACCATCAGCGTGACCACAGAGATCCTGCCTGTGTCCATGACCAAGACCAGCGTGGACTGCACC
ATGTACATCTGCGGCGATTCCACCGAGTGCTCCAACCTGCTGCTGCAGTACGGCAGCTTCTGCACCCAGCTGAATAGA
GCCCTGACAGGGATCGCCGTGGAACAGGACAAGAACACCCAAGAGGTGTTCGCCCAAGTGAAGCAGATCTACAAGACC
CCTCCTATCAAGGACTTCGGCGGCTTCAATTTCAGCCAGATTCTGCCCGATCCTAGCAAGCCCAGCAAGCGGAGCCCC
ATCGAGGACCTGCTGTTCAACAAAGTGACACTGGCCGACGCCGGCTTCATCAAGCAGTATGGCGATTGTCTGGGCGAC
ATTGCCGCCAGGGATCTGATTTGCGCCCAGAAGTTTAACGGACTGACAGTGCTGCCTCCTCTGCTGACCGATGAGATG
ATCGCCCAGTACACATCTGCCCTGCTGGCCGGCACAATCACAAGCGGCTGGACATTTGGAGCTGGCCCCGCTCTGCAG
ATCCCCTTTCCTATGCAGATGGCCTACAGATTCAACGGCATCGGAGTGACCCAGAATGTGCTGTACGAGAACCAGAAG
CTGATCGCCAACCAGTTCAACAGCGCCATCGGCAAGATCCAGGACAGCCTGAGCAGCACACCAAGCGCCCTGGGAAAG
CTGCAGGACGTGGTCAACCAGAATGCCCAGGCACTGAACACCCTGGTCAAGCAGCTGTCCTCCAACTTCGGCGCCATC
AGCTCTGTGCTGAACGATATCCTGGCCAGACTGGACCCTCCTGAGGCCGAGGTGCAGATCGACAGACTGATCACAGGC
AGACTGCAGAGCCTCCAGACATACGTGACCCAGCAGCTGATCAGAGCCGCCGAGATTAGAGCCTCTGCCAATCTGGCC
GCCACCAAGATGTCTGAGTGTGTGCTGGGCCAGAGCAAGAGAGTGGACTTTTGCGGCAAGGGCTACCACCTGATGAGC
TTCCCTCAGTCTGCCCCTCACGGCGTGGTGTTTCTGCACGTGACATACGTTCCCGCTCAAGAGAAGAATTTCACCACC
GCTCCAGCCATCTGCCACGACGGCAAAGCCCACTTTCCTAGAGAAGGCGTGTTCGTGTCCAACGGCACCCATTGGTTC
GTGACACAGCGGAACTTCTACGAGCCCCAGATCATCACCACCCACAACACCTTCGTGTCTGGCAACTGCGACGTCGTG
ATCGGCATTGTGAACAATACCGTGTACGACCCTCTGCAGCCCGAGCTGGACAGCTTCAAAGAGGAACTGGACAAGTAC
TTTAAGAACCACACAAGCCCCGACGTGGACCTGGGCGATATCAGCGGAATCAATGCCAGCGTCGTGAACATCCAGAAA
GAGATCGACCGGCTGAACGAGGTGGCCAAGAATCTGAACGAGAGCCTGATCGACCTGCAAGAACTGGGGAAGTACGAG
CAGTACATCAAGTGGCCCTGGTACATCTGGCTGGGCTTTATCGCCGGACTGATTGCCATCGTGATGGTCACAATCATG
CTGTGTTGCATGACCAGCTGCTGTAGCTGCCTGAAGGGCTGTTGTAGCTGTGGCAGCTGCTGCAAGTTCGACGAGGAC

-continued

GATTCTGAGCCCGTGCTGAAGGGCGTGAAACTGCACTACACATGAGCGGCCGCGAATTGGCAAGCTGCTTACATAGAA

CTCGCGGCGATTGGCATGCCGCCTTAAAATTTTTATTTTATTTTTCTTTTCTTTTCCGAATCGGATTTTGTTTTTAAT

ATTTCAAAAAAAAAAAAAAAAAAAAAAAAAAAAAAAAAAAACGCGTCGAGGGGAATTAATTCTTGAAGACGAAAGGGCC

AGGTGGCACTTTTCGGGGAAATGTGCGCGGAACCCCTATTTGTTTATTTTTCTAAATACATTCAAATATGTATCCGCT

CATGAGACAATAACCCTGATAAATGCTTCAATAATATTGAAAAAGGAAGAGTATGAGTATTCAACATTTCCGTGTCGC

CCTTATTCCCTTTTTTGCGGCATTTTGCCTTCCTGTTTTTGCTCACCCAGAAACGCTGGTGAAAGTAAAAGATGCTGA

AGATCAGTTGGGTGCACGAGTGGGTTACATCGAACTGGATCTCAACAGCGGTAAGATCCTTGAGAGTTTTCGCCCCGA

AGAACGTTTTCCAATGATGAGCACTTTTAAAGTTCTGCTATGTGGCGCGGTATTATCCCGTGTTGACGCCGGGCAAGA

GCAACTCGGTCGCCGCATACACTATTCTCAGAATGACTTGGTTGAGTACTCACCAGTCACAGAAAAGCATCTTACGGA

TGGCATGACAGTAAGAGAATTATGCAGTGCTGCCATAACCATGAGTGATAACACTGCGGCCAACTTACTTCTGACAAC

GATCGGAGGACCGAAGGAGCTAACCGCTTTTTTGCACAACATGGGGGATCATGTAACTCGCCTTGATCGTTGGGAACC

GGAGCTGAATGAAGCCATACCAAACGACGAGCGTGACACCACGATGCCTGTAGCAATGGCAACAACGTTGCGCAAACT

ATTAACTGGCGAACTACTTACTCTAGCTTCCCGGCAACAATTAATAGACTGGATGGAGGCGGATAAAGTTGCAGGACC

ACTTCTGCGCTCGGCCCTTCCGGCTGGCTGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCTACACGACGGGGAGTCAGGCAACTATGGA

TGAACGAAATAGACAGATCGCTGAGATAGGTGCCTCACTGATTAAGCATTGGTAACTGTCAGACCAAGTTTACTCATA

TATACTTTAGATTGATTTAAAACTTCATTTTTAATTTAAAAGGATCTAGGTGAAGATCCTTTTTGATAATCTCATGAC

CAAAATCCCTTAACGTGAGTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGTTTGTTTGCCGGATCAAGA

GCTACCAACTCTTTTTCCGAAGGTAACTGGCTTCAGCAGAGCGCAGATACCAAATACTGTCCTTCTAGTGTAGCCGTA

GTTAGGCCACCACTTCAAGAACTCTGTAGCACCGCCTACATACCTCGCTCTGCTAATCCTGTTACCAGTGGCTGCTGC

CAGTGGCGATAAGTCGTGTCTTACCGGGTTGGACTCAAGACGATAGTTACCGGATAAGGCGCAGCGGTCGGGCTGAAC

GGGGGGTTCGTGCACACAGCCCAGCTTGGAGCGAACGACCTACACCGAACTGAGATACCTACAGCGTGAGCATTGAGA

AAGCGCCACGCTTCCCGAAGGGAGAAAGGCGGACAGGTATCCGGTAAGCGGCAGGGTCGGAACAGGAGAGCGCACGAG

GGAGCTTCCAGGGGGAAACGCCTGGTATCTTTATAGTCCTGTCGGGTTTCGCCACCTCTGACTTGAGCGTCGATTTTT

GTGATGCTCGTCAGGGGGGCGGAGCCTATGGAAAAACGCCATTCTAGAATGGCGCGCCCTTAAGGGGAGAATAGGAGC

CGCAACACACAAGCAACGCGAGGTCGTTTAAACTAATACGACTCACTATAATGGGCGGCGCATGAGAGAAGCCCAGAC

CAATTACCTACCCAAAATGGAGAAAGTTCACGTTGACATCGAGGAAGACAGCCCATTCCTCAGAGCTTTGCAGCGGAG

CTTCCCGCAGTTTGAGGTAGAAGCCAAGCAGGTCACTGATAATGACCATGCTAATGCCAGAGCGTTTTCGCATCTGGC

TTCAAAACTGATCGAAACGGAGGTGGACCCATCCGACACGATCCTTGACATTGGAAGTGCGCCCGCCCGCAGAATGTA

TTCTAAGCACAAGTATCATTGTATCTGTCCGATGAGATGTGCGGAAGATCCGGACAGATTGTATAAGTATGCAACTAA

GCTGAAGAAAAACTGTAAGGAAATAACTGATAAGGAATTGGACAAGAAAATGAAGGAGCTGGCCGCCGTCATGAGCGA

CCCTGACCTGGAAACTGAGACTATGTGCCTCCACGACGACGAGTCGTGTCGCTACGAAGGGCAAGTCGCTGTTTACCA

GGATGTATACGCGGTTGACGGACCGACAAGTCTCTATCACCAAGCCAATAAGGGAGTTAGAGTCGCCTACTGGATAGG

CTTTGACACCACCCCTTTTATGTTTAAGAACTTGGCTGGAGCATATCCATCATACTCTACCAACTGGGCCGACGAAAC

CGTGTTAACGGCTCGTAACATAGGCCTATGCAGCTCTGACGTTATGGAGCGGTCACGTAGAGGGATGTCCATTCTTAG

AAAGAAGTATTTGAAACCATCCAACAATGTTCTATTCTCTGTTGGCTCGACCATCTACCACGAGAAGAGGGACTTACT

GAGGAGCTGGCACCTGCCGTCTGTATTTCACTTACGTGGCAAGCAAAATTACACATGTCGGTGTGAGACTATAGTTAG

TTGCGACGGGTACGTCGTTAAAAGAATAGCTATCAGTCCAGGCCTGTATGGGAAGCCTTCAGGCTATGCTGCTACGAT

GCACCGCGAGGGATTCTTGTGCTGCAAAGTGACAGACACATTGAACGGGGAGAGGGTCTCTTTTCCCGTGTGCACGTA

TGTGCCAGCTACATTGTGTGACCAAATGACTGGCATACTGGCAACAGATGTCAGTGCGGACGACGCGCAAAAACTGCT

-continued

GGTTGGGCTCAACCAGCGTATAGTCGTCAACGGTCGCACCCAGAGAAACACCAATACCATGAAAAATTACCTTTTGCC

CGTAGTGGCCCAGGCATTTGCTAGGTGGGCAAAGGAATATAAGGAAGATCAAGAAGATGAAAGGCCACTAGGACTACG

AGATAGACAGTTAGTCATGGGGTGTTGTTGGGCTTTTAGAAGGCACAAGATAACATCTATTTATAAGCGCCCGGATAC

CCAAACCATCATCAAAGTGAACAGCGATTTCCACTCATTCGTGCTGCCCAGGATAGGCAGTAACACATTGGAGATCGG

GCTGAGAACAAGAATCAGGAAAATGTTAGAGGAGCACAAGGAGCCGTCACCTCTCATTACCGCCGAGGACGTACAAGA

AGCTAAGTGCGCAGCCGATGAGGCTAAGGAGGTGCGTGAAGCCGAGGAGTTGCGCGCAGCTCTACCACCTTTGGCAGC

TGATGTTGAGGAGCCCACTCTGGAGGCAGACGTCGACTTGATGTTACAAGAGGCTGGGGCCGGCTCAGTGGAGACACC

TCGTGGCTTGATAAAGGTTACCAGCTACGATGGCGAGGACAAGATCGGCTCTTACGCTGTGCTTTCTCCGCAGGCTGT

ACTCAAGAGTGAAAAATTATCTTGCATCCACCCTCTCGCTGAACAAGTCATAGTGATAACACACTCTGGCCGAAAAGG

GCGTTATGCCGTGGAACCATACCATGGTAAAGTAGTGGTGCCAGAGGGACATGCAATACCCGTCCAGGACTTTCAAGC

TCTGAGTGAAAGTGCCACCATTGTGTACAACGAACGTGAGTTCGTAAACAGGTACCTGCACCATATTGCCACACATGG

AGGAGCGCTGAACACTGATGAAGAATATTACAAAACTGTCAAGCCCAGCGAGCACGACGGCGAATACCTGTACGACAT

CGACAGGAAACAGTGCGTCAAGAAAGAACTAGTCACTGGGCTAGGGCTCACAGGCGAGCTGGTGGATCCTCCCTTCCA

TGAATTCGCCTACGAGAGTCTGAGAACACGACCAGCCGCTCCTTACCAAGTACCAACCATAGGGGTGTATGGCGTGCC

AGGATCAGGCAAGTCTGGCATCATTAAAAGCGCAGTCACCAAAAAAGATCTAGTGGTGAGCGCCAAGAAAGAAAACTG

TGCAGAAATTATAAGGGACGTCAAGAAAATGAAAGGGCTGGACGTCAATGCCAGAACTGTGGACTCAGTGCTCTTGAA

TGGATGCAAACACCCCGTAGAGACCCTGTATATTGACGAAGCTTTTGCTTGTCATGCAGGTACTCTCAGAGCGCTCAT

AGCCATTATAAGACCTAAAAAGGCAGTGCTCTGCGGGGATCCCAAACAGTGCGGTTTTTTAACATGATGTGCCTGAA

AGTGCATTTTAACCACGAGATTTGCACACAAGTCTTCCACAAAAGCATCTCTCGCCGTTGCACTAAATCTGTGACTTC

GGTCGTCTCAACCTTGTTTTACGACAAAAAAATGAGAACGACGAATCCGAAAGAGACTAAGATTGTGATTGACACTAC

CGGCAGTACCAAACCTAAGCAGGACGATCTCATTCTCACTTGTTTCAGAGGGTGGGTGAAGCAGTTGCAAATAGATTA

CAAAGGCAACGAAATAATGACGGCAGCTGCCTCTCAAGGGCTGACCCGTAAAGGTGTGTATGCCGTTCGGTACAAGGT

GAATGAAA

Accordingly, preferably the vector comprises the nucleotide sequence substantially as set out in SEQ ID NO: 72, or a variant or fragment thereof.

In one embodiment (the B.1.1.7 UK+E484K variant of SARS-CoV-2 glycoprotein), the vector may comprise the nucleic acid sequence of SEQ ID No: 73, as follows:

[SEQ ID No: 73]

ATCCTCTGTACGCACCCACCTCAGAACATGTGAACGTCCTACTGACCCGCACGGAGGACCGCATCGTGTGGAAAACAC

TAGCCGGCGACCCATGGATAAAAACACTGACTGCCAAGTACCCTGGGAATTTCACTGCCACGATAGAGGAGTGGCAAG

CAGAGCATGATGCCATCATGAGGCACATCTTGGAGAGACCGGACCCTACCGACGTCTTCCAGAATAAGGCAAACGTGT

GTTGGGCCAAGGCTTTAGTGCCGGTGCTGAAGACCGCTGGCATAGACATGACCACTGAACAATGGAACACTGTGGATT

ATTTTGAAACGGACAAAGCTCACTCAGCAGAGATAGTATTGAACCAACTATGCGTGAGGTTCTTTGGACTCGATCTGG

ACTCCGGTCTATTTTCTGCACCCACTGTTCCGTTATCCATTAGGAATAATCACTGGGATAACTCCCCGTCGCCTAACA

TGTACGGGCTGAATAAAGAAGTGGTCCGTCAGCTCTCTCGCAGGTACCCACAACTGCCTCGGGCAGTTGCCACTGGAA

GAGTCTATGACATGAACACTGGTACACTGCGCAATTATGATCCGCGCATAAACCTAGTACCTGTAAACAGAAGACTGC

CTCATGCTTTAGTCCTCCACCATAATGAACACCCACAGAGTGACTTTTCTTCATTCGTCAGCAAATTGAAGGGCAGAA

CTGTCCTGGTGGTCGGGGAAAAGTTGTCCGTCCCAGGCAAAATGGTTGACTGGTTGTCAGACCGGCCTGAGGCTACCT

TCAGAGCTCGGCTGGATTTAGGCATCCCAGGTGATGTGCCCAAATATGACATAATATTTGTTAATGTGAGGACCCCAT

ATAAATACCATCACTATCAGCAGTGTGAAGACCATGCCATTAAGCTTAGCATGTTGACCAAGAAAGCTTGTCTGCATC

TGAATCCCGGCGGAACCTGTGTCAGCATAGGTTATGGTTACGCTGACAGGGCCAGCGAAAGCATCATTGGTGCTATAG

-continued

CGCGGCAGTTCAAGTTTTCCCGGGTATGCAAACCGAAATCCTCACTTGAAGAGACGGAAGTTCTGTTTGTATTCATTG

GGTACGATCGCAAGGCCCGTACGCACAATTCTTACAAGCTTTCATCAACCTTGACCAACATTTATACAGGTTCCAGAC

TCCACGAAGCCGGATGTGCACCCTCATATCATGTGGTGCGAGGGGATATTGCCACGGCCACCGAAGGAGTGATTATAA

ATGCTGCTAACAGCAAAGGACAACCTGGCGGAGGGGTGTGCGGAGCGCTGTATAAGAAATTCCCGGAAAGCTTCGATT

TACAGCCGATCGAAGTAGGAAAAGCGCGACTGGTCAAAGGTGCAGCTAAACATATCATTCATGCCGTAGGACCAAACT

TCAACAAAGTTTCGGAGGTTGAAGGTGACAAACAGTTGGCAGAGGCTTATGAGTCCATCGCTAAGATTGTCAACGATA

ACAATTACAAGTCAGTAGCGATTCCACTGTTGTCCACCGGCATCTTTTCCGGGAACAAAGATCGACTAACCCAATCAT

TGAACCATTTGCTGACAGCTTTAGACACCACTGATGCAGATGTAGCCATATACTGCAGGGACAAGAAATGGGAAATGA

CTCTCAAGGAAGCAGTGGCTAGGAGAGAAGCAGTGGAGGAGATATGCATATCCGACGACTCTTCAGTGACAGAACCTG

ATGCAGAGCTGGTGAGGGTGCATCCGAAGAGTTCTTTGGCTGGAAGGAAGGGCTACAGCACAAGCGATGGCAAAACTT

TCTCATATTTGGAAGGGACCAAGTTTCACCAGGCGGCCAAGGATATAGCAGAAATTAATGCCATGTGGCCCGTTGCAA

CGGAGGCCAATGAGCAGGTATGCATGTATATCCTCGGAGAAAGCATGAGCAGTATTAGGTCGAAATGCCCCGTCGAAG

AGTCGGAAGCCTCCACACCACCTAGCACGCTGCCTTGCTTGTGCATCCATGCCATGACTCCAGAAAGAGTACAGCGCC

TAAAAGCCTCACGTCCAGAACAAATTACTGTGTGCTCATCCTTTCCATTGCCGAAGTATAGAATCACTGGTGTGCAGA

AGATCCAATGCTCCCAGCCTATATTGTTCTCACCGAAAGTGCCTGCGTATATTCATCCAAGGAAGTATCTCGTGGAAA

CACCACCGGTAGACGAGACTCCGGAGCCATCGGCAGAGAACCAATCCACAGAGGGGACACCTGAACAACCACCACTTA

TAACCGAGGATGAGACCAGGACTAGAACGCCTGAGCCGATCATCATCGAAGAGGAAGAAGAGGATAGCATAAGTTTGC

TGTCAGATGGCCCGACCCACCAGGTGCTGCAAGTCGAGGCAGACATTCACGGGCCGCCCTCTGTATCTAGCTCATCCT

GGTCCATTCCTCATGCATCCGACTTTGATGTGGACAGTTTATCCATACTTGACACCCTGGAGGGAGCTAGCGTGACCA

GCGGGGCAACGTCAGCCGAGACTAACTCTTACTTCGCAAAGAGTATGGAGTTTCTGGCGCGACCGGTGCCTGCGCCTC

GAACAGTATTCAGGAACCCTCCACATCCCGCTCCGCGCACAAGAACACCGTCACTTGCACCCAGCAGGGCCTGCTCGA

GAACCAGCCTAGTTTCCACCCCGCCAGGCGTGAATAGGGTGATCACTAGAGAGGAGCTCGAGGCGCTTACCCCGTCAC

GCACTCCTAGCAGGTCGGTCTCGAGAACCAGCCTGGTCTCCAACCCGCCAGGCGTAAATAGGGTGATTACAAGAGAGG

AGTTTGAGGCGTTCGTAGCACAACAACAATGACGGTTTGATGCGGGTGCATACATCTTTTCCTCCGACACCGGTCAAG

GGCATTTACAACAAAAATCAGTAAGGCAAACGGTGCTATCCGAAGTGGTGTTGGAGAGGACCGAATTGGAGATTTCGT

ATGCCCCGCGCCTCGACCAAGAAAAAGAAGAATTACTACGCAAGAAATTACAGTTAAATCCCACACCTGCTAACAGAA

GCAGATACCAGTCCAGGAAGGTGGAGAACATGAAAGCCATAACAGCTAGACGTATTCTGCAAGGCCTAGGGCATTATT

TGAAGGCAGAAGGAAAAGTGGAGTGCTACCGAACCCTGCATCCTGTTCCTTTGTATTCATCTAGTGTGAACCGTGCCT

TTTCAAGCCCCAAGGTCGCAGTGGAAGCCTGTAACGCCATGTTGAAAGAGAACTTTCCGACTGTGGCTTCTTACTGTA

TTATTCCAGAGTACGATGCCTATTTGGACATGGTTGACGGAGCTTCATGCTGCTTAGACACTGCCAGTTTTTGCCCTG

CAAAGCTGCGCAGCTTTCCAAAGAAACACTCCTATTTGGAACCCACAATACGATCGGCAGTGCCTTCAGCGATCCAGA

ACACGCTCCAGAACGTCCTGGCAGCTGCCACAAAAAGAAATTGCAATGTCACGCAAATGAGAGAATTGCCCGTATTGG

ATTCGGCGGCCTTTAATGTGGAATGCTTCAAGAAATATGCGTGTAATAATGAATATTGGGAAACGTTTAAAGAAAACC

CCATCAGGCTTACTGAAGAAAACGTGGTAAATTACATTACCAAATTAAAAGGACCAAAAGCTGCTGCTCTTTTTGCGA

AGACACATAATTTGAATATGTTGCAGGACATACCAATGGACAGGTTTGTAATGGACTTAAAGAGAGACGTGAAAGTGA

CTCCAGGAACAAAACATACTGAAGAACGGCCCAAGGTACAGGTGATCCAGGCTGCCGATCCGCTAGCAACAGCGTATC

TGTGCGGAATCCACCGAGAGCTGGTTAGGAGATTAAATGCGGTCCTGCTTCCGAACATTCATACACTGTTTGATATGT

CGGCTGAAGACTTTGACGCTATTATAGCCGAGCACTTCCAGCCTGGGGATTGTGTTCTGGAAACTGACATCGCGTCGT

TTGATAAAAGTGAGGACGACGCCATGGCTCTGACCGCGTTAATGATTCTGGAAGACTTAGGTGTGGACGCAGAGCTGT

TGACGCTGATTGAGGCGGCTTTCGGCGAAATTTCATCAATACATTTGCCCACTAAAACTAAATTTAAATTCGGAGCCA

TGATGAAATCTGGAATGTTCCTCACACTGTTTGTGAACACAGTCATTAACATTGTAATCGCAAGCAGAGTGTTGAGAG

-continued

AACGGCTAACCGGATCACCATGTGCAGCATTCATTGGAGATGACAATATCGTGAAAGGAGTCAAATCGGACAAATTAA

TGGCAGACAGGTGCGCCACCTGGTTGAATATGGAAGTCAAGATTATAGATGCTGTGGTGGGCGAGAAAGCGCCTTATT

TCTGTGGAGGGTTTATTTTGTGTGACTCCGTGACCGGCACAGCGTGCCGTGTGGCAGACCCCCTAAAAAGGCTGTTTA

AGCTTGGCAAACCTCTGGCAGCAGACGATGAACATGATGATGACAGGAGAAGGGCATTGCATGAAGAGTCAACACGCT

GGAACCGAGTGGGTATTCTTTCAGAGCTGTGCAAGGCAGTAGAATCAAGGTATGAAACCGTAGGAACTTCCATCATAG

TTATGGCCATGACTACTCTAGCTAGCAGTGTTAAATCATTCAGCTACCTGAGAGGGGCCCCTATAACTCTCTACGGCT

AACCTGAATGGACTACGACATAGTCTAGTCCGCCAAGTCTAGCATATGGCCACCATGTTCGTGTTTCTGGTGCTGCTG

CCTCTGGTGTCCAGCCAGTGTGTGAACCTGACCACCAGAACACAGCTGCCTCCAGCCTACACCAACAGCTTTACCAGA

GGCGTGTACTACCCCGACAAGGTGTTCAGATCCAGCGTGCTGCACTCTACCCAGGACCTGTTCCTGCCTTTCTTCAGC

AACGTGACCTGGTTCCACGCCATCTCCGGCACCAATGGCACCAAGAGATTCGACAACCCCGTGCTGCCCTTCAACGAC

GGGGTGTACTTTGCCAGCACCGAGAAGTCCAACATCATCAGAGGCTGGATCTTCGGCACCACACTGGACAGCAAGACC

CAGAGCCTGCTGATCGTGAACAACGCCACCAACGTGGTCATCAAAGTGTGCGAGTTCCAGTTCTGCAACGACCCCTTC

CTGGGCGTCTACCACAAGAACAACAAGAGCTGGATGGAAAGCGAGTTCCGGGTGTACAGCAGCGCCAACAACTGCACC

TTCGAGTACGTGTCCCAGCCTTTCCTGATGGACCTGGAAGGCAAGCAGGGCAACTTCAAGAACCTGCGCGAGTTCGTG

TTCAAGAACATCGACGGCTACTTCAAGATCTACAGCAAGCACACCCCTATCAACCTCGTGCGGGATCTGCCTCAGGGC

TTCTCTGCTCTGGAACCCCTGGTGGATCTGCCCATCGGCATCAACATCACCCGGTTTCAGACACTGCTGGCCCTGCAC

AGAAGCTACCTGACACCTGGCGATAGCAGCAGCGGATGGACAGCTGGTGCCGCCGCTTACTATGTGGGCTACCTGCAG

CCTAGAACCTTCCTGCTGAAGTACAACGAGAACGGCACCATCACCGACGCCGTGGATTGTGCCCTTGATCCTCTGAGC

GAGACAAAGTGCACCCTGAAGTCCTTCACCGTGGAAAAGGGCATCTACCAGACCAGCAACTTCCGGGTGCAGCCCACC

GAATCCATCGTGCGGTTCCCCAATATCACCAATCTGTGCCCCTTCGGCGAGGTGTTCAATGCCACCAGATTCGCCTCT

GTGTACGCCTGGAACCGGAAGCGGATCAGCAATTGCGTGGCCGACTACTCCGTGCTGTACAACTCCGCCAGCTTCAGC

ACCTTCAAGTGCTACGGCGTGTCCCCTACCAAGCTGAACGACCTGTGCTTCACAAACGTGTACGCCGACAGCTTCGTG

ATCCGGGGAGATGAAGTGCGGCAGATTGCCCCTGGACAGACAGGCAAGATCGCCGACTACAACTACAAGCTGCCCGAC

GACTTCACCGGCTGTGTGATTGCCTGGAACAGCAACAACCTGGACTCCAAAGTCGGCGGCAACTACAATTACCTGTAC

CGGCTGTTCCGGAAGTCCAATCTGAAGCCCTTCGAGCGGGACATCTCCACCGAGATCTATCAGGCCGGCAGCACCCCT

TGTAACGGCGTGAAAGGCTTCAACTGCTACTTCCCACTGCAGTCCTACGGCTTTCAGCCCACATATGGCGTGGGCTAT

CAGCCCTACAGAGTGGTGGTGCTGAGCTTCGAACTGCTGCATGCCCCTGCCACAGTGTGCGGCCCTAAGAAAAGCACC

AATCTCGTGAAGAACAAATGCGTGAACTTCAACTTCAACGGCCTGACCGGCACAGGCGTGCTGACAGAGAGCAACAAG

AAGTTCCTGCCATTCCAGCAGTTTGGCCGGGATATCGACGATACCACAGACGCCGTTAGAGATCCCCAGACACTGGAA

ATCCTGGACATCACCCCTTGCAGCTTCGGCGGAGTGTCTGTGATCACCCCTGGCACCAACACCAGCAATCAGGTGGCA

GTGCTGTACCAGGGCGTGAACTGTACCGAAGTGCCCGTGGCCATTCACGCCGATCAGCTGACACCTACATGGCGGGTG

TACTCCACCGGCAGCAATGTGTTTCAGACCAGAGCCGGCTGTCTGATCGGAGCCGAGCACGTGAACAATAGCTACGAG

TGCGACATCCCCATCGGCGCTGGCATCTGTGCCAGCTACCAGACACAGACAAACAGCCACTCTCTGGCCAGCTCTGTG

GCCAGCCAGAGCATCATTGCCTACACAATGTCTCTGGGCGCCGAGAACAGCGTGGCCTACTCCAACAACTCTATCGCT

ATCCCCATCAACTTCACCATCAGCGTGACCACAGAGATCCTGCCTGTGTCCATGACCAAGACCAGCGTGGACTGCACC

ATGTACATCTGCGGCGATTCCACCGAGTGCTCCAACCTGCTGCTGCAGTACGGCAGCTTCTGCACCCAGCTGAATAGA

GCCCTGACAGGGATCGCCGTGGAACAGGACAAGAACACCCAAGAGGTGTTCGCCCAAGTGAAGCAGATCTACAAGACC

CCTCCTATCAAGGACTTCGGCGGCTTCAATTTCAGCCAGATTCTGCCCGATCCTAGCAAGCCCAGCAAGCGGAGCCCC

ATCGAGGACCTGCTGTTCAACAAAGTGACACTGGCCGACGCCGGCTTCATCAAGCAGTATGGCGATTGTCTGGGCGAC

ATTGCCGCCAGGGATCTGATTTGCGCCCAGAAGTTTAACGGACTGACAGTGCTGCCTCCTCTGCTGACCGATGAGATG

-continued

ATCGCCCAGTACACATCTGCCCTGCTGGCCGGCACAATCACAAGCGGCTGGACATTTGGAGCTGGCCCCGCTCTGCAG

ATCCCCTTTCCTATGCAGATGGCCTACAGATTCAACGGCATCGGAGTGACCCAGAATGTGCTGTACGAGAACCAGAAG

CTGATCGCCAACCAGTTCAACAGCGCCATCGGCAAGATCCAGGACAGCCTGAGCAGCACACCAAGCGCCCTGGGAAAG

CTGCAGGACGTGGTCAACCAGAATGCCCAGGCACTGAACACCCTGGTCAAGCAGCTGTCCTCCAACTTCGGCGCCATC

AGCTCTGTGCTGAACGATATCCTGGCCAGACTGGACCCTCCTGAGGCCGAGGTGCAGATCGACAGACTGATCACAGGC

AGACTGCAGAGCCTCCAGACATACGTGACCCAGCAGCTGATCAGAGCCGCCGAGATTAGAGCCTCTGCCAATCTGGCC

GCCACCAAGATGTCTGAGTGTGTGCTGGGCCAGAGCAAGAGAGTGGACTTTTGCGGCAAGGGCTACCACCTGATGAGC

TTCCCTCAGTCTGCCCCTCACGGCGTGGTGTTTCTGCACGTGACATACGTTCCCGCTCAAGAGAAGAATTTCACCACC

GCTCCAGCCATCTGCCACGACGGCAAAGCCCACTTTCCTAGAGAAGGCGTGTTCGTGTCCAACGGCACCCATTGGTTC

GTGACACAGCGGAACTTCTACGAGCCCCAGATCATCACCACCCACAACACCTTCGTGTCTGGCAACTGCGACGTCGTG

ATCGGCATTGTGAACAATACCGTGTACGACCCTCTGCAGCCCGAGCTGGACAGCTTCAAAGAGGAACTGGACAAGTAC

TTTAAGAACCACACAAGCCCCGACGTGGACCTGGGCGATATCAGCGGAATCAATGCCAGCGTCGTGAACATCCAGAAA

GAGATCGACCGGCTGAACGAGGTGGCCAAGAATCTGAACGAGAGCCTGATCGACCTGCAAGAACTGGGGAAGTACGAG

CAGTACATCAAGTGGCCCTGGTACATCTGGCTGGGCTTTATCGCCGGACTGATTGCCATCGTGATGGTCACAATCATG

CTGTGTTGCATGACCAGCTGCTGTAGCTGCCTGAAGGGCTGTTGTAGCTGTGGCAGCTGCTGCAAGTTCGACGAGGAC

GATTCTGAGCCCGTGCTGAAGGGCGTGAAACTGCACTACACATGAGCGGCCGCGAATTGGCAAGCTGCTTACATAGAA

CTCGCGGCGATTGGCATGCCGCCTTAAAATTTTTATTTTATTTTTCTTTTCTTTTCCGAATCGGATTTTGTTTTTAAT

ATTTCAAAAAAAAAAAAAAAAAAAAAAAAAAAAAAAAAAACGCGTCGAGGGGAATTAATTCTTGAAGACGAAAGGGCC

AGGTGGCACTTTTCGGGGAAATGTGCGCGGAACCCCTATTTGTTTATTTTTCTAAATACATTCAAATATGTATCCGCT

CATGAGACAATAACCCTGATAAATGCTTCAATAATATTGAAAAAGGAAGAGTATGAGTATTCAACATTTCCGTGTCGC

CCTTATTCCCTTTTTTGCGGCATTTTGCCTTCCTGTTTTTGCTCACCCAGAAACGCTGGTGAAAGTAAAAGATGCTGA

AGATCAGTTGGGTGCACGAGTGGGTTACATCGAACTGGATCTCAACAGCGGTAAGATCCTTGAGAGTTTTCGCCCCGA

AGAACGTTTTCCAATGATGAGCACTTTTAAAGTTCTGCTATGTGGCGCGGTATTATCCCGTGTTGACGCCGGGCAAGA

GCAACTCGGTCGCCGCATACACTATTCTCAGAATGACTTGGTTGAGTACTCACCAGTCACAGAAAAGCATCTTACGGA

TGGCATGACAGTAAGAGAATTATGCAGTGCTGCCATAACCATGAGTGATAACACTGCGGCCAACTTACTTCTGACAAC

GATCGGAGGACCGAAGGAGCTAACCGCTTTTTTGCACAACATGGGGGATCATGTAACTCGCCTTGATCGTTGGGAACC

GGAGCTGAATGAAGCCATACCAAACGACGAGCGTGACACCACGATGCCTGTAGCAATGGCAACAACGTTGCGCAAACT

ATTAACTGGCGAACTACTTACTCTAGCTTCCCGGCAACAATTAATAGACTGGATGGAGGCGGATAAAGTTGCAGGACC

ACTTCTGCGCTCGGCCCTTCCGGCTGGCTGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCTACACGACGGGGAGTCAGGCAACTATGGA

TGAACGAAATAGACAGATCGCTGAGATAGGTGCCTCACTGATTAAGCATTGGTAACTGTCAGACCAAGTTTACTCATA

TATACTTTAGATTGATTTAAAACTTCATTTTTAATTTAAAAGGATCTAGGTGAAGATCCTTTTTGATAATCTCATGAC

CAAAATCCCTTAACGTGAGTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGTTTGTTTGCCGGATCAAGA

GCTACCAACTCTTTTTCCGAAGGTAACTGGCTTCAGCAGAGCGCAGATACCAAATACTGTCCTTCTAGTGTAGCCGTA

GTTAGGCCACCACTTCAAGAACTCTGTAGCACCGCCTACATACCTCGCTCTGCTAATCCTGTTACCAGTGGCTGCTGC

CAGTGGCGATAAGTCGTGTCTTACCGGGTTGGACTCAAGACGATAGTTACCGGATAAGGCGCAGCGGTCGGGCTGAAC

GGGGGGTTCGTGCACACAGCCCAGCTTGGAGCGAACGACCTACACCGAACTGAGATACCTACAGCGTGAGCATTGAGA

AAGCGCCACGCTTCCCGAAGGGAGAAAGGCGGACAGGTATCCGGTAAGCGGCAGGGTCGGAACAGGAGAGCGCACGAG

GGAGCTTCCAGGGGGAAACGCCTGGTATCTTTATAGTCCTGTCGGGTTTCGCCACCTCTGACTTGAGCGTCGATTTTT

GTGATGCTCGTCAGGGGGGCGGAGCCTATGGAAAAACGCCATTCTAGAATGGCGCGCCCTTAAGGGGAGAATAGGAGC

-continued

```
CGCAACACACAAGCAACGCGAGGTCGTTTAAACTAATACGACTCACTATAATGGGCGGCGCATGAGAGAAGCCCAGAC
CAATTACCTACCCAAAATGGAGAAAGTTCACGTTGACATCGAGGAAGACAGCCCATTCCTCAGAGCTTTGCAGCGGAG
CTTCCCGCAGTTTGAGGTAGAAGCCAAGCAGGTCACTGATAATGACCATGCTAATGCCAGAGCGTTTTCGCATCTGGC
TTCAAAACTGATCGAAACGGAGGTGGACCCATCCGACACGATCCTTGACATTGGAAGTGCGCCCGCCCGCAGAATGTA
TTCTAAGCACAAGTATCATTGTATCTGTCCGATGAGATGTGCGGAAGATCCGGACAGATTGTATAAGTATGCAACTAA
GCTGAAGAAAAACTGTAAGGAAATAACTGATAAGGAATTGGACAAGAAAATGAAGGAGCTGGCCGCCGTCATGAGCGA
CCCTGACCTGGAAACTGAGACTATGTGCCTCCACGACGACGAGTCGTGTCGCTACGAAGGGCAAGTCGCTGTTTACCA
GGATGTATACGCGGTTGACGGACCGACAAGTCTCTATCACCAAGCCAATAAGGGAGTTAGAGTCGCCTACTGGATAGG
CTTTGACACCACCCCTTTTATGTTTAAGAACTTGGCTGGAGCATATCCATCATACTCTACCAACTGGGCCGACGAAAC
CGTGTTAACGGCTCGTAACATAGGCCTATGCAGCTCTGACGTTATGGAGCGGTCACGTAGAGGGATGTCCATTCTTAG
AAAGAAGTATTTGAAACCATCCAACAATGTTCTATTCTCTGTTGGCTCGACCATCTACCACGAGAAGAGGGACTTACT
GAGGAGCTGGCACCTGCCGTCTGTATTTCACTTACGTGGCAAGCAAAATTACACATGTCGGTGTGAGACTATAGTTAG
TTGCGACGGGTACGTCGTTAAAAGAATAGCTATCAGTCCAGGCCTGTATGGGAAGCCTTCAGGCTATGCTGCTACGAT
GCACCGCGAGGGATTCTTGTGCTGCAAAGTGACAGACACATTGAACGGGGAGAGGGTCTCTTTTCCCGTGTGCACGTA
TGTGCCAGCTACATTGTGTGACCAAATGACTGGCATACTGGCAACAGATGTCAGTGCGGACGACGCGCAAAAACTGCT
GGTTGGGCTCAACCAGCGTATAGTCGTCAACGGTCGCACCCAGAGAAACACCAATACCATGAAAAATTACCTTTTGCC
CGTAGTGGCCCAGGCATTTGCTAGGTGGGCAAAGGAATATAAGGAAGATCAAGAAGATGAAAGGCCACTAGGACTACG
AGATAGACAGTTAGTCATGGGGTGTTGTTGGGCTTTTAGAAGGCACAAGATAACATCTATTTATAAGCGCCCGGATAC
CCAAACCATCATCAAAGTGAACAGCGATTTCCACTCATTCGTGCTGCCCAGGATAGGCAGTAACACATTGGAGATCGG
GCTGAGAACAAGAATCAGGAAAATGTTAGAGGAGCACAAGGAGCCGTCACCTCTCATTACCGCCGAGGACGTACAAGA
AGCTAAGTGCGCAGCCGATGAGGCTAAGGAGGTGCGTGAAGCCGAGGAGTTGCGCGCAGCTCTACCACCTTTGGCAGC
TGATGTTGAGGAGCCCACTCTGGAGGCAGACGTCGACTTGATGTTACAAGAGGCTGGGGCCGGCTCAGTGGAGACACC
TCGTGGCTTGATAAAGGTTACCAGCTACGATGGCGAGGACAAGATCGGCTCTTACGCTGTGCTTTCTCCGCAGGCTGT
ACTCAAGAGTGAAAAATTATCTTGCATCCACCCTCTCGCTGAACAAGTCATAGTGATAACACACTCTGGCCGAAAAGG
GCGTTATGCCGTGGAACCATACCATGGTAAAGTAGTGGTGCCAGAGGGACATGCAATACCCGTCCAGGACTTTCAAGC
TCTGAGTGAAAGTGCCACCATTGTGTACAACGAACGTGAGTTCGTAAACAGGTACCTGCACCATATTGCCACACATGG
AGGAGCGCTGAACACTGATGAAGAATATTACAAAACTGTCAAGCCCAGCGAGCACGACGGCGAATACCTGTACGACAT
CGACAGGAAACAGTGCGTCAAGAAAGAACTAGTCACTGGGCTAGGGCTCACAGGCGAGCTGGTGGATCCTCCCTTCCA
TGAATTCGCCTACGAGAGTCTGAGAACACGACCAGCCGCTCCTTACCAAGTACCAACCATAGGGGTGTATGGCGTGCC
AGGATCAGGCAAGTCTGGCATCATTAAAAGCGCAGTCACCAAAAAAGATCTAGTGGTGAGCGCCAAGAAAGAAAACTG
TGCAGAAATTATAAGGGACGTCAAGAAAATGAAAGGGCTGGACGTCAATGCCAGAACTGTGGACTCAGTGCTCTTGAA
TGGATGCAAACACCCCGTAGAGACCCTGTATATTGACGAAGCTTTTGCTTGTCATGCAGGTACTCTCAGAGCGCTCAT
AGCCATTATAAGACCTAAAAAGGCAGTGCTCTGCGGGGATCCCAAACAGTGCGGTTTTTTAACATGATGTGCCTGAA
AGTGCATTTTAACCACGAGATTTGCACACAAGTCTTCCACAAAAGCATCTCTCGCCGTTGCACTAAATCTGTGACTTC
GGTCGTCTCAACCTTGTTTTACGACAAAAAAATGAGAACGACGAATCCGAAAGAGACTAAGATTGTGATTGACACTAC
CGGCAGTACCAAACCTAAGCAGGACGATCTCATTCTCACTTGTTTCAGAGGGTGGGTGAAGCAGTTGCAAATAGATTA
CAAAGGCAACGAAATAATGACGGCAGCTGCCTCTCAAGGGCTGACCCGTAAAGGTGTGTATGCCGTTCGGTACAAGGT
GAATGAAA
```

Accordingly, preferably the vector comprises the nucleotide sequence substantially as set out in SEQ ID NO: 73, or a variant or fragment thereof.

In one embodiment (the B.1.351 South African variant of SARS-CoV-2 glycoprotein), the vector may comprise the nucleic acid sequence of SEQ ID No: 74, as follows:

[SEQ ID No: 74]
ATCCTCTGTACGCACCCACCTCAGAACATGTGAACGTCCTACTGACCCGCACGGAGGACCGCATCGTGTGGAAAACAC

TAGCCGGCGACCCATGGATAAAAACACTGACTGCCAAGTACCCTGGGAATTTCACTGCCACGATAGAGGAGTGGCAAG

CAGAGCATGATGCCATCATGAGGCACATCTTGGAGAGACCGGACCCTACCGACGTCTTCCAGAATAAGGCAAACGTGT

GTTGGGCCAAGGCTTTAGTGCCGGTGCTGAAGACCGCTGGCATAGACATGACCACTGAACAATGGAACACTGTGGATT

ATTTTGAAACGGACAAAGCTCACTCAGCAGAGATAGTATTGAACCAACTATGCGTGAGGTTCTTTGGACTCGATCTGG

ACTCCGGTCTATTTTCTGCACCCACTGTTCCGTTATCCATTAGGAATAATCACTGGGATAACTCCCCGTCGCCTAACA

TGTACGGGCTGAATAAAGAAGTGGTCCGTCAGCTCTCTCGCAGGTACCCACAACTGCCTCGGGCAGTTGCCACTGGAA

GAGTCTATGACATGAACACTGGTACACTGCGCAATTATGATCCGCGCATAAACCTAGTACCTGTAAACAGAAGACTGC

CTCATGCTTTAGTCCTCCACCATAATGAACACCCACAGAGTGACTTTTCTTCATTCGTCAGCAAATTGAAGGGCAGAA

CTGTCCTGGTGGTCGGGGAAAAGTTGTCCGTCCCAGGCAAAATGGTTGACTGGTTGTCAGACCGGCCTGAGGCTACCT

TCAGAGCTCGGCTGGATTTAGGCATCCCAGGTGATGTGCCCAAATATGACATAATATTTGTTAATGTGAGGACCCCAT

ATAAATACCATCACTATCAGCAGTGTGAAGACCATGCCATTAAGCTTAGCATGTTGACCAAGAAAGCTTGTCTGCATC

TGAATCCCGGCGGAACCTGTGTCAGCATAGGTTATGGTTACGCTGACAGGGCCAGCGAAAGCATCATTGGTGCTATAG

CGCGGCAGTTCAAGTTTTCCCGGGTATGCAAACCGAAATCCTCACTTGAAGAGACGGAAGTTCTGTTTGTATTCATTG

GGTACGATCGCAAGGCCCGTACGCACAATTCTTACAAGCTTTCATCAACCTTGACCAACATTTATACAGGTTCCAGAC

TCCACGAAGCCGGATGTGCACCCTCATATCATGTGGTGCGAGGGGATATTGCCACGGCCACCGAAGGAGTGATTATAA

ATGCTGCTAACAGCAAAGGACAACCTGGCGGAGGGGTGTGCGGAGCGCTGTATAAGAAATTCCCGGAAAGCTTCGATT

TACAGCCGATCGAAGTAGGAAAAGCGCGACTGGTCAAAGGTGCAGCTAAACATATCATTCATGCCGTAGGACCAAACT

TCAACAAAGTTTCGGAGGTTGAAGGTGACAAACAGTTGGCAGAGGCTTATGAGTCCATCGCTAAGATTGTCAACGATA

ACAATTACAAGTCAGTAGCGATTCCACTGTTGTCCACCGGCATCTTTTCCGGGAACAAAGATCGACTAACCCAATCAT

TGAACCATTIGCTGACAGCTTTAGACACCACTGATGCAGATGTAGCCATATACTGCAGGGACAAGAAATGGGAAATGA

CTCTCAAGGAAGCAGTGGCTAGGAGAGAAGCAGTGGAGGAGATATGCATATCCGACGACTCTTCAGTGACAGAACCTG

ATGCAGAGCTGGTGAGGGTGCATCCGAAGAGTTCTTTGGCTGGAAGGAAGGGCTACAGCACAAGCGATGGCAAAACTT

TCTCATATTTGGAAGGGACCAAGTTTCACCAGGCGGCCAAGGATATAGCAGAAATTAATGCCATGTGGCCCGTTGCAA

CGGAGGCCAATGAGCAGGTATGCATGTATATCCTCGGAGAAAGCATGAGCAGTATTAGGTCGAAATGCCCCGTCGAAG

AGTCGGAAGCCTCCACACCACCTAGCACGCTGCCTTGCTTGTGCATCCATGCCATGACTCCAGAAAGAGTACAGCGCC

TAAAAGCCTCACGTCCAGAACAAATTACTGTGTGCTCATCCTTTCCATTGCCGAAGTATAGAATCACTGGTGTGCAGA

AGATCCAATGCTCCCAGCCTATATTGTTCTCACCGAAAGTGCCTGCGTATATTCATCCAAGGAAGTATCTCGTGGAAA

CACCACCGGTAGACGAGACTCCGGAGCCATCGGCAGAGAACCAATCCACAGAGGGGACACCTGAACAACCACCACTTA

TAACCGAGGATGAGACCAGGACTAGAACGCCTGAGCCGATCATCATCGAAGAGGAAGAAGAGGATAGCATAAGTTTGC

TGTCAGATGGCCCGACCCACCAGGTGCTGCAAGTCGAGGCAGACATTCACGGGCCGCCCTCTGTATCTAGCTCATCCT

GGTCCATTCCTCATGCATCCGACTTTGATGTGGACAGTTTATCCATACTTGACACCCTGGAGGGAGCTAGCGTGACCA

GCGGGGCAACGTCAGCCGAGACTAACTCTTACTTCGCAAAGAGTATGGAGTTTCTGGCGCGACCGGTGCCTGCGCCTC

GAACAGTATTCAGGAACCCTCCACATCCCGCTCCGCGCACAAGAACACCGTCACTTGCACCCAGCAGGGCCTGCTCGA

GAACCAGCCTAGTTTCCACCCCGCCAGGCGTGAATAGGGTGATCACTAGAGAGGAGCTCGAGGCGCTTACCCCGTCAC

GCACTCCTAGCAGGTCGGTCTCGAGAACCAGCCTGGTCTCCAACCCGCCAGGCGTAAATAGGGTGATTACAAGAGAGG

AGTTTGAGGCGTTCGTAGCACAACAACAATGACGGTTTGATGCGGGTGCATACATCTTTTCCTCCGACACCGGTCAAG

GGCATTTACAACAAAAATCAGTAAGGCAAACGGTGCTATCCGAAGTGGTGTTGGAGAGGACCGAATTGGAGATTTCGT

ATGCCCCGCGCCTCGACCAAGAAAAAGAAGAATTACTACGCAAGAAATTACAGTTAAATCCCACACCTGCTAACAGAA

GCAGATACCAGTCCAGGAAGGTGGAGAACATGAAAGCCATAACAGCTAGACGTATTCTGCAAGGCCTAGGGCATTATT

-continued

TGAAGGCAGAAGGAAAAGTGGAGTGCTACCGAACCCTGCATCCTGTTCCTTTGTATTCATCTAGTGTGAACCGTGCCT

TTTCAAGCCCCAAGGTCGCAGTGGAAGCCTGTAACGCCATGTTGAAAGAGAACTTTCCGACTGTGGCTTCTTACTGTA

TTATTCCAGAGTACGATGCCTATTTGGACATGGTTGACGGAGCTTCATGCTGCTTAGACACTGCCAGTTTTTGCCCTG

CAAAGCTGCGCAGCTTTCCAAAGAAACACTCCTATTTGGAACCCACAATACGATCGGCAGTGCCTTCAGCGATCCAGA

ACACGCTCCAGAACGTCCTGGCAGCTGCCACAAAAAGAAATTGCAATGTCACGCAAATGAGAGAATTGCCCGTATTGG

ATTCGGCGGCCTTTAATGTGGAATGCTTCAAGAAATATGCGTGTAATAATGAATATTGGGAAACGTTTAAAGAAAACC

CCATCAGGCTTACTGAAGAAAACGTGGTAAATTACATTACCAAATTAAAAGGACCAAAAGCTGCTGCTCTTTTTGCGA

AGACACATAATTTGAATATGTTGCAGGACATACCAATGGACAGGTTTGTAATGGACTTAAAGAGAGACGTGAAAGTGA

CTCCAGGAACAAAACATACTGAAGAACGGCCCAAGGTACAGGTGATCCAGGCTGCCGATCCGCTAGCAACAGCGTATC

TGTGCGGAATCCACCGAGAGCTGGTTAGGAGATTAAATGCGGTCCTGCTTCCGAACATTCATACACTGTTTGATATGT

CGGCTGAAGACTTTGACGCTATTATAGCCGAGCACTTCCAGCCTGGGGATTGTGTTCTGGAAACTGACATCGCGTCGT

TTGATAAAAGTGAGGACGACGCCATGGCTCTGACCGCGTTAATGATTCTGGAAGACTTAGGTGTGGACGCAGAGCTGT

TGACGCTGATTGAGGCGGCTTTCGGCGAAATTTCATCAATACATTTGCCCACTAAAACTAAATTTAAATTCGGAGCCA

TGATGAAATCTGGAATGTTCCTCACACTGTTTGTGAACACAGTCATTAACATTGTAATCGCAAGCAGAGTGTTGAGAG

AACGGCTAACCGGATCACCATGTGCAGCATTCATTGGAGATGACAATATCGTGAAAGGAGTCAAATCGGACAAATTAA

TGGCAGACAGGTGCGCCACCTGGTTGAATATGGAAGTCAAGATTATAGATGCTGTGGTGGGCGAGAAAGCGCCTTATT

TCTGTGGAGGGTTTATTTTGTGTGACTCCGTGACCGGCACAGCGTGCCGTGTGGCAGACCCCCTAAAAAGGCTGTTTA

AGCTTGGCAAACCTCTGGCAGCAGACGATGAACATGATGATGACAGGAGAAGGGCATTGCATGAAGAGTCAACACGCT

GGAACCGAGTGGGTATTCTTTCAGAGCTGTGCAAGGCAGTAGAATCAAGGTATGAAACCGTAGGAACTTCCATCATAG

TTATGGCCATGACTACTCTAGCTAGCAGTGTTAAATCATTCAGCTACCTGAGAGGGGCCCCTATAACTCTCTACGGCT

AACCTGAATGGACTACGACATAGTCTAGTCCGCCAAGTCTAGCATATGGCCACCATGTTCGTGTTTCTGGTGCTGCTG

CCTCTGGTGTCCAGCCAGTGTGTGAACTTCACCACCAGAACACAGCTGCCTCCAGCCTACACCAACAGCTTTACCAGA

GGCGTGTACTACCCCGACAAGGTGTTCAGATCCAGCGTGCTGCACTCTACCCAGGACCTGTTCCTGCCTTTCTTCAGC

AACGTGACCTGGTTCCACGCCATCCACGTGTCCGGCACCAATGGCACCAAGAGATTCGCCAACCCCGTGCTGCCCTTC

AACGACGGGGTGTACTTTGCCAGCACCGAGAAGTCCAACATCATCAGAGGCTGGATCTTCGGCACCACACTGGACAGC

AAGACCCAGAGCCTGCTGATCGTGAACAACGCCACCAACGTGGTCATCAAAGTGTGCGAGTTCCAGTTCTGCAACGAC

CCCTTCCTGGGCGTCTACTACCACAAGAACAACAAGAGCTGGATGGAAAGCGAGTTCCGGGTGTACAGCAGCGCCAAC

AACTGCACCTTCGAGTACGTGTCCCAGCCTTTCCTGATGGACCTGGAAGGCAAGCAGGGCAACTTCAAGAACCTGCGC

GAGTTCGTGTTCAAGAACATCGACGGCTACTTCAAGATCTACAGCAAGCACACCCCTATCAACCTCGTGCGGGGTCTG

CCTCAGGGCTTCTCTGCTCTGGAACCCCTGGTGGATCTGCCCATCGGCATCAACATCACCCGGTTTCAGACACTGCAC

ATAAGCTACCTGACACCTGGCGATAGCAGCAGCGGATGGACAGCTGGTGCCGCCGCTTACTATGTGGGCTACCTGCAG

CCTAGAACCTTCCTGCTGAAGTACAACGAGAACGGCACCATCACCGACGCCGTGGATTGTGCCCTTGATCCTCTGAGC

GAGACAAAGTGCACCCTGAAGTCCTTCACCGTGGAAAAGGGCATCTACCAGACCAGCAACTTCCGGGTGCAGCCCACC

GAATCCATCGTGCGGTTCCCCAATATCACCAATCTGTGCCCCTTCGGCGAGGTGTTCAATGCCACCAGATTCGCCTCT

GTGTACGCCTGGAACCGGAAGCGGATCAGCAATTGCGTGGCCGACTACTCCGTGCTGTACAACTCCGCCAGCTTCAGC

ACCTTCAAGTGCTACGGCGTGTCCCCTACCAAGCTGAACGACCTGTGCTTCACAAACGTGTACGCCGACAGCTTCGTG

ATCCGGGGAGATGAAGTGCGGCAGATTGCCCCTGGACAGACAGGCAATATCGCCGACTACAACTACAAGCTGCCCGAC

GACTTCACCGGCTGTGTGATTGCCTGGAACAGCAACAACCTGGACTCCAAAGTCGGCGGCAACTACAATTACCTGTAC

CGGCTGTTCCGGAAGTCCAATCTGAAGCCCTTCGAGCGGGACATCTCCACCGAGATCTATCAGGCCGGCAGCACCCCT

TGTAACGGCGTGAAAGGCTTCAACTGCTACTTCCCACTGCAGTCCTACGGCTTTCAGCCCACATATGGCGTGGGCTAT

CAGCCCTACAGAGTGGTGGTGCTGAGCTTCGAACTGCTGCATGCCCCTGCCACAGTGTGCGGCCCTAAGAAAAGCACC

-continued

AATCTCGTGAAGAACAAATGCGTGAACTTCAACTTCAACGGCCTGACCGGCACAGGCGTGCTGACAGAGAGCAACAAG

AAGTTCCTGCCATTCCAGCAGTTTGGCCGGGATATCGCCGATACCACAGACGCCGTTAGAGATCCCCAGACACTGGAA

ATCCTGGACATCACCCCTTGCAGCTTCGGCGGAGTGTCTGTGATCACCCCTGGCACCAACACCAGCAATCAGGTGGCA

GTGCTGTACCAGGACGTGAACTGTACCGAAGTGCCCGTGGCCATTCACGCCGATCAGCTGACACCTACATGGCGGGTG

TACTCCACCGGCAGCAATGTGTTTCAGACCAGAGCCGGCTGTCTGATCGGAGCCGAGCACGTGAACAATAGCTACGAG

TGCGACATCCCCATCGGCGCTGGCATCTGTGCCAGCTACCAGACACAGACAAACAGCCCCTCTCTGGCCAGCTCTGTG

GCCAGCCAGAGCATCATTGCCTACACAATGTCTCTGGGCGTCGAGAACAGCGTGGCCTACTCCAACAACTCTATCGCT

ATCCCCACCAACTTCACCATCAGCGTGACCACAGAGATCCTGCCTGTGTCCATGACCAAGACCAGCGTGGACTGCACC

ATGTACATCTGCGGCGATTCCACCGAGTGCTCCAACCTGCTGCTGCAGTACGGCAGCTTCTGCACCCAGCTGAATAGA

GCCCTGACAGGGATCGCCGTGGAACAGGACAAGAACACCCAAGAGGTGTTCGCCCAAGTGAAGCAGATCTACAAGACC

CCTCCTATCAAGGACTTCGGCGGCTTCAATTTCAGCCAGATTCTGCCCGATCCTAGCAAGCCCAGCAAGCGGAGCCCC

ATCGAGGACCTGCTGTTCAACAAAGTGACACTGGCCGACGCCGGCTTCATCAAGCAGTATGGCGATTGTCTGGGCGAC

ATTGCCGCCAGGGATCTGATTTGCGCCCAGAAGTTTAACGGACTGACAGTGCTGCCTCCTCTGCTGACCGATGAGATG

ATCGCCCAGTACACATCTGCCCTGCTGGCCGGCACAATCACAAGCGGCTGGACATTTGGAGCTGGCCCCGCTCTGCAG

ATCCCCTTTCCTATGCAGATGGCCTACAGATTCAACGGCATCGGAGTGACCCAGAATGTGCTGTACGAGAACCAGAAG

CTGATCGCCAACCAGTTCAACAGCGCCATCGGCAAGATCCAGGACAGCCTGAGCAGCACACCAAGCGCCCTGGGAAAG

CTGCAGGACGTGGTCAACCAGAATGCCCAGGCACTGAACACCCTGGTCAAGCAGCTGTCCTCCAACTTCGGCGCCATC

AGCTCTGTGCTGAACGATATCCTGAGCAGACTGGACCCTCCTGAGGCCGAGGTGCAGATCGACAGACTGATCACAGGC

AGACTGCAGAGCCTCCAGACATACGTGACCCAGCAGCTGATCAGAGCCGCCGAGATTAGAGCCTCTGCCAATCTGGCC

GCCACCAAGATGTCTGAGTGTGTGCTGGGCCAGAGCAAGAGAGTGGACTTTTGCGGCAAGGGCTACCACCTGATGAGC

TTCCCTCAGTCTGCCCCTCACGGCGTGGTGTTTCTGCACGTGACATACGTTCCCGCTCAAGAGAAGAATTTCACCACC

GCTCCAGCCATCTGCCACGACGGCAAAGCCCACTTTCCTAGAGAAGGCGTGTTCGTGTCCAACGGCACCCATTGGTTC

GTGACACAGCGGAACTTCTACGAGCCCCAGATCATCACCACCGACAACACCTTCGTGTCTGGCAACTGCGACGTCGTG

ATCGGCATTGTGAACAATACCGTGTACGACCCTCTGCAGCCCGAGCTGGACAGCTTCAAAGAGGAACTGGACAAGTAC

TTTAAGAACCACACAAGCCCCGACGTGGACCTGGGCGATATCAGCGGAATCAATGCCAGCGTCGTGAACATCCAGAAA

GAGATCGACCGGCTGAACGAGGTGGCCAAGAATCTGAACGAGAGCCTGATCGACCTGCAAGAACTGGGGAAGTACGAG

CAGTACATCAAGTGGCCCTGGTACATCTGGCTGGGCTTTATCGCCGGACTGATTGCCATCGTGATGGTCACAATCATG

CTGTGTTGCATGACCAGCTGCTGTAGCTGCCTGAAGGGCTGTTGTAGCTGTGGCAGCTGCTGCAAGTTCGACGAGGAC

GATTCTGAGCCCGTGCTGAAGGGCGTGAAACTGCACTACACATGAGCGGCCGCGAATTGGCAAGCTGCTTACATAGAA

CTCGCGGCGATTGGCATGCCGCCTTAAAATTTTTATTTTATTTTTCTTTTCTTTTCCGAATCGGATTTTGTTTTTAAT

ATTTCAAAAAAAAAAAAAAAAAAAAAAAAAAAAAAAAAAAACGCGTCGAGGGGAATTAATTCTTGAAGACGAAAGGGCC

AGGTGGCACTTTTCGGGGAAATGTGCGCGGAACCCCTATTTGTTTATTTTTCTAAATACATTCAAATATGTATCCGCT

CATGAGACAATAACCCTGATAAATGCTTCAATAATATTGAAAAAGGAAGAGTATGAGTATTCAACATTTCCGTGTCGC

CCTTATTCCCTTTTTTGCGGCATTTTGCCTTCCTGTTTTTGCTCACCCAGAAACGCTGGTGAAAGTAAAAGATGCTGA

AGATCAGTTGGGTGCACGAGTGGGTTACATCGAACTGGATCTCAACAGCGGTAAGATCCTTGAGAGTTTTCGCCCCGA

AGAACGTTTTCCAATGATGAGCACTTTTAAAGTTCTGCTATGTGGCGCGGTATTATCCCGTGTTGACGCCGGGCAAGA

GCAACTCGGTCGCCGCATACACTATTCTCAGAATGACTTGGTTGAGTACTCACCAGTCACAGAAAAGCATCTTACGGA

TGGCATGACAGTAAGAGAATTATGCAGTGCTGCCATAACCATGAGTGATAACACTGCGGCCAACTTACTTCTGACAAC

GATCGGAGGACCGAAGGAGCTAACCGCTTTTTTGCACAACATGGGGGATCATGTAACTCGCCTTGATCGTTGGGAACC

GGAGCTGAATGAAGCCATACCAAACGACGAGCGTGACACCACGATGCCTGTAGCAATGGCAACAACGTTGCGCAAACT

-continued

ATTAACTGGCGAACTACTTACTCTAGCTTCCCGGCAACAATTAATAGACTGGATGGAGGCGGATAAAGTTGCAGGACC

ACTTCTGCGCTCGGCCCTTCCGGCTGGCTGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCTACACGACGGGGAGTCAGGCAACTATGGA

TGAACGAAATAGACAGATCGCTGAGATAGGTGCCTCACTGATTAAGCATTGGTAACTGTCAGACCAAGTTTACTCATA

TATACTTTAGATTGATTTAAAACTTCATTTTTAATTTAAAAGGATCTAGGTGAAGATCCTTTTTGATAATCTCATGAC

CAAAATCCCTTAACGTGAGTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGTTTGTTTGCCGGATCAAGA

GCTACCAACTCTTTTTCCGAAGGTAACTGGCTTCAGCAGAGCGCAGATACCAAATACTGTCCTTCTAGTGTAGCCGTA

GTTAGGCCACCACTTCAAGAACTCTGTAGCACCGCCTACATACCTCGCTCTGCTAATCCTGTTACCAGTGGCTGCTGC

CAGTGGCGATAAGTCGTGTCTTACCGGGTTGGACTCAAGACGATAGTTACCGGATAAGGCGCAGCGGTCGGGCTGAAC

GGGGGGTTCGTGCACACAGCCCAGCTTGGAGCGAACGACCTACACCGAACTGAGATACCTACAGCGTGAGCATTGAGA

AAGCGCCACGCTTCCCGAAGGGAGAAAGGCGGACAGGTATCCGGTAAGCGGCAGGGTCGGAACAGGAGAGCGCACGAG

GGAGCTTCCAGGGGGAAACGCCTGGTATCTTTATAGTCCTGTCGGGTTTCGCCACCTCTGACTTGAGCGTCGATTTTT

GTGATGCTCGTCAGGGGGGCGGAGCCTATGGAAAAACGCCATTCTAGAATGGCGCGCCCTTAAGGGGAGAATAGGAGC

CGCAACACACAAGCAACGCGAGGTCGTTTAAACTAATACGACTCACTATAATGGGCGGCGCATGAGAGAAGCCCAGAC

CAATTACCTACCCAAAATGGAGAAAGTTCACGTTGACATCGAGGAAGACAGCCCATTCCTCAGAGCTTTGCAGCGGAG

CTTCCCGCAGTTTGAGGTAGAAGCCAAGCAGGTCACTGATAATGACCATGCTAATGCCAGAGCGTTTTCGCATCTGGC

TTCAAAACTGATCGAAACGGAGGTGGACCCATCCGACACGATCCTTGACATTGGAAGTGCGCCCGCCCGCAGAATGTA

TTCTAAGCACAAGTATCATTGTATCTGTCCGATGAGATGTGCGGAAGATCCGGACAGATTGTATAAGTATGCAACTAA

GCTGAAGAAAAACTGTAAGGAAATAACTGATAAGGAATTGGACAAGAAAATGAAGGAGCTGGCCGCCGTCATGAGCGA

CCCTGACCTGGAAACTGAGACTATGTGCCTCCACGACGACGAGTCGTGTCGCTACGAAGGGCAAGTCGCTGTTTACCA

GGATGTATACGCGGTTGACGGACCGACAAGTCTCTATCACCAAGCCAATAAGGGAGTTAGAGTCGCCTACTGGATAGG

CTTTGACACCACCCCTTTTATGTTTAAGAACTTGGCTGGAGCATATCCATCATACTCTACCAACTGGGCCGACGAAAC

CGTGTTAACGGCTCGTAACATAGGCCTATGCAGCTCTGACGTTATGGAGCGGTCACGTAGAGGGATGTCCATTCTTAG

AAAGAAGTATTTGAAACCATCCAACAATGTTCTATTCTCTGTTGGCTCGACCATCTACCACGAGAAGAGGGACTTACT

GAGGAGCTGGCACCTGCCGTCTGTATTTCACTTACGTGGCAAGCAAAATTACACATGTCGGTGTGAGACTATAGTTAG

TTGCGACGGGTACGTCGTTAAAAGAATAGCTATCAGTCCAGGCCTGTATGGGAAGCCTTCAGGCTATGCTGCTACGAT

GCACCGCGAGGGATTCTTGTGCTGCAAAGTGACAGACACATTGAACGGGGAGAGGGTCTCTTTTCCCGTGTGCACGTA

TGTGCCAGCTACATTGTGTGACCAAATGACTGGCATACTGGCAACAGATGTCAGTGCGGACGACGCGCAAAAACTGCT

GGTTGGGCTCAACCAGCGTATAGTCGTCAACGGTCGCACCCAGAGAAACACCAATACCATGAAAAATTACCTTTTGCC

CGTAGTGGCCCAGGCATTTGCTAGGTGGGCAAAGGAATATAAGGAAGATCAAGAAGATGAAAGGCCACTAGGACTACG

AGATAGACAGTTAGTCATGGGGTGTTGTTGGGCTTTTAGAAGGCACAAGATAACATCTATTTATAAGCGCCCGGATAC

CCAAACCATCATCAAAGTGAACAGCGATTTCCACTCATTCGTGCTGCCCAGGATAGGCAGTAACACATTGGAGATCGG

GCTGAGAACAAGAATCAGGAAAATGTTAGAGGAGCACAAGGAGCCGTCACCTCTCATTACCGCCGAGGACGTACAAGA

AGCTAAGTGCGCAGCCGATGAGGCTAAGGAGGTGCGTGAAGCCGAGGAGTTGCGCGCAGCTCTACCACCTTTGGCAGC

TGATGTTGAGGAGCCCACTCTGGAGGCAGACGTCGACTTGATGTTACAAGAGGCTGGGGCCGGCTCAGTGGAGACACC

TCGTGGCTTGATAAAGGTTACCAGCTACGATGGCGAGGACAAGATCGGCTCTTACGCTGTGCTTTCTCCGCAGGCTGT

ACTCAAGAGTGAAAAATTATCTTGCATCCACCCTCTCGCTGAACAAGTCATAGTGATAACACACTCTGGCCGAAAAGG

GCGTTATGCCGTGGAACCATACCATGGTAAAGTAGTGGTGCCAGAGGGACATGCAATACCCGTCCAGGACTTTCAAGC

TCTGAGTGAAAGTGCCACCATTGTGTACAACGAACGTGAGTTCGTAAACAGGTACCTGCACCATATTGCCACACATGG

AGGAGCGCTGAACACTGATGAAGAATATTACAAAACTGTCAAGCCCAGCGAGCACGACGGCGAATACCTGTACGACAT

-continued

```
CGACAGGAAACAGTGCGTCAAGAAAGAACTAGTCACTGGGCTAGGGCTCACAGGCGAGCTGGTGGATCCTCCCTTCCA

TGAATTCGCCTACGAGAGTCTGAGAACACGACCAGCCGCTCCTTACCAAGTACCAACCATAGGGGTGTATGGCGTGCC

AGGATCAGGCAAGTCTGGCATCATTAAAAGCGCAGTCACCAAAAAAGATCTAGTGGTGAGCGCCAAGAAAGAAAACTG

TGCAGAAATTATAAGGGACGTCAAGAAAATGAAAGGGCTGGACGTCAATGCCAGAACTGTGGACTCAGTGCTCTTGAA

TGGATGCAAACACCCCGTAGAGACCCTGTATATTGACGAAGCTTTTGCTTGTCATGCAGGTACTCTCAGAGCGCTCAT

AGCCATTATAAGACCTAAAAAGGCAGTGCTCTGCGGGGATCCCAAACAGTGCGGTTTTTTTAACATGATGTGCCTGAA

AGTGCATTTTAACCACGAGATTTGCACACAAGTCTTCCACAAAAGCATCTCTCGCCGTTGCACTAAATCTGTGACTTC

GGTCGTCTCAACCTTGTTTTACGACAAAAAAATGAGAACGACGAATCCGAAAGAGACTAAGATTGTGATTGACACTAC

CGGCAGTACCAAACCTAAGCAGGACGATCTCATTCTCACTTGTTTCAGAGGGTGGGTGAAGCAGTTGCAAATAGATTA

CAAAGGCAACGAAATAATGACGGCAGCTGCCTCTCAAGGGCTGACCCGTAAAGGTGTGTATGCCGTTCGGTACAAGGT

GAATGAAA
```

20

Accordingly, preferably the vector comprises the nucleotide sequence substantially as set out in SEQ ID NO: 74, or a variant or fragment thereof.

In one embodiment (the B.1.1.28 (P.1) Brazilian variant of SARS-CoV-2 glycoprotein), the vector may comprise the nucleic acid sequence of SEQ ID No: 75, as follows:

[SEQ ID No: 75]

```
ATCCTCTGTACGCACCCACCTCAGAACATGTGAACGTCCTACTGACCCGCACGGAGGACCGCATCGTGTGGAAAACAC

TAGCCGGCGACCCATGGATAAAAACACTGACTGCCAAGTACCCTGGGAATTTCACTGCCACGATAGAGGAGTGGCAAG

CAGAGCATGATGCCATCATGAGGCACATCTTGGAGAGACCGGACCCTACCGACGTCTTCCAGAATAAGGCAAACGTGT

GTTGGGCCAAGGCTTTAGTGCCGGTGCTGAAGACCGCTGGCATAGACATGACCACTGAACAATGGAACACTGTGGATT

ATTTTGAAACGGACAAAGCTCACTCAGCAGAGATAGTATTGAACCAACTATGCGTGAGGTTCTTTGGACTCGATCTGG

ACTCCGGTCTATTTTCTGCACCCACTGTTCCGTTATCCATTAGGAATAATCACTGGGATAACTCCCCGTCGCCTAACA

TGTACGGGCTGAATAAAGAAGTGGTCCGTCAGCTCTCTCGCAGGTACCCACAACTGCCTCGGGCAGTTGCCACTGGAA

GAGTCTATGACATGAACACTGGTACACTGCGCAATTATGATCCGCGCATAAACCTAGTACCTGTAAACAGAAGACTGC

CTCATGCTTTAGTCCTCCACCATAATGAACACCCACAGAGTGACTTTTCTTCATTCGTCAGCAAATTGAAGGGCAGAA

CTGTCCTGGTGGTCGGGGAAAAGTTGTCCGTCCCAGGCAAAATGGTTGACTGGTTGTCAGACCGGCCTGAGGCTACCT

TCAGAGCTCGGCTGGATTTAGGCATCCCAGGTGATGTGCCCAAATATGACATAATATTTGTTAATGTGAGGACCCCAT

ATAAATACCATCACTATCAGCAGTGTGAAGACCATGCCATTAAGCTTAGCATGTTGACCAAGAAAGCTTGTCTGCATC

TGAATCCCGGCGGAACCTGTGTCAGCATAGGTTATGGTTACGCTGACAGGGCCAGCGAAAGCATCATTGGTGCTATAG

CGCGGCAGTTCAAGTTTTCCCGGGTATGCAAACCGAAATCCTCACTTGAAGAGACGGAAGTTCTGTTTGTATTCATTG

GGTACGATCGCAAGGCCCGTACGCACAATTCTTACAAGCTTTCATCAACCTTGACCAACATTTATACAGGTTCCAGAC

TCCACGAAGCCGGATGTGCACCCTCATATCATGTGGTGCGAGGGGATATTGCCACGGCCACCGAAGGAGTGATTATAA

ATGCTGCTAACAGCAAAGGACAACCTGGCGGAGGGGTGTGCGGAGCGCTGTATAAGAAATTCCCGGAAAGCTTCGATT

TACAGCCGATCGAAGTAGGAAAAGCGCGACTGGTCAAAGGTGCAGCTAAACATATCATTCATGCCGTAGGACCAAACT

TCAACAAAGTTTCGGAGGTTGAAGGTGACAAACAGTTGGCAGAGGCTTATGAGTCCATCGCTAAGATTGTCAACGATA

ACAATTACAAGTCAGTAGCGATTCCACTGTTGTCCACCGGCATCTTTTCCGGGAACAAAGATCGACTAACCCAATCAT

TGAACCATTTGCTGACAGCTTTAGACACCACTGATGCAGATGTAGCCATATACTGCAGGGACAAGAAATGGGAAATGA

CTCTCAAGGAAGCAGTGGCTAGGAGAGAAGCAGTGGAGGAGATATGCATATCCGACGACTCTTCAGTGACAGAACCTG

ATGCAGAGCTGGTGAGGGTGCATCCGAAGAGTTCTTTGGCTGGAAGGAAGGGCTACAGCACAAGCGATGGCAAAACTT

TCTCATATTTGGAAGGGACCAAGTTTCACCAGGCGGCCAAGGATATAGCAGAAATTAATGCCATGTGGCCCGTTGCAA

CGGAGGCCAATGAGCAGGTATGCATGTATATCCTCGGAGAAAGCATGAGCAGTATTAGGTCGAAATGCCCCGTCGAAG
```

-continued

AGTCGGAAGCCTCCACACCACCTAGCACGCTGCCTTGCTTGTGCATCCATGCCATGACTCCAGAAAGAGTACAGCGCC

TAAAAGCCTCACGTCCAGAACAAATTACTGTGTGCTCATCCTTTCCATTGCCGAAGTATAGAATCACTGGTGTGCAGA

AGATCCAATGCTCCCAGCCTATATTGTTCTCACCGAAAGTGCCTGCGTATATTCATCCAAGGAAGTATCTCGTGGAAA

CACCACCGGTAGACGAGACTCCGGAGCCATCGGCAGAGAACCAATCCACAGAGGGGACACCTGAACAACCACCACTTA

TAACCGAGGATGAGACCAGGACTAGAACGCCTGAGCCGATCATCATCGAAGAGGAAGAAGAGGATAGCATAAGTTTGC

TGTCAGATGGCCCGACCCACCAGGTGCTGCAAGTCGAGGCAGACATTCACGGGCCGCCCTCTGTATCTAGCTCATCCT

GGTCCATTCCTCATGCATCCGACTTTGATGTGGACAGTTTATCCATACTTGACACCCTGGAGGGAGCTAGCGTGACCA

GCGGGGCAACGTCAGCCGAGACTAACTCTTACTTCGCAAAGAGTATGGAGTTTCTGGCGCGACCGGTGCCTGCGCCTC

GAACAGTATTCAGGAACCCTCCACATCCCGCTCCGCGCACAAGAACACCGTCACTTGCACCCAGCAGGGCCTGCTCGA

GAACCAGCCTAGTTTCCACCCCGCCAGGCGTGAATAGGGTGATCACTAGAGAGGAGCTCGAGGCGCTTACCCCGTCAC

GCACTCCTAGCAGGTCGGTCTCGAGAACCAGCCTGGTCTCCAACCCGCCAGGCGTAAATAGGGTGATTACAAGAGAGG

AGTTTGAGGCGTTCGTAGCACAACAACAATGACGGTTTGATGCGGGTGCATACATCTTTTCCTCCGACACCGGTCAAG

GGCATTTACAACAAAAATCAGTAAGGCAAACGGTGCTATCCGAAGTGGTGTTGGAGAGGACCGAATTGGAGATTTCGT

ATGCCCCGCGCCTCGACCAAGAAAAAGAAGAATTACTACGCAAGAAATTACAGTTAAATCCCACACCTGCTAACAGAA

GCAGATACCAGTCCAGGAAGGTGGAGAACATGAAAGCCATAACAGCTAGACGTATTCTGCAAGGCCTAGGGCATTATT

TGAAGGCAGAAGGAAAAGTGGAGTGCTACCGAACCCTGCATCCTGTTCCTTTGTATTCATCTAGTGTGAACCGTGCCT

TTTCAAGCCCCAAGGTCGCAGTGGAAGCCTGTAACGCCATGTTGAAAGAGAACTTTCCGACTGTGGCTTCTTACTGTA

TTATTCCAGAGTACGATGCCTATTTGGACATGGTTGACGGAGCTTCATGCTGCTTAGACACTGCCAGTTTTTGCCCTG

CAAAGCTGCGCAGCTTTCCAAAGAAACACTCCTATTTGGAACCCACAATACGATCGGCAGTGCCTTCAGCGATCCAGA

ACACGCTCCAGAACGTCCTGGCAGCTGCCACAAAAAGAAATTGCAATGTCACGCAAATGAGAGAATTGCCCGTATTGG

ATTCGGCGGCCTTTAATGTGGAATGCTTCAAGAAATATGCGTGTAATAATGAATATTGGGAAACGTTTAAAGAAAACC

CCATCAGGCTTACTGAAGAAAACGTGGTAAATTACATTACCAAATTAAAAGGACCAAAAGCTGCTGCTCTTTTTGCGA

AGACACATAATTTGAATATGTTGCAGGACATACCAATGGACAGGTTTGTAATGGACTTAAAGAGAGACGTGAAAGTGA

CTCCAGGAACAAAACATACTGAAGAACGGCCCAAGGTACAGGTGATCCAGGCTGCCGATCCGCTAGCAACAGCGTATC

TGTGCGGAATCCACCGAGAGCTGGTTAGGAGATTAAATGCGGTCCTGCTTCCGAACATTCATACACTGTTTGATATGT

CGGCTGAAGACTTTGACGCTATTATAGCCGAGCACTTCCAGCCTGGGGATTGTGTTCTGGAAACTGACATCGCGTCGT

TTGATAAAAGTGAGGACGACGCCATGGCTCTGACCGCGTTAATGATTCTGGAAGACTTAGGTGTGGACGCAGAGCTGT

TGACGCTGATTGAGGCGGCTTTCGGCGAAATTTCATCAATACATTTGCCCACTAAAACTAAATTTAAATTCGGAGCCA

TGATGAAATCTGGAATGTTCCTCACACTGTTTGTGAACACAGTCATTAACATTGTAATCGCAAGCAGAGTGTTGAGAG

AACGGCTAACCGGATCACCATGTGCAGCATTCATTGGAGATGACAATATCGTGAAAGGAGTCAAATCGGACAAATTAA

TGGCAGACAGGTGCGCCACCTGGTTGAATATGGAAGTCAAGATTATAGATGCTGTGGTGGGCGAGAAAGCGCCTTATT

TCTGTGGAGGGTTTATTTTGTGTGACTCCGTGACCGGCACAGCGTGCCGTGTGGCAGACCCCCTAAAAAGGCTGTTTA

AGCTTGGCAAACCTCTGGCAGCAGACGATGAACATGATGATGACAGGAGAAGGGCATTGCATGAAGAGTCAACACGCT

GGAACCGAGTGGGTATTCTTTCAGAGCTGTGCAAGGCAGTAGAATCAAGGTATGAAACCGTAGGAACTTCCATCATAG

TTATGGCCATGACTACTCTAGCTAGCAGTGTTAAATCATTCAGCTACCTGAGAGGGGCCCCTATAACTCTCTACGGCT

AACCTGAATGGACTACGACATAGTCTAGTCCGCCAAGTCTAGCATATGGCCACCATGTTCGTGTTTCTGGTGCTGCTG

CCTCTGGTGTCCAGCCAGTGTGTGAACTTCACCAACAGAACACAGCTGCCTTTCGCCTACACCAACAGCTTTACCAGA

GGCGTGTACTACCCCGACAAGGTGTTCAGATCCAGCGTGCTGCACTCTACCCAGGACCTGTTCCTGCCTTTCTTCAGC

AACGTGACCTGGTTCCACGCCATCCACGTGTCCGGCACCAATGGCACCAAGAGATTCGACAACCCCGTGCTGCCCTTC

AACGACGGGGTGTACTTTGCCAGCACCGAGAAGTCCAACATCATCAGAGGCTGGATCTTCGGCACCACACTGGACAGC

AAGACCCAGAGCCTGCTGATCGTGAACAACGCCACCAACGTGGTCATCAAAGTGTGCGAGTTCCAGTTCTGCAACTAC

-continued

CCCTTCCTGGGCGTCTACTACCACAAGAACAACAAGAGCTGGATGGAAAGCGAGTTCCGGGTGTACAGCAGCGCCAAC
AACTGCACCTTCGAGTACGTGTCCCAGCCTTTCCTGATGGACCTGGAAGGCAAGCAGGGCAACTTCAAGAACCTGAGC
GAGTTCGTGTTCAAGAACATCGACGGCTACTTCAAGATCTACAGCAAGCACACCCCTATCAACCTCGTGCGGGATCTG
CCTCAGGGCTTCTCTGCTCTGGAACCCCTGGTGGATCTGCCCATCGGCATCAACATCACCCGGTTTCAGACACTGCTG
GCCCTGCACAGAAGCTACCTGACACCTGGCGATAGCAGCAGCGGATGGACAGCTGGTGCCGCCGCTTACTATGTGGGC
TACCTGCAGCCTAGAACCTTCCTGCTGAAGTACAACGAGAACGGCACCATCACCGACGCCGTGGATTGTGCCCTTGAT
CCTCTGAGCGAGACAAAGTGCACCCTGAAGTCCTTCACCGTGGAAAAGGGCATCTACCAGACCAGCAACTTCCGGGTG
CAGCCCACCGAATCCATCGTGCGGTTCCCCAATATCACCAATCTGTGCCCCTTCGGCGAGGTGTTCAATGCCACCAGA
TTCGCCTCTGTGTACGCCTGGAACCGGAAGCGGATCAGCAATTGCGTGGCCGACTACTCCGTGCTGTACAACTCCGCC
AGCTTCAGCACCTTCAAGTGCTACGGCGTGTCCCCTACCAAGCTGAACGACCTGTGCTTCACAAACGTGTACGCCGAC
AGCTTCGTGATCCGGGGAGATGAAGTGCGGCAGATTGCCCCTGGACAGACAGGCACGATCGCCGACTACAACTACAAG
CTGCCCGACGACTTCACCGGCTGTGTGATTGCCTGGAACAGCAACAACCTGGACTCCAAAGTCGGCGGCAACTACAAT
TACCTGTACCGGCTGTTCCGGAAGTCCAATCTGAAGCCCTTCGAGCGGGACATCTCCACCGAGATCTATCAGGCCGGC
AGCACCCCTTGTAACGGCGTGAAAGGCTTCAACTGCTACTTCCCACTGCAGTCCTACGGCTTTCAGCCCACATATGGC
GTGGGCTATCAGCCCTACAGAGTGGTGGTGCTGAGCTTCGAACTGCTGCATGCCCCTGCCACAGTGTGCGGCCCTAAG
AAAAGCACCAATCTCGTGAAGAACAAATGCGTGAACTTCAACTTCAACGGCCTGACCGGCACAGGCGTGCTGACAGAG
AGCAACAAGAAGTTCCTGCCATTCCAGCAGTTTGGCCGGGATATCGCCGATACCACAGACGCCGTTAGAGATCCCCAG
ACACTGGAAATCCTGGACATCACCCCTTGCAGCTTCGGCGGAGTGTCTGTGATCACCCCTGGCACCAACACCAGCAAT
CAGGTGGCAGTGCTGTACCAGGGCGTGAACTGTACCGAAGTGCCCGTGGCCATTCACGCCGATCAGCTGACACCTACA
TGGCGGGTGTACTCCACCGGCAGCAATGTGTTTCAGACCAGAGCCGGCTGTCTGATCGGAGCCGAGTACGTGAACAAT
AGCTACGAGTGCGACATCCCCATCGGCGCTGGCATCTGTGCCAGCTACCAGACACAGACAAACAGCCCCTCTCTGGCC
AGCTCTGTGGCCAGCCAGAGCATCATTGCCTACACAATGTCTCTGGGCGCCGAGAACAGCGTGGCCTACTCCAACAAC
TCTATCGCTATCCCCACCAACTTCACCATCAGCGTGACCACAGAGATCCTGCCTGTGTCCATGACCAAGACCAGCGTG
GACTGCACCATGTACATCTGCGGCGATTCCACCGAGTGCTCCAACCTGCTGCTGCAGTACGGCAGCTTCTGCACCCAG
CTGAATAGAGCCCTGACAGGGATCGCCGTGGAACAGGACAAGAACACCCAAGAGGTGTTCGCCCAAGTGAAGCAGATC
TACAAGACCCCTCCTATCAAGGACTTCGGCGGCTTCAATTTCAGCCAGATTCTGCCCGATCCTAGCAAGCCCAGCAAG
CGGAGCCCCATCGAGGACCTGCTGTTCAACAAAGTGACACTGGCCGACGCCGGCTTCATCAAGCAGTATGGCGATTGT
CTGGGCGACATTGCCGCCAGGGATCTGATTTGCGCCCAGAAGTTTAACGGACTGACAGTGCTGCCTCCTCTGCTGACC
GATGAGATGATCGCCCAGTACACATCTGCCCTGCTGGCCGGCACAATCACAAGCGGCTGGACATTTGGAGCTGGCCCC
GCTCTGCAGATCCCCTTTCCTATGCAGATGGCCTACAGATTCAACGGCATCGGAGTGACCCAGAATGTGCTGTACGAG
AACCAGAAGCTGATCGCCAACCAGTTCAACAGCGCCATCGGCAAGATCCAGGACAGCCTGAGCAGCACACCAAGCGCC
CTGGGAAAGCTGCAGGACGTGGTCAACCAGAATGCCCAGGCACTGAACACCCTGGTCAAGCAGCTGTCCTCCAACTTC
GGCGCCATCAGCTCTGTGCTGAACGATATCCTGAGCAGACTGGACCCTCCTGAGGCCGAGGTGCAGATCGACAGACTG
ATCACAGGCAGACTGCAGAGCCTCCAGACATACGTGACCCAGCAGCTGATCAGAGCCGCCGAGATTAGAGCCTCTGCC
AATCTGGCCGCCATCAAGATGTCTGAGTGTGTGCTGGGCCAGAGCAAGAGAGTGGACTTTTGCGGCAAGGGCTACCAC
CTGATGAGCTTCCCTCAGTCTGCCCCTCACGGCGTGGTGTTTCTGCACGTGACATACGTTCCCGCTCAAGAGAAGAAT
TTCACCACCGCTCCAGCCATCTGCCACGACGGCAAAGCCCACTTTCCTAGAGAAGGCGTGTTCGTGTCCAACGGCACC
CATTGGTTCGTGACACAGCGGAACTTCTACGAGCCCCAGATCATCACCACCGACAACACCTTCGTGTCTGGCAACTGC
GACGTCGTGATCGGCATTGTGAACAATACCGTGTACGACCCTCTGCAGCCCGAGCTGGACAGCTTCAAAGAGGAACTG
GACAAGTACTTTAAGAACCACACAAGCCCCGACGTGGACCTGGGCGATATCAGCGGAATCAATGCCAGCTTCGTGAAC

-continued

ATCCAGAAAGAGATCGACCGGCTGAACGAGGTGGCCAAGAATCTGAACGAGAGCCTGATCGACCTGCAAGAACTGGGG

AAGTACGAGCAGTACATCAAGTGGCCCTGGTACATCTGGCTGGGCTTTATCGCCGGACTGATTGCCATCGTGATGGTC

ACAATCATGCTGTGTTGCATGACCAGCTGCTGTAGCTGCCTGAAGGGCTGTTGTAGCTGTGGCAGCTGCTGCAAGTTC

GACGAGGACGATTCTGAGCCCGTGCTGAAGGGCGTGAAACTGCACTACACATGAGCGGCCGCGAATTGGCAAGCTGCT

TACATAGAACTCGCGGCGATTGGCATGCCGCCTTAAAATTTTTATTTTATTTTTCTTTTCTTTTCCGAATCGGATTTT

GTTTTTAATATTTCAAAAAAAAAAAAAAAAAAAAAAAAAAAAAAAAAAAACGCGTCGAGGGGAATTAATTCTTGAAGAC

GAAAGGGCCAGGTGGCACTTTTCGGGGAAATGTGCGCGGAACCCCTATTTGTTTATTTTTCTAAATACATTCAAATAT

GTATCCGCTCATGAGACAATAACCCTGATAAATGCTTCAATAATATTGAAAAAGGAAGAGTATGAGTATTCAACATTT

CCGTGTCGCCCTTATTCCCTTTTTTGCGGCATTTTGCCTTCCTGTTTTTGCTCACCCAGAAACGCTGGTGAAAGTAAA

AGATGCTGAAGATCAGTTGGGTGCACGAGTGGGTTACATCGAACTGGATCTCAACAGCGGTAAGATCCTTGAGAGTTT

TCGCCCCGAAGAACGTTTTCCAATGATGAGCACTTTTAAAGTTCTGCTATGTGGCGCGGTATTATCCCGTGTTGACGC

CGGGCAAGAGCAACTCGGTCGCCGCATACACTATTCTCAGAATGACTTGGTTGAGTACTCACCAGTCACAGAAAAGCA

TCTTACGGATGGCATGACAGTAAGAGAATTATGCAGTGCTGCCATAACCATGAGTGATAACACTGCGGCCAACTTACT

TCTGACAACGATCGGAGGACCGAAGGAGCTAACCGCTTTTTTGCACAACATGGGGGATCATGTAACTCGCCTTGATCG

TTGGGAACCGGAGCTGAATGAAGCCATACCAAACGACGAGCGTGACACCACGATGCCTGTAGCAATGGCAACAACGTT

GCGCAAACTATTAACTGGCGAACTACTTACTCTAGCTTCCCGGCAACAATTAATAGACTGGATGGAGGCGGATAAAGT

TGCAGGACCACTTCTGCGCTCGGCCCTTCCGGCTGGCTGGTTTATTGCTGATAAATCTGGAGCCGGTGAGCGTGGGTC

TCGCGGTATCATTGCAGCACTGGGGCCAGATGGTAAGCCCTCCCGTATCGTAGTTATCTACACGACGGGGAGTCAGGC

AACTATGGATGAACGAAATAGACAGATCGCTGAGATAGGTGCCTCACTGATTAAGCATTGGTAACTGTCAGACCAAGT

TTACTCATATATACTTTAGATTGATTTAAAACTTCATTTTTAATTTAAAAGGATCTAGGTGAAGATCCTTTTTGATAA

TCTCATGACCAAAATCCCTTAACGTGAGTTTTCGTTCCACTGAGCGTCAGACCCCGTAGAAAAGATCAAAGGATCTTC

TTGAGATCCTTTTTTTCTGCGCGTAATCTGCTGCTTGCAAACAAAAAAACCACCGCTACCAGCGGTGGTTTGTTTGCC

GGATCAAGAGCTACCAACTCTTTTTCCGAAGGTAACTGGCTTCAGCAGAGCGCAGATACCAAATACTGTCCTTCTAGT

GTAGCCGTAGTTAGGCCACCACTTCAAGAACTCTGTAGCACCGCCTACATACCTCGCTCTGCTAATCCTGTTACCAGT

GGCTGCTGCCAGTGGCGATAAGTCGTGTCTTACCGGGTTGGACTCAAGACGATAGTTACCGGATAAGGCGCAGCGGTC

GGGCTGAACGGGGGGTTCGTGCACACAGCCCAGCTTGGAGCGAACGACCTACACCGAACTGAGATACCTACAGCGTGA

GCATTGAGAAAGCGCCACGCTTCCCGAAGGGAGAAAGGCGGACAGGTATCCGGTAAGCGGCAGGGTCGGAACAGGAGA

GCGCACGAGGGAGCTTCCAGGGGGAAACGCCTGGTATCTTTATAGTCCTGTCGGGTTTCGCCACCTCTGACTTGAGCG

TCGATTTTTGTGATGCTCGTCAGGGGGGCGGAGCCTATGGAAAAACGCCATTCTAGAATGGCGCGCCCTTAAGGGGAG

AATAGGAGCCGCAACACACAAGCAACGCGAGGTCGTTTAAACTAATACGACTCACTATAATGGGCGGCGCATGAGAGA

AGCCCAGACCAATTACCTACCCAAAATGGAGAAAGTTCACGTTGACATCGAGGAAGACAGCCCATTCCTCAGAGCTTT

GCAGCGGAGCTTCCCGCAGTTTGAGGTAGAAGCCAAGCAGGTCACTGATAATGACCATGCTAATGCCAGAGCGTTTTC

GCATCTGGCTTCAAAACTGATCGAAACGGAGGTGGACCCATCCGACACGATCCTTGACATTGGAAGTGCGCCCGCCCG

CAGAATGTATTCTAAGCACAAGTATCATTGTATCTGTCCGATGAGATGTGCGGAAGATCCGGACAGATTGTATAAGTA

TGCAACTAAGCTGAAGAAAAACTGTAAGGAAATAACTGATAAGGAATTGGACAAGAAAATGAAGGAGCTGGCCGCCGT

CATGAGCGACCCTGACCTGGAAACTGAGACTATGTGCCTCCACGACGACGAGTCGTGTCGCTACGAAGGGCAAGTCGC

TGTTTACCAGGATGTATACGCGGTTGACGGACCGACAAGTCTCTATCACCAAGCCAATAAGGGAGTTAGAGTCGCCTA

CTGGATAGGCTTTGACACCACCCCTTTTATGTTTAAGAACTTGGCTGGAGCATATCCATCATACTCTACCAACTGGGC

CGACGAAACCGTGTTAACGGCTCGTAACATAGGCCTATGCAGCTCTGACGTTATGGAGCGGTCACGTAGAGGGATGTC

CATTCTTAGAAAGAAGTATTTGAAACCATCCAACAATGTTCTATTCTCTGTTGGCTCGACCATCTACCACGAGAAGAG

GGACTTACTGAGGAGCTGGCACCTGCCGTCTGTATTTCACTTACGTGGCAAGCAAAATTACACATGTCGGTGTGAGAC

-continued

TATAGTTAGTTGCGACGGGTACGTCGTTAAAAGAATAGCTATCAGTCCAGGCCTGTATGGGAAGCCTTCAGGCTATGC

TGCTACGATGCACCGCGAGGGATTCTTGTGCTGCAAAGTGACAGACACATTGAACGGGGAGAGGGTCTCTTTTCCCGT

GTGCACGTATGTGCCAGCTACATTGTGTGACCAAATGACTGGCATACTGGCAACAGATGTCAGTGCGGACGACGCGCA

AAAACTGCTGGTTGGGCTCAACCAGCGTATAGTCGTCAACGGTCGCACCCAGAGAAACACCAATACCATGAAAAATTA

CCTTTTGCCCGTAGTGGCCCAGGCATTTGCTAGGTGGGCAAAGGAATATAAGGAAGATCAAGAAGATGAAAGGCCACT

AGGACTACGAGATAGACAGTTAGTCATGGGGTGTTGTTGGGCTTTTAGAAGGCACAAGATAACATCTATTTATAAGCG

CCCGGATACCCAAACCATCATCAAAGTGAACAGCGATTTCCACTCATTCGTGCTGCCCAGGATAGGCAGTAACACATT

GGAGATCGGGCTGAGAACAAGAATCAGGAAAATGTTAGAGGAGCACAAGGAGCCGTCACCTCTCATTACCGCCGAGGA

CGTACAAGAAGCTAAGTGCGCAGCCGATGAGGCTAAGGAGGTGCGTGAAGCCGAGGAGTTGCGCGCAGCTCTACCACC

TTTGGCAGCTGATGTTGAGGAGCCCACTCTGGAGGCAGACGTCGACTTGATGTTACAAGAGGCTGGGGCCGGCTCAGT

GGAGACACCTCGTGGCTTGATAAAGGTTACCAGCTACGATGGCGAGGACAAGATCGGCTCTTACGCTGTGCTTTCTCC

GCAGGCTGTACTCAAGAGTGAAAAATTATCTTGCATCCACCCTCTCGCTGAACAAGTCATAGTGATAACACACTCTGG

CCGAAAAGGGCGTTATGCCGTGGAACCATACCATGGTAAAGTAGTGGTGCCAGAGGGACATGCAATACCCGTCCAGGA

CTTTCAAGCTCTGAGTGAAAGTGCCACCATTGTGTACAACGAACGTGAGTTCGTAAACAGGTACCTGCACCATATTGC

CACACATGGAGGAGCGCTGAACACTGATGAAGAATATTACAAAACTGTCAAGCCCAGCGAGCACGACGGCGAATACCT

GTACGACATCGACAGGAAACAGTGCGTCAAGAAAGAACTAGTCACTGGGCTAGGGCTCACAGGCGAGCTGGTGGATCC

TCCCTTCCATGAATTCGCCTACGAGAGTCTGAGAACACGACCAGCCGCTCCTTACCAAGTACCAACCATAGGGGTGTA

TGGCGTGCCAGGATCAGGCAAGTCTGGCATCATTAAAAGCGCAGTCACCAAAAAAGATCTAGTGGTGAGCGCCAAGAA

AGAAAACTGTGCAGAAATTATAAGGGACGTCAAGAAAATGAAAGGGCTGGACGTCAATGCCAGAACTGTGGACTCAGT

GCTCTTGAATGGATGCAAACACCCCGTAGAGACCCTGTATATTGACGAAGCTTTTGCTTGTCATGCAGGTACTCTCAG

AGCGCTCATAGCCATTATAAGACCTAAAAAGGCAGTGCTCTGCGGGGATCCCAAACAGTGCGGTTTTTTAACATGAT

GTGCCTGAAAGTGCATTTTAACCACGAGATTTGCACACAAGTCTTCCACAAAAGCATCTCTCGCCGTTGCACTAAATC

TGTGACTTCGGTCGTCTCAACCTTGTTTTACGACAAAAAAATGAGAACGACGAATCCGAAAGAGACTAAGATTGTGAT

TGACACTACCGGCAGTACCAAACCTAAGCAGGACGATCTCATTCTCACTTGTTTCAGAGGGTGGGTGAAGCAGTTGCA

AATAGATTACAAAGGCAACGAAATAATGACGGCAGCTGCCTCTCAAGGGCTGACCCGTAAAGGTGTGTATGCCGTTCG

GTACAAGGTGAATGAAA

Accordingly, preferably the vector comprises the nucleotide sequence substantially as set out in SEQ ID NO: 75, or a variant or fragment thereof.

In one embodiment (the SARS-CoV-2 surface glycoprotein with ORF4a IIP), the vector may comprise the nucleic acid sequence of SEQ ID No: 76, as follows:

[SEQ ID No: 76]

ATCCTCTGTACGCACCCACCTCAGAACATGTGAACGTCCTACTGACCCGCACGGAGGACCGCATCGTGTGGAAAACAC

TAGCCGGCGACCCATGGATAAAAACACTGACTGCCAAGTACCCTGGGAATTTCACTGCCACGATAGAGGAGTGGCAAG

CAGAGCATGATGCCATCATGAGGCACATCTTGGAGAGACCGGACCCTACCGACGTCTTCCAGAATAAGGCAAACGTGT

GTTGGGCCAAGGCTTTAGTGCCGGTGCTGAAGACCGCTGGCATAGACATGACCACTGAACAATGGAACACTGTGGATT

ATTTTGAAACGGACAAAGCTCACTCAGCAGAGATAGTATTGAACCAACTATGCGTGAGGTTCTTTGGACTCGATCTGG

ACTCCGGTCTATTTTCTGCACCCACTGTTCCGTTATCCATTAGGAATAATCACTGGGATAACTCCCCGTCGCCTAACA

TGTACGGGCTGAATAAAGAAGTGGTCCGTCAGCTCTCTCGCAGGTACCCACAACTGCCTCGGGCAGTTGCCACTGGAA

GAGTCTATGACATGAACACTGGTACACTGCGCAATTATGATCCGCGCATAAACCTAGTACCTGTAAACAGAAGACTGC

CTCATGCTTTAGTCCTCCACCATAATGAACACCCACAGAGTGACTTTTCTTCATTCGTCAGCAAATTGAAGGGCAGAA

CTGTCCTGGTGGTCGGGGAAAAGTTGTCCGTCCCAGGCAAAATGGTTGACTGGTTGTCAGACCGGCCTGAGGCTACCT

-continued

TCAGAGCTCGGCTGGATTTAGGCATCCCAGGTGATGTGCCCAAATATGACATAATATTTGTTAATGTGAGGACCCCAT

ATAAATACCATCACTATCAGCAGTGTGAAGACCATGCCATTAAGCTTAGCATGTTGACCAAGAAAGCTTGTCTGCATC

TGAATCCCGGCGGAACCTGTGTCAGCATAGGTTATGGTTACGCTGACAGGGCCAGCGAAAGCATCATTGGTGCTATAG

CGCGGCAGTTCAAGTTTTCCCGGGTATGCAAACCGAAATCCTCACTTGAAGAGACGGAAGTTCTGTTTGTATTCATTG

GGTACGATCGCAAGGCCCGTACGCACAATTCTTACAAGCTTTCATCAACCTTGACCAACATTTATACAGGTTCCAGAC

TCCACGAAGCCGGATGTGCACCCTCATATCATGTGGTGCGAGGGGATATTGCCACGGCCACCGAAGGAGTGATTATAA

ATGCTGCTAACAGCAAAGGACAACCTGGCGGAGGGGTGTGCGGAGCGCTGTATAAGAAATTCCCGGAAAGCTTCGATT

TACAGCCGATCGAAGTAGGAAAAGCGCGACTGGTCAAAGGTGCAGCTAAACATATCATTCATGCCGTAGGACCAAACT

TCAACAAAGTTTCGGAGGTTGAAGGTGACAAACAGTTGGCAGAGGCTTATGAGTCCATCGCTAAGATTGTCAACGATA

ACAATTACAAGTCAGTAGCGATTCCACTGTTGTCCACCGGCATCTTTTCCGGGAACAAAGATCGACTAACCCAATCAT

TGAACCATTTGCTGACAGCTTTAGACACCACTGATGCAGATGTAGCCATATACTGCAGGGACAAGAAATGGGAAATGA

CTCTCAAGGAAGCAGTGGCTAGGAGAGAAGCAGTGGAGGAGATATGCATATCCGACGACTCTTCAGTGACAGAACCTG

ATGCAGAGCTGGTGAGGGTGCATCCGAAGAGTTCTTTGGCTGGAAGGAAGGGCTACAGCACAAGCGATGGCAAAACTT

TCTCATATTTGGAAGGGACCAAGTTTCACCAGGCGGCCAAGGATATAGCAGAAATTAATGCCATGTGGCCCGTTGCAA

CGGAGGCCAATGAGCAGGTATGCATGTATATCCTCGGAGAAAGCATGAGCAGTATTAGGTCGAAATGCCCCGTCGAAG

AGTCGGAAGCCTCCACACCACCTAGCACGCTGCCTTGCTTGTGCATCCATGCCATGACTCCAGAAAGAGTACAGCGCC

TAAAAGCCTCACGTCCAGAACAAATTACTGTGTGCTCATCCTTTCCATTGCCGAAGTATAGAATCACTGGTGTGCAGA

AGATCCAATGCTCCCAGCCTATATTGTTCTCACCGAAAGTGCCTGCGTATATTCATCCAAGGAAGTATCTCGTGGAAA

CACCACCGGTAGACGAGACTCCGGAGCCATCGGCAGAGAACCAATCCACAGAGGGGACACCTGAACAACCACCACTTA

TAACCGAGGATGAGACCAGGACTAGAACGCCTGAGCCGATCATCATCGAAGAGGAAGAAGAGGATAGCATAAGTTTGC

TGTCAGATGGCCCGACCCACCAGGTGCTGCAAGTCGAGGCAGACATTCACGGGCCGCCCTCTGTATCTAGCTCATCCT

GGTCCATTCCTCATGCATCCGACTTTGATGTGGACAGTTTATCCATACTTGACACCCTGGAGGGAGCTAGCGTGACCA

GCGGGGCAACGTCAGCCGAGACTAACTCTTACTTCGCAAAGAGTATGGAGTTTCTGGCGCGACCGGTGCCTGCGCCTC

GAACAGTATTCAGGAACCCTCCACATCCCGCTCCGCGCACAAGAACACCGTCACTTGCACCCAGCAGGGCCTGCTCGA

GAACCAGCCTAGTTTCCACCCCGCCAGGCGTGAATAGGGTGATCACTAGAGAGGAGCTCGAGGCGCTTACCCCGTCAC

GCACTCCTAGCAGGTCGGTCTCGAGAACCAGCCTGGTCTCCAACCCGCCAGGCGTAAATAGGGTGATTACAAGAGAGG

AGTTTGAGGCGTTCGTAGCACAACAACAATGACGGTTTGATGCGGGTGCATACATCTTTTCCTCCGACACCGGTCAAG

GGCATTTACAACAAAAATCAGTAAGGCAAACGGTGCTATCCGAAGTGGTGTTGGAGAGGACCGAATTGGAGATTTCGT

ATGCCCCGCGCCTCGACCAAGAAAAAGAAGAATTACTACGCAAGAAATTACAGTTAAATCCCACACCTGCTAACAGAA

GCAGATACCAGTCCAGGAAGGTGGAGAACATGAAAGCCATAACAGCTAGACGTATTCTGCAAGGCCTAGGGCATTATT

TGAAGGCAGAAGGAAAAGTGGAGTGCTACCGAACCCTGCATCCTGTTCCTTTGTATTCATCTAGTGTGAACCGTGCCT

TTTCAAGCCCCAAGGTCGCAGTGGAAGCCTGTAACGCCATGTTGAAAGAGAACTTTCCGACTGTGGCTTCTTACTGTA

TTATTCCAGAGTACGATGCCTATTTGGACATGGTTGACGGAGCTTCATGCTGCTTAGACACTGCCAGTTTTTGCCCTG

CAAAGCTGCGCAGCTTTCCAAAGAAACACTCCTATTTGGAACCCACAATACGATCGGCAGTGCCTTCAGCGATCCAGA

ACACGCTCCAGAACGTCCTGGCAGCTGCCACAAAAAGAAATTGCAATGTCACGCAAATGAGAGAATTGCCCGTATTGG

ATTCGGCGGCCTTTAATGTGGAATGCTTCAAGAAATATGCGTGTAATAATGAATATTGGGAAACGTTTAAAGAAAACC

CCATCAGGCTTACTGAAGAAAACGTGGTAAATTACATTACCAAATTAAAAGGACCAAAAGCTGCTGCTCTTTTTGCGA

AGACACATAATTTGAATATGTTGCAGGACATACCAATGGACAGGTTTGTAATGGACTTAAAGAGAGACGTGAAAGTGA

CTCCAGGAACAAAACATACTGAAGAACGGCCCAAGGTACAGGTGATCCAGGCTGCCGATCCGCTAGCAACAGCGTATC

TGTGCGGAATCCACCGAGAGCTGGTTAGGAGATTAAATGCGGTCCTGCTTCCGAACATTCATACACTGTTTGATATGT

CGGCTGAAGACTTTGACGCTATTATAGCCGAGCACTTCCAGCCTGGGGATTGTGTTCTGGAAACTGACATCGCGTCGT

-continued

TTGATAAAAGTGAGGACGACGCCATGGCTCTGACCGCGTTAATGATTCTGGAAGACTTAGGTGTGGACGCAGAGCTGT

TGACGCTGATTGAGGCGGCTTTCGGCGAAATTTCATCAATACATTTGCCCACTAAAACTAAATTTAAATTCGGAGCCA

TGATGAAATCTGGAATGTTCCTCACACTGTTTGTGAACACAGTCATTAACATTGTAATCGCAAGCAGAGTGTTGAGAG

AACGGCTAACCGGATCACCATGTGCAGCATTCATTGGAGATGACAATATCGTGAAAGGAGTCAAATCGGACAAATTAA

TGGCAGACAGGTGCGCCACCTGGTTGAATATGGAAGTCAAGATTATAGATGCTGTGGTGGGCGAGAAAGCGCCTTATT

TCTGTGGAGGGTTTATTTTGTGTGACTCCGTGACCGGCACAGCGTGCCGTGTGGCAGACCCCCTAAAAAGGCTGTTTA

AGCTTGGCAAACCTCTGGCAGCAGACGATGAACATGATGATGACAGGAGAAGGGCATTGCATGAAGAGTCAACACGCT

GGAACCGAGTGGGTATTCTTTCAGAGCTGTGCAAGGCAGTAGAATCAAGGTATGAAACCGTAGGAACTTCCATCATAG

TTATGGCCATGACTACTCTAGCTAGCAGTGTTAAATCATTCAGCTACCTGAGAGGGGCCCCTATAACTCTCTACGGCT

AACCTGAATGGACTACGACATAGTCTAGTCCGCCAAGTCTAGCATATGGCCACCATGTTCGTGTTTCTGGTGCTGCTG

CCTCTGGTGTCCAGCCAGTGTGTGAACCTGACCACCAGAACACAGCTGCCTCCAGCCTACACCAACAGCTTTACCAGA

GGCGTGTACTACCCCGACAAGGTGTTCAGATCCAGCGTGCTGCACTCTACCCAGGACCTGTTCCTGCCTTTCTTCAGC

AACGTGACCTGGTTCCACGCCATCCACGTGTCCGGCACCAATGGCACCAAGAGATTCGACAACCCCGTGCTGCCCTTC

AACGACGGGGTGTACTTTGCCAGCACCGAGAAGTCCAACATCATCAGAGGCTGGATCTTCGGCACCACACTGGACAGC

AAGACCCAGAGCCTGCTGATCGTGAACAACGCCACCAACGTGGTCATCAAAGTGTGCGAGTTCCAGTTCTGCAACGAC

CCCTTCCTGGGCGTCTACTACCACAAGAACAACAAGAGCTGGATGGAAAGCGAGTTCCGGGTGTACAGCAGCGCCAAC

AACTGCACCTTCGAGTACGTGTCCCAGCCTTTCCTGATGGACCTGGAAGGCAAGCAGGGCAACTTCAAGAACCTGCGC

GAGTTCGTGTTCAAGAACATCGACGGCTACTTCAAGATCTACAGCAAGCACACCCCTATCAACCTCGTGCGGGATCTG

CCTCAGGGCTTCTCTGCTCTGGAACCCCTGGTGGATCTGCCCATCGGCATCAACATCACCCGGTTTCAGACACTGCTG

GCCCTGCACAGAAGCTACCTGACACCTGGCGATAGCAGCAGCGGATGGACAGCTGGTGCCGCCGCTTACTATGTGGGC

TACCTGCAGCCTAGAACCTTCCTGCTGAAGTACAACGAGAACGGCACCATCACCGACGCCGTGGATTGTGCCCTTGAT

CCTCTGAGCGAGACAAAGTGCACCCTGAAGTCCTTCACCGTGGAAAAGGGCATCTACCAGACCAGCAACTTCCGGGTG

CAGCCCACCGAATCCATCGTGCGGTTCCCCAATATCACCAATCTGTGCCCCTTCGGCGAGGTGTTCAATGCCACCAGA

TTCGCCTCTGTGTACGCCTGGAACCGGAAGCGGATCAGCAATTGCGTGGCCGACTACTCCGTGCTGTACAACTCCGCC

AGCTTCAGCACCTTCAAGTGCTACGGCGTGTCCCCTACCAAGCTGAACGACCTGTGCTTCACAAACGTGTACGCCGAC

AGCTTCGTGATCCGGGGAGATGAAGTGCGGCAGATTGCCCCTGGACAGACAGGCAAGATCGCCGACTACAACTACAAG

CTGCCCGACGACTTCACCGGCTGTGTGATTGCCTGGAACAGCAACAACCTGGACTCCAAAGTCGGCGGCAACTACAAT

TACCTGTACCGGCTGTTCCGGAAGTCCAATCTGAAGCCCTTCGAGCGGGACATCTCCACCGAGATCTATCAGGCCGGC

AGCACCCCTTGTAACGGCGTGGAAGGCTTCAACTGCTACTTCCCACTGCAGTCCTACGGCTTTCAGCCCACAAATGGC

GTGGGCTATCAGCCCTACAGAGTGGTGGTGCTGAGCTTCGAACTGCTGCATGCCCCTGCCACAGTGTGCGGCCCTAAG

AAAAGCACCAATCTCGTGAAGAACAAATGCGTGAACTTCAACTTCAACGGCCTGACCGGCACAGGCGTGCTGACAGAG

AGCAACAAGAAGTTCCTGCCATTCCAGCAGTTTGGCCGGGATATCGCCGATACCACAGACGCCGTTAGAGATCCCCAG

ACACTGGAAATCCTGGACATCACCCCTTGCAGCTTCGGCGGAGTGTCTGTGATCACCCCTGGCACCAACACCAGCAAT

CAGGTGGCAGTGCTGTACCAGGACGTGAACTGTACCGAAGTGCCCGTGGCCATTCACGCCGATCAGCTGACACCTACA

TGGCGGGTGTACTCCACCGGCAGCAATGTGTTTCAGACCAGAGCCGGCTGTCTGATCGGAGCCGAGCACGTGAACAAT

AGCTACGAGTGCGACATCCCCATCGGCGCTGGCATCTGTGCCAGCTACCAGACACAGACAAACAGCCCCAGACGGGCC

AGATCTGTGGCCAGCCAGAGCATCATTGCCTACACAATGTCTCTGGGCGCCGAGAACAGCGTGGCCTACTCCAACAAC

TCTATCGCTATCCCCACCAACTTCACCATCAGCGTGACCACAGAGATCCTGCCTGTGTCCATGACCAAGACCAGCGTG

GACTGCACCATGTACATCTGCGGCGATTCCACCGAGTGCTCCAACCTGCTGCTGCAGTACGGCAGCTTCTGCACCCAG

CTGAATAGAGCCCTGACAGGGATCGCCGTGGAACAGGACAAGAACACCCAAGAGGTGTTCGCCCAAGTGAAGCAGATC

-continued

```
TACAAGACCCCTCCTATCAAGGACTTCGGCGGCTTCAATTTCAGCCAGATTCTGCCCGATCCTAGCAAGCCCAGCAAG

CGGAGCTTCATCGAGGACCTGCTGTTCAACAAAGTGACACTGGCCGACGCCGGCTTCATCAAGCAGTATGGCGATTGT

CTGGGCGACATTGCCGCCAGGGATCTGATTTGCGCCCAGAAGTTTAACGGACTGACAGTGCTGCCTCCTCTGCTGACC

GATGAGATGATCGCCCAGTACACATCTGCCCTGCTGGCCGGCACAATCACAAGCGGCTGGACATTTGGAGCTGGCGCC

GCTCTGCAGATCCCCTTTGCTATGCAGATGGCCTACAGATTCAACGGCATCGGAGTGACCCAGAATGTGCTGTACGAG

AACCAGAAGCTGATCGCCAACCAGTTCAACAGCGCCATCGGCAAGATCCAGGACAGCCTGAGCAGCACAGCAAGCGCC

CTGGGAAAGCTGCAGGACGTGGTCAACCAGAATGCCCAGGCACTGAACACCCTGGTCAAGCAGCTGTCCTCCAACTTC

GGCGCCATCAGCTCTGTGCTGAACGATATCCTGAGCAGACTGGACCCTCCTGAGGCCGAGGTGCAGATCGACAGACTG

ATCACAGGCAGACTGCAGAGCCTCCAGACATACGTGACCCAGCAGCTGATCAGAGCCGCCGAGATTAGAGCCTCTGCC

AATCTGGCCGCCACCAAGATGTCTGAGTGTGTGCTGGGCCAGAGCAAGAGAGTGGACTTTTGCGGCAAGGGCTACCAC

CTGATGAGCTTCCCTCAGTCTGCCCCTCACGGCGTGGTGTTTCTGCACGTGACATACGTTCCCGCTCAAGAGAAGAAT

TTCACCACCGCTCCAGCCATCTGCCACGACGGCAAAGCCCACTTTCCTAGAGAAGGCGTGTTCGTGTCCAACGGCACC

CATTGGTTCGTGACACAGCGGAACTTCTACGAGCCCCAGATCATCACCACCGACAACACCTTCGTGTCTGGCAACTGC

GACGTCGTGATCGGCATTGTGAACAATACCGTGTACGACCCTCTGCAGCCCGAGCTGGACAGCTTCAAAGAGGAACTG

GACAAGTACTTTAAGAACCACACAAGCCCCGACGTGGACCTGGGCGATATCAGCGGAATCAATGCCAGCGTCGTGAAC

ATCCAGAAAGAGATCGACCGGCTGAACGAGGTGGCCAAGAATCTGAACGAGAGCCTGATCGACCTGCAAGAACTGGGG

AAGTACGAGCAGTACATCAAGTGGCCCTGGTACATCTGGCTGGGCTTTATCGCCGGACTGATTGCCATCGTGATGGTC

ACAATCATGCTGTGTTGCATGACCAGCTGCTGTAGCTGCCTGAAGGGCTGTTGTAGCTGTGGCAGCTGCTGCAAGTTC

GACGAGGACGATTCTGAGCCCGTGCTGAAGGGCGTGAAACTGCACTACACAGATCGGAGAAAGAGAGGCTCTGGCGAA

GGCAGAGGCAGCCTGCTTACATGTGGCGACGTGGAAGAGAACCCCGGACCTATGGATTATGTGTCCCTGCTGAACCAG

ATTTGGCAGAAGTACCTGAACAGCCCCTACACCACCTGTCTGTACATCCCCAAGCCTACCGCCAAGTACACACCTCTC

GTGGGCACATCTCTGCACCCCGTGCTGTGGAATTGCCAGCTGAGCTTTGCCGGCTACACCGAGTCTGCCGTGAACAGC

ACAAAGGCCCTGGCCAAACAGGACGCCGCTCAGAGAATTGCCTGGCTGCTGCACAAGGATGGCGGCATCCCTGATGGC

TGTAGCCTGTACCTGAGACACAGCAGCCTGTTCGCCCAGAGCGAGGAAGAGGAATCCTTCAGCAACTGAGCGGCCGCG

AATTGGCAAGCTGCTTACATAGAACTCGCGGCGATTGGCATGCCGCCTTAAAATTTTTATTTTATTTTTTCTTTTCTTT

TCCGAATCGGATTTTGTTTTTAATATTTCAAAAAAAAAAAAAAAAAAAAAAAAAAAAAAAAAAAACGCGTCGAGGGGAA

TTAATTCTTGAAGACGAAAGGGCCAGGTGGCACTTTTCGGGGAAATGTGCGCGGAACCCCTATTTGTTTATTTTTCTA

AATACATTCAAATATGTATCCGCTCATGAGACAATAACCCTGATAAATGCTTCAATAATATTGAAAAAGGAAGAGTAT

GAGTATTCAACATTTCCGTGTCGCCCTTATTCCCTTTTTTGCGGCATTTTGCCTTCCTGTTTTTGCTCACCCAGAAAC

GCTGGTGAAAGTAAAAGATGCTGAAGATCAGTTGGGTGCACGAGTGGGTTACATCGAACTGGATCTCAACAGCGGTAA

GATCCTTGAGAGTTTTCGCCCCGAAGAACGTTTTCCAATGATGAGCACTTTTAAAGTTCTGCTATGTGGCGCGGTATT

ATCCCGTGTTGACGCCGGGCAAGAGCAACTCGGTCGCCGCATACACTATTCTCAGAATGACTTGGTTGAGTACTCACC

AGTCACAGAAAAGCATCTTACGGATGGCATGACAGTAAGAGAATTATGCAGTGCTGCCATAACCATGAGTGATAACAC

TGCGGCCAACTTACTTCTGACAACGATCGGAGGACCGAAGGAGCTAACCGCTTTTTTGCACAACATGGGGGATCATGT

AACTCGCCTTGATCGTTGGGAACCGGAGCTGAATGAAGCCATACCAAACGACGAGCGTGACACCACGATGCCTGTAGC

AATGGCAACAACGTTGCGCAAACTATTAACTGGCGAACTACTTACTCTAGCTTCCCGGCAACAATTAATAGACTGGAT

GGAGGCGGATAAAGTTGCAGGACCACTTCTGCGCTCGGCCCTTCCGGCTGGCTGGTTTATTGCTGATAAATCTGGAGC

CGGTGAGCGTGGGTCTCGCGGTATCATTGCAGCACTGGGGCCAGATGGTAAGCCCTCCCGTATCGTAGTTATCTACAC

GACGGGGAGTCAGGCAACTATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATTTAAAAGGATCTAGGTGAA

GATCCTTTTTGATAATCTCATGACCAAAATCCCTTAACGTGAGTTTTCGTTCCACTGAGCGTCAGACCCCGTAGAAAA
```

-continued

GATCAAAGGATCTTCTTGAGATCCTTTTTTTCTGCGCGTAATCTGCTGCTTGCAAACAAAAAAACCACCGCTACCAGC

GGTGGTTTGTTTGCCGGATCAAGAGCTACCAACTCTTTTTCCGAAGGTAACTGGCTTCAGCAGAGCGCAGATACCAAA

TACTGTCCTTCTAGTGTAGCCGTAGTTAGGCCACCACTTCAAGAACTCTGTAGCACCGCCTACATACCTCGCTCTGCT

AATCCTGTTACCAGTGGCTGCTGCCAGTGGCGATAAGTCGTGTCTTACCGGGTTGGACTCAAGACGATAGTTACCGGA

TAAGGCGCAGCGGTCGGGCTGAACGGGGGGTTCGTGCACACAGCCCAGCTTGGAGCGAACGACCTACACCGAACTGAG

ATACCTACAGCGTGAGCATTGAGAAAGCGCCACGCTTCCCGAAGGGAGAAAGGCGGACAGGTATCCGGTAAGCGGCAG

GGTCGGAACAGGAGAGCGCACGAGGGAGCTTCCAGGGGGAAACGCCTGGTATCTTTATAGTCCTGTCGGGTTTCGCCA

CCTCTGACTTGAGCGTCGATTTTTGTGATGCTCGTCAGGGGGGCGGAGCCTATGGAAAAACGCCATTCTAGAATGGCG

CGCCCTTAAGGGGAGAATAGGAGCCGCAACACACAAGCAACGCGAGGTCGTTTAAACTAATACGACTCACTATAATGG

GCGGCGCATGAGAGAAGCCCAGACCAATTACCTACCCAAAATGGAGAAAGTTCACGTTGACATCGAGGAAGACAGCCC

ATTCCTCAGAGCTTTGCAGCGGAGCTTCCCGCAGTTTGAGGTAGAAGCCAAGCAGGTCACTGATAATGACCATGCTAA

TGCCAGAGCGTTTTCGCATCTGGCTTCAAAACTGATCGAAACGGAGGTGGACCCATCCGACACGATCCTTGACATTGG

AAGTGCGCCCGCCCGCAGAATGTATTCTAAGCACAAGTATCATTGTATCTGTCCGATGAGATGTGCGGAAGATCCGGA

CAGATTGTATAAGTATGCAACTAAGCTGAAGAAAAACTGTAAGGAAATAACTGATAAGGAATTGGACAAGAAAATGAA

GGAGCTGGCCGCCGTCATGAGCGACCCTGACCTGGAAACTGAGACTATGTGCCTCCACGACGACGAGTCGTGTCGCTA

CGAAGGGCAAGTCGCTGTTTACCAGGATGTATACGCGGTTGACGGACCGACAAGTCTCTATCACCAAGCCAATAAGGG

AGTTAGAGTCGCCTACTGGATAGGCTTTGACACCACCCCTTTTATGTTTAAGAACTTGGCTGGAGCATATCCATCATA

CTCTACCAACTGGGCCGACGAAACCGTGTTAACGGCTCGTAACATAGGCCTATGCAGCTCTGACGTTATGGAGCGGTC

ACGTAGAGGGATGTCCATTCTTAGAAAGAAGTATTTGAAACCATCCAACAATGTTCTATTCTCTGTTGGCTCGACCAT

CTACCACGAGAAGAGGGACTTACTGAGGAGCTGGCACCTGCCGTCTGTATTTCACTTACGTGGCAAGCAAAATTACAC

ATGTCGGTGTGAGACTATAGTTAGTTGCGACGGGTACGTCGTTAAAAGAATAGCTATCAGTCCAGGCCTGTATGGGAA

GCCTTCAGGCTATGCTGCTACGATGCACCGCGAGGGATTCTTGTGCTGCAAAGTGACAGACACATTGAACGGGGAGAG

GGTCTCTTTTCCCGTGTGCACGTATGTGCCAGCTACATTGTGTGACCAAATGACTGGCATACTGGCAACAGATGTCAG

TGCGGACGACGCGCAAAAACTGCTGGTTGGGCTCAACCAGCGTATAGTCGTCAACGGTCGCACCCAGAGAAACACCAA

TACCATGAAAAATTACCTTTTGCCCGTAGTGGCCCAGGCATTTGCTAGGTGGGCAAAGGAATATAAGGAAGATCAAGA

AGATGAAAGGCCACTAGGACTACGAGATAGACAGTTAGTCATGGGGTGTTGTTGGGCTTTTAGAAGGCACAAGATAAC

ATCTATTTATAAGCGCCCGGATACCCAAACCATCATCAAAGTGAACAGCGATTTCCACTCATTCGTGCTGCCCAGGAT

AGGCAGTAACACATTGGAGATCGGGCTGAGAACAAGAATCAGGAAAATGTTAGAGGAGCACAAGGAGCCGTCACCTCT

CATTACCGCCGAGGACGTACAAGAAGCTAAGTGCGCAGCCGATGAGGCTAAGGAGGTGCGTGAAGCCGAGGAGTTGCG

CGCAGCTCTACCACCTTTGGCAGCTGATGTTGAGGAGCCCACTCTGGAGGCAGACGTCGACTTGATGTTACAAGAGGC

TGGGGCCGGCTCAGTGGAGACACCTCGTGGCTTGATAAAGGTTACCAGCTACGATGGCGAGGACAAGATCGGCTCTTA

CGCTGTGCTTTCTCCGCAGGCTGTACTCAAGAGTGAAAAATTATCTTGCATCCACCCTCTCGCTGAACAAGTCATAGT

GATAACACACTCTGGCCGAAAAGGGCGTTATGCCGTGGAACCATACCATGGTAAAGTAGTGGTGCCAGAGGGACATGC

AATACCCGTCCAGGACTTTCAAGCTCTGAGTGAAAGTGCCACCATTGTGTACAACGAACGTGAGTTCGTAAACAGGTA

CCTGCACCATATTGCCACACATGGAGGAGCGCTGAACACTGATGAAGAATATTACAAAACTGTCAAGCCCAGCGAGCA

CGACGGCGAATACCTGTACGACATCGACAGGAAACAGTGCGTCAAGAAAGAACTAGTCACTGGGCTAGGGCTCACAGG

CGAGCTGGTGGATCCTCCCTTCCATGAATTCGCCTACGAGAGTCTGAGAACACGACCAGCCGCTCCTTACCAAGTACC

AACCATAGGGGTGTATGGCGTGCCAGGATCAGGCAAGTCTGGCATCATTAAAAGCGCAGTCACCAAAAAAGATCTAGT

GGTGAGCGCCAAGAAAGAAAACTGTGCAGAAATTATAAGGGACGTCAAGAAAATGAAAGGGCTGGACGTCAATGCCAG

AACTGTGGACTCAGTGCTCTTGAATGGATGCAAACACCCCGTAGAGACCCTGTATATTGACGAAGCTTTTGCTTGTCA

-continued

TGCAGGTACTCTCAGAGCGCTCATAGCCATTATAAGACCTAAAAAGGCAGTGCTCTGCGGGGATCCCAAACAGTGCGG

TTTTTTTAACATGATGTGCCTGAAAGTGCATTTTAACCACGAGATTTGCACACAAGTCTTCCACAAAAGCATCTCTCG

CCGTTGCACTAAATCTGTGACTTCGGTCGTCTCAACCTTGTTTTACGACAAAAAAATGAGAACGACGAATCCGAAAGA

GACTAAGATTGTGATTGACACTACCGGCAGTACCAAACCTAAGCAGGACGATCTCATTCTCACTTGTTTCAGAGGGTG

GGTGAAGCAGTTGCAAATAGATTACAAAGGCAACGAAATAATGACGGCAGCTGCCTCTCAAGGGCTGACCCGTAAAGG

TGTGTATGCCGTTCGGTACAAGGTGAATGAAA

Accordingly, preferably the vector comprises the nucleotide sequence substantially as set out in SEQ ID NO: 76, or a variant or fragment thereof.

The saRNA constructs of the invention may be made using a DNA plasmid, which is shown in FIG. 3, 7-11, as a template. RNA copies may then be made by in vitro transcription using a polymerase, such as T7 polymerase, and the T7 promoter is shown upstream of the saRNA in the plasmid map in FIG. 3, 7-11. Hence, the saRNA constructs of the first aspect may be made using the DNA plasmid having a nucleic acid sequence as set out in SEQ ID No: 35, or a variant or fragment thereof, which is shown in FIG. 3, 7-11, as the template.

The vector of the fourth aspect encoding the RNA construct of the first aspect may for example be a plasmid, cosmid or phage and/or be a viral vector. Such recombinant vectors are highly useful in the delivery systems of the invention for transforming cells with the 50 nucleotide sequences. The nucleotide sequences may preferably be a DNA sequence, and it is this DNA sequence which encodes the RNA sequence forming the RNA construct of the first aspect.

Recombinant vectors encoding the RNA construct of the first aspect may also include other functional elements. For example, they may further comprise a variety of other functional elements including a suitable promoter for initiating transgene expression upon introduction of the vector in a host cell. For instance, the vector is preferably capable of autonomously replicating in the nucleus of the host cell, such as bacterial cell. In this case, elements which induce or regulate DNA replication may be required in the so recombinant vector. Alternatively, the recombinant vector may be designed such that it integrates into the genome of a host cell. In this case, DNA sequences which favour targeted integration (e.g. by homologous recombination) are envisaged. Suitable promoters may include the SV40 promoter, CMV, EF1a, PGK, viral long terminal repeats, as well as inducible promoters, such as the Tetracycline inducible system, as examples. The cassette or vector may also comprise a terminator, such as the Beta globin, SV40 polyadenylation sequences or synthetic polyadenylation sequences. The recombinant vector may also comprise a promoter or regulator or enhancer to control expression of the nucleic acid as required.

The vector may also comprise DNA coding for a gene that may be used as a selectable marker in the cloning process, i.e. to enable selection of cells that have been transfected or transformed, and to enable the selection of cells harbouring vectors incorporating heterologous DNA. For example, ampicillin, neomycin, puromycin or chloramphenicol resistance is envisaged. The vector shown in FIG. 3, 7-11 includes an ampicillin resistant marker, which is useful for selecting the plasmid in bacteria. Alternatively, the selectable marker gene may be in a different vector to be used simultaneously with the vector containing the transgene(s). The cassette or vector may also comprise DNA involved with regulating expression of the nucleotide sequence, or for targeting the expressed polypeptide to a certain part of the host cell.

Purified vector may be inserted directly into a host cell by suitable means, e.g. direct endocytotic uptake. The vector may be introduced directly into a host cell (e.g. a eukaryotic or prokaryotic cell) by transfection, infection, electroporation, microinjection, cell fusion, protoplast fusion or ballistic bombardment. Alternatively, vectors of the invention may be introduced directly into a host cell using a particle gun.

The nucleic acid molecule may (but not necessarily) be one, which becomes incorporated in the DNA of the host cell. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated. When this is the case, regulation of expression may be less important because expression of the DNA molecule will stop when the transformed cells die or stop expressing the.

Alternatively, the delivery system may provide the nucleic acid molecule to the host cell without it being incorporated in a vector. For instance, the nucleic acid molecule may be incorporated within a liposome or virus particle. Alternatively a "naked" nucleic acid molecule may be inserted into a host cell by a suitable means, e.g. direct endocytotic uptake.

In a fifth aspect, there is provided a pharmaceutical composition comprising the RNA construct of the first aspect, the nucleic acid sequence of the second aspect, the expression cassette of the third aspect or the vector of the fourth aspect, and a pharmaceutically acceptable vehicle.

In a sixth aspect, there is provided a process for making the pharmaceutical composition according to the fifth aspect, the method comprising contacting the RNA construct of the first aspect, the nucleic acid sequence of the second aspect, the expression cassette of the third aspect or the vector of the fourth aspect, with a pharmaceutically acceptable vehicle.

In a seventh aspect, there is provided a method of preparing the saRNA construct of the first aspect, the method comprising:

(a) (i) introducing, into a host cell, the vector of the fourth aspect; and
   (ii) culturing the host cell under conditions to result in the production of the RNA construct of the first aspect; or
(b) transcribing the RNA construct from the vector according to the fourth aspect.

The host cell of step (a) may be a eukaryotic or prokaryotic host cell. Suitable prokaryotic cells are bacterial cell, such as *E. coli*. Preferably, the host cell is a eukaryotic host cell. More preferably, the host cell is a mammalian host cell such as Human embryonic kidney 293 cells or Chinese hamster ovary (CHO) cells. Step (b) may be performed in vitro or in vivo, preferably in vitro.

The saRNA constructs of the invention may be made using the DNA plasmid, which is shown in FIG. 3, 7-11, as a template. RNA copies may be made by in vitro transcription using a polymerase, such as T7 polymerase. For example, the T7 promoter is shown upstream of the saRNA in the plasmid map in FIG. 3, 7-11. Hence, the method of the seventh aspect preferably comprises preparing the saRNA construct of the first aspect using the DNA plasmid having a nucleic acid sequence as set out in SEQ ID No: 35, or a variant or fragment thereof, which is shown in FIG. 3, 7-11, as the template.

Suitable methods of in vitro transcription are well-known in the art and would be known to those skilled in the art. For example, as described in Molecular Cloning, A Laboratory Manual, 2nd edition. (1989) editor C Nolan, Cold Spring Harbor Laboratory Press.

The saRNA construct of the first aspect is particularly suitable for therapy or prophylaxis. While the inventors envisaged that the RNA construct of the first aspect would be generated by in vitro transcription for in vivo use in prophylaxis or therapy, those experienced in the art will recognise that the RNA construct can be generated in vivo in a subject for prophylaxis and/or therapy, by in vivo delivery of the nucleic acid according to the second aspect, the expression cassette according to the third aspect, the vector according to the fourth aspect to a subject.

Hence, according to an eighth aspect, there is provided a RNA construct according to the first aspect, the nucleic acid according to the second aspect, the expression cassette according to the third aspect, the vector according to the fourth aspect or the pharmaceutical composition according to the fifth aspect, for use as a medicament, or in therapy or prophylaxis.

The RNA construct described herein provides an effective means of vaccinating a subject against a coronavirus infection.

Accordingly, in a ninth aspect of the invention, there is provided a vaccine comprising the saRNA construct according to the first aspect, the nucleic acid according to the second aspect, the expression cassette according to the third aspect, the vector according to the fourth aspect or the pharmaceutical composition according to the fifth aspect.

As shown in FIGS. 6A and 6C, the inventors investigated the delivery of the saRNA construct when encapsulated in Lipid Nano Particles (LNPs), and surprisingly observed robust binding antibody responses following vaccinations. Accordingly, preferably the saRNA construct, nucleic acid, expression cassette, vector of pharmaceutical composition is formulated in a lipid, i.e. the formulation is lipid-based. Preferably, the saRNA construct, nucleic acid, expression cassette, vector of pharmaceutical composition is formulated in a nanoparticle, which preferably comprises lipid. The formulation of nanoparticle may comprise one or more components selected from a group consisting of: a cationic lipid (which is preferably ionisable); phosphatidylcholine; cholesterol; and polyethylene glycol (PEG)-lipid. A preferred formulation or nanoparticle comprises an ionisable cationic lipid, phosphatidylcholine, cholesterol, and polyethylene glycol (PEG)-lipid. The average diameter of the nanoparticle may be between 50 and 200 nm, and preferably between 50 and 150 nm.

In another embodiment, the saRNA construct, nucleic acid, expression cassette, vector of pharmaceutical composition is formulated within a liposome. Liposomes are known to the skilled person as being a sac of phospholipid molecules which encapsulated the active agent, i.e. the RNA construct, nucleic acid, vector etc.

In yet another embodiment, the saRNA construct, nucleic acid, expression cassette, vector of pharmaceutical composition is formulated within a polyplex, for example pABOL, as exemplified herein, the data for which are shown in FIG. 5.

In some embodiments, the vaccine may not comprise an adjuvant. For example, this may be the situation in which the saRNA is formulated in a lipid-based nanoparticle or Lipid Nano Particle (LNP).

However, in other embodiments, the vaccine may comprise an adjuvant. The adjuvant may be selected form the group consisting of a bacterial lipopeptide, lipoprotein and lipoteichoic acid; mycobacterial lipoglycan; yeast zymosan, porin, Lipopolysaccharide, Lipid A, monophosphoryl lipid A (MPL), Flagellin, CpG DNA, hemozoin, Saponins (Quil-A, QS-21, Tomatine, ISCOM, ISCOMATRIX™), squalene based emulsions, polymers such as PEI, Carbopol, lipid nanoparticles and bacterial toxins (CT, LT).

As described in Example 3, in order to determine the immunogenicity of the saRNA construct of the invention, female Balb/c mice were immunized intramuscularly with the saRNA formulated in a cationic polymer 8 kDa pABOL (i.e. poly(CBA-4-amino-1-butanol in which "CBA" is N,N'-cystaminebisacrylamide) (polymer/RNA=45:1, w/w) with and without MPLA (monophosphoryl lipid A) acting as an adjuvant. As can be seen from the data, robust binding antibody responses were induced when saRNA was formulated in pABOL plus MPLA at two and four weeks post a single vaccination. Hence, in some embodiments, the saRNA may be formulated with pABOL (poly(CBA-4-amino-1-butanol), and optionally in combination with monophosphoryl lipid A (MPLA).

The average molecular mass of the pABOL may be at least 5.5 kg $mol^{-1}$, at least 6 kg $mol^{-1}$, at least 7 kg $mol^{-1}$, at least 8 kg $mol^{-1}$ or at least 9 kg $mol^{-1}$. The average molecular mass of the pABOL may be at least 10 kg $mol^{-1}$, at least 20 kg $mol^{-1}$, at least 30 kg $mol^{-1}$, at least 40 kg $mol^{-1}$ or at least 50 kg $mol^{-1}$. The average molecular mass of the pABOL may be at least 75 kg $mol^{-1}$, at least 100 kg $mol^{-1}$, at least 125 kg $mol^{-1}$, at least 150 kg $mol^{-1}$ or at least 160 kg $mol^{-1}$. As explained in the examples, the inventors have found that pABOL with an average molecular mass of about 8 kg $mol^{-1}$ (8 kDa) is surprisingly effective at delivering the saRNA.

In a tenth aspect of the invention, there is provided an RNA construct according to the first aspect, the nucleic acid according to the second aspect, the expression cassette according to the third aspect, the vector according to the fourth aspect, the pharmaceutical composition according to the fifth aspect, or the vaccine of the ninth aspect, for use in stimulating an immune response in a subject.

It will be appreciated that the RNA construct according to the first aspect, the nucleic acid according to the second aspect, the expression cassette according to the third aspect, the vector according to the fourth aspect or the pharmaceutical composition according to the fifth aspect (herein known as the active agents) may be used in a medicament, which may be used as a monotherapy (i.e. use of the active agent), for vaccination against a coronavirus infection. Alternatively, the active agents according to the invention may be used as an adjunct to, or in combination with, known therapies for treating, ameliorating, or preventing coronavirus infections.

The RNA construct, nucleic acid sequence, expression cassette, vector or pharmaceutical composition of the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension, polyplex, emulsion, lipid nanoparticles (with RNA on the surface or encapsulated) or any other suitable form that may be administered to a person or animal in need of vaccination. It will be appreciated that the vehicle of medicaments according to the invention should be one so which is well-tolerated by the subject to whom it is given.

The RNA construct, nucleic acid sequence, expression cassette, vector or pharmaceutical composition of the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with the genetic construct or the recombinant vector is required and which would normally require frequent administration (e.g. at least daily injection).

In a preferred embodiment, however, medicaments according to the invention may be administered to a subject by injection into the blood stream, muscle, skin or directly into a site requiring treatment. Injections may be intravenous (bolus or infusion) or subcutaneous (bolus or infusion), or intradermal (bolus or infusion), or intramuscular (bolus or infusion).

It will be appreciated that the amount of RNA construct, nucleic acid sequence, expression cassette, vector or pharmaceutical composition that is required is determined by its biological activity and bioavailability, which in turn depends on the mode of administration, the physiochemical properties of the RNA construct, nucleic acid sequence, expression cassette, vector or pharmaceutical composition and whether it is being used as a monotherapy or in a combined therapy. The frequency of administration will also be influenced by the half-life of the active agent within the subject being treated. Optimal dosages to be administered may be determined by those skilled in the art, and will vary with the particular the RNA construct, nucleic acid sequence, expression cassette, vector or pharmaceutical composition in use, the strength of the pharmaceutical composition, the mode of administration, and the type and advancement of the viral infection. Additional factors depending on the particular subject being treated will result in a need to adjust dosages, including subject age, weight, gender, diet, and time of administration.

Generally, a daily dose of between 0.001 μg/kg of body weight and 1 mg/kg of body weight, or between 0.01 μg/kg of body weight and 0.1 mg/kg of body weight, of the RNA construct, nucleic acid sequence, expression cassette, vector or pharmaceutical composition of the invention may be used for the immunisation, depending upon the active agent used.

Daily doses may be given as a single administration (e.g. a single daily injection or inhalation of a nasal spray). Alternatively, the RNA construct, nucleic acid sequence, expression cassette, vector or pharmaceutical composition may require administration twice or more times during a day. As an example, the RNA construct, nucleic acid sequence, expression cassette, vector or pharmaceutical composition may be administered as an initial primer and a subsequent boost, or two boosts administered at between a week or monthly intervals. In a typical example, the active agent may be administered between 0 and 4 weeks apart.

Known procedures, such as those conventionally employed by the pharmaceutical industry (e.g. in vivo experimentation, clinical trials, etc.), may be used to form specific formulations of the RNA construct, nucleic acid sequence, expression cassette or vector according to the invention and precise therapeutic regimes (such as daily doses of the agents and the frequency of administration).

A "subject" may be a vertebrate, mammal, or domestic animal. Hence, compositions and medicaments according to the invention may be used to treat any mammal, for example livestock (e.g. a horse), pets, or may be used in other veterinary applications. Most preferably, however, the subject is a human being.

A "therapeutically effective amount" of the RNA construct, nucleic acid sequence, expression cassette, vector or pharmaceutical composition is any amount which, when administered to a subject, is the amount of the aforementioned that is needed to ameliorate, prevent or treat any given disease, preferably prophylactically.

For example, the RNA construct, nucleic acid sequence, expression cassette, vector or pharmaceutical composition of the invention may be used may be from about 0.001 μg to about 1 mg, and preferably from about 0.001 μg to about 500 μg. It is preferred that the amount of the replicon, nucleic acid sequence, expression cassette, vector or pharmaceutical composition is an amount from about 0.01 μg to about 250 μg, and most preferably from about 0.1 μg to about 100 μg. Preferably, the RNA construct, nucleic acid sequence, expression cassette, vector or pharmaceutical composition according to the invention is administered at a dose of 1-50 μg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent (e.g. RNA construct, nucleic acid sequence, expression cassette, vector or pharmaceutical composition according to the invention) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The RNA construct, nucleic acid sequence, expression cassette, vector or pharmaceutical composition according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, subcutaneous, intradermal, intrathecal, epidural, intraperitoneal, intravenous and particularly intramuscular injection. The nucleic acid sequence, or expression cassette of the invention may be prepared as a sterile solid composition that may be dissolved or suspended at the time of administration using sterile water, saline, or other appropriate sterile injectable medium.

The RNA construct, nucleic acid sequence, expression cassette, vector or pharmaceutical composition of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The RNA construct, nucleic acid sequence, expression cassette, vector or pharmaceutical composition according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

It will be appreciated that the invention extends to any nucleic acid or peptide or variant, derivative or analogue thereof, which comprises substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the sequence identified as SEQ ID Nos: 1-86 and so on.

Amino acid/polynucleotide/polypeptide sequences with a sequence identity which is greater than 65%, more preferably greater than 70%, even more preferably greater than 75%, and still more preferably greater than 80% sequence identity to any of the so sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (v) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps and either including or excluding overhangs. Preferably, overhangs are included in the calculation. Hence, a most preferred method for calculating percentage identity between two sequences comprises (i) preparing a sequence alignment using the ClustalW program using a suitable set of parameters, for example, as set out above; and (ii) inserting the values of N and T into the following formula:—Sequence Identity=(N/T)*100.

Alternative methods for identifying similar sequences will be known to those skilled in the art. For example, a substantially similar nucleotide sequence will be encoded by a sequence which hybridizes to DNA sequences or their complements under stringent conditions. By stringent conditions, the inventors mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in, for example, SEQ ID Nos: 1-86.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent (synonymous) change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example, small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The so positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

FIG. 1A is a schematic representation of a self-amplifying RNA replicon derived from VEEV containing a 5'cap, an 5' untranslated region (5'UTR), non-structural genes (nsP1-4) encoding the RNA dependent RNA polymerase machinery, a sub-genomic promoter (SGP), an antigen of interest, a 3' untranslated region (3'UTR) and a poly(A) tail.

FIG. 1B is a schematic representation of the steps in replication and expression of the self-amplifying RNA replicon shown in FIG. 1A. (1) The RNA replicon is first delivered to the cytoplasm. (2) Translation of the open reading frame encoding the four non-structural proteins (nsP1-4) that forms the RNA-dependent polymerase (RDRP), then occurs, which produces the negative-sense copy of the genome and triggers innate sensing of the double stranded RNA intermediate. (3) RDRP catalysis of the production of positive-sense genomes from the negative sense copy. (4) RDRP transcription of the subgenome leading to extremely high amplification. (5) Translation of the vaccine antigen leading to protein expression.

FIG. 2 shows a schematic of one embodiment of a self-amplifying RNA replicon or construct based on the Venezuelan Equine Encephalitis Virus (VEEV) backbone known as a “Stealthicon”. The vector is a saRNA replicon encoding four Non-structural Proteins (NSP1-4), which are either upstream or downstream of the GOI (Gene of Interest), i.e. an antigen which stimulates an immune response.

FIG. 3 shows the construct map of one embodiment of a DNA expression vector according to the invention encoding one embodiment of the saRNA construct of the invention. The vector comprises a VEEV backbone as shown in FIG. 2, but harbouring the gene encoding the SARS-CoV-2 (COVID-19 nCoV) native coronavirus surface S glycoprotein as the antigen or GOI. In other embodiments (not shown), the antigen could be the MERS-CoV or SARS-CoV coronavirus surface glycoprotein.

FIG. 4 shows Flow Cytometry analysis of HEK 293T cells transfected with Lipofectamine Max and saRNA encoding the S glycoprotein of SARS-CoV-2. Left hand panels depict non-transfected cells, and right hand panels depict cells transfected with saRNA encoding the S glycoprotein of SARS-CoV-2 stained with polyclonal sera (antibody A) and a monoclonal (antibody B) known to bind to shared epitopes between SARS and SARS-CoV2.

Figure 2:
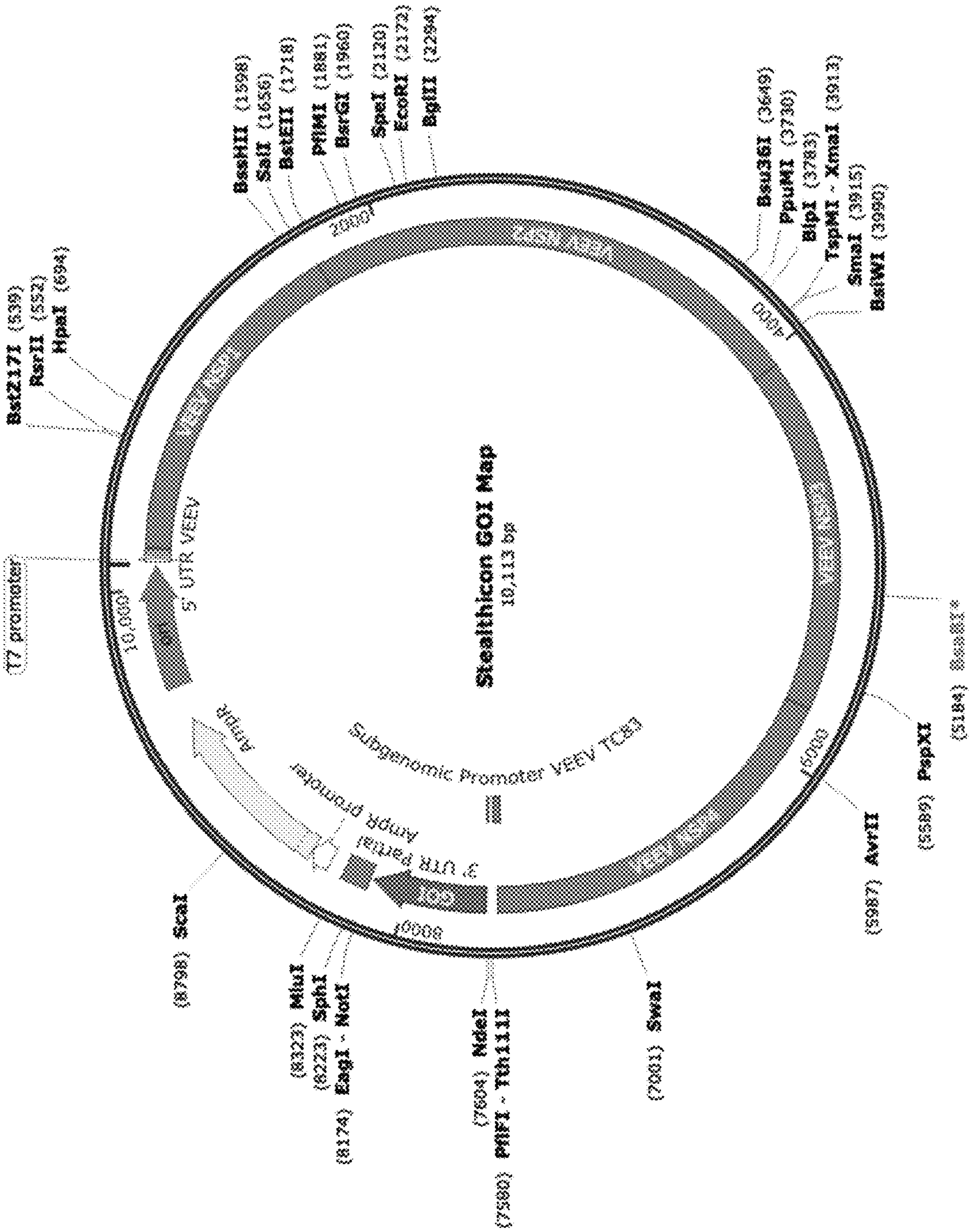
Figure 7:
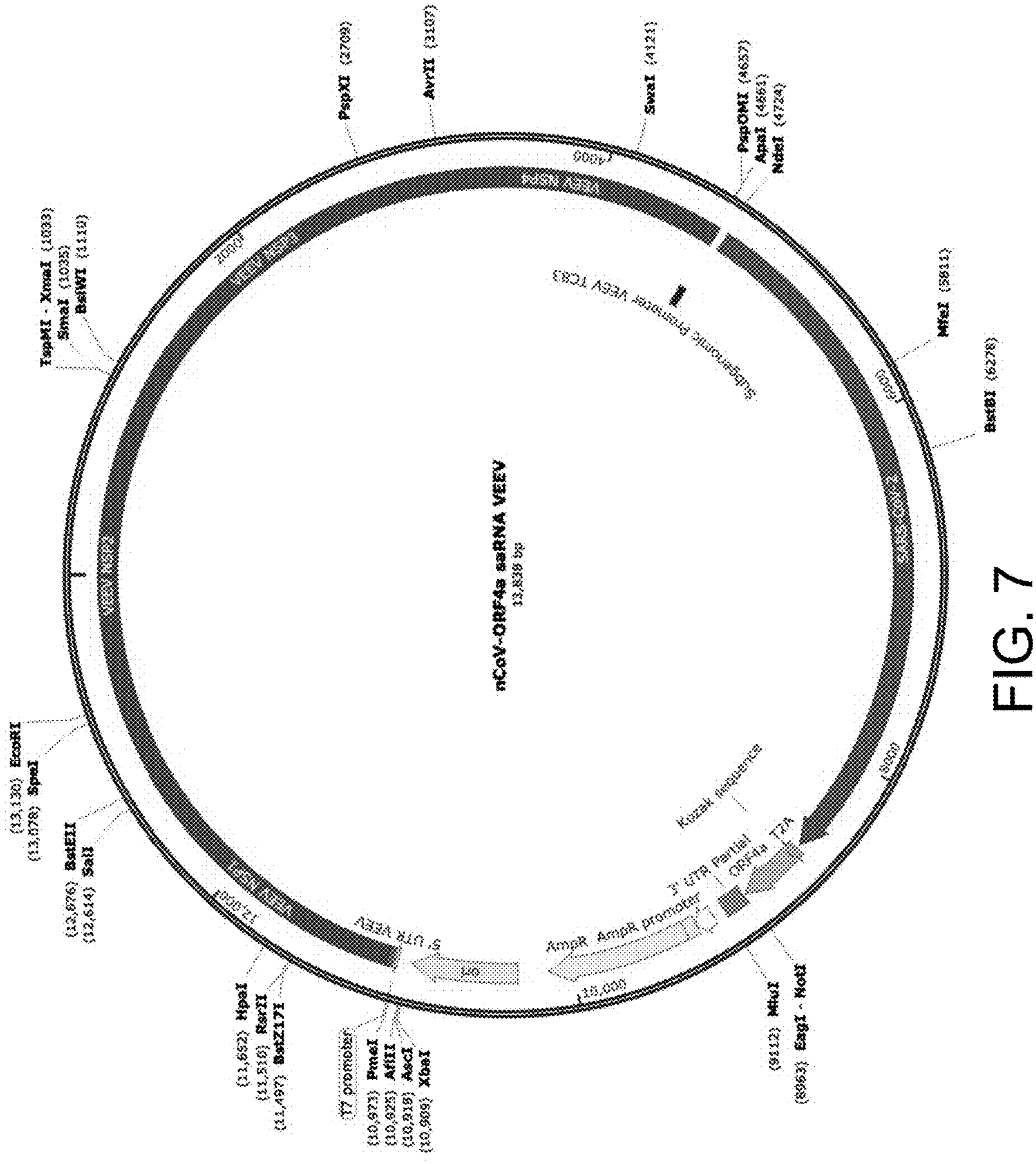

FIG. 7 shows the construct map of another embodiment of the DNA expression vector according to the invention encoding another embodiment of the saRNA construct of the invention. The vector comprises a VEEV backbone as shown in FIG. 2, harbouring the gene encoding the SARS-CoV-2 native coronavirus surface S glycoprotein as the antigen or GOI, and also ORF4a, which acts as an innate inhibitor protein (IIP) to suppress the innate response in a subject treated with the construct.

Figure 8:
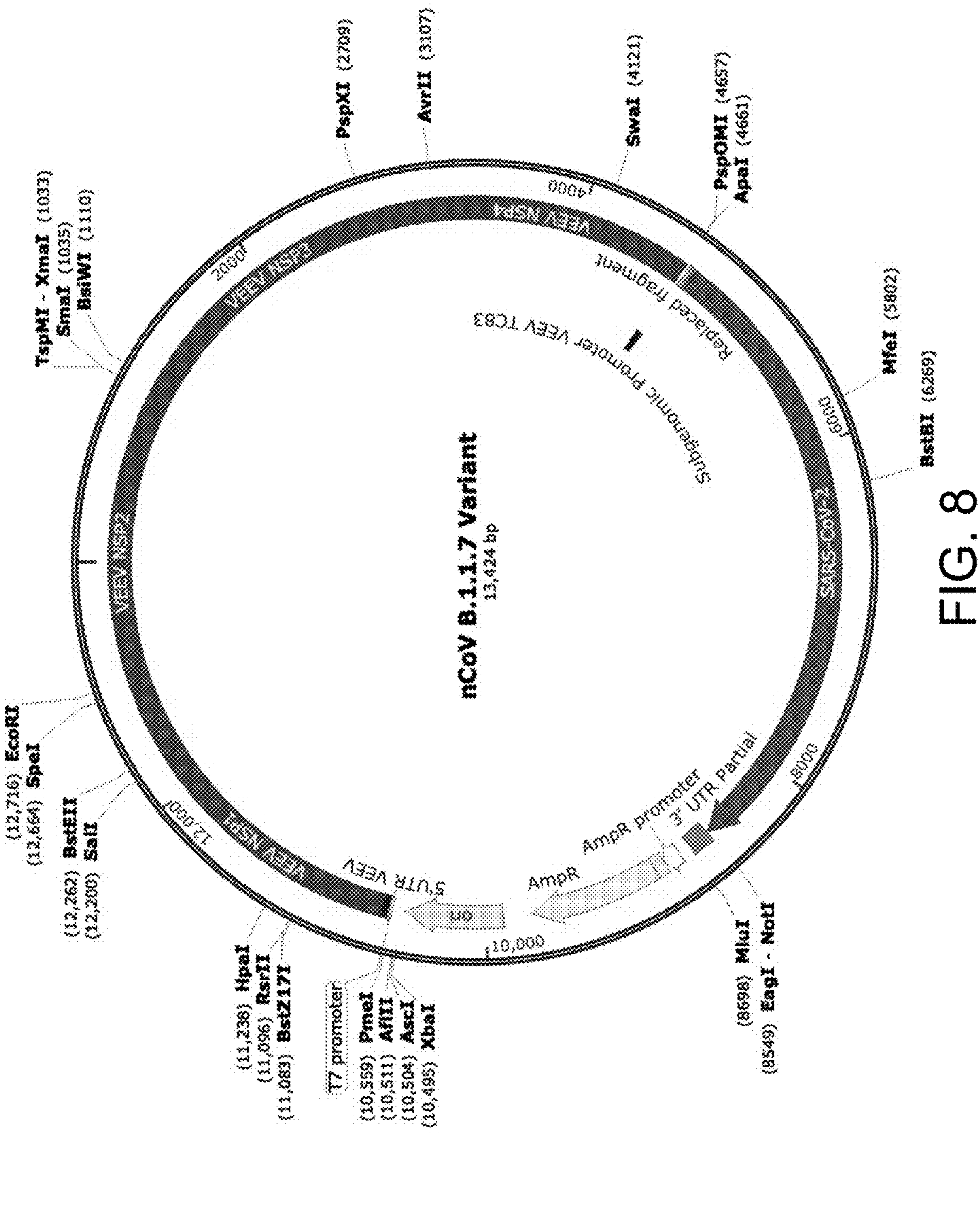

FIG. 8 shows the construct map of another embodiment of the DNA expression vector according to the invention encoding another embodiment of the saRNA construct of the invention. The construct comprises a VEEV backbone as shown in FIG. 2, harbouring the gene encoding the nCov B.1.1.7 variant (i.e. the UK variant) of SARS-CoV-2 native coronavirus surface S glycoprotein as the antigen or GOI.

Figure 9:
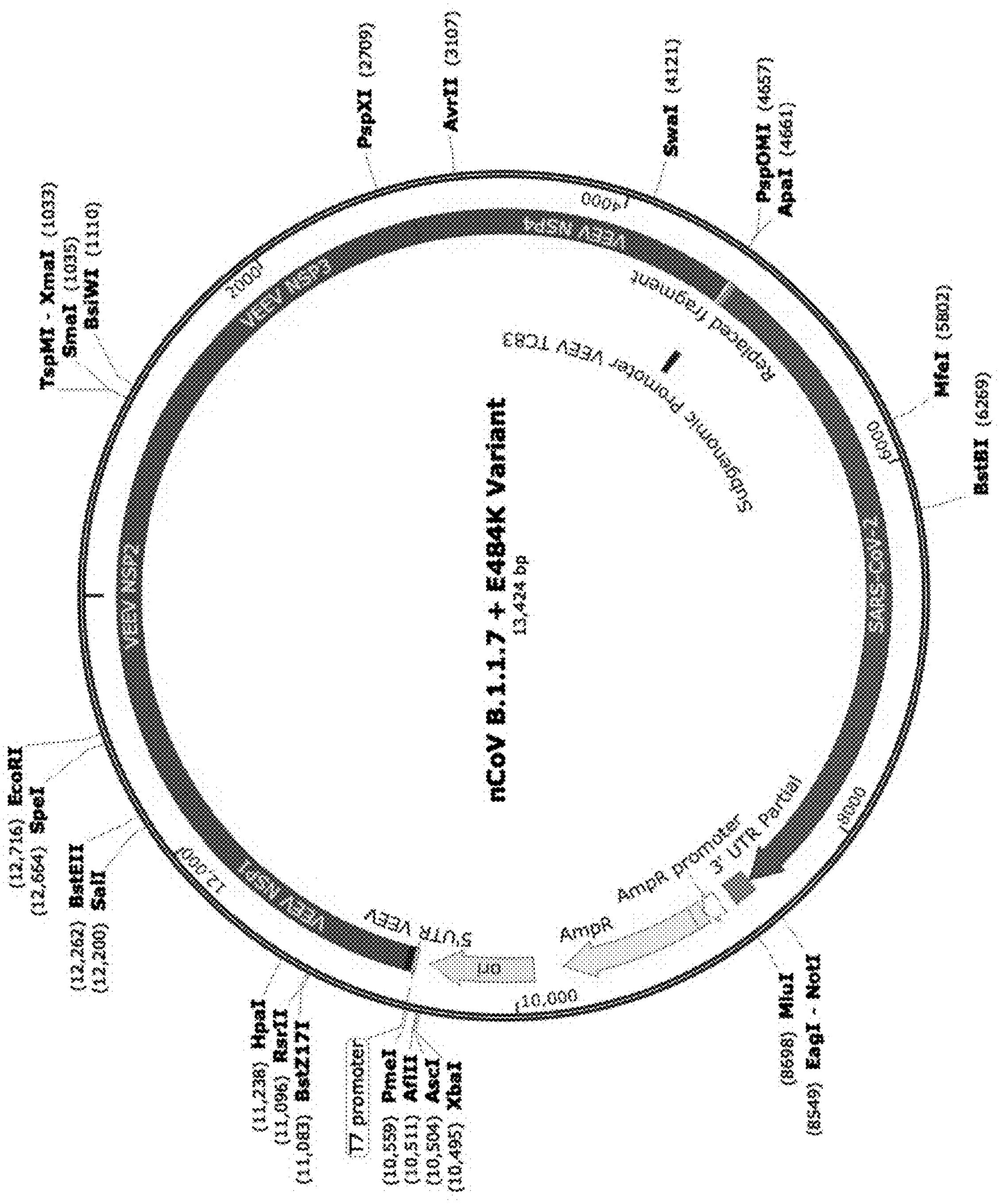

FIG. 9 shows the construct map of another embodiment of the DNA expression vector according to the invention encoding another embodiment of the saRNA construct of the invention. The construct comprises a VEEV backbone as shown in FIG. 2, harbouring the gene encoding the nCov B.1.1.7+E484K variant (i.e. the UK variant) of SARS-CoV-2 native coronavirus surface S glycoprotein as the antigen or GOI.

Figure 10:
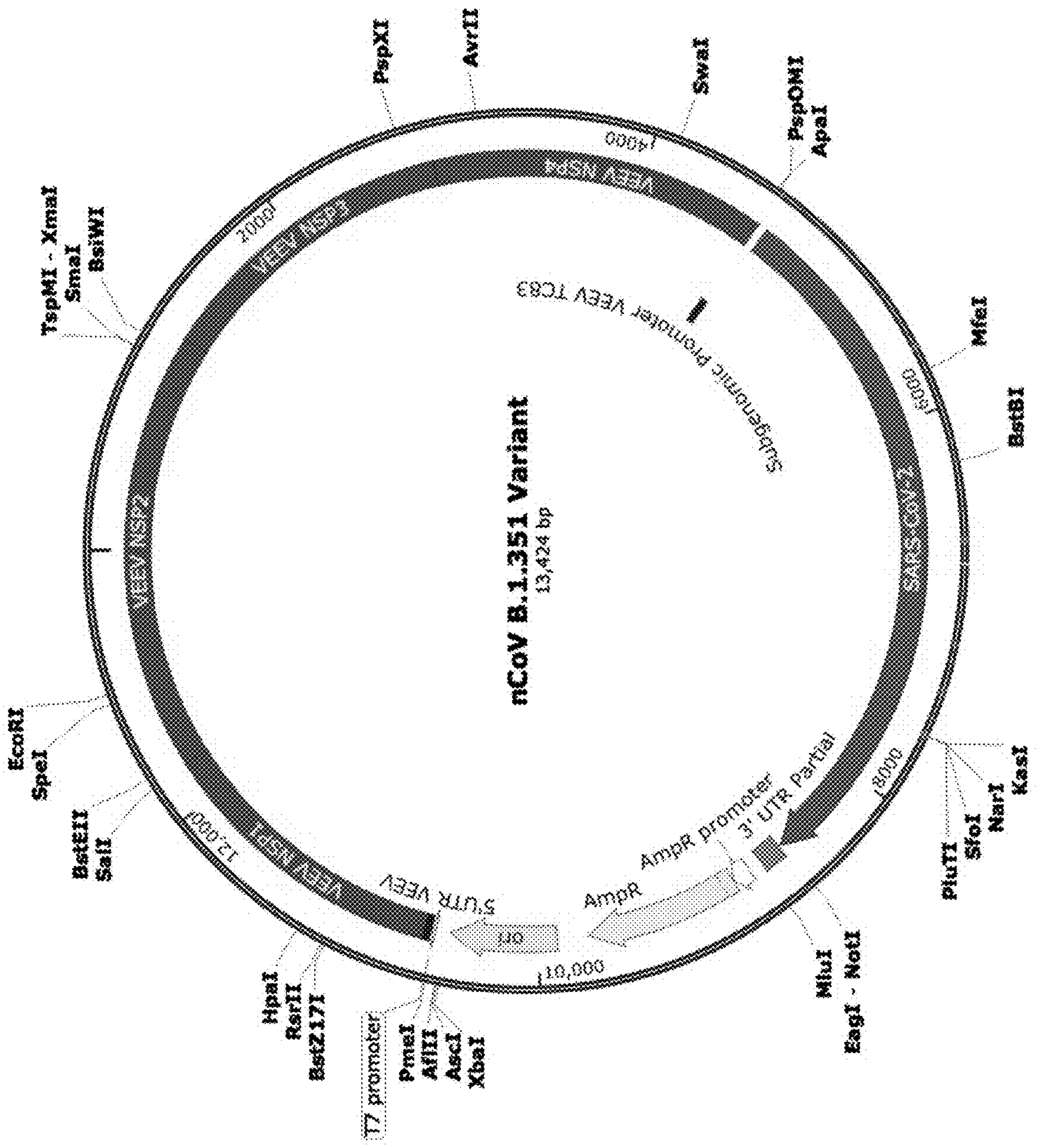

FIG. 10 shows the construct map of another embodiment of the DNA expression vector according to the invention encoding another embodiment of the saRNA construct of the invention. The construct comprises a VEEV backbone as shown in FIG. 2, harbouring the gene encoding the nCov B.1.351 variant (i.e. the South African variant) of SARS-CoV-2 native coronavirus surface S glycoprotein as the antigen or GOI.

Figure 11:
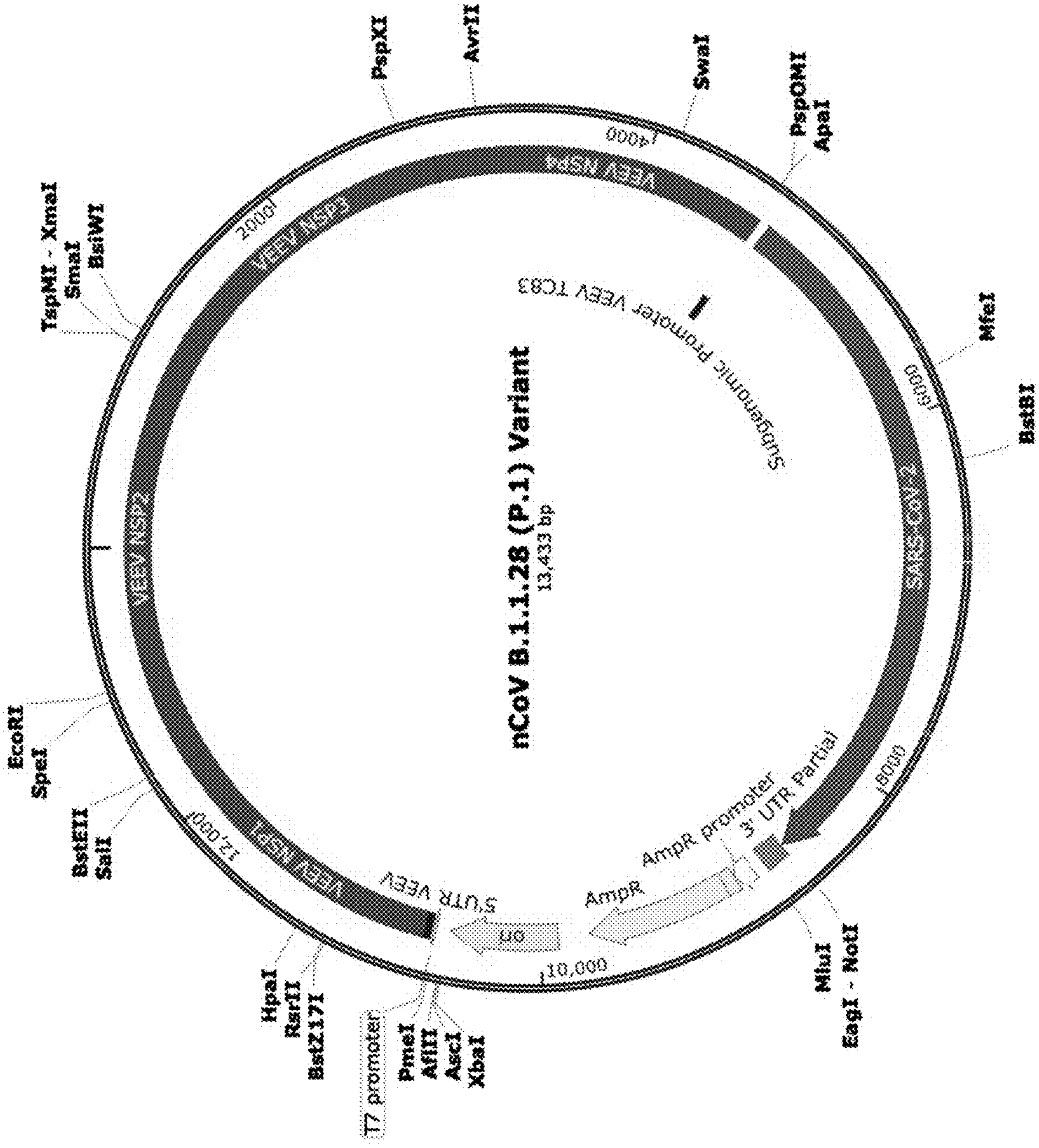

FIG. 11 shows the construct map of another embodiment of the DNA expression vector according to the invention encoding another embodiment of the saRNA construct of the invention. The construct comprises a VEEV backbone as shown in FIG. 2, harbouring the gene encoding the nCov B.1.1.28 (P.1) variant (i.e. the Brazil variant) of SARS-CoV-2 native coronavirus surface S glycoprotein as the antigen or GOI.

EXAMPLES

The inventors have designed and developed a self-amplifying RNA vaccine against the SARS-CoV-2 virus, the causative agent of COVID-19. Specifically, the saRNA is based on the backbone sequence of Venezuelan Equine Encephalitis Virus (VEEV) where the structural genes have been replaced by the full-length codon optimized sequence of the SARS-CoV-2 surface S1 glycoprotein containing two point mutations required to stabilise the protein in its pre-fusion conformation.

Figure 1A:
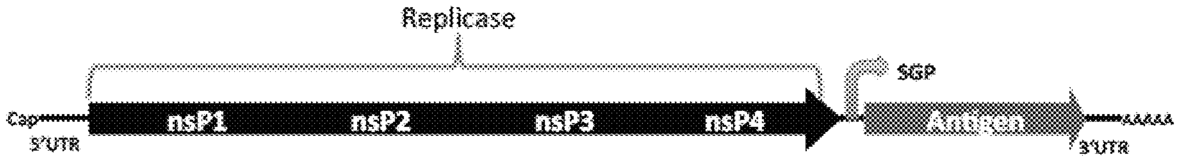
Figure 1B:
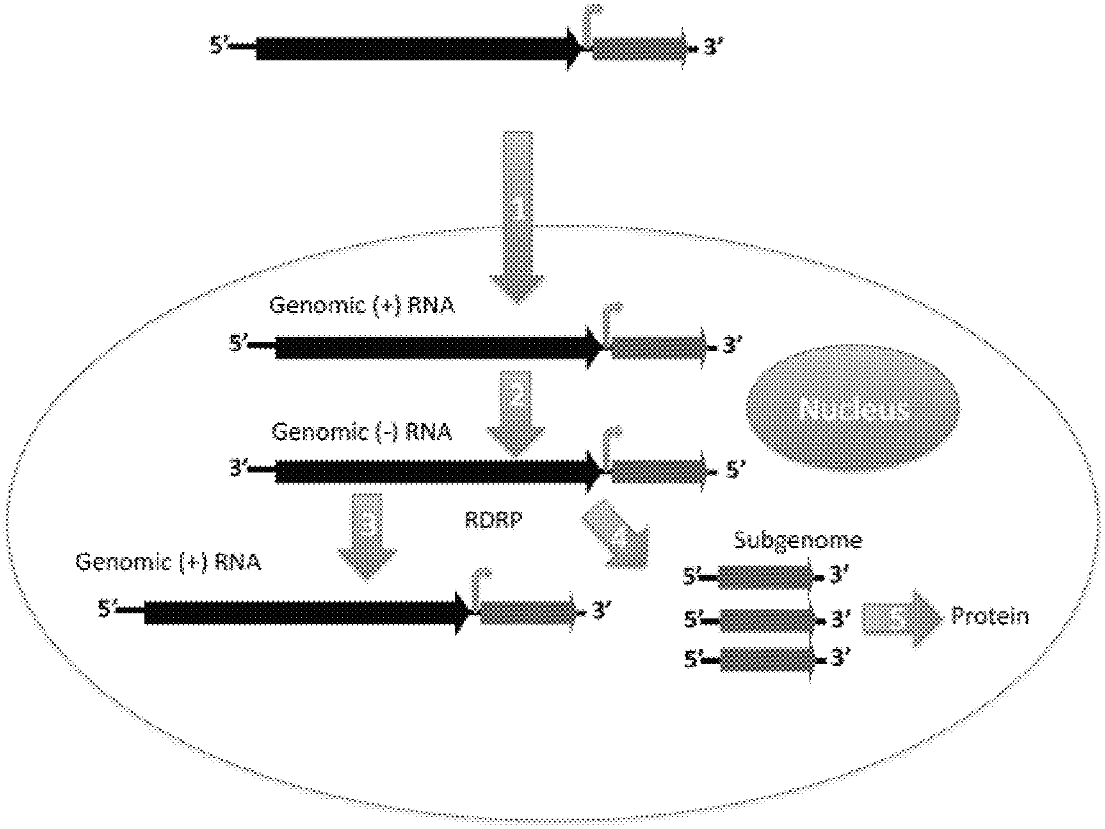

Referring to FIG. 1, there is shown one embodiment of a self-amplifying RNA replicon according to the invention.

(1) The RNA replicon is first delivered to the cytoplasm;
(2) In the cytoplasm, the open reading frame encoding the four non-structural proteins (nsP1-4) that forms the RNA-dependent polymerase (RDRP), is then translated which results in the production of a negative-sense copy of the genome. Innate sensing of the double stranded RNA intermediate is then triggered;
(3) RNA-dependent polymerase catalysis produces positive-sense genomes from the negative sense copy;
(4) RNA-dependent polymerase transcription of the sub-genome leads to extremely high amplification; and
(5) The SARS-CoV-2 surface S1 glycoprotein antigen is then translated leading to protein expression, which results in an immune response to that antigen.

Materials and Methods

Cloning of SARS-CoV-2 saRNA

Four DNA strings covering the entire S glycoprotein (sequence 2) and including the K986P and V987P stabilisation mutations were designed and codon optimized using the GeneArt Gene Otimizer software. These strings were synthesized by GeneArt (Invitrogen, UK) assembled into a single sequence by Gibson assembly and cloned into the Venezuelan Equine Encephalitis Virus (VEEV) replicon. pDNA was then transformed into *Escherichia coli*, grown in 50 mL LB culture with 1 mg/mL carbenicillin (Sigma Aldrich, UK) and purified using a Plasmid Plus Maxiprep kit (QIAGEN, UK). pDNA concentration and purity were measured on a NanoDrop One (ThermoFisher, UK) prior to use.

In Vitro Transcription of saRNA

Self-amplifying RNA was produced using in vitro transcription (IVT). pDNA was linearized using MluIO for 2 h at 37° C. and heat inactivated at 80° C. for 20 min. For in vitro transfections, co-transcriptionally capped RNA was synthesized using 1 μg of linearized DNA template in a mMessage mMachine™ reaction (Promega, UK) and purified using a MEGAClear™ column (Promega, UK) according to the manufacturer's protocol. For in vivo experiments, uncapped IVT RNA was synthesized using 1 μg of linearized DNA template in a MEGAScript™ reaction (Promega, UK) according to the manufacturer's protocol. Transcripts were then purified by overnight LiCl precipitation at −20° C., pelleted by centrifugation at 14,000 RPM for 20 min, washed with 70% EtOH, centrifuged at 14,000 RPM for 5 min and then resuspended in UltraPure H2O. Purified transcripts were then capped using the ScriptCap™ m7G Capping System (CellScript, Madison, WI, USA) and ScriptCapt™ 2'-O-Methyltransferase Kit (CellScript, Madison, WI, USA) simultaneously according to the manufacturer's protocol. Capped transcripts were then purified by LiCl precipitation as detailed above, resuspended in UltraPure H2O and stored at −80° C. until further use.

saRNA Formulation saRNA was formulated with 8 kDa poly(CBA-4-amino-1-butanol) (pABOL) at a ratio of 45:1 polymer to RNA (w/w) in a buffer of 20 mM HEPES (pH 7.4) with 5% glucose plus or minus 10 ug MPLA (invitrogen). saRNA was formulated in LNPs. LNPs made from a mixture of ionizable cationic lipid, phosphatidylcholine, cholesterol, and polyethylene glycol (PEG)-lipid.

Clinical Manufacture

Clinical grade saRNA vaccine substance was manufactured under contract by Trilink (San Diego) using the same pDNA template for in vitro transcription with co-capping using Trilink's AU clean-cap technology. LNP formulation was performed by Polymun.

In Vitro Transfections

Transfections were performed in HEK293T.17 cells (ATCC, USA), HeLa cells (ATCC, USA) or MRC5 (ATCC, USA) that were maintained in culture in either complete Dulbecco's Modified Eagle's Medium (cDMEM) (Gibco, Thermo Fisher, UK) (HEK, HeLa cells) or Modified Eagle's Medium (cMEM) (Gibco, Thermo Fisher, UK) containing 10% fetal calf serum (FCS), 5 mg/mL L-glutamine and 5 mg/mL penicillin/streptomycin (Thermo Fisher, UK). Cells were plated at a density of 50,000 cells per well in a clear 96 well plate 24 h prior to transfection. For the transfection, the media was completely removed and replace with 50 μL of pre-warmed transfection medium (DMEM or MEM with 5 mg/mL L-glutamine). 100 μL of the polyplex solution was added to each well and allowed to incubate for four hours, then the transfection media was completely removed and replaced with 100 μL of cDMEM. After 48 h from the initial transfection cells were assessed for expression by Flow cytometry.

Flow Cytometry

Flow cytometry was performed to assess surface expression of the S glycoprotein following transfect of HEK293T cells. Transient expression of S glycoprotein was assessed by FC. 48 h post transfection, 293T.17 cells were rinsed with PBS, dissociated with cell dissociation buffer (GIBCO), washed with FACS buffer (2.5% FBS, 1 mM EDTA, 25 mM HEPES in 1×PBS) and pelleted at 600× g, 5 min. Cells were resuspended in FACS buffer and counted using trypan blue. Cells were then stained with aqua viability dye (1:400) for 20 min at RT in the dark, then washed twice with FACS buffer. 2.5 μg/mL in 100 μL FACS buffer of primary polyclonal or monoclonal anti-Env Ab were used to stain 1×10^6 cells per well in U bottom 96-well plates, 30 min at RT in the dark. Antibody A is a rabbit polyclonal/PA1-41165, Antibody B is a mouse monoclonal MA1-41173 (ThermoFisher). Cells were then washed twice with 125 μL FACS buffer and secondary detection antibody was added onto the cells at 0.5 μg/10^6 cells in 100 μL FACS buffer per well. Antibody A was detected BD Pharmigen FITIC goat anti-rabbit IgG, cat 554020 and antibody B with BD Pharmigen APC goat anti-mouse Ig, cat 550826 and antibody. After 20 min incubation in the dark, cells were washed twice, resuspended in 100 μL PBS and fixed with an additional 100 μL 3% paraformaldehyde (Polysciences), final 1.5%. Samples were acquired on a LSRFortessa FC (BD) using FACSDiva (BD) and data interpreted using FlowJo v.10.1 software (Treestar). Mean fluorescence intensity (MFI) values of the 'live cells' gate were used to analyze the results.

In Vivo Immunogenicity of the COVID-19 nCoV VEEV saRNA Replicon

BALB/c mice were immunized IM in one hind leg with either 1 or 0.1 μg of HA saRNA formulated with either PABOL-8 (FIG. 5) or in LNPs (FIGS. 6A and 6B) in a total volume of 50 μL. Blood was collected after 2 and 4 weeks from study onset via tail bleeding, centrifuged at 10,000 rpm for 5 min and then the serum was removed and stored at −80° C. until further use.

S Glycoprotein-Specific ELISA

A semi-quantitative immunoglobulin ELISA protocol was performed. Briefly, 0.5 μg/mL of soluble trimeric S-glycoprotein (deleted for the transmembrane and cytoplasmic tail) was used to coated ELISA plates were blocked with 1% BSA/0.05% Tween-20 in PBS. After washing, diluted samples were added to the plates and incubated for 2 h, washed, and a 1:4,000 dilution of anti-mouse IgG-HRP (Southern Biotech, UK) was used. Standards were prepared by coating ELISA plate wells with anti-mouse Kappa (1:1,000) and Lambda (1:1,000) light chain (Serotec, UK), blocking with PBS/1% BSA/0.05% Tween-20, washing and adding purified IgG (Southern Biotech, UK) starting at 1,000 ng/mL and titrating down with a 5-fold dilution series. Samples and standard were developed using TMB (3,3'-5,5'-tetramethylbenzidine) and the reaction was stopped after 5 min with Stop solution (Insight Biotechnologies, UK). Absorbance was read on a spectrophotometer (VersaMax, Molecular Devices) with SoftMax Pro GxP v5 software.

Example 1—Construction of the COVID-19 nCoV VEEV saRNA Replicon

The saRNA replicon-based vaccine of the invention is based on the published sequence of the SARS-CoV-2 envelope, published online on Jan. 10, 2020 (QHD43416.1)—SEQ ID No: 3.

The inventors made two amino acid mutations (K986P and V987P) identified for stabilisation of the SARS-CoV-2 S glycoprotein trimer in its native-like pre-fusion conformation (Science; 2020; 367:1260), as set out in SEQ ID No: 4. This protein sequence was then codon optimised using GeneArt's GeneOptimizer™ software for human expression, and the corresponding DNA sequence is shown as SEQ ID No: 6.

Figure 3:
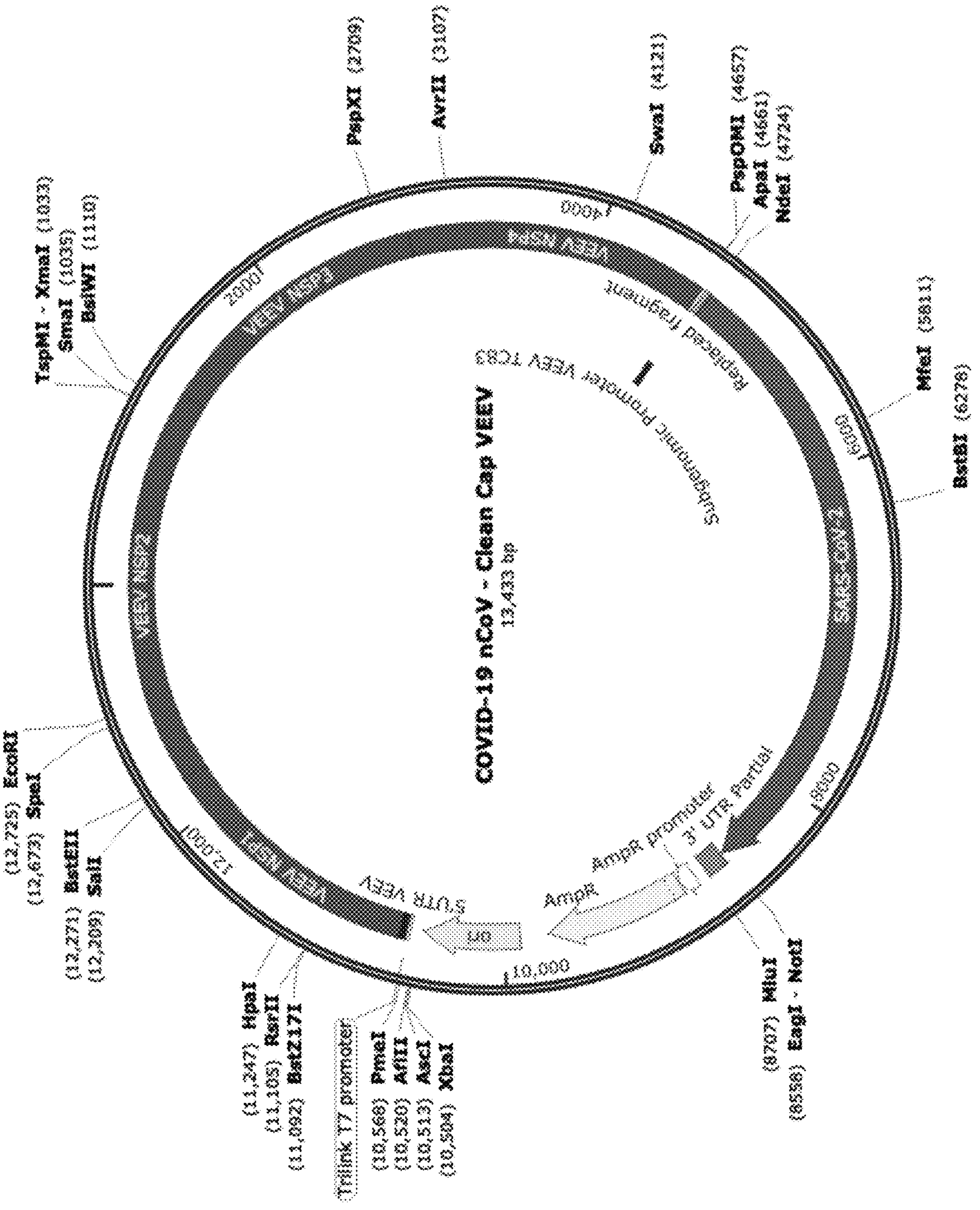

SEQ ID No: 6 was then inserted into the expression plasmid based on the VEEV backbone, as shown in FIG. 2, to thereby provide the saRNA replicon shown in FIG. 3. The resultant plasmid is designed for production of saRNA by in vitro transcription. The correct insertion of the SARS-CoV-2 S glycoprotein sequence (i.e. the antigen) in the plasmid shown in FIG. 3 was confirmed by Sanger Sequencing. The full plasmid sequence is given as SEQ ID No: 34, which encodes the saRNA sequence given as SEQ ID No: 33.

Figure 4:
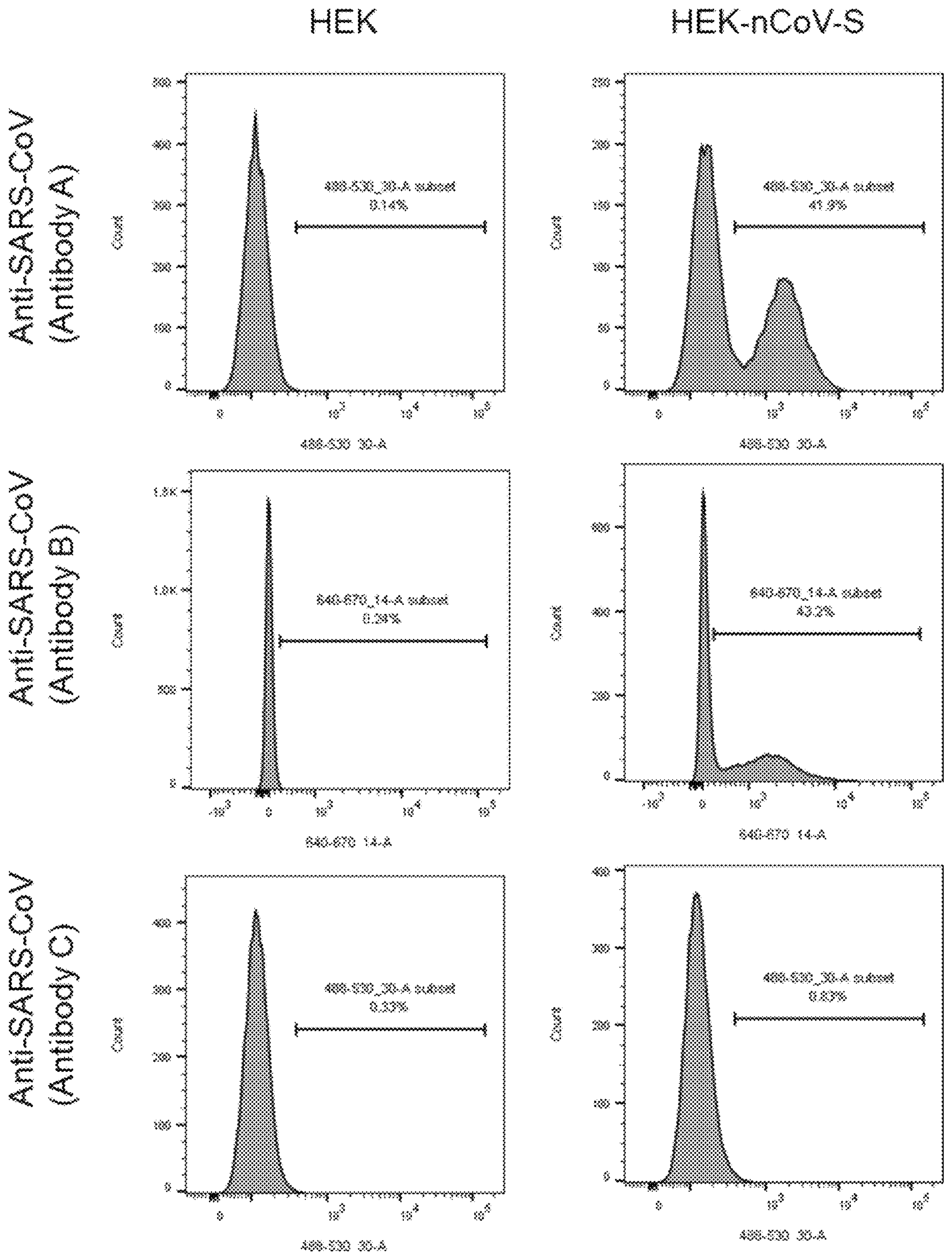

Example 2—Expression of SARS-CoB-2 S Protein from the COVID-19 nCoV VEEV saRNA Replicon Expression levels of the SARS-CoV-2 S antigen protein was assessed in HEK cells by Flow Cytometry following transfection of HEK 293T cells with the saRNA replicon shown in FIG. 3. Expression was detected using polyclonal and monoclonal antibodies, and the results are shown in FIG. 4. The left hand panels depict non-transfected cells, and the right hand panels show cells transfected with saRNA encoding the S glycoprotein of SARS-CoV-2 stained with polyclonal sera (antibody A) and a monoclonal (antibody B) known to bind to shared epitopes between SARS and SARS-CoV2. As can be seen from the data, distinct peaks are observed using both the polyclonal and monoclonal antibodies (in the right hand panels of FIG. 4), and so it is clear that SARS-CoV-2 S protein is being expressed at high levels.

Example 3—Immunogenicity of the COVID-19 nCoV VEEV saRNA Replicon

In order to determine the immunogenicity of the saRNA replicon, female Balb/c mice (n=8 per group) were immunized intramuscularly with 10 ug of saRNA formulated in a cationic polymer pABOL with and without MPLA (monophosphoryl lipid A) acting as an adjuvant.

Figure 5:
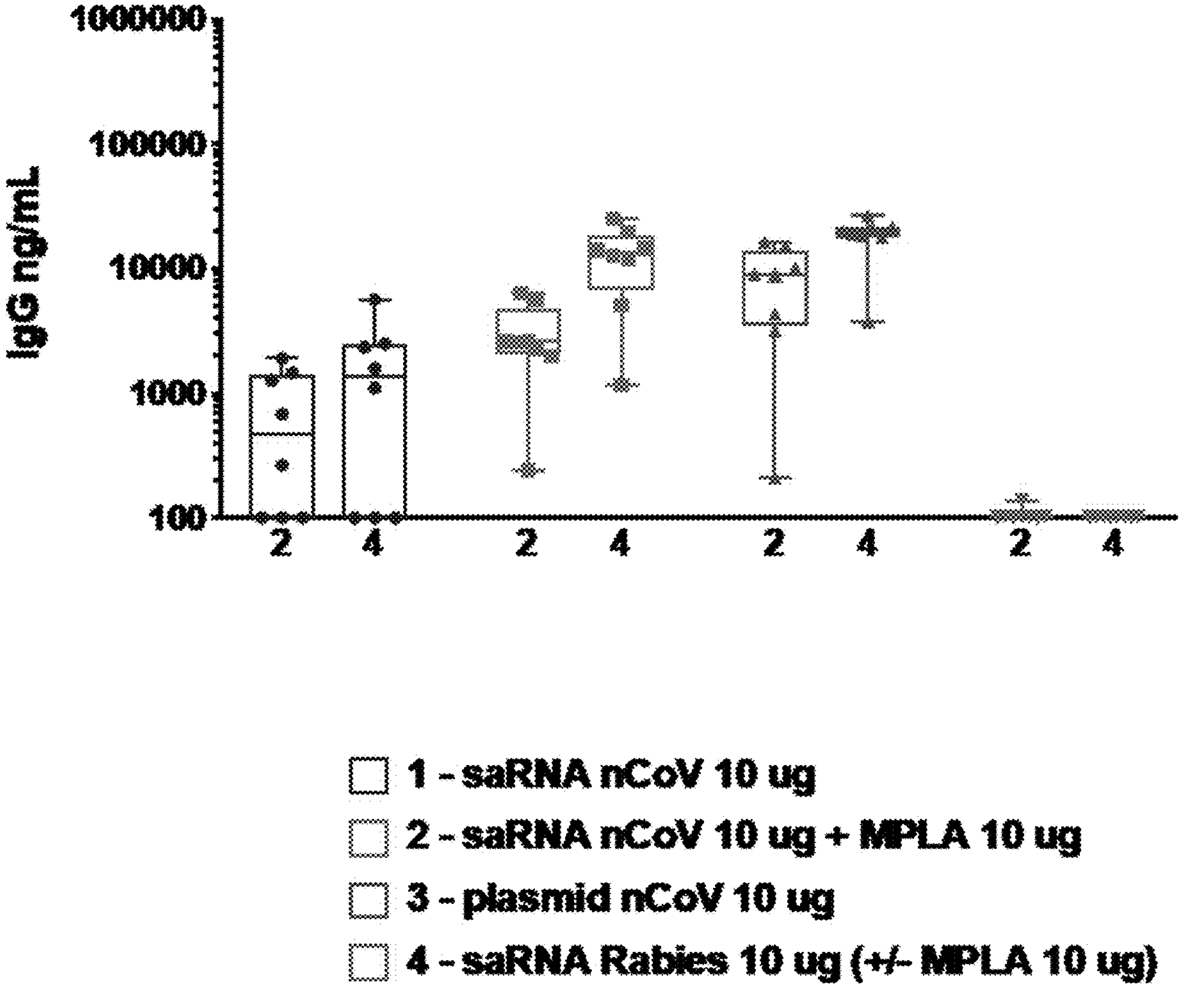
FIG. 5 shows binding antibody responses following the administration of saRNA formulated in pABOL plus/minus MPLA or plasmid DNA administered with electroporation. The table shows mean responses (ng/ml) and SEM.

Responses were compared to a DNA expression plasmid also encoding the modified S glycoprotein and delivered with electroporation. SaRNA encoding the rabies glycoprotein was used as a negative control, and the results are shown in FIG. 5, and Table 1.

TABLE 1

Antibody responses to administration of the saRNA COVID-19 vaccine

| | Mean 2 Weeks | SEM | Mean 2 Weeks | SEM |
|---|---|---|---|---|
| 1—saRNA nCoV 10 ug | 707.69 | 265.06 | 1652.32 | 677.7 |
| 2—saRNA nCoV 10 ug + MPLA 10 ug | 3026.43 | 696.43 | 13040.3 | 2658.57 |
| 3—plasmid nCoV 10 ug | 8398.91 | 1969.72 | 18561.73 | 2343.22 |
| 4—saRNA Rabies 10 ug (+/− MPLA 10 ug) | 45.36 | 14.09 | 0 | 0 |

As can be seen from the data, robust binding antibody responses determined by ELISA were induced when saRNA was formulated in pABOL plus MPLA at two and four weeks post a single vaccination. These were equivalent to the responses induced by plasmid DNA administered by electroporation (a gold standard in this model). There were no (or only background) responses to saRNA encoding the rabies glycoprotein, acting as a negative control.

Example 4—Clinical Trials—Delivery of the COVID-19 nCoV VEEV saRNA Replicon

The inventors then investigated the delivery of saRNA encoding the modified SARS-CoV-2 S glycoprotein when encapsulated in Lipid Nano Particles (LNPs) in human clinical trials.

These LNPs contain an ionizable cationic lipid, phosphatidylcholine/cholesterol/PEG-lipid and the saRNA encapsulation self-assembly process in which an aqueous solution of saRNA is rapidly mixed with a solution of lipids dissolved in ethanol.

Figure 6A:
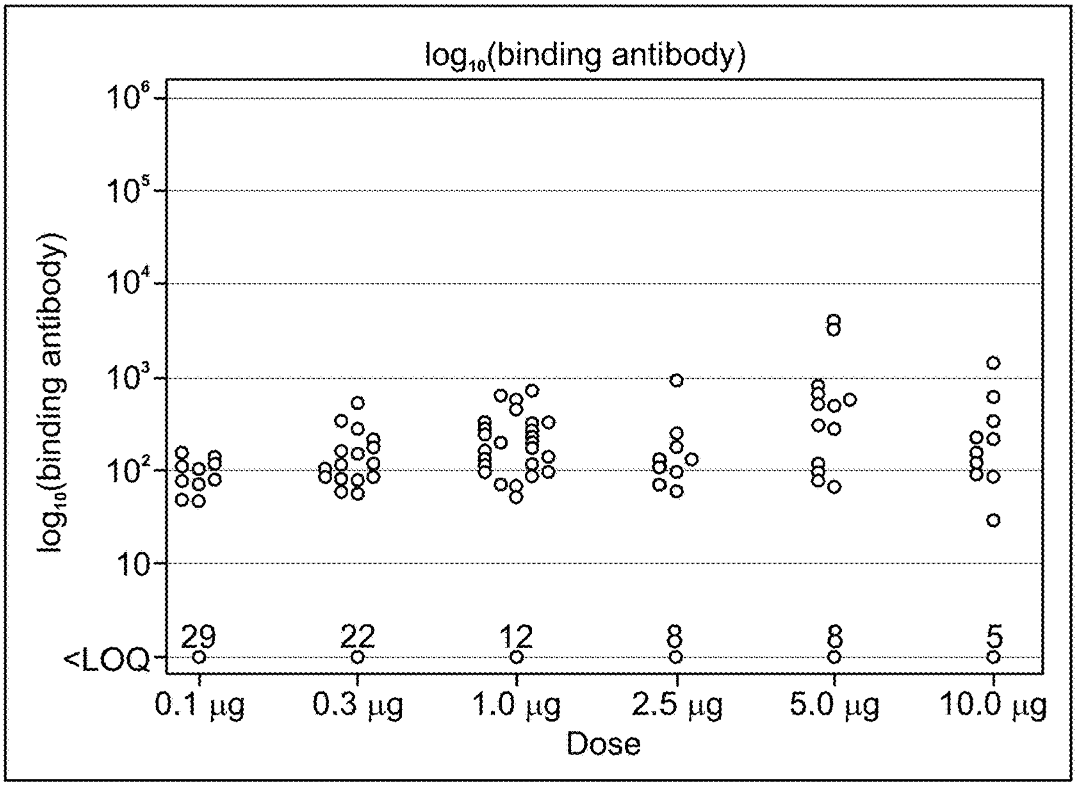
FIG. 6A shows dose response to vaccination in humans with one embodiment of the SARS-CoV-2-saRNA construct when encapsulated in Lipid Nano Particles (LNP).

Referring to FIG. 6A, there is shown the dose response to vaccination in humans with the CoV-saRNA construct when encapsulated in Lipid Nano Particles (LNPs). Human volunteers were immunized with an escalating dose (0.1-10 ug) of the CoV-saRNA vaccine at 0 and 4 weeks and the level of binding antibodies (ELISA) determined at 6 weeks. As can be seen, increasing responses were observed up to a 10 ug dose with >70% seroconversion.

Figure 6B:
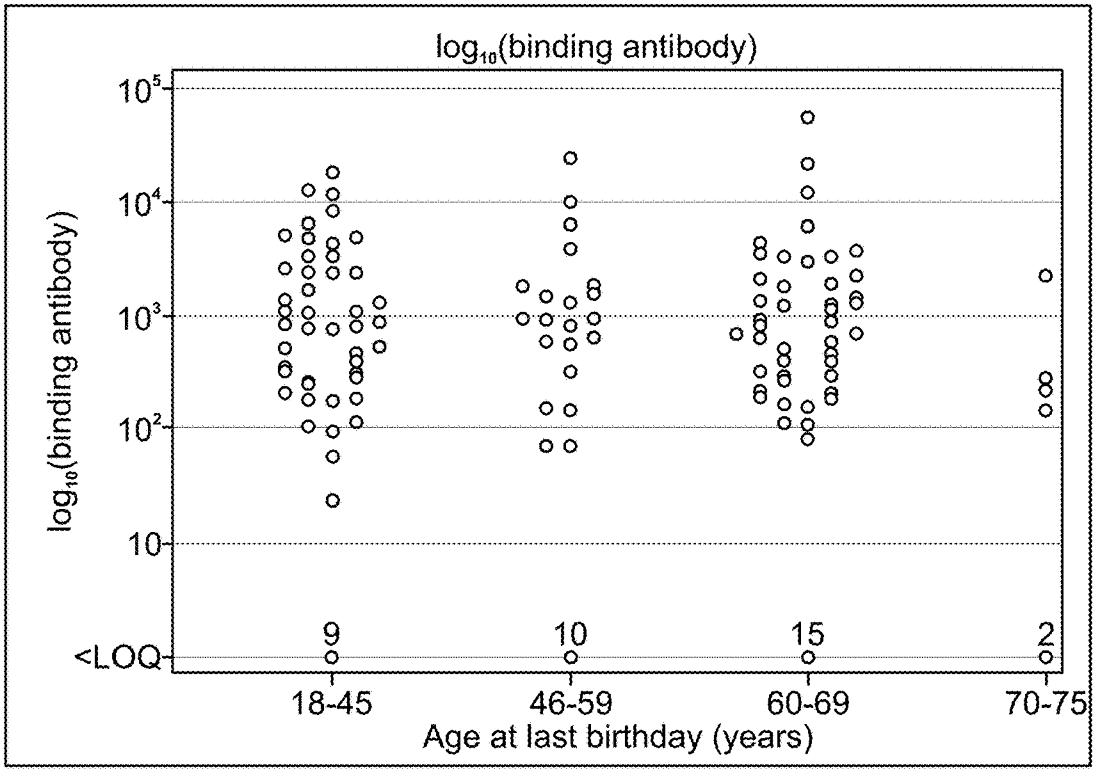
FIG. 6B shows age response to vaccination in humans with the CoV-saRNA construct when encapsulated in LNPs.

Referring to FIG. 6B, there is shown the age response to vaccination in humans with the CoV-saRNA construct when encapsulated in LNPs. Human volunteers were immunized with 1 ug of formulated CoV-saRNA vaccine at week 0, boosted with 10 ug at week 12, and the level of binding antibodies (using ELISA) was determined at 14 weeks. Responses were observed across all age groups, percentage seroconversion ranged from 67-85%. The mean level of serum binding responses in the 18-45 year old cohort were high in this cohort given the vaccine at 0 and 12 weeks than in the previous cohort immunized at 0 and 4 weeks.

Taken together, these data demonstrate that the saRNA vaccine of the invention (for immunising against any coronavirus infection, but especially COVID-19) can induce robust antibody responses when administered in two different formulations, pABOL+MPLA and LNPs.

Conclusions

The invention described herein is the development of a self-amplifying RNA (saRNA) vaccine designed to prevent COVID-19 caused by infection with the SARS-CoV-2 virus. Specifically, the saRNA vaccine carries the genetic sequence for the spike glycoprotein disposed on the surface of the virus, i.e. S1. When the vaccine is injected into the muscle, the saRNA provides the genetic blueprint that instructs cells to make this viral protein, which is recognised by the immune system which makes protective antibodies. These antibodies work to protect the vaccinated individual such that they are immune to the virus when exposed in the community.

Advantageously, the use of a specific codon optimised sequence of a prefusion stabilised version of the S glycoprotein of SARS-CoV-2 virus which in a saRNA vaccine vector means that antibodies are produced by the host which are immunospecific for the prefusion version of the glycoprotein and not the attached or fused version of the glycoprotein. The specific sequence and its combination within an saRNA vector are unique and would not have been obvious. The inventors believe that this is the first saRNA vaccine developed against COVID-19. Furthermore, the codon optimisation, sequence modification and membrane tethered presentation are designed to optimise the induction of effective neutralising antibodies. The COVID-19 saRNA vaccine has been shown to induce optimal responses in mice. The inventors also envisage delivering this vaccine as a saRNA which co-expresses the innate inhibitor protein blocking or reducing the binding of PACT to RNA, i.e. OFR4a (NS4a) of any coronaviruses, as discussed in Example 5.

Example 5—saRNA Constructs for SARS-CoV2 with Innate Inhibitor Protein (IIP)

The inventors constructed a COVID-19 nCoV VEEV saRNA replicon in which the antigen was co-expressed with an innate inhibitor protein. The IIP blocks or reduces the binding of PACT to RNA, and thereby reduces the innate immune response.

Referring to FIG. 7, there is shown the construct map of one embodiment of the saRNA construct of the invention on the VEEV backbone harbouring the gene encoding the SARS-CoV-2 native coronavirus surface S glycoprotein as the antigen (or GOI), and also ORF4a, which acts as an innate inhibitor protein (IIP) to suppress the innate response in a subject treated with the construct.

Example 6—saRNA Constructs for SARS-CoV2 Variants/Mutants

The inventors constructed a series of additional COVID-19 nCoV VEEV saRNA replicons in which the antigen was a variant of the SARS-CoV-2 surface glycoprotein, such as the B.1.1.7 UK variant (FIG. 8), the B.1.1.7 UK+E484K variant (FIG. 9), the B.1.351 South African variant (FIG. 10), or the B.1.1.28 (P.1) Brazilian variant (FIG. 11).

The invention claimed is:

1. A self-amplifying RNA (saRNA) construct comprising a nucleic acid sequence encoding a coronavirus surface glycoprotein, or a fragment or variant thereof, wherein the RNA construct comprises a sequence, which encodes an innate inhibitor protein (IIP), which is capable of reducing or blocking the innate immune response to the saRNA.

2. The saRNA according to claim 1, wherein the RNA construct comprises or is derived from a positive stranded RNA virus selected from the group of genus consisting of: alphavirus, picornavirus, flavivirus; rubivirus; pestivirus; hepacivirus; calicivirus and coronavirus; optionally wherein the RNA construct comprises or is derived from a virus selected from the group of species consisting of: Venezuelan Equine Encephalitis Virus (VEEV); enterovirus 71; Encephalomyocarditis virus; Kunjin virus; and Middle East respiratory syndrome virus.

3. The saRNA according to claim 1, wherein the RNA construct comprises or is derived from Venezuelan Equine Encephalitis Virus.

4. The saRNA according to claim 1, wherein the saRNA comprises a nucleic acid sequence encoding a coronavirus surface glycoprotein, or a fragment or variant thereof, selected from a group consisting of SARS-COV-2 surface glycoprotein, or a fragment or variant thereof; SARS-COV surface glycoprotein, or a fragment or variant thereof; and MERS-COV surface glycoprotein, or a fragment or variant thereof.

5. The saRNA according to claim 1, wherein the saRNA comprises a nucleic acid sequence encoding SARS-COV-2 surface glycoprotein having an amino acid sequence as set out in any of SEQ ID No: 3, 47, 50, 53 or 56, or a fragment or variant thereof.

6. The saRNA according to claim 1, wherein the saRNA comprises a nucleic acid sequence encoding MERS-COV surface glycoprotein having an amino acid sequence as set out in SEQ ID No: 1, or a fragment or variant thereof, optionally wherein the saRNA comprises a nucleic acid sequence encoding modified MERS-COV surface glycoprotein comprising an amino acid sequence which has at least one modification in amino acid 1060 or amino acid 1061 of SEQ ID No: 1.

7. The saRNA according to claim 1, wherein the saRNA comprises a nucleic acid sequence encoding SARS-COV surface glycoprotein having an amino acid sequence as set out in SEQ ID No: 2, or a fragment or variant thereof, optionally wherein the modified SARS-COV surface glycoprotein comprises a modification in amino acid 968 and amino acid 969 of SEQ ID No: 2.

8. The saRNA according to claim 1, wherein the saRNA comprises a nucleic acid sequence encoding coronavirus surface glycoprotein or a fragment or variant thereof in its pre-fusion conformation, optionally wherein the saRNA comprises a nucleic acid sequence encoding coronavirus surface glycoprotein trimer.

9. The saRNA according to claim 1, wherein the saRNA comprises a nucleic acid sequence encoding modified SARS-COV-2 surface glycoprotein comprising an amino acid sequence which has at least one modification in amino acid 986 and/or amino acid 987 of any of SEQ ID No: 3, 47, 50, 53 or 56, optionally wherein the modification at amino acid K986 comprises a substitution with a proline, i.e. K986P; and/or wherein the modification at amino acid V987 comprises a substitution with a proline, i.e. V987P.

10. The saRNA according to claim 9, wherein the saRNA comprises a nucleic acid sequence encoding SARS-COV-2 surface glycoprotein having an amino acid sequence as set out in SEQ ID No: 4, or a fragment or variant thereof.

11. The saRNA according to claim 1, wherein the saRNA comprises a nucleic acid sequence encoding modified SARS-COV-2 surface glycoprotein comprising a mutated furin cleavage site, optionally wherein the saRNA comprises a nucleic acid sequence encoding modified SARS-COV-2 surface glycoprotein comprising an amino acid sequence which has at least one, two, three or four modifications in amino acids 681, 682, 683 and 684 of any of SEQ ID No: 3, 47, 50, 53 or 56.

12. The saRNA according to claim 1, wherein the saRNA is encoded by a DNA sequence as set out in SEQ ID No: 6, or a fragment or variant thereof, and/or wherein the saRNA comprises a sequence as set out in SEQ ID No: 36, or a fragment or variant thereof.

13. The saRNA according to claim 1, wherein:

(a) the saRNA comprises a nucleotide sequence encoding SARS-COV-2, MERS-COV or SARS-COV surface glycoprotein which lacks the transmembrane domain and/or the cytoplasmic domain, or a truncation thereof;

(b) the saRNA construct comprises a nucleic acid sequence encoding truncated SARS-CoV-2 or SARS-COV surface glycoprotein having an amino acid sequence which lacks the amino acid sequence as set out in SEQ ID No: 37, or a fragment or variant thereof; and/or wherein the saRNA construct comprises a nucleic acid sequence encoding truncated SARS-COV-2 surface glycoprotein having an amino acid sequence as set out in SEQ ID No: 38, or a fragment or variant thereof; and/or (c) the saRNA is encoded by a DNA sequence as set out in SEQ ID No: 39, or a fragment or variant thereof, and/or wherein the saRNA comprises a sequence as set out in SEQ ID No: 40, or a fragment or variant thereof.

14. The saRNA according to claim 1, wherein:

(a) the saRNA comprises a nucleotide sequence encoding SARS-COV-2, MERS-COV or SARS-COV surface glycoprotein which lacks an endoplasmic reticulum (ER) retrieval motif (KxHxx) from the cytoplasmic tail of the glycoprotein;

(b) at least one, two, three of four of the cysteines in the cytoplasmic tail of the glycoprotein remain present, optionally at least five, six, seven or eight of the cysteines in the cytoplasmic tail of the glycoprotein remain present; and/or (c) no more than 5, 6, 7, 8 or 9 amino acids are deleted from the C-terminus of the cytoplasmic tail of the glycoprotein, or no more 10, 11, 12, 13, 14 or 15 amino acids are deleted from the C-terminus of the cytoplasmic tail of the glycoprotein, or no more than 16, 17, 18, or 19 amino acids are deleted from the C-terminus of the cytoplasmic tail of the glycoprotein.

15. The saRNA according to claim 1, wherein:

(a) the saRNA construct comprises a nucleic acid sequence encoding truncated SARS-CoV-2 surface glycoprotein having an amino acid sequence as set out in SEQ ID No: 78, 81 or 84, or a fragment or variant thereof;

(b) the saRNA is encoded by a DNA sequence as set out in SEQ ID No: 79, 82, or 85 or a fragment or variant thereof; and/or (c) the saRNA comprises a sequence as set out in SEQ ID No: 80, 83 or 86, or a fragment or variant thereof.

16. The saRNA according to claim 1, wherein the saRNA comprises a nucleotide sequence which encodes a glycoprotein which comprises a trimerization motif, wherein:

(a) the trimerisation motif comprises a Foldon motif and an optional linker for enhancing trimerization, optionally wherein (i) the saRNA is encoded by a DNA sequence as set out in SEQ ID No: 41, or a fragment or variant thereof;

(ii) the saRNA comprises a sequence as set out in SEQ ID No: 42, or a fragment or variant thereof; and/or (iii) the saRNA construct comprises a nucleic acid sequence encoding a trimerization sequence having an amino acid sequence as set out in SEQ ID No: 43, or a fragment or variant thereof; and/or (b) the trimerization motif comprises a GCN4 motif and an optional linker for enhancing trimerization, optionally wherein (i) the saRNA is encoded by a DNA sequence as set out in SEQ ID No: 44, or a fragment or variant thereof;

the saRNA comprises a sequence as set out in SEQ ID No: 45, or a fragment or variant thereof; and/or (iii) the saRNA construct comprises a nucleic acid sequence encoding a trimerization sequence having an amino acid sequence as set out in SEQ ID No: 46, or a fragment or variant thereof.

17. The saRNA according to claim 1, wherein the innate inhibitor protein is Parainfluenza virus type 5 V protein (PIV5 V), optionally wherein: (i) the PIV5 V polypeptide comprises an amino acid sequence as set out in SEQ ID NO: 7, or a biologically active variant or fragment thereof, and/or (ii) the PIV5 V polypeptide is encoded by the nucleotide sequence as set out in SEQ ID NO: 8, or a variant or fragment thereof, and/or (iii) the RNA construct comprises an RNA nucleotide sequence as set out as SEQ ID No: 9, or a variant or fragment thereof.

18. The saRNA according to claim 1, wherein the innate inhibitor protein is selected from the group consisting of: ORF4a (NS4a) of any coronaviruses, or the nucleocapsid proteins of mouse hepatitis virus and SARS (coronavirus); and orthologues thereof.

19. The saRNA according to claim 1, wherein the RNA construct comprises a sequence, which encodes an innate inhibitor protein (IIP), which is a coronavirus ORF4a (NS4a), optionally wherein: (i) the MERS-COV ORF4a polypeptide comprises an amino acid sequence as set out in SEQ ID NO: 10, or a biologically active variant or fragment thereof; and/or (ii) the RNA construct of the first aspect comprises an RNA nucleotide sequence which encodes SEQ ID No: 10, or 59, or a variant or fragment thereof; and/or (iii) the MERS-COV ORF4a polypeptide is encoded by the nucleotide sequence as set out in SEQ ID NO: 11, or 60, or a variant or fragment thereof; and/or (iv) the RNA construct comprises an RNA nucleotide sequence as set out as SEQ ID No: 12, or 61, or a variant or fragment thereof.

20. The saRNA according to claim 1, wherein the RNA construct comprises at least one promotor, either genomic or sub-genomic, optionally wherein the promoter is as as set out in SEQ ID NO: 13, or a variant or fragment thereof.

21. The saRNA according to claim 1, wherein the RNA construct comprises a nucleotide sequence as set out in any of SEQ ID No: 33, or 62-66, or a fragment or variant thereof.

22. A nucleic acid sequence encoding the RNA construct according to claim 1, optionally wherein the nucleic acid sequence comprises a nucleotide sequence as set out in any of SEQ ID No: 34, or 67-71, or a fragment or variant thereof.

23. An expression cassette comprising a nucleic acid sequence according to claim 22.

24. A recombinant vector comprising the expression cassette according to claim 23, optionally wherein the vector comprises the nucleotide sequence as set out in any of SEQ ID NO: 35, or 72-76, or a variant or fragment thereof.

25. A pharmaceutical composition comprising the RNA construct according to claim 1, and a pharmaceutically acceptable vehicle.

26. A method of preparing the saRNA construct according to claim 1, the method comprising:

(a) (i) introducing, into a host cell, the vector according to claim 24; and
 (ii) culturing the host cell under conditions to result in the production of the RNA construct of the first aspect; or (b) transcribing the RNA construct from the vector the vector according to claim 24.

27. A method according to claim 26, wherein the method comprises preparing the saRNA construct using the DNA plasmid having a nucleic acid sequence as set out in SEQ ID No: 35, or 72-76, or a variant or fragment thereof, as the template.

28. The saRNA construct according to claim 1 for use as a medicament, or in therapy, or prophylaxis.

29. A vaccine comprising the saRNA construct according to claim 1.

30. The vaccine according to claim 29, wherein the saRNA construct is formulated in a lipid, liposome or a nanoparticle which comprises lipid, optionally wherein the formulation, liposome or nanoparticle comprises one or more components selected from a group consisting of: a cationic lipid; phosphatidylcholine; cholesterol; and polyethylene glycol (PEG)-lipid.

31. The vaccine according to claim 29, wherein the saRNA construct is formulated in a polyplex, optionally pABOL (poly(CBA-4-amino-1-butanol in which "CBA" is N,N'-cystaminebisacrylamide).

32. The saRNA construct according to claim 1 for use in stimulating an immune response in a subject.

* * * * *

SEQUENCE LISTING

```
<160> NUMBER OF SEQ ID NOS: 86

<210> SEQ ID NO 1
<211> LENGTH: 1353
<212> TYPE: PRT
<213> ORGANISM: MERS-CoV

<400> SEQUENCE: 1

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175
```

```
Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Phe Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590
```

-continued

```
Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
            645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
    690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
            725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
        755                 760                 765

Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
            805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
    850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
            885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
            965                 970                 975

Phe Tyr Arg Leu Asn Gly Val Gly Ile Thr Gln Gln Val Leu Ser Glu
            980                 985                 990

Asn Gln Lys Leu Ile Ala Asn Lys  Phe Asn Gln Ala Leu  Gly Ala Met
        995                 1000                1005

Gln Thr  Gly Phe Thr Thr Thr  Asn Glu Ala Phe His  Lys Val Gln
```

1010 1015 1020

Asp Ala Val Asn Asn Asn Ala Gln Ala Leu Ser Lys Leu Ala Ser
1025 1030 1035

Glu Leu Ser Asn Thr Phe Gly Ala Ile Ser Ala Ser Ile Gly Asp
1040 1045 1050

Ile Ile Gln Arg Leu Asp Val Leu Glu Gln Asp Ala Gln Ile Asp
1055 1060 1065

Arg Leu Ile Asn Gly Arg Leu Thr Thr Leu Asn Ala Phe Val Ala
1070 1075 1080

Gln Gln Leu Val Arg Ser Glu Ser Ala Ala Leu Ser Ala Gln Leu
1085 1090 1095

Ala Lys Asp Lys Val Asn Glu Cys Val Lys Ala Gln Ser Lys Arg
1100 1105 1110

Ser Gly Phe Cys Gly Gln Gly Thr His Ile Val Ser Phe Val Val
1115 1120 1125

Asn Ala Pro Asn Gly Leu Tyr Phe Met His Val Gly Tyr Tyr Pro
1130 1135 1140

Ser Asn His Ile Glu Val Val Ser Ala Tyr Gly Leu Cys Asp Ala
1145 1150 1155

Ala Asn Pro Thr Asn Cys Ile Ala Pro Val Asn Gly Tyr Phe Ile
1160 1165 1170

Lys Thr Asn Asn Thr Arg Ile Val Asp Glu Trp Ser Tyr Thr Gly
1175 1180 1185

Ser Ser Phe Tyr Ala Pro Glu Pro Ile Thr Ser Leu Asn Thr Lys
1190 1195 1200

Tyr Val Ala Pro Gln Val Thr Tyr Gln Asn Ile Ser Thr Asn Leu
1205 1210 1215

Pro Pro Pro Leu Leu Gly Asn Ser Thr Gly Ile Asp Phe Gln Asp
1220 1225 1230

Glu Leu Asp Glu Phe Phe Lys Asn Val Ser Thr Ser Ile Pro Asn
1235 1240 1245

Phe Gly Ser Leu Thr Gln Ile Asn Thr Thr Leu Leu Asp Leu Thr
1250 1255 1260

Tyr Glu Met Leu Ser Leu Gln Gln Val Val Lys Ala Leu Asn Glu
1265 1270 1275

Ser Tyr Ile Asp Leu Lys Glu Leu Gly Asn Tyr Thr Tyr Tyr Asn
1280 1285 1290

Lys Trp Pro Trp Tyr Ile Trp Leu Gly Phe Ile Ala Gly Leu Val
1295 1300 1305

Ala Leu Ala Leu Cys Val Phe Phe Ile Leu Cys Cys Thr Gly Cys
1310 1315 1320

Gly Thr Asn Cys Met Gly Lys Leu Lys Cys Asn Arg Cys Cys Asp
1325 1330 1335

Arg Tyr Glu Glu Tyr Asp Leu Glu Pro His Lys Val His Val His
1340 1345 1350

<210> SEQ ID NO 2
<211> LENGTH: 1255
<212> TYPE: PRT
<213> ORGANISM: SARS-CoV

<400> SEQUENCE: 2

Met Phe Ile Phe Leu Leu Phe Leu Thr Leu Thr Ser Gly Ser Asp Leu
1 5 10 15

-continued

```
Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
```

```
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860
```

-continued

```
Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
    1025                1030                1035

Pro His  Gly Val Val Phe Leu  His Val Thr Tyr Val  Pro Ser Gln
    1040                1045                1050

Glu Arg  Asn Phe Thr Thr Ala  Pro Ala Ile Cys His  Glu Gly Lys
    1055                1060                1065

Ala Tyr  Phe Pro Arg Glu Gly  Val Phe Val Phe Asn  Gly Thr Ser
    1070                1075                1080

Trp Phe  Ile Thr Gln Arg Asn  Phe Phe Ser Pro Gln  Ile Ile Thr
    1085                1090                1095

Thr Asp  Asn Thr Phe Val Ser  Gly Asn Cys Asp Val  Val Ile Gly
    1100                1105                1110

Ile Ile  Asn Asn Thr Val Tyr  Asp Pro Leu Gln Pro  Glu Leu Asp
    1115                1120                1125

Ser Phe  Lys Glu Glu Leu Asp  Lys Tyr Phe Lys Asn  His Thr Ser
    1130                1135                1140

Pro Asp  Val Asp Leu Gly Asp  Ile Ser Gly Ile Asn  Ala Ser Val
    1145                1150                1155

Val Asn  Ile Gln Lys Glu Ile  Asp Arg Leu Asn Glu  Val Ala Lys
    1160                1165                1170

Asn Leu  Asn Glu Ser Leu Ile  Asp Leu Gln Glu Leu  Gly Lys Tyr
    1175                1180                1185

Glu Gln  Tyr Ile Lys Trp Pro  Trp Tyr Val Trp Leu  Gly Phe Ile
    1190                1195                1200

Ala Gly  Leu Ile Ala Ile Val  Met Val Thr Ile Leu  Leu Cys Cys
    1205                1210                1215

Met Thr  Ser Cys Cys Ser Cys  Leu Lys Gly Ala Cys  Ser Cys Gly
    1220                1225                1230

Ser Cys  Cys Lys Phe Asp Glu  Asp Asp Ser Glu Pro  Val Leu Lys
    1235                1240                1245

Gly Val  Lys Leu His Tyr Thr
    1250                1255
```

<210> SEQ ID NO 3
<211> LENGTH: 1273
<212> TYPE: PRT
<213> ORGANISM: SARS-CoV-2

<400> SEQUENCE: 3

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Cys Ala Leu Asp Pro Leu Ser Glu Thr Lys Cys Thr Leu Lys
290 295 300

Ser Phe Thr Val Glu Lys Gly Ile Tyr Gln Thr Ser Asn Phe Arg Val
305 310 315 320

Gln Pro Thr Glu Ser Ile Val Arg Phe Pro Asn Ile Thr Asn Leu Cys
325 330 335

Pro Phe Gly Glu Val Phe Asn Ala Thr Arg Phe Ala Ser Val Tyr Ala
340 345 350

Trp Asn Arg Lys Arg Ile Ser Asn Cys Val Ala Asp Tyr Ser Val Leu
355 360 365

Tyr Asn Ser Ala Ser Phe Ser Thr Phe Lys Cys Tyr Gly Val Ser Pro
370 375 380

-continued

```
Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800
```

-continued

```
Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
```

```
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr
    1265                1270


<210> SEQ ID NO 4
<211> LENGTH: 1273
<212> TYPE: PRT
<213> ORGANISM: modified SARS-CoV-2

<400> SEQUENCE: 4

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300
```

-continued

```
Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
```

-continued

```
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140
```

-continued

```
Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270


<210> SEQ ID NO 5
<211> LENGTH: 4
<212> TYPE: PRT
<213> ORGANISM: SARS-CoV-2

<400> SEQUENCE: 5

Pro Arg Arg Ala
1


<210> SEQ ID NO 6
<211> LENGTH: 3822
<212> TYPE: DNA
<213> ORGANISM: Artificial Sequence
<220> FEATURE:
<223> OTHER INFORMATION: Synthetised Sequence

<400> SEQUENCE: 6

atgttcgtgt ttctggtgct gctgcctctg gtgtccagcc agtgtgtgaa cctgaccacc     60

agaacacagc tgcctccagc ctacaccaac agctttacca gaggcgtgta ctaccccgac    120

aaggtgttca gatccagcgt gctgcactct acccaggacc tgttcctgcc tttcttcagc    180

aacgtgacct ggttccacgc catccacgtg tccggcacca atggcaccaa gagattcgac    240

aaccccgtgc tgcccttcaa cgacggggtg tactttgcca gcaccgagaa gtccaacatc    300

atcagaggct ggatcttcgg caccacactg gacagcaaga cccagagcct gctgatcgtg    360

aacaacgcca ccaacgtggt catcaaagtg tgcgagttcc agttctgcaa cgaccccttc    420

ctgggcgtct actaccacaa gaacaacaag agctggatgg aaagcgagtt ccgggtgtac    480

agcagcgcca acaactgcac cttcgagtac gtgtcccagc ctttcctgat ggacctggaa    540

ggcaagcagg gcaacttcaa gaacctgcgc gagttcgtgt tcaagaacat cgacggctac    600

ttcaagatct acagcaagca cacccctatc aacctcgtgc gggatctgcc tcagggcttc    660

tctgctctgg aacccctggt ggatctgccc atcggcatca acatcacccg gtttcagaca    720

ctgctggccc tgcacagaag ctacctgaca cctggcgata gcagcagcgg atggacagct    780

ggtgccgccg cttactatgt gggctacctg cagcctagaa ccttcctgct gaagtacaac    840

gagaacggca ccatcaccga cgccgtggat tgtgcccttg atcctctgag cgagacaaag    900
```

-continued

```
tgcaccctga agtccttcac cgtggaaaag ggcatctacc agaccagcaa cttccgggtg    960
cagcccaccg aatccatcgt gcggttcccc aatatcacca atctgtgccc cttcggcgag   1020
gtgttcaatg ccaccagatt cgcctctgtg tacgcctgga accggaagcg gatcagcaat   1080
tgcgtggccg actactccgt gctgtacaac tccgccagct tcagcacctt caagtgctac   1140
ggcgtgtccc ctaccaagct gaacgacctg tgcttcacaa acgtgtacgc cgacagcttc   1200
gtgatccggg gagatgaagt gcggcagatt gcccctggac agacaggcaa gatcgccgac   1260
tacaactaca agctgcccga cgacttcacc ggctgtgtga ttgcctggaa cagcaacaac   1320
ctggactcca aagtcggcgg caactacaat tacctgtacc ggctgttccg gaagtccaat   1380
ctgaagccct tcgagcggga catctccacc gagatctatc aggccggcag caccccttgt   1440
aacggcgtgg aaggcttcaa ctgctacttc ccactgcagt cctacggctt tcagcccaca   1500
aatggcgtgg gctatcagcc ctacagagtg gtggtgctga gcttcgaact gctgcatgcc   1560
cctgccacag tgtgcggccc taagaaaagc accaatctcg tgaagaacaa atgcgtgaac   1620
ttcaacttca acggcctgac cggcacaggc gtgctgacag agagcaacaa gaagttcctg   1680
ccattccagc agtttggccg ggatatcgcc gataccacag acgccgttag agatccccag   1740
acactggaaa tcctggacat caccccttgc agcttcggcg gagtgtctgt gatcacccct   1800
ggcaccaaca ccagcaatca ggtggcagtg ctgtaccagg acgtgaactg taccgaagtg   1860
cccgtggcca ttcacgccga tcagctgaca cctacatggc gggtgtactc caccggcagc   1920
aatgtgtttc agaccagagc cggctgtctg atcggagccg agcacgtgaa caatagctac   1980
gagtgcgaca tccccatcgg cgctggcatc tgtgccagct accagacaca gacaaacagc   2040
cccagacggg ccagatctgt ggccagccag agcatcattg cctacacaat gtctctgggc   2100
gccgagaaca gcgtggccta ctccaacaac tctatcgcta tccccaccaa cttcaccatc   2160
agcgtgacca cagagatcct gcctgtgtcc atgaccaaga ccagcgtgga ctgcaccatg   2220
tacatctgcg gcgattccac cgagtgctcc aacctgctgc tgcagtacgg cagcttctgc   2280
acccagctga atagagccct gacagggatc gccgtggaac aggacaagaa cacccaagag   2340
gtgttcgccc aagtgaagca gatctacaag accccctccta tcaaggactt cggcggcttc   2400
aatttcagcc agattctgcc cgatcctagc aagcccagca agcggagctt catcgaggac   2460
ctgctgttca acaaagtgac actggccgac gccggcttca tcaagcagta tggcgattgt   2520
ctgggcgaca ttgccgccag ggatctgatt tgcgcccaga agtttaacgg actgacagtg   2580
ctgcctcctc tgctgaccga tgagatgatc gcccagtaca catctgccct gctggccggc   2640
acaatcacaa gcggctggac atttggagct ggcgccgctc tgcagatccc ctttgctatg   2700
cagatggcct acagattcaa cggcatcgga gtgacccaga atgtgctgta cgagaaccag   2760
aagctgatcg ccaaccagtt caacagcgcc atcggcaaga tccaggacag cctgagcagc   2820
acagcaagcg ccctgggaaa gctgcaggac gtggtcaacc agaatgccca ggcactgaac   2880
accctggtca agcagctgtc ctccaacttc ggcgccatca gctctgtgct gaacgatatc   2940
ctgagcagac tggaccctcc tgaggccgag gtgcagatcg acagactgat cacaggcaga   3000
ctgcagagcc tccagacata cgtgacccag cagctgatca gagccgccga gattagagcc   3060
tctgccaatc tggccgccac caagatgtct gagtgtgtgc tgggccagag caagagagtg   3120
gacttttgcg gcaagggcta ccacctgatg agcttccctc agtctgcccc tcacggcgtg   3180
gtgtttctgc acgtgacata cgttcccgct caagagaaga atttcaccac cgctccagcc   3240
atctgccacg acggcaaagc ccactttcct agagaaggcg tgttcgtgtc caacggcacc   3300
```

cattggttcg tgacacagcg gaacttctac gagccccaga tcatcaccac cgacaacacc 3360
ttcgtgtctg gcaactgcga cgtcgtgatc ggcattgtga acaataccgt gtacgaccct 3420
ctgcagcccg agctggacag cttcaaagag gaactggaca agtactttaa gaaccacaca 3480
agccccgacg tggacctggg cgatatcagc ggaatcaatg ccagcgtcgt gaacatccag 3540
aaagagatcg accggctgaa cgaggtggcc aagaatctga acgagagcct gatcgacctg 3600
caagaactgg ggaagtacga gcagtacatc aagtggccct ggtacatctg gctgggcttt 3660
atcgccggac tgattgccat cgtgatggtc acaatcatgc tgtgttgcat gaccagctgc 3720
tgtagctgcc tgaagggctg ttgtagctgt ggcagctgct gcaagttcga cgaggacgat 3780
tctgagcccg tgctgaaggg cgtgaaactg cactacacat ga 3822

<210> SEQ ID NO 7
<211> LENGTH: 222
<212> TYPE: PRT
<213> ORGANISM: Parainfluenza virus type 5

<400> SEQUENCE: 7

Met Asp Pro Thr Asp Leu Ser Phe Ser Pro Asp Glu Ile Asn Lys Leu
1 5 10 15

Ile Glu Thr Gly Leu Asn Thr Val Glu Tyr Phe Thr Ser Gln Gln Val
20 25 30

Thr Gly Thr Ser Ser Leu Gly Lys Asn Thr Ile Pro Pro Gly Val Thr
35 40 45

Gly Leu Leu Thr Asn Ala Ala Glu Ala Lys Ile Gln Glu Ser Thr Asn
50 55 60

His Gln Lys Gly Ser Val Gly Gly Gly Ala Lys Pro Lys Lys Pro Arg
65 70 75 80

Pro Lys Ile Ala Ile Val Pro Ala Asp Asp Lys Thr Val Pro Gly Lys
85 90 95

Pro Ile Pro Asn Pro Leu Leu Gly Leu Asp Ser Thr Pro Ser Thr Gln
100 105 110

Thr Val Leu Asp Leu Ser Gly Lys Thr Leu Pro Ser Gly Ser Tyr Lys
115 120 125

Gly Val Lys Leu Ala Lys Phe Gly Lys Glu Asn Leu Met Thr Arg Phe
130 135 140

Ile Glu Glu Pro Arg Glu Asn Pro Ile Ala Thr Ser Ser Pro Ile Asp
145 150 155 160

Phe Lys Arg Gly Arg Asp Thr Gly Gly Phe His Arg Arg Glu Tyr Ser
165 170 175

Ile Gly Trp Val Gly Asp Glu Val Lys Val Thr Glu Trp Cys Asn Pro
180 185 190

Ser Cys Ser Pro Ile Thr Ala Ala Ala Arg Arg Phe Glu Cys Thr Cys
195 200 205

His Gln Cys Pro Val Thr Cys Ser Glu Cys Glu Arg Asp Thr
210 215 220

<210> SEQ ID NO 8
<211> LENGTH: 666
<212> TYPE: DNA
<213> ORGANISM: Artificial Sequence
<220> FEATURE:
<223> OTHER INFORMATION: Synthetised Sequence

<400> SEQUENCE: 8

-continued

```
atggacccta ccgacctgag cttcagcccc gacgagatca acaagctgat cgagacaggc     60

ctgaacaccg tggaatactt caccagccag caagtgaccg gcacaagcag cctgggcaag    120

aacacaattc ctccaggcgt gaccggcctg ctgacaaatg ctgccgaggc caagatccaa    180

gagagcacca accaccagaa gggctctgtt ggaggcggag ccaagcctaa gaagcccaga    240

cctaagatcg ccatcgtgcc cgccgacgat aagacagtgc ctggcaagcc cattcctaat    300

cctctgctgg gcctcgacag caccccctagc acacagacag tgctggatct gagcggcaag    360

acactgccta gcggcagcta taagggcgtg aagctggcca agttcggcaa agaaaacctg    420

atgacccggt tcatcgagga acccagagag aaccctatcg ccaccagctc tcccatcgac    480

ttcaagagag gcagagacac cggcggcttc cacagaagag agtacagcat tggctgggtc    540

ggagatgaag tgaaagtgac cgagtggtgc aaccccagct gcagccctat tacagccgcc    600

gctagaagat tcgagtgcac ctgtcaccag tgtcctgtga cctgtagcga gtgcgagcgg    660

gacaca                                                               666
```

<210> SEQ ID NO 9
<211> LENGTH: 666
<212> TYPE: RNA
<213> ORGANISM: Artificial Sequence
<220> FEATURE:
<223> OTHER INFORMATION: Synthetised Sequence

<400> SEQUENCE: 9

```
auggacccua ccgaccugag cuucagcccc gacgagauca acaagcugau cgagacaggc     60

cugaacaccg uggaauacuu caccagccag caagugaccg gcacaagcag ccugggcaag    120

aacacaauuc cuccaggcgu gaccggccug cugacaaaug cugccgaggc caagauccaa    180

gagagcacca accaccagaa gggcucuguu ggaggcggag ccaagccuaa gaagcccaga    240

ccuaagaucg ccaucgugcc cgccgacgau aagacagugc cuggcaagcc cauuccuaau    300

ccucugcugg gccucgacag caccccuagc acacagacag ugcuggaucu gagcggcaag    360

acacugccua gcggcagcua uaagggcgug aagcuggcca aguucggcaa agaaaaccug    420

augacccggu ucaucgagga acccagagag aacccuaucg ccaccagcuc ucccaucgac    480

uucaagagag gcagagacac cggcggcuuc cacagaagag aguacagcau uggcuggguc    540

ggagaugaag ugaaagugac cgaguggugc aaccccagcu gcagcccuau uacagccgcc    600

gcuagaagau ucgagugcac cugucaccag uguccuguga ccuguagcga gugcgagcgg    660

gacaca                                                               666
```

<210> SEQ ID NO 10
<211> LENGTH: 109
<212> TYPE: PRT
<213> ORGANISM: MERS-CoV

<400> SEQUENCE: 10

```
Met Asp Tyr Val Ser Leu Leu Asn Gln Ile Trp Gln Lys Tyr Leu Asn
1               5                   10                  15

Ser Pro Tyr Thr Thr Cys Leu Tyr Ile Pro Lys Pro Thr Ala Lys Tyr
            20                  25                  30

Thr Pro Leu Val Gly Thr Ser Leu His Pro Val Leu Trp Asn Cys Gln
        35                  40                  45

Leu Ser Phe Ala Gly Tyr Thr Glu Ser Ala Val Asn Ser Thr Lys Ala
    50                  55                  60

Leu Ala Lys Gln Asp Ala Ala Gln Arg Ile Ala Trp Leu Leu His Lys
```

-continued

```
65                  70                  75                  80

Asp Gly Gly Ile Pro Asp Gly Cys Ser Leu Tyr Leu Arg His Ser Ser
                85                  90                  95

Leu Phe Ala Gln Ser Glu Glu Glu Glu Ser Phe Ser Asn
            100                 105


<210> SEQ ID NO 11
<211> LENGTH: 327
<212> TYPE: DNA
<213> ORGANISM: Artificial Sequence
<220> FEATURE:
<223> OTHER INFORMATION: Synthetised Sequence

<400> SEQUENCE: 11

atggactacg tgtccctgct gaaccagatt tggcagaagt acctgaacag cccctacacc      60

acctgtctgt acatccccaa gcctaccgcc aagtacacac ctctcgtggg cacatctctg     120

caccccgtgc tgtggaattg ccagctgagc tttgccggct acaccgagtc tgccgtgaac     180

agcacaaagg ccctggccaa acaggacgcc gctcagagaa ttgcctggct gctgcacaag     240

gatggcggca tccctgatgg ctgtagcctg tacctgagac acagcagcct gttcgcccag     300

agcgaggaag aggaatcctt cagcaac                                         327


<210> SEQ ID NO 12
<211> LENGTH: 327
<212> TYPE: RNA
<213> ORGANISM: Artificial Sequence
<220> FEATURE:
<223> OTHER INFORMATION: Synthetised Sequence

<400> SEQUENCE: 12

auggacuacg ugucccugcu gaaccagauu uggcagaagu accugaacag ccccuacacc      60

accugucugu acauccccaa gccuaccgcc aaguacacac cucucguggg cacaucucug     120

caccccgugc uguggaauug ccagcugagc uuugccggcu acaccgaguc ugccgugaac     180

agcacaaagg cccuggccaa acaggacgcc gcucagagaa uugccuggcu gcugcacaag     240

gauggcggca ucccugaugg cuguagccug uaccugagac acagcagccu guucgcccag     300

agcgaggaag aggaauccuu cagcaac                                         327


<210> SEQ ID NO 13
<211> LENGTH: 45
<212> TYPE: DNA
<213> ORGANISM: Artificial Sequence
<220> FEATURE:
<223> OTHER INFORMATION: Synthetised Sequence

<400> SEQUENCE: 13

gggcccctat aactctctac ggctaacctg aatggactac gacat                      45


<210> SEQ ID NO 14
<211> LENGTH: 19
<212> TYPE: PRT
<213> ORGANISM: Porcine teschovirus-1

<400> SEQUENCE: 14

Ala Thr Asn Phe Ser Leu Leu Lys Gln Ala Gly Asp Val Glu Glu Asn
1               5                   10                  15

Pro Gly Pro


<210> SEQ ID NO 15
```

-continued

<211> LENGTH: 20
<212> TYPE: PRT
<213> ORGANISM: Thosea asigna virus

<400> SEQUENCE: 15

Gln Cys Thr Asn Tyr Ala Leu Leu Lys Leu Ala Gly Asp Val Glu Ser
1               5                   10                  15

Asn Pro Gly Pro
            20

<210> SEQ ID NO 16
<211> LENGTH: 22
<212> TYPE: PRT
<213> ORGANISM: Foot and mouth disease virus

<400> SEQUENCE: 16

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 17
<211> LENGTH: 6
<212> TYPE: PRT
<213> ORGANISM: Artificial Sequence
<220> FEATURE:
<223> OTHER INFORMATION: Synthetised Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 17

Arg Xaa Arg Lys Xaa Arg
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetised Sequence

<400> SEQUENCE: 18

Arg Arg Arg Arg Arg Arg
1               5

<210> SEQ ID NO 19
<211> LENGTH: 27
<212> TYPE: PRT
<213> ORGANISM: Thosea asigna virus

<400> SEQUENCE: 19

Arg Arg Arg Arg Arg Arg Gly Ser Gly Glu Gly Arg Gly Ser Leu Leu
1               5                   10                  15

Thr Cys Gly Asp Val Glu Glu Asn Pro Gly Pro
            20                  25

<210> SEQ ID NO 20
<211> LENGTH: 535
<212> TYPE: PRT
<213> ORGANISM: Coronavirus

<400> SEQUENCE: 20

Met Glu Lys Val His Val Asp Ile Glu Glu Asp Ser Pro Phe Leu Arg
1               5                   10                  15

Ala Leu Gln Arg Ser Phe Pro Gln Phe Glu Val Glu Ala Lys Gln Val
            20                  25                  30

Thr Asp Asn Asp His Ala Asn Ala Arg Ala Phe Ser His Leu Ala Ser
        35                  40                  45

Lys Leu Ile Glu Thr Glu Val Asp Pro Ser Asp Thr Ile Leu Asp Ile
    50                  55                  60

Gly Ser Ala Pro Ala Arg Arg Met Tyr Ser Lys His Lys Tyr His Cys
65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
        115                 120                 125

Glu Thr Glu Thr Met Cys Leu His Asp Asp Glu Ser Cys Arg Tyr Glu
    130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
            180                 185                 190

Pro Ser Tyr Ser Thr Asn Trp Ala Asp Glu Thr Val Leu Thr Ala Arg
        195                 200                 205

Asn Ile Gly Leu Cys Ser Ser Asp Val Met Glu Arg Ser Arg Arg Gly
    210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
        275                 280                 285

Arg Ile Ala Ile Ser Pro Gly Leu Tyr Gly Lys Pro Ser Gly Tyr Ala
    290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val

-continued

```
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
        435                 440                 445

Ser Phe Val Leu Pro Arg Ile Gly Ser Asn Thr Leu Glu Ile Gly Leu
    450                 455                 460

Arg Thr Arg Ile Arg Lys Met Leu Glu Glu His Lys Glu Pro Ser Pro
465                 470                 475                 480

Leu Ile Thr Ala Glu Asp Val Gln Glu Ala Lys Cys Ala Ala Asp Glu
                485                 490                 495

Ala Lys Glu Val Arg Glu Ala Glu Glu Leu Arg Ala Ala Leu Pro Pro
            500                 505                 510

Leu Ala Ala Asp Val Glu Glu Pro Thr Leu Glu Ala Asp Val Asp Leu
        515                 520                 525

Met Leu Gln Glu Ala Gly Ala
    530                 535


<210> SEQ ID NO 21
<211> LENGTH: 1605
<212> TYPE: DNA
<213> ORGANISM: Artificial Sequence
<220> FEATURE:
<223> OTHER INFORMATION: Synthetised Sequence

<400> SEQUENCE: 21

atggagaaag ttcacgttga catcgaggaa gacagcccat tcctcagagc tttgcagcgg      60

agcttcccgc agtttgaggt agaagccaag caggtcactg ataatgacca tgctaatgcc     120

agagcgtttt cgcatctggc ttcaaaactg atcgaaacgg aggtggaccc atccgacacg     180

atccttgaca ttggaagtgc gcccgcccgc agaatgtatt ctaagcacaa gtatcattgt     240

atctgtccga tgagatgtgc ggaagatccg gacagattgt ataagtatgc aactaagctg     300

aagaaaaact gtaaggaaat aactgataag gaattggaca agaaaatgaa ggagctggcc     360

gccgtcatga gcgaccctga cctggaaact gagactatgt gcctccacga cgacgagtcg     420

tgtcgctacg aagggcaagt cgctgtttac caggatgtat acgcggttga cggaccgaca     480

agtctctatc accaagccaa taagggagtt agagtcgcct actggatagg ctttgacacc     540

accccttta tgtttaagaa cttggctgga gcatatccat catactctac caactgggcc      600

gacgaaaccg tgttaacggc tcgtaacata ggcctatgca gctctgacgt tatggagcgg     660

tcacgtagag ggatgtccat tcttagaaag aagtatttga aaccatccaa caatgttcta     720

ttctctgttg gctcgaccat ctaccacgag aagagggact tactgaggag ctggcacctg     780

ccgtctgtat ttcacttacg tggcaagcaa aattacacat gtcggtgtga gactatagtt     840

agttgcgacg ggtacgtcgt taaaagaata gctatcagtc caggcctgta tgggaagcct     900

tcaggctatg ctgctacgat gcaccgcgag ggattcttgt gctgcaaagt gacagacaca     960

ttgaacgggg agagggtctc ttttcccgtg tgcacgtatg tgccagctac attgtgtgac    1020

caaatgactg gcatactggc aacagatgtc agtgcggacg acgcgcaaaa actgctggtt    1080

gggctcaacc agcgtatagt cgtcaacggt cgcacccaga gaaacaccaa taccatgaaa    1140

aattaccttt tgcccgtagt ggcccaggca tttgctaggt gggcaaagga atataaggaa    1200

gatcaagaag atgaaaggcc actaggacta cgagatagac agttagtcat ggggtgttgt    1260

tgggctttta gaaggcacaa gataacatct atttataagc gcccggatac ccaaaccatc    1320
```

atcaaagtga acagcgattt ccactcattc gtgctgccca ggataggcag taacacattg 1380
gagatcgggc tgagaacaag aatcaggaaa atgttagagg agcacaagga gccgtcacct 1440
ctcattaccg ccgaggacgt acaagaagct aagtgcgcag ccgatgaggc taaggaggtg 1500
cgtgaagccg aggagttgcg cgcagctcta ccacctttgg cagctgatgt tgaggagccc 1560
actctggaag ccgatgtcga cttgatgtta caagaggctg gggcc 1605

<210> SEQ ID NO 22
<211> LENGTH: 1605
<212> TYPE: RNA
<213> ORGANISM: Artificial Sequence
<220> FEATURE:
<223> OTHER INFORMATION: Synthetised Sequence

<400> SEQUENCE: 22
auggagaaag uucacguuga caucgaggaa gacagcccau uccucagagc uuugcagcgg 60
agcuucccgc aguuugaggu agaagccaag caggucacug auaaugacca ugcuaaugcc 120
agagcguuuu cgcaucuggc uucaaaacug aucgaaacgg agguggaccc auccgacacg 180
auccuugaca uuggaagugc gcccgcccgc agaauguauu cuaagcacaa guaucauugu 240
aucuguccga ugagaugugc ggaagauccg gacagauugu auaaguaugc aacuaagcug 300
aagaaaaacu guaaggaaau aacugauaag gaauuggaca agaaaaugaa ggagcuggcc 360
gccgucauga gcgacccuga ccuggaaacu gagacuaugu gccuccacga cgacgagucg 420
ugucgcuacg aagggcaagu cgcuguuuac caggauguau acgcgguuga cggaccgaca 480
agucucuauc accaagccaa uaagggaguu agagucgccu acuggauagg cuuugacacc 540
accccuuuua uguuuaagaa cuuggcugga gcauauccau cauacucuac caacugggcc 600
gacgaaaccg uguuaacggc ucguaacaua ggccuaugca gcucugacgu uauggagcgg 660
ucacguagag ggauguccau ucuuagaaag aaguauuuga aaccauccaa caauguucua 720
uucucuguug gcucgaccau cuaccacgag aagagggacu uacugaggag cuggcaccug 780
ccgucuguau uucacuuacg uggcaagcaa aauuacacau gucggugug a gacuauaguu 840 aguugcgacg gguacgucgu uaaaagaaua gcuaucaguc caggccugua ugggaagccu 900
ucaggcuaug cugcuacgau gcaccgcgag ggauucuugu gcugcaaagu gacagacaca 960
uugaacgggg agagggucuc uuuucccgug ugcacguaug ugccagcuac auugugugac 1020
caaaugacug gcauacuggc aacagauguc agugcggacg acgcgcaaaa acugcugguu 1080
gggcucaacc agcguauagu cgucaacggu cgcacccaga gaaacaccaa uaccaugaaa 1140
aauuaccuuu ugcccguagu ggcccaggca uuugcuaggu gggcaaagga auauaaggaa 1200
gaucaagaag augaaaggcc acuaggacua cgagauagac aguuagucau ggggguguugu 1260 ugggcuuuua gaaggcacaa gauaacaucu auuuauaagc gcccggauac ccaaaccauc 1320
aucaaaguga acagcgauuu ccacucauuc gugcugccca ggauaggcag uaacacauug 1380
gagaucgggc ugagaacaag aaucaggaaa auguuagagg agcacaagga gccgucaccu 1440
cucauuaccg ccgaggacgu acaagaagcu aagugcgcag ccgaugaggc uaaggaggug 1500
cgugaagccg aggaguugcg cgcagcucua ccaccuuugg cagcugaugu ugaggagccc 1560
acucuggaag ccgaugucga cuugauguua caagaggcug gggcc 1605

<210> SEQ ID NO 23
<211> LENGTH: 794
<212> TYPE: PRT

<213> ORGANISM: Coronavirus

<400> SEQUENCE: 23

```
Gly Ser Val Glu Thr Pro Arg Gly Leu Ile Lys Val Thr Ser Tyr Asp
1               5                   10                  15

Gly Glu Asp Lys Ile Gly Ser Tyr Ala Val Leu Ser Pro Gln Ala Val
            20                  25                  30

Leu Lys Ser Glu Lys Leu Ser Cys Ile His Pro Leu Ala Glu Gln Val
        35                  40                  45

Ile Val Ile Thr His Ser Gly Arg Lys Gly Arg Tyr Ala Val Glu Pro
    50                  55                  60

Tyr His Gly Lys Val Val Val Pro Glu Gly His Ala Ile Pro Val Gln
65                  70                  75                  80

Asp Phe Gln Ala Leu Ser Glu Ser Ala Thr Ile Val Tyr Asn Glu Arg
                85                  90                  95

Glu Phe Val Asn Arg Tyr Leu His His Ile Ala Thr His Gly Gly Ala
            100                 105                 110

Leu Asn Thr Asp Glu Glu Tyr Tyr Lys Thr Val Lys Pro Ser Glu His
        115                 120                 125

Asp Gly Glu Tyr Leu Tyr Asp Ile Asp Arg Lys Gln Cys Val Lys Lys
    130                 135                 140

Glu Leu Val Thr Gly Leu Gly Leu Thr Gly Glu Leu Val Asp Pro Pro
145                 150                 155                 160

Phe His Glu Phe Ala Tyr Glu Ser Leu Arg Thr Arg Pro Ala Ala Pro
                165                 170                 175

Tyr Gln Val Pro Thr Ile Gly Val Tyr Gly Val Pro Gly Ser Gly Lys
            180                 185                 190

Ser Gly Ile Ile Lys Ser Ala Val Thr Lys Lys Asp Leu Val Val Ser
        195                 200                 205

Ala Lys Lys Glu Asn Cys Ala Glu Ile Ile Arg Asp Val Lys Lys Met
    210                 215                 220

Lys Gly Leu Asp Val Asn Ala Arg Thr Val Asp Ser Val Leu Leu Asn
225                 230                 235                 240

Gly Cys Lys His Pro Val Glu Thr Leu Tyr Ile Asp Glu Ala Phe Ala
                245                 250                 255

Cys His Ala Gly Thr Leu Arg Ala Leu Ile Ala Ile Ile Arg Pro Lys
            260                 265                 270

Lys Ala Val Leu Cys Gly Asp Pro Lys Gln Cys Gly Phe Phe Asn Met
        275                 280                 285

Met Cys Leu Lys Val His Phe Asn His Glu Ile Cys Thr Gln Val Phe
    290                 295                 300

His Lys Ser Ile Ser Arg Arg Cys Thr Lys Ser Val Thr Ser Val Val
305                 310                 315                 320

Ser Thr Leu Phe Tyr Asp Lys Lys Met Arg Thr Thr Asn Pro Lys Glu
                325                 330                 335

Thr Lys Ile Val Ile Asp Thr Thr Gly Ser Thr Lys Pro Lys Gln Asp
            340                 345                 350

Asp Leu Ile Leu Thr Cys Phe Arg Gly Trp Val Lys Gln Leu Gln Ile
        355                 360                 365

Asp Tyr Lys Gly Asn Glu Ile Met Thr Ala Ala Ala Ser Gln Gly Leu
    370                 375                 380

Thr Arg Lys Gly Val Tyr Ala Val Arg Tyr Lys Val Asn Glu Asn Pro
385                 390                 395                 400
```

```
Leu Tyr Ala Pro Thr Ser Glu His Val Asn Val Leu Leu Thr Arg Thr
                405                 410                 415

Glu Asp Arg Ile Val Trp Lys Thr Leu Ala Gly Asp Pro Trp Ile Lys
            420                 425                 430

Thr Leu Thr Ala Lys Tyr Pro Gly Asn Phe Thr Ala Thr Ile Glu Glu
        435                 440                 445

Trp Gln Ala Glu His Asp Ala Ile Met Arg His Ile Leu Glu Arg Pro
    450                 455                 460

Asp Pro Thr Asp Val Phe Gln Asn Lys Ala Asn Val Cys Trp Ala Lys
465                 470                 475                 480

Ala Leu Val Pro Val Leu Lys Thr Ala Gly Ile Asp Met Thr Thr Glu
                485                 490                 495

Gln Trp Asn Thr Val Asp Tyr Phe Glu Thr Asp Lys Ala His Ser Ala
            500                 505                 510

Glu Ile Val Leu Asn Gln Leu Cys Val Arg Phe Phe Gly Leu Asp Leu
        515                 520                 525

Asp Ser Gly Leu Phe Ser Ala Pro Thr Val Pro Leu Ser Ile Arg Asn
    530                 535                 540

Asn His Trp Asp Asn Ser Pro Ser Pro Asn Met Tyr Gly Leu Asn Lys
545                 550                 555                 560

Glu Val Val Arg Gln Leu Ser Arg Arg Tyr Pro Gln Leu Pro Arg Ala
                565                 570                 575

Val Ala Thr Gly Arg Val Tyr Asp Met Asn Thr Gly Thr Leu Arg Asn
            580                 585                 590

Tyr Asp Pro Arg Ile Asn Leu Val Pro Val Asn Arg Arg Leu Pro His
        595                 600                 605

Ala Leu Val Leu His His Asn Glu His Pro Gln Ser Asp Phe Ser Ser
    610                 615                 620

Phe Val Ser Lys Leu Lys Gly Arg Thr Val Leu Val Val Gly Glu Lys
625                 630                 635                 640

Leu Ser Val Pro Gly Lys Met Val Asp Trp Leu Ser Asp Arg Pro Glu
                645                 650                 655

Ala Thr Phe Arg Ala Arg Leu Asp Leu Gly Ile Pro Gly Asp Val Pro
            660                 665                 670

Lys Tyr Asp Ile Ile Phe Val Asn Val Arg Thr Pro Tyr Lys Tyr His
        675                 680                 685

His Tyr Gln Gln Cys Glu Asp His Ala Ile Lys Leu Ser Met Leu Thr
    690                 695                 700

Lys Lys Ala Cys Leu His Leu Asn Pro Gly Gly Thr Cys Val Ser Ile
705                 710                 715                 720

Gly Tyr Gly Tyr Ala Asp Arg Ala Ser Glu Ser Ile Ile Gly Ala Ile
                725                 730                 735

Ala Arg Gln Phe Lys Phe Ser Arg Val Cys Lys Pro Lys Ser Ser Leu
            740                 745                 750

Glu Glu Thr Glu Val Leu Phe Val Phe Ile Gly Tyr Asp Arg Lys Ala
        755                 760                 765

Arg Thr His Asn Ser Tyr Lys Leu Ser Ser Thr Leu Thr Asn Ile Tyr
    770                 775                 780

Thr Gly Ser Arg Leu His Glu Ala Gly Cys
785                 790
```

<210> SEQ ID NO 24
<211> LENGTH: 2382
<212> TYPE: DNA

-continued

<213> ORGANISM: Artificial Sequence
<220> FEATURE:
<223> OTHER INFORMATION: Synthetised Sequence

<400> SEQUENCE: 24
ggctcagtgg agacacctcg tggcttgata aaggttacca gctacgatgg cgaggacaag 60
atcggctctt acgctgtgct ttctccgcag gctgtactca agagtgaaaa attatcttgc 120
atccaccctc tcgctgaaca agtcatagtg ataacacact ctggccgaaa agggcgttat 180
gccgtggaac cataccatgg taaagtagtg gtgccagagg gacatgcaat acccgtccag 240
gactttcaag ctctgagtga aagtgccacc attgtgtaca acgaacgtga gttcgtaaac 300
aggtacctgc accatattgc cacacatgga ggagcgctga acactgatga agaatattac 360
aaaactgtca agcccagcga gcacgacggc gaatacctgt acgacatcga caggaaacag 420
tgcgtcaaga aagaactagt cactgggcta gggctcacag gcgagctggt ggatcctccc 480
ttccatgaat tcgcctacga gagtctgaga acacgaccag ccgctcctta ccaagtacca 540
accatagggg tgtatggcgt gccaggatca ggcaagtctg gcatcattaa aagcgcagtc 600
accaaaaaag atctagtggt gagcgccaag aaagaaaact gtgcagaaat tataagggac 660
gtcaagaaaa tgaaagggct ggacgtcaat gccagaactg tggactcagt gctcttgaat 720
ggatgcaaac accccgtaga gaccctgtat attgacgaag cttttgcttg tcatgcaggt 780
actctcagag cgctcatagc cattataaga cctaaaaagg cagtgctctg cggggatccc 840
aaacagtgcg gtttttttaa catgatgtgc ctgaaagtgc attttaacca cgagatttgc 900
acacaagtct tccacaaaag catctctcgc cgttgcacta aatctgtgac ttcggtcgtc 960
tcaaccttgt tttacgacaa aaaaatgaga acgacgaatc cgaaagagac taagattgtg 1020
attgacacta ccggcagtac caaacctaag caggacgatc tcattctcac ttgtttcaga 1080
gggtgggtga agcagttgca aatagattac aaaggcaacg aaataatgac ggcagctgcc 1140
tctcaagggc tgacccgtaa aggtgtgtat gccgttcggt acaaggtgaa tgaaaatcct 1200
ctgtacgcac ccacctcaga acatgtgaac gtcctactga cccgcacgga ggaccgcatc 1260
gtgtggaaaa cactagccgg cgacccatgg ataaaaacac tgactgccaa gtaccctggg 1320
aatttcactg ccacgataga ggagtggcaa gcagagcatg atgccatcat gaggcacatc 1380
ttggagagac cggaccctac cgacgtcttc cagaataagg caaacgtgtg ttgggccaag 1440
gctttagtgc cggtgctgaa gaccgctggc atagacatga ccactgaaca atggaacact 1500
gtggattatt ttgaaacgga caaagctcac tcagcagaga tagtattgaa ccaactatgc 1560
gtgaggttct ttggactcga tctggactcc ggtctatttt ctgcacccac tgttccgtta 1620
tccattagga ataatcactg ggataactcc ccgtcgccta acatgtacgg gctgaataaa 1680
gaagtggtcc gtcagctctc tcgcaggtac ccacaactgc ctcgggcagt tgccactgga 1740
agagtctatg acatgaacac tggtacactg cgcaattatg atccgcgcat aaacctagta 1800
cctgtaaaca gaagactgcc tcatgcttta gtcctccacc ataatgaaca cccacagagt 1860
gacttttctt cattcgtcag caaattgaag ggcagaactg tcctggtggt cggggaaaag 1920
ttgtccgtcc caggcaaaat ggttgactgg ttgtcagacc ggcctgaggc taccttcaga 1980
gctcggctgg atttaggcat cccaggtgat gtgcccaaat atgacataat atttgttaat 2040
gtgaggaccc catataaata ccatcactat cagcagtgtg aagaccatgc cattaagctt 2100
agcatgttga ccaagaaagc ttgtctgcat ctgaatcccg gcggaacctg tgtcagcata 2160
ggttatggtt acgctgacag ggccagcgaa agcatcattg gtgctatagc gcggcagttc 2220

```
aagttttccc gggtatgcaa accgaaatcc tcacttgaag agacggaagt tctgtttgta   2280

ttcattgggt acgatcgcaa ggcccgtacg cacaattctt acaagctttc atcaaccttg   2340

accaacattt atacaggttc cagactccac gaagccggat gt                      2382
```

<210> SEQ ID NO 25
<211> LENGTH: 2382
<212> TYPE: RNA
<213> ORGANISM: Artificial Sequence
<220> FEATURE:
<223> OTHER INFORMATION: Synthetised Sequence

<400> SEQUENCE: 25

```
ggcucagugg agacaccucg uggcuugaua aagguuacca gcuacgaugg cgaggacaag     60

aucggcucuu acgcugugcu uucuccgcag gcuguacuca agagugaaaa auuaucuugc    120

auccacccuc ucgcugaaca agucauagug auaacacacu cuggccgaaa agggcguuau    180

gccguggaac cauaccaugg uaaaguagug gugccagagg gacaugcaau acccguccag    240

gacuuucaag cucugaguga aagugccacc auuguguaca acgaacguga guucguaaac    300

agguaccugc accauauugc cacacaugga ggagcgcuga acacugauga agaauauuac    360

aaaacuguca agcccagcga gcacgacggc gaauaccugu acgacaucga caggaaacag    420

ugcgucaaga aagaacuagu cacugggcua gggcucacag gcgagcuggu ggauccuccc    480

uuccaugaau ucgccuacga gagucugaga acacgaccag ccgcuccuua ccaaguacca    540

accauagggg uguauggcgu gccaggauca ggcaagucug gcaucauuaa aagcgcaguc    600

accaaaaaag aucuaguggu gagcgccaag aaagaaaacu gugcagaaau uauaagggac    660

gucaagaaaa ugaaagggcu ggacgucaau gccagaacug uggacucagu gcucuugaau    720

ggaugcaaac accccguaga gacccuguau auugacgaag cuuuugcuug ucaugcaggu    780

acucucagag cgcucauagc cauuauaaga ccuaaaaagg cagugcucug cggggauccc    840

aaacagugcg guuuuuuaa caugaugugc cugaaagugc auuuuaacca cgagauuugc    900

acacaagucu uccacaaaag caucucucgc cguugcacua aaucugugac uucggucguc    960

ucaaccuugu uuuacgacaa aaaaaugaga acgacgaauc cgaaagagac uaagauugug   1020

auugacacua ccggcaguac caaaccuaag caggacgauc ucauucucac uuguuucaga   1080

gggugggugga agcaguugca aauagauuac aaaggcaacg aaauaaugac ggcagcugcc   1140

ucucaagggc ugacccguaa aggugugua gccguucggu acaaggugaa ugaaaauccu   1200

cuguacgcac ccaccucaga acaugugaac guccuacuga cccgcacgga ggaccgcauc   1260

guguggaaaa cacuagccgg cgacccaugg auaaaaacac ugacugccaa guacccuggg   1320

aauuucacug ccacgauaga ggaguggcaa gcagagcaug augccaucau gaggcacauc   1380

uuggagagac cggacccuac cgacgucuuc cagaauaagg caaacgugug uugggccaag   1440

gcuuuagugc cggugcugaa gaccgcuggc auagacauga ccacugaaca auggaacacu   1500

guggauuauu uugaaacgga caaagcucac ucagcagaga uaguauugaa ccaacuaugc   1560

gugagguucu uuggacucga ucuggacucc ggucuauuuu cugcacccac uguuccguua   1620

uccauuagga auaaucacug ggauaacucc ccgucgccua acauguacgg gcugaauaaa   1680

gaaguggucc gucagcucuc ucgcagguac ccacaacugc cucgggcagu ugccacugga   1740

agagucuaug acaugaacac ugguacacug cgcaauuaug auccgcgcau aaaccuagua   1800

ccuguaaaca gaagacugcc ucaugcuuua guccuccacc auaaugaaca cccacagagu   1860
```

```
gacuuuucuu cauucgucag caaauugaag ggcagaacug uccugguggu cggggaaaag   1920

uuguccgucc caggcaaaau gguugacugg uugucagacc ggccugaggc uaccuucaga   1980

gcucggcugg auuuaggcau cccaggugau gugcccaaau augacauaau auuuguuaau   2040

gugaggaccc cauauaaaua ccaucacuau cagcagugug aagaccaugc cauuaagcuu   2100

agcauguuga ccaagaaagc uugucugcau cugaaucccg gcggaaccug ugucagcaua   2160

gguuaugguu acgcugacag ggccagcgaa agcaucauug gugcuauagc gcggcaguuc   2220

aaguuucccc ggguaugcaa accgaaaucc ucacuugaag agacggaagu ucuguuugua   2280

uucauugggu acgaucgcaa ggcccguacg cacaauucuu acaagcuuuc aucaaccuug   2340

accaacauuu auacagguuc cagacuccac gaagccggau gu                      2382
```

```
<210> SEQ ID NO 26
<211> LENGTH: 556
<212> TYPE: PRT
<213> ORGANISM: Coronavirus

<400> SEQUENCE: 26

Ala Pro Ser Tyr His Val Val Arg Gly Asp Ile Ala Thr Ala Thr Glu
1               5                   10                  15

Gly Val Ile Ile Asn Ala Ala Asn Ser Lys Gly Gln Pro Gly Gly Gly
            20                  25                  30

Val Cys Gly Ala Leu Tyr Lys Lys Phe Pro Glu Ser Phe Asp Leu Gln
        35                  40                  45

Pro Ile Glu Val Gly Lys Ala Arg Leu Val Lys Gly Ala Ala Lys His
    50                  55                  60

Ile Ile His Ala Val Gly Pro Asn Phe Asn Lys Val Ser Glu Val Glu
65                  70                  75                  80

Gly Asp Lys Gln Leu Ala Glu Ala Tyr Glu Ser Ile Ala Lys Ile Val
                85                  90                  95

Asn Asp Asn Asn Tyr Lys Ser Val Ala Ile Pro Leu Leu Ser Thr Gly
            100                 105                 110

Ile Phe Ser Gly Asn Lys Asp Arg Leu Thr Gln Ser Leu Asn His Leu
        115                 120                 125

Leu Thr Ala Leu Asp Thr Thr Asp Ala Asp Val Ala Ile Tyr Cys Arg
    130                 135                 140

Asp Lys Lys Trp Glu Met Thr Leu Lys Glu Ala Val Ala Arg Arg Glu
145                 150                 155                 160

Ala Val Glu Glu Ile Cys Ile Ser Asp Asp Ser Ser Val Thr Glu Pro
                165                 170                 175

Asp Ala Glu Leu Val Arg Val His Pro Lys Ser Ser Leu Ala Gly Arg
            180                 185                 190

Lys Gly Tyr Ser Thr Ser Asp Gly Lys Thr Phe Ser Tyr Leu Glu Gly
        195                 200                 205

Thr Lys Phe His Gln Ala Ala Lys Asp Ile Ala Glu Ile Asn Ala Met
    210                 215                 220

Trp Pro Val Ala Thr Glu Ala Asn Glu Gln Val Cys Met Tyr Ile Leu
225                 230                 235                 240

Gly Glu Ser Met Ser Ser Ile Arg Ser Lys Cys Pro Val Glu Glu Ser
                245                 250                 255

Glu Ala Ser Thr Pro Pro Ser Thr Leu Pro Cys Leu Cys Ile His Ala
            260                 265                 270

Met Thr Pro Glu Arg Val Gln Arg Leu Lys Ala Ser Arg Pro Glu Gln
        275                 280                 285
```

```
Ile Thr Val Cys Ser Ser Phe Pro Leu Pro Lys Tyr Arg Ile Thr Gly
    290                 295                 300

Val Gln Lys Ile Gln Cys Ser Gln Pro Ile Leu Phe Ser Pro Lys Val
305                 310                 315                 320

Pro Ala Tyr Ile His Pro Arg Lys Tyr Leu Val Glu Thr Pro Pro Val
                325                 330                 335

Asp Glu Thr Pro Glu Pro Ser Ala Glu Asn Gln Ser Thr Glu Gly Thr
            340                 345                 350

Pro Glu Gln Pro Pro Leu Ile Thr Glu Asp Glu Thr Arg Thr Arg Thr
        355                 360                 365

Pro Glu Pro Ile Ile Ile Glu Glu Glu Glu Glu Asp Ser Ile Ser Leu
    370                 375                 380

Leu Ser Asp Gly Pro Thr His Gln Val Leu Gln Val Glu Ala Asp Ile
385                 390                 395                 400

His Gly Pro Pro Ser Val Ser Ser Ser Ser Trp Ser Ile Pro His Ala
                405                 410                 415

Ser Asp Phe Asp Val Asp Ser Leu Ser Ile Leu Asp Thr Leu Glu Gly
            420                 425                 430

Ala Ser Val Thr Ser Gly Ala Thr Ser Ala Glu Thr Asn Ser Tyr Phe
        435                 440                 445

Ala Lys Ser Met Glu Phe Leu Ala Arg Pro Val Pro Ala Pro Arg Thr
    450                 455                 460

Val Phe Arg Asn Pro Pro His Pro Ala Pro Arg Thr Arg Thr Pro Ser
465                 470                 475                 480

Leu Ala Pro Ser Arg Ala Cys Ser Arg Thr Ser Leu Val Ser Thr Pro
                485                 490                 495

Pro Gly Val Asn Arg Val Ile Thr Arg Glu Glu Leu Glu Ala Leu Thr
            500                 505                 510

Pro Ser Arg Thr Pro Ser Arg Ser Val Ser Arg Thr Ser Leu Val Ser
        515                 520                 525

Asn Pro Pro Gly Val Asn Arg Val Ile Thr Arg Glu Glu Phe Glu Ala
    530                 535                 540

Phe Val Ala Gln Gln Gln Arg Phe Asp Ala Gly Ala
545                 550                 555


<210> SEQ ID NO 27
<211> LENGTH: 1671
<212> TYPE: DNA
<213> ORGANISM: Artificial Sequence
<220> FEATURE:
<223> OTHER INFORMATION: Synthetised Sequence

<400> SEQUENCE: 27

gcaccctcat atcatgtggt gcgaggggat attgccacgg ccaccgaagg agtgattata      60

aatgctgcta acagcaaagg acaacctggc ggaggggtgt gcggagcgct gtataagaaa     120

ttcccggaaa gcttcgattt acagccgatc gaagtaggaa aagcgcgact ggtcaaaggt     180

gcagctaaac atatcattca tgccgtagga ccaaacttca acaaagtttc ggaggttgaa     240

ggtgacaaac agttggcaga ggcttatgag tccatcgcta agattgtcaa cgataacaat     300

tacaagtcag tagcgattcc actgttgtcc accggcatct tttccgggaa caaagatcga     360

ctaacccaat cattgaacca tttgctgaca gctttagaca ccactgatgc agatgtagcc     420

atatactgca gggacaagaa atgggaaatg actctcaagg aagcagtggc taggagagaa     480

gcagtggagg agatatgcat atccgacgac tcttcagtga cagaacctga tgcagagctg     540
```

-continued

```
gtgagggtgc atccgaagag ttctttggct ggaaggaagg gctacagcac aagcgatggc    600

aaaactttct catatttgga agggaccaag tttcaccagg cggccaagga tatagcagaa    660

attaatgcca tgtggcccgt tgcaacggag gccaatgagc aggtatgcat gtatatcctc    720

ggagaaagca tgagcagtat taggtcgaaa tgccccgtcg aagagtcgga agcctccaca    780

ccacctagca cgctgccttg cttgtgcatc catgccatga ctccagaaag agtacagcgc    840

ctaaaagcct cacgtccaga acaaattact gtgtgctcat cctttccatt gccgaagtat    900

agaatcactg gtgtgcagaa gatccaatgc tcccagccta tattgttctc accgaaagtg    960

cctgcgtata ttcatccaag gaagtatctc gtggaaacac caccggtaga cgagactccg   1020

gagccatcgg cagagaacca atccacagag ggacacctg aacaaccacc acttataacc   1080

gaggatgaga ccaggactag aacgcctgag ccgatcatca tcgaagagga agaagaggat   1140

agcataagtt tgctgtcaga tggcccgacc caccaggtgc tgcaagtcga ggcagacatt   1200

cacgggccgc cctctgtatc tagctcatcc tggtccattc ctcatgcatc cgactttgat   1260

gtggacagtt tatccatact tgacaccctg gagggagcta gcgtgaccag cggggcaacg   1320

tcagccgaga ctaactctta cttcgcaaag agtatggagt ttctggcgcg accggtgcct   1380

gcgcctcgaa cagtattcag gaaccctcca catcccgctc cgcgcacaag aacaccgtca   1440

cttgcaccca gcagggcctg ctcgagaacc agcctagttt ccaccccgcc aggcgtgaat   1500

agggtgatca ctagagagga gctcgaggcg cttaccccgt cacgcactcc tagcaggtcg   1560

gtctcgagaa ccagcctggt ctccaacccg ccaggcgtaa atagggtgat tacaagagag   1620

gagtttgagg cgttcgtagc acaacaacaa tgacggtttg atgcgggtgc a            1671
```

<210> SEQ ID NO 28
<211> LENGTH: 1671
<212> TYPE: RNA
<213> ORGANISM: Artificial Sequence
<220> FEATURE:
<223> OTHER INFORMATION: Synthetised Sequence

<400> SEQUENCE: 28

```
gcacccucau aucauguggu gcgaggggau auugccacgg ccaccgaagg agugauuaua     60

aaugcugcua acagcaaagg acaaccuggc ggaggggugu gcggagcgcu guauaagaaa    120

uucccggaaa gcuucgauuu acagccgauc gaaguaggaa aagcgcgacu ggucaaaggu    180

gcagcuaaac auaucauuca ugccguagga ccaaacuuca acaaaguuuc ggagguugaa    240

ggugacaaac aguuggcaga ggcuuaugag uccaucgcua agauugucaa cgauaacaau    300

uacaagucag uagcgauucc acuguugucc accggcaucu uuuccgggaa caaagaucga    360

cuaacccaau cauugaacca uuugcugaca gcuuuagaca ccacugaugc agauguagcc    420

auauacugca gggacaagaa augggaaaug acucucaagg aagcaguggc uaggagagaa    480

gcaguggagg agauaugcau auccgacgac ucuucaguga cagaaccuga ugcagagcug    540

gugagggugc auccgaagag uucuuuggcu ggaaggaagg gcuacagcac aagcgauggc    600

aaaacuuucu cauauuugga agggaccaag uuucaccagg cggccaagga uauagcagaa    660

auuaaugcca uguggcccgu ugcaacggag gccaaugagc agguaugcau guauauccuc    720

ggagaaagca ugagcaguau uaggucgaaa ugccccgucg aagagucgga agccuccaca    780

ccaccuagca cgcugccuug cuugugcauc caugccauga cuccagaaag aguacagcgc    840

cuaaaagccu cacguccaga acaaauuacu gugugcucau ccuuuccauu gccgaaguau    900
```

```
agaaucacug gugugcagaa gauccaaugc ucccagccua uauuguucuc accgaaagug     960

ccugcguaua uucauccaag gaaguaucuc guggaaacac caccgguaga cgagacuccg    1020

gagccaucgg cagagaacca auccacagag gggacaccug aacaaccacc acuuauaacc    1080

gaggaugaga ccaggacuag aacgccugag ccgaucauca ucgaagagga agaagaggau    1140

agcauaaguu ugcugucaga uggcccgacc caccaggugc ugcaagucga ggcagacauu    1200

cacgggccgc ccucuguauc uagcucaucc ugguccauuc cucaugcauc cgacuuugau    1260

guggacaguu uauccauacu ugacacccug gagggagcua gcgugaccag cggggcaacg    1320

ucagccgaga cuaacucuua cuucgcaaag aguauggagu uucuggcgcg accggugccu    1380

gcgccucgaa caguauucag gaacccucca caucccgcuc cgcgcacaag aacaccguca    1440

cuugcaccca gcagggccug cucgagaacc agccuaguuu ccacccccgcc aggcgugaau    1500

agggugauca cuagagagga gcucgaggcg cuuaccccgu cacgcacucc uagcaggucg    1560

gucucgagaa ccagccuggu cuccaacccg ccaggcguaa auagggugau uacaagagag    1620

gaguuugagg cguucguagc acaacaacaa ugacgguuug augcgggugc a             1671
```

<210> SEQ ID NO 29
<211> LENGTH: 607
<212> TYPE: PRT
<213> ORGANISM: Coronavirus

<400> SEQUENCE: 29

```
Tyr Ile Phe Ser Ser Asp Thr Gly Gln Gly His Leu Gln Gln Lys Ser
1               5                   10                  15

Val Arg Gln Thr Val Leu Ser Glu Val Val Leu Glu Arg Thr Glu Leu
            20                  25                  30

Glu Ile Ser Tyr Ala Pro Arg Leu Asp Gln Glu Lys Glu Glu Leu Leu
        35                  40                  45

Arg Lys Lys Leu Gln Leu Asn Pro Thr Pro Ala Asn Arg Ser Arg Tyr
    50                  55                  60

Gln Ser Arg Lys Val Glu Asn Met Lys Ala Ile Thr Ala Arg Arg Ile
65                  70                  75                  80

Leu Gln Gly Leu Gly His Tyr Leu Lys Ala Glu Gly Lys Val Glu Cys
                85                  90                  95

Tyr Arg Thr Leu His Pro Val Pro Leu Tyr Ser Ser Ser Val Asn Arg
            100                 105                 110

Ala Phe Ser Ser Pro Lys Val Ala Val Glu Ala Cys Asn Ala Met Leu
        115                 120                 125

Lys Glu Asn Phe Pro Thr Val Ala Ser Tyr Cys Ile Ile Pro Glu Tyr
    130                 135                 140

Asp Ala Tyr Leu Asp Met Val Asp Gly Ala Ser Cys Cys Leu Asp Thr
145                 150                 155                 160

Ala Ser Phe Cys Pro Ala Lys Leu Arg Ser Phe Pro Lys Lys His Ser
                165                 170                 175

Tyr Leu Glu Pro Thr Ile Arg Ser Ala Val Pro Ser Ala Ile Gln Asn
            180                 185                 190

Thr Leu Gln Asn Val Leu Ala Ala Ala Thr Lys Arg Asn Cys Asn Val
        195                 200                 205

Thr Gln Met Arg Glu Leu Pro Val Leu Asp Ser Ala Ala Phe Asn Val
    210                 215                 220

Glu Cys Phe Lys Lys Tyr Ala Cys Asn Asn Glu Tyr Trp Glu Thr Phe
225                 230                 235                 240
```

-continued

```
Lys Glu Asn Pro Ile Arg Leu Thr Glu Glu Asn Val Val Asn Tyr Ile
                245                 250                 255

Thr Lys Leu Lys Gly Pro Lys Ala Ala Ala Leu Phe Ala Lys Thr His
            260                 265                 270

Asn Leu Asn Met Leu Gln Asp Ile Pro Met Asp Arg Phe Val Met Asp
        275                 280                 285

Leu Lys Arg Asp Val Lys Val Thr Pro Gly Thr Lys His Thr Glu Glu
    290                 295                 300

Arg Pro Lys Val Gln Val Ile Gln Ala Ala Asp Pro Leu Ala Thr Ala
305                 310                 315                 320

Tyr Leu Cys Gly Ile His Arg Glu Leu Val Arg Arg Leu Asn Ala Val
                325                 330                 335

Leu Leu Pro Asn Ile His Thr Leu Phe Asp Met Ser Ala Glu Asp Phe
            340                 345                 350

Asp Ala Ile Ile Ala Glu His Phe Gln Pro Gly Asp Cys Val Leu Glu
        355                 360                 365

Thr Asp Ile Ala Ser Phe Asp Lys Ser Glu Asp Asp Ala Met Ala Leu
    370                 375                 380

Thr Ala Leu Met Ile Leu Glu Asp Leu Gly Val Asp Ala Glu Leu Leu
385                 390                 395                 400

Thr Leu Ile Glu Ala Ala Phe Gly Glu Ile Ser Ser Ile His Leu Pro
                405                 410                 415

Thr Lys Thr Lys Phe Lys Phe Gly Ala Met Met Lys Ser Gly Met Phe
            420                 425                 430

Leu Thr Leu Phe Val Asn Thr Val Ile Asn Ile Val Ile Ala Ser Arg
        435                 440                 445

Val Leu Arg Glu Arg Leu Thr Gly Ser Pro Cys Ala Ala Phe Ile Gly
    450                 455                 460

Asp Asp Asn Ile Val Lys Gly Val Lys Ser Asp Lys Leu Met Ala Asp
465                 470                 475                 480

Arg Cys Ala Thr Trp Leu Asn Met Glu Val Lys Ile Ile Asp Ala Val
                485                 490                 495

Val Gly Glu Lys Ala Pro Tyr Phe Cys Gly Gly Phe Ile Leu Cys Asp
            500                 505                 510

Ser Val Thr Gly Thr Ala Cys Arg Val Ala Asp Pro Leu Lys Arg Leu
        515                 520                 525

Phe Lys Leu Gly Lys Pro Leu Ala Ala Asp Asp Glu His Asp Asp Asp
    530                 535                 540

Arg Arg Arg Ala Leu His Glu Glu Ser Thr Arg Trp Asn Arg Val Gly
545                 550                 555                 560

Ile Leu Ser Glu Leu Cys Lys Ala Val Glu Ser Arg Tyr Glu Thr Val
                565                 570                 575

Gly Thr Ser Ile Ile Val Met Ala Met Thr Thr Leu Ala Ser Ser Val
            580                 585                 590

Lys Ser Phe Ser Tyr Leu Arg Gly Ala Pro Ile Thr Leu Tyr Gly
        595                 600                 605
```

<210> SEQ ID NO 30
<211> LENGTH: 1821
<212> TYPE: DNA
<213> ORGANISM: Artificial Sequence
<220> FEATURE:
<223> OTHER INFORMATION: Synthetised Sequence

<400> SEQUENCE: 30

-continued

```
tacatctttt cctccgacac cggtcaaggg catttacaac aaaaatcagt aaggcaaacg     60
gtgctatccg aagtggtgtt ggagaggacc gaattggaga tttcgtatgc cccgcgcctc    120
gaccaagaaa aagaagaatt actacgcaag aaattacagt taaatcccac acctgctaac    180
agaagcagat accagtccag gaaggtggag aacatgaaag ccataacagc tagacgtatt    240
ctgcaaggcc tagggcatta tttgaaggca gaaggaaaag tggagtgcta ccgaaccctg    300
catcctgttc ctttgtattc atctagtgtg aaccgtgcct tttcaagccc caaggtcgca    360
gtggaagcct gtaacgccat gttgaaagag aactttccga ctgtggcttc ttactgtatt    420
attccagagt acgatgccta tttggacatg gttgacggag cttcatgctg cttagacact    480
gccagttttt gccctgcaaa gctgcgcagc tttccaaaga aacactccta tttggaaccc    540
acaatacgat cggcagtgcc ttcagcgatc cagaacacgc tccagaacgt cctggcagct    600
gccacaaaaa gaaattgcaa tgtcacgcaa atgagagaat tgcccgtatt ggattcggcg    660
gcctttaatg tggaatgctt caagaaatat gcgtgtaata atgaatattg ggaaacgttt    720
aaagaaaacc ccatcaggct tactgaagaa aacgtggtaa attacattac caaattaaaa    780
ggaccaaaag ctgctgctct tttgcgaag acacataatt tgaatatgtt gcaggacata    840
ccaatggaca ggtttgtaat ggacttaaag agagacgtga aagtgactcc aggaacaaaa    900
catactgaag aacggcccaa ggtacaggtg atccaggctg ccgatccgct agcaacagcg    960
tatctgtgcg gaatccaccg agagctggtt aggagattaa atgcggtcct gcttccgaac   1020
attcatacac tgtttgatat gtcggctgaa gactttgacg ctattatagc cgagcacttc   1080
cagcctgggg attgtgttct ggaaactgac atcgcgtcgt ttgataaaag tgaggacgac   1140
gccatggctc tgaccgcgtt aatgattctg gaagacttag gtgtggacgc agagctgttg   1200
acgctgattg aggcggcttt cggcgaaatt tcatcaatac atttgcccac taaaactaaa   1260
tttaaattcg gagccatgat gaaatctgga atgttcctca cactgtttgt gaacacagtc   1320
attaacattg taatcgcaag cagagtgttg agagaacggc taaccggatc accatgtgca   1380
gcattcattg gagatgacaa tatcgtgaaa ggagtcaaat cggacaaatt aatggcagac   1440
aggtgcgcca cctggttgaa tatggaagtc aagattatag atgctgtggt gggcgagaaa   1500
gcgccttatt tctgtggagg gtttattttg tgtgactccg tgaccggcac agcgtgccgt   1560
gtggcagacc ccctaaaaag gctgtttaag cttggcaaac ctctggcagc agacgatgaa   1620
catgatgatg acaggagaag ggcattgcat gaagagtcaa cacgctggaa ccgagtgggt   1680
attctttcag agctgtgcaa ggcagtagaa tcaaggtatg aaaccgtagg aacttccatc   1740
atagttatgg ccatgactac tctagctagc agtgttaaat cattcagcta cctgagaggg   1800
gcccctataa ctctctacgg c                                             1821
```

<210> SEQ ID NO 31
<211> LENGTH: 1821
<212> TYPE: RNA
<213> ORGANISM: Artificial Sequence
<220> FEATURE:
<223> OTHER INFORMATION: Synthetised Sequence

<400> SEQUENCE: 31

```
uacaucuuuu ccuccgacac cggucaaggg cauuuacaac aaaaaucagu aaggcaaacg     60
gugcuauccg aagugguguu ggagaggacc gaauuggaga uuucguaugc cccgcgccuc    120
gaccaagaaa aagaagaauu acuacgcaag aaauuacagu uaaaucccac accugcuaac    180
agaagcagau accaguccag gaagguggag aacaugaaag ccauaacagc uagacguauu    240
```

cugcaaggcc uagggcauua uuugaaggca gaaggaaaag uggagugcua ccgaacccug 300
cauccuguuc cuuuguauuc aucuagugug aaccgugccu uuucaagccc caaggucgca 360
guggaagccu guaacgccau guugaaagag aacuuuccga cuguggcuuc uuacuguauu 420
auuccagagu acgaugccua uuuggacaug guugacggag cuucaugcug cuuagacacu 480
gccaguuuuu gcccugcaaa gcugcgcagc uuuccaaaga aacacuccua uuuggaaccc 540
acaauacgau cggcagugcc uucagcgauc cagaacacgc uccagaacgu ccuggcagcu 600
gccacaaaaa gaaauugcaa ugucacgcaa augagagaau ugcccguauu ggauucggcg 660
gccuuuaaug uggaaugcuu caagaaauau gcguguaaua augaauauug ggaaacguuu 720
aaagaaaacc ccaucaggcu uacugaagaa aacgugguaa auuacauuac caaauuaaaa 780
ggaccaaaag cugcugcucu uuuugcgaag acacauaauu ugaauauguu gcaggacaua 840
ccaauggaca gguuuguaau ggacuuaaag agagacguga aagugacucc aggaacaaaa 900
cauacugaag aacggcccaa gguacaggug auccaggcug ccgauccgcu agcaacagcg 960
uaucugugcg gaauccaccg agagcugguu aggagauuaa augcgguccu gcuuccgaac 1020
auucauacac uguuugauau gucggcugaa gacuuugacg cuauuauagc cgagcacuuc 1080
cagccugggg auuguguucu ggaaacugac aucgcgucgu uugauaaaag ugaggacgac 1140
gccauggcuc ugaccgcguu aaugauucug gaagacuuag guguggacgc agagcuguug 1200
acgcugauug aggcggcuuu cggcgaaauu ucaucaauac auuugcccac uaaaacuaaa 1260
uuuaaauucg gagccaugau gaaaucugga auguuccuca cacuguuugu gaacacaguc 1320
auuaacauug uaaucgcaag cagaguguug agagaacggc uaaccggauc accaugugca 1380
gcauucauug gagaugacaa uaucgugaaa ggagucaaau cggacaaauu aauggcagac 1440
aggugcgcca ccugguugaa uauggaaguc aagauuauag augcuguggu gggcgagaaa 1500
gcgccuuauu ucuguggagg guuuauuuug ugugacuccg ugaccggcac agcgugccgu 1560
guggcagacc cccuaaaaag gcuguuuaag cuuggcaaac cucuggcagc agacgaugaa 1620
caugaugaug acaggagaag ggcauugcau gaagagucaa cacgcuggaa ccgaguggguu 1680 auucuuucag agcugugcaa ggcaguagaa ucaagguaug aaaccguagg aacuuccauc 1740
auaguuaugg ccaugacuac ucuagcuagc aguguuaaau cauucagcua ccugagaggg 1800
gccccuauaa cucucuacgg c 1821

<210> SEQ ID NO 32
<211> LENGTH: 44
<212> TYPE: RNA
<213> ORGANISM: Artificial Sequence
<220> FEATURE:
<223> OTHER INFORMATION: Synthetised Sequence

<400> SEQUENCE: 32
augggcggcg caugagagaa gcccagacca auuaccuacc caaa 44

<210> SEQ ID NO 33
<211> LENGTH: 11507
<212> TYPE: RNA
<213> ORGANISM: Artificial Sequence
<220> FEATURE:
<223> OTHER INFORMATION: Synthetised Sequence

<400> SEQUENCE: 33
auggagaaag uucacguuga caucgaggaa gacagcccau uccucagagc uuugcagcgg 60

-continued

```
agcuucccgc aguuugaggu agaagccaag caggucacug auaaugacca ugcuaaugcc    120
agagcguuuu cgcaucuggc uucaaaacug aucgaaacgg agguggaccc auccgacacg    180
auccuugaca uuggaagugc gcccgcccgc agaauguauu cuaagcacaa guaucauugu    240
aucuguccga ugagaugugc ggaagauccg gacagauugu auaaguaugc aacuaagcug    300
aagaaaaacu guaaggaaau aacugauaag gaauuggaca agaaaaugaa ggagcuggcc    360
gccgucauga gcgacccuga ccuggaaacu gagacuaugu gccuccacga cgacgagucg    420
ugucgcuacg aagggcaagu cgcuguuuac caggauguau acgcgguuga cggaccgaca    480
agucucuauc accaagccaa uaagggaguu agagucgccu acuggauagg cuuugacacc    540
accccuuuua uguuuaagaa cuuggcugga gcauauccau cauacucuac caacugggcc    600
gacgaaaccg uguuaacggc ucguaacaua ggccuaugca gcucugacgu uauggagcgg    660
ucacguagag ggauguccau ucuuagaaag aaguauuuga aaccauccaa caauguucua    720
uucucuguug gcucgaccau cuaccacgag aagagggacu uacugaggag cuggcaccug    780
ccgucuguau uucacuuacg uggcaagcaa aauuacacau gucggugu ga gacuauaguu    840
aguugcgacg gguacgucgu uaaaagaaua gcuaucaguc caggccugua ugggaagccu    900
ucaggcuaug cugcuacgau gcaccgcgag ggauucuugu gcugcaaagu gacagacaca    960
uugaacgggg agagggucuc uuuucccgug ugcacguaug ugccagcuac auugugugac   1020
caaaugacug gcauacuggc aacagauguc agugcggacg acgcgcaaaa acugcugguu   1080
gggcucaacc agcguauagu cgucaacggu cgcacccaga gaaacaccaa uaccaugaaa   1140
aauuaccuuu ugcccguagu ggcccaggca uuugcuaggu gggcaaagga auauaaggaa   1200
gaucaagaag augaaaggcc acuaggacua cgagauagac aguuagucau gggguguugu   1260
ugggcuuuua gaaggcacaa gauaacaucu auuuauaagc gcccggauac ccaaaccauc   1320
aucaaaguga acagcgauuu ccacucauuc gugcugccca ggauaggcag uaacacauug   1380
gagaucgggc ugagaacaag aaucaggaaa auguuagagg agcacaagga gccgucaccu   1440
cucauuaccg ccgaggacgu acaagaagcu aagugcgcag ccgaugaggc uaaggaggug   1500
cgugaagccg aggaguugcg cgcagcucua ccaccuuugg cagcugaugu ugaggagccc   1560
acucuggaag ccgaugucga cuugauguua caagaggcug gggccggcuc aguggagaca   1620
ccucguggcu ugauaaaggu uaccagcuac gauggcgagg acaagaucgg cucuuacgcu   1680
gugcuuucuc cgcaggcugu acucaagagu gaaaaauuau cuugcaucca cccucucgcu   1740
gaacaaguca uagugauaac acacucuggc cgaaaagggc guuaugccgu ggaaccauac   1800
caugguaaag uaguggugcc agagggacau gcaauacccg uccaggacuu ucaagcucug   1860
agugaaagug ccaccauugu guacaacgaa cgugaguucg uaaacaggua ccugcaccau   1920
auugccacac auggaggagc gcugaacacu gaugaagaau auuacaaaac ugucaagccc   1980
agcgagcacg acggcgaaua ccuguacgac aucgacagga aacagugcgu caagaaagaa   2040
cuagucacug ggcuagggcu cacaggcgag cugguggauc cucccuucca ugaauucgcc   2100
uacgagaguc ugagaacacg accagccgcu ccuuaccaag uaccaaccau aggggguguau   2160
ggcgugccag gaucaggcaa gucuggcauc auuaaaagcg cagucaccaa aaaagaucua   2220
guggugagcg ccaagaaaga aaacugugca gaaauuauaa gggacgucaa gaaaaugaaa   2280
gggcuggacg ucaaugccag aacuguggac ucagugcucu ugaauggaug caaacacccc   2340
guagagaccc uguauauuga cgaagcuuuu gcuugucaug cagguacucu cagagcgcuc   2400
auagccauua uaagaccuaa aaaggcagug cucugcgggg aucccaaaca gugcgguuuu   2460
```

-continued

```
uuuaacauga ugugccugaa agugcauuuu aaccacgaga uuugcacaca agucuuccac   2520
aaaagcaucu cucgccguug cacuaaaucu gugacuucgg ucgucucaac cuuguuuuac   2580
gacaaaaaaa ugagaacgac gaauccgaaa gagacuaaga uugugauuga cacuaccggc   2640
aguaccaaac cuaagcagga cgaucucauu cucacuuguu ucagagggug ggugaagcag   2700
uugcaaauag auuacaaagg caacgaaaua augacggcag cugccucuca agggcugacc   2760
cguaaaggug uguaugccgu ucgguacaag gugaaugaaa auccucugua cgcacccacc   2820
ucagaacaug ugaacguccu acugacccgc acggaggacc gcaucgugug gaaaacacua   2880
gccggcgacc cauggauaaa aacacugacu gccaaguacc cugggaauuu cacugccacg   2940
auagaggagu ggcaagcaga gcaugaugcc aucaugaggc acaucuugga gagaccggac   3000
ccuaccgacg ucuuccagaa uaaggcaaac guguguuggg ccaaggcuuu agugccggug   3060
cugaagaccg cuggcauaga caugaccacu gaacaaugga acacugugga uuauuuugaa   3120
acggacaaag cucacucagc agagauagua uugaaccaac uaugcgugag guucuuugga   3180
cucgaucugg acuccggucu auuuucugca cccacuguuc cguuauccau uaggaauaau   3240
cacugggaua acuccccguc gccuaacaug uacgggcuga auaaagaagu gguccgucag   3300
cucucucgca gguacccaca acugccucgg gcaguugcca cuggaagagu cuaugacaug   3360
aacacuggua cacugcgcaa uuaugauccg cgcauaaacc uaguaccugu aaacagaaga   3420
cugccucaug cuuuaguccu ccaccauaau gaacacccac agagugacuu uucuucauuc   3480
gucagcaaau ugaagggcag aacuguccug gugguucgggg aaaaguuguc cgucccaggc   3540
aaaaugguug acugguuguc agaccggccu gaggcuaccu ucagagcucg gcuggauuua   3600
ggcaucccag gugaugugcc caaauaugac auaauauuug uuaaugugag gaccccauau   3660
aaauaccauc acuaucagca gugugaagac caugccauua agcuuagcau guugaccaag   3720
aaagcuuguc ugcaucugaa ucccggcgga accuguguca gcauagguua ugguuacgcu   3780
gacagggcca gcgaaagcau cauuggugcu auagcgcggc aguucaaguu uucccgggua   3840
ugcaaaccga aauccucacu ugaagagacg gaaguucugu uuguauucau uggguacgau   3900
cgcaaggccc guacgcacaa uucuuacaag cuuucaucaa ccuugaccaa cauuuauaca   3960
gguuccagac uccacgaagc cggaugugca cccucauauc augugguggcg aggggauauu   4020
gccacggcca ccgaaggagu gauuauaaau gcugcuaaca gcaaaggaca accuggcgga   4080
ggggugugcg gagcgcugua uaagaaauuc ccggaaagcu ucgauuuaca gccgaucgaa   4140
guaggaaaag cgcgacuggu caaaggugca gcuaaacaua ucauucaugc cguaggacca   4200
aacuucaaca aaguuucgga gguugaaggu gacaaacagu uggcagaggc uuaugagucc   4260
aucgcuaaga uugucaacga uaacaauuac aagucaguag cgauuccacu guuguccacc   4320
ggcaucuuuu ccgggaacaa agaucgacua acccaaucau ugaaccauuu gcugacagcu   4380
uuagacacca cugaugcaga uguagccaua uacugcaggg acaagaaaug ggaaaugacu   4440
cucaaggaag caguggcuag gagagaagca guggaggaga uaugcauauc cgacgacucu   4500
ucagugacag aaccugaugc agagcuggug agggugcauc cgaagaguuc uuuggcugga   4560
aggaagggcu acagcacaag cgauggcaaa acuuucucau auuuggaagg gaccaaguuu   4620
caccaggcgg ccaaggauau agcagaaauu aaugccaugu ggcccguugc aacggaggcc   4680
aaugagcagg uaugcaugua uauccucgga gaaagcauga gcaguauuag gucgaaaugc   4740
cccgucgaag agucggaagc cuccacacca ccuagcacgc ugccuugcuu gugcauccau   4800
```

-continued gccaugacuc cagaaagagu acagcgccua aaagccucac guccagaaca aauuacugug 4860
ugcucauccu uuccauugcc gaaguauaga aucacuggug ugcagaagau ccaaugcucc 4920
cagccuauau uguucucacc gaaagugccu gcguauauuc auccaaggaa guaucucgug 4980
gaaacaccac cgguagacga gacuccggag ccaucggcag agaaccaauc cacagagggg 5040
acaccugaac aaccaccacu uauaaccgag gaugagacca ggacuagaac gccugagccg 5100
aucaucaucg aagaggaaga agaggauagc auaaguuugc ugucagaugg cccgacccac 5160
caggugcugc aagucgaggc agacauucac gggccgcccu cuguaucuag cucauccugg 5220
uccauuccuc augcauccga cuuugaugug gacaguuuau ccauacuuga cacccuggag 5280
ggagcuagcg ugaccagcgg ggcaacguca gccgagacua acucuuacuu cgcaaagagu 5340
auggaguuuc uggcgcgacc ggugccugcg ccucgaacag uauucaggaa cccuccacau 5400
cccgcuccgc gcacaagaac accgucacuu gcacccagca gggccugcuc gagaaccagc 5460
cuaguuucca ccccgccagg cgugaauagg gugaucacua gagaggagcu cgaggcgcuu 5520
accccgucac gcacuccuag caggucgguc ucgagaacca gccuggucuc caacccgcca 5580
ggcguaaaua gggugauuac aagagaggag uuugaggcgu ucguagcaca acaacaauga 5640
cgguuugaug cgggugcaua caucuuuucc uccgacaccg gucaagggca uuuacaacaa 5700
aaaucaguaa ggcaaacggu gcuauccgaa guggguuugg agaggaccga auuggagauu 5760
ucguaugccc cgcgccucga ccaagaaaaa gaagaauuac uacgcaagaa auuacaguua 5820
aaucccacac cugcuaacag aagcagauac caguccagga agguggagaa caugaaagcc 5880
auaacagcua gacguauucu gcaaggccua gggcauuauu ugaaggcaga aggaaaagug 5940
gagugcuacc gaacccugca uccuguuccu uuguauucau cuagugugaa ccgugccuuu 6000
ucaagcccca aggucgcagu ggaagccugu aacgccaugu ugaaagagaa cuuuccgacu 6060
guggcuucuu acuguauuau uccagaguac gaugccuauu uggacauggu ugacggagcu 6120
ucaugcugcu uagacacugc caguuuuugc ccugcaaagc ugcgcagcuu uccaaagaaa 6180
cacuccuauu uggaacccac aauacgaucg gcagugccuu cagcgaucca gaacacgcuc 6240
cagaacgucc uggcagcugc cacaaaaaga aauugcaaug ucacgcaaau gagagaauug 6300
cccguauugg auucggcggc cuuuaaugug gaaugcuuca agaaauaugc guguaauaau 6360
gaauauuggg aaacguuuaa agaaaacccc aucaggcuua cugaagaaaa cgugguaaau 6420
uacauuacca aauuaaaagg accaaaagcu gcugcucuuu uugcgaagac acauaauuug 6480
aauauguugc aggacauacc aauggacagg uuuguaaugg acuuaaagag agacgugaaa 6540
gugacuccag gaacaaaaca uacugaagaa cggcccaagg uacaggugau ccaggcugcc 6600
gauccgcuag caacagcgua ucugugcgga auccaccgag agcugguuag gagauuaaau 6660
gcgguccugc uuccgaacau ucauacacug uuugauaugu cggcugaaga cuuugacgcu 6720
auuauagccg agcacuucca gccuggggau uguguucugg aaacugacau cgcgucguuu 6780
gauaaaagug aggacgacgc cauggcucug accgcguuaa ugauucugga agacuuaggu 6840
guggacgcag agcuguugac gcugauugag gcggcuuucg gcgaaauuuc aucaauacau 6900
uugcccacua aaacuaaauu uaaauucgga gccaugauga aaucuggaau guuccucaca 6960
cuguuuguga acacagucau uaacauugua aucgcaagca gaguguugag agaacggcua 7020
accggaucac caugugcagc auucauugga gaugacaaua ucgugaaagg agucaaaucg 7080
gacaaauuaa uggcagacag gugcgccacc ugguugaaua uggaagucaa gauuauagau 7140
gcugugguggg gcgagaaagc gccuuauuuc uguggagggu uuauuuugug ugacuccgug 7200

-continued accggcacag cgugccgugu ggcagacccc cuaaaaaggc uguuuaagcu uggcaaaccu 7260
cuggcagcag acgaugaaca ugaugaugac aggagaaggg cauugcauga agagucaaca 7320
cgcuggaacc gagugggu au ucuuucagag cugugcaagg caguagaauc aagguaugaa 7380
accguaggaa cuuccaucau aguuauggcc augacuacuc uagcuagcag uguuaaauca 7440
uucagcuacc ugagaggggc cccuauaacu cucuacggcu aaccugaaug gacuacgaca 7500
uagucuaguc cgccaagucu agcauauggc caccauguuc guguuucugg ugcugcugcc 7560
ucuggugucc agccagugug ugaaccugac caccagaaca cagcugccuc cagccuacac 7620
caacagcuuu accagaggcg uguacuaccc cgacaaggug uucagaucca gcgugcugca 7680
cucuacccag gaccuguucc ugccuuucuu cagcaacgug accugguucc acgccaucca 7740
cguguccggc accaauggca ccaagagauu cgacaacccc gugcugcccu ucaacgacgg 7800
gguguacuuu gccagcaccg agaaguccaa caucaucaga ggcuggaucu ucggcaccac 7860
acuggacagc aagacccaga gccugcugau cgugaacaac gccaccaacg uggucaucaa 7920
agugugcgag uuccaguucu gcaacgaccc cuuccugggc gucuacuacc acaagaacaa 7980
caagagcugg auggaaagcg aguuccgggu guacagcagc gccaacaacu gcaccuucga 8040
guacgugucc cagccuuucc ugauggaccu ggaaggcaag cagggcaacu ucaagaaccu 8100
gcgcgaguuc guguucaaga acaucgacgg cuacuucaag aucuacagca agcacacccc 8160
uaucaaccuc gugcgggauc ugccucaggg cuucucugcu cuggaacccc ugguggaucu 8220
gcccaucggc aucaacauca cccgguuuca gacacugcug gcccugcaca gaagcuaccu 8280
gacaccuggc gauagcagca gcggauggac agcuggugcc gccgcuuacu augugggcua 8340
ccugcagccu agaaccuucc ugcugaagua caacgagaac ggcaccauca ccgacgccgu 8400
ggauugugcc cuugauccuc ugagcgagac aaagugcacc cugaaguccu ucaccgugga 8460
aaagggcauc uaccagacca gcaacuuccg ggugcagccc accgaaucca ucgugcgguu 8520
ccccaauauc accaaucugu gccccuucgg cgagguguuc aaugccacca gauucgccuc 8580
uguguacgcc uggaaccgga agcggaucag caauugcgug gccgacuacu ccgugcugua 8640
caacuccgcc agcuucagca ccuucaagug cuacggcgug uccccuacca agcugaacga 8700
ccugugcuuc acaaacgugu acgccgacag cuucgugauc cggggagaug aagugcggca 8760
gauugccccu ggacagacag gcaagaucgc cgacuacaac uacaagcugc ccgacgacuu 8820
caccggcugu gugauugccu ggaacagcaa caaccuggac uccaaagucg gcggcaacua 8880
caauuaccug uaccggcugu uccggaaguc caaucugaag cccuucgagc gggacaucuc 8940
caccgagauc uaucaggccg gcagcacccc uuguaacggc guggaaggcu ucaacugcua 9000
cuucccacug caguccuacg gcuuucagcc cacaaauggc gugggcuauc agcccuacag 9060
agugguggug cugagcuucg aacugcugca ugccccugcc acagugugcg gcccuaagaa 9120
aagcaccaau cucgugaaga acaaaugcgu gaacuucaac uucaacggcc ugaccggcac 9180
aggcgugcug acagagagca acaagaaguu ccugccauuc cagcaguuug gccgggauau 9240
cgccgauacc acagacgccg uuagagaucc ccagacacug gaaauccugg acaucacccc 9300
uugcagcuuc ggcggagugu cugugaucac cccuggcacc aacaccagca aucagguggc 9360
agugcuguac caggacguga acuguaccga agugcccgug gccauucacg ccgaucagcu 9420
gacaccuaca uggcgggugu acuccaccgg cagcaaugug uuucagacca gagccggcug 9480
ucugaucgga gccgagcacg ugaacaauag cuacgagugc gacaucccca ucggcgcugg 9540
caucugugcc agcuaccaga cacagacaaa cagccccaga cgggccagau cuguggccag 9600
ccagagcauc auugccuaca caaugucucu gggcgccgag aacagcgugg ccuacuccaa 9660
caacucuauc gcuaucccca ccaacuucac caucagcgug accacagaga uccugccugu 9720
guccaugacc aagaccagcg uggacugcac cauguacauc ugcggcgauu ccaccgagug 9780
cuccaaccug cugcugcagu acggcagcuu cugcacccag cugaauagag cccugacagg 9840
gaucgccgug gaacaggaca agaacaccca agagguguuc gcccaaguga agcagaucua 9900
caagaccccu ccuaucaagg acuucggcgg cuucaauuuc agccagauuc ugcccgaucc 9960
uagcaagccc agcaagcgga gcuucaucga ggaccugcug uucaacaaag ugacacuggc 10020
cgacgccggc uucaucaagc aguauggcga uugucugggc gacauugccg ccagggaucu 10080
gauuugcgcc cagaaguuua acggacugac agugcugccu ccucugcuga ccgaugagau 10140
gaucgcccag uacacaucug cccugcuggc cggcacaauc acaagcggcu ggacauuugg 10200
agcuggcgcc gcucugcaga uccccuuugc uaugcagaug gccuacagau ucaacggcau 10260
cggagugacc cagaaugugc uguacgagaa ccagaagcug aucgccaacc aguucaacag 10320
cgccaucggc aagauccagg acagccugag cagcacagca agcgcccugg gaaagcugca 10380
ggacgugguc aaccagaaug cccaggcacu gaacacccug gucaagcagc uguccuccaa 10440
cuucggcgcc aucagcucug ugcugaacga uauccugagc agacuggacc cuccugaggc 10500
cgaggugcag aucgacagac ugaucacagg cagacugcag agccuccaga cauacgugac 10560
ccagcagcug aucagagccg ccgagauuag agccucugcc aaucuggccg ccaccaagau 10620
gucugagugu gugcugggcc agagcaagag aguggacuuu ugcggcaagg gcuaccaccu 10680
gaugagcuuc ccucagucug ccccucacgg cgugguguuu cugcacguga cauacguucc 10740
cgcucaagag aagaauuuca ccaccgcucc agccaucugc cacgacggca aagcccacuu 10800
uccuagagaa ggcguguucg uguccaacgg cacccauugg uucgugacac agcggaacuu 10860
cuacgagccc cagaucauca ccaccgacaa caccuucgug ucuggcaacu gcgacgucgu 10920
gaucggcauu gugaacaaua ccguguacga cccucugcag cccgagcugg acagcuucaa 10980
agaggaacug gacaaguacu uuaagaacca cacaagcccc gacguggacc ugggcgauau 11040
cagcggaauc aaugccagcg ucgugaacau ccagaaagag aucgaccggc ugaacgaggu 11100
ggccaagaau cugaacgaga gccugaucga ccugcaagaa cuggggaagu acgagcagua 11160
caucaagugg cccugguaca ucuggcuggg cuuuaucgcc ggacugauug ccaucgugau 11220
ggucacaauc augcuguguu gcaugaccag cugcuguagc ugccugaagg gcuguuguag 11280
cuguggcagc ugcugcaagu ucgacgagga cgauucugag cccgugcuga agggcgugaa 11340
acugcacuac acaugagcgg ccgcgaauug gcaagcugcu uacauagaac ucgcggcgau 11400
uggcaugccg ccuuaaaauu uuuauuuuau uuuucuuuuc uuuuccgaau cggauuuugu 11460
uuuuaauauu ucaaaaaaaa aaaaaaaaaa aaaaaaaaaa aaaaaaa 11507

<210> SEQ ID NO 34
<211> LENGTH: 11507
<212> TYPE: DNA
<213> ORGANISM: Artificial Sequence
<220> FEATURE:
<223> OTHER INFORMATION: Synthetised Sequence

<400> SEQUENCE: 34
atggagaaag ttcacgttga catcgaggaa gacagcccat tcctcagagc tttgcagcgg 60
agcttcccgc agtttgaggt agaagccaag caggtcactg ataatgacca tgctaatgcc 120

-continued

```
agagcgtttt cgcatctggc ttcaaaactg atcgaaacgg aggtggaccc atccgacacg    180
atccttgaca ttggaagtgc gcccgcccgc agaatgtatt ctaagcacaa gtatcattgt    240
atctgtccga tgagatgtgc ggaagatccg gacagattgt ataagtatgc aactaagctg    300
aagaaaaact gtaaggaaat aactgataag gaattggaca agaaaatgaa ggagctggcc    360
gccgtcatga gcgaccctga cctggaaact gagactatgt gcctccacga cgacgagtcg    420
tgtcgctacg aagggcaagt cgctgtttac caggatgtat acgcggttga cggaccgaca    480
agtctctatc accaagccaa taagggagtt agagtcgcct actggatagg ctttgacacc    540
acccctttta tgtttaagaa cttggctgga gcatatccat catactctac caactgggcc    600
gacgaaaccg tgttaacggc tcgtaacata ggcctatgca gctctgacgt tatggagcgg    660
tcacgtagag ggatgtccat tcttagaaag aagtatttga aaccatccaa caatgttcta    720
ttctctgttg gctcgaccat ctaccacgag aagagggact tactgaggag ctggcacctg    780
ccgtctgtat ttcacttacg tggcaagcaa aattacacat gtcggtgtga gactatagtt    840
agttgcgacg ggtacgtcgt taaaagaata gctatcagtc caggcctgta tgggaagcct    900
tcaggctatg ctgctacgat gcaccgcgag ggattcttgt gctgcaaagt gacagacaca    960
ttgaacgggg agagggtctc ttttcccgtg tgcacgtatg tgccagctac attgtgtgac   1020
caaatgactg gcatactggc aacagatgtc agtgcggacg acgcgcaaaa actgctggtt   1080
gggctcaacc agcgtatagt cgtcaacggt cgcacccaga gaaacaccaa taccatgaaa   1140
aattaccttt tgcccgtagt ggcccaggca tttgctaggt gggcaaagga atataaggaa   1200
gatcaagaag atgaaaggcc actaggacta cgagatagac agttagtcat ggggtgttgt   1260
tgggctttta gaaggcacaa gataacatct atttataagc gcccggatac ccaaaccatc   1320
atcaaagtga acagcgattt ccactcattc gtgctgccca ggataggcag taacacattg   1380
gagatcgggc tgagaacaag aatcaggaaa atgttagagg agcacaagga gccgtcacct   1440
ctcattaccg ccgaggacgt acaagaagct aagtgcgcag ccgatgaggc taaggaggtg   1500
cgtgaagccg aggagttgcg cgcagctcta ccacctttgg cagctgatgt tgaggagccc   1560
actctggaag ccgatgtcga cttgatgtta caagaggctg gggccggctc agtggagaca   1620
cctcgtggct tgataaaggt taccagctac gatggcgagg acaagatcgg ctcttacgct   1680
gtgctttctc cgcaggctgt actcaagagt gaaaaattat cttgcatcca ccctctcgct   1740
gaacaagtca tagtgataac acactctggc cgaaaagggc gttatgccgt ggaaccatac   1800
catggtaaag tagtggtgcc agagggacat gcaatacccg tccaggactt tcaagctctg   1860
agtgaaagtg ccaccattgt gtacaacgaa cgtgagttcg taaacaggta cctgcaccat   1920
attgccacac atggaggagc gctgaacact gatgaagaat attacaaaac tgtcaagccc   1980
agcgagcacg acggcgaata cctgtacgac atcgacagga aacagtgcgt caagaaagaa   2040
ctagtcactg ggctagggct cacaggcgag ctggtggatc ctcccttcca tgaattcgcc   2100
tacgagagtc tgagaacacg accagccgct ccttaccaag taccaaccat aggggtgtat   2160
ggcgtgccag gatcaggcaa gtctggcatc attaaaagcg cagtcaccaa aaaagatcta   2220
gtggtgagcg ccaagaaaga aaactgtgca gaaattataa gggacgtcaa gaaaatgaaa   2280
gggctggacg tcaatgccag aactgtggac tcagtgctct tgaatggatg caaacacccc   2340
gtagagaccc tgtatattga cgaagctttt gcttgtcatg caggtactct cagagcgctc   2400
atagccatta taagacctaa aaaggcagtg ctctgcgggg atcccaaaca gtgcggtttt   2460
```

-continued

```
tttaacatga tgtgcctgaa agtgcatttt aaccacgaga tttgcacaca agtcttccac   2520
aaaagcatct ctcgccgttg cactaaatct gtgacttcgg tcgtctcaac cttgttttac   2580
gacaaaaaaa tgagaacgac gaatccgaaa gagactaaga ttgtgattga cactaccggc   2640
agtaccaaac ctaagcagga cgatctcatt ctcacttgtt tcagagggtg ggtgaagcag   2700
ttgcaaatag attacaaagg caacgaaata atgacggcag ctgcctctca agggctgacc   2760
cgtaaaggtg tgtatgccgt tcggtacaag gtgaatgaaa atcctctgta cgcacccacc   2820
tcagaacatg tgaacgtcct actgacccgc acggaggacc gcatcgtgtg gaaaacacta   2880
gccggcgacc catggataaa aacactgact gccaagtacc ctgggaattt cactgccacg   2940
atagaggagt ggcaagcaga gcatgatgcc atcatgaggc acatcttgga gagaccggac   3000
cctaccgacg tcttccagaa taaggcaaac gtgtgttggg ccaaggcttt agtgccggtg   3060
ctgaagaccg ctggcataga catgaccact gaacaatgga acactgtgga ttattttgaa   3120
acggacaaag ctcactcagc agagatagta ttgaaccaac tatgcgtgag gttctttgga   3180
ctcgatctgg actccggtct attttctgca cccactgttc cgttatccat taggaataat   3240
cactgggata actccccgtc gcctaacatg tacgggctga ataaagaagt ggtccgtcag   3300
ctctctcgca ggtacccaca actgcctcgg gcagttgcca ctggaagagt ctatgacatg   3360
aacactggta cactgcgcaa ttatgatccg cgcataaacc tagtacctgt aaacagaaga   3420
ctgcctcatg ctttagtcct ccaccataat gaacacccac agagtgactt ttcttcattc   3480
gtcagcaaat tgaagggcag aactgtcctg gtggtcgggg aaaagttgtc cgtcccaggc   3540
aaaatggttg actggttgtc agaccggcct gaggctacct tcagagctcg gctggattta   3600
ggcatcccag gtgatgtgcc caaatatgac ataatatttg ttaatgtgag gaccccatat   3660
aaataccatc actatcagca gtgtgaagac catgccatta agcttagcat gttgaccaag   3720
aaagcttgtc tgcatctgaa tcccggcgga acctgtgtca gcataggtta tggttacgct   3780
gacagggcca gcgaaagcat cattggtgct atagcgcggc agttcaagtt ttcccgggta   3840
tgcaaaccga aatcctcact tgaagagacg gaagttctgt ttgtattcat tgggtacgat   3900
cgcaaggccc gtacgcacaa ttcttacaag ctttcatcaa ccttgaccaa catttataca   3960
ggttccagac tccacgaagc cggatgtgca ccctcatatc atgtggtgcg aggggatatt   4020
gccacggcca ccgaaggagt gattataaat gctgctaaca gcaaaggaca acctggcgga   4080
ggggtgtgcg gagcgctgta taagaaattc ccggaaagct tcgatttaca gccgatcgaa   4140
gtaggaaaag cgcgactggt caaaggtgca gctaaacata tcattcatgc cgtaggacca   4200
aacttcaaca aagtttcgga ggttgaaggt gacaaacagt tggcagaggc ttatgagtcc   4260
atcgctaaga ttgtcaacga taacaattac aagtcagtag cgattccact gttgtccacc   4320
ggcatctttt ccgggaacaa agatcgacta acccaatcat tgaaccattt gctgacagct   4380
ttagacacca ctgatgcaga tgtagccata tactgcaggg acaagaaatg ggaaatgact   4440
ctcaaggaag cagtggctag gagagaagca gtggaggaga tatgcatatc cgacgactct   4500
tcagtgacag aacctgatgc agagctggtg agggtgcatc cgaagagttc tttggctgga   4560
aggaagggct acagcacaag cgatggcaaa actttctcat atttggaagg gaccaagttt   4620
caccaggcgg ccaaggatat agcagaaatt aatgccatgt ggcccgttgc aacggaggcc   4680
aatgagcagg tatgcatgta tatcctcgga gaaagcatga gcagtattag gtcgaaatgc   4740
cccgtcgaag agtcggaagc ctccacacca cctagcacgc tgccttgctt gtgcatccat   4800
gccatgactc cagaaagagt acagcgccta aaagcctcac gtccagaaca aattactgtg   4860
```

```
tgctcatcct ttccattgcc gaagtataga atcactggtg tgcagaagat ccaatgctcc   4920
cagcctatat tgttctcacc gaaagtgcct gcgtatattc atccaaggaa gtatctcgtg   4980
gaaacaccac cggtagacga gactccggag ccatcggcag agaaccaatc cacagagggg   5040
acacctgaac aaccaccact tataaccgag gatgagacca ggactagaac gcctgagccg   5100
atcatcatcg aagaggaaga agaggatagc ataagtttgc tgtcagatgg cccgacccac   5160
caggtgctgc aagtcgaggc agacattcac gggccgccct ctgtatctag ctcatcctgg   5220
tccattcctc atgcatccga ctttgatgtg gacagtttat ccatacttga caccctggag   5280
ggagctagcg tgaccagcgg ggcaacgtca gccgagacta actcttactt cgcaaagagt   5340
atggagtttc tggcgcgacc ggtgcctgcg cctcgaacag tattcaggaa ccctccacat   5400
cccgctccgc gcacaagaac accgtcactt gcacccagca gggcctgctc gagaaccagc   5460
ctagtttcca ccccgccagg cgtgaatagg gtgatcacta gagaggagct cgaggcgctt   5520
accccgtcac gcactcctag caggtcggtc tcgagaacca gcctggtctc caacccgcca   5580
ggcgtaaata gggtgattac aagagaggag tttgaggcgt tcgtagcaca acaacaatga   5640
cggtttgatg cgggtgcata catcttttcc tccgacaccg gtcaagggca tttacaacaa   5700
aaatcagtaa ggcaaacggt gctatccgaa gtggtgttgg agaggaccga attggagatt   5760
tcgtatgccc cgcgcctcga ccaagaaaaa gaagaattac tacgcaagaa attacagtta   5820
aatcccacac ctgctaacag aagcagatac cagtccagga aggtggagaa catgaaagcc   5880
ataacagcta gacgtattct gcaaggccta gggcattatt tgaaggcaga aggaaaagtg   5940
gagtgctacc gaaccctgca tcctgttcct ttgtattcat ctagtgtgaa ccgtgccttt   6000
tcaagcccca aggtcgcagt ggaagcctgt aacgccatgt tgaaagagaa ctttccgact   6060
gtggcttctt actgtattat tccagagtac gatgcctatt tggacatggt tgacggagct   6120
tcatgctgct tagacactgc cagtttttgc cctgcaaagc tgcgcagctt tccaaagaaa   6180
cactcctatt tggaacccac aatacgatcg gcagtgcctt cagcgatcca gaacacgctc   6240
cagaacgtcc tggcagctgc cacaaaaaga aattgcaatg tcacgcaaat gagagaattg   6300
cccgtattgg attcggcggc ctttaatgtg gaatgcttca agaaatatgc gtgtaataat   6360
gaatattggg aaacgtttaa agaaaacccc atcaggctta ctgaagaaaa cgtggtaaat   6420
tacattacca aattaaaagg accaaaagct gctgctcttt ttgcgaagac acataatttg   6480
aatatgttgc aggacatacc aatggacagg tttgtaatgg acttaaagag agacgtgaaa   6540
gtgactccag gaacaaaaca tactgaagaa cggcccaagg tacaggtgat ccaggctgcc   6600
gatccgctag caacagcgta tctgtgcgga atccaccgag agctggttag gagattaaat   6660
gcggtcctgc ttccgaacat tcatacactg tttgatatgt cggctgaaga ctttgacgct   6720
attatagccg agcacttcca gcctggggat tgtgttctgg aaactgacat cgcgtcgttt   6780
gataaaagtg aggacgacgc catggctctg accgcgttaa tgattctgga agacttaggt   6840
gtggacgcag agctgttgac gctgattgag gcggctttcg gcgaaatttc atcaatacat   6900
ttgcccacta aaactaaatt taaattcgga gccatgatga aatctggaat gttcctcaca   6960
ctgtttgtga acacagtcat taacattgta atcgcaagca gagtgttgag agaacggcta   7020
accggatcac catgtgcagc attcattgga gatgacaata tcgtgaaagg agtcaaatcg   7080
gacaaattaa tggcagacag gtgcgccacc tggttgaata tggaagtcaa gattatagat   7140
gctgtggtgg gcgagaaagc gccttatttc tgtggagggt ttattttgtg tgactccgtg   7200
```

-continued

```
accggcacag cgtgccgtgt ggcagacccc ctaaaaaggc tgtttaagct tggcaaacct   7260
ctggcagcag acgatgaaca tgatgatgac aggagaaggg cattgcatga agagtcaaca   7320
cgctggaacc gagtgggtat tctttcagag ctgtgcaagg cagtagaatc aaggtatgaa   7380
accgtaggaa cttccatcat agttatggcc atgactactc tagctagcag tgttaaatca   7440
ttcagctacc tgagaggggc ccctataact ctctacggct aacctgaatg gactacgaca   7500
tagtctagtc cgccaagtct agcatatggc caccatgttc gtgtttctgg tgctgctgcc   7560
tctggtgtcc agccagtgtg tgaacctgac caccagaaca cagctgcctc cagcctacac   7620
caacagcttt accagaggcg tgtactaccc cgacaaggtg ttcagatcca gcgtgctgca   7680
ctctacccag gacctgttcc tgcctttctt cagcaacgtg acctggttcc acgccatcca   7740
cgtgtccggc accaatggca ccaagagatt cgacaacccc gtgctgccct tcaacgacgg   7800
ggtgtacttt gccagcaccg agaagtccaa catcatcaga ggctggatct tcggcaccac   7860
actggacagc aagacccaga gcctgctgat cgtgaacaac gccaccaacg tggtcatcaa   7920
agtgtgcgag ttccagttct gcaacgaccc cttcctgggc gtctactacc acaagaacaa   7980
caagagctgg atggaaagcg agttccgggt gtacagcagc gccaacaact gcaccttcga   8040
gtacgtgtcc cagcctttcc tgatggacct ggaaggcaag cagggcaact tcaagaacct   8100
gcgcgagttc gtgttcaaga acatcgacgg ctacttcaag atctacagca agcacacccc   8160
tatcaacctc gtgcgggatc tgcctcaggg cttctctgct ctggaacccc tggtggatct   8220
gcccatcggc atcaacatca cccggtttca gacactgctg gccctgcaca gaagctacct   8280
gacacctggc gatagcagca gcggatggac agctggtgcc gccgcttact atgtgggcta   8340
cctgcagcct agaaccttcc tgctgaagta caacgagaac ggcaccatca ccgacgccgt   8400
ggattgtgcc cttgatcctc tgagcgagac aaagtgcacc ctgaagtcct tcaccgtgga   8460
aaagggcatc taccagacca gcaacttccg ggtgcagccc accgaatcca tcgtgcggtt   8520
ccccaatatc accaatctgt gccccttcgg cgaggtgttc aatgccacca gattcgcctc   8580
tgtgtacgcc tggaaccgga agcggatcag caattgcgtg gccgactact ccgtgctgta   8640
caactccgcc agcttcagca ccttcaagtg ctacggcgtg tcccctacca agctgaacga   8700
cctgtgcttc acaaacgtgt acgccgacag cttcgtgatc cggggagatg aagtgcggca   8760
gattgcccct ggacagacag gcaagatcgc cgactacaac tacaagctgc ccgacgactt   8820
caccggctgt gtgattgcct ggaacagcaa caacctggac tccaaagtcg gcggcaacta   8880
caattacctg taccggctgt tccggaagtc caatctgaag cccttcgagc gggacatctc   8940
caccgagatc tatcaggccg gcagcacccc ttgtaacggc gtggaaggct tcaactgcta   9000
cttcccactg cagtcctacg gctttcagcc cacaaatggc gtgggctatc agccctacag   9060
agtggtggtg ctgagcttcg aactgctgca tgcccctgcc acagtgtgcg gccctaagaa   9120
aagcaccaat ctcgtgaaga acaaatgcgt gaacttcaac ttcaacggcc tgaccggcac   9180
aggcgtgctg acagagagca acaagaagtt cctgccattc cagcagtttg gccgggatat   9240
cgccgatacc acagacgccg ttagagatcc ccagacactg gaaatcctgg acatcacccc   9300
ttgcagcttc ggcggagtgt ctgtgatcac ccctggcacc aacaccagca atcaggtggc   9360
agtgctgtac caggacgtga actgtaccga agtgcccgtg gccattcacg ccgatcagct   9420
gacacctaca tggcgggtgt actccaccgg cagcaatgtg tttcagacca gagccggctg   9480
tctgatcgga gccgagcacg tgaacaatag ctacgagtgc gacatcccca tcggcgctgg   9540
catctgtgcc agctaccaga cacagacaaa cagccccaga cgggccagat ctgtggccag   9600
```

ccagagcatc attgcctaca caatgtctct gggcgccgag aacagcgtgg cctactccaa 9660
caactctatc gctatcccca ccaacttcac catcagcgtg accacagaga tcctgcctgt 9720
gtccatgacc aagaccagcg tggactgcac catgtacatc tgcggcgatt ccaccgagtg 9780
ctccaacctg ctgctgcagt acggcagctt ctgcacccag ctgaatagag ccctgacagg 9840
gatcgccgtg gaacaggaca agaacaccca agaggtgttc gcccaagtga agcagatcta 9900
caagacccct cctatcaagg acttcggcgg cttcaatttc agccagattc tgcccgatcc 9960
tagcaagccc agcaagcgga gcttcatcga ggacctgctg ttcaacaaag tgacactggc 10020
cgacgccggc ttcatcaagc agtatggcga ttgtctgggc gacattgccg ccagggatct 10080
gatttgcgcc cagaagttta acggactgac agtgctgcct cctctgctga ccgatgagat 10140
gatcgcccag tacacatctg ccctgctggc cggcacaatc acaagcggct ggacatttgg 10200
agctggcgcc gctctgcaga tcccctttgc tatgcagatg gcctacagat tcaacggcat 10260
cggagtgacc cagaatgtgc tgtacgagaa ccagaagctg atcgccaacc agttcaacag 10320
cgccatcggc aagatccagg acagcctgag cagcacagca agcgccctgg gaaagctgca 10380
ggacgtggtc aaccagaatg cccaggcact gaacaccctg gtcaagcagc tgtcctccaa 10440
cttcggcgcc atcagctctg tgctgaacga tatcctgagc agactggacc ctcctgaggc 10500
cgaggtgcag atcgacagac tgatcacagg cagactgcag agcctccaga catacgtgac 10560
ccagcagctg atcagagccg ccgagattag agcctctgcc aatctggccg ccaccaagat 10620
gtctgagtgt gtgctgggcc agagcaagag agtggacttt tgcggcaagg gctaccacct 10680
gatgagcttc cctcagtctg cccctcacgg cgtggtgttt ctgcacgtga catacgttcc 10740
cgctcaagag aagaatttca ccaccgctcc agccatctgc cacgacggca aagcccactt 10800
tcctagagaa ggcgtgttcg tgtccaacgg cacccattgg ttcgtgacac agcggaactt 10860
ctacgagccc cagatcatca ccaccgacaa caccttcgtg tctggcaact gcgacgtcgt 10920
gatcggcatt gtgaacaata ccgtgtacga ccctctgcag cccgagctgg acagcttcaa 10980
agaggaactg gacaagtact ttaagaacca cacaagcccc gacgtggacc tgggcgatat 11040
cagcggaatc aatgccagcg tcgtgaacat ccagaaagag atcgaccggc tgaacgaggt 11100
ggccaagaat ctgaacgaga gcctgatcga cctgcaagaa ctggggaagt acgagcagta 11160
catcaagtgg ccctggtaca tctggctggg ctttatcgcc ggactgattg ccatcgtgat 11220
ggtcacaatc atgctgtgtt gcatgaccag ctgctgtagc tgcctgaagg gctgttgtag 11280
ctgtggcagc tgctgcaagt tcgacgagga cgattctgag cccgtgctga agggcgtgaa 11340
actgcactac acatgagcgg ccgcgaattg gcaagctgct tacatagaac tcgcggcgat 11400
tggcatgccg ccttaaaatt tttattttat ttttcttttc ttttccgaat cggattttgt 11460
ttttaatatt tcaaaaaaaa aaaaaaaaaa aaaaaaaaaa aaaaaaa 11507

<210> SEQ ID NO 35
<211> LENGTH: 13377
<212> TYPE: DNA
<213> ORGANISM: Artificial Sequence
<220> FEATURE:
<223> OTHER INFORMATION: Synthetised Sequence

<400> SEQUENCE: 35
cgccagcaac gcgagctcta atacgactca ctatagatgg gcggcgcatg agagaagccc 60
agaccaatta cctacccaaa atggagaaag ttcacgttga catcgaggaa gacagcccat 120

-continued

```
tcctcagagc tttgcagcgg agcttcccgc agtttgaggt agaagccaag caggtcactg    180
ataatgacca tgctaatgcc agagcgtttt cgcatctggc ttcaaaactg atcgaaacgg    240
aggtggaccc atccgacacg atccttgaca ttggaagtgc gcccgcccgc agaatgtatt    300
ctaagcacaa gtatcattgt atctgtccga tgagatgtgc ggaagatccg gacagattgt    360
ataagtatgc aactaagctg aagaaaaact gtaaggaaat aactgataag gaattggaca    420
agaaaatgaa ggagctggcc gccgtcatga gcgaccctga cctggaaact gagactatgt    480
gcctccacga cgacgagtcg tgtcgctacg aagggcaagt cgctgtttac caggatgtat    540
acgcggttga cggaccgaca agtctctatc accaagccaa taagggagtt agagtcgcct    600
actggatagg ctttgacacc acccctttta tgtttaagaa cttggctgga gcatatccat    660
catactctac caactgggcc gacgaaaccg tgttaacggc tcgtaacata ggcctatgca    720
gctctgacgt tatggagcgg tcacgtagag ggatgtccat tcttagaaag aagtatttga    780
aaccatccaa caatgttcta ttctctgttg gctcgaccat ctaccacgag aagagggact    840
tactgaggag ctggcacctg ccgtctgtat ttcacttacg tggcaagcaa aattacacat    900
gtcggtgtga gactatagtt agttgcgacg ggtacgtcgt taaaagaata gctatcagtc    960
caggcctgta tgggaagcct tcaggctatg ctgctacgat gcaccgcgag ggattcttgt   1020
gctgcaaagt gacagacaca ttgaacgggg agagggtctc ttttcccgtg tgcacgtatg   1080
tgccagctac attgtgtgac caaatgactg gcatactggc aacagatgtc agtgcggacg   1140
acgcgcaaaa actgctggtt gggctcaacc agcgtatagt cgtcaacggt cgcacccaga   1200
gaaacaccaa taccatgaaa aattaccttt tgcccgtagt ggcccaggca tttgctaggt   1260
gggcaaagga atataaggaa gatcaagaag atgaaaggcc actaggacta cgagatagac   1320
agttagtcat ggggtgttgt tgggctttta gaaggcacaa gataacatct atttataagc   1380
gcccggatac ccaaaccatc atcaaagtga acagcgattt ccactcattc gtgctgccca   1440
ggataggcag taacacattg gagatcgggc tgagaacaag aatcaggaaa atgttagagg   1500
agcacaagga gccgtcacct ctcattaccg ccgaggacgt acaagaagct aagtgcgcag   1560
ccgatgaggc taaggaggtg cgtgaagccg aggagttgcg cgcagctcta ccacctttgg   1620
cagctgatgt tgaggagccc actctggaag ccgatgtcga cttgatgtta caagaggctg   1680
gggccggctc agtggagaca cctcgtggct tgataaaggt taccagctac gatggcgagg   1740
acaagatcgg ctcttacgct gtgctttctc cgcaggctgt actcaagagt gaaaaattat   1800
cttgcatcca ccctctcgct gaacaagtca tagtgataac acactctggc cgaaaagggc   1860
gttatgccgt ggaaccatac catggtaaag tagtggtgcc agagggacat gcaatacccg   1920
tccaggactt tcaagctctg agtgaaagtg ccaccattgt gtacaacgaa cgtgagttcg   1980
taaacaggta cctgcaccat attgccacac atggaggagc gctgaacact gatgaagaat   2040
attacaaaac tgtcaagccc agcgagcacg acggcgaata cctgtacgac atcgacagga   2100
aacagtgcgt caagaaagaa ctagtcactg ggctagggct cacaggcgag ctggtggatc   2160
ctcccttcca tgaattcgcc tacgagagtc tgagaacacg accagccgct ccttaccaag   2220
taccaaccat aggggtgtat ggcgtgccag gatcaggcaa gtctggcatc attaaaagcg   2280
cagtcaccaa aaaagatcta gtggtgagcg ccaagaaaga aaactgtgca gaaattataa   2340
gggacgtcaa gaaaatgaaa gggctggacg tcaatgccag aactgtggac tcagtgctct   2400
tgaatggatg caaacacccc gtagagaccc tgtatattga cgaagctttt gcttgtcatg   2460
caggtactct cagagcgctc atagccatta taagacctaa aaaggcagtg ctctgcgggg   2520
```

-continued

```
atcccaaaca gtgcggtttt tttaacatga tgtgcctgaa agtgcatttt aaccacgaga   2580
tttgcacaca agtcttccac aaaagcatct ctcgccgttg cactaaatct gtgacttcgg   2640
tcgtctcaac cttgttttac gacaaaaaaa tgagaacgac gaatccgaaa gagactaaga   2700
ttgtgattga cactaccggc agtaccaaac ctaagcagga cgatctcatt ctcacttgtt   2760
tcagagggtg ggtgaagcag ttgcaaatag attacaaagg caacgaaata atgacggcag   2820
ctgcctctca agggctgacc cgtaaaggtg tgtatgccgt tcggtacaag gtgaatgaaa   2880
atcctctgta cgcacccacc tcagaacatg tgaacgtcct actgacccgc acggaggacc   2940
gcatcgtgtg gaaaacacta gccggcgacc catggataaa aacactgact gccaagtacc   3000
ctgggaattt cactgccacg atagaggagt ggcaagcaga gcatgatgcc atcatgaggc   3060
acatcttgga gagaccggac cctaccgacg tcttccagaa taaggcaaac gtgtgttggg   3120
ccaaggcttt agtgccggtg ctgaagaccg ctggcataga catgaccact gaacaatgga   3180
acactgtgga ttattttgaa acggacaaag ctcactcagc agagatagta ttgaaccaac   3240
tatgcgtgag gttctttgga ctcgatctgg actccggtct attttctgca cccactgttc   3300
cgttatccat taggaataat cactgggata actccccgtc gcctaacatg tacgggctga   3360
ataaagaagt ggtccgtcag ctctctcgca ggtacccaca actgcctcgg gcagttgcca   3420
ctggaagagt ctatgacatg aacactggta cactgcgcaa ttatgatccg cgcataaacc   3480
tagtacctgt aaacagaaga ctgcctcatg ctttagtcct ccaccataat gaacacccac   3540
agagtgactt ttcttcattc gtcagcaaat tgaagggcag aactgtcctg gtggtcgggg   3600
aaaagttgtc cgtcccaggc aaaatggttg actggttgtc agaccggcct gaggctacct   3660
tcagagctcg gctggattta ggcatcccag gtgatgtgcc caaatatgac ataatatttg   3720
ttaatgtgag gaccccatat aaataccatc actatcagca gtgtgaagac catgccatta   3780
agcttagcat gttgaccaag aaagcttgtc tgcatctgaa tcccggcgga acctgtgtca   3840
gcataggtta tggttacgct gacagggcca gcgaaagcat cattggtgct atagcgcggc   3900
agttcaagtt ttcccgggta tgcaaaccga aatcctcact tgaagagacg gaagttctgt   3960
ttgtattcat tgggtacgat cgcaaggccc gtacgcacaa ttcttacaag ctttcatcaa   4020
ccttgaccaa catttataca ggttccagac tccacgaagc cggatgtgca ccctcatatc   4080
atgtggtgcg aggggatatt gccacggcca ccgaaggagt gattataaat gctgctaaca   4140
gcaaaggaca acctggcgga ggggtgtgcg gagcgctgta taagaaattc ccggaaagct   4200
tcgatttaca gccgatcgaa gtaggaaaag cgcgactggt caaaggtgca gctaaacata   4260
tcattcatgc cgtaggacca aacttcaaca aagtttcgga ggttgaaggt gacaaacagt   4320
tggcagaggc ttatgagtcc atcgctaaga ttgtcaacga taacaattac aagtcagtag   4380
cgattccact gttgtccacc ggcatctttt ccgggaacaa agatcgacta acccaatcat   4440
tgaaccattt gctgacagct ttagacacca ctgatgcaga tgtagccata tactgcaggg   4500
acaagaaatg ggaaatgact ctcaaggaag cagtggctag gagagaagca gtggaggaga   4560
tatgcatatc cgacgactct tcagtgacag aacctgatgc agagctggtg agggtgcatc   4620
cgaagagttc tttggctgga aggaagggct acagcacaag cgatggcaaa actttctcat   4680
atttggaagg gaccaagttt caccaggcgg ccaaggatat agcagaaatt aatgccatgt   4740
ggcccgttgc aacggaggcc aatgagcagg tatgcatgta tatcctcgga gaaagcatga   4800
gcagtattag gtcgaaatgc ccgtcgaagg agtcggaagc ctccacacca cctagcacgc   4860
```

-continued

```
tgccttgctt gtgcatccat gccatgactc cagaaagagt acagcgccta aaagcctcac   4920
gtccagaaca aattactgtg tgctcatcct ttccattgcc gaagtataga atcactggtg   4980
tgcagaagat ccaatgctcc cagcctatat tgttctcacc gaaagtgcct gcgtatattc   5040
atccaaggaa gtatctcgtg gaaacaccac cggtagacga gactccggag ccatcggcag   5100
agaaccaatc cacagagggg acacctgaac aaccaccact tataaccgag gatgagacca   5160
ggactagaac gcctgagccg atcatcatcg aagaggaaga agaggatagc ataagtttgc   5220
tgtcagatgg cccgacccac caggtgctgc aagtcgaggc agacattcac gggccgccct   5280
ctgtatctag ctcatcctgg tccattcctc atgcatccga ctttgatgtg gacagtttat   5340
ccatacttga caccctggag ggagctagcg tgaccagcgg ggcaacgtca gccgagacta   5400
actcttactt cgcaaagagt atggagtttc tggcgcgacc ggtgcctgcg cctcgaacag   5460
tattcaggaa ccctccacat cccgctccgc gcacaagaac accgtcactt gcacccagca   5520
gggcctgctc gagaaccagc ctagtttcca ccccgccagg cgtgaatagg gtgatcacta   5580
gagaggagct cgaggcgctt accccgtcac gcactcctag caggtcggtc tcgagaacca   5640
gcctggtctc caacccgcca ggcgtaaata gggtgattac aagagaggag tttgaggcgt   5700
tcgtagcaca acaacaatga cggtttgatg cgggtgcata catcttttcc tccgacaccg   5760
gtcaagggca tttacaacaa aaatcagtaa ggcaaacggt gctatccgaa gtggtgttgg   5820
agaggaccga attggagatt tcgtatgccc cgcgcctcga ccaagaaaaa gaagaattac   5880
tacgcaagaa attacagtta aatcccacac ctgctaacag aagcagatac cagtccagga   5940
aggtggagaa catgaaagcc ataacagcta gacgtattct gcaaggccta gggcattatt   6000
tgaaggcaga aggaaaagtg gagtgctacc gaaccctgca tcctgttcct ttgtattcat   6060
ctagtgtgaa ccgtgccttt tcaagcccca aggtcgcagt ggaagcctgt aacgccatgt   6120
tgaaagagaa ctttccgact gtggcttctt actgtattat tccagagtac gatgcctatt   6180
tggacatggt tgacggagct tcatgctgct tagacactgc cagtttttgc cctgcaaagc   6240
tgcgcagctt tccaaagaaa cactcctatt tggaacccac aatacgatcg gcagtgcctt   6300
cagcgatcca gaacacgctc cagaacgtcc tggcagctgc cacaaaaaga aattgcaatg   6360
tcacgcaaat gagagaattg cccgtattgg attcggcggc ctttaatgtg gaatgcttca   6420
agaaatatgc gtgtaataat gaatattggg aaacgtttaa agaaaacccc atcaggctta   6480
ctgaagaaaa cgtggtaaat tacattacca aattaaaagg accaaaagct gctgctcttt   6540
ttgcgaagac acataatttg aatatgttgc aggacatacc aatggacagg tttgtaatgg   6600
acttaaagag agacgtgaaa gtgactccag gaacaaaaca tactgaagaa cggcccaagg   6660
tacaggtgat ccaggctgcc gatccgctag caacagcgta tctgtgcgga atccaccgag   6720
agctggttag gagattaaat gcggtcctgc ttccgaacat tcatacactg tttgatatgt   6780
cggctgaaga ctttgacgct attatagccg agcacttcca gcctggggat tgtgttctgg   6840
aaactgacat cgcgtcgttt gataaaagtg aggacgacgc catggctctg accgcgttaa   6900
tgattctgga agacttaggt gtggacgcag agctgttgac gctgattgag gcggctttcg   6960
gcgaaatttc atcaatacat ttgcccacta aaactaaatt taaattcgga gccatgatga   7020
aatctggaat gttcctcaca ctgtttgtga acacagtcat taacattgta atcgcaagca   7080
gagtgttgag agaacggcta accggatcac catgtgcagc attcattgga gatgacaata   7140
tcgtgaaagg agtcaaatcg gacaaattaa tggcagacag gtgcgccacc tggttgaata   7200
tggaagtcaa gattatagat gctgtggtgg gcgagaaagc gccttatttc tgtggagggt   7260
```

```
ttattttgtg tgactccgtg accggcacag cgtgccgtgt ggcagacccc ctaaaaaggc   7320
tgtttaagct tggcaaacct ctggcagcag acgatgaaca tgatgatgac aggagaaggg   7380
cattgcatga agagtcaaca cgctggaacc gagtgggtat tctttcagag ctgtgcaagg   7440
cagtagaatc aaggtatgaa accgtaggaa cttccatcat agttatggcc atgactactc   7500
tagctagcag tgttaaatca ttcagctacc tgagaggggc ccctataact ctctacggct   7560
aacctgaatg gactacgaca tagtctagtc cgccaagtct agcatatggc caccatgttc   7620
gtgtttctgg tgctgctgcc tctggtgtcc agccagtgtg tgaacctgac caccagaaca   7680
cagctgcctc cagcctacac caacagcttt accagaggcg tgtactaccc cgacaaggtg   7740
ttcagatcca gcgtgctgca ctctacccag gacctgttcc tgcctttctt cagcaacgtg   7800
acctggttcc acgccatcca cgtgtccggc accaatggca ccaagagatt cgacaacccc   7860
gtgctgccct tcaacgacgg ggtgtacttt gccagcaccg agaagtccaa catcatcaga   7920
ggctggatct tcggcaccac actggacagc aagacccaga gcctgctgat cgtgaacaac   7980
gccaccaacg tggtcatcaa agtgtgcgag ttccagttct gcaacgaccc cttcctgggc   8040
gtctactacc acaagaacaa caagagctgg atggaaagcg agttccgggt gtacagcagc   8100
gccaacaact gcaccttcga gtacgtgtcc cagcctttcc tgatggacct ggaaggcaag   8160
cagggcaact tcaagaacct gcgcgagttc gtgttcaaga acatcgacgg ctacttcaag   8220
atctacagca agcacacccc tatcaacctc gtgcgggatc tgcctcaggg cttctctgct   8280
ctggaacccc tggtggatct gcccatcggc atcaacatca cccggtttca gacactgctg   8340
gccctgcaca gaagctacct gacacctggc gatagcagca gcggatggac agctggtgcc   8400
gccgcttact atgtgggcta cctgcagcct agaaccttcc tgctgaagta caacgagaac   8460
ggcaccatca ccgacgccgt ggattgtgcc cttgatcctc tgagcgagac aaagtgcacc   8520
ctgaagtcct tcaccgtgga aaagggcatc taccagacca gcaacttccg ggtgcagccc   8580
accgaatcca tcgtgcggtt ccccaatatc accaatctgt gccccttcgg cgaggtgttc   8640
aatgccacca gattcgcctc tgtgtacgcc tggaaccgga agcggatcag caattgcgtg   8700
gccgactact ccgtgctgta caactccgcc agcttcagca ccttcaagtg ctacggcgtg   8760
tcccctacca agctgaacga cctgtgcttc acaaacgtgt acgccgacag cttcgtgatc   8820
cggggagatg aagtgcggca gattgcccct ggacagacag gcaagatcgc cgactacaac   8880
tacaagctgc ccgacgactt caccggctgt gtgattgcct ggaacagcaa caacctggac   8940
tccaaagtcg gcggcaacta caattacctg taccggctgt tccggaagtc caatctgaag   9000
cccttcgagc gggacatctc caccgagatc tatcaggccg gcagcacccc ttgtaacggc   9060
gtggaaggct tcaactgcta cttcccactg cagtcctacg gctttcagcc cacaaatggc   9120
gtgggctatc agccctacag agtggtggtg ctgagcttcg aactgctgca tgcccctgcc   9180
acagtgtgcg gccctaagaa aagcaccaat ctcgtgaaga acaaatgcgt gaacttcaac   9240
ttcaacggcc tgaccggcac aggcgtgctg acagagagca acaagaagtt cctgccattc   9300
cagcagtttg gccgggatat cgccgatacc acagacgccg ttagagatcc ccagacactg   9360
gaaatcctgg acatcacccc ttgcagcttc ggcggagtgt ctgtgatcac ccctggcacc   9420
aacaccagca atcaggtggc agtgctgtac caggacgtga actgtaccga agtgcccgtg   9480
gccattcacg ccgatcagct gacacctaca tggcgggtgt actccaccgg cagcaatgtg   9540
tttcagacca gagccggctg tctgatcgga gccgagcacg tgaacaatag ctacgagtgc   9600
```

-continued

```
gacatcccca tcggcgctgg catctgtgcc agctaccaga cacagacaaa cagccccaga   9660
cgggccagat ctgtggccag ccagagcatc attgcctaca caatgtctct gggcgccgag   9720
aacagcgtgg cctactccaa caactctatc gctatcccca ccaacttcac catcagcgtg   9780
accacagaga tcctgcctgt gtccatgacc aagaccagcg tggactgcac catgtacatc   9840
tgcggcgatt ccaccgagtg ctccaacctg ctgctgcagt acggcagctt ctgcacccag   9900
ctgaatagag ccctgacagg gatcgccgtg gaacaggaca agaacaccca agaggtgttc   9960
gcccaagtga agcagatcta caagacccct cctatcaagg acttcggcgg cttcaatttc  10020
agccagattc tgcccgatcc tagcaagccc agcaagcgga gcttcatcga ggacctgctg  10080
ttcaacaaag tgacactggc cgacgccggc ttcatcaagc agtatggcga ttgtctgggc  10140
gacattgccg ccagggatct gatttgcgcc cagaagttta acggactgac agtgctgcct  10200
cctctgctga ccgatgagat gatcgcccag tacacatctg ccctgctggc cggcacaatc  10260
acaagcggct ggacatttgg agctggcgcc gctctgcaga tcccctttgc tatgcagatg  10320
gcctacagat tcaacggcat cggagtgacc cagaatgtgc tgtacgagaa ccagaagctg  10380
atcgccaacc agttcaacag cgccatcggc aagatccagg acagcctgag cagcacagca  10440
agcgccctgg gaaagctgca ggacgtggtc aaccagaatg cccaggcact gaacaccctg  10500
gtcaagcagc tgtcctccaa cttcggcgcc atcagctctg tgctgaacga tatcctgagc  10560
agactggacc ctcctgaggc cgaggtgcag atcgacagac tgatcacagg cagactgcag  10620
agcctccaga catacgtgac ccagcagctg atcagagccg ccgagattag agcctctgcc  10680
aatctggccg ccaccaagat gtctgagtgt gtgctgggcc agagcaagag agtggacttt  10740
tgcggcaagg gctaccacct gatgagcttc cctcagtctg cccctcacgg cgtggtgttt  10800
ctgcacgtga catacgttcc cgctcaagag aagaatttca ccaccgctcc agccatctgc  10860
cacgacggca aagcccactt tcctagagaa ggcgtgttcg tgtccaacgg cacccattgg  10920
ttcgtgacac agcggaactt ctacgagccc cagatcatca ccaccgacaa caccttcgtg  10980
tctggcaact gcgacgtcgt gatcggcatt gtgaacaata ccgtgtacga ccctctgcag  11040
cccgagctgg acagcttcaa agaggaactg gacaagtact ttaagaacca cacaagcccc  11100
gacgtggacc tgggcgatat cagcggaatc aatgccagcg tcgtgaacat ccagaaagag  11160
atcgaccggc tgaacgaggt ggccaagaat ctgaacgaga gcctgatcga cctgcaagaa  11220
ctggggaagt acgagcagta catcaagtgg ccctggtaca tctggctggg ctttatcgcc  11280
ggactgattg ccatcgtgat ggtcacaatc atgctgtgtt gcatgaccag ctgctgtagc  11340
tgcctgaagg gctgttgtag ctgtggcagc tgctgcaagt tcgacgagga cgattctgag  11400
cccgtgctga agggcgtgaa actgcactac acatgagcgg ccgcgaattg gcaagctgct  11460
tacatagaac tcgcggcgat tggcatgccg ccttaaaatt tttattttat tttctttttc  11520
ttttccgaat cggattttgt ttttaatatt tcaaaaaaaa aaaaaaaaaa aaaaaaaaaa  11580
aaaaaaacgc gtcgagggga attaattctt gaagacgaaa gggccaggtg gcacttttcg  11640
gggaaatgtg cgcggaaccc ctatttgttt atttttctaa atacattcaa atatgtatcc  11700
gctcatgaga caataaccct gataaatgct tcaataatat tgaaaaagga agagtatgag  11760
tattcaacat ttccgtgtcg cccttattcc cttttttgcg gcattttgcc ttcctgtttt  11820
tgctcaccca gaaacgctgg tgaaagtaaa agatgctgaa gatcagttgg gtgcacgagt  11880
gggttacatc gaactggatc tcaacagcgg taagatcctt gagagttttc gccccgaaga  11940
acgttttcca atgatgagca cttttaaagt tctgctatgt ggcgcggtat tatcccgtgt  12000
```

tgacgccggg caagagcaac tcggtcgccg catacactat tctcagaatg acttggttga 12060
gtactcacca gtcacagaaa agcatcttac ggatggcatg acagtaagag aattatgcag 12120
tgctgccata accatgagtg ataacactgc ggccaactta cttctgacaa cgatcggagg 12180
accgaaggag ctaaccgctt ttttgcacaa catgggggat catgtaactc gccttgatcg 12240
ttgggaaccg gagctgaatg aagccatacc aaacgacgag cgtgacacca cgatgcctgt 12300
agcaatggca acaacgttgc gcaaactatt aactggcgaa ctacttactc tagcttcccg 12360
gcaacaatta atagactgga tggaggcgga taaagttgca ggaccacttc tgcgctcggc 12420
ccttccggct ggctggttta ttgctgataa atctggagcc ggtgagcgtg ggtctcgcgg 12480
tatcattgca gcactggggc cagatggtaa gccctcccgt atcgtagtta tctacacgac 12540
ggggagtcag gcaactatgg atgaacgaaa tagacagatc gctgagatag gtgcctcact 12600
gattaagcat tggtaactgt cagaccaagt ttactcatat atactttaga ttgatttaaa 12660
acttcatttt taatttaaaa ggatctaggt gaagatcctt tttgataatc tcatgaccaa 12720
aatcccttaa cgtgagtttt cgttccactg agcgtcagac cccgtagaaa agatcaaagg 12780
atcttcttga gatccttttt ttctgcgcgt aatctgctgc ttgcaaacaa aaaaaccacc 12840
gctaccagcg gtggtttgtt tgccggatca agagctacca actctttttc cgaaggtaac 12900
tggcttcagc agagcgcaga taccaaatac tgtccttcta gtgtagccgt agttaggcca 12960
ccacttcaag aactctgtag caccgcctac atacctcgct ctgctaatcc tgttaccagt 13020
ggctgctgcc agtggcgata agtcgtgtct taccgggttg gactcaagac gatagttacc 13080
ggataaggcg cagcggtcgg gctgaacggg gggttcgtgc acacagccca gcttggagcg 13140
aacgacctac accgaactga gatacctaca gcgtgagcat tgagaaagcg ccacgcttcc 13200
cgaagggaga aaggcggaca ggtatccggt aagcggcagg gtcggaacag gagagcgcac 13260
gagggagctt ccagggggaa acgcctggta tctttatagt cctgtcgggt ttcgccacct 13320
ctgacttgag cgtcgatttt tgtgatgctc gtcagggggg cggagcctat ggaaaaa 13377

<210> SEQ ID NO 36
<211> LENGTH: 3822
<212> TYPE: RNA
<213> ORGANISM: Artificial Sequence
<220> FEATURE:
<223> OTHER INFORMATION: Synthetised Sequence

<400> SEQUENCE: 36
auguucgugu uucuggugcu gcugccucug guguccagcc agugugugaa ccugaccacc 60
agaacacagc ugccuccagc cuacaccaac agcuuuacca gaggcgugua cuaccccgac 120
aagguguuca gauccagcgu gcugcacucu acccaggacc uguuccugcc uuucuucagc 180
aacgugaccu gguuccacgc cauccacgug uccggcacca auggcaccaa gagauucgac 240
aaccccgugc ugcccuucaa cgacggggug uacuuugcca gcaccgagaa guccaacauc 300
aucagaggcu ggaucuucgg caccacacug gacagcaaga cccagagccu gcugaucgug 360
aacaacgcca ccaacguggu caucaaagug ugcgaguucc aguucugcaa cgaccccuuc 420
cugggcgucu acuaccacaa gaacaacaag agcuggaugg aaagcgaguu ccggguguac 480
agcagcgcca acaacugcac cuucgaguac gugucccagc cuuuccugau ggaccuggaa 540
ggcaagcagg gcaacuucaa gaaccugcgc gaguucgugu ucaagaacau cgacggcuac 600
uucaagaucu acagcaagca caccccuauc aaccucgugc gggaucugcc ucagggcuuc 660

-continued ucugcucugg aaccccuggu ggaucugccc aucggcauca acaucacccg guuucagaca 720
cugcuggccc ugcacagaag cuaccugaca ccuggcgaua gcagcagcgg auggacagcu 780
ggugccgccg cuuacuaugu gggcuaccug cagccuagaa ccuuccugcu gaaguacaac 840
gagaacggca ccaucaccga cgccguggau ugugcccuug auccucugag cgagacaaag 900
ugcacccuga aguccuucac cguggaaaag ggcaucuacc agaccagcaa cuuccgggug 960
cagcccaccg aauccaucgu gcgguucccc aauaucacca aucugugccc cuucggcgag 1020
guguucaaug ccaccagauu cgccucugug uacgccugga accggaagcg gaucagcaau 1080
ugcguggccg acuacuccgu gcuguacaac uccgccagcu ucagcaccuu caagugcuac 1140
ggcguguccc cuaccaagcu gaacgaccug ugcuucacaa acguguacgc cgacagcuuc 1200
gugauccggg gagaugaagu gcggcagauu gccccuggac agacaggcaa gaucgccgac 1260
uacaacuaca agcugcccga cgacuucacc ggcuguguga uugccuggaa cagcaacaac 1320
cuggacucca aagucggcgg caacuacaau uaccuguacc ggcuguuccg gaaguccaau 1380
cugaagcccu ucgagcggga caucuccacc gagaucuauc aggccggcag caccccuugu 1440
aacggcgugg aaggcuucaa cugcuacuuc ccacugcagu ccuacggcuu ucagcccaca 1500
aauggcgugg gcuaucagcc cuacagagug guggugcuga gcuucgaacu gcugcaugcc 1560
ccugccacag ugugcggccc uaagaaaagc accaaucucg ugaagaacaa augcgugaac 1620
uucaacuuca acggccugac cggcacaggc gugcugacag agagcaacaa gaaguuccug 1680
ccauuccagc aguuuggccg ggauaucgcc gauaccacag acgccguuag agaucccag 1740 acacuggaaa uccuggacau caccccuugc agcuucggcg gagugucugu gaucaccccu 1800
ggcaccaaca ccagcaauca gguggcagug cuguaccagg acgugaacug uaccgaagug 1860
cccguggcca uucacgccga ucagcugaca ccuacauggc ggguguacuc caccggcagc 1920
aauguguuuc agaccagagc cggcugucug aucggagccg agcacgugaa caauagcuac 1980
gagugcgaca uccccaucgg cgcuggcauc ugugccagcu accagacaca gacaaacagc 2040
cccagacggg ccagaucugu ggccagccag agcaucauug ccuacacaau gucucugggc 2100
gccgagaaca gcguggccua cuccaacaac ucuaucgcua uccccaccaa cuucaccauc 2160
agcgugacca cagagauccu gccuguguce augaccaaga ccagcgugga cugcaccaug 2220
uacaucugcg gcgauuccac cgagugcucc aaccugcugc ugcaguacgg cagcuucugc 2280
acccagcuga auagagcccu gacagggauc gccguggaac aggacaagaa cacccaagag 2340
guguucgccc aagugaagca gaucuacaag accccuccua ucaaggacuu cggcggcuuc 2400
aauuucagcc agauucugcc cgauccuagc aagcccagca agcggagcuu caucgaggac 2460
cugcuguuca acaaagugac acuggccgac gccggcuuca ucaagcagua uggcgauugu 2520
cugggcgaca uugccgccag ggaucugauu ugcgcccaga aguuuaacgg acugacagug 2580
cugccuccuc ugcugaccga ugagaugauc gcccaguaca caucugcccu gcuggccggc 2640
acaaucacaa gcggcuggac auuuggagcu ggcgccgcuc ugcagauccc cuuugcuaug 2700
cagauggccu acagauucaa cggcaucgga gugacccaga augugcugua cgagaaccag 2760
aagcugaucg ccaaccaguu caacagcgcc aucggcaaga uccaggacag ccugagcagc 2820
acagcaagcg cccugggaaa gcugcaggac guggucaacc agaaugccca ggcacugaac 2880
acccugguca agcagcuguc cuccaacuuc ggcgccauca gcucugugcu gaacgauauc 2940
cugagcagac uggacccucc ugaggccgag gugcagaucg acagacugau cacaggcaga 3000
cugcagagcc uccagacaua cgugacccag cagcugauca gagccgccga gauuagagcc 3060

```
ucugccaauc uggccgccac caagaugucu gagugugugc ugggccagag caagagagug   3120

gacuuuugcg gcaagggcua ccaccugaug agcuucccuc agucugcccc ucacggcgug   3180

guguuucugc acgugacaua cguucccgcu caagagaaga auuucaccac cgcuccagcc   3240

aucugccacg acggcaaagc ccacuuuccu agagaaggcg uguucguguc caacggcacc   3300

cauugguucg ugacacagcg gaacuucuac gagccccaga ucaucaccac cgacaacacc   3360

uucgugucug gcaacugcga cgucgugauc ggcauuguga acaauaccgu guacgacccu   3420

cugcagcccg agcuggacag cuucaaagag gaacuggaca aguacuuuaa gaaccacaca   3480

agccccgacg uggaccuggg cgauaucagc ggaaucaaug ccagcgucgu gaacauccag   3540

aaagagaucg accggcugaa cgagguggcc aagaaucuga acgagagccu gaucgaccug   3600

caagaacugg ggaaguacga gcaguacauc aaguggcccu gguacaucug gcugggcuuu   3660

aucgccggac ugauugccau cgugaugguc acaaucaugc uguguugcau gaccagcugc   3720

uguagcugcc ugaagggcug uuguagcugu ggcagcugcu gcaaguucga cgaggacgau   3780

ucugagcccg ugcugaaggg cgugaaacug cacuacacau ga                      3822


<210> SEQ ID NO 37
<211> LENGTH: 60
<212> TYPE: PRT
<213> ORGANISM: SARS-CoV-2

<400> SEQUENCE: 37

Trp Tyr Ile Trp Leu Gly Phe Ile Ala Gly Leu Ile Ala Ile Val Met
1               5                   10                  15

Val Thr Ile Met Leu Cys Cys Met Thr Ser Cys Cys Ser Cys Leu Lys
            20                  25                  30

Gly Cys Cys Ser Cys Gly Ser Cys Cys Lys Phe Asp Glu Asp Asp Ser
        35                  40                  45

Glu Pro Val Leu Lys Gly Val Lys Leu His Tyr Thr
    50                  55                  60


<210> SEQ ID NO 38
<211> LENGTH: 1213
<212> TYPE: PRT
<213> ORGANISM: SARS-CoV-2

<400> SEQUENCE: 38

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125
```

-continued

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu

-continued

```
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975
```

```
Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro
    1205                 1210
```

<210> SEQ ID NO 39
<211> LENGTH: 3624
<212> TYPE: DNA
<213> ORGANISM: Artificial Sequence
<220> FEATURE:
<223> OTHER INFORMATION: Synthetised Sequence

<400> SEQUENCE: 39

```
atgttcgtgt ttctggtgct gctgcctctg gtgtccagcc agtgtgtgaa cctgaccacc     60

agaacacagc tgcctccagc ctacaccaac agctttacca gaggcgtgta ctaccccgac    120

aaggtgttca gatccagcgt gctgcactct acccaggacc tgttcctgcc tttcttcagc    180

aacgtgacct ggttccacgc catccacgtg tccggcacca atggcaccaa gagattcgac    240

aaccccgtgc tgcccttcaa cgacggggtg tactttgcca gcaccgagaa gtccaacatc    300

atcagaggct ggatcttcgg caccacactg gacagcaaga cccagagcct gctgatcgtg    360

aacaacgcca ccaacgtggt catcaaagtg tgcgagttcc agttctgcaa cgaccccttc    420

ctgggcgtct actaccacaa gaacaacaag agctggatgg aaagcgagtt ccgggtgtac    480

agcagcgcca acaactgcac cttcgagtac gtgtcccagc ctttcctgat ggacctggaa    540

ggcaagcagg gcaacttcaa gaacctgcgc gagttcgtgt tcaagaacat cgacggctac    600
```

ttcaagatct acagcaagca caccoctatc aacctcgtgc gggatctgcc tcagggcttc 660
tctgctctgg aacccctggt ggatctgccc atcggcatca acatcacccg gtttcagaca 720
ctgctggccc tgcacagaag ctacctgaca cctggcgata gcagcagcgg atggacagct 780
ggtgccgccg cttactatgt gggctacctg cagcctagaa ccttcctgct gaagtacaac 840
gagaacggca ccatcaccga cgccgtggat tgtgcccttg atcctctgag cgagacaaag 900
tgcaccctga agtccttcac cgtggaaaag ggcatctacc agaccagcaa cttccgggtg 960
cagcccaccg aatccatcgt gcggttcccc aatatcacca atctgtgccc cttcggcgag 1020
gtgttcaatg ccaccagatt cgcctctgtg tacgcctgga accggaagcg gatcagcaat 1080
tgcgtggccg actactccgt gctgtacaac tccgccagct tcagcacctt caagtgctac 1140
ggcgtgtccc ctaccaagct gaacgacctg tgcttcacaa acgtgtacgc cgacagcttc 1200
gtgatccggg gagatgaagt gcggcagatt gcccctggac agacaggcaa gatcgccgac 1260
tacaactaca agctgcccga cgacttcacc ggctgtgtga ttgcctggaa cagcaacaac 1320
ctggactcca aagtcggcgg caactacaat tacctgtacc ggctgttccg gaagtccaat 1380
ctgaagccct tcgagcggga catctccacc gagatctatc aggccggcag caccccttgt 1440
aacggcgtgg aaggcttcaa ctgctacttc ccactgcagt cctacggctt tcagcccaca 1500
aatggcgtgg gctatcagcc ctacagagtg gtggtgctga gcttcgaact gctgcatgcc 1560
cctgccacag tgtgcggccc taagaaaagc accaatctcg tgaagaacaa atgcgtgaac 1620
ttcaacttca acggcctgac cggcacaggc gtgctgacag agagcaacaa gaagttcctg 1680
ccattccagc agtttggccg ggatatcgcc gataccacag acgccgttag agatccccag 1740
acactggaaa tcctggacat caccccttgc agcttcggcg gagtgtctgt gatcacccct 1800
ggcaccaaca ccagcaatca ggtggcagtg ctgtaccagg acgtgaactg taccgaagtg 1860
cccgtggcca ttcacgccga tcagctgaca cctacatggc gggtgtactc caccggcagc 1920
aatgtgtttc agaccagagc cggctgtctg atcggagccg agcacgtgaa caatagctac 1980
gagtgcgaca tccccatcgg cgctggcatc tgtgccagct accagacaca gacaaacagc 2040
cccagacggg ccagatctgt ggccagccag agcatcattg cctacacaat gtctctgggc 2100
gccgagaaca gcgtggccta ctccaacaac tctatcgcta tccccaccaa cttcaccatc 2160
agcgtgacca cagagatcct gcctgtgtcc atgaccaaga ccagcgtgga ctgcaccatg 2220
tacatctgcg gcgattccac cgagtgctcc aacctgctgc tgcagtacgg cagcttctgc 2280
acccagctga atagagccct gacagggatc gccgtggaac aggacaagaa cacccaagag 2340
gtgttcgccc aagtgaagca gatctacaag acccctccta tcaaggactt cggcggcttc 2400
aatttcagcc agattctgcc cgatcctagc aagcccagca agcggagctt catcgaggac 2460
ctgctgttca acaaagtgac actggccgac gccggcttca tcaagcagta tggcgattgt 2520
ctgggcgaca ttgccgccag ggatctgatt tgcgcccaga agtttaacgg actgacagtg 2580
ctgcctcctc tgctgaccga tgagatgatc gcccagtaca catctgccct gctggccggc 2640
acaatcacaa gcggctggac atttggagct ggcgccgctc tgcagatccc ctttgctatg 2700
cagatggcct acagattcaa cggcatcgga gtgacccaga atgtgctgta cgagaaccag 2760
aagctgatcg ccaaccagtt caacagcgcc atcggcaaga tccaggacag cctgagcagc 2820
acagcaagcg ccctgggaaa gctgcaggac gtggtcaacc agaatgccca ggcactgaac 2880
accctggtca agcagctgtc ctccaacttc ggcgccatca gctctgtgct gaacgatatc 2940
ctgagcagac tggaccctcc tgaggccgag gtgcagatcg acagactgat cacaggcaga 3000
ctgcagagcc tccagacata cgtgacccag cagctgatca gagccgccga gattagagcc 3060
tctgccaatc tggccgccac caagatgtct gagtgtgtgc tgggccagag caagagagtg 3120
gacttttgcg gcaagggcta ccacctgatg agcttccctc agtctgcccc tcacggcgtg 3180
gtgtttctgc acgtgacata cgttcccgct caagagaaga atttcaccac cgctccagcc 3240
atctgccacg acggcaaagc ccactttcct agagaaggcg tgttcgtgtc caacggcacc 3300
cattggttcg tgacacagcg gaacttctac gagccccaga tcatcaccac cgacaacacc 3360
ttcgtgtctg gcaactgcga cgtcgtgatc ggcattgtga acaataccgt gtacgaccct 3420
ctgcagcccg agctggacag cttcaaagag gaactggaca agtactttaa gaaccacaca 3480
agccccgacg tggacctggg cgatatcagc ggaatcaatg ccagcgtcgt gaacatccag 3540
aaagagatcg accggctgaa cgaggtggcc aagaatctga acgagagcct gatcgacctg 3600
caagaactgg ggaagtacga gcag 3624

<210> SEQ ID NO 40
<211> LENGTH: 3624
<212> TYPE: RNA
<213> ORGANISM: Artificial Sequence
<220> FEATURE:
<223> OTHER INFORMATION: Synthetised Sequence

<400> SEQUENCE: 40
auguucgugu uucuggugcu gcugccucug guguccagcc agugugugaa ccugaccacc 60
agaacacagc ugccuccagc cuacaccaac agcuuuacca gaggcgugua cuaccccgac 120
aagguguuca gauccagcgu gcugcacucu acccaggacc uguuccugcc uuucuucagc 180
aacgugaccu gguuccacgc cauccacgug uccggcacca auggcaccaa gagauucgac 240
aaccccgugc ugcccuucaa cgacggggug uacuuugcca gcaccgagaa guccaacauc 300
aucagaggcu ggaucuucgg caccacacug gacagcaaga cccagagccu gcugaucgug 360
aacaacgcca ccaacguggu caucaaagug ugcgaguucc aguucugcaa cgaccccuuc 420
cugggcgucu acuaccacaa gaacaacaag agcuggaugg aaagcgaguu ccggguguac 480
agcagcgcca acaacugcac cuucgaguac guguccccagc cuuuccugau ggaccuggaa 540
ggcaagcagg gcaacuucaa gaaccugcgc gaguucgugu ucaagaacau cgacggcuac 600
uucaagaucu acagcaagca caccccuauc aaccucgugc gggaucugcc ucagggcuuc 660
ucugcucugg aaccccuggu ggaucugccc aucggcauca acaucacccg guuucagaca 720
cugcuggccc ugcacagaag cuaccugaca ccuggcgaua gcagcagcgg auggacagcu 780
ggugccgccg cuuacuaugu gggcuaccug cagccuagaa ccuuccugcu gaaguacaac 840
gagaacggca ccaucaccga cgccguggau ugugcccuug auccucugag cgagacaaag 900
ugcacccuga aguccuucac cguggaaaag ggcaucuacc agaccagcaa cuuccgggug 960
cagcccaccg aauccaucgu gcgguucccc aauaucacca aucugugccc cuucggcgag 1020
guguucaaug ccaccagauu cgccucugug uacgccugga accggaagcg gaucagcaau 1080
ugcguggccg acuacuccgu gcuguacaac uccgccagcu ucagcaccuu caagugcuac 1140
ggcguguccc cuaccaagcu gaacgaccug ugcuucacaa acguguacgc cgacagcuuc 1200
gugauccggg gagaugaagu gcggcagauu gccccuggac agacaggcaa gaucgccgac 1260
uacaacuaca agcugcccga cgacuucacc ggcuguguga uugccuggaa cagcaacaac 1320
cuggacucca aagucggcgg caacuacaau uaccuguacc ggcuguuccg gaaguccaau 1380

-continued cugaagcccu ucgagcggga caucuccacc gagaucuauc aggccggcag caccccuugu 1440
aacggcgugg aaggcuucaa cugcuacuuc ccacugcagu ccuacggcuu ucagcccaca 1500
aauggcgugg gcuaucagcc cuacagagug gugguggcuga gcuucgaacu gcugcaugcc 1560
ccugccacag ugugcggccc uaagaaaagc accaaucucg ugaagaacaa augcgugaac 1620
uucaacuuca acggccugac cggcacaggc gugcugacag agagcaacaa gaaguuccug 1680
ccauuccagc aguuuggccg ggauaucgcc gauaccacag acgccguuag agaucccccag 1740 acacuggaaa uccuggacau caccccuugc agcuucggcg gagugucugu gaucaccccu 1800
ggcaccaaca ccagcaauca gguggcagug cuguaccagg acgugaacug uaccgaagug 1860
cccguggcca uucacgccga ucagcugaca ccuacauggc ggguguacuc caccggcagc 1920
aauguguuuc agaccagagc cggcugucug aucggagccg agcacgugaa caauagcuac 1980
gagugcgaca uccccaucgg cgcuggcauc ugugccagcu accagacaca gacaaacagc 2040
cccagacggg ccagaucugu ggccagccag agcaucauug ccuacacaau gucucugggc 2100
gccgagaaca gcguggccua cuccaacaac ucuaucgcua uccccaccaa cuucaccauc 2160
agcgugacca cagagauccu gccuguguccc augaccaaga ccagcgugga cugcaccaug 2220
uacaucugcg gcgauuccac cgagugcucc aaccugcugc ugcaguacgg cagcuucugc 2280
acccagcuga auagagcccu gacagggauc gccguggaac aggacaagaa cacccaagag 2340
guguucgccc aagugaagca gaucuacaag accccuccua ucaaggacuu cggcggcuuc 2400
aauuucagcc agauucugcc cgauccuagc aagcccagca agcggagcuu caucgaggac 2460
cugcuguuca acaaagugac acuggccgac gccggcuuca ucaagcagua uggcgauugu 2520
cugggcgaca uugccgccag ggaucugauu ugcgcccaga aguuuaacgg acugacagug 2580
cugccuccuc ugcugaccga ugagaugauc gcccaguaca caucugcccu gcuggccggc 2640
acaaucacaa gcggcuggac auuuggagcu ggcgccgcuc ugcagauccc cuuugcuaug 2700
cagauggccu acagauucaa cggcaucgga gugacccaga augugcugua cgagaaccag 2760
aagcugaucg ccaaccaguu caacagcgcc aucggcaaga uccaggacag ccugagcagc 2820
acagcaagcg cccugggaaa gcugcaggac guggucaacc agaaugccca ggcacugaac 2880
acccugguca agcagcuguc cuccaacuuc ggcgccauca gcucugugcu gaacgauauc 2940
cugagcagac uggacccucc ugaggccgag gugcagaucg acagacugau cacaggcaga 3000
cugcagagcc uccagacaua cgugacccag cagcugauca gagccgccga gauuagagcc 3060
ucugccaauc uggccgccac caagaugucu gagugugugc ugggccagag caagagagug 3120
gacuuuugcg gcaagggcua ccaccugaug agcuucccuc agucugcccc ucacggcgug 3180
guguuucugc acgugacaua cguucccgcu caagagaaga auuucaccac cgcuccagcc 3240
aucugccacg acggcaaagc ccacuuuccu agagaaggcg uguucguguc caacggcacc 3300
cauugguucg ugacacagcg gaacuucuac gagccccaga ucaucaccac cgacaacacc 3360
uucgugucug gcaacugcga cgucgugauc ggcauuguga acaauaccgu guacgacccu 3420
cugcagcccg agcuggacag cuucaaagag gaacuggaca aguacuuuaa gaaccacaca 3480
agccccgacg uggaccuggg cgauaucagc ggaaucaaug ccagcgucgu gaacauccag 3540
aaagagaucg accggcugaa cgagguggcc aagaaucuga acgagagccu gaucgaccug 3600
caagaacugg ggaaguacga gcag 3624

<210> SEQ ID NO 41
<211> LENGTH: 120

-continued

<212> TYPE: DNA
<213> ORGANISM: Artificial Sequence
<220> FEATURE:
<223> OTHER INFORMATION: Synthetised Sequence

<400> SEQUENCE: 41
ggaggcggag gatctggcgg aggcggaagt ggatctggct atatccctga ggctcccaga 60
gatggccagg cctatgttcg gaaggatggc gaatgggtgc tgctgagcac attcctcggt 120

<210> SEQ ID NO 42
<211> LENGTH: 120
<212> TYPE: RNA
<213> ORGANISM: Artificial Sequence
<220> FEATURE:
<223> OTHER INFORMATION: Synthetised Sequence

<400> SEQUENCE: 42
ggaggcggag gaucuggcgg aggcggaagu ggaucuggcu auaucccuga ggcucccaga 60
gauggccagg ccuauguucg gaaggauggc gaaugggugc ugcugagcac auuccucggu 120

<210> SEQ ID NO 43
<211> LENGTH: 39
<212> TYPE: PRT
<213> ORGANISM: Artificial Sequence
<220> FEATURE:
<223> OTHER INFORMATION: Synthetised Sequence

<400> SEQUENCE: 43

```
Gly Gly Gly Gly Ser Gly Gly Gly Gly Ser Gly Ser Gly Tyr Ile Pro
1               5                   10                  15

Glu Ala Pro Arg Asp Gly Gln Ala Tyr Val Arg Lys Asp Glu Trp Val
            20                  25                  30

Leu Leu Ser Thr Phe Leu Gly
        35
```

<210> SEQ ID NO 44
<211> LENGTH: 129
<212> TYPE: DNA
<213> ORGANISM: Artificial Sequence
<220> FEATURE:
<223> OTHER INFORMATION: Synthetised Sequence

<400> SEQUENCE: 44
ggctctggct ctggcaatgg aaccggcaga atgaagcaga tcgaggacaa gatcgagaac 60
atcaccagca agatctacaa tatcaccaac gagatcgccc ggatcaagaa gctgatcggc 120
aacagaaca 129

<210> SEQ ID NO 45
<211> LENGTH: 129
<212> TYPE: RNA
<213> ORGANISM: Artificial Sequence
<220> FEATURE:
<223> OTHER INFORMATION: Synthetised Sequence

<400> SEQUENCE: 45
ggcucuggcu cuggcaaugg aaccggcaga augaagcaga ucgaggacaa gaucgagaac 60
aucaccagca agaucuacaa uaucaccaac gagaucgccc ggaucaagaa gcugaucggc 120
aacagaaca 129

<210> SEQ ID NO 46
<211> LENGTH: 43

<212> TYPE: PRT
<213> ORGANISM: Artificial Sequence
<220> FEATURE:
<223> OTHER INFORMATION: Synthetised Sequence

<400> SEQUENCE: 46

Gly Ser Gly Ser Gly Asn Gly Thr Gly Arg Met Lys Gln Ile Glu Asp
1 5 10 15

Lys Ile Glu Asn Ile Thr Ser Lys Ile Tyr Asn Ile Thr Asn Glu Ile
20 25 30

Ala Arg Ile Lys Lys Leu Ile Gly Asn Arg Thr
35 40

<210> SEQ ID NO 47
<211> LENGTH: 1270
<212> TYPE: PRT
<213> ORGANISM: SARS-CoV-2 UK variant B.1.1.7

<400> SEQUENCE: 47

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile Ser Gly Thr Asn Gly Thr Lys Arg Phe Asp Asn Pro
65 70 75 80

Val Leu Pro Phe Asn Asp Gly Val Tyr Phe Ala Ser Thr Glu Lys Ser
85 90 95

Asn Ile Ile Arg Gly Trp Ile Phe Gly Thr Thr Leu Asp Ser Lys Thr
100 105 110

Gln Ser Leu Leu Ile Val Asn Asn Ala Thr Asn Val Val Ile Lys Val
115 120 125

Cys Glu Phe Gln Phe Cys Asn Asp Pro Phe Leu Gly Val Tyr His Lys
130 135 140

Asn Asn Lys Ser Trp Met Glu Ser Glu Phe Arg Val Tyr Ser Ser Ala
145 150 155 160

Asn Asn Cys Thr Phe Glu Tyr Val Ser Gln Pro Phe Leu Met Asp Leu
165 170 175

Glu Gly Lys Gln Gly Asn Phe Lys Asn Leu Arg Glu Phe Val Phe Lys
180 185 190

Asn Ile Asp Gly Tyr Phe Lys Ile Tyr Ser Lys His Thr Pro Ile Asn
195 200 205

Leu Val Arg Asp Leu Pro Gln Gly Phe Ser Ala Leu Glu Pro Leu Val
210 215 220

Asp Leu Pro Ile Gly Ile Asn Ile Thr Arg Phe Gln Thr Leu Leu Ala
225 230 235 240

Leu His Arg Ser Tyr Leu Thr Pro Gly Asp Ser Ser Ser Gly Trp Thr
245 250 255

Ala Gly Ala Ala Ala Tyr Tyr Val Gly Tyr Leu Gln Pro Arg Thr Phe
260 265 270

Leu Leu Lys Tyr Asn Glu Asn Gly Thr Ile Thr Asp Ala Val Asp Cys
275 280 285

Ala Leu Asp Pro Leu Ser Glu Thr Lys Cys Thr Leu Lys Ser Phe Thr

-continued

```
    290                 295                 300

Val Glu Lys Gly Ile Tyr Gln Thr Ser Asn Phe Arg Val Gln Pro Thr
305                 310                 315                 320

Glu Ser Ile Val Arg Phe Pro Asn Ile Thr Asn Leu Cys Pro Phe Gly
                325                 330                 335

Glu Val Phe Asn Ala Thr Arg Phe Ala Ser Val Tyr Ala Trp Asn Arg
            340                 345                 350

Lys Arg Ile Ser Asn Cys Val Ala Asp Tyr Ser Val Leu Tyr Asn Ser
        355                 360                 365

Ala Ser Phe Ser Thr Phe Lys Cys Tyr Gly Val Ser Pro Thr Lys Leu
    370                 375                 380

Asn Asp Leu Cys Phe Thr Asn Val Tyr Ala Asp Ser Phe Val Ile Arg
385                 390                 395                 400

Gly Asp Glu Val Arg Gln Ile Ala Pro Gly Gln Thr Gly Lys Ile Ala
                405                 410                 415

Asp Tyr Asn Tyr Lys Leu Pro Asp Asp Phe Thr Gly Cys Val Ile Ala
            420                 425                 430

Trp Asn Ser Asn Asn Leu Asp Ser Lys Val Gly Gly Asn Tyr Asn Tyr
        435                 440                 445

Leu Tyr Arg Leu Phe Arg Lys Ser Asn Leu Lys Pro Phe Glu Arg Asp
    450                 455                 460

Ile Ser Thr Glu Ile Tyr Gln Ala Gly Ser Thr Pro Cys Asn Gly Val
465                 470                 475                 480

Glu Gly Phe Asn Cys Tyr Phe Pro Leu Gln Ser Tyr Gly Phe Gln Pro
                485                 490                 495

Thr Tyr Gly Val Gly Tyr Gln Pro Tyr Arg Val Val Val Leu Ser Phe
            500                 505                 510

Glu Leu Leu His Ala Pro Ala Thr Val Cys Gly Pro Lys Lys Ser Thr
        515                 520                 525

Asn Leu Val Lys Asn Lys Cys Val Asn Phe Asn Phe Asn Gly Leu Thr
    530                 535                 540

Gly Thr Gly Val Leu Thr Glu Ser Asn Lys Lys Phe Leu Pro Phe Gln
545                 550                 555                 560

Gln Phe Gly Arg Asp Ile Asp Asp Thr Thr Asp Ala Val Arg Asp Pro
                565                 570                 575

Gln Thr Leu Glu Ile Leu Asp Ile Thr Pro Cys Ser Phe Gly Gly Val
            580                 585                 590

Ser Val Ile Thr Pro Gly Thr Asn Thr Ser Asn Gln Val Ala Val Leu
        595                 600                 605

Tyr Gln Gly Val Asn Cys Thr Glu Val Pro Val Ala Ile His Ala Asp
    610                 615                 620

Gln Leu Thr Pro Thr Trp Arg Val Tyr Ser Thr Gly Ser Asn Val Phe
625                 630                 635                 640

Gln Thr Arg Ala Gly Cys Leu Ile Gly Ala Glu His Val Asn Asn Ser
                645                 650                 655

Tyr Glu Cys Asp Ile Pro Ile Gly Ala Gly Ile Cys Ala Ser Tyr Gln
            660                 665                 670

Thr Gln Thr Asn Ser His Ser Leu Ala Ser Ser Val Ala Ser Gln Ser
        675                 680                 685

Ile Ile Ala Tyr Thr Met Ser Leu Gly Ala Glu Asn Ser Val Ala Tyr
    690                 695                 700

Ser Asn Asn Ser Ile Ala Ile Pro Ile Asn Phe Thr Ile Ser Val Thr
705                 710                 715                 720
```

-continued

```
Thr Glu Ile Leu Pro Val Ser Met Thr Lys Thr Ser Val Asp Cys Thr
                725                 730                 735

Met Tyr Ile Cys Gly Asp Ser Thr Glu Cys Ser Asn Leu Leu Leu Gln
            740                 745                 750

Tyr Gly Ser Phe Cys Thr Gln Leu Asn Arg Ala Leu Thr Gly Ile Ala
        755                 760                 765

Val Glu Gln Asp Lys Asn Thr Gln Glu Val Phe Ala Gln Val Lys Gln
    770                 775                 780

Ile Tyr Lys Thr Pro Pro Ile Lys Asp Phe Gly Gly Phe Asn Phe Ser
785                 790                 795                 800

Gln Ile Leu Pro Asp Pro Ser Lys Pro Ser Lys Arg Ser Pro Ile Glu
                805                 810                 815

Asp Leu Leu Phe Asn Lys Val Thr Leu Ala Asp Ala Gly Phe Ile Lys
            820                 825                 830

Gln Tyr Gly Asp Cys Leu Gly Asp Ile Ala Ala Arg Asp Leu Ile Cys
        835                 840                 845

Ala Gln Lys Phe Asn Gly Leu Thr Val Leu Pro Pro Leu Leu Thr Asp
    850                 855                 860

Glu Met Ile Ala Gln Tyr Thr Ser Ala Leu Leu Ala Gly Thr Ile Thr
865                 870                 875                 880

Ser Gly Trp Thr Phe Gly Ala Gly Pro Ala Leu Gln Ile Pro Phe Pro
                885                 890                 895

Met Gln Met Ala Tyr Arg Phe Asn Gly Ile Gly Val Thr Gln Asn Val
            900                 905                 910

Leu Tyr Glu Asn Gln Lys Leu Ile Ala Asn Gln Phe Asn Ser Ala Ile
        915                 920                 925

Gly Lys Ile Gln Asp Ser Leu Ser Ser Thr Pro Ser Ala Leu Gly Lys
    930                 935                 940

Leu Gln Asp Val Val Asn Gln Asn Ala Gln Ala Leu Asn Thr Leu Val
945                 950                 955                 960

Lys Gln Leu Ser Ser Asn Phe Gly Ala Ile Ser Ser Val Leu Asn Asp
                965                 970                 975

Ile Leu Ala Arg Leu Asp Pro Pro Glu Ala Glu Val Gln Ile Asp Arg
            980                 985                 990

Leu Ile Thr Gly Arg Leu Gln Ser  Leu Gln Thr Tyr Val  Thr Gln Gln
        995                 1000                1005

Leu Ile  Arg Ala Ala Glu Ile  Arg Ala Ser Ala Asn  Leu Ala Ala
    1010                1015                1020

Thr Lys  Met Ser Glu Cys Val  Leu Gly Gln Ser Lys  Arg Val Asp
    1025                1030                1035

Phe Cys  Gly Lys Gly Tyr His  Leu Met Ser Phe Pro  Gln Ser Ala
    1040                1045                1050

Pro His  Gly Val Val Phe Leu  His Val Thr Tyr Val  Pro Ala Gln
    1055                1060                1065

Glu Lys  Asn Phe Thr Thr Ala  Pro Ala Ile Cys His  Asp Gly Lys
    1070                1075                1080

Ala His  Phe Pro Arg Glu Gly  Val Phe Val Ser Asn  Gly Thr His
    1085                1090                1095

Trp Phe  Val Thr Gln Arg Asn  Phe Tyr Glu Pro Gln  Ile Ile Thr
    1100                1105                1110

Thr His  Asn Thr Phe Val Ser  Gly Asn Cys Asp Val  Val Ile Gly
    1115                1120                1125
```

Ile Val Asn Asn Thr Val Tyr Asp Pro Leu Gln Pro Glu Leu Asp
1130 1135 1140

Ser Phe Lys Glu Glu Leu Asp Lys Tyr Phe Lys Asn His Thr Ser
1145 1150 1155

Pro Asp Val Asp Leu Gly Asp Ile Ser Gly Ile Asn Ala Ser Val
1160 1165 1170

Val Asn Ile Gln Lys Glu Ile Asp Arg Leu Asn Glu Val Ala Lys
1175 1180 1185

Asn Leu Asn Glu Ser Leu Ile Asp Leu Gln Glu Leu Gly Lys Tyr
1190 1195 1200

Glu Gln Tyr Ile Lys Trp Pro Trp Tyr Ile Trp Leu Gly Phe Ile
1205 1210 1215

Ala Gly Leu Ile Ala Ile Val Met Val Thr Ile Met Leu Cys Cys
1220 1225 1230

Met Thr Ser Cys Cys Ser Cys Leu Lys Gly Cys Cys Ser Cys Gly
1235 1240 1245

Ser Cys Cys Lys Phe Asp Glu Asp Asp Ser Glu Pro Val Leu Lys
1250 1255 1260

Gly Val Lys Leu His Tyr Thr
1265 1270

<210> SEQ ID NO 48
<211> LENGTH: 3813
<212> TYPE: DNA
<213> ORGANISM: Artificial Sequence
<220> FEATURE:
<223> OTHER INFORMATION: Synthetised Sequence

<400> SEQUENCE: 48
atgttcgtgt ttctggtgct gctgcctctg gtgtccagcc agtgtgtgaa cctgaccacc 60
agaacacagc tgcctccagc ctacaccaac agctttacca gaggcgtgta ctaccccgac 120
aaggtgttca gatccagcgt gctgcactct acccaggacc tgttcctgcc tttcttcagc 180
aacgtgacct ggttccacgc catctccggc accaatggca ccaagagatt cgacaacccc 240
gtgctgccct tcaacgacgg ggtgtacttt gccagcaccg agaagtccaa catcatcaga 300
ggctggatct tcggcaccac actggacagc aagacccaga gcctgctgat cgtgaacaac 360
gccaccaacg tggtcatcaa agtgtgcgag ttccagttct gcaacgaccc cttcctgggc 420
gtctaccaca agaacaacaa gagctggatg gaaagcgagt tccgggtgta cagcagcgcc 480
aacaactgca ccttcgagta cgtgtcccag cctttcctga tggacctgga aggcaagcag 540
ggcaacttca agaacctgcg cgagttcgtg ttcaagaaca tcgacggcta cttcaagatc 600
tacagcaagc acacccctat caacctcgtg cgggatctgc ctcagggctt ctctgctctg 660
gaacccctgg tggatctgcc catcggcatc aacatcaccc ggtttcagac actgctggcc 720
ctgcacagaa gctacctgac acctggcgat agcagcagcg gatggacagc tggtgccgcc 780
gcttactatg tgggctacct gcagcctaga accttcctgc tgaagtacaa cgagaacggc 840
accatcaccg acgccgtgga ttgtgccctt gatcctctga gcgagacaaa gtgcaccctg 900
aagtccttca ccgtggaaaa gggcatctac cagaccagca acttccgggt gcagcccacc 960
gaatccatcg tgcggttccc caatatcacc aatctgtgcc ccttcggcga ggtgttcaat 1020
gccaccagat tcgcctctgt gtacgcctgg aaccggaagc ggatcagcaa ttgcgtggcc 1080
gactactccg tgctgtacaa ctccgccagc ttcagcacct tcaagtgcta cggcgtgtcc 1140
cctaccaagc tgaacgacct gtgcttcaca aacgtgtacg ccgacagctt cgtgatccgg 1200

-continued

```
ggagatgaag tgcggcagat tgcccctgga cagacaggca agatcgccga ctacaactac   1260
aagctgcccg acgacttcac cggctgtgtg attgcctgga acagcaacaa cctggactcc   1320
aaagtcggcg gcaactacaa ttacctgtac cggctgttcc ggaagtccaa tctgaagccc   1380
ttcgagcggg acatctccac cgagatctat caggccggca gcaccccttg taacggcgtg   1440
gaaggcttca actgctactt cccactgcag tcctacggct ttcagcccac atatggcgtg   1500
ggctatcagc cctacagagt ggtggtgctg agcttcgaac tgctgcatgc ccctgccaca   1560
gtgtgcggcc ctaagaaaag caccaatctc gtgaagaaca aatgcgtgaa cttcaacttc   1620
aacggcctga ccggcacagg cgtgctgaca gagagcaaca agaagttcct gccattccag   1680
cagtttggcc gggatatcga cgataccaca gacgccgtta gagatcccca gacactggaa   1740
atcctggaca tcaccccttg cagcttcggc ggagtgtctg tgatcacccc tggcaccaac   1800
accagcaatc aggtggcagt gctgtaccag ggcgtgaact gtaccgaagt gcccgtggcc   1860
attcacgccg atcagctgac acctacatgg cgggtgtact ccaccggcag caatgtgttt   1920
cagaccagag ccggctgtct gatcggagcc gagcacgtga acaatagcta cgagtgcgac   1980
atccccatcg gcgctggcat ctgtgccagc taccagacac agacaaacag ccactctctg   2040
gccagctctg tggccagcca gagcatcatt gcctacacaa tgtctctggg cgccgagaac   2100
agcgtggcct actccaacaa ctctatcgct atccccatca acttcaccat cagcgtgacc   2160
acagagatcc tgcctgtgtc catgaccaag accagcgtgg actgcaccat gtacatctgc   2220
ggcgattcca ccgagtgctc caacctgctg ctgcagtacg gcagcttctg cacccagctg   2280
aatagagccc tgacagggat cgccgtggaa caggacaaga acacccaaga ggtgttcgcc   2340
caagtgaagc agatctacaa gacccctcct atcaaggact tcggcggctt caatttcagc   2400
cagattctgc ccgatcctag caagcccagc aagcggagcc ccatcgagga cctgctgttc   2460
aacaaagtga cactggccga cgccggcttc atcaagcagt atggcgattg tctgggcgac   2520
attgccgcca gggatctgat ttgcgcccag aagtttaacg gactgacagt gctgcctcct   2580
ctgctgaccg atgagatgat cgcccagtac acatctgccc tgctggccgg cacaatcaca   2640
agcggctgga catttggagc tggccccgct ctgcagatcc cctttcctat gcagatggcc   2700
tacagattca acggcatcgg agtgacccag aatgtgctgt acgagaacca gaagctgatc   2760
gccaaccagt tcaacagcgc catcggcaag atccaggaca gcctgagcag cacaccaagc   2820
gccctgggaa agctgcagga cgtggtcaac cagaatgccc aggcactgaa caccctggtc   2880
aagcagctgt cctccaactt cggcgccatc agctctgtgc tgaacgatat cctggccaga   2940
ctggaccctc ctgaggccga ggtgcagatc gacagactga tcacaggcag actgcagagc   3000
ctccagacat acgtgaccca gcagctgatc agagccgccg agattagagc ctctgccaat   3060
ctggccgcca ccaagatgtc tgagtgtgtg ctgggccaga gcaagagagt ggacttttgc   3120
ggcaagggct accacctgat gagcttccct cagtctgccc ctcacggcgt ggtgtttctg   3180
cacgtgacat acgttcccgc tcaagagaag aatttcacca ccgctccagc catctgccac   3240
gacggcaaag cccactttcc tagagaaggc gtgttcgtgt ccaacggcac ccattggttc   3300
gtgacacagc ggaacttcta cgagccccag atcatcacca cccacaacac cttcgtgtct   3360
ggcaactgcg acgtcgtgat cggcattgtg aacaataccg tgtacgaccc tctgcagccc   3420
gagctggaca gcttcaaaga ggaactggac aagtacttta agaaccacac aagccccgac   3480
gtggacctgg gcgatatcag cggaatcaat gccagcgtcg tgaacatcca gaaagagatc   3540
```

gaccggctga acgaggtggc caagaatctg aacgagagcc tgatcgacct gcaagaactg 3600
gggaagtacg agcagtacat caagtggccc tggtacatct ggctgggctt tatcgccgga 3660
ctgattgcca tcgtgatggt cacaatcatg ctgtgttgca tgaccagctg ctgtagctgc 3720
ctgaagggct gttgtagctg tggcagctgc tgcaagttcg acgaggacga ttctgagccc 3780
gtgctgaagg gcgtgaaact gcactacaca tga 3813

<210> SEQ ID NO 49
<211> LENGTH: 3813
<212> TYPE: RNA
<213> ORGANISM: Artificial Sequence
<220> FEATURE:
<223> OTHER INFORMATION: Synthetised Sequence

<400> SEQUENCE: 49
auguucgugu uucuggugcu gcugccucug guguccagcc agugugugaa ccugaccacc 60
agaacacagc ugccuccagc cuacaccaac agcuuuacca gaggcgugua cuaccccgac 120
aagguguuca gauccagcgu gcugcacucu acccaggacc uguuccugcc uuucuucagc 180
aacgugaccu gguuccacgc caucuccggc accaauggca ccaagagauu cgacaacccc 240
gugcugcccu ucaacgacgg gguguacuuu gccagcaccg agaaguccaa caucaucaga 300
ggcuggaucu ucggcaccac acuggacagc aagacccaga gccugcugau cgugaacaac 360
gccaccaacg uggucaucaa agugugcgag uuccaguucu gcaacgaccc cuuccugggc 420
gucuaccaca agaacaacaa gagcuggaug gaaagcgagu uccgggugua cagcagcgcc 480
aacaacugca ccuucgagua cgugucccag ccuuuccuga uggaccugga aggcaagcag 540
ggcaacuuca agaaccugcg cgaguucgug uucaagaaca ucgacggcua cuucaagauc 600
uacagcaagc acaccccuau caaccucgug cgggaucugc cucagggcuu cucugcucug 660
gaaccccugg uggaucugcc caucggcauc aacaucaccc gguuucagac acugcuggcc 720
cugcacagaa gcuaccugac accuggcgau agcagcagcg gauggacagc uggugccgcc 780
gcuuacuaug ugggcuaccu gcagccuaga accuuccugc ugaaguacaa cgagaacggc 840
accaucaccg acgccgugga uugugcccuu gauccucuga gcgagacaaa gugcacccug 900
aaguccuuca ccguggaaaa gggcaucuac cagaccagca acuuccgggu gcagcccacc 960
gaauccaucg ugcgguuccc caauaucacc aaucugugcc ccuucggcga gguguucaau 1020
gccaccagau ucgccucugu guacgccugg aaccggaagc ggaucagcaa uugcguggcc 1080
gacuacuccg ugcuguacaa cuccgccagc uucagcaccu ucaagugcua cggcgugucc 1140
ccuaccaagc ugaacgaccu gugcuucaca aacguguacg ccgacagcuu cgugauccgg 1200
ggagaugaag ugcggcagau ugccccugga cagacaggca agaucgccga cuacaacuac 1260
aagcugcccg acgacuucac cggcugugug auugccugga acagcaacaa ccuggacucc 1320
aaagucggcg gcaacuacaa uuaccuguac cggcuguucc ggaaguccaa ucugaagccc 1380
uucgagcggg acaucuccac cgagaucuau caggccggca gcaccccuug uaacggcgug 1440
gaaggcuuca acugcuacuu cccacugcag uccuacggcu uucagcccac auauggcgug 1500
ggcuaucagc ccuacagagu gguggugcug agcuucgaac ugcugcaugc cccugccaca 1560
gugugcggcc cuaagaaaag caccaaucuc gugaagaaca aaugcgugaa cuucaacuuc 1620
aacggccuga ccggcacagg cgugcugaca gagagcaaca agaaguuccu gccauuccag 1680
caguuuggcc gggauaucga cgauaccaca gacgccguua gagaucccca gacacuggaa 1740
auccuggaca ucaccccuug cagcuucggc ggagugucug ugaucacccc uggcaccaac 1800
accagcaauc agguggcagu gcuguaccag ggcgugaacu guaccgaagu gcccguggcc 1860
auucacgccg aucagcugac accuacaugg cgggguguacu ccaccggcag caauguguuu 1920
cagaccagag ccggcugucu gaucggagcc gagcacguga acaauagcua cgagugcgac 1980
auccccaucg gcgcuggcau cugugccagc uaccagacac agacaaacag ccacucucug 2040
gccagcucug uggccagcca gagcaucauu gccuacacaa ugucucuggg cgccgagaac 2100
agcguggccu acuccaacaa cucuaucgcu auccccauca acuucaccau cagcgugacc 2160
acagagaucc ugccugugu c caugaccaag accagcgugg acugcaccau guacaucugc 2220
ggcgauucca ccgagugcuc caaccugcug cugcaguacg gcagcuucug cacccagcug 2280
aauagagccc ugacagggau cgccguggaa caggacaaga acacccaaga gguguucgcc 2340
caagugaagc agaucuacaa gaccccuccu aucaaggacu ucggcggcuu caauuucagc 2400
cagauucugc ccgauccuag caagcccagc aagcggagcc ccaucgagga ccugcuguuc 2460
aacaaaguga cacuggccga cgccggcuuc aucaagcagu auggcgauug ucugggcgac 2520
auugccgcca gggaucugau uugcgcccag aaguuuaacg gacugacagu gcugccuccu 2580
cugcugaccg augagaugau cgcccaguac acaucugccc ugcuggccgg cacaaucaca 2640
agcggcugga cauuuggagc uggccccgcu cugcagaucc ccuuuccuau gcagauggcc 2700
uacagauuca acggcaucgg agugacccag aaugugcugu acgagaacca gaagcugauc 2760
gccaaccagu ucaacagcgc caucggcaag auccaggaca gccugagcag cacaccaagc 2820
gcccugggaa agcugcagga cgugguc aac cagaaugccc aggcacugaa cacccugguc 2880
aagcagcugu ccuccaacuu cggcgccauc agcucugugc ugaacgauau ccuggccaga 2940
cuggacccuc cugaggccga ggugcagauc gacagacuga ucacaggcag acugcagagc 3000
cuccagacau acgugaccca gcagcugauc agagccgccg agauuagagc cucugccaau 3060
cuggccgcca ccaagauguc ugagugugug cugggccaga gcaagagagu ggacuuuugc 3120
ggcaagggcu accaccugau gagcuucccu cagucugccc cucacggcgu ggguguuucug 3180 cacgugacau acguucccgc ucaagagaag aauuucacca ccgcuccagc caucugccac 3240
gacggcaaag cccacuuucc uagagaaggc guguucgugu ccaacggcac ccauugguuc 3300
gugacacagc ggaacuucua cgagccccag aucaucacca cccacaacac cuucgugucu 3360
ggcaacugcg acgucgugau cggcauugug aacaauaccg uguacgaccc ucugcagccc 3420
gagcuggaca gcuucaaaga ggaacuggac aaguacuuua agaaccacac aagccccgac 3480
guggaccugg gcgauaucag cggaaucaau gccagcgucg ugaacaucca gaaagagauc 3540
gaccggcuga acgagguggc caagaaucug aacgagagcc ugaucgaccu gcaagaacug 3600
gggaaguacg agcaguacau caaguggccc ugguacaucu ggcugggcuu uaucgccgga 3660
cugauugcca ucgugauggu cacaaucaug cuguguugca ugaccagcug cuguagcugc 3720
cugaagggcu guuguagcug uggcagcugc ugcaaguucg acgaggacga uucugagccc 3780
gugcugaagg gcgugaaacu gcacuacaca uga 3813

<210> SEQ ID NO 50
<211> LENGTH: 1270
<212> TYPE: PRT
<213> ORGANISM: SARS-CoV-2 UK variant B.1.1.7 and variant E484K

<400> SEQUENCE: 50

Met Phe Val Phe Leu Val Leu Leu Pro Leu Val Ser Ser Gln Cys Val
1 5 10 15

-continued

```
Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile Ser Gly Thr Asn Gly Thr Lys Arg Phe Asp Asn Pro
65                  70                  75                  80

Val Leu Pro Phe Asn Asp Gly Val Tyr Phe Ala Ser Thr Glu Lys Ser
                85                  90                  95

Asn Ile Ile Arg Gly Trp Ile Phe Gly Thr Thr Leu Asp Ser Lys Thr
            100                 105                 110

Gln Ser Leu Leu Ile Val Asn Asn Ala Thr Asn Val Val Ile Lys Val
        115                 120                 125

Cys Glu Phe Gln Phe Cys Asn Asp Pro Phe Leu Gly Val Tyr His Lys
    130                 135                 140

Asn Asn Lys Ser Trp Met Glu Ser Glu Phe Arg Val Tyr Ser Ser Ala
145                 150                 155                 160

Asn Asn Cys Thr Phe Glu Tyr Val Ser Gln Pro Phe Leu Met Asp Leu
                165                 170                 175

Glu Gly Lys Gln Gly Asn Phe Lys Asn Leu Arg Glu Phe Val Phe Lys
            180                 185                 190

Asn Ile Asp Gly Tyr Phe Lys Ile Tyr Ser Lys His Thr Pro Ile Asn
        195                 200                 205

Leu Val Arg Asp Leu Pro Gln Gly Phe Ser Ala Leu Glu Pro Leu Val
    210                 215                 220

Asp Leu Pro Ile Gly Ile Asn Ile Thr Arg Phe Gln Thr Leu Leu Ala
225                 230                 235                 240

Leu His Arg Ser Tyr Leu Thr Pro Gly Asp Ser Ser Ser Gly Trp Thr
                245                 250                 255

Ala Gly Ala Ala Ala Tyr Tyr Val Gly Tyr Leu Gln Pro Arg Thr Phe
            260                 265                 270

Leu Leu Lys Tyr Asn Glu Asn Gly Thr Ile Thr Asp Ala Val Asp Cys
        275                 280                 285

Ala Leu Asp Pro Leu Ser Glu Thr Lys Cys Thr Leu Lys Ser Phe Thr
    290                 295                 300

Val Glu Lys Gly Ile Tyr Gln Thr Ser Asn Phe Arg Val Gln Pro Thr
305                 310                 315                 320

Glu Ser Ile Val Arg Phe Pro Asn Ile Thr Asn Leu Cys Pro Phe Gly
                325                 330                 335

Glu Val Phe Asn Ala Thr Arg Phe Ala Ser Val Tyr Ala Trp Asn Arg
            340                 345                 350

Lys Arg Ile Ser Asn Cys Val Ala Asp Tyr Ser Val Leu Tyr Asn Ser
        355                 360                 365

Ala Ser Phe Ser Thr Phe Lys Cys Tyr Gly Val Ser Pro Thr Lys Leu
    370                 375                 380

Asn Asp Leu Cys Phe Thr Asn Val Tyr Ala Asp Ser Phe Val Ile Arg
385                 390                 395                 400

Gly Asp Glu Val Arg Gln Ile Ala Pro Gly Gln Thr Gly Lys Ile Ala
                405                 410                 415

Asp Tyr Asn Tyr Lys Leu Pro Asp Asp Phe Thr Gly Cys Val Ile Ala
            420                 425                 430
```

-continued

```
Trp Asn Ser Asn Asn Leu Asp Ser Lys Val Gly Gly Asn Tyr Asn Tyr
        435                 440                 445

Leu Tyr Arg Leu Phe Arg Lys Ser Asn Leu Lys Pro Phe Glu Arg Asp
    450                 455                 460

Ile Ser Thr Glu Ile Tyr Gln Ala Gly Ser Thr Pro Cys Asn Gly Val
465                 470                 475                 480

Lys Gly Phe Asn Cys Tyr Phe Pro Leu Gln Ser Tyr Gly Phe Gln Pro
                485                 490                 495

Thr Tyr Gly Val Gly Tyr Gln Pro Tyr Arg Val Val Val Leu Ser Phe
            500                 505                 510

Glu Leu Leu His Ala Pro Ala Thr Val Cys Gly Pro Lys Lys Ser Thr
        515                 520                 525

Asn Leu Val Lys Asn Lys Cys Val Asn Phe Asn Phe Asn Gly Leu Thr
    530                 535                 540

Gly Thr Gly Val Leu Thr Glu Ser Asn Lys Lys Phe Leu Pro Phe Gln
545                 550                 555                 560

Gln Phe Gly Arg Asp Ile Asp Asp Thr Thr Asp Ala Val Arg Asp Pro
                565                 570                 575

Gln Thr Leu Glu Ile Leu Asp Ile Thr Pro Cys Ser Phe Gly Gly Val
            580                 585                 590

Ser Val Ile Thr Pro Gly Thr Asn Thr Ser Asn Gln Val Ala Val Leu
        595                 600                 605

Tyr Gln Gly Val Asn Cys Thr Glu Val Pro Val Ala Ile His Ala Asp
    610                 615                 620

Gln Leu Thr Pro Thr Trp Arg Val Tyr Ser Thr Gly Ser Asn Val Phe
625                 630                 635                 640

Gln Thr Arg Ala Gly Cys Leu Ile Gly Ala Glu His Val Asn Asn Ser
                645                 650                 655

Tyr Glu Cys Asp Ile Pro Ile Gly Ala Gly Ile Cys Ala Ser Tyr Gln
            660                 665                 670

Thr Gln Thr Asn Ser His Ser Leu Ala Ser Ser Val Ala Ser Gln Ser
        675                 680                 685

Ile Ile Ala Tyr Thr Met Ser Leu Gly Ala Glu Asn Ser Val Ala Tyr
    690                 695                 700

Ser Asn Asn Ser Ile Ala Ile Pro Ile Asn Phe Thr Ile Ser Val Thr
705                 710                 715                 720

Thr Glu Ile Leu Pro Val Ser Met Thr Lys Thr Ser Val Asp Cys Thr
                725                 730                 735

Met Tyr Ile Cys Gly Asp Ser Thr Glu Cys Ser Asn Leu Leu Leu Gln
            740                 745                 750

Tyr Gly Ser Phe Cys Thr Gln Leu Asn Arg Ala Leu Thr Gly Ile Ala
        755                 760                 765

Val Glu Gln Asp Lys Asn Thr Gln Glu Val Phe Ala Gln Val Lys Gln
    770                 775                 780

Ile Tyr Lys Thr Pro Pro Ile Lys Asp Phe Gly Gly Phe Asn Phe Ser
785                 790                 795                 800

Gln Ile Leu Pro Asp Pro Ser Lys Pro Ser Lys Arg Ser Pro Ile Glu
                805                 810                 815

Asp Leu Leu Phe Asn Lys Val Thr Leu Ala Asp Ala Gly Phe Ile Lys
            820                 825                 830

Gln Tyr Gly Asp Cys Leu Gly Asp Ile Ala Ala Arg Asp Leu Ile Cys
        835                 840                 845

Ala Gln Lys Phe Asn Gly Leu Thr Val Leu Pro Pro Leu Leu Thr Asp
```

```
    850                 855                 860

Glu Met Ile Ala Gln Tyr Thr Ser Ala Leu Leu Ala Gly Thr Ile Thr
865                 870                 875                 880

Ser Gly Trp Thr Phe Gly Ala Gly Pro Ala Leu Gln Ile Pro Phe Pro
                885                 890                 895

Met Gln Met Ala Tyr Arg Phe Asn Gly Ile Gly Val Thr Gln Asn Val
            900                 905                 910

Leu Tyr Glu Asn Gln Lys Leu Ile Ala Asn Gln Phe Asn Ser Ala Ile
        915                 920                 925

Gly Lys Ile Gln Asp Ser Leu Ser Ser Thr Pro Ser Ala Leu Gly Lys
    930                 935                 940

Leu Gln Asp Val Val Asn Gln Asn Ala Gln Ala Leu Asn Thr Leu Val
945                 950                 955                 960

Lys Gln Leu Ser Ser Asn Phe Gly Ala Ile Ser Ser Val Leu Asn Asp
                965                 970                 975

Ile Leu Ala Arg Leu Asp Pro Pro Glu Ala Glu Val Gln Ile Asp Arg
            980                 985                 990

Leu Ile Thr Gly Arg Leu Gln Ser  Leu Gln Thr Tyr Val  Thr Gln Gln
        995                 1000                1005

Leu Ile  Arg Ala Ala Glu Ile  Arg Ala Ser Ala Asn  Leu Ala Ala
    1010                 1015                 1020

Thr Lys  Met Ser Glu Cys Val  Leu Gly Gln Ser Lys  Arg Val Asp
    1025                 1030                 1035

Phe Cys  Gly Lys Gly Tyr His  Leu Met Ser Phe Pro  Gln Ser Ala
    1040                 1045                 1050

Pro His  Gly Val Val Phe Leu  His Val Thr Tyr Val  Pro Ala Gln
    1055                 1060                 1065

Glu Lys  Asn Phe Thr Thr Ala  Pro Ala Ile Cys His  Asp Gly Lys
    1070                 1075                 1080

Ala His  Phe Pro Arg Glu Gly  Val Phe Val Ser Asn  Gly Thr His
    1085                 1090                 1095

Trp Phe  Val Thr Gln Arg Asn  Phe Tyr Glu Pro Gln  Ile Ile Thr
    1100                 1105                 1110

Thr His  Asn Thr Phe Val Ser  Gly Asn Cys Asp Val  Val Ile Gly
    1115                 1120                 1125

Ile Val  Asn Asn Thr Val Tyr  Asp Pro Leu Gln Pro  Glu Leu Asp
    1130                 1135                 1140

Ser Phe  Lys Glu Glu Leu Asp  Lys Tyr Phe Lys Asn  His Thr Ser
    1145                 1150                 1155

Pro Asp  Val Asp Leu Gly Asp  Ile Ser Gly Ile Asn  Ala Ser Val
    1160                 1165                 1170

Val Asn  Ile Gln Lys Glu Ile  Asp Arg Leu Asn Glu  Val Ala Lys
    1175                 1180                 1185

Asn Leu  Asn Glu Ser Leu Ile  Asp Leu Gln Glu Leu  Gly Lys Tyr
    1190                 1195                 1200

Glu Gln  Tyr Ile Lys Trp Pro  Trp Tyr Ile Trp Leu  Gly Phe Ile
    1205                 1210                 1215

Ala Gly  Leu Ile Ala Ile Val  Met Val Thr Ile Met  Leu Cys Cys
    1220                 1225                 1230

Met Thr  Ser Cys Cys Ser Cys  Leu Lys Gly Cys Cys  Ser Cys Gly
    1235                 1240                 1245

Ser Cys  Cys Lys Phe Asp Glu  Asp Asp Ser Glu Pro  Val Leu Lys
    1250                 1255                 1260
```

Gly Val Lys Leu His Tyr Thr
1265 1270

<210> SEQ ID NO 51
<211> LENGTH: 3813
<212> TYPE: DNA
<213> ORGANISM: Artificial Sequence
<220> FEATURE:
<223> OTHER INFORMATION: Synthetised Sequence

<400> SEQUENCE: 51
atgttcgtgt ttctggtgct gctgcctctg gtgtccagcc agtgtgtgaa cctgaccacc 60
agaacacagc tgcctccagc ctacaccaac agctttacca gaggcgtgta ctaccccgac 120
aaggtgttca gatccagcgt gctgcactct acccaggacc tgttcctgcc tttcttcagc 180
aacgtgacct ggttccacgc catctccggc accaatggca ccaagagatt cgacaacccc 240
gtgctgccct tcaacgacgg ggtgtacttt gccagcaccg agaagtccaa catcatcaga 300
ggctggatct tcggcaccac actggacagc aagacccaga gcctgctgat cgtgaacaac 360
gccaccaacg tggtcatcaa agtgtgcgag ttccagttct gcaacgaccc cttcctgggc 420
gtctaccaca agaacaacaa gagctggatg gaaagcgagt tccgggtgta cagcagcgcc 480
aacaactgca ccttcgagta cgtgtcccag cctttcctga tggacctgga aggcaagcag 540
ggcaacttca agaacctgcg cgagttcgtg ttcaagaaca tcgacggcta cttcaagatc 600
tacagcaagc acacccctat caacctcgtg cgggatctgc ctcagggctt ctctgctctg 660
gaacccctgg tggatctgcc catcggcatc aacatcaccc ggtttcagac actgctggcc 720
ctgcacagaa gctacctgac acctggcgat agcagcagcg gatggacagc tggtgccgcc 780
gcttactatg tgggctacct gcagcctaga accttcctgc tgaagtacaa cgagaacggc 840
accatcaccg acgccgtgga ttgtgccctt gatcctctga gcgagacaaa gtgcaccctg 900
aagtccttca ccgtggaaaa gggcatctac cagaccagca acttccgggt gcagcccacc 960
gaatccatcg tgcggttccc caatatcacc aatctgtgcc ccttcggcga ggtgttcaat 1020
gccaccagat tcgcctctgt gtacgcctgg aaccggaagc ggatcagcaa ttgcgtggcc 1080
gactactccg tgctgtacaa ctccgccagc ttcagcacct tcaagtgcta cggcgtgtcc 1140
cctaccaagc tgaacgacct gtgcttcaca aacgtgtacg ccgacagctt cgtgatccgg 1200
ggagatgaag tgcggcagat tgcccctgga cagacaggca agatcgccga ctacaactac 1260
aagctgcccg acgacttcac cggctgtgtg attgcctgga acagcaacaa cctggactcc 1320
aaagtcggcg gcaactacaa ttacctgtac cggctgttcc ggaagtccaa tctgaagccc 1380
ttcgagcggg acatctccac cgagatctat caggccggca gcaccccttg taacggcgtg 1440
aaaggcttca actgctactt cccactgcag tcctacggct ttcagcccac atatggcgtg 1500
ggctatcagc cctacagagt ggtggtgctg agcttcgaac tgctgcatgc ccctgccaca 1560
gtgtgcggcc ctaagaaaag caccaatctc gtgaagaaca aatgcgtgaa cttcaacttc 1620
aacggcctga ccggcacagg cgtgctgaca gagagcaaca agaagttcct gccattccag 1680
cagtttggcc gggatatcga cgataccaca gacgccgtta gagatcccca gacactggaa 1740
atcctggaca tcaccccttg cagcttcggc ggagtgtctg tgatcacccc tggcaccaac 1800
accagcaatc aggtggcagt gctgtaccag ggcgtgaact gtaccgaagt gcccgtggcc 1860
attcacgccg atcagctgac acctacatgg cgggtgtact ccaccggcag caatgtgttt 1920
cagaccagag ccggctgtct gatcggagcc gagcacgtga acaatagcta cgagtgcgac 1980

-continued

```
atccccatcg gcgctggcat ctgtgccagc taccagacac agacaaacag ccactctctg   2040

gccagctctg tggccagcca gagcatcatt gcctacacaa tgtctctggg cgccgagaac   2100

agcgtggcct actccaacaa ctctatcgct atccccatca acttcaccat cagcgtgacc   2160

acagagatcc tgcctgtgtc catgaccaag accagcgtgg actgcaccat gtacatctgc   2220

ggcgattcca ccgagtgctc caacctgctg ctgcagtacg gcagcttctg cacccagctg   2280

aatagagccc tgacagggat cgccgtggaa caggacaaga acacccaaga ggtgttcgcc   2340

caagtgaagc agatctacaa gacccctcct atcaaggact tcggcggctt caatttcagc   2400

cagattctgc ccgatcctag caagcccagc aagcggagcc ccatcgagga cctgctgttc   2460

aacaaagtga cactggccga cgccggcttc atcaagcagt atggcgattg tctgggcgac   2520

attgccgcca gggatctgat ttgcgcccag aagtttaacg gactgacagt gctgcctcct   2580

ctgctgaccg atgagatgat cgcccagtac acatctgccc tgctggccgg cacaatcaca   2640

agcggctgga catttggagc tggccccgct ctgcagatcc cctttcctat gcagatggcc   2700

tacagattca acggcatcgg agtgacccag aatgtgctgt acgagaacca gaagctgatc   2760

gccaaccagt tcaacagcgc catcggcaag atccaggaca gcctgagcag cacaccaagc   2820

gccctgggaa agctgcagga cgtggtcaac cagaatgccc aggcactgaa caccctggtc   2880

aagcagctgt cctccaactt cggcgccatc agctctgtgc tgaacgatat cctggccaga   2940

ctggaccctc ctgaggccga ggtgcagatc gacagactga tcacaggcag actgcagagc   3000

ctccagacat acgtgaccca gcagctgatc agagccgccg agattagagc ctctgccaat   3060

ctggccgcca ccaagatgtc tgagtgtgtg ctgggccaga gcaagagagt ggacttttgc   3120

ggcaagggct accacctgat gagcttccct cagtctgccc ctcacggcgt ggtgtttctg   3180

cacgtgacat acgttcccgc tcaagagaag aatttcacca ccgctccagc catctgccac   3240

gacggcaaag cccactttcc tagagaaggc gtgttcgtgt ccaacggcac ccattggttc   3300

gtgacacagc ggaacttcta cgagccccag atcatcacca cccacaacac cttcgtgtct   3360

ggcaactgcg acgtcgtgat cggcattgtg aacaataccg tgtacgaccc tctgcagccc   3420

gagctggaca gcttcaaaga ggaactggac aagtacttta agaaccacac aagccccgac   3480

gtggacctgg gcgatatcag cggaatcaat gccagcgtcg tgaacatcca gaaagagatc   3540

gaccggctga acgaggtggc caagaatctg aacgagagcc tgatcgacct gcaagaactg   3600

gggaagtacg agcagtacat caagtggccc tggtacatct ggctgggctt tatcgccgga   3660

ctgattgcca tcgtgatggt cacaatcatg ctgtgttgca tgaccagctg ctgtagctgc   3720

ctgaagggct gttgtagctg tggcagctgc tgcaagttcg acgaggacga ttctgagccc   3780

gtgctgaagg gcgtgaaact gcactacaca tga                              3813
```

<210> SEQ ID NO 52
<211> LENGTH: 3813
<212> TYPE: RNA
<213> ORGANISM: Artificial Sequence
<220> FEATURE:
<223> OTHER INFORMATION: Synthetised Sequence

<400> SEQUENCE: 52

```
auguucgugu uucuggugcu gcugccucug guguccagcc agugugugaa ccugaccacc     60

agaacacagc ugccuccagc cuacaccaac agcuuuacca gaggcgugua cuaccccgac    120

aagguguuca gauccagcgu gcugcacucu acccaggacc uguuccugcc uuucuucagc    180
```

-continued aacgugaccu gguuccacgc caucuccggc accaauggca ccaagagauu cgacaacccc 240
gugcugcccu ucaacgacgg gguguacuuu gccagcaccg agaaguccaa caucaucaga 300
ggcuggaucu ucggcaccac acuggacagc aagacccaga gccugcugau cgugaacaac 360
gccaccaacg uggucaucaa agugugcgag uuccaguucu gcaacgaccc cuuccugggc 420
gucuaccaca agaacaacaa gagcuggaug gaaagcgagu uccgggugua cagcagcgcc 480
aacaacugca ccuucgagua cguguccccag ccuuuccuga uggaccugga aggcaagcag 540
ggcaacuuca agaaccugcg cgaguucgug uucaagaaca ucgacggcua cuucaagauc 600
uacagcaagc acaccccuau caaccucgug cgggaucugc cucagggcuu cucugcucug 660
gaaccccugg uggaucugcc caucggcauc aacaucaccc gguuucagac acugcuggcc 720
cugcacagaa gcuaccugac accuggcgau agcagcagcg gauggacagc uggugccgcc 780
gcuuacuaug ugggcuaccu gcagccuaga accuuccugc ugaaguacaa cgagaacggc 840
accaucaccg acgccgugga uugugcccuu gauccucuga gcgagacaaa gugcacccug 900
aaguccuuca ccguggaaaa gggcaucuac cagaccagca acuuccgggu gcagcccacc 960
gaauccaucg ugcgguuccc caauaucacc aaucugugcc ccuucggcga gguguucaau 1020
gccaccagau ucgccucugu guacgccugg aaccggaagc ggaucagcaa uugcguggcc 1080
gacuacuccg ugcuguacaa cuccgccagc uucagcaccu ucaagugcua cggcgugucc 1140
ccuaccaagc ugaacgaccu gugcuucaca aacguguacg ccgacagcuu cgugauccgg 1200
ggagaugaag ugcggcagau ugccccugga cagacaggca agaucgccga cuacaacuac 1260
aagcugcccg acgacuucac cggcugugug auugccugga acagcaacaa ccuggacucc 1320
aaagucggcg gcaacuacaa uuaccuguac cggcuguucc ggaaguccaa ucugaagccc 1380
uucgagcggg acaucuccac cgagaucuau caggccggca gcaccccuug uaacggcgug 1440
aaaggcuuca acugcuacuu cccacugcag uccuacggcu uucagcccac auauggcgug 1500
ggcuaucagc ccuacagagu gguggugcug agcuucgaac ugcugcaugc cccugccaca 1560
gugugcggcc cuaagaaaag caccaaucuc gugaagaaca aaugcgugaa cuucaacuuc 1620
aacggccuga ccggcacagg cgugcugaca gagagcaaca agaaguuccu gccauuccag 1680
caguuuggcc gggauaucga cgauaccaca gacgccguua gagaucccca gacacuggaa 1740
auccuggaca ucaccccuug cagcuucggc ggagugucug ugaucacccc uggcaccaac 1800
accagcaauc agguggcagu gcuguaccag ggcgugaacu guaccgaagu gcccguggcc 1860
auucacgccg aucagcugac accuacaugg cggguguacu ccaccggcag caauguguuu 1920
cagaccagag ccggcugucu gaucggagcc gagcacguga acaauagcua cgagugcgac 1980
auccccaucg gcgcuggcau cugugccagc uaccagacac agacaaacag ccacucucug 2040
gccagcucug uggccagcca gagcaucauu gccuacacaa ugucucuggg cgccgagaac 2100
agcguggccu acuccaacaa cucuaucgcu auccccauca acuucaccau cagcgugacc 2160
acagagaucc ugccuguguc caugaccaag accagcgugg acugcaccau guacaucugc 2220
ggcgauucca ccgagugcuc caaccugcug cugcaguacg gcagcuucug cacccagcug 2280
aauagagccc ugacagggau cgccguggaa caggacaaga acacccaaga gguguucgcc 2340
caagugaagc agaucuacaa gaccccuccu aucaaggacu ucggcggcuu caauuucagc 2400
cagauucugc ccgauccuag caagcccagc aagcggagcc ccaucgagga ccugcuguuc 2460
aacaaaguga cacuggccga cgccggcuuc aucaagcagu auggcgauug ucugggcgac 2520
auugccgcca gggaucugau uugcgcccag aaguuuaacg gacugacagu gcugccuccu 2580

-continued cugcugaccg augagaugau cgcccaguac acaucugccc ugcuggccgg cacaaucaca 2640
agcggcugga cauuuggagc uggccccgcu cugcagaucc ccuuuccuau gcagauggcc 2700
uacagauuca acggcaucgg agugacccag aaugugcugu acgagaacca gaagcugauc 2760
gccaaccagu ucaacagcgc caucggcaag auccaggaca gccugagcag cacaccaagc 2820
gcccugggaa agcugcagga cguggucaac cagaaugccc aggcacugaa cacccugguc 2880
aagcagcugu ccuccaacuu cggcgccauc agcucugugc ugaacgauau ccuggccaga 2940
cuggacccuc cugaggccga ggugcagauc gacagacuga ucacaggcag acugcagagc 3000
cuccagacau acgugaccca gcagcugauc agagccgccg agauuagagc cucugccaau 3060
cuggccgcca ccaagauguc ugagugugug cugggccaga gcaagagagu ggacuuuugc 3120
ggcaagggcu accaccugau gagcuucccu cagucugccc cucacggcgu gguguuucug 3180
cacgugacau acguucccgc ucaagagaag aauuucacca ccgcuccagc caucugccac 3240
gacggcaaag cccacuuucc uagagaaggc guguucgugu ccaacggcac ccauugguuc 3300
gugacacagc ggaacuucua cgagccccag aucaucacca cccacaacac cuucgugucu 3360
ggcaacugcg acgucgugau cggcauugug aacaauaccg uguacgaccc ucugcagccc 3420
gagcuggaca gcuucaaaga ggaacuggac aaguacuuua agaaccacac aagccccgac 3480
guggaccugg gcgauaucag cggaaucaau gccagcgucg ugaacaucca gaaagagauc 3540
gaccggcuga acgagguggc caagaaucug aacgagagcc ugaucgaccu gcaagaacug 3600
gggaaguacg agcaguacau caaguggccc ugguacaucu ggcugggcuu uaucgccgga 3660
cugauugcca ucgugauggu cacaaucaug cuguguugca ugaccagcug cuguagcugc 3720
cugaagggcu guuguagcug uggcagcugc ugcaaguucg acgaggacga uucugagccc 3780
gugcugaagg gcgugaaacu gcacuacaca uga 3813

<210> SEQ ID NO 53
<211> LENGTH: 1270
<212> TYPE: PRT
<213> ORGANISM: SARS-CoV-2 South African variant B.1.351

<400> SEQUENCE: 53

Met Phe Val Phe Leu Val Leu Leu Pro Leu Val Ser Ser Gln Cys Val
1               5                   10                  15

Asn Phe Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Ala
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr

```
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Gly Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu His Ile Ser Tyr Leu Thr Pro Gly Asp Ser Ser Ser Gly Trp Thr
                245                 250                 255

Ala Gly Ala Ala Ala Tyr Tyr Val Gly Tyr Leu Gln Pro Arg Thr Phe
            260                 265                 270

Leu Leu Lys Tyr Asn Glu Asn Gly Thr Ile Thr Asp Ala Val Asp Cys
        275                 280                 285

Ala Leu Asp Pro Leu Ser Glu Thr Lys Cys Thr Leu Lys Ser Phe Thr
    290                 295                 300

Val Glu Lys Gly Ile Tyr Gln Thr Ser Asn Phe Arg Val Gln Pro Thr
305                 310                 315                 320

Glu Ser Ile Val Arg Phe Pro Asn Ile Thr Asn Leu Cys Pro Phe Gly
                325                 330                 335

Glu Val Phe Asn Ala Thr Arg Phe Ala Ser Val Tyr Ala Trp Asn Arg
            340                 345                 350

Lys Arg Ile Ser Asn Cys Val Ala Asp Tyr Ser Val Leu Tyr Asn Ser
        355                 360                 365

Ala Ser Phe Ser Thr Phe Lys Cys Tyr Gly Val Ser Pro Thr Lys Leu
    370                 375                 380

Asn Asp Leu Cys Phe Thr Asn Val Tyr Ala Asp Ser Phe Val Ile Arg
385                 390                 395                 400

Gly Asp Glu Val Arg Gln Ile Ala Pro Gly Gln Thr Gly Asn Ile Ala
                405                 410                 415

Asp Tyr Asn Tyr Lys Leu Pro Asp Asp Phe Thr Gly Cys Val Ile Ala
            420                 425                 430

Trp Asn Ser Asn Asn Leu Asp Ser Lys Val Gly Gly Asn Tyr Asn Tyr
        435                 440                 445

Leu Tyr Arg Leu Phe Arg Lys Ser Asn Leu Lys Pro Phe Glu Arg Asp
    450                 455                 460

Ile Ser Thr Glu Ile Tyr Gln Ala Gly Ser Thr Pro Cys Asn Gly Val
465                 470                 475                 480

Lys Gly Phe Asn Cys Tyr Phe Pro Leu Gln Ser Tyr Gly Phe Gln Pro
                485                 490                 495

Thr Tyr Gly Val Gly Tyr Gln Pro Tyr Arg Val Val Val Leu Ser Phe
            500                 505                 510

Glu Leu Leu His Ala Pro Ala Thr Val Cys Gly Pro Lys Lys Ser Thr
        515                 520                 525

Asn Leu Val Lys Asn Lys Cys Val Asn Phe Asn Phe Asn Gly Leu Thr
    530                 535                 540

Gly Thr Gly Val Leu Thr Glu Ser Asn Lys Lys Phe Leu Pro Phe Gln
545                 550                 555                 560

Gln Phe Gly Arg Asp Ile Ala Asp Thr Thr Asp Ala Val Arg Asp Pro
                565                 570                 575
```

-continued

```
Gln Thr Leu Glu Ile Leu Asp Ile Thr Pro Cys Ser Phe Gly Gly Val
            580                 585                 590

Ser Val Ile Thr Pro Gly Thr Asn Thr Ser Asn Gln Val Ala Val Leu
        595                 600                 605

Tyr Gln Asp Val Asn Cys Thr Glu Val Pro Val Ala Ile His Ala Asp
    610                 615                 620

Gln Leu Thr Pro Thr Trp Arg Val Tyr Ser Thr Gly Ser Asn Val Phe
625                 630                 635                 640

Gln Thr Arg Ala Gly Cys Leu Ile Gly Ala Glu His Val Asn Asn Ser
                645                 650                 655

Tyr Glu Cys Asp Ile Pro Ile Gly Ala Gly Ile Cys Ala Ser Tyr Gln
            660                 665                 670

Thr Gln Thr Asn Ser Pro Ser Leu Ala Ser Ser Val Ala Ser Gln Ser
        675                 680                 685

Ile Ile Ala Tyr Thr Met Ser Leu Gly Val Glu Asn Ser Val Ala Tyr
    690                 695                 700

Ser Asn Asn Ser Ile Ala Ile Pro Thr Asn Phe Thr Ile Ser Val Thr
705                 710                 715                 720

Thr Glu Ile Leu Pro Val Ser Met Thr Lys Thr Ser Val Asp Cys Thr
                725                 730                 735

Met Tyr Ile Cys Gly Asp Ser Thr Glu Cys Ser Asn Leu Leu Leu Gln
            740                 745                 750

Tyr Gly Ser Phe Cys Thr Gln Leu Asn Arg Ala Leu Thr Gly Ile Ala
        755                 760                 765

Val Glu Gln Asp Lys Asn Thr Gln Glu Val Phe Ala Gln Val Lys Gln
    770                 775                 780

Ile Tyr Lys Thr Pro Pro Ile Lys Asp Phe Gly Gly Phe Asn Phe Ser
785                 790                 795                 800

Gln Ile Leu Pro Asp Pro Ser Lys Pro Ser Lys Arg Ser Pro Ile Glu
                805                 810                 815

Asp Leu Leu Phe Asn Lys Val Thr Leu Ala Asp Ala Gly Phe Ile Lys
            820                 825                 830

Gln Tyr Gly Asp Cys Leu Gly Asp Ile Ala Ala Arg Asp Leu Ile Cys
        835                 840                 845

Ala Gln Lys Phe Asn Gly Leu Thr Val Leu Pro Pro Leu Leu Thr Asp
    850                 855                 860

Glu Met Ile Ala Gln Tyr Thr Ser Ala Leu Leu Ala Gly Thr Ile Thr
865                 870                 875                 880

Ser Gly Trp Thr Phe Gly Ala Gly Pro Ala Leu Gln Ile Pro Phe Pro
                885                 890                 895

Met Gln Met Ala Tyr Arg Phe Asn Gly Ile Gly Val Thr Gln Asn Val
            900                 905                 910

Leu Tyr Glu Asn Gln Lys Leu Ile Ala Asn Gln Phe Asn Ser Ala Ile
        915                 920                 925

Gly Lys Ile Gln Asp Ser Leu Ser Ser Thr Pro Ser Ala Leu Gly Lys
    930                 935                 940

Leu Gln Asp Val Val Asn Gln Asn Ala Gln Ala Leu Asn Thr Leu Val
945                 950                 955                 960

Lys Gln Leu Ser Ser Asn Phe Gly Ala Ile Ser Ser Val Leu Asn Asp
                965                 970                 975

Ile Leu Ser Arg Leu Asp Pro Pro Glu Ala Glu Val Gln Ile Asp Arg
            980                 985                 990
```

```
Leu Ile Thr Gly Arg Leu Gln Ser  Leu Gln Thr Tyr Val  Thr Gln Gln
        995                 1000                 1005

Leu Ile  Arg Ala Ala Glu Ile  Arg Ala Ser Ala Asn  Leu Ala Ala
    1010                 1015                 1020

Thr Lys  Met Ser Glu Cys Val  Leu Gly Gln Ser Lys  Arg Val Asp
    1025                 1030                 1035

Phe Cys  Gly Lys Gly Tyr His  Leu Met Ser Phe Pro  Gln Ser Ala
    1040                 1045                 1050

Pro His  Gly Val Val Phe Leu  His Val Thr Tyr Val  Pro Ala Gln
    1055                 1060                 1065

Glu Lys  Asn Phe Thr Thr Ala  Pro Ala Ile Cys His  Asp Gly Lys
    1070                 1075                 1080

Ala His  Phe Pro Arg Glu Gly  Val Phe Val Ser Asn  Gly Thr His
    1085                 1090                 1095

Trp Phe  Val Thr Gln Arg Asn  Phe Tyr Glu Pro Gln  Ile Ile Thr
    1100                 1105                 1110

Thr Asp  Asn Thr Phe Val Ser  Gly Asn Cys Asp Val  Val Ile Gly
    1115                 1120                 1125

Ile Val  Asn Asn Thr Val Tyr  Asp Pro Leu Gln Pro  Glu Leu Asp
    1130                 1135                 1140

Ser Phe  Lys Glu Glu Leu Asp  Lys Tyr Phe Lys Asn  His Thr Ser
    1145                 1150                 1155

Pro Asp  Val Asp Leu Gly Asp  Ile Ser Gly Ile Asn  Ala Ser Val
    1160                 1165                 1170

Val Asn  Ile Gln Lys Glu Ile  Asp Arg Leu Asn Glu  Val Ala Lys
    1175                 1180                 1185

Asn Leu  Asn Glu Ser Leu Ile  Asp Leu Gln Glu Leu  Gly Lys Tyr
    1190                 1195                 1200

Glu Gln  Tyr Ile Lys Trp Pro  Trp Tyr Ile Trp Leu  Gly Phe Ile
    1205                 1210                 1215

Ala Gly  Leu Ile Ala Ile Val  Met Val Thr Ile Met  Leu Cys Cys
    1220                 1225                 1230

Met Thr  Ser Cys Cys Ser Cys  Leu Lys Gly Cys Cys  Ser Cys Gly
    1235                 1240                 1245

Ser Cys  Cys Lys Phe Asp Glu  Asp Asp Ser Glu Pro  Val Leu Lys
    1250                 1255                 1260

Gly Val  Lys Leu His Tyr Thr
    1265                 1270
```

<210> SEQ ID NO 54
<211> LENGTH: 3813
<212> TYPE: DNA
<213> ORGANISM: Artificial Sequence
<220> FEATURE:
<223> OTHER INFORMATION: Synthetised Sequence

<400> SEQUENCE: 54

```
atgttcgtgt ttctggtgct gctgcctctg gtgtccagcc agtgtgtgaa cttcaccacc     60

agaacacagc tgcctccagc ctacaccaac agctttacca gaggcgtgta ctaccccgac    120

aaggtgttca gatccagcgt gctgcactct acccaggacc tgttcctgcc tttcttcagc    180

aacgtgacct ggttccacgc catccacgtg tccggcacca atggcaccaa gagattcgcc    240

aaccccgtgc tgcccttcaa cgacggggtg tactttgcca gcaccgagaa gtccaacatc    300

atcagaggct ggatcttcgg caccacactg gacagcaaga cccagagcct gctgatcgtg    360
```

-continued

```
aacaacgcca ccaacgtggt catcaaagtg tgcgagttcc agttctgcaa cgacccccttc    420
ctgggcgtct actaccacaa gaacaacaag agctggatgg aaagcgagtt ccgggtgtac    480
agcagcgcca acaactgcac cttcgagtac gtgtcccagc ctttcctgat ggacctggaa    540
ggcaagcagg gcaacttcaa gaacctgcgc gagttcgtgt tcaagaacat cgacggctac    600
ttcaagatct acagcaagca cacccctatc aacctcgtgc ggggtctgcc tcagggcttc    660
tctgctctgg aacccctggt ggatctgccc atcggcatca acatcacccg gtttcagaca    720
ctgcacataa gctacctgac acctggcgat agcagcagcg gatggacagc tggtgccgcc    780
gcttactatg tgggctacct gcagcctaga accttcctgc tgaagtacaa cgagaacggc    840
accatcaccg acgccgtgga ttgtgccctt gatcctctga gcgagacaaa gtgcaccctg    900
aagtccttca ccgtggaaaa gggcatctac cagaccagca acttccgggt gcagcccacc    960
gaatccatcg tgcggttccc caatatcacc aatctgtgcc ccttcggcga ggtgttcaat   1020
gccaccagat tcgcctctgt gtacgcctgg aaccggaagc ggatcagcaa ttgcgtggcc   1080
gactactccg tgctgtacaa ctccgccagc ttcagcacct tcaagtgcta cggcgtgtcc   1140
cctaccaagc tgaacgacct gtgcttcaca aacgtgtacg ccgacagctt cgtgatccgg   1200
ggagatgaag tgcggcagat tgcccctgga cagacaggca atatcgccga ctacaactac   1260
aagctgcccg acgacttcac cggctgtgtg attgcctgga acagcaacaa cctggactcc   1320
aaagtcggcg gcaactacaa ttacctgtac cggctgttcc ggaagtccaa tctgaagccc   1380
ttcgagcggg acatctccac cgagatctat caggccggca gcaccccttg taacggcgtg   1440
aaaggcttca actgctactt cccactgcag tcctacggct ttcagcccac atatggcgtg   1500
ggctatcagc cctacagagt ggtggtgctg agcttcgaac tgctgcatgc ccctgccaca   1560
gtgtgcggcc ctaagaaaag caccaatctc gtgaagaaca aatgcgtgaa cttcaacttc   1620
aacggcctga ccggcacagg cgtgctgaca gagagcaaca agaagttcct gccattccag   1680
cagtttggcc gggatatcgc cgataccaca gacgccgtta gagatcccca gacactggaa   1740
atcctggaca tcaccccttg cagcttcggc ggagtgtctg tgatcacccc tggcaccaac   1800
accagcaatc aggtggcagt gctgtaccag gacgtgaact gtaccgaagt gcccgtggcc   1860
attcacgccg atcagctgac acctacatgg cgggtgtact ccaccggcag caatgtgttt   1920
cagaccagag ccggctgtct gatcggagcc gagcacgtga acaatagcta cgagtgcgac   1980
atccccatcg gcgctggcat ctgtgccagc taccagacac agacaaacag cccctctctg   2040
gccagctctg tggccagcca gagcatcatt gcctacacaa tgtctctggg cgtcgagaac   2100
agcgtggcct actccaacaa ctctatcgct atccccacca acttcaccat cagcgtgacc   2160
acagagatcc tgcctgtgtc catgaccaag accagcgtgg actgcaccat gtacatctgc   2220
ggcgattcca ccgagtgctc caacctgctg ctgcagtacg gcagcttctg cacccagctg   2280
aatagagccc tgacagggat cgccgtggaa caggacaaga acacccaaga ggtgttcgcc   2340
caagtgaagc agatctacaa gacccctcct atcaaggact tcggcggctt caatttcagc   2400
cagattctgc ccgatcctag caagcccagc aagcggagcc ccatcgagga cctgctgttc   2460
aacaaagtga cactggccga cgccggcttc atcaagcagt atggcgattg tctgggcgac   2520
attgccgcca gggatctgat ttgcgcccag aagtttaacg gactgacagt gctgcctcct   2580
ctgctgaccg atgagatgat cgcccagtac acatctgccc tgctggccgg cacaatcaca   2640
agcggctgga catttggagc tggccccgct ctgcagatcc cctttcctat gcagatggcc   2700
tacagattca acggcatcgg agtgacccag aatgtgctgt acgagaacca gaagctgatc   2760
```

gccaaccagt tcaacagcgc catcggcaag atccaggaca gcctgagcag cacaccaagc 2820
gccctgggaa agctgcagga cgtggtcaac cagaatgccc aggcactgaa caccctggtc 2880
aagcagctgt cctccaactt cggcgccatc agctctgtgc tgaacgatat cctgagcaga 2940
ctggaccctc ctgaggccga ggtgcagatc gacagactga tcacaggcag actgcagagc 3000
ctccagacat acgtgaccca gcagctgatc agagccgccg agattagagc ctctgccaat 3060
ctggccgcca ccaagatgtc tgagtgtgtg ctgggccaga gcaagagagt ggacttttgc 3120
ggcaagggct accacctgat gagcttccct cagtctgccc ctcacggcgt ggtgtttctg 3180
cacgtgacat acgttcccgc tcaagagaag aatttcacca ccgctccagc catctgccac 3240
gacggcaaag cccactttcc tagagaaggc gtgttcgtgt ccaacggcac ccattggttc 3300
gtgacacagc ggaacttcta cgagccccag atcatcacca ccgacaacac cttcgtgtct 3360
ggcaactgcg acgtcgtgat cggcattgtg aacaataccg tgtacgaccc tctgcagccc 3420
gagctggaca gcttcaaaga ggaactggac aagtacttta agaaccacac aagccccgac 3480
gtggacctgg gcgatatcag cggaatcaat gccagcgtcg tgaacatcca gaaagagatc 3540
gaccggctga acgaggtggc caagaatctg aacgagagcc tgatcgacct gcaagaactg 3600
gggaagtacg agcagtacat caagtggccc tggtacatct ggctgggctt tatcgccgga 3660
ctgattgcca tcgtgatggt cacaatcatg ctgtgttgca tgaccagctg ctgtagctgc 3720
ctgaagggct gttgtagctg tggcagctgc tgcaagttcg acgaggacga ttctgagccc 3780
gtgctgaagg gcgtgaaact gcactacaca tga 3813

<210> SEQ ID NO 55
<211> LENGTH: 3813
<212> TYPE: RNA
<213> ORGANISM: Artificial Sequence
<220> FEATURE:
<223> OTHER INFORMATION: Synthetised Sequence

<400> SEQUENCE: 55
auguucgugu uucuggugcu gcugccucug guguccagcc agugugugaa cuucaccacc 60
agaacacagc ugccuccagc cuacaccaac agcuuuacca gaggcgugua cuaccccgac 120
aagguguuca gauccagcgu gcugcacucu acccaggacc uguuccugcc uuucuucagc 180
aacgugaccu gguuccacgc cauccacgug uccggcacca auggcaccaa gagauucgcc 240
aaccccgugc ugcccuucaa cgacggggug uacuuugcca gcaccgagaa guccaacauc 300
aucagaggcu ggaucuucgg caccacacug gacagcaaga cccagagccu gcugaucgug 360
aacaacgcca ccaacguggu caucaaagug ugcgaguucc aguucugcaa cgaccccuuc 420
cugggcgucu acuaccacaa gaacaacaag agcuggaugg aaagcgaguu ccggguguac 480
agcagcgcca acaacugcac cuucgaguac gugucccagc cuuuccugau ggaccuggaa 540
ggcaagcagg gcaacuucaa gaaccugcgc gaguucgugu ucaagaacau cgacggcuac 600
uucaagaucu acagcaagca caccccuauc aaccucgugc ggggucugcc ucagggcuuc 660
ucugcucugg aaccccuggu ggaucugccc aucggcauca acaucacccg guuucagaca 720
cugcacauaa gcuaccugac accuggcgau agcagcagcg gauggacagc uggugccgcc 780
gcuuacuaug ugggcuaccu gcagccuaga accuuccugc ugaaguacaa cgagaacggc 840
accaucaccg acgccgugga uugugcccuu gauccucuga gcgagacaaa gugcacccug 900
aaguccuuca ccguggaaaa gggcaucuac cagaccagca acuuccgggu gcagcccacc 960

-continued gaauccaucg ugcgguuccc caauaucacc aaucugugcc ccuucggcga gguguucaau 1020
gccaccagau ucgccucugu guacgccugg aaccggaagc ggaucagcaa uugcguggcc 1080
gacuacuccg ugcuguacaa cuccgccagc uucagcaccu ucaagugcua cggcgugucc 1140
ccuaccaagc ugaacgaccu gugcuucaca aacguguacg ccgacagcuu cgugauccgg 1200
ggagaugaag ugcggcagau ugccccugga cagacaggca auaucgccga cuacaacuac 1260
aagcugcccg acgacuucac cggcugugug auugccugga acagcaacaa ccuggacucc 1320
aaagucggcg gcaacuacaa uuaccuguac cggcuguucc ggaaguccaa ucugaagccc 1380
uucgagcggg acaucuccac cgagaucuau caggccggca gcaccccuug uaacggcgug 1440
aaaggcuuca acugcuacuu cccacugcag uccuacggcu uucagcccac auauggcgug 1500
ggcuaucagc ccuacagagu gguggugcug agcuucgaac ugcugcaugc cccugccaca 1560
gugugcggcc cuaagaaaag caccaaucuc gugaagaaca aaugcgugaa cuucaacuuc 1620
aacggccuga ccggcacagg cgugcugaca gagagcaaca agaaguuccu gccauuccag 1680
caguuuggcc gggauaucgc cgauaccaca gacgccguua gagaucccca gacacuggaa 1740
auccuggaca ucaccccuug cagcuucggc ggagugucug ugaucacccc uggcaccaac 1800
accagcaauc agguggcagu gcuguaccag gacgugaacu guaccgaagu gcccguggcc 1860
auucacgccg aucagcugac accuacaugg cggguguacu ccaccggcag caauguguuu 1920
cagaccagag ccggcugucu gaucggagcc gagcacguga acaauagcua cgagugcgac 1980
auccccaucg gcgcuggcau cugugccagc uaccagacac agacaaacag ccccucucug 2040
gccagcucug uggccagcca gagcaucauu gccuacacaa ugucucuggg cgucgagaac 2100
agcguggccu acuccaacaa cucuaucgcu aucccccacca acuucaccau cagcgugacc 2160
acagagaucc ugccuguguc caugaccaag accagcgugg acugcaccau guacaucugc 2220
ggcgauucca ccgagugcuc caaccugcug cugcaguacg gcagcuucug cacccagcug 2280
aauagagccc ugacagggau cgccguggaa caggacaaga acacccaaga gguguucgcc 2340
caagugaagc agaucuacaa gaccccuccu aucaaggacu ucggcggcuu caauuucagc 2400
cagauucugc ccgauccuag caagcccagc aagcggagcc ccaucgagga ccugcuguuc 2460
aacaaaguga cacuggccga cgccggcuuc aucaagcagu auggcgauug ucugggcgac 2520
auugccgcca gggaucugau uugcgcccag aaguuuaacg gacugacagu gcugccuccu 2580
cugcugaccg augagaugau cgcccaguac acaucugccc ugcuggccgg cacaaucaca 2640
agcggcugga cauuuggagc uggccccgcu cugcagaucc ccuuuccuau gcagauggcc 2700
uacagauuca acggcaucgg agugacccag aaugugcugu acgagaacca gaagcugauc 2760
gccaaccagu ucaacagcgc caucggcaag auccaggaca gccugagcag cacaccaagc 2820
gcccugggaa agcugcagga cgugguucaac cagaaugccc aggcacugaa cacccugguc 2880
aagcagcugu ccuccaacuu cggcgccauc agcucugugc ugaacgauau ccugagcaga 2940
cuggacccuc cugaggccga ggugcagauc gacagacuga ucacaggcag acugcagagc 3000
cuccagacau acgugaccca gcagcugauc agagccgccg agauuagagc cucugccaau 3060
cuggccgcca ccaagauguc ugagugugug cugggccaga gcaagagagu ggacuuuugc 3120
ggcaagggcu accaccugau gagcuucccu cagucugccc cucacggcgu ggguguuucug 3180
cacgugacau acguucccgc ucaagagaag aauuucacca ccgcuccagc caucugccac 3240
gacggcaaag cccacuuucc uagagaaggc guguucgugu ccaacggcac ccauugguuc 3300
gugacacagc ggaacuucua cgagccccag aucaucacca ccgacaacac cuucgugucu 3360

```
ggcaacugcg acgucgugau cggcauugug aacaauaccg uguacgaccc ucugcagccc   3420

gagcuggaca gcuucaaaga ggaacuggac aaguacuuua agaaccacac aagccccgac   3480

guggaccugg gcgauaucag cggaaucaau gccagcgucg ugaacaucca gaaagagauc   3540

gaccggcuga acgagguggc caagaaucug aacgagagcc ugaucgaccu gcaagaacug   3600

gggaaguacg agcaguacau caaguggccc ugguacaucu ggcugggcuu uaucgccgga   3660

cugauugcca ucgugauggu cacaaucaug cuguguugca ugaccagcug cuguagcugc   3720

cugaagggcu guuguagcug uggcagcugc ugcaaguucg acgaggacga uucugagccc   3780

gugcugaagg gcgugaaacu gcacuacaca uga                                3813
```

<210> SEQ ID NO 56
<211> LENGTH: 1273
<212> TYPE: PRT
<213> ORGANISM: SARS-CoV-2 Brazilian variant B.1.1.28 (P.1)

<400> SEQUENCE: 56

```
Met Phe Val Phe Leu Val Leu Leu Pro Leu Val Ser Ser Gln Cys Val
1               5                   10                  15

Asn Phe Thr Asn Arg Thr Gln Leu Pro Phe Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Tyr Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Ser Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285
```

```
Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Thr Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Lys Gly Phe Asn Cys Tyr Phe Pro Leu Gln Ser Tyr Gly
                485                 490                 495

Phe Gln Pro Thr Tyr Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Gly Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu Tyr Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Ser Leu Ala Ser Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
```

-continued

```
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Pro Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Pro Ala Leu Gln Ile
                885                 890                 895

Pro Phe Pro Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Pro Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                1020

Leu Ala  Ala Ile Lys Met Ser  Glu Cys Val Leu Gly  Gln Ser Lys
    1025                 1030                1035

Arg Val  Asp Phe Cys Gly Lys  Gly Tyr His Leu Met  Ser Phe Pro
    1040                 1045                1050

Gln Ser  Ala Pro His Gly Val  Val Phe Leu His Val  Thr Tyr Val
    1055                 1060                1065

Pro Ala  Gln Glu Lys Asn Phe  Thr Thr Ala Pro Ala  Ile Cys His
    1070                 1075                1080

Asp Gly  Lys Ala His Phe Pro  Arg Glu Gly Val Phe  Val Ser Asn
    1085                 1090                1095

Gly Thr  His Trp Phe Val Thr  Gln Arg Asn Phe Tyr  Glu Pro Gln
    1100                 1105                1110

Ile Ile  Thr Thr Asp Asn Thr  Phe Val Ser Gly Asn  Cys Asp Val
    1115                 1120                1125
```

-continued

```
Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Phe Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270
```

<210> SEQ ID NO 57
<211> LENGTH: 3822
<212> TYPE: DNA
<213> ORGANISM: Artificial Sequence
<220> FEATURE:
<223> OTHER INFORMATION: Synthetised Sequence

<400> SEQUENCE: 57

```
atgttcgtgt ttctggtgct gctgcctctg gtgtccagcc agtgtgtgaa cttcaccaac     60

agaacacagc tgcctttcgc ctacaccaac agctttacca gaggcgtgta ctaccccgac    120

aaggtgttca gatccagcgt gctgcactct acccaggacc tgttcctgcc tttcttcagc    180

aacgtgacct ggttccacgc catccacgtg tccggcacca atggcaccaa gagattcgac    240

aaccccgtgc tgcccttcaa cgacggggtg tactttgcca gcaccgagaa gtccaacatc    300

atcagaggct ggatcttcgg caccacactg gacagcaaga cccagagcct gctgatcgtg    360

aacaacgcca ccaacgtggt catcaaagtg tgcgagttcc agttctgcaa ctaccccttc    420

ctgggcgtct actaccacaa gaacaacaag agctggatgg aaagcgagtt ccgggtgtac    480

agcagcgcca acaactgcac cttcgagtac gtgtcccagc ctttcctgat ggacctggaa    540

ggcaagcagg gcaacttcaa gaacctgagc gagttcgtgt tcaagaacat cgacggctac    600

ttcaagatct acagcaagca cacccctatc aacctcgtgc gggatctgcc tcagggcttc    660

tctgctctgg aacccctggt ggatctgccc atcggcatca acatcacccg gtttcagaca    720

ctgctggccc tgcacagaag ctacctgaca cctggcgata gcagcagcgg atggacagct    780

ggtgccgccg cttactatgt gggctacctg cagcctagaa ccttcctgct gaagtacaac    840

gagaacggca ccatcaccga cgccgtggat tgtgcccttg atcctctgag cgagacaaag    900

tgcaccctga agtccttcac cgtggaaaag ggcatctacc agaccagcaa cttccgggtg    960

cagcccaccg aatccatcgt gcggttcccc aatatcacca atctgtgccc cttcggcgag   1020

gtgttcaatg ccaccagatt cgcctctgtg tacgcctgga accggaagcg gatcagcaat   1080

tgcgtggccg actactccgt gctgtacaac tccgccagct tcagcacctt caagtgctac   1140
```

-continued

```
ggcgtgtccc ctaccaagct gaacgacctg tgcttcacaa acgtgtacgc cgacagcttc   1200
gtgatccggg gagatgaagt gcggcagatt gcccctggac agacaggcac gatcgccgac   1260
tacaactaca agctgcccga cgacttcacc ggctgtgtga ttgcctggaa cagcaacaac   1320
ctggactcca aagtcggcgg caactacaat tacctgtacc ggctgttccg gaagtccaat   1380
ctgaagccct tcgagcggga catctccacc gagatctatc aggccggcag caccccttgt   1440
aacggcgtga aaggcttcaa ctgctacttc ccactgcagt cctacggctt tcagcccaca   1500
tatggcgtgg gctatcagcc ctacagagtg gtggtgctga gcttcgaact gctgcatgcc   1560
cctgccacag tgtgcggccc taagaaaagc accaatctcg tgaagaacaa atgcgtgaac   1620
ttcaacttca acggcctgac cggcacaggc gtgctgacag agagcaacaa gaagttcctg   1680
ccattccagc agtttggccg ggatatcgcc gataccacag acgccgttag agatccccag   1740
acactggaaa tcctggacat caccccttgc agcttcggcg gagtgtctgt gatcacccct   1800
ggcaccaaca ccagcaatca ggtggcagtg ctgtaccagg gcgtgaactg taccgaagtg   1860
cccgtggcca ttcacgccga tcagctgaca cctacatggc gggtgtactc caccggcagc   1920
aatgtgtttc agaccagagc cggctgtctg atcggagccg agtacgtgaa caatagctac   1980
gagtgcgaca tccccatcgg cgctggcatc tgtgccagct accagacaca gacaaacagc   2040
ccctctctgg ccagctctgt ggccagccag agcatcattg cctacacaat gtctctgggc   2100
gccgagaaca gcgtggccta ctccaacaac tctatcgcta tccccaccaa cttcaccatc   2160
agcgtgacca cagagatcct gcctgtgtcc atgaccaaga ccagcgtgga ctgcaccatg   2220
tacatctgcg gcgattccac cgagtgctcc aacctgctgc tgcagtacgg cagcttctgc   2280
acccagctga atagagccct gacagggatc gccgtggaac aggacaagaa cacccaagag   2340
gtgttcgccc aagtgaagca gatctacaag acccctccta tcaaggactt cggcggcttc   2400
aatttcagcc agattctgcc cgatcctagc aagcccagca agcggagccc catcgaggac   2460
ctgctgttca acaaagtgac actggccgac gccggcttca tcaagcagta tggcgattgt   2520
ctgggcgaca ttgccgccag ggatctgatt tgcgcccaga agtttaacgg actgacagtg   2580
ctgcctcctc tgctgaccga tgagatgatc gcccagtaca catctgccct gctggccggc   2640
acaatcacaa gcggctggac atttggagct ggccccgctc tgcagatccc ctttcctatg   2700
cagatggcct acagattcaa cggcatcgga gtgacccaga atgtgctgta cgagaaccag   2760
aagctgatcg ccaaccagtt caacagcgcc atcggcaaga tccaggacag cctgagcagc   2820
acaccaagcg ccctgggaaa gctgcaggac gtggtcaacc agaatgccca ggcactgaac   2880
accctggtca agcagctgtc ctccaacttc ggcgccatca gctctgtgct gaacgatatc   2940
ctgagcagac tggaccctcc tgaggccgag gtgcagatcg acagactgat cacaggcaga   3000
ctgcagagcc tccagacata cgtgacccag cagctgatca gagccgccga gattagagcc   3060
tctgccaatc tggccgccat caagatgtct gagtgtgtgc tgggccagag caagagagtg   3120
gacttttgcg gcaagggcta ccacctgatg agcttccctc agtctgcccc tcacggcgtg   3180
gtgtttctgc acgtgacata cgttcccgct caagagaaga atttcaccac cgctccagcc   3240
atctgccacg acggcaaagc ccactttcct agagaaggcg tgttcgtgtc caacggcacc   3300
cattggttcg tgacacagcg gaacttctac gagccccaga tcatcaccac cgacaacacc   3360
ttcgtgtctg gcaactgcga cgtcgtgatc ggcattgtga acaataccgt gtacgaccct   3420
ctgcagcccg agctggacag cttcaaagag gaactggaca agtactttaa gaaccacaca   3480
agccccgacg tggacctggg cgatatcagc ggaatcaatg ccagcttcgt gaacatccag   3540
```

aaagagatcg accggctgaa cgaggtggcc aagaatctga acgagagcct gatcgacctg 3600
caagaactgg ggaagtacga gcagtacatc aagtggccct ggtacatctg gctgggcttt 3660
atcgccggac tgattgccat cgtgatggtc acaatcatgc tgtgttgcat gaccagctgc 3720
tgtagctgcc tgaagggctg ttgtagctgt ggcagctgct gcaagttcga cgaggacgat 3780
tctgagcccg tgctgaaggg cgtgaaactg cactacacat ga 3822

<210> SEQ ID NO 58
<211> LENGTH: 3822
<212> TYPE: RNA
<213> ORGANISM: Artificial Sequence
<220> FEATURE:
<223> OTHER INFORMATION: Synthetised Sequence

<400> SEQUENCE: 58
auguucgugu uucuggugcu gcugccucug guguccagcc agugugugaa cuucaccaac 60
agaacacagc ugccuuucgc cuacaccaac agcuuuacca gaggcgugua cuaccccgac 120
aagguguuca gauccagcgu gcugcacucu acccaggacc uguuccugcc uuucuucagc 180
aacgugaccu gguuccacgc cauccacgug uccggcacca auggcaccaa gagauucgac 240
aaccccgugc ugcccuucaa cgacggggug uacuuugcca gcaccgagaa guccaacauc 300
aucagaggcu ggaucuucgg caccacacug gacagcaaga cccagagccu gcugaucgug 360
aacaacgcca ccaacguggu caucaaagug ugcgaguucc aguucugcaa cuaccccuuc 420
cugggcgucu acuaccacaa gaacaacaag agcuggaugg aaagcgaguu ccggguguac 480
agcagcgcca acaacugcac cuucgaguac gugucccagc cuuuccugau ggaccuggaa 540
ggcaagcagg gcaacuucaa gaaccugagc gaguucgugu ucaagaacau cgacggcuac 600
uucaagaucu acagcaagca caccccuauc aaccucgugc gggaucugcc ucagggcuuc 660
ucugcucugg aaccccuggu ggaucugccc aucggcauca acaucacccg guuucagaca 720
cugcuggccc ugcacagaag cuaccugaca ccuggcgaua gcagcagcgg auggacagcu 780
ggugccgccg cuuacuaugu gggcuaccug cagccuagaa ccuuccugcu gaaguacaac 840
gagaacggca ccaucaccga cgccguggau ugugcccuug auccucugag cgagacaaag 900
ugcacccuga aguccuucac cguggaaaag ggcaucuacc agaccagcaa cuuccgggug 960
cagcccaccg aauccaucgu gcgguucccc aauaucacca aucugugccc cuucggcgag 1020
guguucaaug ccaccagauu cgccucugug uacgccugga accggaagcg gaucagcaau 1080
ugcguggccg acuacuccgu gcuguacaac uccgccagcu ucagcaccuu caagugcuac 1140
ggcguguccc cuaccaagcu gaacgaccug ugcuucacaa acguguacgc cgacagcuuc 1200
gugauccggg gagaugaagu gcggcagauu gccccuggac agacaggcac gaucgccgac 1260
uacaacuaca agcugcccga cgacuucacc ggcuguguga uugccuggaa cagcaacaac 1320
cuggacucca aagucggcgg caacuacaau uaccuguacc ggcuguuccg gaaguccaau 1380
cugaagcccu ucgagcggga caucuccacc gagaucuauc aggccggcag caccccuugu 1440
aacggcguga aaggcuucaa cugcuacuuc ccacugcagu ccuacggcuu ucagcccaca 1500
uauggcgugg gcuaucagcc cuacagagug guggugcuga gcuucgaacu gcugcaugcc 1560
ccugccacag ugugcggccc uaagaaaagc accaaucucg ugaagaacaa augcgugaac 1620
uucaacuuca acggccugac cggcacaggc gugcugacag agagcaacaa gaaguuccug 1680
ccauuccagc aguuuggccg ggauaucgcc gauaccacag acgccguuag agauccccag 1740

-continued acacuggaaa uccuggacau caccccuugc agcuucggcg gagugucugu gaucaccccu 1800
ggcaccaaca ccagcaauca gguggcagug cuguaccagg gcgugaacug uaccgaagug 1860
cccguggcca uucacgccga ucagcugaca ccuacauggc ggguguacuc caccggcagc 1920
aauguguuuc agaccagagc cggcugucug aucggagccg aguacgugaa caauagcuac 1980
gagugcgaca uccccaucgg cgcuggcauc ugugccagcu accagacaca gacaaacagc 2040
cccucucugg ccagcucugu ggccagccag agcaucauug ccuacacaau gucucugggc 2100
gccgagaaca gcguggccua cuccaacaac ucuaucgcua uccccaccaa cuucaccauc 2160
agcgugacca cagagauccu gccugugucc augaccaaga ccagcgugga cugcaccaug 2220
uacaucugcg gcgauuccac cgagugcucc aaccugcugc ugcaguacgg cagcuucugc 2280
acccagcuga auagagcccu gacagggauc gccguggaac aggacaagaa cacccaagag 2340
guguucgccc aagugaagca gaucuacaag accccuccua ucaaggacuu cggcggcuuc 2400
aauuucagcc agauucugcc cgauccuagc aagcccagca agcggagccc caucgaggac 2460
cugcuguuca acaaagugac acuggccgac gccggcuuca ucaagcagua uggcgauugu 2520
cugggcgaca uugccgccag ggaucugauu ugcgcccaga aguuuaacgg acugacagug 2580
cugccuccuc ugcugaccga ugagaugauc gcccaguaca caucugcccu gcuggccggc 2640
acaaucacaa gcggcuggac auuuggagcu ggccccgcuc ugcagauccc cuuuccuaug 2700
cagauggccu acagauucaa cggcaucgga gugacccaga augugcugua cgagaaccag 2760
aagcugaucg ccaaccaguu caacagcgcc aucggcaaga uccaggacag ccugagcagc 2820
acaccaagcg cccugggaaa gcugcaggac guggucaacc agaaugccca ggcacugaac 2880
acccugguca agcagcuguc cuccaacuuc ggcgccauca gcucugugcu gaacgauauc 2940
cugagcagac uggacccucc ugaggccgag gugcagaucg acagacugau cacaggcaga 3000
cugcagagcc uccagacaua cgugacccag cagcugauca gagccgccga gauuagagcc 3060
ucugccaauc uggccgccau caagaugucu gagugugugc ugggccagag caagagagug 3120
gacuuuugcg gcaagggcua ccaccugaug agcuucccuc agucugcccc ucacggcgug 3180
guguuucugc acgugacaua cguucccgcu caagagaaga auuucaccac cgcuccagcc 3240
aucugccacg acggcaaagc ccacuuuccu agagaaggcg uguucguguc caacggcacc 3300
cauugguucg ugacacagcg gaacuucuac gagccccaga ucaucaccac cgacaacacc 3360
uucgugucug gcaacugcga cgucgugauc ggcauuguga acaauaccgu guacgacccu 3420
cugcagcccg agcuggacag cuucaaagag gaacuggaca aguacuuuaa gaaccacaca 3480
agccccgacg uggaccuggg cgauaucagc ggaaucaaug ccagcuucgu gaacauccag 3540
aaagagaucg accggcugaa cgagguggcc aagaaucuga acgagagccu gaucgaccug 3600
caagaacugg ggaaguacga gcaguacauc aaguggcccu gguacaucug gcugggcuuu 3660
aucgccggac ugauugccau cgugauggug acaaucaugc uguguugcau gaccagcugc 3720
uguagcugcc ugaagggcug uuguagcugu ggcagcugcu gcaaguucga cgaggacgau 3780
ucugagcccg ugcugaaggg cgugaaacug cacuacacau ga 3822

<210> SEQ ID NO 59
<211> LENGTH: 1408
<212> TYPE: PRT
<213> ORGANISM: SARS-CoV-2

<400> SEQUENCE: 59

Met Phe Val Phe Leu Val Leu Leu Pro Leu Val Ser Ser Gln Cys Val

-continued 1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

-continued

```
Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845
```

-continued

```
Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                1020

Leu Ala  Ala Thr Lys Met Ser  Glu Cys Val Leu Gly  Gln Ser Lys
    1025                 1030                1035

Arg Val  Asp Phe Cys Gly Lys  Gly Tyr His Leu Met  Ser Phe Pro
    1040                 1045                1050

Gln Ser  Ala Pro His Gly Val  Val Phe Leu His Val  Thr Tyr Val
    1055                 1060                1065

Pro Ala  Gln Glu Lys Asn Phe  Thr Thr Ala Pro Ala  Ile Cys His
    1070                 1075                1080

Asp Gly  Lys Ala His Phe Pro  Arg Glu Gly Val Phe  Val Ser Asn
    1085                 1090                1095

Gly Thr  His Trp Phe Val Thr  Gln Arg Asn Phe Tyr  Glu Pro Gln
    1100                 1105                1110

Ile Ile  Thr Thr Asp Asn Thr  Phe Val Ser Gly Asn  Cys Asp Val
    1115                 1120                1125

Val Ile  Gly Ile Val Asn Asn  Thr Val Tyr Asp Pro  Leu Gln Pro
    1130                 1135                1140

Glu Leu  Asp Ser Phe Lys Glu  Glu Leu Asp Lys Tyr  Phe Lys Asn
    1145                 1150                1155

His Thr  Ser Pro Asp Val Asp  Leu Gly Asp Ile Ser  Gly Ile Asn
    1160                 1165                1170

Ala Ser  Val Val Asn Ile Gln  Lys Glu Ile Asp Arg  Leu Asn Glu
    1175                 1180                1185

Val Ala  Lys Asn Leu Asn Glu  Ser Leu Ile Asp Leu  Gln Glu Leu
    1190                 1195                1200

Gly Lys  Tyr Glu Gln Tyr Ile  Lys Trp Pro Trp Tyr  Ile Trp Leu
    1205                 1210                1215

Gly Phe  Ile Ala Gly Leu Ile  Ala Ile Val Met Val  Thr Ile Met
    1220                 1225                1230

Leu Cys  Cys Met Thr Ser Cys  Cys Ser Cys Leu Lys  Gly Cys Cys
    1235                 1240                1245

Ser Cys  Gly Ser Cys Cys Lys  Phe Asp Glu Asp Asp  Ser Glu Pro
```

```
    1250                1255                1260

Val Leu  Lys Gly Val Lys Leu  His Tyr Thr Asp Arg  Arg Lys Arg
    1265                1270                1275

Gly Ser  Gly Glu Gly Arg Gly  Ser Leu Leu Thr Cys  Gly Asp Val
    1280                1285                1290

Glu Glu  Asn Pro Gly Pro Met  Asp Tyr Val Ser Leu  Leu Asn Gln
    1295                1300                1305

Ile Trp  Gln Lys Tyr Leu Asn  Ser Pro Tyr Thr Thr  Cys Leu Tyr
    1310                1315                1320

Ile Pro  Lys Pro Thr Ala Lys  Tyr Thr Pro Leu Val  Gly Thr Ser
    1325                1330                1335

Leu His  Pro Val Leu Trp Asn  Cys Gln Leu Ser Phe  Ala Gly Tyr
    1340                1345                1350

Thr Glu  Ser Ala Val Asn Ser  Thr Lys Ala Leu Ala  Lys Gln Asp
    1355                1360                1365

Ala Ala  Gln Arg Ile Ala Trp  Leu Leu His Lys Asp  Gly Gly Ile
    1370                1375                1380

Pro Asp  Gly Cys Ser Leu Tyr  Leu Arg His Ser Ser  Leu Phe Ala
    1385                1390                1395

Gln Ser  Glu Glu Glu Glu Ser  Phe Ser Asn
    1400                1405
```

<210> SEQ ID NO 60
<211> LENGTH: 4227
<212> TYPE: DNA
<213> ORGANISM: Artificial Sequence
<220> FEATURE:
<223> OTHER INFORMATION: Synthetised Sequence

<400> SEQUENCE: 60

```
atgttcgtgt ttctggtgct gctgcctctg gtgtccagcc agtgtgtgaa cctgaccacc     60

agaacacagc tgcctccagc ctacaccaac agctttacca gaggcgtgta ctaccccgac    120

aaggtgttca gatccagcgt gctgcactct acccaggacc tgttcctgcc tttcttcagc    180

aacgtgacct ggttccacgc catccacgtg tccggcacca atggcaccaa gagattcgac    240

aaccccgtgc tgcccttcaa cgacggggtg tactttgcca gcaccgagaa gtccaacatc    300

atcagaggct ggatcttcgg caccacactg gacagcaaga cccagagcct gctgatcgtg    360

aacaacgcca ccaacgtggt catcaaagtg tgcgagttcc agttctgcaa cgaccccttc    420

ctgggcgtct actaccacaa gaacaacaag agctggatgg aaagcgagtt ccgggtgtac    480

agcagcgcca acaactgcac cttcgagtac gtgtcccagc ctttcctgat ggacctggaa    540

ggcaagcagg gcaacttcaa gaacctgcgc gagttcgtgt tcaagaacat cgacggctac    600

ttcaagatct acagcaagca cacccctatc aacctcgtgc gggatctgcc tcagggcttc    660

tctgctctgg aacccctggt ggatctgccc atcggcatca acatcacccg gtttcagaca    720

ctgctggccc tgcacagaag ctacctgaca cctggcgata gcagcagcgg atggacagct    780

ggtgccgccg cttactatgt gggctacctg cagcctagaa ccttcctgct gaagtacaac    840

gagaacggca ccatcaccga cgccgtggat tgtgcccttg atcctctgag cgagacaaag    900

tgcaccctga agtccttcac cgtggaaaag ggcatctacc agaccagcaa cttccgggtg    960

cagcccaccg aatccatcgt gcggttcccc aatatcacca atctgtgccc cttcggcgag   1020

gtgttcaatg ccaccagatt cgcctctgtg tacgcctgga accggaagcg gatcagcaat   1080

tgcgtggccg actactccgt gctgtacaac tccgccagct tcagcacctt caagtgctac   1140
```

-continued

```
ggcgtgtccc ctaccaagct gaacgacctg tgcttcacaa acgtgtacgc cgacagcttc   1200
gtgatccggg gagatgaagt gcggcagatt gcccctggac agacaggcaa gatcgccgac   1260
tacaactaca agctgcccga cgacttcacc ggctgtgtga ttgcctggaa cagcaacaac   1320
ctggactcca aagtcggcgg caactacaat tacctgtacc ggctgttccg gaagtccaat   1380
ctgaagccct tcgagcggga catctccacc gagatctatc aggccggcag cacccccttgt  1440
aacggcgtgg aaggcttcaa ctgctacttc ccactgcagt cctacggctt tcagcccaca   1500
aatggcgtgg gctatcagcc ctacagagtg gtggtgctga gcttcgaact gctgcatgcc   1560
cctgccacag tgtgcggccc taagaaaagc accaatctcg tgaagaacaa atgcgtgaac   1620
ttcaacttca acggcctgac cggcacaggc gtgctgacag agagcaacaa gaagttcctg   1680
ccattccagc agtttggccg ggatatcgcc gataccacag acgccgttag agatccccag   1740
acactggaaa tcctggacat cacccccttgc agcttcggcg gagtgtctgt gatcacccct  1800
ggcaccaaca ccagcaatca ggtggcagtg ctgtaccagg acgtgaactg taccgaagtg   1860
cccgtggcca ttcacgccga tcagctgaca cctacatggc gggtgtactc caccggcagc   1920
aatgtgtttc agaccagagc cggctgtctg atcggagccg agcacgtgaa caatagctac   1980
gagtgcgaca tccccatcgg cgctggcatc tgtgccagct accagacaca gacaaacagc   2040
cccagacggg ccagatctgt ggccagccag agcatcattg cctacacaat gtctctgggc   2100
gccgagaaca gcgtggccta ctccaacaac tctatcgcta tccccaccaa cttcaccatc   2160
agcgtgacca cagagatcct gcctgtgtcc atgaccaaga ccagcgtgga ctgcaccatg   2220
tacatctgcg gcgattccac cgagtgctcc aacctgctgc tgcagtacgg cagcttctgc   2280
acccagctga atagagccct gacagggatc gccgtggaac aggacaagaa cacccaagag   2340
gtgttcgccc aagtgaagca gatctacaag accccctccta tcaaggactt cggcggcttc  2400
aatttcagcc agattctgcc cgatcctagc aagcccagca agcggagctt catcgaggac   2460
ctgctgttca acaaagtgac actggccgac gccggcttca tcaagcagta tggcgattgt   2520
ctgggcgaca ttgccgccag ggatctgatt tgcgcccaga agtttaacgg actgacagtg   2580
ctgcctcctc tgctgaccga tgagatgatc gcccagtaca catctgccct gctggccggc   2640
acaatcacaa gcggctggac atttggagct ggcgccgctc tgcagatccc ctttgctatg   2700
cagatggcct acagattcaa cggcatcgga gtgacccaga atgtgctgta cgagaaccag   2760
aagctgatcg ccaaccagtt caacagcgcc atcggcaaga tccaggacag cctgagcagc   2820
acagcaagcg ccctgggaaa gctgcaggac gtggtcaacc agaatgccca ggcactgaac   2880
accctggtca agcagctgtc ctccaacttc ggcgccatca gctctgtgct gaacgatatc   2940
ctgagcagac tggaccctcc tgaggccgag gtgcagatcg acagactgat cacaggcaga   3000
ctgcagagcc tccagacata cgtgacccag cagctgatca gagccgccga gattagagcc   3060
tctgccaatc tggccgccac caagatgtct gagtgtgtgc tgggccagag caagagagtg   3120
gacttttgcg gcaagggcta ccacctgatg agcttccctc agtctgcccc tcacggcgtg   3180
gtgtttctgc acgtgacata cgttcccgct caagagaaga atttcaccac cgctccagcc   3240
atctgccacg acggcaaagc ccactttcct agagaaggcg tgttcgtgtc caacggcacc   3300
cattggttcg tgacacagcg gaacttctac gagccccaga tcatcaccac cgacaacacc   3360
ttcgtgtctg gcaactgcga cgtcgtgatc ggcattgtga acaataccgt gtacgaccct   3420
ctgcagcccg agctggacag cttcaaagag gaactggaca agtactttaa gaaccacaca   3480
```

agccccgacg tggacctggg cgatatcagc ggaatcaatg ccagcgtcgt gaacatccag 3540
aaagagatcg accggctgaa cgaggtggcc aagaatctga acgagagcct gatcgacctg 3600
caagaactgg ggaagtacga gcagtacatc aagtggccct ggtacatctg gctgggcttt 3660
atcgccggac tgattgccat cgtgatggtc acaatcatgc tgtgttgcat gaccagctgc 3720
tgtagctgcc tgaagggctg ttgtagctgt ggcagctgct gcaagttcga cgaggacgat 3780
tctgagcccg tgctgaaggg cgtgaaactg cactacacag atcggagaaa gagaggctct 3840
ggcgaaggca gaggcagcct gcttacatgt ggcgacgtgg aagagaaccc cggacctatg 3900
gattatgtgt ccctgctgaa ccagatttgg cagaagtacc tgaacagccc ctacaccacc 3960
tgtctgtaca tccccaagcc taccgccaag tacacacctc tcgtgggcac atctctgcac 4020
cccgtgctgt ggaattgcca gctgagcttt gccggctaca ccgagtctgc cgtgaacagc 4080
acaaaggccc tggccaaaca ggacgccgct cagagaattg cctggctgct gcacaaggat 4140
ggcggcatcc ctgatggctg tagcctgtac ctgagacaca gcagcctgtt cgcccagagc 4200
gaggaagagg aatccttcag caactga 4227

<210> SEQ ID NO 61
<211> LENGTH: 4227
<212> TYPE: RNA
<213> ORGANISM: Artificial Sequence
<220> FEATURE:
<223> OTHER INFORMATION: Synthetised Sequence

<400> SEQUENCE: 61
auguucgugu uucuggugcu gcugccucug guguccagcc agugugugaa ccugaccacc 60
agaacacagc ugccuccagc cuacaccaac agcuuuacca gaggcgugua cuaccccgac 120
aagguguuca gauccagcgu gcugcacucu acccaggacc uguuccugcc uuucuucagc 180
aacgugaccu gguuccacgc cauccacgug uccggcacca auggcaccaa gagauucgac 240
aaccccgugc ugcccuucaa cgacggggug uacuuugcca gcaccgagaa guccaacauc 300
aucagaggcu ggaucuucgg caccacacug gacagcaaga cccagagccu gcugaucgug 360
aacaacgcca ccaacguggu caucaaagug ugcgaguucc aguucugcaa cgaccccuuc 420
cugggcgucu acuaccacaa gaacaacaag agcuggaugg aaagcgaguu ccggguguac 480
agcagcgcca acaacugcac cuucgaguac gugucccagc cuuuccugau ggaccuggaa 540
ggcaagcagg gcaacuucaa gaaccugcgc gaguucgugu ucaagaacau cgacggcuac 600
uucaagaucu acagcaagca caccccuauc aaccucgugc gggaucugcc ucagggcuuc 660
ucugcucugg aaccccuggu ggaucugccc aucggcauca acaucacccg guuucagaca 720
cugcuggccc ugcacagaag cuaccugaca ccuggcgaua gcagcagcgg auggacagcu 780
ggugccgccg cuuacuaugu gggcuaccug cagccuagaa ccuuccugcu gaaguacaac 840
gagaacggca ccaucaccga cgccguggau ugugcccuug auccucugag cgagacaaag 900
ugcacccuga aguccuucac cguggaaaag ggcaucuacc agaccagcaa cuuccgggug 960
cagcccaccg aauccaucgu gcgguucccc aauaucacca aucugugccc cuucggcgag 1020
guguucaaug ccaccagauu cgccucugug uacgccugga accggaagcg gaucagcaau 1080
ugcguggccg acuacuccgu gcuguacaac uccgccagcu ucagcaccuu caagugcuac 1140
ggcgcguccc cuaccaagcu gaacgaccug ugcuucacaa acguguacgc cgacagcuuc 1200
gugauccggg gagaugaagu gcggcagauu gccccuggac agacaggcaa gaucgccgac 1260
uacaacuaca agcugcccga cgacuucacc ggcuguguga uugccuggaa cagcaacaac 1320

-continued

```
cuggacucca aagucggcgg caacuacaau uaccuguacc ggcuguuccg gaaguccaau   1380
cugaagcccu ucgagcggga caucuccacc gagaucuauc aggccggcag caccccuugu   1440
aacggcgugg aaggcuucaa cugcuacuuc ccacugcagu ccuacggcuu ucagcccaca   1500
aauggcgugg gcuaucagcc cuacagagug guggugcuga gcuucgaacu gcugcaugcc   1560
ccugccacag ugugcggccc uaagaaaagc accaaucucg ugaagaacaa augcgugaac   1620
uucaacuuca acggccugac cggcacaggc gugcugacag agagcaacaa gaaguuccug   1680
ccauuccagc aguuuggccg ggauaucgcc gauaccacag acgccguuag agauccccag   1740
acacuggaaa uccuggacau caccccuugc agcuucggcg gagugucugu gaucaccccu   1800
ggcaccaaca ccagcaauca gguggcagug cuguaccagg acgugaacug uaccgaagug   1860
cccguggcca uucacgccga ucagcugaca ccuacauggc ggguguacuc caccggcagc   1920
aauguguuuc agaccagagc cggcugucug aucggagccg agcacgugaa caauagcuac   1980
gagugcgaca uccccaucgg cgcuggcauc ugugccagcu accagacaca gacaaacagc   2040
cccagacggg ccagaucugu ggccagccag agcaucauug ccuacacaau gucucugggc   2100
gccgagaaca gcguggccua cuccaacaac ucuaucgcua uccccaccaa cuucaccauc   2160
agcgugacca cagagauccu gccuguguc  augaccaaga ccagcgugga cugcaccaug   2220
uacaucugcg gcgauuccac cgagugcucc aaccugcugc ugcaguacgg cagcuucugc   2280
acccagcuga auagagcccu gacagggauc gccguggaac aggacaagaa cacccaagag   2340
guguucgccc aagugaagca gaucuacaag accccuccua ucaaggacuu cggcggcuuc   2400
aauuucagcc agauucugcc cgauccuagc aagcccagca agcggagcuu caucgaggac   2460
cugcuguuca acaaagugac acuggccgac gccggcuuca ucaagcagua uggcgauugu   2520
cugggcgaca uugccgccag ggaucugauu ugcgcccaga aguuuaacgg acugacagug   2580
cugccuccuc ugcugaccga ugagaugauc gcccaguaca caucugcccu gcuggccggc   2640
acaaucacaa gcggcuggac auuuggagcu ggcgccgcuc ugcagauccc cuuugcuaug   2700
cagauggccu acagauucaa cggcaucgga gugacccaga augugcugua cgagaaccag   2760
aagcugaucg ccaaccaguu caacagcgcc aucggcaaga uccaggacag ccugagcagc   2820
acagcaagcg cccugggaaa gcugcaggac guggucaacc agaaugccca ggcacugaac   2880
acccugguca agcagcuguc cuccaacuuc ggcgccauca gcucugugcu gaacgauauc   2940
cugagcagac uggacccucc ugaggccgag gugcagaucg acagacugau cacaggcaga   3000
cugcagagcc uccagacaua cgugacccag cagcugauca gagccgccga gauuagagcc   3060
ucugccaauc uggccgccac caagaugucu gagugugugc ugggccagag caagagagug   3120
gacuuuugcg gcaagggcua ccaccugaug agcuucccuc agucugcccc ucacggcgug   3180
guguuucugc acgugacaua cguucccgcu caagagaaga auuucaccac cgcuccagcc   3240
aucugccacg acggcaaagc ccacuuuccu agagaaggcg uguucguguc caacggcacc   3300
cauugguucg ugacacagcg gaacuucuac gagccccaga ucaucaccac cgacaacacc   3360
uucgugucug gcaacugcga cgucgugauc ggcauuguga acaauaccgu guacgacccu   3420
cugcagcccg agcuggacag cuucaaagag gaacuggaca aguacuuuaa gaaccacaca   3480
agccccgacg uggaccuggg cgauaucagc ggaaucaaug ccagcgucgu gaacauccag   3540
aaagagaucg accggcugaa cgagguggcc aagaaucuga acgagagccu gaucgaccug   3600
caagaacugg ggaaguacga gcaguacauc aaguggcccu gguacaucug gcugggcuuu   3660
```

-continued aucgccggac ugauugccau cgugaugguc acaaucaugc uguguugcau gaccagcugc 3720
uguagcugcc ugaagggcug uuguagcugu ggcagcugcu gcaaguucga cgaggacgau 3780
ucugagcccg ugcugaaggg cgugaaacug cacuacacag aucggagaaa gagaggcucu 3840
ggcgaaggca gaggcagccu gcuuacaugu ggcgacgugg aagagaaccc cggaccuaug 3900
gauuaugugu cccugcugaa ccagauuugg cagaaguacc ugaacagccc cuacaccacc 3960
ugucuguaca ucccccaagcc uaccgccaag uacacaccuc ucgugggcac aucucugcac 4020
cccgugcugu ggaauugcca gcugagcuuu gccggcuaca ccgagucugc cgugaacagc 4080
acaaaggccc uggccaaaca ggacgccgcu cagagaauug ccuggcugcu gcacaaggau 4140
ggcggcaucc cugauggcug uagccuguac cugagacaca gcagccuguu cgcccagagc 4200
gaggaagagg aauccuucag caacuga 4227

<210> SEQ ID NO 62
<211> LENGTH: 11542
<212> TYPE: RNA
<213> ORGANISM: Artificial Sequence
<220> FEATURE:
<223> OTHER INFORMATION: Synthetised Sequence

<400> SEQUENCE: 62
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu ggccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu agguggggcaa aggaauauaa ggaagaucaa gaagaugaaa 1260
ggccacuagg acuacgagau agacaguuag ucauggggug uuguugggcu uuuagaaggc 1320
acaagauaac aucuauuuau aagcgcccgg auacccaaac caucaucaaa gugaacagcg 1380
auuuccacuc auucgugcug cccaggauag gcaguaacac auuggagauc gggcugagaa 1440
caagaaucag gaaaauguua gaggagcaca aggagccguc accucucauu accgccgagg 1500

-continued

```
acguacaaga agcuaagugc gcagccgaug aggcuaagga ggugcgugaa gccgaggagu   1560
ugcgcgcagc ucuaccaccu uuggcagcug auguugagga gcccacucug gaggcagacg   1620
ucgacuugau guuacaagag gcugggggccg gcucagugga gacaccucgu ggcuugauaa   1680
agguuaccag cuacgauggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa ggugugua ug   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aaguggu ccg ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuuucuuc auucgucagc aaauugaagg   3540
gcagaacugu ccugguggu c ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
agcagugug a agaccaugcc auuaagcuua gcauguugac caagaaagcu ugucugcauc   3780
ugaaucccgg cggaaccugu gucagcauag guuaugguua cgcugacagg gccagcgaaa   3840
```

-continued

```
gcaucauugg ugcuauagcg cggcaguuca aguuuucccg gguaugcaaa ccgaaauccu   3900
cacuugaaga gacggaaguu cuguuuguau ucauugggua cgaucgcaag gcccguacgc   3960
acaauucuua caagcuuuca ucaaccuuga ccaacauuua uacagguucc agacuccacg   4020
aagccggaug ugcacccuca uaucaugugg ugcgagggga uauugccacg gccaccgaag   4080
gagugauuau aaaugcugcu aacagcaaag gacaaccugg cggagggggug ugcggagcgc  4140
uguauaagaa auucccggaa agcuucgauu uacagccgau cgaaguagga aaagcgcgac   4200
uggucaaagg ugcagcuaaa cauaucauuc augccguagg accaaacuuc aacaaaguuu   4260
cggagguuga aggugacaaa caguuggcag aggcuuauga guccaucgcu aagauuguca   4320
acgauaacaa uuacaaguca guagcgauuc cacuguuguc caccggcauc uuuuccggga   4380
acaaagaucg acuaacccaa ucauugaacc auuugcugac agcuuuagac accacugaug   4440
cagauguagc cauauacugc agggacaaga aaugggaaau gacucucaag gaagcagugg   4500
cuaggagaga agcaguggag gagauaugca uauccgacga cucuucagug acagaaccug   4560
augcagagcu ggugagggug cauccgaaga guucuuuggc uggaaggaag ggcuacagca   4620
caagcgaugg caaaacuuuc ucauauuugg aagggaccaa guuucaccag gcggccaagg   4680
auauagcaga aauuaaugcc auguggcccg uugcaacgga ggccaaugag cagguaugca   4740
uguauauccu cggagaaagc augagcagua uuaggucgaa augccccguc gaagagucgg   4800
aagccuccac accaccuagc acgcugccuu gcuugugcau ccaugccaug acuccagaaa   4860
gaguacagcg ccuaaaagcc ucacguccag aacaaauuac ugugugcuca uccuuuccau   4920
ugccgaagua uagaaucacu ggugugcaga agauccaaug cucccagccu auauuguucu   4980
caccgaaagu gccugcguau auucauccaa ggaaguaucu cguggaaaca ccaccgguag   5040
acgagacucc ggagccaucg gcagagaacc aauccacaga ggggacaccu gaacaaccac   5100
cacuuauaac cgaggaugag accaggacua gaacgccuga gccgaucauc aucgaagagg   5160
aagaagagga uagcauaagu uugcugucag auggcccgac ccaccaggug cugcaagucg   5220
aggcagacau ucacgggccg cccucuguau cuagcucauc cugguccauu ccucaugcau   5280
ccgacuuuga uguggacagu uuauccauac uugacacccu ggagggagcu agcgugacca   5340
gcggggcaac gucagccgag acuaacucuu acuucgcaaa gaguauggag uuucuggcgc   5400
gaccggugcc ugcgccucga acaguauuca ggaacccucc acaucccgcu ccgcgcacaa   5460
gaacaccguc acuugcaccc agcagggccu gcucgagaac cagccuaguu uccaccccgc   5520
caggcgugaa uagggugauc acuagagagg agcucgaggc gcuuaccccg ucacgcacuc   5580
cuagcagguc ggucucgaga accagccugg ucuccaaccc gccaggcgua aauagggu ga  5640
uuacaagaga ggaguuugag gcguucguag cacaacaaca augacgguuu gaugcgggug   5700
cauacaucuu uuccuccgac accggucaag ggcauuuaca acaaaaauca guaaggcaaa   5760
cggugcuauc cgaaguggug uuggagagga ccgaauugga gauuucguau gccccgcgcc   5820
ucgaccaaga aaaagaagaa uuacuacgca agaaauuaca guuaaauccc acaccugcua   5880
acagaagcag auaccagucc aggaaggugg agaacaugaa agccauaaca gcuagacgua   5940
uucugcaagg ccuagggcau uauuugaagg cagaaggaaa aguggagugc uaccgaaccc   6000
ugcauccugu uccuuuguau ucaucuagug ugaaccgugc cuuuucaagc cccaaggucg   6060
caguggaagc cuguaacgcc auguugaaag agaacuuucc gacuguggcu ucuuacugua   6120
uuauuccaga guacgaugcc uauuuggaca ugguugacgg agcuucaugc ugcuuagaca   6180
cugccaguuu uugcccugca aagcugcgca gcuuuccaaa gaaacacucc uauuuggaac   6240
```

-continued

```
ccacaauacg aucggcagug ccuucagcga uccagaacac gcuccagaac guccuggcag   6300
cugccacaaa aagaaauugc aaugucacgc aaaugagaga auugcccgua uuggauucgg   6360
cggccuuuaa uguggaaugc uucaagaaau augcguguaa uaaugaauau ugggaaacgu   6420
uuaaagaaaa ccccaucagg cuuacugaag aaaacguggu aaauuacauu accaaauuaa   6480
aaggaccaaa agcugcugcu cuuuuugcga agacacauaa uuugaauaug uugcaggaca   6540
uaccaaugga cagguuugua auggacuuaa agagagacgu gaaagugacu ccaggaacaa   6600
aacauacuga agaacggccc aagguacagg ugauccaggc ugccgauccg cuagcaacag   6660
cguaucugug cggaauccac cgagagcugg uuaggagauu aaaugcgguc cugcuuccga   6720
acauucauac acuguuugau augucggcug aagacuuuga cgcuauuaua gccgagcacu   6780
uccagccugg ggauuguguu cuggaaacug acaucgcguc guuugauaaa agugaggacg   6840
acgccauggc ucugaccgcg uuaaugauuc uggaagacuu aggugugggac gcagagcugu   6900
ugacgcugau ugaggcggcu uucggcgaaa uuucaucaau acauuugccc acuaaaacua   6960
aauuuaaauu cggagccaug augaaaucug gaauguuccu cacacuguuu gugaacacag   7020
ucauuaacau uguaaucgca agcagagugu ugagagaacg gcuaaccgga ucaccaugug   7080
cagcauucau uggagaugac aauaucguga aaggagucaa aucggacaaa uuaauggcag   7140
acaggugcgc caccugguug aauauggaag ucaagauuau agaugcugug guggggcgaga   7200
aagcgccuua uuucugugga ggguuuauuu ugugugacuc cgugaccggc acagcgugcc   7260
guguggcaga cccccuaaaa aggcuguuua agcuuggcaa accucuggca gcagacgaug   7320
aacaugauga ugacaggaga agggcauugc augaagaguc aacacgcugg aaccgagugg   7380
guauucuuuc agagcugugc aaggcaguag aaucaaggua ugaaaccgua ggaacuucca   7440
ucauaguuau ggccaugacu acucuagcua gcaguguuaa aucauucagc uaccugagag   7500
gggccccuau aacucucuac ggcuaaccug aauggacuac gacauagucu aguccgccaa   7560
gucuagcaua uggccaccau guucguguuu cuggugcugc ugccucuggu guccagccag   7620
ugugugaacc ugaccaccag aacacagcug ccuccagccu acaccaacag cuuuaccaga   7680
ggcguguacu accccgacaa gguguucaga uccagcgugc ugcacucuac ccaggaccug   7740
uuccugccuu ucuucagcaa cgugaccugg uuccacgcca ucuccggcac caauggcacc   7800
aagagauucg acaaccccgu gcugcccuuc aacgacgggg uguacuuugc cagcaccgag   7860
aaguccaaca ucaucagagg cuggaucuuc ggcaccacac uggacagcaa gacccagagc   7920
cugcugaucg ugaacaacgc caccaacgug gucaucaaag ugugcgaguu ccaguucugc   7980
aacgaccccu uccugggcgu cuaccacaag aacaacaaga gcuggaugga aagcgaguuc   8040
cggguguaca gcagcgccaa caacugcacc uucgaguacg ugucccagcc uuuccugaug   8100
gaccuggaag gcaagcaggg caacuucaag aaccugcgcg aguucguguu caagaacauc   8160
gacggcuacu ucaagaucua cagcaagcac accccuauca accucgugcg ggaucugccu   8220
cagggcuucu cugcucugga accccuggug gaucugccca ucggcaucaa caucacccgg   8280
uuucagacac ugcuggcccu gcacagaagc uaccugacac cuggcgauag cagcagcgga   8340
uggacagcug gugccgccgc uuacuaugug ggcuaccugc agccuagaac cuuccugcug   8400
aaguacaacg agaacggcac caucaccgac gccguggauu gugcccuuga ucccugagc   8460
gagacaaagu gcacccugaa guccuucacc guggaaaagg gcaucuacca gaccagcaac   8520
uuccgggugc agcccaccga auccaucgug cgguucccca auaucaccaa ucugugcccc   8580
```

-continued

```
uucggcgagg uguucaaugc caccagauuc gccucugugu acgccuggaa ccggaagcgg   8640
aucagcaauu gcguggccga cuacuccgug cuguacaacu ccgccagcuu cagcaccuuc   8700
aagugcuacg gcguguccc uaccaagcug aacgaccugu gcuucacaaa cguguacgcc   8760
gacagcuucg ugauccgggg agaugaagug cggcagauug ccccuggaca gacaggcaag   8820
aucgccgacu acaacuacaa gcugcccgac gacuucaccg gcugugugau ugccuggaac   8880
agcaacaacc uggacuccaa agucggcggc aacuacaauu accuguaccg gcuguuccgg   8940
aaguccaauc ugaagcccuu cgagcgggac aucuccaccg agaucuauca ggccggcagc   9000
accccuugua acggcgugga aggcuucaac ugcuacuucc cacugcaguc cuacggcuuu   9060
cagcccacau auggcguggg cuaucagccc uacagagugg uggugcugag cuucgaacug   9120
cugcaugccc cugccacagu gugcggcccu aagaaaagca ccaaucucgu gaagaacaaa   9180
ugcgugaacu ucaacuucaa cggccugacc ggcacaggcg ugcugacaga gagcaacaag   9240
aaguuccugc cauuccagca guuuggccgg gauaucgacg auaccacaga cgccguuaga   9300
gaucccccaga cacuggaaau ccuggacauc accccuugca gcuucggcgg agugucugug   9360
aucaccccug gcaccaacac cagcaaucag guggcagugc uguaccaggg cgugaacugu   9420
accgaagugc ccguggccau ucacgccgau cagcugacac cuacauggcg gguguacucc   9480
accggcagca auguguuuca gaccagagcc ggcugucuga ucggagccga gcacgugaac   9540
aauagcuacg agugcgacau ccccaucggc gcuggcaucu gugccagcua ccagacacag   9600
acaaacagcc acucucuggc cagcucugug gccagccaga gcaucauugc cuacacaaug   9660
ucucugggcg ccgagaacag cguggccuac uccaacaacu cuaucgcuau ccccaucaac   9720
uucaccauca gcgugaccac agagauccug ccuguguucca ugaccaagac cagcguggac   9780
ugcaccaugu acaucugcgg cgauuccacc gagugcucca accugcugcu gcaguacggc   9840
agcuucugca cccagcugaa uagagcccug acagggaucg ccguggaaca ggacaagaac   9900
acccaagagg uguucgccca agugaagcag aucuacaaga ccccuccuau caaggacuuc   9960
ggcggcuuca auuucagcca gauucugccc gauccuagca agcccagcaa gcggagcccc  10020
aucgaggacc ugcuguucaa caaagugaca cuggccgacg ccggcuucau caagcaguau  10080
ggcgauuguc ugggcgacau ugccgccagg gaucugauuu gcgcccagaa guuuaacgga  10140
cugacagugc ugccuccucu gcugaccgau gagaugaucg cccaguacac aucugcccug  10200
cuggccggca caaucacaag cggcuggaca uuuggagcug gccccgcucu gcagaucccc  10260
uuuccuaugc agauggccua cagauucaac ggcaucggag ugacccagaa ugugcuguac  10320
gagaaccaga agcugaucgc caaccaguuc aacagcgcca ucggcaagau ccaggacagc  10380
cugagcagca caccaagcgc ccugggaaag cugcaggacg uggucaacca gaaugcccag  10440
gcacugaaca cccuggucaa gcagcugucc uccaacuucg gcgccaucag cucugugcug  10500
aacgauaucc uggccagacu ggacccuccu gaggccgagg ugcagaucga cagacugauc  10560
acaggcagac ugcagagccu ccagacauac gugacccagc agcugaucag agccgccgag  10620
auuagagccu cugccaaucu ggccgccacc aagaugucug agugugugcu gggccagagc  10680
aagagagugg acuuuugcgg caagggcuac caccugauga gcuucccuca gucugccccu  10740
cacggcgugg uguuucugca cgugacauac guucccgcuc aagagaagaa uuucaccacc  10800
gcuccagcca ucugccacga cggcaaagcc cacuuuccua gagaaggcgu guucgugucc  10860
aacggcaccc auugguucgu gacacagcgg aacuucuacg agccccagau caucaccacc  10920
cacaacaccu ucgugucugg caacugcgac gucgugaucg gcauugugaa caauaccgug  10980
```

uacgacccuc ugcagcccga gcuggacagc uucaaagagg aacuggacaa guacuuuaag 11040
aaccacacaa gccccgacgu ggaccugggc gauaucagcg gaaucaaugc cagcgucgug 11100
aacauccaga aagagaucga ccggcugaac gagguggcca agaaucugaa cgagagccug 11160
aucgaccugc aagaacuggg gaaguacgag caguacauca aguggcccug guacaucugg 11220
cugggcuuua ucgccggacu gauugccauc gugaugguca caaucaugcu guguugcaug 11280
accagcugcu guagcugccu gaagggcugu uguagcugug gcagcugcug caaguucgac 11340
gaggacgauu cugagcccgu gcugaagggc gugaaacugc acuacacaug agcggccgcg 11400
aauuggcaag cugcuuacau agaacucgcg gcgauuggca ugccgccuua aaauuuuuau 11460
uuuauuuuuc uuuucuuuuc cgaaucggau uuuguuuuua auauuucaaa aaaaaaaaaa 11520
aaaaaaaaaa aaaaaaaaaa aa 11542

<210> SEQ ID NO 63
<211> LENGTH: 11542
<212> TYPE: RNA
<213> ORGANISM: Artificial Sequence
<220> FEATURE:
<223> OTHER INFORMATION: Synthetised Sequence

<400> SEQUENCE: 63
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu ggccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucaugggggug uuguugggcu uuuagaaggc 1320
acaagauaac aucuauuuau aagcgcccgg auacccaaac caucaucaaa gugaacagcg 1380
auuuccacuc auucgugcug cccaggauag gcaguaacac auuggagauc gggcugagaa 1440

-continued caagaaucag gaaaauguua gaggagcaca aggagccguc accucucauu accgccgagg 1500
acguacaaga agcuaagugc gcagccgaug aggcuaagga ggugcgugaa gccgaggagu 1560
ugcgcgcagc ucuaccaccu uuggcagcug auguugagga gcccacucug gaggcagacg 1620
ucgacuugau guuacaagag gcuggggccg gcucagugga gacaccucgu ggcuugauaa 1680
agguuaccag cuacgauggc gaggacaaga ucggcucuua cgcugugcuu ucuccgcagg 1740
cuguacucaa gagugaaaaa uuaucuugca uccacccucu cgcugaacaa gucauaguga 1800
uaacacacuc uggccgaaaa gggcguuaug ccguggaacc auaccauggu aaaguagugg 1860
ugccagaggg acaugcaaua cccguccagg acuuucaagc ucugagugaa agugccacca 1920
uuguguacaa cgaacgugag uucguaaaca gguaccugca ccauauugcc acacauggag 1980
gagcgcugaa cacugaugaa gaauauuaca aaacugucaa gcccagcgag cacgacggcg 2040
aauaccugua cgacaucgac aggaaacagu gcgucaagaa agaacuaguc acugggcuag 2100
ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuaguggug agcgccaaga 2280
aagaaaacug ugcagaaauu auaagggacg ucaagaaaau gaaagggcug gacgucaaug 2340
ccagaacugu ggacucagug cucuugaaug gaugcaaaca ccccguagag acccuguaua 2400
uugacgaagc uuuugcuugu caugcaggua cucucagagc gcucauagcc auuauaagac 2460
cuaaaaaggc agugcucugc ggggauccca aacagugcgg uuuuuuuaac augaugugcc 2520
ugaaagugca uuuuaaccac gagauuugca cacaagucuu ccacaaaagc aucucucgcc 2580
guugcacuaa aucugugacu ucggucgucu caaccuuguu uuacgacaaa aaaaugagaa 2640
cgacgaaucc gaaagagacu aagauuguga uugacacuac cggcaguacc aaaccuaagc 2700
aggacgaucu cauucucacu uguuucagag ggugggugaa gcaguugcaa auagauuaca 2760
aaggcaacga aauaaugacg gcagcugccu cucaagggcu gacccguaaa ggugugua ug 2820 ccguucggua caaggugaau gaaaauccuc uguacgcacc caccucagaa caugugaacg 2880
uccuacugac ccgcacggag gaccgcaucg uguggaaaac acuagccggc gacccaugga 2940
uaaaaacacu gacugccaag uacccuggga auuucacugc cacgauagag gaguggcaag 3000
cagagcauga ugccaucaug aggcacaucu uggagagacc ggacccuacc gacgucuucc 3060
agaauaaggc aaacguguguu ugggccaagg cuuuagugcc ggugcugaag accgcuggca 3120
uagacaugac cacugaacaa uggaacacug uggauuauuu ugaaacggac aaagcucacu 3180
cagcagagau aguauugaac caacuaugcg ugagguucuu uggacucgau cuggacuccg 3240
gucuauuuuc ugcacccacu guuccguuau ccauuaggaa uaaucacugg gauaacuccc 3300
cgucgccuaa cauguacggg cugaauaaag aaguggucccg ucagcucucu cgcagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccuggugguc ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720 agcagugga agaccaugcc auuaagcuua gcauguugac caagaaagcu ugucugcauc 3780
ugaaucccgg cggaaccugu gucagcauag guuaugguua cgcugacagg gccagcgaaa 3840

-continued gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauucuua caagcuuuca ucaaccuuga ccaacauuua uacagguucc agacuccacg 4020
aagccggaug ugcacccuca uaucaugugg ugcgagggga uauugccacg gccaccgaag 4080
gagugauuau aaaugcugcu aacagcaaag gacaaccugg cggagggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauaggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180

-continued

```
cugccaguuu uugcccugca aagcugcgca gcuuuccaaa gaaacacucc uauuuggaac   6240
ccacaauacg aucggcagug ccuucagcga uccagaacac gcuccagaac guccuggcag   6300
cugccacaaa aagaaauugc aaugucacgc aaaugagaga auugcccgua uuggauucgg   6360
cggccuuuaa uguggaaugc uucaagaaau augcguguaa uaaugaauau ugggaaacgu   6420
uuaaagaaaa ccccaucagg cuuacugaag aaaacguggu aaauuacauu accaaauuaa   6480
aaggaccaaa agcugcugcu cuuuuugcga agacacauaa uuugaauaug uugcaggaca   6540
uaccaaugga cagguuugua auggacuuaa agagagacgu gaaagugacu ccaggaacaa   6600
aacauacuga agaacggccc aagguacagg ugauccaggc ugccgauccg cuagcaacag   6660
cguaucugug cggaauccac cgagagcugg uuaggagauu aaaugcgguc cugcuuccga   6720
acauucauac acuguuugau augucggcug aagacuuuga cgcuauuaua gccgagcacu   6780
uccagccugg ggauugucuu cuggaaacug acaucgcguc guuugauaaa agugaggacg   6840
acgccauggc ucugaccgcg uuaaugauuc uggaagacuu agguguggac gcagagcugu   6900
ugacgcugau ugaggcggcu uucggcgaaa uuucaucaau acauuugccc acuaaaacua   6960
aauuuaaauu cggagccaug augaaaucug gaauguuccu cacacuguuu gugaacacag   7020
ucauuaacau uguaaucgca agcagagugu ugagagaacg gcuaaccgga ucaccaugug   7080
cagcauucau uggagaugac aauaucguga aaggagucaa aucggacaaa uuaauggcag   7140
acaggugcgc caccugguug aauauggaag ucaagauuau agaugcugug gugggcgaga   7200
aagcgccuua uuucugugga ggguuuauuu ugugugacuc cgugaccggc acagcgugcc   7260
guguggcaga cccccuaaaa aggcuguuua agcuuggcaa accucuggca gcagacgaug   7320
aacaugauga ugacaggaga agggcauugc augaagaguc aacacgcugg aaccgagugg   7380
guauucuuuc agagcugugc aaggcaguag aaucaaggua ugaaaccgua ggaacuucca   7440
ucauaguuau ggccaugacu acucuagcua gcaguguuaa aucauucagc uaccugagag   7500
gggccccuau aacucucuac ggcuaaccug aauggacuac gacauagucu aguccgccaa   7560
gucuagcaua uggccaccau guucguguuu cuggugcugc ugccucuggu guccagccag   7620
ugugugaacc ugaccaccag aacacagcug ccuccagccu acaccaacag cuuuaccaga   7680
ggcguguacu accccgacaa gguguucaga uccagcgugc ugcacucuac ccaggaccug   7740
uuccugccuu ucuucagcaa cgugaccugg uuccacgcca ucuccggcac caauggcacc   7800
aagagauucg acaaccccgu gcugcccuuc aacgacgggg uguacuuugc cagcaccgag   7860
aaguccaaca ucaucagagg cuggaucuuc ggcaccacac uggacagcaa gacccagagc   7920
cugcugaucg ugaacaacgc caccaacgug gucaucaaag ugugcgaguu ccaguucugc   7980
aacgaccccu uccugggcgu cuaccacaag aacaacaaga gcuggaugga aagcgaguuc   8040
cgggguguaca gcagcgccaa caacugcacc uucgaguacg ugucccagcc uuuccugaug   8100
gaccuggaag gcaagcaggg caacuucaag aaccugcgcg aguucguguu caagaacauc   8160
gacggcuacu ucaagaucua cagcaagcac accccuauca accucgugcg ggaucugccu   8220
cagggcuucu cugcucugga accccuggug gaucugccca ucggcaucaa caucacccgg   8280
uuucagacac ugcuggcccu gcacagaagc uaccugacac cuggcgauag cagcagcgga   8340
uggacagcug gugccgccgc uuacuaugug ggcuaccugc agccuagaac cuuccugcug   8400
aaguacaacg agaacggcac caucaccgac gccguggauu gugcccuuga uccucugagc   8460
gagacaaagu gcacccugaa guccuucacc guggaaaagg gcaucuacca gaccagcaac   8520
uuccgggugc agcccaccga auccaucgug cgguucccca auaucaccaa ucugugcccc   8580
```

-continued uucggcgagg uguucaaugc caccagauuc gccucugugu acgccuggaa ccggaagcgg 8640
aucagcaauu gcguggccga cuacuccgug cuguacaacu ccgccagcuu cagcaccuuc 8700
aagugcuacg gcgugucccc uaccaagcug aacgaccugu gcuucacaaa cguguacgcc 8760
gacagcuucg ugauccgggg agaugaagug cggcagauug ccccuggaca gacaggcaag 8820
aucgccgacu acaacuacaa gcugcccgac gacuucaccg gcugugugau ugccuggaac 8880
agcaacaacc uggacuccaa agucggcggc aacuacaauu accuguaccg gcuguuccgg 8940
aaguccaauc ugaagcccuu cgagcgggac aucuccaccg agaucuauca ggccggcagc 9000
accccuugua acggcgugaa aggcuucaac ugcuacuucc cacugcaguc cuacggcuuu 9060
cagcccacau auggcguggg cuaucagccc uacagagugg uggugcugag cuucgaacug 9120
cugcaugccc cugccacagu gugcggcccu aagaaaagca ccaaucucgu gaagaacaaa 9180
ugcgugaacu ucaacuucaa cggccugacc ggcacaggcg ugcugacaga gagcaacaag 9240
aaguuccugc cauuccagca guuuggccgg gauaucgacg auaccacaga cgccguuaga 9300
gauccccaga cacuggaaau ccuggacauc accccuugca gcuucggcgg agugucugug 9360
aucaccccug gcaccaacac cagcaaucag guggcagugc uguaccaggg cgugaacugu 9420
accgaagugc ccguggccau ucacgccgau cagcugacac cuacauggcg gguguacucc 9480
accggcagca auguguuuca gaccagagcc ggcugucuga ucggagccga gcacgugaac 9540
aauagcuacg agugcgacau ccccaucggc gcuggcaucu gugccagcua ccagacacag 9600
acaaacagcc acucucuggc cagcucugug gccagccaga gcaucauugc cuacacaaug 9660
ucucugggcg ccgagaacag cguggccuac uccaacaacu cuaucgcuau ccccaucaac 9720
uucaccauca gcgugaccac agagauccug ccugugucca ugaccaagac cagcguggac 9780
ugcaccaugu acaucugcgg cgauuccacc gagugcucca accugcugcu gcaguacggc 9840
agcuucugca cccagcugaa uagagcccug acagggaucg ccguggaaca ggacaagaac 9900
acccaagagg uguucgccca agugaagcag aucuacaaga ccccuccuau caaggacuuc 9960
ggcggcuuca auuucagcca gauucugccc gauccuagca agcccagcaa gcggagcccc 10020
aucgaggacc ugcuguucaa caaagugaca cuggccgacg ccggcuucau caagcaguau 10080
ggcgauuguc ugggcgacau ugccgccagg gaucugauuu gcgcccagaa guuuaacgga 10140
cugacagugc ugccuccucu gcugaccgau gagaugaucg cccaguacac aucugcccug 10200
cuggccggca caaucacaag cggcuggaca uuuggagcug gccccgcucu gcagaucccc 10260
uuuccuaugc agauggccua cagauucaac ggcaucggag ugacccagaa ugugcuguac 10320
gagaaccaga agcugaucgc caaccaguuc aacagcgcca ucggcaagau ccaggacagc 10380
cugagcagca caccaagcgc ccugggaaag cugcaggacg uggucaacca gaaugcccag 10440
gcacugaaca cccuggucaa gcagcugucc uccaacuucg gcgccaucag cucugugcug 10500
aacgauaucc uggccagacu ggacccuccu gaggccgagg ugcagaucga cagacugauc 10560
acaggcagac ugcagagccu ccagacauac gugacccagc agcugaucag agccgccgag 10620
auuagagccu cugccaaucu ggccgccacc aagaugucug agugugugcu gggccagagc 10680
aagagagugg acuuuugcgg caagggcuac caccugauga gcuucccuca gucugccccu 10740
cacggcgugg uguuucugca cgugacauac guucccgcuc aagagaagaa uuucaccacc 10800
gcuccagcca ucugccacga cggcaaagcc cacuuuccua gagaaggcgu guucgugucc 10860
aacggcaccc auugguucgu gacacagcgg aacuucuacg agccccagau caucaccacc 10920
cacaacaccu ucgugucugg caacugcgac gucgugaucg gcauugugaa caauaccgug 10980
uacgacccuc ugcagcccga gcuggacagc uucaaagagg aacuggacaa guacuuuaag 11040
aaccacacaa gccccgacgu ggaccugggc gauaucagcg gaaucaaugc cagcgucgug 11100
aacauccaga aagagaucga ccggcugaac gagguggcca agaaucugaa cgagagccug 11160
aucgaccugc aagaacuggg gaaguacgag caguacauca aguggcccug guacaucugg 11220
cugggcuuua ucgccggacu gauugccauc gugaugguca caaucaugcu guguugcaug 11280
accagcugcu guagcugccu gaagggcugu uguagcugug gcagcugcug caaguucgac 11340
gaggacgauu cugagcccgu gcugaagggc gugaaacugc acuacacaug agcggccgcg 11400
aauuggcaag cugcuuacau agaacucgcg gcgauuggca ugccgccuua aaauuuuuau 11460
uuuauuuuuc uuuucuuuuc cgaaucggau uuuguuuuua auauuucaaa aaaaaaaaaa 11520
aaaaaaaaaa aaaaaaaaaa aa 11542

<210> SEQ ID NO 64
<211> LENGTH: 11542
<212> TYPE: RNA
<213> ORGANISM: Artificial Sequence
<220> FEATURE:
<223> OTHER INFORMATION: Synthetised Sequence

<400> SEQUENCE: 64
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu ggccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucaugggggug uuguugggcu uuuagaaggc 1320
acaagauaac aucuauuuau aagcgcccgg auacccaaac caucaucaaa gugaacagcg 1380
auuuccacuc auucgugcug cccaggauag gcaguaacac auuggagauc gggcugagaa 1440

-continued caagaaucag gaaaauguua gaggagcaca aggagccguc accucucauu accgccgagg 1500
acguacaaga agcuaagugc gcagccgaug aggcuaagga ggugcgugaa gccgaggagu 1560
ugcgcgcagc ucuaccaccu uuggcagcug auguugagga gcccacucug gaggcagacg 1620
ucgacuugau guuacaagag gcuggggccg gcucagugga gacaccucgu ggcuugauaa 1680
agguuaccag cuacgauggc gaggacaaga ucggcucuua cgcugugcuu ucuccgcagg 1740
cuguacucaa gagugaaaaa uuaucuugca uccacccucu cgcugaacaa gucauaguga 1800
uaacacacuc uggccgaaaa gggcguuaug ccguggaacc auaccauggu aaaguagugg 1860
ugccagaggg acaugcaaua cccguccagg acuuucaagc ucugagugaa agugccacca 1920
uuguguacaa cgaacgugag uucguaaaca gguaccugca ccauauugcc acacauggag 1980
gagcgcugaa cacugaugaa gaauauuaca aaacugucaa gcccagcgag cacgacggcg 2040
aauaccugua cgacaucgac aggaaacagu gcgucaagaa agaacuaguc acugggcuag 2100
ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuaguggug agcgccaaga 2280
aagaaaacug ugcagaaauu auaagggacg ucaagaaaau gaaagggcug gacgucaaug 2340
ccagaacugu ggacucagug cucuugaaug gaugcaaaca ccccguagag acccuguaua 2400
uugacgaagc uuuugcuugu caugcaggua cucucagagc gcucauagcc auuauaagac 2460
cuaaaaaggc agugcucugc ggggauccca aacagugcgg uuuuuuuaac augaugugcc 2520
ugaaagugca uuuuaaccac gagauuugca cacaagucuu ccacaaaagc aucucucgcc 2580
guugcacuaa aucugugacu ucggucgucu caaccuuguu uuacgacaaa aaaaugagaa 2640
cgacgaaucc gaaagagacu aagauuguga uugacacuac cggcaguacc aaaccuaagc 2700
aggacgaucu cauucucacu uguuucagag ggugggugaa gcaguugcaa auagauuaca 2760
aaggcaacga aauaaugacg gcagcugccu cucaagggcu gacccguaaa ggugugguaug 2820 ccguucggua caaggugaau gaaaauccuc uguacgcacc caccucagaa caugugaacg 2880
uccuacugac ccgcacggag gaccgcaucg uguggaaaac acuagccggc gacccaugga 2940
uaaaaacacu gacugccaag uacccuggga auuucacugc cacgauagag gaguggcaag 3000
cagagcauga ugccaucaug aggcacaucu uggagagacc ggacccuacc gacgucuucc 3060
agaauaaggc aaacgugugu ugggccaagg cuuuagugcc ggugcugaag accgcuggca 3120
uagacaugac cacugaacaa uggaacacug uggauuauuu ugaaacggac aaagcucacu 3180
cagcagagau aguauugaac caacuaugcg ugagguucuu uggacucgau cuggacuccg 3240
gucuauuuuc ugcacccacu guuccguuau ccauuaggaa uaaucacugg gauaacuccc 3300
cgucgccuaa cauguacggg cugaauaaag aaguggucccg ucagcucucu cgcagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccugguggguc ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720 agcagugugua agaccaugcc auuaagcuua gcauguugac caagaaagcu ugucugcauc 3780

-continued ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauucuua caagcuuuca ucaaccuuga ccaacauuua uacagguucc agacuccacg 4020
aagccggaug ugcacccuca uaucaugugg ugcgagggga uauugccacg gccaccgaag 4080
gagugauuau aaaugcugcu aacagcaaag gacaaccugg cggaggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauagggguga 5640 uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180

-continued

```
cugccaguuu uugcccugca aagcugcgca gcuuuccaaa gaaacacucc uauuuggaac   6240
ccacaauacg aucggcagug ccuucagcga uccagaacac gcuccagaac guccuggcag   6300
cugccacaaa aagaaauugc aaugucacgc aaaugagaga auugcccgua uuggauucgg   6360
cggccuuuaa uguggaaugc uucaagaaau augcguguaa uaaugaauau ugggaaacgu   6420
uuaaagaaaa ccccaucagg cuuacugaag aaaacguggu aaauuacauu accaaauuaa   6480
aaggaccaaa agcugcugcu cuuuuugcga agacacauaa uuugaauaug uugcaggaca   6540
uaccaaugga cagguuugua auggacuuaa agagagacgu gaaagugacu ccaggaacaa   6600
aacauacuga agaacggccc aagguacagg ugauccaggc ugccgauccg cuagcaacag   6660
cguaucugug cggaauccac cgagagcugg uuaggagauu aaaugcgguc cugcuuccga   6720
acauucauac acuguuugau augucggcug aagacuuuga cgcuauuaua gccgagcacu   6780
uccagccugg ggauuguguu cuggaaacug acaucgcguc guuugauaaa agugaggacg   6840
acgccauggc ucugaccgcg uuaaugauuc uggaagacuu agguguggac gcagagcugu   6900
ugacgcugau ugaggcggcu uucggcgaaa uuucaucaau acauuugccc acuaaaacua   6960
aauuuaaauu cggagccaug augaaaucug gaauguuccu cacacuguuu gugaacacag   7020
ucauuaacau uguaaucgca agcagagugu ugagagaacg gcuaaccgga ucaccaugug   7080
cagcauucau uggagaugac aauaucguga aaggagucaa aucggacaaa uuaauggcag   7140
acaggugcgc caccugguug aauauggaag ucaagauuau agaugcugug gugggcgaga   7200
aagcgccuua uuucugugga ggguuuauuu ugugugacuc cgugaccggc acagcgugcc   7260
guguggcaga cccccuaaaa aggcuguuua agcuuggcaa accucuggca gcagacgaug   7320
aacaugauga ugacaggaga agggcauugc augaagaguc aacacgcugg aaccgagugg   7380
guauucuuuc agagcugugc aaggcaguag aaucaaggua ugaaaccgua ggaacuucca   7440
ucauaguuau ggccaugacu acucuagcua gcaguguuaa aucauucagc uaccugagag   7500
gggccccuau aacucucuac ggcuaaccug aauggacuac gacauagucu aguccgccaa   7560
gucuagcaua uggccaccau guucguguuu cuggugcugc ugccucuggu guccagccag   7620
ugugugaacu ucaccaccag aacacagcug ccuccagccu acaccaacag cuuuaccaga   7680
ggcguguacu accccgacaa gguguucaga uccagcgugc ugcacucuac ccaggaccug   7740
uuccugccuu ucuucagcaa cgugaccugg uuccacgcca uccacguguc cggcaccaau   7800
ggcaccaaga gauucgccaa ccccgugcug cccuucaacg acgggguggua cuuugccagc   7860
accgagaagu ccaacaucau cagaggcugg aucuucggca ccacacugga cagcaagacc   7920
cagagccugc ugaucgugaa caacgccacc aacgugguca ucaaagugug cgaguuccag   7980
uucugcaacg accccuuccu gggcgucuac uaccacaaga acaacaagag cuggauggaa   8040
agcgaguucc ggguguacag cagcgccaac aacugcaccu ucgaguacgu gucccagccu   8100
uuccugaugg accuggaagg caagcagggc aacuucaaga accugcgcga guucguguuc   8160
aagaacaucg acggcuacuu caagaucuac agcaagcaca ccccuaucaa ccucgugcgg   8220
ggucugccuc agggcuucuc ugcucuggaa ccccuggugg aucugcccau cggcaucaac   8280
aucacccggu uucagacacu gcacauaagc uaccugacac cuggcgauag cagcagcgga   8340
uggacagcug gugccgccgc uuacuaugug ggcuaccugc agccuagaac cuuccugcug   8400
aaguacaacg agaacggcac caucaccgac gccguggauu gugcccuuga uccucugagc   8460
gagacaaagu gcacccugaa guccuucacc guggaaaagg gcaucuacca gaccagcaac   8520
```

-continued

```
uuccgggugc agcccaccga auccaucgug cgguucccca auaucaccaa ucugugcccc   8580
uucggcgagg uguucaaugc caccagauuc gccucugugu acgccuggaa ccggaagcgg   8640
aucagcaauu gcguggccga cuacuccgug cuguacaacu ccgccagcuu cagcaccuuc   8700
aagugcuacg gcguguccc uaccaagcug aacgaccugu gcuucacaaa cguguacgcc   8760
gacagcuucg ugauccgggg agaugaagug cggcagauug ccccuggaca gacaggcaau   8820
aucgccgacu acaacuacaa gcugcccgac gacuucaccg gcugugugau ugccuggaac   8880
agcaacaacc uggacuccaa agucggcggc aacuacaauu accuguaccg gcuguuccgg   8940
aaguccaauc ugaagcccuu cgagcgggac aucuccaccg agaucuauca ggccggcagc   9000
accccuugua acggcgugaa aggcuucaac ugcuacuucc cacugcaguc cuacggcuuu   9060
cagcccacau auggcguggg cuaucagccc uacagagugg uggugcugag cuucgaacug   9120
cugcaugccc cugccacagu gugcggcccu aagaaaagca ccaaucucgu gaagaacaaa   9180
ugcgugaacu ucaacuucaa cggccugacc ggcacaggcg ugcugacaga gagcaacaag   9240
aaguuccugc cauuccagca guuuggccgg gauaucgccg auaccacaga cgccguuaga   9300
gauccccaga cacuggaaau ccuggacauc accccuugca gcuucggcgg agugucugug   9360
aucaccccug gcaccaacac cagcaaucag guggcagugc uguaccagga cgugaacugu   9420
accgaagugc ccguggccau ucacgccgau cagcugacac cuacauggcg gguguacucc   9480
accggcagca auguguuuca gaccagagcc ggcugucuga ucggagccga gcacgugaac   9540
aauagcuacg agugcgacau ccccaucggc gcuggcaucu gugccagcua ccagacacag   9600
acaaacagcc ccucucuggc cagcucugug gccagccaga gcaucauugc cuacacaaug   9660
ucucugggcg ucgagaacag cguggccuac uccaacaacu cuaucgcuau ccccaccaac   9720
uucaccauca gcgugaccac agagauccug ccugugucca ugaccaagac cagcguggac   9780
ugcaccaugu acaucugcgg cgauuccacc gagugcucca accugcugcu gcaguacggc   9840
agcuucugca cccagcugaa uagagcccug acagggaucg ccguggaaca ggacaagaac   9900
acccaagagg uguucgccca agugaagcag aucuacaaga ccccuccuau caaggacuuc   9960
ggcggcuuca auuucagcca gauucugccc gauccuagca agcccagcaa gcggagcccc  10020
aucgaggacc ugcuguucaa caaagugaca cuggccgacg ccggcuucau caagcaguau  10080
ggcgauuguc ugggcgacau ugccgccagg gaucugauuu gcgcccagaa guuuaacgga  10140
cugacagugc ugccuccucu gcugaccgau gagaugaucg cccaguacac aucugcccug  10200
cuggccggca caaucacaag cggcuggaca uuuggagcug gccccgcucu gcagaucccc  10260
uuuccuaugc agauggccua cagauucaac ggcaucggag ugacccagaa ugugcuguac  10320
gagaaccaga agcugaucgc caaccaguuc aacagcgcca ucggcaagau ccaggacagc  10380
cugagcagca caccaagcgc ccugggaaag cugcaggacg uggucaacca gaaugcccag  10440
gcacugaaca cccuggucaa gcagcugucc uccaacuucg gcgccaucag cucugugcug  10500
aacgauaucc ugagcagacu ggacccuccu gaggccgagg ugcagaucga cagacugauc  10560
acaggcagac ugcagagccu ccagacauac gugacccagc agcugaucag agccgccgag  10620
auuagagccu cugccaaucu ggccgccacc aagaugucug agugugugcu gggccagagc  10680
aagagagugg acuuuugcgg caagggcuac caccugauga gcuucccuca gucugcccu  10740
cacggcgugg uguuucugca cgugacauac guucccgcuc aagagaagaa uuucaccacc  10800
gcuccagcca ucugccacga cggcaaagcc cacuuuccua gagaaggcgu guucgugucc  10860
aacggcaccc auugguucgu gacacagcgg aacuucuacg agccccagau caucaccacc  10920
```

-continued gacaacaccu ucgugucugg caacugcgac gucgugaucg gcauugugaa caauaccgug 10980
uacgacccuc ugcagcccga gcuggacagc uucaaagagg aacuggacaa guacuuuaag 11040
aaccacacaa gccccgacgu ggaccugggc gauaucagcg gaaucaaugc cagcgucgug 11100
aacauccaga aagagaucga ccggcugaac gagguggcca agaaucugaa cgagagccug 11160
aucgaccugc aagaacuggg gaaguacgag caguacauca aguggcccug guacaucugg 11220
cugggcuuua ucgccggacu gauugccauc gugaugguca caaucaugcu guguugcaug 11280
accagcugcu guagcugccu gaagggcugu uguagcugug gcagcugcug caaguucgac 11340
gaggacgauu cugagcccgu gcugaagggc gugaaacugc acuacacaug agcggccgcg 11400
aauuggcaag cugcuuacau agaacucgcg gcgauuggca ugccgccuua aaauuuuuau 11460
uuuauuuuuc uuuucuuuuc cgaaucggau uuuguuuuua auauuucaaa aaaaaaaaaa 11520
aaaaaaaaaa aaaaaaaaaa aa 11542

<210> SEQ ID NO 65
<211> LENGTH: 11551
<212> TYPE: RNA
<213> ORGANISM: Artificial Sequence
<220> FEATURE:
<223> OTHER INFORMATION: Synthetised Sequence

<400> SEQUENCE: 65
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu ggccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucaugggggug uuguugggcu uuuagaaggc 1320
acaagauaac aucuauuuau aagcgcccgg auacccaaac caucaucaaa gugaacagcg 1380

-continued

```
auuuccacuc auucgugcug cccaggauag gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaggcagacg   1620
ucgacuugau guuacaagag gcuggggccg gcucagugga gacaccucgu ggcuugauaa   1680
agguuaccag cuacgauggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa ggugugua ug  2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aaguggucog ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuuucuuc auucgucagc aaauugaagg   3540
gcagaacugu ccuggugguc ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
agcagugug a agaccaugcc auuaagcuua gcauguugac caagaaagcu ugucugcauc   3780
```

-continued ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauucuua caagcuuuca ucaaccuuga ccaacauuua uacagguucc agacuccacg 4020
aagccggaug ugcacccuca uaucaugugg ugcgagggga uauugccacg gccaccgaag 4080
gagugauuau aaaugcugcu aacagcaaag gacaaccugg cggaggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccacccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauaggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120

-continued

```
uuauuccaga guacgaugcc uauuuggaca ugguugacgg agcuucaugc ugcuuagaca   6180

cugccaguuu uugcccugca aagcugcgca gcuuuccaaa gaaacacucc uauuuggaac   6240

ccacaauacg aucggcagug ccuucagcga uccagaacac gcuccagaac guccuggcag   6300

cugccacaaa aagaaauugc aaugucacgc aaaugagaga auugcccgua uuggauucgg   6360

cggccuuuaa uguggaaugc uucaagaaau augcguguaa uaaugaauau ugggaaacgu   6420

uuaaagaaaa ccccaucagg cuuacugaag aaaacguggu aaauuacauu accaaauuaa   6480

aaggaccaaa agcugcugcu cuuuuugcga agacacauaa uuugaauaug uugcaggaca   6540

uaccaaugga cagguuugua auggacuuaa agagagacgu gaaagugacu ccaggaacaa   6600

aacauacuga agaacggccc aagguacagg ugauccaggc ugccgauccg cuagcaacag   6660

cguaucugug cggaauccac cgagagcugg uuaggagauu aaaugcgguc cugcuuccga   6720

acauucauac acuguuugau augucggcug aagacuuuga cgcuauuaua gccgagcacu   6780

uccagccugg ggauuguguu cuggaaacug acaucgcguc guuugauaaa agugaggacg   6840

acgccauggc ucugaccgcg uuaaugauuc uggaagacuu aggugugggac gcagagcugu   6900

ugacgcugau ugaggcggcu uucggcgaaa uuucaucaau acauuugccc acuaaaacua   6960

aauuuaaauu cggagccaug augaaaucug gaauguuccu cacacuguuu gugaacacag   7020

ucauuaacau uguaaucgca agcagagugu ugagagaacg gcuaaccgga ucaccaugug   7080

cagcauucau uggagaugac aauaucguga aaggagucaa aucggacaaa uuaauggcag   7140

acaggugcgc caccugguug aauauggaag ucaagauuau agaugcugug gugggcgaga   7200

aagcgccuua uuucugugga ggguuuauuu ugugugacuc cgugaccggc acagcgugcc   7260

guguggcaga cccccuaaaa aggcuguuua agcuuggcaa accucuggca gcagacgaug   7320

aacaugauga ugacaggaga agggcauugc augaagaguc aacacgcugg aaccgagugg   7380

guauucuuuc agagcugugc aaggcaguag aaucaaggua ugaaaccgua ggaacuucca   7440

ucauaguuau ggccaugacu acucuagcua gcaguguuaa aucauucagc uaccugagag   7500

gggccccuau aacucucuac ggcuaaccug aauggacuac gacauagucu aguccgccaa   7560

gucuagcaua uggccaccau guucguguuu cuggugcugc ugccucuggu guccagccag   7620

ugugugaacu ucaccaacag aacacagcug ccuuucgccu acaccaacag cuuuaccaga   7680

ggcguguacu accccgacaa gguguucaga uccagcgugc ugcacucuac ccaggaccug   7740

uuccugccuu ucuucagcaa cgugaccugg uuccacgcca uccacguguc cggcaccaau   7800

ggcaccaaga gauucgacaa ccccgugcug cccuucaacg acgggggugua cuuugccagc   7860

accgagaagu ccaacaucau cagaggcugg aucuucggca ccacacugga cagcaagacc   7920

cagagccugc ugaucgugaa caacgccacc aacgugguca ucaaagugug cgaguuccag   7980

uucugcaacu accccuuccu gggcgucuac uaccacaaga acaacaagag cuggauggaa   8040

agcgaguucc ggguguacag cagcgccaac aacugcaccu ucgaguacgu gucccagccu   8100

uuccugaugg accuggaagg caagcagggc aacuucaaga accugagcga guucguguuc   8160

aagaacaucg acggcuacuu caagaucuac agcaagcaca ccccuaucaa ccucgugcgg   8220

gaucugccuc agggcuucuc ugcucuggaa ccccuggugg aucugcccau cggcaucaac   8280

aucacccggu uucagacacu gcuggcccug cacagaagcu accugacacc uggcgauagc   8340

agcagcggau ggacagcugg ugccgccgcu uacuaugugg gcuaccugca gccuagaacc   8400

uuccugcuga aguacaacga gaacggcacc aucaccgacg ccguggauug ugcccuugau   8460

ccucugagcg agacaaagug cacccugaag uccuucaccg uggaaaaggg caucuaccag   8520
```

-continued

```
accagcaacu uccgggugca gcccaccgaa uccaucgugc gguuccccaa uaucaccaau   8580
cugugccccu ucggcgaggu guucaaugcc accagauucg ccucugugua cgccuggaac   8640
cggaagcgga ucagcaauug cguggccgac uacuccgugc uguacaacuc cgccagcuuc   8700
agcaccuuca agugcuacgg cguguccccu accaagcuga acgaccugug cuucacaaac   8760
guguacgccg acagcuucgu gauccgggga gaugaagugc ggcagauugc cccuggacag   8820
acaggcacga ucgccgacua caacuacaag cugcccgacg acuucaccgg cugugugauu   8880
gccuggaaca gcaacaaccu ggacuccaaa gucggcggca acuacaauua ccuguaccgg   8940
cuguuccgga aguccaaucu gaagcccuuc gagcgggaca ucuccaccga gaucuaucag   9000
gccggcagca ccccuuguaa cggcgugaaa ggcuucaacu gcuacuuccc acugcagucc   9060
uacggcuuuc agcccacaua uggcgugggc uaucagcccu acagaguggu ggugcugagc   9120
uucgaacugc ugcaugcccc ugccacagug ugcggcccua agaaaagcac caaucucgug   9180
aagaacaaau gcgugaacuu caacuucaac ggccugaccg gcacaggcgu gcugacagag   9240
agcaacaaga aguuccugcc auuccagcag uuuggccggg auaucgccga uaccacagac   9300
gccguuagag auccccagac acuggaaauc cuggacauca ccccuugcag cuucggcgga   9360
gugucuguga ucaccccugg caccaacacc agcaaucagg uggcagugcu guaccagggc   9420
gugaacugua ccgaagugcc cguggccauu cacgccgauc agcugacacc uacauggcgg   9480
guguacucca ccggcagcaa uguguuucag accagagccg gcugucugau cggagccgag   9540
uacgugaaca auagcuacga gugcgacauc cccaucggcg cuggcaucug ugccagcuac   9600
cagacacaga caaacagccc cucucuggcc agcucugugg ccagccagag caucauugcc   9660
uacacaaugu cucugggcgc cgagaacagc guggccuacu ccaacaacuc uaucgcuauc   9720
cccaccaacu ucaccaucag cgugaccaca gagauccugc cuguguccau gaccaagacc   9780
agcguggacu gcaccaugua caucugcggc gauuccaccg agugcuccaa ccugcugcug   9840
caguacggca gcuucugcac ccagcugaau agagcccuga cagggaucgc cguggaacag   9900
gacaagaaca cccaagaggu guucgcccaa gugaagcaga ucuacaagac cccuccuauc   9960
aaggacuucg gcggcuucaa uuucagccag auucugcccg auccuagcaa gcccagcaag  10020
cggagcccca ucgaggaccu gcuguucaac aaagugacac uggccgacgc cggcuucauc  10080
aagcaguaug gcgauugucu gggcgacauu gccgccaggg aucugauuug cgcccagaag  10140
uuuaacggac ugacagugcu gccuccucug cugaccgaug agaugaucgc ccaguacaca  10200
ucugcccugc uggccggcac aaucacaagc ggcuggacau uuggagcugg ccccgcucug  10260
cagaucccu uuccuaugca gauggccuac agauucaacg gcaucggagu gacccagaau  10320
gugcuguacg agaaccagaa gcugaucgcc aaccaguuca acagcgccau cggcaagauc  10380
caggacagcc ugagcagcac accaagcgcc cugggaaagc ugcaggacgu ggucaaccag  10440
aaugcccagg cacugaacac ccuggucaag cagcuguccu ccaacuucgg cgccaucagc  10500
ucugugcuga acgauauccu gagcagacug gacccuccug aggccgaggu gcagaucgac  10560
agacugauca caggcagacu gcagagccuc cagacauacg ugacccagca gcugaucaga  10620
gccgccgaga uuagagccuc ugccaaucug gccgccauca agaugucuga gugugugcug  10680
ggccagagca agagagugga cuuuugcggc aagggcuacc accugaugag cuucccucag  10740
ucugccccuc acggcguggu guuucugcac gugacauacg uucccgcuca agagaagaau  10800
uucaccaccg cuccagccau cugccacgac ggcaaagccc acuuuccuag agaaggcgug  10860
```

-continued

```
uucgugucca acggcaccca uugguucgug acacagcgga acuucuacga gccccagauc    10920

aucaccaccg acaacaccuu cgugucuggc aacugcgacg ucgugaucgg cauugugaac    10980

aauaccgugu acgacccucu gcagcccgag cuggacagcu ucaaagagga acuggacaag    11040

uacuuuaaga accacacaag ccccgacgug gaccugggcg auaucagcgg aaucaaugcc    11100

agcuucguga acauccagaa agagaucgac cggcugaacg agguggccaa gaaucugaac    11160

gagagccuga ucgaccugca agaacugggg aaguacgagc aguacaucaa guggcccugg    11220

uacaucuggc ugggcuuuau cgccggacug auugccaucg ugauggucac aaucaugcug    11280

uguugcauga ccagcugcug uagcugccug aagggcuguu guagcugugg cagcugcugc    11340

aaguucgacg aggacgauuc ugagcccgug cugaagggcg ugaaacugca cuacacauga    11400

gcggccgcga auuggcaagc ugcuuacaua gaacucgcgg cgauuggcau gccgccuuaa    11460

aauuuuuauu uuauuuuucu uuucuuuucc gaaucggauu uuguuuuuaa uauuucaaaa    11520

aaaaaaaaaa aaaaaaaaaa aaaaaaaaaa a                                   11551

<210> SEQ ID NO 66
<211> LENGTH: 11956
<212> TYPE: RNA
<213> ORGANISM: Artificial Sequence
<220> FEATURE:
<223> OTHER INFORMATION: Synthetised Sequence

<400> SEQUENCE: 66

augggcggcg caugagagaa gcccagacca auuaccuacc caaaauggag aaaguucacg      60

uugacaucga ggaagacagc ccauuccuca gagcuuugca gcggagcuuc ccgcaguuug     120

agguagaagc caagcagguc acugauaaug accaugcuaa ugccagagcg uuuucgcauc     180

uggcuucaaa acugaucgaa acggaggugg acccauccga cacgauccuu gacauuggaa     240

gugcgcccgc ccgcagaaug uauucuaagc acaaguauca uuguaucugu ccgaugagau     300

gugcggaaga uccggacaga uuguauaagu augcaacuaa gcugaagaaa aacuguaagg     360

aaauaacuga uaaggaauug gacaagaaaa ugaaggagcu ggccgccguc augagcgacc     420

cugaccugga aacugagacu augugccucc acgacgacga gucgugucgc uacgaagggc     480

aagucgcugu uuaccaggau guauacgcgg uugacggacc gacaagucuc uaucaccaag     540

ccaauaaggg aguuagaguc gccuacugga uaggcuuuga caccacccccu uuuauguuua     600

agaacuuggc uggagcauau ccaucauacu cuaccaacug ggccgacgaa accguguuaa     660

cggcucguaa cauaggccua ugcagcucug acguuaugga gcggucacgu agagggaugu     720

ccauucuuag aaagaaguau uugaaaccau ccaacaaugu ucuauucucu guuggcucga     780

ccaucuacca cgagaagagg gacuuacuga ggagcuggca ccugccgucu guauuucacu     840

uacguggcaa gcaaaauuac acaugucggu gugagacuau aguuaguugc gacggguacg     900

ucguuaaaag aauagcuauc aguccaggcc uguaugggaa gccuucaggc uaugcugcua     960

cgaugcaccg cgagggauuc uugugcugca aagugacaga cacauugaac ggggagaggg    1020

ucucuuuucc cgugugcacg uaugugccag cuacauugug ugaccaaaug acuggcauac    1080

uggcaacaga ugucagugcg gacgacgcgc aaaaacugcu gguugggcuc aaccagcgua    1140

uagucgucaa cggucgcacc cagagaaaca ccaauaccau gaaaaauuac cuuuugcccg    1200

uaguggccca ggcauuugcu aggugggcaa aggaauauaa ggaagaucaa gaagaugaaa    1260

ggccacuagg acuacgagau agacaguuag ucauggggug uuguugggcu uuuagaaggc    1320

acaagauaac aucuauuuau aagcgcccgg auacccaaac caucaucaaa gugaacagcg    1380
```

auuuccacuc auucgugcug cccaggauag gcaguaacac auuggagauc gggcugagaa 1440
caagaaucag gaaaauguua gaggagcaca aggagccguc accucucauu accgccgagg 1500
acguacaaga agcuaagugc gcagccgaug aggcuaagga ggugcgugaa gccgaggagu 1560
ugcgcgcagc ucuaccaccu uuggcagcug auguugagga gcccacucug gaggcagacg 1620
ucgacuugau guuacaagag gcuggggccg gcucagugga gacaccucgu ggcuugauaa 1680
agguuaccag cuacgauggc gaggacaaga ucggcucuua cgcugugcuu ucuccgcagg 1740
cuguacucaa gagugaaaaa uuaucuugca uccacccucu cgcugaacaa gucauaguga 1800
uaacacacuc uggccgaaaa gggcguuaug ccguggaacc auaccauggu aaaguagugg 1860
ugccagaggg acaugcaaua cccguccagg acuuucaagc ucugagugaa agugccacca 1920
uuguguacaa cgaacgugag uucguaaaca gguaccugca ccauauugcc acacauggag 1980
gagcgcugaa cacugaugaa gaauauuaca aaacugucaa gcccagcgag cacgacggcg 2040
aauaccugua cgacaucgac aggaaacagu gcgucaagaa agaacuaguc acugggcuag 2100
ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuaguggug agcgccaaga 2280
aagaaaacug ugcagaaauu auaagggacg ucaagaaaau gaaagggcug gacgucaaug 2340
ccagaacugu ggacucagug cucuugaaug gaugcaaaca ccccguagag acccuguaua 2400
uugacgaagc uuuugcuugu caugcaggua cucucagagc gcucauagcc auuauaagac 2460
cuaaaaaggc agugcucugc ggggauccca aacagugcgg uuuuuuuaac augaugugcc 2520
ugaaagugca uuuuaaccac gagauuugca cacaagucuu ccacaaaagc aucucucgcc 2580
guugcacuaa aucugugacu ucggucgucu caaccuuguu uuacgacaaa aaaaugagaa 2640
cgacgaaucc gaaagagacu aagauuguga uugacacuac cggcaguacc aaaccuaagc 2700
aggacgaucu cauucucacu uguuucagag ggugggugaa gcaguugcaa auagauuaca 2760
aaggcaacga aauaaugacg gcagcugccu cucaagggcu gacccguaaa ggugugguaug 2820
ccguucggua caaggugaau gaaaauccuc uguacgcacc caccucagaa caugugaacg 2880
uccuacugac ccgcacggag gaccgcaucg uguggaaaac acuagccggc gacccaugga 2940
uaaaaacacu gacugccaag uacccuggga auuucacugc cacgauagag gaguggcaag 3000
cagagcauga ugccaucaug aggcacaucu uggagagacc ggacccuacc gacgucuucc 3060
agaauaaggc aaacgugugu ugggccaagg cuuuagugcc ggugcugaag accgcuggca 3120
uagacaugac cacugaacaa uggaacacug uggauuauuu ugaaacggac aaagcucacu 3180
cagcagagau aguauugaac caacuaugcg ugagguucuu uggacucgau cuggacuccg 3240
gucuauuuuc ugcacccacu guuccguuau ccauuaggaa uaaucacugg gauaacuccc 3300
cgucgccuaa cauguacggg cugaauaaag aaguggucog ucagcucucu cgcagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccuggugguc ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720
agcagugugu agaccaugcc auuaagcuua gcauguugac caagaaagcu ugucugcauc 3780
ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauucuua caagcuuuca ucaaccuuga ccaacauuua uacagguucc agacuccacg 4020
aagccggaug ugcacccuca uaucaugugg ugcgaggga uauugccacg gccaccgaag 4080
gagugauuau aaaugcugcu aacagcaaag gacaaccugg cggagggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauagggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu aggugugac gcagagcugu 6900 ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug guggggcgaga 7200 aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
gucuagcaua uggccaccau guucguguuu cuggugcugc ugccucuggu guccagccag 7620
ugugugaacc ugaccaccag aacacagcug ccuccagccu acaccaacag cuuuaccaga 7680
ggcguguacu accccgacaa gguguucaga uccagcgugc ugcacucuac ccaggaccug 7740
uuccugccuu ucuucagcaa cgugaccugg uuccacgcca uccacguguc cggcaccaau 7800
ggcaccaaga gauucgacaa ccccgugcug cccuucaacg acgggggugua cuuugccagc 7860 accgagaagu ccaacaucau cagaggcugg aucuucggca ccacacugga cagcaagacc 7920
cagagccugc ugaucgugaa caacgccacc aacgugguca ucaaagugug cgaguuccag 7980
uucugcaacg accccuuccu gggcgucuac uaccacaaga acaacaagag cuggauggaa 8040
agcgaguucc ggguguacag cagcgccaac aacugcaccu ucgaguacgu gucccagccu 8100
uuccugaugg accuggaagg caagcagggc aacuucaaga accugcgcga guucguguuc 8160
aagaacaucg acggcuacuu caagaucuac agcaagcaca ccccuaucaa ccucgugcgg 8220
gaucugccuc agggcuucuc ugcucuggaa ccccuggugg aucugcccau cggcaucaac 8280
aucacccggu uucagacacu gcuggcccug cacagaagcu accugacacc uggcgauagc 8340
agcagcggau ggacagcugg ugccgccgcu uacuaugugg gcuaccugca gccuagaacc 8400
uuccugcuga aguacaacga gaacggcacc aucaccgacg ccguggauug ugcccuugau 8460

-continued ccucugagcg agacaaagug cacccugaag uccuucaccg uggaaaaggg caucuaccag 8520
accagcaacu uccgggugca gcccaccgaa uccaucgugc gguuccccaa uaucaccaau 8580
cugugccccu ucggcgaggu guucaaugcc accagauucg ccucugugua cgccuggaac 8640
cggaagcgga ucagcaauug cguggccgac uacuccgugc uguacaacuc cgccagcuuc 8700
agcaccuuca agugcuacgg cguguccccu accaagcuga acgaccugug cuucacaaac 8760
guguacgccg acagcuucgu gauccgggga gaugaagugc ggcagauugc cccuggacag 8820
acaggcaaga ucgccgacua caacuacaag cugcccgacg acuucaccgg cugugugauu 8880
gccuggaaca gcaacaaccu ggacuccaaa gucggcggca acuacaauua ccuguaccgg 8940
cuguuccgga aguccaaucu gaagcccuuc gagcgggaca ucuccaccga gaucuaucag 9000
gccggcagca ccccuuguaa cggcguggaa ggcuucaacu gcuacuuccc acugcagucc 9060
uacggcuuuc agcccacaaa uggcgugggc uaucagcccu acagaguggu ggugcugagc 9120
uucgaacugc ugcaugcccc ugccacagug ugcggcccua agaaaagcac caaucucgug 9180
aagaacaaau gcgugaacuu caacuucaac ggccugaccg gcacaggcgu gcugacagag 9240
agcaacaaga aguuccugcc auuccagcag uuuggccggg auaucgccga uaccacagac 9300
gccguuagag auccccagac acuggaaauc cuggacauca ccccuugcag cuucggcgga 9360
gugucuguga ucaccccugg caccaacacc agcaaucagg uggcagugcu guaccaggac 9420
gugaacugua ccgaagugcc cguggccauu cacgccgauc agcugacacc uacauggcgg 9480
guguacucca ccggcagcaa uguguuucag accagagccg gcugucugau cggagccgag 9540
cacgugaaca auagcuacga gugcgacauc cccaucggcg cuggcaucug ugccagcuac 9600
cagacacaga caaacagccc cagacgggcc agaucugugg ccagccagag caucauugcc 9660
uacacaaugu cucugggcgc cgagaacagc guggccuacu ccaacaacuc uaucgcuauc 9720
cccaccaacu ucaccaucag cgugaccaca gagauccugc cuguguccau gaccaagacc 9780
agcguggacu gcaccaugua caucugcggc gauuccaccg agugcuccaa ccugcugcug 9840
caguacggca gcuucugcac ccagcugaau agagcccuga cagggaucgc cguggaacag 9900
gacaagaaca cccaagaggu guucgcccaa gugaagcaga ucuacaagac cccuccuauc 9960
aaggacuucg gcggcuucaa uuucagccag auucugcccg auccuagcaa gcccagcaag 10020
cggagcuuca ucgaggaccu gcuguucaac aaagugacac uggccgacgc cggcuucauc 10080
aagcaguaug gcgauugucu gggcgacauu gccgccaggg aucugauuug cgcccagaag 10140
uuuaacggac ugacagugcu gccuccucug cugaccgaug agaugaucgc ccaguacaca 10200
ucugcccugc uggccggcac aaucacaagc ggcuggacau uuggagcugg cgccgcucug 10260
cagaucccuu uugcuaugca gauggccuac agauucaacg gcaucggagu gacccagaau 10320
gugcuguacg agaaccagaa gcugaucgcc aaccaguuca acagcgccau cggcaagauc 10380
caggacagcc ugagcagcac agcaagcgcc cugggaaagc ugcaggacgu ggucaaccag 10440
aaugcccagg cacugaacac ccuggucaag cagcuguccu ccaacuucgg cgccaucagc 10500
ucugugcuga acgauauccu gagcagacug gacccuccug aggccgaggu gcagaucgac 10560
agacugauca caggcagacu gcagagccuc cagacauacg ugacccagca gcugaucaga 10620
gccgccgaga uuagagccuc ugccaaucug gccgccacca agaugucuga gugugugcug 10680
ggccagagca agagagugga cuuuugcggc aagggcuacc accugaugag cuucccucag 10740
ucugccccuc acggcguggu guuucugcac gugacauacg uucccgcuca agagaagaau 10800
uucaccaccg cuccagccau cugccacgac ggcaaagccc acuuuccuag agaaggcgug 10860

```
uucguguccca acggcaccca uugguucgug acacagcgga acuucuacga gccccagauc  10920

aucaccaccg acaacaccuu cgugucuggc aacugcgacg ucgugaucgg cauugugaac  10980

aauaccgugu acgacccucu gcagcccgag cuggacagcu ucaaagagga acuggacaag  11040

uacuuuaaga accacacaag ccccgacgug gaccugggcg auaucagcgg aaucaaugcc  11100

agcgucguga acauccagaa agagaucgac cggcugaacg agguggccaa gaaucugaac  11160

gagagccuga ucgaccugca agaacugggg aaguacgagc aguacaucaa guggcccugg  11220

uacaucuggc ugggcuuuau cgccggacug auugccaucg ugauggucac aaucaugcug  11280

uguugcauga ccagcugcug uagcugccug aagggcuguu guagcugugg cagcugcugc  11340

aaguucgacg aggacgauuc ugagcccgug cugaagggcg ugaaacugca cuacacagau  11400

cggagaaaga gaggcucugg cgaaggcaga ggcagccugc uuacaugugg cgacguggaa  11460

gagaaccccg gaccuaugga uuaugugucc cugcugaacc agauuuggca gaaguaccug  11520

aacagccccu acaccaccug ucuguacauc cccaagccua ccgccaagua cacaccucuc  11580

gugggcacau cucugcaccc cgugcugugg aauugccagc ugagcuuugc cggcuacacc  11640

gagucugccg ugaacagcac aaaggcccug gccaaacagg acgccgcuca gagaauugcc  11700

uggcugcugc acaaggaugg cggcaucccu gauggcugua gccuguaccu gagacacagc  11760

agccuguucg cccagagcga ggaagaggaa uccuucagca acugagcggc cgcgaauugg  11820

caagcugcuu acauagaacu cgcggcgauu ggcaugccgc cuuaaaauuu uuauuuuauu  11880

uuucuuuucu uuuccgaauc ggauuuuguu uuuaauauuu caaaaaaaaa aaaaaaaaaa  11940

aaaaaaaaaa aaaaaa                                                  11956
```

<210> SEQ ID NO 67
<211> LENGTH: 11542
<212> TYPE: DNA
<213> ORGANISM: Artificial Sequence
<220> FEATURE:
<223> OTHER INFORMATION: Synthetised Sequence

<400> SEQUENCE: 67

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct ggccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900
```

-continued

```
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
```

```
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
```

-continued

```
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aacccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tggccaccat gttcgtgttt ctggtgctgc tgcctctggt gtccagccag   7620
tgtgtgaacc tgaccaccag aacacagctg cctccagcct acaccaacag ctttaccaga   7680
ggcgtgtact accccgacaa ggtgttcaga tccagcgtgc tgcactctac ccaggacctg   7740
ttcctgcctt tcttcagcaa cgtgacctgg ttccacgcca tctccggcac caatggcacc   7800
aagagattcg acaaccccgt gctgcccttc aacgacgggg tgtactttgc cagcaccgag   7860
aagtccaaca tcatcagagg ctggatcttc ggcaccacac tggacagcaa gacccagagc   7920
ctgctgatcg tgaacaacgc caccaacgtg gtcatcaaag tgtgcgagtt ccagttctgc   7980
aacgacccct tcctgggcgt ctaccacaag aacaacaaga gctggatgga aagcgagttc   8040
```

cgggtgtaca gcagcgccaa caactgcacc ttcgagtacg tgtcccagcc tttcctgatg 8100
gacctggaag gcaagcaggg caacttcaag aacctgcgcg agttcgtgtt caagaacatc 8160
gacggctact tcaagatcta cagcaagcac acccctatca acctcgtgcg ggatctgcct 8220
cagggcttct ctgctctgga acccctggtg gatctgccca tcggcatcaa catcacccgg 8280
tttcagacac tgctggccct gcacagaagc tacctgacac ctggcgatag cagcagcgga 8340
tggacagctg gtgccgccgc ttactatgtg ggctacctgc agcctagaac cttcctgctg 8400
aagtacaacg agaacggcac catcaccgac gccgtggatt gtgcccttga tcctctgagc 8460
gagacaaagt gcaccctgaa gtccttcacc gtggaaaagg gcatctacca gaccagcaac 8520
ttccgggtgc agcccaccga atccatcgtg cggttcccca atatcaccaa tctgtgcccc 8580
ttcggcgagg tgttcaatgc caccagattc gcctctgtgt acgcctggaa ccggaagcgg 8640
atcagcaatt gcgtggccga ctactccgtg ctgtacaact ccgccagctt cagcaccttc 8700
aagtgctacg gcgtgtcccc taccaagctg aacgacctgt gcttcacaaa cgtgtacgcc 8760
gacagcttcg tgatccgggg agatgaagtg cggcagattg cccctggaca gacaggcaag 8820
atcgccgact acaactacaa gctgcccgac gacttcaccg gctgtgtgat tgcctggaac 8880
agcaacaacc tggactccaa agtcggcggc aactacaatt acctgtaccg gctgttccgg 8940
aagtccaatc tgaagccctt cgagcgggac atctccaccg agatctatca ggccggcagc 9000
acccccttgta acggcgtgga aggcttcaac tgctacttcc cactgcagtc ctacggcttt 9060
cagcccacat atggcgtggg ctatcagccc tacagagtgg tggtgctgag cttcgaactg 9120
ctgcatgccc ctgccacagt gtgcggccct aagaaaagca ccaatctcgt gaagaacaaa 9180
tgcgtgaact tcaacttcaa cggcctgacc ggcacaggcg tgctgacaga gagcaacaag 9240
aagttcctgc cattccagca gtttggccgg gatatcgacg ataccacaga cgccgttaga 9300
gatccccaga cactggaaat cctggacatc accccttgca gcttcggcgg agtgtctgtg 9360
atcacccctg gcaccaacac cagcaatcag gtggcagtgc tgtaccaggg cgtgaactgt 9420
accgaagtgc ccgtggccat tcacgccgat cagctgacac ctacatggcg ggtgtactcc 9480
accggcagca atgtgtttca gaccagagcc ggctgtctga tcggagccga gcacgtgaac 9540
aatagctacg agtgcgacat ccccatcggc gctggcatct gtgccagcta ccagacacag 9600
acaaacagcc actctctggc cagctctgtg gccagccaga gcatcattgc ctacacaatg 9660
tctctgggcg ccgagaacag cgtggcctac tccaacaact ctatcgctat ccccatcaac 9720
ttcaccatca gcgtgaccac agagatcctg cctgtgtcca tgaccaagac cagcgtggac 9780
tgcaccatgt acatctgcgg cgattccacc gagtgctcca acctgctgct gcagtacggc 9840
agcttctgca cccagctgaa tagagccctg acagggatcg ccgtggaaca ggacaagaac 9900
acccaagagg tgttcgccca agtgaagcag atctacaaga cccctcctat caaggacttc 9960
ggcggcttca atttcagcca gattctgccc gatcctagca agcccagcaa gcggagcccc 10020
atcgaggacc tgctgttcaa caaagtgaca ctggccgacg ccggcttcat caagcagtat 10080
ggcgattgtc tgggcgacat tgccgccagg gatctgattt gcgcccagaa gtttaacgga 10140
ctgacagtgc tgcctcctct gctgaccgat gagatgatcg cccagtacac atctgccctg 10200
ctggccggca caatcacaag cggctggaca tttggagctg gccccgctct gcagatcccc 10260
tttcctatgc agatggccta cagattcaac ggcatcggag tgacccagaa tgtgctgtac 10320
gagaaccaga agctgatcgc caaccagttc aacagcgcca tcggcaagat ccaggacagc 10380

```
ctgagcagca caccaagcgc cctgggaaag ctgcaggacg tggtcaacca gaatgcccag  10440
gcactgaaca ccctggtcaa gcagctgtcc tccaacttcg gcgccatcag ctctgtgctg  10500
aacgatatcc tggccagact ggaccctcct gaggccgagg tgcagatcga cagactgatc  10560
acaggcagac tgcagagcct ccagacatac gtgacccagc agctgatcag agccgccgag  10620
attagagcct ctgccaatct ggccgccacc aagatgtctg agtgtgtgct gggccagagc  10680
aagagagtgg acttttgcgg caagggctac cacctgatga gcttccctca gtctgcccct  10740
cacggcgtgg tgtttctgca cgtgacatac gttcccgctc aagagaagaa tttcaccacc  10800
gctccagcca tctgccacga cggcaaagcc cactttccta gagaaggcgt gttcgtgtcc  10860
aacggcaccc attggttcgt gacacagcgg aacttctacg agccccagat catcaccacc  10920
cacaacacct tcgtgtctgg caactgcgac gtcgtgatcg gcattgtgaa caataccgtg  10980
tacgaccctc tgcagcccga gctggacagc ttcaaagagg aactggacaa gtactttaag  11040
aaccacacaa gccccgacgt ggacctgggc gatatcagcg gaatcaatgc cagcgtcgtg  11100
aacatccaga aagagatcga ccggctgaac gaggtggcca agaatctgaa cgagagcctg  11160
atcgacctgc aagaactggg gaagtacgag cagtacatca agtggccctg gtacatctgg  11220
ctgggcttta tcgccggact gattgccatc gtgatggtca caatcatgct gtgttgcatg  11280
accagctgct gtagctgcct gaagggctgt tgtagctgtg gcagctgctg caagttcgac  11340
gaggacgatt ctgagcccgt gctgaagggc gtgaaactgc actacacatg agcggccgcg  11400
aattggcaag ctgcttacat agaactcgcg gcgattggca tgccgcctta aaatttttat  11460
tttatttttc ttttcttttc cgaatcggat tttgttttta atatttcaaa aaaaaaaaaa  11520
aaaaaaaaaa aaaaaaaaaa aa                                            11542
```

<210> SEQ ID NO 68
<211> LENGTH: 11542
<212> TYPE: DNA
<213> ORGANISM: Artificial Sequence
<220> FEATURE:
<223> OTHER INFORMATION: Synthetised Sequence

<400> SEQUENCE: 68

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa catagggcta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
```

```
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
```

-continued

```
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
```

ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gtctagcata tggccaccat gttcgtgttt ctggtgctgc tgcctctggt gtccagccag 7620
tgtgtgaacc tgaccaccag aacacagctg cctccagcct acaccaacag ctttaccaga 7680
ggcgtgtact accccgacaa ggtgttcaga tccagcgtgc tgcactctac ccaggacctg 7740
ttcctgcctt tcttcagcaa cgtgacctgg ttccacgcca tctccggcac caatggcacc 7800
aagagattcg acaaccccgt gctgcccttc aacgacgggg tgtactttgc cagcaccgag 7860
aagtccaaca tcatcagagg ctggatcttc ggcaccacac tggacagcaa gacccagagc 7920
ctgctgatcg tgaacaacgc caccaacgtg gtcatcaaag tgtgcgagtt ccagttctgc 7980

-continued

```
aacgacccct tcctgggcgt ctaccacaag aacaacaaga gctggatgga aagcgagttc   8040
cgggtgtaca gcagcgccaa caactgcacc ttcgagtacg tgtcccagcc tttcctgatg   8100
gacctggaag gcaagcaggg caacttcaag aacctgcgcg agttcgtgtt caagaacatc   8160
gacggctact tcaagatcta cagcaagcac acccctatca acctcgtgcg ggatctgcct   8220
cagggcttct ctgctctgga acccctggtg gatctgccca tcggcatcaa catcacccgg   8280
tttcagacac tgctggccct gcacagaagc tacctgacac ctggcgatag cagcagcgga   8340
tggacagctg gtgccgccgc ttactatgtg ggctacctgc agcctagaac cttcctgctg   8400
aagtacaacg agaacggcac catcaccgac gccgtggatt gtgcccttga tcctctgagc   8460
gagacaaagt gcaccctgaa gtccttcacc gtggaaaagg gcatctacca gaccagcaac   8520
ttccgggtgc agcccaccga atccatcgtg cggttcccca atatcaccaa tctgtgcccc   8580
ttcggcgagg tgttcaatgc caccagattc gcctctgtgt acgcctggaa ccggaagcgg   8640
atcagcaatt gcgtggccga ctactccgtg ctgtacaact ccgccagctt cagcaccttc   8700
aagtgctacg gcgtgtcccc taccaagctg aacgacctgt gcttcacaaa cgtgtacgcc   8760
gacagcttcg tgatccgggg agatgaagtg cggcagattg cccctggaca gacaggcaag   8820
atcgccgact acaactacaa gctgcccgac gacttcaccg gctgtgtgat tgcctggaac   8880
agcaacaacc tggactccaa agtcggcggc aactacaatt acctgtaccg gctgttccgg   8940
aagtccaatc tgaagccctt cgagcgggac atctccaccg agatctatca ggccggcagc   9000
accccttgta acggcgtgaa aggcttcaac tgctacttcc cactgcagtc ctacggcttt   9060
cagcccacat atggcgtggg ctatcagccc tacagagtgg tggtgctgag cttcgaactg   9120
ctgcatgccc ctgccacagt gtgcggccct aagaaaagca ccaatctcgt gaagaacaaa   9180
tgcgtgaact tcaacttcaa cggcctgacc ggcacaggcg tgctgacaga gagcaacaag   9240
aagttcctgc cattccagca gtttggccgg gatatcgacg ataccacaga cgccgttaga   9300
gatccccaga cactggaaat cctggacatc accccttgca gcttcggcgg agtgtctgtg   9360
atcacccctg gcaccaacac cagcaatcag gtggcagtgc tgtaccaggg cgtgaactgt   9420
accgaagtgc ccgtggccat tcacgccgat cagctgacac ctacatggcg ggtgtactcc   9480
accggcagca atgtgtttca gaccagagcc ggctgtctga tcggagccga gcacgtgaac   9540
aatagctacg agtgcgacat ccccatcggc gctggcatct gtgccagcta ccagacacag   9600
acaaacagcc actctctggc cagctctgtg gccagccaga gcatcattgc ctacacaatg   9660
tctctgggcg ccgagaacag cgtggcctac tccaacaact ctatcgctat ccccatcaac   9720
ttcaccatca gcgtgaccac agagatcctg cctgtgtcca tgaccaagac cagcgtggac   9780
tgcaccatgt acatctgcgg cgattccacc gagtgctcca acctgctgct gcagtacggc   9840
agcttctgca cccagctgaa tagagccctg acagggatcg ccgtggaaca ggacaagaac   9900
acccaagagg tgttcgccca agtgaagcag atctacaaga cccctcctat caaggacttc   9960
ggcggcttca atttcagcca gattctgccc gatcctagca agcccagcaa gcggagcccc  10020
atcgaggacc tgctgttcaa caaagtgaca ctggccgacg ccggcttcat caagcagtat  10080
ggcgattgtc tgggcgacat tgccgccagg gatctgattt gcgcccagaa gtttaacgga  10140
ctgacagtgc tgcctcctct gctgaccgat gagatgatcg cccagtacac atctgccctg  10200
ctggccggca caatcacaag cggctggaca tttggagctg gccccgctct gcagatcccc  10260
tttcctatgc agatggccta cagattcaac ggcatcggag tgacccagaa tgtgctgtac  10320
gagaaccaga agctgatcgc caaccagttc aacagcgcca tcggcaagat ccaggacagc  10380
```

ctgagcagca caccaagcgc cctgggaaag ctgcaggacg tggtcaacca gaatgcccag 10440
gcactgaaca ccctggtcaa gcagctgtcc tccaacttcg gcgccatcag ctctgtgctg 10500
aacgatatcc tggccagact ggaccctcct gaggccgagg tgcagatcga cagactgatc 10560
acaggcagac tgcagagcct ccagacatac gtgacccagc agctgatcag agccgccgag 10620
attagagcct ctgccaatct ggccgccacc aagatgtctg agtgtgtgct gggccagagc 10680
aagagagtgg acttttgcgg caagggctac cacctgatga gcttccctca gtctgcccct 10740
cacggcgtgg tgtttctgca cgtgacatac gttcccgctc aagagaagaa tttcaccacc 10800
gctccagcca tctgccacga cggcaaagcc cactttccta gagaaggcgt gttcgtgtcc 10860
aacggcaccc attggttcgt gacacagcgg aacttctacg agccccagat catcaccacc 10920
cacaacacct tcgtgtctgg caactgcgac gtcgtgatcg gcattgtgaa caataccgtg 10980
tacgaccctc tgcagcccga gctggacagc ttcaaagagg aactggacaa gtactttaag 11040
aaccacacaa gccccgacgt ggacctgggc gatatcagcg gaatcaatgc cagcgtcgtg 11100
aacatccaga aagagatcga ccggctgaac gaggtggcca agaatctgaa cgagagcctg 11160
atcgacctgc aagaactggg gaagtacgag cagtacatca agtggccctg gtacatctgg 11220
ctgggcttta tcgccggact gattgccatc gtgatggtca caatcatgct gtgttgcatg 11280
accagctgct gtagctgcct gaagggctgt tgtagctgtg gcagctgctg caagttcgac 11340
gaggacgatt ctgagcccgt gctgaagggc gtgaaactgc actacacatg agcggccgcg 11400
aattggcaag ctgcttacat agaactcgcg gcgattggca tgccgcctta aaatttttat 11460
tttatttttc ttttcttttc cgaatcggat tttgttttta atatttcaaa aaaaaaaaaa 11520
aaaaaaaaaa aaaaaaaaaa aa 11542

<210> SEQ ID NO 69
<211> LENGTH: 11542
<212> TYPE: DNA
<213> ORGANISM: Artificial Sequence
<220> FEATURE:
<223> OTHER INFORMATION: Synthetised Sequence

<400> SEQUENCE: 69
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct ggccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaggcagacg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg ttttttaac atgatgtgcc 2520 tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaattctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580

-continued ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gtctagcata tggccaccat gttcgtgttt ctggtgctgc tgcctctggt gtccagccag 7620
tgtgtgaact tcaccaccag aacacagctg cctccagcct acaccaacag ctttaccaga 7680
ggcgtgtact accccgacaa ggtgttcaga tccagcgtgc tgcactctac ccaggacctg 7740
ttcctgcctt tcttcagcaa cgtgacctgg ttccacgcca tccacgtgtc cggcaccaat 7800
ggcaccaaga gattcgccaa ccccgtgctg cccttcaacg acggggtgta ctttgccagc 7860
accgagaagt ccaacatcat cagaggctgg atcttcggca ccacactgga cagcaagacc 7920
cagagcctgc tgatcgtgaa caacgccacc aacgtggtca tcaaagtgtg cgagttccag 7980

-continued

```
ttctgcaacg accccttcct gggcgtctac taccacaaga acaacaagag ctggatggaa   8040
agcgagttcc gggtgtacag cagcgccaac aactgcacct tcgagtacgt gtcccagcct   8100
ttcctgatgg acctggaagg caagcagggc aacttcaaga acctgcgcga gttcgtgttc   8160
aagaacatcg acggctactt caagatctac agcaagcaca cccctatcaa cctcgtgcgg   8220
ggtctgcctc agggcttctc tgctctggaa cccctggtgg atctgcccat cggcatcaac   8280
atcacccggt ttcagacact gcacataagc tacctgacac ctggcgatag cagcagcgga   8340
tggacagctg gtgccgccgc ttactatgtg ggctacctgc agcctagaac cttcctgctg   8400
aagtacaacg agaacggcac catcaccgac gccgtggatt gtgcccttga tcctctgagc   8460
gagacaaagt gcaccctgaa gtccttcacc gtggaaaagg gcatctacca gaccagcaac   8520
ttccgggtgc agcccaccga atccatcgtg cggttcccca atatcaccaa tctgtgcccc   8580
ttcggcgagg tgttcaatgc caccagattc gcctctgtgt acgcctggaa ccggaagcgg   8640
atcagcaatt gcgtggccga ctactccgtg ctgtacaact ccgccagctt cagcaccttc   8700
aagtgctacg gcgtgtcccc taccaagctg aacgacctgt gcttcacaaa cgtgtacgcc   8760
gacagcttcg tgatccgggg agatgaagtg cggcagattg cccctggaca gacaggcaat   8820
atcgccgact acaactacaa gctgcccgac gacttcaccg gctgtgtgat tgcctggaac   8880
agcaacaacc tggactccaa agtcggcggc aactacaatt acctgtaccg gctgttccgg   8940
aagtccaatc tgaagccctt cgagcgggac atctccaccg agatctatca ggccggcagc   9000
accccttgta acggcgtgaa aggcttcaac tgctacttcc cactgcagtc ctacggcttt   9060
cagcccacat atggcgtggg ctatcagccc tacagagtgg tggtgctgag cttcgaactg   9120
ctgcatgccc ctgccacagt gtgcggccct aagaaaagca ccaatctcgt gaagaacaaa   9180
tgcgtgaact tcaacttcaa cggcctgacc ggcacaggcg tgctgacaga gagcaacaag   9240
aagttcctgc cattccagca gtttggccgg gatatcgccg ataccacaga cgccgttaga   9300
gatccccaga cactggaaat cctggacatc accccttgca gcttcggcgg agtgtctgtg   9360
atcacccctg gcaccaacac cagcaatcag gtggcagtgc tgtaccagga cgtgaactgt   9420
accgaagtgc ccgtggccat tcacgccgat cagctgacac ctacatggcg ggtgtactcc   9480
accggcagca atgtgtttca gaccagagcc ggctgtctga tcggagccga gcacgtgaac   9540
aatagctacg agtgcgacat ccccatcggc gctggcatct gtgccagcta ccagacacag   9600
acaaacagcc cctctctggc cagctctgtg gccagccaga gcatcattgc ctacacaatg   9660
tctctgggcg tcgagaacag cgtggcctac tccaacaact ctatcgctat ccccaccaac   9720
ttcaccatca gcgtgaccac agagatcctg cctgtgtcca tgaccaagac cagcgtggac   9780
tgcaccatgt acatctgcgg cgattccacc gagtgctcca acctgctgct gcagtacggc   9840
agcttctgca cccagctgaa tagagccctg acagggatcg ccgtggaaca ggacaagaac   9900
acccaagagg tgttcgccca agtgaagcag atctacaaga cccctcctat caaggacttc   9960
ggcggcttca atttcagcca gattctgccc gatcctagca agcccagcaa gcggagcccc  10020
atcgaggacc tgctgttcaa caaagtgaca ctggccgacg ccggcttcat caagcagtat  10080
ggcgattgtc tgggcgacat tgccgccagg gatctgattt gcgcccagaa gtttaacgga  10140
ctgacagtgc tgcctcctct gctgaccgat gagatgatcg cccagtacac atctgccctg  10200
ctggccggca caatcacaag cggctggaca tttggagctg gccccgctct gcagatcccc  10260
tttcctatgc agatggccta cagattcaac ggcatcggag tgacccagaa tgtgctgtac  10320
```

-continued gagaaccaga agctgatcgc caaccagttc aacagcgcca tcggcaagat ccaggacagc 10380
ctgagcagca caccaagcgc cctgggaaag ctgcaggacg tggtcaacca gaatgcccag 10440
gcactgaaca ccctggtcaa gcagctgtcc tccaacttcg gcgccatcag ctctgtgctg 10500
aacgatatcc tgagcagact ggaccctcct gaggccgagg tgcagatcga cagactgatc 10560
acaggcagac tgcagagcct ccagacatac gtgacccagc agctgatcag agccgccgag 10620
attagagcct ctgccaatct ggccgccacc aagatgtctg agtgtgtgct gggccagagc 10680
aagagagtgg acttttgcgg caagggctac cacctgatga gcttccctca gtctgcccct 10740
cacggcgtgg tgtttctgca cgtgacatac gttcccgctc aagagaagaa tttcaccacc 10800
gctccagcca tctgccacga cggcaaagcc cactttccta gagaaggcgt gttcgtgtcc 10860
aacggcaccc attggttcgt gacacagcgg aacttctacg agccccagat catcaccacc 10920
gacaacacct tcgtgtctgg caactgcgac gtcgtgatcg gcattgtgaa caataccgtg 10980
tacgaccctc tgcagcccga gctggacagc ttcaaagagg aactggacaa gtactttaag 11040
aaccacacaa gccccgacgt ggacctgggc gatatcagcg gaatcaatgc cagcgtcgtg 11100
aacatccaga aagagatcga ccggctgaac gaggtggcca agaatctgaa cgagagcctg 11160
atcgacctgc aagaactggg gaagtacgag cagtacatca agtggccctg gtacatctgg 11220
ctgggcttta tcgccggact gattgccatc gtgatggtca caatcatgct gtgttgcatg 11280
accagctgct gtagctgcct gaagggctgt tgtagctgtg gcagctgctg caagttcgac 11340
gaggacgatt ctgagcccgt gctgaagggc gtgaaactgc actacacatg agcggccgcg 11400
aattggcaag ctgcttacat agaactcgcg gcgattggca tgccgcctta aaatttttat 11460
tttatttttc ttttcttttc cgaatcggat tttgttttta atatttcaaa aaaaaaaaaa 11520
aaaaaaaaaa aaaaaaaaaa aa 11542

<210> SEQ ID NO 70
<211> LENGTH: 11551
<212> TYPE: DNA
<213> ORGANISM: Artificial Sequence
<220> FEATURE:
<223> OTHER INFORMATION: Synthetised Sequence

<400> SEQUENCE: 70
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct ggccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840

-continued

```
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
```

-continued

```
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
```

-continued

```
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tggccaccat gttcgtgttt ctggtgctgc tgcctctggt gtccagccag   7620
tgtgtgaact tcaccaacag aacacagctg cctttcgcct acaccaacag ctttaccaga   7680
ggcgtgtact accccgacaa ggtgttcaga tccagcgtgc tgcactctac ccaggacctg   7740
ttcctgcctt tcttcagcaa cgtgacctgg ttccacgcca tccacgtgtc cggcaccaat   7800
ggcaccaaga gattcgacaa ccccgtgctg cccttcaacg acggggtgta ctttgccagc   7860
accgagaagt ccaacatcat cagaggctgg atcttcggca ccacactgga cagcaagacc   7920
```

-continued

```
cagagcctgc tgatcgtgaa caacgccacc aacgtggtca tcaaagtgtg cgagttccag   7980
ttctgcaact acccccttcct gggcgtctac taccacaaga acaacaagag ctggatggaa   8040
agcgagttcc gggtgtacag cagcgccaac aactgcacct tcgagtacgt gtcccagcct   8100
ttcctgatgg acctggaagg caagcagggc aacttcaaga acctgagcga gttcgtgttc   8160
aagaacatcg acggctactt caagatctac agcaagcaca cccctatcaa cctcgtgcgg   8220
gatctgcctc agggcttctc tgctctggaa cccctggtgg atctgcccat cggcatcaac   8280
atcacccggt ttcagacact gctggccctg cacagaagct acctgacacc tggcgatagc   8340
agcagcggat ggacagctgg tgccgccgct tactatgtgg gctacctgca gcctagaacc   8400
ttcctgctga agtacaacga gaacggcacc atcaccgacg ccgtggattg tgcccttgat   8460
cctctgagcg agacaaagtg caccctgaag tccttcaccg tggaaaaggg catctaccag   8520
accagcaact tccgggtgca gcccaccgaa tccatcgtgc ggttccccaa tatcaccaat   8580
ctgtgcccct tcggcgaggt gttcaatgcc accagattcg cctctgtgta cgcctggaac   8640
cggaagcgga tcagcaattg cgtggccgac tactccgtgc tgtacaactc cgccagcttc   8700
agcaccttca agtgctacgg cgtgtcccct accaagctga acgacctgtg cttcacaaac   8760
gtgtacgccg acagcttcgt gatccgggga gatgaagtgc ggcagattgc ccctggacag   8820
acaggcacga tcgccgacta caactacaag ctgcccgacg acttcaccgg ctgtgtgatt   8880
gcctggaaca gcaacaacct ggactccaaa gtcggcggca actacaatta cctgtaccgg   8940
ctgttccgga agtccaatct gaagcccttc gagcgggaca tctccaccga gatctatcag   9000
gccggcagca ccccttgtaa cggcgtgaaa ggcttcaact gctacttccc actgcagtcc   9060
tacggctttc agcccacata tggcgtgggc tatcagccct acagagtggt ggtgctgagc   9120
ttcgaactgc tgcatgcccc tgccacagtg tgcggcccta agaaaagcac caatctcgtg   9180
aagaacaaat gcgtgaactt caacttcaac ggcctgaccg gcacaggcgt gctgacagag   9240
agcaacaaga agttcctgcc attccagcag tttggccggg atatcgccga taccacagac   9300
gccgttagag atccccagac actggaaatc ctggacatca ccccttgcag cttcggcgga   9360
gtgtctgtga tcacccctgg caccaacacc agcaatcagg tggcagtgct gtaccagggc   9420
gtgaactgta ccgaagtgcc cgtggccatt cacgccgatc agctgacacc tacatggcgg   9480
gtgtactcca ccggcagcaa tgtgtttcag accagagccg gctgtctgat cggagccgag   9540
tacgtgaaca atagctacga gtgcgacatc cccatcggcg ctggcatctg tgccagctac   9600
cagacacaga caaacagccc ctctctggcc agctctgtgg ccagccagag catcattgcc   9660
tacacaatgt ctctgggcgc cgagaacagc gtggcctact ccaacaactc tatcgctatc   9720
cccaccaact tcaccatcag cgtgaccaca gagatcctgc ctgtgtccat gaccaagacc   9780
agcgtggact gcaccatgta catctgcggc gattccaccg agtgctccaa cctgctgctg   9840
cagtacggca gcttctgcac ccagctgaat agagccctga cagggatcgc cgtggaacag   9900
gacaagaaca cccaagaggt gttcgcccaa gtgaagcaga tctacaagac ccctcctatc   9960
aaggacttcg gcggcttcaa tttcagccag attctgcccg atcctagcaa gcccagcaag  10020
cggagcccca tcgaggacct gctgttcaac aaagtgacac tggccgacgc cggcttcatc  10080
aagcagtatg gcgattgtct gggcgacatt gccgccaggg atctgatttg cgcccagaag  10140
tttaacggac tgacagtgct gcctcctctg ctgaccgatg agatgatcgc ccagtacaca  10200
tctgccctgc tggccggcac aatcacaagc ggctggacat ttggagctgg ccccgctctg  10260
cagatcccct ttcctatgca gatggcctac agattcaacg gcatcggagt gacccagaat  10320
```

```
gtgctgtacg agaaccagaa gctgatcgcc aaccagttca acagcgccat cggcaagatc  10380
caggacagcc tgagcagcac accaagcgcc ctgggaaagc tgcaggacgt ggtcaaccag  10440
aatgcccagg cactgaacac cctggtcaag cagctgtcct ccaacttcgg cgccatcagc  10500
tctgtgctga acgatatcct gagcagactg gaccctcctg aggccgaggt gcagatcgac  10560
agactgatca caggcagact gcagagcctc cagacatacg tgacccagca gctgatcaga  10620
gccgccgaga ttagagcctc tgccaatctg gccgccatca agatgtctga gtgtgtgctg  10680
ggccagagca agagagtgga cttttgcggc aagggctacc acctgatgag cttccctcag  10740
tctgcccctc acggcgtggt gtttctgcac gtgacatacg ttcccgctca agagaagaat  10800
ttcaccaccg ctccagccat ctgccacgac ggcaaagccc actttcctag agaaggcgtg  10860
ttcgtgtcca acggcaccca ttggttcgtg acacagcgga acttctacga gccccagatc  10920
atcaccaccg acaacacctt cgtgtctggc aactgcgacg tcgtgatcgg cattgtgaac  10980
aataccgtgt acgaccctct gcagcccgag ctggacagct tcaaagagga actggacaag  11040
tactttaaga accacacaag ccccgacgtg gacctgggcg atatcagcgg aatcaatgcc  11100
agcttcgtga acatccagaa agagatcgac cggctgaacg aggtggccaa gaatctgaac  11160
gagagcctga tcgacctgca agaactgggg aagtacgagc agtacatcaa gtggccctgg  11220
tacatctggc tgggctttat cgccggactg attgccatcg tgatggtcac aatcatgctg  11280
tgttgcatga ccagctgctg tagctgcctg aagggctgtt gtagctgtgg cagctgctgc  11340
aagttcgacg aggacgattc tgagcccgtg ctgaagggcg tgaaactgca ctacacatga  11400
gcggccgcga attggcaagc tgcttacata gaactcgcgg cgattggcat gccgccttaa  11460
aatttttatt ttatttttct tttcttttcc gaatcggatt ttgtttttaa tatttcaaaa  11520
aaaaaaaaaa aaaaaaaaaa aaaaaaaaaa a                                 11551
```

<210> SEQ ID NO 71
<211> LENGTH: 11956
<212> TYPE: DNA
<213> ORGANISM: Artificial Sequence
<220> FEATURE:
<223> OTHER INFORMATION: Synthetised Sequence

<400> SEQUENCE: 71

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
```

```
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
```

cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaattctta caagctttca tcaaccttga ccaacattta tacaggttcc agactccacg 4020
aagccggatg tgcaccctca tatcatgtgg tgcgaggggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520

-continued

```
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tggccaccat gttcgtgttt ctggtgctgc tgcctctggt gtccagccag   7620
tgtgtgaacc tgaccaccag aacacagctg cctccagcct acaccaacag ctttaccaga   7680
ggcgtgtact accccgacaa ggtgttcaga tccagcgtgc tgcactctac ccaggacctg   7740
ttcctgcctt tcttcagcaa cgtgacctgg ttccacgcca tccacgtgtc cggcaccaat   7800
ggcaccaaga gattcgacaa ccccgtgctg cccttcaacg acggggtgta ctttgccagc   7860
accgagaagt ccaacatcat cagaggctgg atcttcggca ccacactgga cagcaagacc   7920
```

-continued

```
cagagcctgc tgatcgtgaa caacgccacc aacgtggtca tcaaagtgtg cgagttccag   7980
ttctgcaacg accccttcct gggcgtctac taccacaaga acaacaagag ctggatggaa   8040
agcgagttcc gggtgtacag cagcgccaac aactgcacct tcgagtacgt gtcccagcct   8100
ttcctgatgg acctggaagg caagcagggc aacttcaaga acctgcgcga gttcgtgttc   8160
aagaacatcg acggctactt caagatctac agcaagcaca cccctatcaa cctcgtgcgg   8220
gatctgcctc agggcttctc tgctctggaa cccctggtgg atctgcccat cggcatcaac   8280
atcacccggt ttcagacact gctggccctg cacagaagct acctgacacc tggcgatagc   8340
agcagcggat ggacagctgg tgccgccgct tactatgtgg gctacctgca gcctagaacc   8400
ttcctgctga agtacaacga gaacggcacc atcaccgacg ccgtggattg tgcccttgat   8460
cctctgagcg agacaaagtg caccctgaag tccttcaccg tggaaaaggg catctaccag   8520
accagcaact tccgggtgca gcccaccgaa tccatcgtgc ggttccccaa tatcaccaat   8580
ctgtgcccct tcggcgaggt gttcaatgcc accagattcg cctctgtgta cgcctggaac   8640
cggaagcgga tcagcaattg cgtggccgac tactccgtgc tgtacaactc cgccagcttc   8700
agcaccttca agtgctacgg cgtgtcccct accaagctga acgacctgtg cttcacaaac   8760
gtgtacgccg acagcttcgt gatccgggga gatgaagtgc ggcagattgc ccctggacag   8820
acaggcaaga tcgccgacta caactacaag ctgcccgacg acttcaccgg ctgtgtgatt   8880
gcctggaaca gcaacaacct ggactccaaa gtcggcggca actacaatta cctgtaccgg   8940
ctgttccgga agtccaatct gaagcccttc gagcgggaca tctccaccga gatctatcag   9000
gccggcagca ccccttgtaa cggcgtggaa ggcttcaact gctacttccc actgcagtcc   9060
tacggctttc agcccacaaa tggcgtgggc tatcagccct acagagtggt ggtgctgagc   9120
ttcgaactgc tgcatgcccc tgccacagtg tgcggcccta agaaaagcac caatctcgtg   9180
aagaacaaat gcgtgaactt caacttcaac ggcctgaccg gcacaggcgt gctgacagag   9240
agcaacaaga agttcctgcc attccagcag tttggccggg atatcgccga taccacagac   9300
gccgttagag atccccagac actggaaatc ctggacatca ccccttgcag cttcggcgga   9360
gtgtctgtga tcacccctgg caccaacacc agcaatcagg tggcagtgct gtaccaggac   9420
gtgaactgta ccgaagtgcc cgtggccatt cacgccgatc agctgacacc tacatggcgg   9480
gtgtactcca ccggcagcaa tgtgtttcag accagagccg gctgtctgat cggagccgag   9540
cacgtgaaca atagctacga gtgcgacatc cccatcggcg ctggcatctg tgccagctac   9600
cagacacaga caaacagccc cagacgggcc agatctgtgg ccagccagag catcattgcc   9660
tacacaatgt ctctgggcgc cgagaacagc gtggcctact ccaacaactc tatcgctatc   9720
cccaccaact tcaccatcag cgtgaccaca gagatcctgc ctgtgtccat gaccaagacc   9780
agcgtggact gcaccatgta catctgcggc gattccaccg agtgctccaa cctgctgctg   9840
cagtacggca gcttctgcac ccagctgaat agagccctga cagggatcgc cgtggaacag   9900
gacaagaaca cccaagaggt gttcgcccaa gtgaagcaga tctacaagac ccctcctatc   9960
aaggacttcg gcggcttcaa tttcagccag attctgcccg atcctagcaa gcccagcaag  10020
cggagcttca tcgaggacct gctgttcaac aaagtgacac tggccgacgc cggcttcatc  10080
aagcagtatg gcgattgtct gggcgacatt gccgccaggg atctgatttg cgcccagaag  10140
tttaacggac tgacagtgct gcctcctctg ctgaccgatg agatgatcgc ccagtacaca  10200
tctgccctgc tggccggcac aatcacaagc ggctggacat ttggagctgg cgccgctctg  10260
```

-continued

```
cagatcccct ttgctatgca gatggcctac agattcaacg gcatcggagt gacccagaat  10320

gtgctgtacg agaaccagaa gctgatcgcc aaccagttca acagcgccat cggcaagatc  10380

caggacagcc tgagcagcac agcaagcgcc ctgggaaagc tgcaggacgt ggtcaaccag  10440

aatgcccagg cactgaacac cctggtcaag cagctgtcct ccaacttcgg cgccatcagc  10500

tctgtgctga acgatatcct gagcagactg gaccctcctg aggccgaggt gcagatcgac  10560

agactgatca caggcagact gcagagcctc cagacatacg tgacccagca gctgatcaga  10620

gccgccgaga ttagagcctc tgccaatctg gccgccacca agatgtctga gtgtgtgctg  10680

ggccagagca agagagtgga cttttgcggc aagggctacc acctgatgag cttccctcag  10740

tctgcccctc acggcgtggt gtttctgcac gtgacatacg ttcccgctca agagaagaat  10800

ttcaccaccg ctccagccat ctgccacgac ggcaaagccc actttcctag agaaggcgtg  10860

ttcgtgtcca acggcaccca ttggttcgtg acacagcgga acttctacga gccccagatc  10920

atcaccaccg acaacacctt cgtgtctggc aactgcgacg tcgtgatcgg cattgtgaac  10980

aataccgtgt acgaccctct gcagcccgag ctggacagct tcaaagagga actggacaag  11040

tactttaaga accacacaag ccccgacgtg gacctgggcg atatcagcgg aatcaatgcc  11100

agcgtcgtga acatccagaa agagatcgac cggctgaacg aggtggccaa gaatctgaac  11160

gagagcctga tcgacctgca agaactgggg aagtacgagc agtacatcaa gtggccctgg  11220

tacatctggc tgggctttat cgccggactg attgccatcg tgatggtcac aatcatgctg  11280

tgttgcatga ccagctgctg tagctgcctg aagggctgtt gtagctgtgg cagctgctgc  11340

aagttcgacg aggacgattc tgagcccgtg ctgaagggcg tgaaactgca ctacacagat  11400

cggagaaaga gaggctctgg cgaaggcaga ggcagcctgc ttacatgtgg cgacgtggaa  11460

gagaaccccg gacctatgga ttatgtgtcc ctgctgaacc agatttggca gaagtacctg  11520

aacagcccct acaccacctg tctgtacatc cccaagccta ccgccaagta cacacctctc  11580

gtgggcacat ctctgcaccc cgtgctgtgg aattgccagc tgagctttgc cggctacacc  11640

gagtctgccg tgaacagcac aaaggccctg gccaaacagg acgccgctca gagaattgcc  11700

tggctgctgc acaaggatgg cggcatccct gatggctgta gcctgtacct gagacacagc  11760

agcctgttcg cccagagcga ggaagaggaa tccttcagca actgagcggc cgcgaattgg  11820

caagctgctt acatagaact cgcggcgatt ggcatgccgc cttaaaattt ttattttatt  11880

tttcttttct tttccgaatc ggattttgtt tttaatattt caaaaaaaaa aaaaaaaaaa  11940

aaaaaaaaaa aaaaaa                                                  11956
```

<210> SEQ ID NO 72
<211> LENGTH: 13424
<212> TYPE: DNA
<213> ORGANISM: Artificial Sequence
<220> FEATURE:
<223> OTHER INFORMATION: Synthetised Sequence

<400> SEQUENCE: 72

```
atcctctgta cgcacccacc tcagaacatg tgaacgtcct actgacccgc acggaggacc     60

gcatcgtgtg gaaaacacta gccggcgacc catggataaa aacactgact gccaagtacc    120

ctgggaattt cactgccacg atagaggagt ggcaagcaga gcatgatgcc atcatgaggc    180

acatcttgga gagaccggac cctaccgacg tcttccagaa taaggcaaac gtgtgttggg    240

ccaaggcttt agtgccggtg ctgaagaccg ctggcataga catgaccact gaacaatgga    300

acactgtgga ttattttgaa acggacaaag ctcactcagc agagatagta ttgaaccaac    360
```

```
tatgcgtgag gttctttgga ctcgatctgg actccggtct attttctgca cccactgttc    420
cgttatccat taggaataat cactgggata actccccgtc gcctaacatg tacgggctga    480
ataaagaagt ggtccgtcag ctctctcgca ggtacccaca actgcctcgg gcagttgcca    540
ctggaagagt ctatgacatg aacactggta cactgcgcaa ttatgatccg cgcataaacc    600
tagtacctgt aaacagaaga ctgcctcatg ctttagtcct ccaccataat gaacacccac    660
agagtgactt ttcttcattc gtcagcaaat tgaagggcag aactgtcctg gtggtcgggg    720
aaaagttgtc cgtcccaggc aaaatggttg actggttgtc agaccggcct gaggctacct    780
tcagagctcg gctggattta ggcatcccag gtgatgtgcc caaatatgac ataatatttg    840
ttaatgtgag gaccccatat aaataccatc actatcagca gtgtgaagac catgccatta    900
agcttagcat gttgaccaag aaagcttgtc tgcatctgaa tcccggcgga acctgtgtca    960
gcataggtta tggttacgct gacagggcca gcgaaagcat cattggtgct atagcgcggc   1020
agttcaagtt ttcccgggta tgcaaaccga aatcctcact tgaagagacg gaagttctgt   1080
ttgtattcat tgggtacgat cgcaaggccc gtacgcacaa ttcttacaag ctttcatcaa   1140
ccttgaccaa catttataca ggttccagac tccacgaagc cggatgtgca ccctcatatc   1200
atgtggtgcg aggggatatt gccacggcca ccgaaggagt gattataaat gctgctaaca   1260
gcaaaggaca acctggcgga ggggtgtgcg gagcgctgta taagaaattc ccggaaagct   1320
tcgatttaca gccgatcgaa gtaggaaaag cgcgactggt caaaggtgca gctaaacata   1380
tcattcatgc cgtaggacca aacttcaaca aagtttcgga ggttgaaggt gacaaacagt   1440
tggcagaggc ttatgagtcc atcgctaaga ttgtcaacga taacaattac aagtcagtag   1500
cgattccact gttgtccacc ggcatctttt ccgggaacaa agatcgacta acccaatcat   1560
tgaaccattt gctgacagct ttagacacca ctgatgcaga tgtagccata tactgcaggg   1620
acaagaaatg ggaaatgact ctcaaggaag cagtggctag gagagaagca gtggaggaga   1680
tatgcatatc cgacgactct tcagtgacag aacctgatgc agagctggtg agggtgcatc   1740
cgaagagttc tttggctgga aggaagggct acagcacaag cgatggcaaa actttctcat   1800
atttggaagg gaccaagttt caccaggcgg ccaaggatat agcagaaatt aatgccatgt   1860
ggcccgttgc aacggaggcc aatgagcagg tatgcatgta tatcctcgga gaaagcatga   1920
gcagtattag gtcgaaatgc cccgtcgaag agtcggaagc ctccacacca cctagcacgc   1980
tgccttgctt gtgcatccat gccatgactc cagaaagagt acagcgccta aaagcctcac   2040
gtccagaaca aattactgtg tgctcatcct ttccattgcc gaagtataga atcactggtg   2100
tgcagaagat ccaatgctcc cagcctatat tgttctcacc gaaagtgcct gcgtatattc   2160
atccaaggaa gtatctcgtg gaaacaccac cggtagacga gactccggag ccatcggcag   2220
agaaccaatc cacagagggg acacctgaac aaccaccact tataaccgag gatgagacca   2280
ggactagaac gcctgagccg atcatcatcg aagaggaaga agaggatagc ataagtttgc   2340
tgtcagatgg cccgacccac caggtgctgc aagtcgaggc agacattcac gggccgccct   2400
ctgtatctag ctcatcctgg tccattcctc atgcatccga ctttgatgtg gacagtttat   2460
ccatacttga caccctggag ggagctagcg tgaccagcgg ggcaacgtca gccgagacta   2520
actcttactt cgcaaagagt atggagtttc tggcgcgacc ggtgcctgcg cctcgaacag   2580
tattcaggaa ccctccacat cccgctccgc gcacaagaac accgtcactt gcacccagca   2640
gggcctgctc gagaaccagc ctagtttcca ccccgccagg cgtgaatagg gtgatcacta   2700
```

gagaggagct cgaggcgctt accccgtcac gcactcctag caggtcggtc tcgagaacca 2760
gcctggtctc caacccgcca ggcgtaaata gggtgattac aagagaggag tttgaggcgt 2820
tcgtagcaca acaacaatga cggtttgatg cgggtgcata catcttttcc tccgacaccg 2880
gtcaagggca tttacaacaa aaatcagtaa ggcaaacggt gctatccgaa gtggtgttgg 2940
agaggaccga attggagatt tcgtatgccc cgcgcctcga ccaagaaaaa gaagaattac 3000
tacgcaagaa attacagtta aatcccacac ctgctaacag aagcagatac cagtccagga 3060
aggtggagaa catgaaagcc ataacagcta gacgtattct gcaaggccta gggcattatt 3120
tgaaggcaga aggaaaagtg gagtgctacc gaaccctgca tcctgttcct ttgtattcat 3180
ctagtgtgaa ccgtgccttt tcaagcccca aggtcgcagt ggaagcctgt aacgccatgt 3240
tgaaagagaa ctttccgact gtggcttctt actgtattat tccagagtac gatgcctatt 3300
tggacatggt tgacggagct tcatgctgct tagacactgc cagtttttgc cctgcaaagc 3360
tgcgcagctt tccaaagaaa cactcctatt tggaacccac aatacgatcg gcagtgcctt 3420
cagcgatcca gaacacgctc cagaacgtcc tggcagctgc cacaaaaaga aattgcaatg 3480
tcacgcaaat gagagaattg cccgtattgg attcggcggc ctttaatgtg gaatgcttca 3540
agaaatatgc gtgtaataat gaatattggg aaacgtttaa agaaaacccc atcaggctta 3600
ctgaagaaaa cgtggtaaat tacattacca aattaaaagg accaaaagct gctgctcttt 3660
ttgcgaagac acataatttg aatatgttgc aggacatacc aatggacagg tttgtaatgg 3720
acttaaagag agacgtgaaa gtgactccag gaacaaaaca tactgaagaa cggcccaagg 3780
tacaggtgat ccaggctgcc gatccgctag caacagcgta tctgtgcgga atccaccgag 3840
agctggttag gagattaaat gcggtcctgc ttccgaacat tcatacactg tttgatatgt 3900
cggctgaaga ctttgacgct attatagccg agcacttcca gcctggggat tgtgttctgg 3960
aaactgacat cgcgtcgttt gataaaagtg aggacgacgc catggctctg accgcgttaa 4020
tgattctgga agacttaggt gtggacgcag agctgttgac gctgattgag gcggctttcg 4080
gcgaaatttc atcaatacat ttgcccacta aaactaaatt taaattcgga gccatgatga 4140
aatctggaat gttcctcaca ctgtttgtga acacagtcat taacattgta atcgcaagca 4200
gagtgttgag agaacggcta accggatcac catgtgcagc attcattgga gatgacaata 4260
tcgtgaaagg agtcaaatcg gacaaattaa tggcagacag gtgcgccacc tggttgaata 4320
tggaagtcaa gattatagat gctgtggtgg gcgagaaagc gccttatttc tgtggagggt 4380
ttattttgtg tgactccgtg accggcacag cgtgccgtgt ggcagacccc ctaaaaaggc 4440
tgtttaagct tggcaaacct ctggcagcag acgatgaaca tgatgatgac aggagaaggg 4500
cattgcatga agagtcaaca cgctggaacc gagtgggtat tctttcagag ctgtgcaagg 4560
cagtagaatc aaggtatgaa accgtaggaa cttccatcat agttatggcc atgactactc 4620
tagctagcag tgttaaatca ttcagctacc tgagaggggc ccctataact ctctacggct 4680
aacctgaatg gactacgaca tagtctagtc cgccaagtct agcatatggc caccatgttc 4740
gtgtttctgg tgctgctgcc tctggtgtcc agccagtgtg tgaacctgac caccagaaca 4800
cagctgcctc cagcctacac caacagcttt accagaggcg tgtactaccc cgacaaggtg 4860
ttcagatcca gcgtgctgca ctctacccag gacctgttcc tgcctttctt cagcaacgtg 4920
acctggttcc acgccatctc cggcaccaat ggcaccaaga gattcgacaa ccccgtgctg 4980
cccttcaacg acggggtgta ctttgccagc accgagaagt ccaacatcat cagaggctgg 5040
atcttcggca ccacactgga cagcaagacc cagagcctgc tgatcgtgaa caacgccacc 5100

-continued

```
aacgtggtca tcaaagtgtg cgagttccag ttctgcaacg accccttcct gggcgtctac   5160
cacaagaaca acaagagctg gatggaaagc gagttccggg tgtacagcag cgccaacaac   5220
tgcaccttcg agtacgtgtc ccagcctttc ctgatggacc tggaaggcaa gcagggcaac   5280
ttcaagaacc tgcgcgagtt cgtgttcaag aacatcgacg gctacttcaa gatctacagc   5340
aagcacaccc ctatcaacct cgtgcgggat ctgcctcagg gcttctctgc tctggaaccc   5400
ctggtggatc tgcccatcgg catcaacatc acccggtttc agacactgct ggccctgcac   5460
agaagctacc tgacacctgg cgatagcagc agcggatgga cagctggtgc cgccgcttac   5520
tatgtgggct acctgcagcc tagaaccttc ctgctgaagt acaacgagaa cggcaccatc   5580
accgacgccg tggattgtgc ccttgatcct ctgagcgaga caaagtgcac cctgaagtcc   5640
ttcaccgtgg aaaagggcat ctaccagacc agcaacttcc gggtgcagcc caccgaatcc   5700
atcgtgcggt tccccaatat caccaatctg tgccccttcg gcgaggtgtt caatgccacc   5760
agattcgcct ctgtgtacgc ctggaaccgg aagcggatca gcaattgcgt ggccgactac   5820
tccgtgctgt acaactccgc cagcttcagc accttcaagt gctacggcgt gtcccctacc   5880
aagctgaacg acctgtgctt cacaaacgtg tacgccgaca gcttcgtgat ccggggagat   5940
gaagtgcggc agattgcccc tggacagaca ggcaagatcg ccgactacaa ctacaagctg   6000
cccgacgact tcaccggctg tgtgattgcc tggaacagca acaacctgga ctccaaagtc   6060
ggcggcaact acaattacct gtaccggctg ttccggaagt ccaatctgaa gcccttcgag   6120
cgggacatct ccaccgagat ctatcaggcc ggcagcaccc cttgtaacgg cgtggaaggc   6180
ttcaactgct acttcccact gcagtcctac ggctttcagc ccacatatgg cgtgggctat   6240
cagccctaca gagtggtggt gctgagcttc gaactgctgc atgcccctgc cacagtgtgc   6300
ggccctaaga aaagcaccaa tctcgtgaag aacaaatgcg tgaacttcaa cttcaacggc   6360
ctgaccggca caggcgtgct gacagagagc aacaagaagt tcctgccatt ccagcagttt   6420
ggccgggata tcgacgatac cacagacgcc gttagagatc cccagacact ggaaatcctg   6480
gacatcaccc cttgcagctt cggcggagtg tctgtgatca cccctggcac caacaccagc   6540
aatcaggtgg cagtgctgta ccagggcgtg aactgtaccg aagtgcccgt ggccattcac   6600
gccgatcagc tgacacctac atggcgggtg tactccaccg gcagcaatgt gtttcagacc   6660
agagccggct gtctgatcgg agccgagcac gtgaacaata gctacgagtg cgacatcccc   6720
atcggcgctg gcatctgtgc cagctaccag acacagacaa acagccactc tctggccagc   6780
tctgtggcca gccagagcat cattgcctac acaatgtctc tgggcgccga gaacagcgtg   6840
gcctactcca acaactctat cgctatcccc atcaacttca ccatcagcgt gaccacagag   6900
atcctgcctg tgtccatgac caagaccagc gtggactgca ccatgtacat ctgcggcgat   6960
tccaccgagt gctccaacct gctgctgcag tacggcagct tctgcaccca gctgaataga   7020
gccctgacag ggatcgccgt ggaacaggac aagaacaccc aagaggtgtt cgcccaagtg   7080
aagcagatct acaagacccc tcctatcaag gacttcggcg gcttcaattt cagccagatt   7140
ctgcccgatc ctagcaagcc cagcaagcgg agccccatcg aggacctgct gttcaacaaa   7200
gtgacactgg ccgacgccgg cttcatcaag cagtatggcg attgtctggg cgacattgcc   7260
gccagggatc tgatttgcgc ccagaagttt aacggactga cagtgctgcc tcctctgctg   7320
accgatgaga tgatcgccca gtacacatct gccctgctgg ccggcacaat cacaagcggc   7380
tggacatttg gagctggccc cgctctgcag atcccctttc ctatgcagat ggcctacaga   7440
```

-continued

```
ttcaacggca tcggagtgac ccagaatgtg ctgtacgaga accagaagct gatcgccaac   7500
cagttcaaca gcgccatcgg caagatccag gacagcctga gcagcacacc aagcgccctg   7560
ggaaagctgc aggacgtggt caaccagaat gcccaggcac tgaacaccct ggtcaagcag   7620
ctgtcctcca acttcggcgc catcagctct gtgctgaacg atatcctggc cagactggac   7680
cctcctgagg ccgaggtgca gatcgacaga ctgatcacag gcagactgca gagcctccag   7740
acatacgtga cccagcagct gatcagagcc gccgagatta gagcctctgc caatctggcc   7800
gccaccaaga tgtctgagtg tgtgctgggc cagagcaaga gagtggactt ttgcggcaag   7860
ggctaccacc tgatgagctt ccctcagtct gcccctcacg gcgtggtgtt tctgcacgtg   7920
acatacgttc ccgctcaaga gaagaatttc accaccgctc cagccatctg ccacgacggc   7980
aaagcccact ttcctagaga aggcgtgttc gtgtccaacg gcacccattg gttcgtgaca   8040
cagcggaact tctacgagcc ccagatcatc accacccaca acaccttcgt gtctggcaac   8100
tgcgacgtcg tgatcggcat tgtgaacaat accgtgtacg accctctgca gcccgagctg   8160
gacagcttca aagaggaact ggacaagtac tttaagaacc acacaagccc cgacgtggac   8220
ctgggcgata tcagcggaat caatgccagc gtcgtgaaca tccagaaaga gatcgaccgg   8280
ctgaacgagg tggccaagaa tctgaacgag agcctgatcg acctgcaaga actggggaag   8340
tacgagcagt acatcaagtg gccctggtac atctggctgg gctttatcgc cggactgatt   8400
gccatcgtga tggtcacaat catgctgtgt tgcatgacca gctgctgtag ctgcctgaag   8460
ggctgttgta gctgtggcag ctgctgcaag ttcgacgagg acgattctga gcccgtgctg   8520
aagggcgtga aactgcacta cacatgagcg gccgcgaatt ggcaagctgc ttacatagaa   8580
ctcgcggcga ttggcatgcc gccttaaaat ttttatttta tttttctttt cttttccgaa   8640
tcggattttg tttttaatat ttcaaaaaaa aaaaaaaaaa aaaaaaaaaa aaaaaaaacg   8700
cgtcgagggg aattaattct tgaagacgaa agggccaggt ggcacttttc ggggaaatgt   8760
gcgcggaacc cctatttgtt tatttttcta aatacattca aatatgtatc cgctcatgag   8820
acaataaccc tgataaatgc ttcaataata ttgaaaaagg aagagtatga gtattcaaca   8880
tttccgtgtc gcccttattc ccttttttgc ggcattttgc cttcctgttt ttgctcaccc   8940
agaaacgctg gtgaaagtaa aagatgctga agatcagttg ggtgcacgag tgggttacat   9000
cgaactggat ctcaacagcg gtaagatcct tgagagtttt cgccccgaag aacgttttcc   9060
aatgatgagc acttttaaag ttctgctatg tggcgcggta ttatcccgtg ttgacgccgg   9120
gcaagagcaa ctcggtcgcc gcatacacta ttctcagaat gacttggttg agtactcacc   9180
agtcacagaa aagcatctta cggatggcat gacagtaaga gaattatgca gtgctgccat   9240
aaccatgagt gataacactg cggccaactt acttctgaca acgatcggag gaccgaagga   9300
gctaaccgct tttttgcaca acatggggga tcatgtaact cgccttgatc gttgggaacc   9360
ggagctgaat gaagccatac caaacgacga gcgtgacacc acgatgcctg tagcaatggc   9420
aacaacgttg cgcaaactat taactggcga actacttact ctagcttccc ggcaacaatt   9480
aatagactgg atggaggcgg ataaagttgc aggaccactt ctgcgctcgg cccttccggc   9540
tggctggttt attgctgata aatctggagc cggtgagcgt gggtctcgcg gtatcattgc   9600
agcactgggg ccagatggta agccctcccg tatcgtagtt atctacacga cggggagtca   9660
ggcaactatg gatgaacgaa atagacagat cgctgagata ggtgcctcac tgattaagca   9720
ttggtaactg tcagaccaag tttactcata tatactttag attgatttaa aacttcattt   9780
ttaatttaaa aggatctagg tgaagatcct ttttgataat ctcatgacca aaatccctta   9840
```

-continued

```
acgtgagttt tcgttccact gagcgtcaga ccccgtagaa aagatcaaag gatcttcttg   9900
agatcctttt tttctgcgcg taatctgctg cttgcaaaca aaaaaaccac cgctaccagc   9960
ggtggtttgt ttgccggatc aagagctacc aactcttttt ccgaaggtaa ctggcttcag  10020
cagagcgcag ataccaaata ctgtccttct agtgtagccg tagttaggcc accacttcaa  10080
gaactctgta gcaccgccta catacctcgc tctgctaatc ctgttaccag tggctgctgc  10140
cagtggcgat aagtcgtgtc ttaccgggtt ggactcaaga cgatagttac cggataaggc  10200
gcagcggtcg ggctgaacgg ggggttcgtg cacacagccc agcttggagc gaacgaccta  10260
caccgaactg agatacctac agcgtgagca ttgagaaagc gccacgcttc ccgaagggag  10320
aaaggcggac aggtatccgg taagcggcag ggtcggaaca ggagagcgca cgagggagct  10380
tccaggggga aacgcctggt atctttatag tcctgtcggg tttcgccacc tctgacttga  10440
gcgtcgattt ttgtgatgct cgtcaggggg gcggagccta tggaaaaacg ccattctaga  10500
atggcgcgcc cttaagggga gaataggagc cgcaacacac aagcaacgcg aggtcgttta  10560
aactaatacg actcactata atgggcggcg catgagagaa gcccagacca attacctacc  10620
caaaatggag aaagttcacg ttgacatcga ggaagacagc ccattcctca gagctttgca  10680
gcggagcttc ccgcagtttg aggtagaagc caagcaggtc actgataatg accatgctaa  10740
tgccagagcg ttttcgcatc tggcttcaaa actgatcgaa acggaggtgg acccatccga  10800
cacgatcctt gacattggaa gtgcgcccgc ccgcagaatg tattctaagc acaagtatca  10860
ttgtatctgt ccgatgagat gtgcggaaga tccggacaga ttgtataagt atgcaactaa  10920
gctgaagaaa aactgtaagg aaataactga taaggaattg gacaagaaaa tgaaggagct  10980
ggccgccgtc atgagcgacc ctgacctgga aactgagact atgtgcctcc acgacgacga  11040
gtcgtgtcgc tacgaagggc aagtcgctgt ttaccaggat gtatacgcgg ttgacggacc  11100
gacaagtctc tatcaccaag ccaataaggg agttagagtc gcctactgga taggctttga  11160
caccacccct tttatgttta agaacttggc tggagcatat ccatcatact ctaccaactg  11220
ggccgacgaa accgtgttaa cggctcgtaa cataggccta tgcagctctg acgttatgga  11280
gcggtcacgt agagggatgt ccattcttag aaagaagtat ttgaaaccat ccaacaatgt  11340
tctattctct gttggctcga ccatctacca cgagaagagg gacttactga ggagctggca  11400
cctgccgtct gtatttcact tacgtggcaa gcaaaattac acatgtcggt gtgagactat  11460
agttagttgc gacgggtacg tcgttaaaag aatagctatc agtccaggcc tgtatgggaa  11520
gccttcaggc tatgctgcta cgatgcaccg cgagggattc ttgtgctgca aagtgacaga  11580
cacattgaac ggggagaggg tctcttttcc cgtgtgcacg tatgtgccag ctacattgtg  11640
tgaccaaatg actggcatac tggcaacaga tgtcagtgcg gacgacgcgc aaaaactgct  11700
ggttgggctc aaccagcgta tagtcgtcaa cggtcgcacc cagagaaaca ccaataccat  11760
gaaaaattac cttttgcccg tagtggccca ggcatttgct aggtgggcaa aggaatataa  11820
ggaagatcaa gaagatgaaa ggccactagg actacgagat agacagttag tcatggggtg  11880
ttgttgggct tttagaaggc acaagataac atctatttat aagcgcccgg atacccaaac  11940
catcatcaaa gtgaacagcg atttccactc attcgtgctg cccaggatag gcagtaacac  12000
attggagatc gggctgagaa caagaatcag gaaaatgtta gaggagcaca aggagccgtc  12060
acctctcatt accgccgagg acgtacaaga agctaagtgc gcagccgatg aggctaagga  12120
ggtgcgtgaa gccgaggagt tgcgcgcagc tctaccacct ttggcagctg atgttgagga  12180
```

gcccactctg gaggcagacg tcgacttgat gttacaagag gctggggccg gctcagtgga 12240
gacacctcgt ggcttgataa aggttaccag ctacgatggc gaggacaaga tcggctctta 12300
cgctgtgctt tctccgcagg ctgtactcaa gagtgaaaaa ttatcttgca tccaccctct 12360
cgctgaacaa gtcatagtga taacacactc tggccgaaaa gggcgttatg ccgtggaacc 12420
ataccatggt aaagtagtgg tgccagaggg acatgcaata cccgtccagg actttcaagc 12480
tctgagtgaa agtgccacca ttgtgtacaa cgaacgtgag ttcgtaaaca ggtacctgca 12540
ccatattgcc acacatggag gagcgctgaa cactgatgaa gaatattaca aaactgtcaa 12600
gcccagcgag cacgacggcg aatacctgta cgacatcgac aggaaacagt gcgtcaagaa 12660
agaactagtc actgggctag ggctcacagg cgagctggtg gatcctccct tccatgaatt 12720
cgcctacgag agtctgagaa cacgaccagc cgctccttac caagtaccaa ccataggggt 12780
gtatggcgtg ccaggatcag gcaagtctgg catcattaaa agcgcagtca ccaaaaaaga 12840
tctagtggtg agcgccaaga aagaaaactg tgcagaaatt ataagggacg tcaagaaaat 12900
gaaagggctg gacgtcaatg ccagaactgt ggactcagtg ctcttgaatg gatgcaaaca 12960
ccccgtagag accctgtata ttgacgaagc ttttgcttgt catgcaggta ctctcagagc 13020
gctcatagcc attataagac ctaaaaaggc agtgctctgc ggggatccca aacagtgcgg 13080
tttttttaac atgatgtgcc tgaaagtgca ttttaaccac gagatttgca cacaagtctt 13140
ccacaaaagc atctctcgcc gttgcactaa atctgtgact tcggtcgtct caaccttgtt 13200
ttacgacaaa aaaatgagaa cgacgaatcc gaaagagact aagattgtga ttgacactac 13260
cggcagtacc aaacctaagc aggacgatct cattctcact tgtttcagag ggtgggtgaa 13320
gcagttgcaa atagattaca aaggcaacga aataatgacg gcagctgcct ctcaagggct 13380
gacccgtaaa ggtgtgtatg ccgttcggta caaggtgaat gaaa 13424

<210> SEQ ID NO 73
<211> LENGTH: 13424
<212> TYPE: DNA
<213> ORGANISM: Artificial Sequence
<220> FEATURE:
<223> OTHER INFORMATION: Synthetised Sequence

<400> SEQUENCE: 73
atcctctgta cgcacccacc tcagaacatg tgaacgtcct actgacccgc acggaggacc 60
gcatcgtgtg gaaaacacta gccggcgacc catggataaa aacactgact gccaagtacc 120
ctgggaattt cactgccacg atagaggagt ggcaagcaga gcatgatgcc atcatgaggc 180
acatcttgga gagaccggac cctaccgacg tcttccagaa taaggcaaac gtgtgttggg 240
ccaaggcttt agtgccggtg ctgaagaccg ctggcataga catgaccact gaacaatgga 300
acactgtgga ttattttgaa acggacaaag ctcactcagc agagatagta ttgaaccaac 360
tatgcgtgag gttctttgga ctcgatctgg actccggtct attttctgca cccactgttc 420
cgttatccat taggaataat cactgggata actccccgtc gcctaacatg tacgggctga 480
ataaagaagt ggtccgtcag ctctctcgca ggtacccaca actgcctcgg gcagttgcca 540
ctggaagagt ctatgacatg aacactggta cactgcgcaa ttatgatccg cgcataaacc 600
tagtacctgt aaacagaaga ctgcctcatg ctttagtcct ccaccataat gaacacccac 660
agagtgactt ttcttcattc gtcagcaaat tgaagggcag aactgtcctg gtggtcgggg 720
aaaagttgtc cgtcccaggc aaaatggttg actggttgtc agaccggcct gaggctacct 780
tcagagctcg gctggattta ggcatcccag gtgatgtgcc caaatatgac ataatatttg 840

-continued

```
ttaatgtgag gaccccatat aaataccatc actatcagca gtgtgaagac catgccatta    900
agcttagcat gttgaccaag aaagcttgtc tgcatctgaa tcccggcgga acctgtgtca    960
gcataggtta tggttacgct gacagggcca gcgaaagcat cattggtgct atagcgcggc   1020
agttcaagtt ttcccgggta tgcaaaccga aatcctcact tgaagagacg gaagttctgt   1080
ttgtattcat tgggtacgat cgcaaggccc gtacgcacaa ttcttacaag ctttcatcaa   1140
ccttgaccaa catttataca ggttccagac tccacgaagc cggatgtgca ccctcatatc   1200
atgtggtgcg aggggatatt gccacggcca ccgaaggagt gattataaat gctgctaaca   1260
gcaaaggaca acctggcgga ggggtgtgcg gagcgctgta taagaaattc ccggaaagct   1320
tcgatttaca gccgatcgaa gtaggaaaag cgcgactggt caaaggtgca gctaaacata   1380
tcattcatgc cgtaggacca aacttcaaca aagtttcgga ggttgaaggt gacaaacagt   1440
tggcagaggc ttatgagtcc atcgctaaga ttgtcaacga taacaattac aagtcagtag   1500
cgattccact gttgtccacc ggcatctttt ccgggaacaa agatcgacta acccaatcat   1560
tgaaccattt gctgacagct ttagacacca ctgatgcaga tgtagccata tactgcaggg   1620
acaagaaatg ggaaatgact ctcaaggaag cagtggctag gagagaagca gtggaggaga   1680
tatgcatatc cgacgactct tcagtgacag aacctgatgc agagctggtg agggtgcatc   1740
cgaagagttc tttggctgga aggaagggct acagcacaag cgatggcaaa actttctcat   1800
atttggaagg gaccaagttt caccaggcgg ccaaggatat agcagaaatt aatgccatgt   1860
ggcccgttgc aacggaggcc aatgagcagg tatgcatgta tatcctcgga gaaagcatga   1920
gcagtattag gtcgaaatgc cccgtcgaag agtcggaagc ctccacacca cctagcacgc   1980
tgccttgctt gtgcatccat gccatgactc cagaaagagt acagcgccta aaagcctcac   2040
gtccagaaca aattactgtg tgctcatcct ttccattgcc gaagtataga atcactggtg   2100
tgcagaagat ccaatgctcc cagcctatat tgttctcacc gaaagtgcct gcgtatattc   2160
atccaaggaa gtatctcgtg gaaacaccac cggtagacga gactccggag ccatcggcag   2220
agaaccaatc cacagagggg acacctgaac aaccaccact tataaccgag gatgagacca   2280
ggactagaac gcctgagccg atcatcatcg aagaggaaga agaggatagc ataagtttgc   2340
tgtcagatgg cccgacccac caggtgctgc aagtcgaggc agacattcac gggccgccct   2400
ctgtatctag ctcatcctgg tccattcctc atgcatccga ctttgatgtg gacagtttat   2460
ccatacttga caccctggag ggagctagcg tgaccagcgg ggcaacgtca gccgagacta   2520
actcttactt cgcaaagagt atggagtttc tggcgcgacc ggtgcctgcg cctcgaacag   2580
tattcaggaa ccctccacat cccgctccgc gcacaagaac accgtcactt gcacccagca   2640
gggcctgctc gagaaccagc ctagtttcca ccccgccagg cgtgaatagg gtgatcacta   2700
gagaggagct cgaggcgctt accccgtcac gcactcctag caggtcggtc tcgagaacca   2760
gcctggtctc caacccgcca ggcgtaaata gggtgattac aagagaggag tttgaggcgt   2820
tcgtagcaca acaacaatga cggtttgatg cgggtgcata catcttttcc tccgacaccg   2880
gtcaagggca tttacaacaa aaatcagtaa ggcaaacggt gctatccgaa gtggtgttgg   2940
agaggaccga attggagatt tcgtatgccc cgcgcctcga ccaagaaaaa gaagaattac   3000
tacgcaagaa attacagtta aatcccacac ctgctaacag aagcagatac cagtccagga   3060
aggtggagaa catgaaagcc ataacagcta gacgtattct gcaaggccta gggcattatt   3120
tgaaggcaga aggaaaagtg gagtgctacc gaaccctgca tcctgttcct ttgtattcat   3180
```

-continued

```
ctagtgtgaa ccgtgccttt tcaagcccca aggtcgcagt ggaagcctgt aacgccatgt   3240
tgaaagagaa ctttccgact gtggcttctt actgtattat tccagagtac gatgcctatt   3300
tggacatggt tgacggagct tcatgctgct tagacactgc cagtttttgc cctgcaaagc   3360
tgcgcagctt tccaaagaaa cactcctatt tggaacccac aatacgatcg gcagtgcctt   3420
cagcgatcca gaacacgctc cagaacgtcc tggcagctgc cacaaaaaga aattgcaatg   3480
tcacgcaaat gagagaattg cccgtattgg attcggcggc ctttaatgtg gaatgcttca   3540
agaaatatgc gtgtaataat gaatattggg aaacgtttaa agaaaacccc atcaggctta   3600
ctgaagaaaa cgtggtaaat tacattacca aattaaaagg accaaaagct gctgctcttt   3660
ttgcgaagac acataatttg aatatgttgc aggacatacc aatggacagg tttgtaatgg   3720
acttaaagag agacgtgaaa gtgactccag gaacaaaaca tactgaagaa cggcccaagg   3780
tacaggtgat ccaggctgcc gatccgctag caacagcgta tctgtgcgga atccaccgag   3840
agctggttag gagattaaat gcggtcctgc ttccgaacat tcatacactg tttgatatgt   3900
cggctgaaga ctttgacgct attatagccg agcacttcca gcctggggat tgtgttctgg   3960
aaactgacat cgcgtcgttt gataaaagtg aggacgacgc catggctctg accgcgttaa   4020
tgattctgga agacttaggt gtggacgcag agctgttgac gctgattgag gcggctttcg   4080
gcgaaatttc atcaatacat ttgcccacta aaactaaatt taaattcgga gccatgatga   4140
aatctggaat gttcctcaca ctgtttgtga acacagtcat taacattgta atcgcaagca   4200
gagtgttgag agaacggcta accggatcac catgtgcagc attcattgga gatgacaata   4260
tcgtgaaagg agtcaaatcg gacaaattaa tggcagacag gtgcgccacc tggttgaata   4320
tggaagtcaa gattatagat gctgtggtgg gcgagaaagc gccttatttc tgtggagggt   4380
ttattttgtg tgactccgtg accggcacag cgtgccgtgt ggcagacccc ctaaaaaggc   4440
tgtttaagct tggcaaacct ctggcagcag acgatgaaca tgatgatgac aggagaaggg   4500
cattgcatga agagtcaaca cgctggaacc gagtgggtat tctttcagag ctgtgcaagg   4560
cagtagaatc aaggtatgaa accgtaggaa cttccatcat agttatggcc atgactactc   4620
tagctagcag tgttaaatca ttcagctacc tgagaggggc ccctataact ctctacggct   4680
aacctgaatg gactacgaca tagtctagtc cgccaagtct agcatatggc caccatgttc   4740
gtgtttctgg tgctgctgcc tctggtgtcc agccagtgtg tgaacctgac caccagaaca   4800
cagctgcctc cagcctacac caacagcttt accagaggcg tgtactaccc cgacaaggtg   4860
ttcagatcca gcgtgctgca ctctacccag gacctgttcc tgcctttctt cagcaacgtg   4920
acctggttcc acgccatctc cggcaccaat ggcaccaaga gattcgacaa ccccgtgctg   4980
cccttcaacg acggggtgta ctttgccagc accgagaagt ccaacatcat cagaggctgg   5040
atcttcggca ccacactgga cagcaagacc cagagcctgc tgatcgtgaa caacgccacc   5100
aacgtggtca tcaaagtgtg cgagttccag ttctgcaacg accccttcct gggcgtctac   5160
cacaagaaca acaagagctg gatggaaagc gagttccggg tgtacagcag cgccaacaac   5220
tgcaccttcg agtacgtgtc ccagcctttc ctgatggacc tggaaggcaa gcagggcaac   5280
ttcaagaacc tgcgcgagtt cgtgttcaag aacatcgacg gctacttcaa gatctacagc   5340
aagcacaccc ctatcaacct cgtgcgggat ctgcctcagg gcttctctgc tctggaaccc   5400
ctggtggatc tgcccatcgg catcaacatc acccggtttc agacactgct ggccctgcac   5460
agaagctacc tgacacctgg cgatagcagc agcggatgga cagctggtgc cgccgcttac   5520
tatgtgggct acctgcagcc tagaaccttc ctgctgaagt acaacgagaa cggcaccatc   5580
```

-continued accgacgccg tggattgtgc ccttgatcct ctgagcgaga caaagtgcac cctgaagtcc 5640
ttcaccgtgg aaaagggcat ctaccagacc agcaacttcc gggtgcagcc caccgaatcc 5700
atcgtgcggt tccccaatat caccaatctg tgccccttcg gcgaggtgtt caatgccacc 5760
agattcgcct ctgtgtacgc ctggaaccgg aagcggatca gcaattgcgt ggccgactac 5820
tccgtgctgt acaactccgc cagcttcagc accttcaagt gctacggcgt gtcccctacc 5880
aagctgaacg acctgtgctt cacaaacgtg tacgccgaca gcttcgtgat ccggggagat 5940
gaagtgcggc agattgcccc tggacagaca ggcaagatcg ccgactacaa ctacaagctg 6000
cccgacgact tcaccggctg tgtgattgcc tggaacagca acaacctgga ctccaaagtc 6060
ggcggcaact acaattacct gtaccggctg ttccggaagt ccaatctgaa gcccttcgag 6120
cgggacatct ccaccgagat ctatcaggcc ggcagcaccc cttgtaacgg cgtgaaaggc 6180
ttcaactgct acttcccact gcagtcctac ggctttcagc ccacatatgg cgtgggctat 6240
cagccctaca gagtggtggt gctgagcttc gaactgctgc atgcccctgc cacagtgtgc 6300
ggccctaaga aaagcaccaa tctcgtgaag aacaaatgcg tgaacttcaa cttcaacggc 6360
ctgaccggca caggcgtgct gacagagagc aacaagaagt tcctgccatt ccagcagttt 6420
ggccgggata tcgacgatac cacagacgcc gttagagatc cccagacact ggaaatcctg 6480
gacatcaccc cttgcagctt cggcggagtg tctgtgatca cccctggcac caacaccagc 6540
aatcaggtgg cagtgctgta ccagggcgtg aactgtaccg aagtgcccgt ggccattcac 6600
gccgatcagc tgacacctac atggcgggtg tactccaccg gcagcaatgt gtttcagacc 6660
agagccggct gtctgatcgg agccgagcac gtgaacaata gctacgagtg cgacatcccc 6720
atcggcgctg gcatctgtgc cagctaccag acacagacaa acagccactc tctggccagc 6780
tctgtggcca gccagagcat cattgcctac acaatgtctc tgggcgccga gaacagcgtg 6840
gcctactcca acaactctat cgctatcccc atcaacttca ccatcagcgt gaccacagag 6900
atcctgcctg tgtccatgac caagaccagc gtggactgca ccatgtacat ctgcggcgat 6960
tccaccgagt gctccaacct gctgctgcag tacggcagct tctgcaccca gctgaataga 7020
gccctgacag ggatcgccgt ggaacaggac aagaacaccc aagaggtgtt cgcccaagtg 7080
aagcagatct acaagacccc tcctatcaag gacttcggcg gcttcaattt cagccagatt 7140
ctgcccgatc ctagcaagcc cagcaagcgg agccccatcg aggacctgct gttcaacaaa 7200
gtgacactgg ccgacgccgg cttcatcaag cagtatggcg attgtctggg cgacattgcc 7260
gccagggatc tgatttgcgc ccagaagttt aacggactga cagtgctgcc tcctctgctg 7320
accgatgaga tgatcgccca gtacacatct gccctgctgg ccggcacaat cacaagcggc 7380
tggacatttg gagctggccc cgctctgcag atcccctttc ctatgcagat ggcctacaga 7440
ttcaacggca tcggagtgac ccagaatgtg ctgtacgaga accagaagct gatcgccaac 7500
cagttcaaca gcgccatcgg caagatccag gacagcctga gcagcacacc aagcgccctg 7560
ggaaagctgc aggacgtggt caaccagaat gcccaggcac tgaacaccct ggtcaagcag 7620
ctgtcctcca acttcggcgc catcagctct gtgctgaacg atatcctggc cagactggac 7680
cctcctgagg ccgaggtgca gatcgacaga ctgatcacag gcagactgca gagcctccag 7740
acatacgtga cccagcagct gatcagagcc gccgagatta gagcctctgc caatctggcc 7800
gccaccaaga tgtctgagtg tgtgctgggc cagagcaaga gagtggactt ttgcggcaag 7860
ggctaccacc tgatgagctt ccctcagtct gcccctcacg gcgtggtgtt tctgcacgtg 7920

-continued

```
acatacgttc ccgctcaaga gaagaatttc accaccgctc cagccatctg ccacgacggc   7980
aaagcccact ttcctagaga aggcgtgttc gtgtccaacg gcacccattg gttcgtgaca   8040
cagcggaact tctacgagcc ccagatcatc accacccaca acaccttcgt gtctggcaac   8100
tgcgacgtcg tgatcggcat tgtgaacaat accgtgtacg accctctgca gcccgagctg   8160
gacagcttca aagaggaact ggacaagtac tttaagaacc acacaagccc cgacgtggac   8220
ctgggcgata tcagcggaat caatgccagc gtcgtgaaca tccagaaaga gatcgaccgg   8280
ctgaacgagg tggccaagaa tctgaacgag agcctgatcg acctgcaaga actggggaag   8340
tacgagcagt acatcaagtg gccctggtac atctggctgg gctttatcgc cggactgatt   8400
gccatcgtga tggtcacaat catgctgtgt tgcatgacca gctgctgtag ctgcctgaag   8460
ggctgttgta gctgtggcag ctgctgcaag ttcgacgagg acgattctga gcccgtgctg   8520
aagggcgtga aactgcacta cacatgagcg gccgcgaatt ggcaagctgc ttacatagaa   8580
ctcgcggcga ttggcatgcc gccttaaaat ttttatttta tttttctttt cttttccgaa   8640
tcggattttg tttttaatat ttcaaaaaaa aaaaaaaaaa aaaaaaaaaa aaaaaaaacg   8700
cgtcgagggg aattaattct tgaagacgaa agggccaggt ggcacttttc ggggaaatgt   8760
gcgcggaacc cctatttgtt tatttttcta aatacattca aatatgtatc cgctcatgag   8820
acaataaccc tgataaatgc ttcaataata ttgaaaaagg aagagtatga gtattcaaca   8880
tttccgtgtc gcccttattc ccttttttgc ggcattttgc cttcctgttt ttgctcaccc   8940
agaaacgctg gtgaaagtaa aagatgctga agatcagttg ggtgcacgag tgggttacat   9000
cgaactggat ctcaacagcg gtaagatcct tgagagtttt cgccccgaag aacgttttcc   9060
aatgatgagc acttttaaag ttctgctatg tggcgcggta ttatcccgtg ttgacgccgg   9120
gcaagagcaa ctcggtcgcc gcatacacta ttctcagaat gacttggttg agtactcacc   9180
agtcacagaa aagcatctta cggatggcat gacagtaaga gaattatgca gtgctgccat   9240
aaccatgagt gataacactg cggccaactt acttctgaca acgatcggag gaccgaagga   9300
gctaaccgct tttttgcaca acatggggga tcatgtaact cgccttgatc gttgggaacc   9360
ggagctgaat gaagccatac caaacgacga gcgtgacacc acgatgcctg tagcaatggc   9420
aacaacgttg cgcaaactat taactggcga actacttact ctagcttccc ggcaacaatt   9480
aatagactgg atggaggcgg ataaagttgc aggaccactt ctgcgctcgg cccttccggc   9540
tggctggttt attgctgata aatctggagc cggtgagcgt gggtctcgcg gtatcattgc   9600
agcactgggg ccagatggta agccctcccg tatcgtagtt atctacacga cggggagtca   9660
ggcaactatg gatgaacgaa atagacagat cgctgagata ggtgcctcac tgattaagca   9720
ttggtaactg tcagaccaag tttactcata tatactttag attgatttaa aacttcattt   9780
ttaatttaaa aggatctagg tgaagatcct ttttgataat ctcatgacca aaatccctta   9840
acgtgagttt tcgttccact gagcgtcaga ccccgtagaa aagatcaaag gatcttcttg   9900
agatcctttt tttctgcgcg taatctgctg cttgcaaaca aaaaaaccac cgctaccagc   9960
ggtggtttgt ttgccggatc aagagctacc aactcttttt ccgaaggtaa ctggcttcag  10020
cagagcgcag ataccaaata ctgtccttct agtgtagccg tagttaggcc accacttcaa  10080
gaactctgta gcaccgccta catacctcgc tctgctaatc ctgttaccag tggctgctgc  10140
cagtggcgat aagtcgtgtc ttaccgggtt ggactcaaga cgatagttac cggataaggc  10200
gcagcggtcg ggctgaacgg ggggttcgtg cacacagccc agcttggagc gaacgaccta  10260
caccgaactg agatacctac agcgtgagca ttgagaaagc gccacgcttc ccgaagggag  10320
```

-continued

```
aaaggcggac aggtatccgg taagcggcag ggtcggaaca ggagagcgca cgagggagct  10380
tccaggggga aacgcctggt atctttatag tcctgtcggg tttcgccacc tctgacttga  10440
gcgtcgattt ttgtgatgct cgtcaggggg gcggagccta tggaaaaacg ccattctaga  10500
atggcgcgcc cttaagggga gaataggagc cgcaacacac aagcaacgcg aggtcgttta  10560
aactaatacg actcactata atgggcggcg catgagagaa gcccagacca attacctacc  10620
caaaatggag aaagttcacg ttgacatcga ggaagacagc ccattcctca gagctttgca  10680
gcggagcttc ccgcagtttg aggtagaagc caagcaggtc actgataatg accatgctaa  10740
tgccagagcg ttttcgcatc tggcttcaaa actgatcgaa acggaggtgg acccatccga  10800
cacgatcctt gacattggaa gtgcgcccgc ccgcagaatg tattctaagc acaagtatca  10860
ttgtatctgt ccgatgagat gtgcggaaga tccggacaga ttgtataagt atgcaactaa  10920
gctgaagaaa aactgtaagg aaataactga taaggaattg gacaagaaaa tgaaggagct  10980
ggccgccgtc atgagcgacc ctgacctgga aactgagact atgtgcctcc acgacgacga  11040
gtcgtgtcgc tacgaagggc aagtcgctgt ttaccaggat gtatacgcgg ttgacggacc  11100
gacaagtctc tatcaccaag ccaataaggg agttagagtc gcctactgga taggctttga  11160
caccacccct tttatgttta agaacttggc tggagcatat ccatcatact ctaccaactg  11220
ggccgacgaa accgtgttaa cggctcgtaa cataggccta tgcagctctg acgttatgga  11280
gcggtcacgt agagggatgt ccattcttag aaagaagtat ttgaaaccat ccaacaatgt  11340
tctattctct gttggctcga ccatctacca cgagaagagg gacttactga ggagctggca  11400
cctgccgtct gtatttcact tacgtggcaa gcaaaattac acatgtcggt gtgagactat  11460
agttagttgc gacgggtacg tcgttaaaag aatagctatc agtccaggcc tgtatgggaa  11520
gccttcaggc tatgctgcta cgatgcaccg cgagggattc ttgtgctgca aagtgacaga  11580
cacattgaac ggggagaggg tctcttttcc cgtgtgcacg tatgtgccag ctacattgtg  11640
tgaccaaatg actggcatac tggcaacaga tgtcagtgcg gacgacgcgc aaaaactgct  11700
ggttgggctc aaccagcgta tagtcgtcaa cggtcgcacc cagagaaaca ccaataccat  11760
gaaaaattac cttttgcccg tagtggccca ggcatttgct aggtgggcaa aggaatataa  11820
ggaagatcaa gaagatgaaa ggccactagg actacgagat agacagttag tcatggggtg  11880
ttgttgggct tttagaaggc acaagataac atctatttat aagcgcccgg atacccaaac  11940
catcatcaaa gtgaacagcg atttccactc attcgtgctg cccaggatag gcagtaacac  12000
attggagatc gggctgagaa caagaatcag gaaaatgtta gaggagcaca aggagccgtc  12060
acctctcatt accgccgagg acgtacaaga agctaagtgc gcagccgatg aggctaagga  12120
ggtgcgtgaa gccgaggagt tgcgcgcagc tctaccacct ttggcagctg atgttgagga  12180
gcccactctg gaggcagacg tcgacttgat gttacaagag gctggggccg gctcagtgga  12240
gacacctcgt ggcttgataa aggttaccag ctacgatggc gaggacaaga tcggctctta  12300
cgctgtgctt tctccgcagg ctgtactcaa gagtgaaaaa ttatcttgca tccaccctct  12360
cgctgaacaa gtcatagtga taacacactc tggccgaaaa gggcgttatg ccgtggaacc  12420
ataccatggt aaagtagtgg tgccagaggg acatgcaata cccgtccagg actttcaagc  12480
tctgagtgaa agtgccacca ttgtgtacaa cgaacgtgag ttcgtaaaca ggtacctgca  12540
ccatattgcc acacatggag gagcgctgaa cactgatgaa gaatattaca aaactgtcaa  12600
gcccagcgag cacgacggcg aatacctgta cgacatcgac aggaaacagt gcgtcaagaa  12660
```

```
agaactagtc actgggctag ggctcacagg cgagctggtg gatcctccct tccatgaatt  12720
cgcctacgag agtctgagaa cacgaccagc cgctccttac caagtaccaa ccataggggt  12780
gtatggcgtg ccaggatcag gcaagtctgg catcattaaa agcgcagtca ccaaaaaaga  12840
tctagtggtg agcgccaaga aagaaaactg tgcagaaatt ataagggacg tcaagaaaat  12900
gaaagggctg gacgtcaatg ccagaactgt ggactcagtg ctcttgaatg gatgcaaaca  12960
ccccgtagag accctgtata ttgacgaagc ttttgcttgt catgcaggta ctctcagagc  13020
gctcatagcc attataagac ctaaaaaggc agtgctctgc ggggatccca aacagtgcgg  13080
tttttttaac atgatgtgcc tgaaagtgca ttttaaccac gagatttgca cacaagtctt  13140
ccacaaaagc atctctcgcc gttgcactaa atctgtgact tcggtcgtct caaccttgtt  13200
ttacgacaaa aaaatgagaa cgacgaatcc gaaagagact aagattgtga ttgacactac  13260
cggcagtacc aaacctaagc aggacgatct cattctcact tgtttcagag ggtgggtgaa  13320
gcagttgcaa atagattaca aaggcaacga aataatgacg gcagctgcct ctcaagggct  13380
gacccgtaaa ggtgtgtatg ccgttcggta caaggtgaat gaaa                  13424
```

<210> SEQ ID NO 74
<211> LENGTH: 13424
<212> TYPE: DNA
<213> ORGANISM: Artificial Sequence
<220> FEATURE:
<223> OTHER INFORMATION: Synthetised Sequence

<400> SEQUENCE: 74

```
atcctctgta cgcacccacc tcagaacatg tgaacgtcct actgacccgc acggaggacc     60
gcatcgtgtg gaaaacacta gccggcgacc catggataaa aacactgact gccaagtacc    120
ctgggaattt cactgccacg atagaggagt ggcaagcaga gcatgatgcc atcatgaggc    180
acatcttgga gagaccggac cctaccgacg tcttccagaa taaggcaaac gtgtgttggg    240
ccaaggcttt agtgccggtg ctgaagaccg ctggcataga catgaccact gaacaatgga    300
acactgtgga ttattttgaa acggacaaag ctcactcagc agagatagta ttgaaccaac    360
tatgcgtgag gttctttgga ctcgatctgg actccggtct attttctgca cccactgttc    420
cgttatccat taggaataat cactgggata actccccgtc gcctaacatg tacgggctga    480
ataaagaagt ggtccgtcag ctctctcgca ggtacccaca actgcctcgg gcagttgcca    540
ctggaagagt ctatgacatg aacactggta cactgcgcaa ttatgatccg cgcataaacc    600
tagtacctgt aaacagaaga ctgcctcatg ctttagtcct ccaccataat gaacacccac    660
agagtgactt ttcttcattc gtcagcaaat tgaagggcag aactgtcctg gtggtcgggg    720
aaaagttgtc cgtcccaggc aaaatggttg actggttgtc agaccggcct gaggctacct    780
tcagagctcg gctggattta ggcatcccag gtgatgtgcc caaatatgac ataatatttg    840
ttaatgtgag gaccccatat aaataccatc actatcagca gtgtgaagac catgccatta    900
agcttagcat gttgaccaag aaagcttgtc tgcatctgaa tcccggcgga acctgtgtca    960
gcataggtta tggttacgct gacagggcca gcgaaagcat cattggtgct atagcgcggc   1020
agttcaagtt ttcccgggta tgcaaaccga aatcctcact tgaagagacg gaagttctgt   1080
ttgtattcat tgggtacgat cgcaaggccc gtacgcacaa ttcttacaag ctttcatcaa   1140
ccttgaccaa catttataca ggttccagac tccacgaagc cggatgtgca ccctcatatc   1200
atgtggtgcg aggggatatt gccacggcca ccgaaggagt gattataaat gctgctaaca   1260
gcaaaggaca acctggcgga ggggtgtgcg gagcgctgta taagaaattc ccggaaagct   1320
```

tcgatttaca gccgatcgaa gtaggaaaag cgcgactggt caaaggtgca gctaaacata 1380
tcattcatgc cgtaggacca aacttcaaca aagtttcgga ggttgaaggt gacaaacagt 1440
tggcagaggc ttatgagtcc atcgctaaga ttgtcaacga taacaattac aagtcagtag 1500
cgattccact gttgtccacc ggcatctttt ccgggaacaa agatcgacta acccaatcat 1560
tgaaccattt gctgacagct ttagacacca ctgatgcaga tgtagccata tactgcaggg 1620
acaagaaatg ggaaatgact ctcaaggaag cagtggctag gagagaagca gtggaggaga 1680
tatgcatatc cgacgactct tcagtgacag aacctgatgc agagctggtg agggtgcatc 1740
cgaagagttc tttggctgga aggaagggct acagcacaag cgatggcaaa actttctcat 1800
atttggaagg gaccaagttt caccaggcgg ccaaggatat agcagaaatt aatgccatgt 1860
ggcccgttgc aacggaggcc aatgagcagg tatgcatgta tatcctcgga gaaagcatga 1920
gcagtattag gtcgaaatgc cccgtcgaag agtcggaagc ctccacacca cctagcacgc 1980
tgccttgctt gtgcatccat gccatgactc cagaaagagt acagcgccta aaagcctcac 2040
gtccagaaca aattactgtg tgctcatcct ttccattgcc gaagtataga atcactggtg 2100
tgcagaagat ccaatgctcc cagcctatat tgttctcacc gaaagtgcct gcgtatattc 2160
atccaaggaa gtatctcgtg gaaacaccac cggtagacga gactccggag ccatcggcag 2220
agaaccaatc cacagagggg acacctgaac aaccaccact tataaccgag gatgagacca 2280
ggactagaac gcctgagccg atcatcatcg aagaggaaga agaggatagc ataagtttgc 2340
tgtcagatgg cccgacccac caggtgctgc aagtcgaggc agacattcac gggccgccct 2400
ctgtatctag ctcatcctgg tccattcctc atgcatccga ctttgatgtg gacagtttat 2460
ccatacttga caccctggag ggagctagcg tgaccagcgg ggcaacgtca gccgagacta 2520
actcttactt cgcaaagagt atggagtttc tggcgcgacc ggtgcctgcg cctcgaacag 2580
tattcaggaa ccctccacat cccgctccgc gcacaagaac accgtcactt gcacccagca 2640
gggcctgctc gagaaccagc ctagtttcca ccccgccagg cgtgaatagg gtgatcacta 2700
gagaggagct cgaggcgctt accccgtcac gcactcctag caggtcggtc tcgagaacca 2760
gcctggtctc caacccgcca ggcgtaaata gggtgattac aagagaggag tttgaggcgt 2820
tcgtagcaca acaacaatga cggtttgatg cgggtgcata catcttttcc tccgacaccg 2880
gtcaagggca tttacaacaa aaatcagtaa ggcaaacggt gctatccgaa gtggtgttgg 2940
agaggaccga attggagatt tcgtatgccc cgcgcctcga ccaagaaaaa gaagaattac 3000
tacgcaagaa attacagtta aatcccacac ctgctaacag aagcagatac cagtccagga 3060
aggtggagaa catgaaagcc ataacagcta gacgtattct gcaaggccta gggcattatt 3120
tgaaggcaga aggaaaagtg gagtgctacc gaaccctgca tcctgttcct ttgtattcat 3180
ctagtgtgaa ccgtgccttt tcaagcccca aggtcgcagt ggaagcctgt aacgccatgt 3240
tgaaagagaa ctttccgact gtggcttctt actgtattat tccagagtac gatgcctatt 3300
tggacatggt tgacggagct tcatgctgct tagacactgc cagtttttgc cctgcaaagc 3360
tgcgcagctt tccaaagaaa cactcctatt tggaacccac aatacgatcg gcagtgcctt 3420
cagcgatcca gaacacgctc cagaacgtcc tggcagctgc cacaaaaaga aattgcaatg 3480
tcacgcaaat gagagaattg cccgtattgg attcggcggc ctttaatgtg gaatgcttca 3540
agaaatatgc gtgtaataat gaatattggg aaacgtttaa agaaaacccc atcaggctta 3600
ctgaagaaaa cgtggtaaat tacattacca aattaaaagg accaaaagct gctgctcttt 3660
ttgcgaagac acataatttg aatatgttgc aggacatacc aatggacagg tttgtaatgg 3720
acttaaagag agacgtgaaa gtgactccag gaacaaaaca tactgaagaa cggcccaagg 3780
tacaggtgat ccaggctgcc gatccgctag caacagcgta tctgtgcgga atccaccgag 3840
agctggttag gagattaaat gcggtcctgc ttccgaacat tcatacactg tttgatatgt 3900
cggctgaaga ctttgacgct attatagccg agcacttcca gcctggggat tgtgttctgg 3960
aaactgacat cgcgtcgttt gataaaagtg aggacgacgc catggctctg accgcgttaa 4020
tgattctgga agacttaggt gtggacgcag agctgttgac gctgattgag gcggctttcg 4080
gcgaaatttc atcaatacat ttgcccacta aaactaaatt taaattcgga gccatgatga 4140
aatctggaat gttcctcaca ctgtttgtga acacagtcat taacattgta atcgcaagca 4200
gagtgttgag agaacggcta accggatcac catgtgcagc attcattgga gatgacaata 4260
tcgtgaaagg agtcaaatcg gacaaattaa tggcagacag gtgcgccacc tggttgaata 4320
tggaagtcaa gattatagat gctgtggtgg gcgagaaagc gccttatttc tgtggagggt 4380
ttattttgtg tgactccgtg accggcacag cgtgccgtgt ggcagacccc ctaaaaaggc 4440
tgtttaagct tggcaaacct ctggcagcag acgatgaaca tgatgatgac aggagaaggg 4500
cattgcatga agagtcaaca cgctggaacc gagtgggtat tctttcagag ctgtgcaagg 4560
cagtagaatc aaggtatgaa accgtaggaa cttccatcat agttatggcc atgactactc 4620
tagctagcag tgttaaatca ttcagctacc tgagaggggc ccctataact ctctacggct 4680
aacctgaatg gactacgaca tagtctagtc cgccaagtct agcatatggc caccatgttc 4740
gtgtttctgg tgctgctgcc tctggtgtcc agccagtgtg tgaacttcac caccagaaca 4800
cagctgcctc cagcctacac caacagcttt accagaggcg tgtactaccc cgacaaggtg 4860
ttcagatcca gcgtgctgca ctctacccag gacctgttcc tgcctttctt cagcaacgtg 4920
acctggttcc acgccatcca cgtgtccggc accaatggca ccaagagatt cgccaacccc 4980
gtgctgccct tcaacgacgg ggtgtacttt gccagcaccg agaagtccaa catcatcaga 5040
ggctggatct tcggcaccac actggacagc aagacccaga gcctgctgat cgtgaacaac 5100
gccaccaacg tggtcatcaa agtgtgcgag ttccagttct gcaacgaccc cttcctgggc 5160
gtctactacc acaagaacaa caagagctgg atggaaagcg agttccgggt gtacagcagc 5220
gccaacaact gcaccttcga gtacgtgtcc cagcctttcc tgatggacct ggaaggcaag 5280
cagggcaact tcaagaacct gcgcgagttc gtgttcaaga acatcgacgg ctacttcaag 5340
atctacagca agcacacccc tatcaacctc gtgcggggtc tgcctcaggg cttctctgct 5400
ctggaacccc tggtggatct gcccatcggc atcaacatca cccggtttca gacactgcac 5460
ataagctacc tgacacctgg cgatagcagc agcggatgga cagctggtgc cgccgcttac 5520
tatgtgggct acctgcagcc tagaaccttc ctgctgaagt acaacgagaa cggcaccatc 5580
accgacgccg tggattgtgc ccttgatcct ctgagcgaga caaagtgcac cctgaagtcc 5640
ttcaccgtgg aaaagggcat ctaccagacc agcaacttcc gggtgcagcc caccgaatcc 5700
atcgtgcggt tccccaatat caccaatctg tgccccttcg gcgaggtgtt caatgccacc 5760
agattcgcct ctgtgtacgc ctggaaccgg aagcggatca gcaattgcgt ggccgactac 5820
tccgtgctgt acaactccgc cagcttcagc accttcaagt gctacggcgt gtcccctacc 5880
aagctgaacg acctgtgctt cacaaacgtg tacgccgaca gcttcgtgat ccggggagat 5940
gaagtgcggc agattgcccc tggacagaca ggcaatatcg ccgactacaa ctacaagctg 6000
cccgacgact tcaccggctg tgtgattgcc tggaacagca acaacctgga ctccaaagtc 6060
ggcggcaact acaattacct gtaccggctg ttccggaagt ccaatctgaa gcccttcgag 6120
cgggacatct ccaccgagat ctatcaggcc ggcagcaccc cttgtaacgg cgtgaaaggc 6180
ttcaactgct acttcccact gcagtcctac ggctttcagc ccacatatgg cgtgggctat 6240
cagccctaca gagtggtggt gctgagcttc gaactgctgc atgcccctgc cacagtgtgc 6300
ggccctaaga aaagcaccaa tctcgtgaag aacaaatgcg tgaacttcaa cttcaacggc 6360
ctgaccggca caggcgtgct gacagagagc aacaagaagt tcctgccatt ccagcagttt 6420
ggccgggata tcgccgatac cacagacgcc gttagagatc cccagacact ggaaatcctg 6480
gacatcaccc cttgcagctt cggcggagtg tctgtgatca cccctggcac caacaccagc 6540
aatcaggtgg cagtgctgta ccaggacgtg aactgtaccg aagtgcccgt ggccattcac 6600
gccgatcagc tgacacctac atggcgggtg tactccaccg gcagcaatgt gtttcagacc 6660
agagccggct gtctgatcgg agccgagcac gtgaacaata gctacgagtg cgacatcccc 6720
atcggcgctg gcatctgtgc cagctaccag acacagacaa acagcccctc tctggccagc 6780
tctgtggcca gccagagcat cattgcctac acaatgtctc tgggcgtcga gaacagcgtg 6840
gcctactcca acaactctat cgctatcccc accaacttca ccatcagcgt gaccacagag 6900
atcctgcctg tgtccatgac caagaccagc gtggactgca ccatgtacat ctgcggcgat 6960
tccaccgagt gctccaacct gctgctgcag tacggcagct tctgcaccca gctgaataga 7020
gccctgacag ggatcgccgt ggaacaggac aagaacaccc aagaggtgtt cgcccaagtg 7080
aagcagatct acaagacccc tcctatcaag gacttcggcg gcttcaattt cagccagatt 7140
ctgcccgatc ctagcaagcc cagcaagcgg agccccatcg aggacctgct gttcaacaaa 7200
gtgacactgg ccgacgccgg cttcatcaag cagtatggcg attgtctggg cgacattgcc 7260
gccagggatc tgatttgcgc ccagaagttt aacggactga cagtgctgcc tcctctgctg 7320
accgatgaga tgatcgccca gtacacatct gccctgctgg ccggcacaat cacaagcggc 7380
tggacatttg gagctggccc cgctctgcag atcccctttc ctatgcagat ggcctacaga 7440
ttcaacggca tcggagtgac ccagaatgtg ctgtacgaga accagaagct gatcgccaac 7500
cagttcaaca gcgccatcgg caagatccag gacagcctga gcagcacacc aagcgccctg 7560
ggaaagctgc aggacgtggt caaccagaat gcccaggcac tgaacaccct ggtcaagcag 7620
ctgtcctcca acttcggcgc catcagctct gtgctgaacg atatcctgag cagactggac 7680
cctcctgagg ccgaggtgca gatcgacaga ctgatcacag gcagactgca gagcctccag 7740
acatacgtga cccagcagct gatcagagcc gccgagatta gagcctctgc caatctggcc 7800
gccaccaaga tgtctgagtg tgtgctgggc cagagcaaga gagtggactt ttgcggcaag 7860
ggctaccacc tgatgagctt ccctcagtct gcccctcacg gcgtggtgtt tctgcacgtg 7920
acatacgttc ccgctcaaga gaagaatttc accaccgctc cagccatctg ccacgacggc 7980
aaagcccact ttcctagaga aggcgtgttc gtgtccaacg gcacccattg gttcgtgaca 8040
cagcggaact tctacgagcc ccagatcatc accaccgaca acaccttcgt gtctggcaac 8100
tgcgacgtcg tgatcggcat tgtgaacaat accgtgtacg accctctgca gcccgagctg 8160
gacagcttca aagaggaact ggacaagtac tttaagaacc acacaagccc cgacgtggac 8220
ctgggcgata tcagcggaat caatgccagc gtcgtgaaca tccagaaaga gatcgaccgg 8280
ctgaacgagg tggccaagaa tctgaacgag agcctgatcg acctgcaaga actggggaag 8340
tacgagcagt acatcaagtg gccctggtac atctggctgg gctttatcgc cggactgatt 8400

-continued

```
gccatcgtga tggtcacaat catgctgtgt tgcatgacca gctgctgtag ctgcctgaag   8460
ggctgttgta gctgtggcag ctgctgcaag ttcgacgagg acgattctga gcccgtgctg   8520
aagggcgtga aactgcacta cacatgagcg gccgcgaatt ggcaagctgc ttacatagaa   8580
ctcgcggcga ttggcatgcc gccttaaaat ttttatttta tttttctttt cttttccgaa   8640
tcggattttg tttttaatat ttcaaaaaaa aaaaaaaaaa aaaaaaaaaa aaaaaaaacg   8700
cgtcgagggg aattaattct tgaagacgaa agggccaggt ggcacttttc ggggaaatgt   8760
gcgcggaacc cctatttgtt tatttttcta aatacattca aatatgtatc cgctcatgag   8820
acaataaccc tgataaatgc ttcaataata ttgaaaaagg aagagtatga gtattcaaca   8880
tttccgtgtc gcccttattc cctttttgc ggcattttgc cttcctgttt ttgctcaccc   8940
agaaacgctg gtgaaagtaa aagatgctga agatcagttg ggtgcacgag tgggttacat   9000
cgaactggat ctcaacagcg gtaagatcct tgagagtttt cgccccgaag aacgttttcc   9060
aatgatgagc acttttaaag ttctgctatg tggcgcggta ttatcccgtg ttgacgccgg   9120
gcaagagcaa ctcggtcgcc gcatacacta ttctcagaat gacttggttg agtactcacc   9180
agtcacagaa aagcatctta cggatggcat gacagtaaga gaattatgca gtgctgccat   9240
aaccatgagt gataacactg cggccaactt acttctgaca acgatcggag gaccgaagga   9300
gctaaccgct tttttgcaca acatggggga tcatgtaact cgccttgatc gttgggaacc   9360
ggagctgaat gaagccatac caaacgacga gcgtgacacc acgatgcctg tagcaatggc   9420
aacaacgttg cgcaaactat taactggcga actacttact ctagcttccc ggcaacaatt   9480
aatagactgg atggaggcgg ataaagttgc aggaccactt ctgcgctcgg cccttccggc   9540
tggctggttt attgctgata aatctggagc cggtgagcgt gggtctcgcg gtatcattgc   9600
agcactgggg ccagatggta agccctcccg tatcgtagtt atctacacga cggggagtca   9660
ggcaactatg gatgaacgaa atagacagat cgctgagata ggtgcctcac tgattaagca   9720
ttggtaactg tcagaccaag tttactcata tatactttag attgatttaa aacttcattt   9780
ttaatttaaa aggatctagg tgaagatcct ttttgataat ctcatgacca aaatccctta   9840
acgtgagttt tcgttccact gagcgtcaga ccccgtagaa aagatcaaag gatcttcttg   9900
agatcctttt tttctgcgcg taatctgctg cttgcaaaca aaaaaaccac cgctaccagc   9960
ggtggtttgt ttgccggatc aagagctacc aactcttttt ccgaaggtaa ctggcttcag  10020
cagagcgcag ataccaaata ctgtccttct agtgtagccg tagttaggcc accacttcaa  10080
gaactctgta gcaccgccta catacctcgc tctgctaatc ctgttaccag tggctgctgc  10140
cagtggcgat aagtcgtgtc ttaccgggtt ggactcaaga cgatagttac cggataaggc  10200
gcagcggtcg ggctgaacgg ggggttcgtg cacacagccc agcttggagc gaacgaccta  10260
caccgaactg agatacctac agcgtgagca ttgagaaagc gccacgcttc ccgaagggag  10320
aaaggcggac aggtatccgg taagcggcag ggtcggaaca ggagagcgca cgagggagct  10380
tccaggggga aacgcctggt atctttatag tcctgtcggg tttcgccacc tctgacttga  10440
gcgtcgattt ttgtgatgct cgtcaggggg gcggagccta tggaaaaacg ccattctaga  10500
atggcgcgcc cttaagggga gaataggagc cgcaacacac aagcaacgcg aggtcgttta  10560
aactaatacg actcactata atgggcggcg catgagagaa gcccagacca attacctacc  10620
caaaatggag aaagttcacg ttgacatcga ggaagacagc ccattcctca gagctttgca  10680
gcggagcttc ccgcagtttg aggtagaagc caagcaggtc actgataatg accatgctaa  10740
tgccagagcg ttttcgcatc tggcttcaaa actgatcgaa acggaggtgg acccatccga  10800
```

```
cacgatcctt gacattggaa gtgcgcccgc ccgcagaatg tattctaagc acaagtatca  10860
ttgtatctgt ccgatgagat gtgcggaaga tccggacaga ttgtataagt atgcaactaa  10920
gctgaagaaa aactgtaagg aaataactga taaggaattg gacaagaaaa tgaaggagct  10980
ggccgccgtc atgagcgacc ctgacctgga aactgagact atgtgcctcc acgacgacga  11040
gtcgtgtcgc tacgaagggc aagtcgctgt ttaccaggat gtatacgcgg ttgacggacc  11100
gacaagtctc tatcaccaag ccaataaggg agttagagtc gcctactgga taggctttga  11160
caccacccct tttatgttta agaacttggc tggagcatat ccatcatact ctaccaactg  11220
ggccgacgaa accgtgttaa cggctcgtaa cataggccta tgcagctctg acgttatgga  11280
gcggtcacgt agagggatgt ccattcttag aaagaagtat ttgaaaccat ccaacaatgt  11340
tctattctct gttggctcga ccatctacca cgagaagagg gacttactga ggagctggca  11400
cctgccgtct gtatttcact tacgtggcaa gcaaaattac acatgtcggt gtgagactat  11460
agttagttgc gacgggtacg tcgttaaaag aatagctatc agtccaggcc tgtatgggaa  11520
gccttcaggc tatgctgcta cgatgcaccg cgagggattc ttgtgctgca aagtgacaga  11580
cacattgaac ggggagaggg tctcttttcc cgtgtgcacg tatgtgccag ctacattgtg  11640
tgaccaaatg actggcatac tggcaacaga tgtcagtgcg gacgacgcgc aaaaactgct  11700
ggttgggctc aaccagcgta tagtcgtcaa cggtcgcacc cagagaaaca ccaataccat  11760
gaaaaattac cttttgcccg tagtggccca ggcatttgct aggtgggcaa aggaatataa  11820
ggaagatcaa gaagatgaaa ggccactagg actacgagat agacagttag tcatggggtg  11880
ttgttgggct tttagaaggc acaagataac atctatttat aagcgcccgg atacccaaac  11940
catcatcaaa gtgaacagcg atttccactc attcgtgctg cccaggatag gcagtaacac  12000
attggagatc gggctgagaa caagaatcag gaaaatgtta gaggagcaca aggagccgtc  12060
acctctcatt accgccgagg acgtacaaga agctaagtgc gcagccgatg aggctaagga  12120
ggtgcgtgaa gccgaggagt tgcgcgcagc tctaccacct ttggcagctg atgttgagga  12180
gcccactctg gaggcagacg tcgacttgat gttacaagag gctggggccg gctcagtgga  12240
gacacctcgt ggcttgataa aggttaccag ctacgatggc gaggacaaga tcggctctta  12300
cgctgtgctt tctccgcagg ctgtactcaa gagtgaaaaa ttatcttgca tccaccctct  12360
cgctgaacaa gtcatagtga taacacactc tggccgaaaa gggcgttatg ccgtggaacc  12420
ataccatggt aaagtagtgg tgccagaggg acatgcaata cccgtccagg actttcaagc  12480
tctgagtgaa agtgccacca ttgtgtacaa cgaacgtgag ttcgtaaaca ggtacctgca  12540
ccatattgcc acacatggag gagcgctgaa cactgatgaa gaatattaca aaactgtcaa  12600
gcccagcgag cacgacggcg aatacctgta cgacatcgac aggaaacagt gcgtcaagaa  12660
agaactagtc actgggctag ggctcacagg cgagctggtg gatcctccct tccatgaatt  12720
cgcctacgag agtctgagaa cacgaccagc cgctccttac caagtaccaa ccataggggt  12780
gtatggcgtg ccaggatcag gcaagtctgg catcattaaa agcgcagtca ccaaaaaaga  12840
tctagtggtg agcgccaaga aagaaaactg tgcagaaatt ataagggacg tcaagaaaat  12900
gaaagggctg gacgtcaatg ccagaactgt ggactcagtg ctcttgaatg gatgcaaaca  12960
ccccgtagag accctgtata ttgacgaagc ttttgcttgt catgcaggta ctctcagagc  13020
gctcatagcc attataagac ctaaaaaggc agtgctctgc ggggatccca aacagtgcgg  13080
ttttttttaac atgatgtgcc tgaaagtgca ttttaaccac gagatttgca cacaagtctt  13140
```

```
ccacaaaagc atctctcgcc gttgcactaa atctgtgact tcggtcgtct caaccttgtt  13200

ttacgacaaa aaaatgagaa cgacgaatcc gaaagagact aagattgtga ttgacactac  13260

cggcagtacc aaacctaagc aggacgatct cattctcact tgtttcagag ggtgggtgaa  13320

gcagttgcaa atagattaca aaggcaacga aataatgacg gcagctgcct ctcaagggct  13380

gacccgtaaa ggtgtgtatg ccgttcggta caaggtgaat gaaa                   13424
```

<210> SEQ ID NO 75
<211> LENGTH: 13433
<212> TYPE: DNA
<213> ORGANISM: Artificial Sequence
<220> FEATURE:
<223> OTHER INFORMATION: Synthetised Sequence

<400> SEQUENCE: 75

```
atcctctgta cgcacccacc tcagaacatg tgaacgtcct actgacccgc acggaggacc     60

gcatcgtgtg gaaaacacta gccggcgacc catggataaa aacactgact gccaagtacc    120

ctgggaattt cactgccacg atagaggagt ggcaagcaga gcatgatgcc atcatgaggc    180

acatcttgga gagaccggac cctaccgacg tcttccagaa taaggcaaac gtgtgttggg    240

ccaaggcttt agtgccggtg ctgaagaccg ctggcataga catgaccact gaacaatgga    300

acactgtgga ttattttgaa acggacaaag ctcactcagc agagatagta ttgaaccaac    360

tatgcgtgag gttctttgga ctcgatctgg actccggtct attttctgca cccactgttc    420

cgttatccat taggaataat cactgggata actccccgtc gcctaacatg tacgggctga    480

ataaagaagt ggtccgtcag ctctctcgca ggtacccaca actgcctcgg gcagttgcca    540

ctggaagagt ctatgacatg aacactggta cactgcgcaa ttatgatccg cgcataaacc    600

tagtacctgt aaacagaaga ctgcctcatg ctttagtcct ccaccataat gaacacccac    660

agagtgactt ttcttcattc gtcagcaaat tgaagggcag aactgtcctg gtggtcgggg    720

aaaagttgtc cgtcccaggc aaaatggttg actggttgtc agaccggcct gaggctacct    780

tcagagctcg gctggattta ggcatcccag gtgatgtgcc caaatatgac ataatatttg    840

ttaatgtgag gaccccatat aaataccatc actatcagca gtgtgaagac catgccatta    900

agcttagcat gttgaccaag aaagcttgtc tgcatctgaa tcccggcgga acctgtgtca    960

gcataggtta tggttacgct gacagggcca gcgaaagcat cattggtgct atagcgcggc   1020

agttcaagtt ttcccgggta tgcaaaccga aatcctcact tgaagagacg gaagttctgt   1080

ttgtattcat tgggtacgat cgcaaggccc gtacgcacaa ttcttacaag ctttcatcaa   1140

ccttgaccaa catttataca ggttccagac tccacgaagc cggatgtgca ccctcatatc   1200

atgtggtgcg aggggatatt gccacggcca ccgaaggagt gattataaat gctgctaaca   1260

gcaaaggaca acctggcgga ggggtgtgcg gagcgctgta taagaaattc ccggaaagct   1320

tcgatttaca gccgatcgaa gtaggaaaag cgcgactggt caaaggtgca gctaaacata   1380

tcattcatgc cgtaggacca aacttcaaca aagtttcgga ggttgaaggt gacaaacagt   1440

tggcagaggc ttatgagtcc atcgctaaga ttgtcaacga taacaattac aagtcagtag   1500

cgattccact gttgtccacc ggcatctttt ccgggaacaa agatcgacta acccaatcat   1560

tgaaccattt gctgacagct ttagacacca ctgatgcaga tgtagccata tactgcaggg   1620

acaagaaatg ggaaatgact ctcaaggaag cagtggctag gagagaagca gtggaggaga   1680

tatgcatatc cgacgactct tcagtgacag aacctgatgc agagctggtg agggtgcatc   1740

cgaagagttc tttggctgga aggaagggct acagcacaag cgatggcaaa actttctcat   1800
```

atttggaagg gaccaagttt caccaggcgg ccaaggatat agcagaaatt aatgccatgt 1860
ggcccgttgc aacggaggcc aatgagcagg tatgcatgta tatcctcgga gaaagcatga 1920
gcagtattag gtcgaaatgc cccgtcgaag agtcggaagc ctccacacca cctagcacgc 1980
tgccttgctt gtgcatccat gccatgactc cagaaagagt acagcgccta aaagcctcac 2040
gtccagaaca aattactgtg tgctcatcct ttccattgcc gaagtataga atcactggtg 2100
tgcagaagat ccaatgctcc cagcctatat tgttctcacc gaaagtgcct gcgtatattc 2160
atccaaggaa gtatctcgtg gaaacaccac cggtagacga gactccggag ccatcggcag 2220
agaaccaatc cacagagggg acacctgaac aaccaccact tataaccgag gatgagacca 2280
ggactagaac gcctgagccg atcatcatcg aagaggaaga agaggatagc ataagtttgc 2340
tgtcagatgg cccgacccac caggtgctgc aagtcgaggc agacattcac gggccgccct 2400
ctgtatctag ctcatcctgg tccattcctc atgcatccga ctttgatgtg gacagtttat 2460
ccatacttga caccctggag ggagctagcg tgaccagcgg ggcaacgtca gccgagacta 2520
actcttactt cgcaaagagt atggagtttc tggcgcgacc ggtgcctgcg cctcgaacag 2580
tattcaggaa ccctccacat cccgctccgc gcacaagaac accgtcactt gcacccagca 2640
gggcctgctc gagaaccagc ctagtttcca ccccgccagg cgtgaatagg gtgatcacta 2700
gagaggagct cgaggcgctt accccgtcac gcactcctag caggtcggtc tcgagaacca 2760
gcctggtctc caacccgcca ggcgtaaata gggtgattac aagagaggag tttgaggcgt 2820
tcgtagcaca acaacaatga cggtttgatg cgggtgcata catcttttcc tccgacaccg 2880
gtcaagggca tttacaacaa aaatcagtaa ggcaaacggt gctatccgaa gtggtgttgg 2940
agaggaccga attggagatt tcgtatgccc cgcgcctcga ccaagaaaaa gaagaattac 3000
tacgcaagaa attacagtta aatcccacac ctgctaacag aagcagatac cagtccagga 3060
aggtggagaa catgaaagcc ataacagcta gacgtattct gcaaggccta gggcattatt 3120
tgaaggcaga aggaaaagtg gagtgctacc gaaccctgca tcctgttcct ttgtattcat 3180
ctagtgtgaa ccgtgccttt tcaagcccca aggtcgcagt ggaagcctgt aacgccatgt 3240
tgaaagagaa ctttccgact gtggcttctt actgtattat tccagagtac gatgcctatt 3300
tggacatggt tgacggagct tcatgctgct tagacactgc cagtttttgc cctgcaaagc 3360
tgcgcagctt tccaaagaaa cactcctatt tggaacccac aatacgatcg gcagtgcctt 3420
cagcgatcca gaacacgctc cagaacgtcc tggcagctgc cacaaaaaga aattgcaatg 3480
tcacgcaaat gagagaattg cccgtattgg attcggcggc ctttaatgtg gaatgcttca 3540
agaaatatgc gtgtaataat gaatattggg aaacgtttaa agaaaacccc atcaggctta 3600
ctgaagaaaa cgtggtaaat tacattacca aattaaaagg accaaaagct gctgctcttt 3660
ttgcgaagac acataatttg aatatgttgc aggacatacc aatggacagg tttgtaatgg 3720
acttaaagag agacgtgaaa gtgactccag gaacaaaaca tactgaagaa cggcccaagg 3780
tacaggtgat ccaggctgcc gatccgctag caacagcgta tctgtgcgga atccaccgag 3840
agctggttag gagattaaat gcggtcctgc ttccgaacat tcatacactg tttgatatgt 3900
cggctgaaga ctttgacgct attatagccg agcacttcca gcctggggat tgtgttctgg 3960
aaactgacat cgcgtcgttt gataaaagtg aggacgacgc catggctctg accgcgttaa 4020
tgattctgga agacttaggt gtggacgcag agctgttgac gctgattgag gcggctttcg 4080
gcgaaatttc atcaatacat ttgcccacta aaactaaatt taaattcgga gccatgatga 4140

-continued

```
aatctggaat gttcctcaca ctgtttgtga acacagtcat taacattgta atcgcaagca   4200
gagtgttgag agaacggcta accggatcac catgtgcagc attcattgga gatgacaata   4260
tcgtgaaagg agtcaaatcg gacaaattaa tggcagacag gtgcgccacc tggttgaata   4320
tggaagtcaa gattatagat gctgtggtgg gcgagaaagc gccttatttc tgtggagggt   4380
ttattttgtg tgactccgtg accggcacag cgtgccgtgt ggcagacccc ctaaaaaggc   4440
tgtttaagct tggcaaacct ctggcagcag acgatgaaca tgatgatgac aggagaaggg   4500
cattgcatga agagtcaaca cgctggaacc gagtgggtat tctttcagag ctgtgcaagg   4560
cagtagaatc aaggtatgaa accgtaggaa cttccatcat agttatggcc atgactactc   4620
tagctagcag tgttaaatca ttcagctacc tgagaggggc ccctataact ctctacggct   4680
aacctgaatg gactacgaca tagtctagtc cgccaagtct agcatatggc caccatgttc   4740
gtgtttctgg tgctgctgcc tctggtgtcc agccagtgtg tgaacttcac caacagaaca   4800
cagctgcctt tcgcctacac caacagcttt accagaggcg tgtactaccc cgacaaggtg   4860
ttcagatcca gcgtgctgca ctctacccag gacctgttcc tgcctttctt cagcaacgtg   4920
acctggttcc acgccatcca cgtgtccggc accaatggca ccaagagatt cgacaacccc   4980
gtgctgccct tcaacgacgg ggtgtacttt gccagcaccg agaagtccaa catcatcaga   5040
ggctggatct tcggcaccac actggacagc aagacccaga gcctgctgat cgtgaacaac   5100
gccaccaacg tggtcatcaa agtgtgcgag ttccagttct gcaactaccc cttcctgggc   5160
gtctactacc acaagaacaa caagagctgg atggaaagcg agttccgggt gtacagcagc   5220
gccaacaact gcaccttcga gtacgtgtcc cagcctttcc tgatggacct ggaaggcaag   5280
cagggcaact tcaagaacct gagcgagttc gtgttcaaga acatcgacgg ctacttcaag   5340
atctacagca agcacacccc tatcaacctc gtgcgggatc tgcctcaggg cttctctgct   5400
ctggaacccc tggtggatct gcccatcggc atcaacatca cccggtttca gacactgctg   5460
gccctgcaca gaagctacct gacacctggc gatagcagca gcggatggac agctggtgcc   5520
gccgcttact atgtgggcta cctgcagcct agaaccttcc tgctgaagta caacgagaac   5580
ggcaccatca ccgacgccgt ggattgtgcc cttgatcctc tgagcgagac aaagtgcacc   5640
ctgaagtcct tcaccgtgga aaagggcatc taccagacca gcaacttccg ggtgcagccc   5700
accgaatcca tcgtgcggtt ccccaatatc accaatctgt gccccttcgg cgaggtgttc   5760
aatgccacca gattcgcctc tgtgtacgcc tggaaccgga agcggatcag caattgcgtg   5820
gccgactact ccgtgctgta caactccgcc agcttcagca ccttcaagtg ctacggcgtg   5880
tcccctacca agctgaacga cctgtgcttc acaaacgtgt acgccgacag cttcgtgatc   5940
cggggagatg aagtgcggca gattgcccct ggacagacag gcacgatcgc cgactacaac   6000
tacaagctgc ccgacgactt caccggctgt gtgattgcct ggaacagcaa caacctggac   6060
tccaaagtcg gcggcaacta caattacctg taccggctgt tccggaagtc caatctgaag   6120
cccttcgagc gggacatctc caccgagatc tatcaggccg gcagcacccc ttgtaacggc   6180
gtgaaaggct tcaactgcta cttcccactg cagtcctacg gctttcagcc cacatatggc   6240
gtgggctatc agccctacag agtggtggtg ctgagcttcg aactgctgca tgcccctgcc   6300
acagtgtgcg gccctaagaa aagcaccaat ctcgtgaaga acaaatgcgt gaacttcaac   6360
ttcaacggcc tgaccggcac aggcgtgctg acagagagca acaagaagtt cctgccattc   6420
cagcagtttg gccgggatat cgccgatacc acagacgccg ttagagatcc ccagacactg   6480
gaaatcctgg acatcacccc ttgcagcttc ggcggagtgt ctgtgatcac ccctggcacc   6540
```

-continued

```
aacaccagca atcaggtggc agtgctgtac cagggcgtga actgtaccga agtgcccgtg   6600
gccattcacg ccgatcagct gacacctaca tggcgggtgt actccaccgg cagcaatgtg   6660
tttcagacca gagccggctg tctgatcgga gccgagtacg tgaacaatag ctacgagtgc   6720
gacatcccca tcggcgctgg catctgtgcc agctaccaga cacagacaaa cagcccctct   6780
ctggccagct ctgtggccag ccagagcatc attgcctaca caatgtctct gggcgccgag   6840
aacagcgtgg cctactccaa caactctatc gctatcccca ccaacttcac catcagcgtg   6900
accacagaga tcctgcctgt gtccatgacc aagaccagcg tggactgcac catgtacatc   6960
tgcggcgatt ccaccgagtg ctccaacctg ctgctgcagt acggcagctt ctgcacccag   7020
ctgaatagag ccctgacagg gatcgccgtg gaacaggaca agaacaccca agaggtgttc   7080
gcccaagtga agcagatcta caagacccct cctatcaagg acttcggcgg cttcaatttc   7140
agccagattc tgcccgatcc tagcaagccc agcaagcgga gccccatcga ggacctgctg   7200
ttcaacaaag tgacactggc cgacgccggc ttcatcaagc agtatggcga ttgtctgggc   7260
gacattgccg ccagggatct gatttgcgcc cagaagttta acggactgac agtgctgcct   7320
cctctgctga ccgatgagat gatcgcccag tacacatctg ccctgctggc cggcacaatc   7380
acaagcggct ggacatttgg agctggcccc gctctgcaga tcccctttcc tatgcagatg   7440
gcctacagat tcaacggcat cggagtgacc cagaatgtgc tgtacgagaa ccagaagctg   7500
atcgccaacc agttcaacag cgccatcggc aagatccagg acagcctgag cagcacacca   7560
agcgccctgg gaaagctgca ggacgtggtc aaccagaatg cccaggcact gaacaccctg   7620
gtcaagcagc tgtcctccaa cttcggcgcc atcagctctg tgctgaacga tatcctgagc   7680
agactggacc ctcctgaggc cgaggtgcag atcgacagac tgatcacagg cagactgcag   7740
agcctccaga catacgtgac ccagcagctg atcagagccg ccgagattag agcctctgcc   7800
aatctggccg ccatcaagat gtctgagtgt gtgctgggcc agagcaagag agtggacttt   7860
tgcggcaagg gctaccacct gatgagcttc cctcagtctg cccctcacgg cgtggtgttt   7920
ctgcacgtga catacgttcc cgctcaagag aagaatttca ccaccgctcc agccatctgc   7980
cacgacggca aagcccactt tcctagagaa ggcgtgttcg tgtccaacgg cacccattgg   8040
ttcgtgacac agcggaactt ctacgagccc cagatcatca ccaccgacaa caccttcgtg   8100
tctggcaact gcgacgtcgt gatcggcatt gtgaacaata ccgtgtacga ccctctgcag   8160
cccgagctgg acagcttcaa agaggaactg gacaagtact ttaagaacca cacaagcccc   8220
gacgtggacc tgggcgatat cagcggaatc aatgccagct tcgtgaacat ccagaaagag   8280
atcgaccggc tgaacgaggt ggccaagaat ctgaacgaga gcctgatcga cctgcaagaa   8340
ctggggaagt acgagcagta catcaagtgg ccctggtaca tctggctggg ctttatcgcc   8400
ggactgattg ccatcgtgat ggtcacaatc atgctgtgtt gcatgaccag ctgctgtagc   8460
tgcctgaagg gctgttgtag ctgtggcagc tgctgcaagt tcgacgagga cgattctgag   8520
cccgtgctga agggcgtgaa actgcactac acatgagcgg ccgcgaattg gcaagctgct   8580
tacatagaac tcgcggcgat tggcatgccg ccttaaaatt tttattttat tttcttttc    8640
ttttccgaat cggattttgt ttttaatatt tcaaaaaaaa aaaaaaaaaa aaaaaaaaaa   8700
aaaaaaacgc gtcgagggga attaattctt gaagacgaaa gggccaggtg gcacttttcg   8760
gggaaatgtg cgcggaaccc ctatttgttt atttttctaa atacattcaa atatgtatcc   8820
gctcatgaga caataaccct gataaatgct tcaataatat tgaaaaagga agagtatgag   8880
```

-continued

```
tattcaacat ttccgtgtcg cccttattcc cttttttgcg gcattttgcc ttcctgtttt   8940
tgctcaccca gaaacgctgg tgaaagtaaa agatgctgaa gatcagttgg gtgcacgagt   9000
gggttacatc gaactggatc tcaacagcgg taagatcctt gagagttttc gccccgaaga   9060
acgttttcca atgatgagca cttttaaagt tctgctatgt ggcgcggtat tatcccgtgt   9120
tgacgccggg caagagcaac tcggtcgccg catacactat tctcagaatg acttggttga   9180
gtactcacca gtcacagaaa agcatcttac ggatggcatg acagtaagag aattatgcag   9240
tgctgccata accatgagtg ataacactgc ggccaactta cttctgacaa cgatcggagg   9300
accgaaggag ctaaccgctt ttttgcacaa catgggggat catgtaactc gccttgatcg   9360
ttgggaaccg gagctgaatg aagccatacc aaacgacgag cgtgacacca cgatgcctgt   9420
agcaatggca acaacgttgc gcaaactatt aactggcgaa ctacttactc tagcttcccg   9480
gcaacaatta atagactgga tggaggcgga taaagttgca ggaccacttc tgcgctcggc   9540
ccttccggct ggctggttta ttgctgataa atctggagcc ggtgagcgtg ggtctcgcgg   9600
tatcattgca gcactggggc cagatggtaa gccctcccgt atcgtagtta tctacacgac   9660
ggggagtcag gcaactatgg atgaacgaaa tagacagatc gctgagatag gtgcctcact   9720
gattaagcat tggtaactgt cagaccaagt ttactcatat atactttaga ttgatttaaa   9780
acttcatttt taatttaaaa ggatctaggt gaagatcctt tttgataatc tcatgaccaa   9840
aatcccttaa cgtgagtttt cgttccactg agcgtcagac cccgtagaaa agatcaaagg   9900
atcttcttga gatccttttt ttctgcgcgt aatctgctgc ttgcaaacaa aaaaaccacc   9960
gctaccagcg gtggtttgtt tgccggatca agagctacca actctttttc cgaaggtaac  10020
tggcttcagc agagcgcaga taccaaatac tgtccttcta gtgtagccgt agttaggcca  10080
ccacttcaag aactctgtag caccgcctac atacctcgct ctgctaatcc tgttaccagt  10140
ggctgctgcc agtggcgata agtcgtgtct taccgggttg gactcaagac gatagttacc  10200
ggataaggcg cagcggtcgg gctgaacggg gggttcgtgc acacagccca gcttggagcg  10260
aacgacctac accgaactga gatacctaca gcgtgagcat tgagaaagcg ccacgcttcc  10320
cgaagggaga aaggcggaca ggtatccggt aagcggcagg gtcggaacag gagagcgcac  10380
gagggagctt ccagggggaa acgcctggta tctttatagt cctgtcgggt ttcgccacct  10440
ctgacttgag cgtcgatttt tgtgatgctc gtcagggggg cggagcctat ggaaaaacgc  10500
cattctagaa tggcgcgccc ttaaggggag aataggagcc gcaacacaca agcaacgcga  10560
ggtcgtttaa actaatacga ctcactataa tgggcggcgc atgagagaag cccagaccaa  10620
ttacctaccc aaaatggaga aagttcacgt tgacatcgag gaagacagcc cattcctcag  10680
agctttgcag cggagcttcc cgcagtttga ggtagaagcc aagcaggtca ctgataatga  10740
ccatgctaat gccagagcgt tttcgcatct ggcttcaaaa ctgatcgaaa cggaggtgga  10800
cccatccgac acgatccttg acattggaag tgcgcccgcc cgcagaatgt attctaagca  10860
caagtatcat tgtatctgtc cgatgagatg tgcggaagat ccggacagat tgtataagta  10920
tgcaactaag ctgaagaaaa actgtaagga aataactgat aaggaattgg acaagaaaat  10980
gaaggagctg gccgccgtca tgagcgaccc tgacctggaa actgagacta tgtgcctcca  11040
cgacgacgag tcgtgtcgct acgaagggca agtcgctgtt taccaggatg tatacgcggt  11100
tgacggaccg acaagtctct atcaccaagc caataaggga gttagagtcg cctactggat  11160
aggctttgac accacccctt ttatgtttaa gaacttggct ggagcatatc catcatactc  11220
taccaactgg gccgacgaaa ccgtgttaac ggctcgtaac ataggcctat gcagctctga  11280
```

-continued cgttatggag cggtcacgta gagggatgtc cattcttaga aagaagtatt tgaaaccatc 11340
caacaatgtt ctattctctg ttggctcgac catctaccac gagaagaggg acttactgag 11400
gagctggcac ctgccgtctg tatttcactt acgtggcaag caaaattaca catgtcggtg 11460
tgagactata gttagttgcg acgggtacgt cgttaaaaga atagctatca gtccaggcct 11520
gtatgggaag ccttcaggct atgctgctac gatgcaccgc gagggattct tgtgctgcaa 11580
agtgacagac acattgaacg gggagagggt ctcttttccc gtgtgcacgt atgtgccagc 11640
tacattgtgt gaccaaatga ctggcatact ggcaacagat gtcagtgcgg acgacgcgca 11700
aaaactgctg gttgggctca accagcgtat agtcgtcaac ggtcgcaccc agagaaacac 11760
caataccatg aaaaattacc ttttgcccgt agtggcccag gcatttgcta ggtgggcaaa 11820
ggaatataag gaagatcaag aagatgaaag gccactagga ctacgagata gacagttagt 11880
catggggtgt tgttgggctt ttagaaggca caagataaca tctatttata agcgcccgga 11940
tacccaaacc atcatcaaag tgaacagcga tttccactca ttcgtgctgc ccaggatagg 12000
cagtaacaca ttggagatcg ggctgagaac aagaatcagg aaaatgttag aggagcacaa 12060
ggagccgtca cctctcatta ccgccgagga cgtacaagaa gctaagtgcg cagccgatga 12120
ggctaaggag gtgcgtgaag ccgaggagtt gcgcgcagct ctaccacctt tggcagctga 12180
tgttgaggag cccactctgg aggcagacgt cgacttgatg ttacaagagg ctggggccgg 12240
ctcagtggag acacctcgtg gcttgataaa ggttaccagc tacgatggcg aggacaagat 12300
cggctcttac gctgtgcttt ctccgcaggc tgtactcaag agtgaaaaat tatcttgcat 12360
ccaccctctc gctgaacaag tcatagtgat aacacactct ggccgaaaag ggcgttatgc 12420
cgtggaacca taccatggta aagtagtggt gccagaggga catgcaatac ccgtccagga 12480
ctttcaagct ctgagtgaaa gtgccaccat tgtgtacaac gaacgtgagt tcgtaaacag 12540
gtacctgcac catattgcca cacatggagg agcgctgaac actgatgaag aatattacaa 12600
aactgtcaag cccagcgagc acgacggcga atacctgtac gacatcgaca ggaaacagtg 12660
cgtcaagaaa gaactagtca ctgggctagg gctcacaggc gagctggtgg atcctccctt 12720
ccatgaattc gcctacgaga gtctgagaac acgaccagcc gctccttacc aagtaccaac 12780
cataggggtg tatggcgtgc caggatcagg caagtctggc atcattaaaa gcgcagtcac 12840
caaaaaagat ctagtggtga gcgccaagaa agaaaactgt gcagaaatta taagggacgt 12900
caagaaaatg aaagggctgg acgtcaatgc cagaactgtg gactcagtgc tcttgaatgg 12960
atgcaaacac cccgtagaga ccctgtatat tgacgaagct tttgcttgtc atgcaggtac 13020
tctcagagcg ctcatagcca ttataagacc taaaaaggca gtgctctgcg gggatcccaa 13080
acagtgcggt ttttttaaca tgatgtgcct gaaagtgcat tttaaccacg agatttgcac 13140
acaagtcttc cacaaaagca tctctcgccg ttgcactaaa tctgtgactt cggtcgtctc 13200
aaccttgttt tacgacaaaa aaatgagaac gacgaatccg aaagagacta agattgtgat 13260
tgacactacc ggcagtacca aacctaagca ggacgatctc attctcactt gtttcagagg 13320
gtgggtgaag cagttgcaaa tagattacaa aggcaacgaa ataatgacgg cagctgcctc 13380
tcaagggctg acccgtaaag gtgtgtatgc cgttcggtac aaggtgaatg aaa 13433

<210> SEQ ID NO 76
<211> LENGTH: 13838
<212> TYPE: DNA
<213> ORGANISM: Artificial Sequence
<220> FEATURE:

<223> OTHER INFORMATION: Synthetised Sequence

<400> SEQUENCE: 76

```
atcctctgta cgcacccacc tcagaacatg tgaacgtcct actgacccgc acggaggacc     60
gcatcgtgtg gaaaacacta gccggcgacc catggataaa aacactgact gccaagtacc    120
ctgggaattt cactgccacg atagaggagt ggcaagcaga gcatgatgcc atcatgaggc    180
acatcttgga gagaccggac cctaccgacg tcttccagaa taaggcaaac gtgtgttggg    240
ccaaggcttt agtgccggtg ctgaagaccg ctggcataga catgaccact gaacaatgga    300
acactgtgga ttattttgaa acggacaaag ctcactcagc agagatagta ttgaaccaac    360
tatgcgtgag gttctttgga ctcgatctgg actccggtct attttctgca cccactgttc    420
cgttatccat taggaataat cactgggata actccccgtc gcctaacatg tacgggctga    480
ataaagaagt ggtccgtcag ctctctcgca ggtacccaca actgcctcgg gcagttgcca    540
ctggaagagt ctatgacatg aacactggta cactgcgcaa ttatgatccg cgcataaacc    600
tagtacctgt aaacagaaga ctgcctcatg ctttagtcct ccaccataat gaacacccac    660
agagtgactt ttcttcattc gtcagcaaat tgaagggcag aactgtcctg gtggtcgggg    720
aaaagttgtc cgtcccaggc aaaatggttg actggttgtc agaccggcct gaggctacct    780
tcagagctcg gctggattta ggcatcccag gtgatgtgcc caaatatgac ataatatttg    840
ttaatgtgag gaccccatat aaataccatc actatcagca gtgtgaagac catgccatta    900
agcttagcat gttgaccaag aaagcttgtc tgcatctgaa tcccggcgga acctgtgtca    960
gcataggtta tggttacgct gacagggcca gcgaaagcat cattggtgct atagcgcggc   1020
agttcaagtt ttcccgggta tgcaaaccga aatcctcact tgaagagacg gaagttctgt   1080
ttgtattcat tgggtacgat cgcaaggccc gtacgcacaa ttcttacaag ctttcatcaa   1140
ccttgaccaa catttataca ggttccagac tccacgaagc cggatgtgca ccctcatatc   1200
atgtggtgcg aggggatatt gccacggcca ccgaaggagt gattataaat gctgctaaca   1260
gcaaaggaca acctggcgga ggggtgtgcg gagcgctgta taagaaattc ccggaaagct   1320
tcgatttaca gccgatcgaa gtaggaaaag cgcgactggt caaaggtgca gctaaacata   1380
tcattcatgc cgtaggacca aacttcaaca aagtttcgga ggttgaaggt gacaaacagt   1440
tggcagaggc ttatgagtcc atcgctaaga ttgtcaacga taacaattac aagtcagtag   1500
cgattccact gttgtccacc ggcatctttt ccgggaacaa agatcgacta acccaatcat   1560
tgaaccattt gctgacagct ttagacacca ctgatgcaga tgtagccata tactgcaggg   1620
acaagaaatg ggaaatgact ctcaaggaag cagtggctag gagagaagca gtggaggaga   1680
tatgcatatc cgacgactct tcagtgacag aacctgatgc agagctggtg agggtgcatc   1740
cgaagagttc tttggctgga aggaagggct acagcacaag cgatggcaaa actttctcat   1800
atttggaagg gaccaagttt caccaggcgg ccaaggatat agcagaaatt aatgccatgt   1860
ggcccgttgc aacggaggcc aatgagcagg tatgcatgta tatcctcgga gaaagcatga   1920
gcagtattag gtcgaaatgc ccgtcgaag agtcggaagc ctccacacca cctagcacgc    1980
tgccttgctt gtgcatccat gccatgactc cagaaagagt acagcgccta aaagcctcac   2040
gtccagaaca aattactgtg tgctcatcct ttccattgcc gaagtataga atcactggtg   2100
tgcagaagat ccaatgctcc cagcctatat tgttctcacc gaaagtgcct gcgtatattc   2160
atccaaggaa gtatctcgtg gaaacaccac cggtagacga gactccggag ccatcggcag   2220
agaaccaatc cacagagggg acacctgaac aaccaccact tataaccgag gatgagacca   2280
```

ggactagaac gcctgagccg atcatcatcg aagaggaaga agaggatagc ataagtttgc 2340
tgtcagatgg cccgacccac caggtgctgc aagtcgaggc agacattcac gggccgccct 2400
ctgtatctag ctcatcctgg tccattcctc atgcatccga ctttgatgtg gacagtttat 2460
ccatacttga caccctggag ggagctagcg tgaccagcgg ggcaacgtca gccgagacta 2520
actcttactt cgcaaagagt atggagtttc tggcgcgacc ggtgcctgcg cctcgaacag 2580
tattcaggaa ccctccacat cccgctccgc gcacaagaac accgtcactt gcacccagca 2640
gggcctgctc gagaaccagc ctagtttcca ccccgccagg cgtgaatagg gtgatcacta 2700
gagaggagct cgaggcgctt accccgtcac gcactcctag caggtcggtc tcgagaacca 2760
gcctggtctc caacccgcca ggcgtaaata gggtgattac aagagaggag tttgaggcgt 2820
tcgtagcaca acaacaatga cggtttgatg cgggtgcata catcttttcc tccgacaccg 2880
gtcaagggca tttacaacaa aaatcagtaa ggcaaacggt gctatccgaa gtggtgttgg 2940
agaggaccga attggagatt tcgtatgccc cgcgcctcga ccaagaaaaa gaagaattac 3000
tacgcaagaa attacagtta aatcccacac ctgctaacag aagcagatac cagtccagga 3060
aggtggagaa catgaaagcc ataacagcta gacgtattct gcaaggccta gggcattatt 3120
tgaaggcaga aggaaaagtg gagtgctacc gaaccctgca tcctgttcct ttgtattcat 3180
ctagtgtgaa ccgtgccttt tcaagcccca aggtcgcagt ggaagcctgt aacgccatgt 3240
tgaaagagaa ctttccgact gtggcttctt actgtattat tccagagtac gatgcctatt 3300
tggacatggt tgacggagct tcatgctgct tagacactgc cagtttttgc cctgcaaagc 3360
tgcgcagctt tccaaagaaa cactcctatt tggaacccac aatacgatcg gcagtgcctt 3420
cagcgatcca gaacacgctc cagaacgtcc tggcagctgc cacaaaaaga aattgcaatg 3480
tcacgcaaat gagagaattg cccgtattgg attcggcggc ctttaatgtg gaatgcttca 3540
agaaatatgc gtgtaataat gaatattggg aaacgtttaa agaaaacccc atcaggctta 3600
ctgaagaaaa cgtggtaaat tacattacca aattaaaagg accaaaagct gctgctcttt 3660
ttgcgaagac acataatttg aatatgttgc aggacatacc aatggacagg tttgtaatgg 3720
acttaaagag agacgtgaaa gtgactccag gaacaaaaca tactgaagaa cggcccaagg 3780
tacaggtgat ccaggctgcc gatccgctag caacagcgta tctgtgcgga atccaccgag 3840
agctggttag gagattaaat gcggtcctgc ttccgaacat tcatacactg tttgatatgt 3900
cggctgaaga ctttgacgct attatagccg agcacttcca gcctggggat tgtgttctgg 3960
aaactgacat cgcgtcgttt gataaaagtg aggacgacgc catggctctg accgcgttaa 4020
tgattctgga agacttaggt gtggacgcag agctgttgac gctgattgag gcggctttcg 4080
gcgaaatttc atcaatacat ttgcccacta aaactaaatt taaattcgga gccatgatga 4140
aatctggaat gttcctcaca ctgtttgtga acacagtcat taacattgta atcgcaagca 4200
gagtgttgag agaacggcta accggatcac catgtgcagc attcattgga gatgacaata 4260
tcgtgaaagg agtcaaatcg gacaaattaa tggcagacag gtgcgccacc tggttgaata 4320
tggaagtcaa gattatagat gctgtggtgg gcgagaaagc gccttatttc tgtggagggt 4380
ttattttgtg tgactccgtg accggcacag cgtgccgtgt ggcagacccc ctaaaaaggc 4440
tgtttaagct tggcaaacct ctggcagcag acgatgaaca tgatgatgac aggagaaggg 4500
cattgcatga agagtcaaca cgctggaacc gagtgggtat tctttcagag ctgtgcaagg 4560
cagtagaatc aaggtatgaa accgtaggaa cttccatcat agttatggcc atgactactc 4620

-continued

```
tagctagcag tgttaaatca ttcagctacc tgagaggggc ccctataact ctctacggct   4680
aacctgaatg gactacgaca tagtctagtc cgccaagtct agcatatggc caccatgttc   4740
gtgtttctgg tgctgctgcc tctggtgtcc agccagtgtg tgaacctgac caccagaaca   4800
cagctgcctc cagcctacac caacagcttt accagaggcg tgtactaccc cgacaaggtg   4860
ttcagatcca gcgtgctgca ctctacccag gacctgttcc tgcctttctt cagcaacgtg   4920
acctggttcc acgccatcca cgtgtccggc accaatggca ccaagagatt cgacaacccc   4980
gtgctgccct tcaacgacgg ggtgtacttt gccagcaccg agaagtccaa catcatcaga   5040
ggctggatct tcggcaccac actggacagc aagacccaga gcctgctgat cgtgaacaac   5100
gccaccaacg tggtcatcaa agtgtgcgag ttccagttct gcaacgaccc cttcctgggc   5160
gtctactacc acaagaacaa caagagctgg atggaaagcg agttccgggt gtacagcagc   5220
gccaacaact gcaccttcga gtacgtgtcc cagcctttcc tgatggacct ggaaggcaag   5280
cagggcaact tcaagaacct gcgcgagttc gtgttcaaga acatcgacgg ctacttcaag   5340
atctacagca agcacacccc tatcaacctc gtgcgggatc tgcctcaggg cttctctgct   5400
ctggaacccc tggtggatct gcccatcggc atcaacatca cccggtttca gacactgctg   5460
gccctgcaca gaagctacct gacacctggc gatagcagca gcggatggac agctggtgcc   5520
gccgcttact atgtgggcta cctgcagcct agaaccttcc tgctgaagta caacgagaac   5580
ggcaccatca ccgacgccgt ggattgtgcc cttgatcctc tgagcgagac aaagtgcacc   5640
ctgaagtcct tcaccgtgga aaagggcatc taccagacca gcaacttccg ggtgcagccc   5700
accgaatcca tcgtgcggtt ccccaatatc accaatctgt gccccttcgg cgaggtgttc   5760
aatgccacca gattcgcctc tgtgtacgcc tggaaccgga agcggatcag caattgcgtg   5820
gccgactact ccgtgctgta caactccgcc agcttcagca ccttcaagtg ctacggcgtg   5880
tcccctacca agctgaacga cctgtgcttc acaaacgtgt acgccgacag cttcgtgatc   5940
cggggagatg aagtgcggca gattgcccct ggacagacag gcaagatcgc cgactacaac   6000
tacaagctgc ccgacgactt caccggctgt gtgattgcct ggaacagcaa caacctggac   6060
tccaaagtcg gcggcaacta caattacctg taccggctgt tccggaagtc caatctgaag   6120
cccttcgagc gggacatctc caccgagatc tatcaggccg gcagcacccc ttgtaacggc   6180
gtggaaggct tcaactgcta cttcccactg cagtcctacg gctttcagcc cacaaatggc   6240
gtgggctatc agccctacag agtggtggtg ctgagcttcg aactgctgca tgcccctgcc   6300
acagtgtgcg gccctaagaa aagcaccaat ctcgtgaaga acaaatgcgt gaacttcaac   6360
ttcaacggcc tgaccggcac aggcgtgctg acagagagca acaagaagtt cctgccattc   6420
cagcagtttg gccgggatat cgccgatacc acagacgccg ttagagatcc ccagacactg   6480
gaaatcctgg acatcacccc ttgcagcttc ggcggagtgt ctgtgatcac ccctggcacc   6540
aacaccagca atcaggtggc agtgctgtac caggacgtga actgtaccga agtgcccgtg   6600
gccattcacg ccgatcagct gacacctaca tggcgggtgt actccaccgg cagcaatgtg   6660
tttcagacca gagccggctg tctgatcgga gccgagcacg tgaacaatag ctacgagtgc   6720
gacatcccca tcggcgctgg catctgtgcc agctaccaga cacagacaaa cagccccaga   6780
cgggccagat ctgtggccag ccagagcatc attgcctaca caatgtctct gggcgccgag   6840
aacagcgtgg cctactccaa caactctatc gctatcccca ccaacttcac catcagcgtg   6900
accacagaga tcctgcctgt gtccatgacc aagaccagcg tggactgcac catgtacatc   6960
tgcggcgatt ccaccgagtg ctccaacctg ctgctgcagt acggcagctt ctgcacccag   7020
```

```
ctgaatagag ccctgacagg gatcgccgtg gaacaggaca agaacaccca agaggtgttc   7080
gcccaagtga agcagatcta caagacccct cctatcaagg acttcggcgg cttcaatttc   7140
agccagattc tgcccgatcc tagcaagccc agcaagcgga gcttcatcga ggacctgctg   7200
ttcaacaaag tgacactggc cgacgccggc ttcatcaagc agtatggcga ttgtctgggc   7260
gacattgccg ccagggatct gatttgcgcc cagaagttta acggactgac agtgctgcct   7320
cctctgctga ccgatgagat gatcgcccag tacacatctg ccctgctggc cggcacaatc   7380
acaagcggct ggacatttgg agctggcgcc gctctgcaga tcccctttgc tatgcagatg   7440
gcctacagat tcaacggcat cggagtgacc cagaatgtgc tgtacgagaa ccagaagctg   7500
atcgccaacc agttcaacag cgccatcggc aagatccagg acagcctgag cagcacagca   7560
agcgccctgg gaaagctgca ggacgtggtc aaccagaatg cccaggcact gaacaccctg   7620
gtcaagcagc tgtcctccaa cttcggcgcc atcagctctg tgctgaacga tatcctgagc   7680
agactggacc ctcctgaggc cgaggtgcag atcgacagac tgatcacagg cagactgcag   7740
agcctccaga catacgtgac ccagcagctg atcagagccg ccgagattag agcctctgcc   7800
aatctggccg ccaccaagat gtctgagtgt gtgctgggcc agagcaagag agtggacttt   7860
tgcggcaagg gctaccacct gatgagcttc cctcagtctg cccctcacgg cgtggtgttt   7920
ctgcacgtga catacgttcc cgctcaagag aagaatttca ccaccgctcc agccatctgc   7980
cacgacggca aagcccactt tcctagagaa ggcgtgttcg tgtccaacgg cacccattgg   8040
ttcgtgacac agcggaactt ctacgagccc cagatcatca ccaccgacaa caccttcgtg   8100
tctggcaact gcgacgtcgt gatcggcatt gtgaacaata ccgtgtacga ccctctgcag   8160
cccgagctgg acagcttcaa agaggaactg gacaagtact ttaagaacca cacaagcccc   8220
gacgtggacc tgggcgatat cagcggaatc aatgccagcg tcgtgaacat ccagaaagag   8280
atcgaccggc tgaacgaggt ggccaagaat ctgaacgaga gcctgatcga cctgcaagaa   8340
ctggggaagt acgagcagta catcaagtgg ccctggtaca tctggctggg ctttatcgcc   8400
ggactgattg ccatcgtgat ggtcacaatc atgctgtgtt gcatgaccag ctgctgtagc   8460
tgcctgaagg gctgttgtag ctgtggcagc tgctgcaagt tcgacgagga cgattctgag   8520
cccgtgctga agggcgtgaa actgcactac acagatcgga gaaagagagg ctctggcgaa   8580
ggcagaggca gcctgcttac atgtggcgac gtggaagaga accccggacc tatggattat   8640
gtgtccctgc tgaaccagat ttggcagaag tacctgaaca gcccctacac cacctgtctg   8700
tacatcccca agcctaccgc caagtacaca cctctcgtgg gcacatctct gcaccccgtg   8760
ctgtggaatt gccagctgag ctttgccggc tacaccgagt ctgccgtgaa cagcacaaag   8820
gccctggcca aacaggacgc cgctcagaga attgcctggc tgctgcacaa ggatggcggc   8880
atccctgatg gctgtagcct gtacctgaga cacagcagcc tgttcgccca gagcgaggaa   8940
gaggaatcct tcagcaactg agcggccgcg aattggcaag ctgcttacat agaactcgcg   9000
gcgattggca tgccgcctta aaatttttat tttattttc ttttcttttc cgaatcggat   9060
tttgttttta atatttcaaa aaaaaaaaaa aaaaaaaaaa aaaaaaaaaa aacgcgtcga   9120
ggggaattaa ttcttgaaga cgaaagggcc aggtggcact tttcggggaa atgtgcgcgg   9180
aacccctatt tgtttatttt tctaaataca ttcaaatatg tatccgctca tgagacaata   9240
accctgataa atgcttcaat aatattgaaa aaggaagagt atgagtattc aacatttccg   9300
tgtcgccctt attccctttt ttgcggcatt ttgccttcct gtttttgctc acccagaaac   9360
```

-continued

```
gctggtgaaa gtaaaagatg ctgaagatca gttgggtgca cgagtgggtt acatcgaact   9420
ggatctcaac agcggtaaga tccttgagag ttttcgcccc gaagaacgtt ttccaatgat   9480
gagcactttt aaagttctgc tatgtggcgc ggtattatcc cgtgttgacg ccgggcaaga   9540
gcaactcggt cgccgcatac actattctca gaatgacttg gttgagtact caccagtcac   9600
agaaaagcat cttacggatg gcatgacagt aagagaatta tgcagtgctg ccataaccat   9660
gagtgataac actgcggcca acttacttct gacaacgatc ggaggaccga aggagctaac   9720
cgcttttttg cacaacatgg gggatcatgt aactcgcctt gatcgttggg aaccggagct   9780
gaatgaagcc ataccaaacg acgagcgtga caccacgatg cctgtagcaa tggcaacaac   9840
gttgcgcaaa ctattaactg gcgaactact tactctagct tcccggcaac aattaataga   9900
ctggatggag gcggataaag ttgcaggacc acttctgcgc tcggcccttc cggctggctg   9960
gtttattgct gataaatctg gagccggtga gcgtgggtct cgcggtatca ttgcagcact  10020
ggggccagat ggtaagccct cccgtatcgt agttatctac acgacgggga gtcaggcaac  10080
tatggatgaa cgaaatagac agatcgctga gataggtgcc tcactgatta agcattggta  10140
actgtcagac caagtttact catatatact ttagattgat ttaaaacttc atttttaatt  10200
taaaaggatc taggtgaaga tcctttttga taatctcatg accaaaatcc cttaacgtga  10260
gttttcgttc cactgagcgt cagaccccgt agaaaagatc aaaggatctt cttgagatcc  10320
tttttttctg cgcgtaatct gctgcttgca aacaaaaaaa ccaccgctac cagcggtggt  10380
ttgtttgccg gatcaagagc taccaactct ttttccgaag gtaactggct tcagcagagc  10440
gcagatacca aatactgtcc ttctagtgta gccgtagtta ggccaccact tcaagaactc  10500
tgtagcaccg cctacatacc tcgctctgct aatcctgtta ccagtggctg ctgccagtgg  10560
cgataagtcg tgtcttaccg ggttggactc aagacgatag ttaccggata aggcgcagcg  10620
gtcgggctga acggggggtt cgtgcacaca gcccagcttg gagcgaacga cctacaccga  10680
actgagatac ctacagcgtg agcattgaga aagcgccacg cttcccgaag ggagaaaggc  10740
ggacaggtat ccggtaagcg gcagggtcgg aacaggagag cgcacgaggg agcttccagg  10800
gggaaacgcc tggtatcttt atagtcctgt cgggtttcgc cacctctgac ttgagcgtcg  10860
atttttgtga tgctcgtcag gggggcggag cctatggaaa aacgccattc tagaatggcg  10920
cgcccttaag ggagaatag gagccgcaac acacaagcaa cgcgaggtcg tttaaactaa  10980
tacgactcac tataatgggc ggcgcatgag agaagcccag accaattacc tacccaaaat  11040
ggagaaagtt cacgttgaca tcgaggaaga cagcccattc ctcagagctt tgcagcggag  11100
cttcccgcag tttgaggtag aagccaagca ggtcactgat aatgaccatg ctaatgccag  11160
agcgttttcg catctggctt caaaactgat cgaaacggag gtggacccat ccgacacgat  11220
ccttgacatt ggaagtgcgc ccgcccgcag aatgtattct aagcacaagt atcattgtat  11280
ctgtccgatg agatgtgcgg aagatccgga cagattgtat aagtatgcaa ctaagctgaa  11340
gaaaaactgt aaggaaataa ctgataagga attggacaag aaaatgaagg agctggccgc  11400
cgtcatgagc gaccctgacc tggaaactga gactatgtgc ctccacgacg acgagtcgtg  11460
tcgctacgaa gggcaagtcg ctgtttacca ggatgtatac gcggttgacg gaccgacaag  11520
tctctatcac caagccaata agggagttag agtcgcctac tggataggct ttgacaccac  11580
ccttttatg tttaagaact tggctggagc atatccatca tactctacca actgggccga  11640
cgaaaccgtg ttaacggctc gtaacatagg cctatgcagc tctgacgtta tggagcggtc  11700
acgtagaggg atgtccattc ttagaaagaa gtatttgaaa ccatccaaca atgttctatt  11760
```

-continued

```
ctctgttggc tcgaccatct accacgagaa gagggactta ctgaggagct ggcacctgcc  11820
gtctgtattt cacttacgtg gcaagcaaaa ttacacatgt cggtgtgaga ctatagttag  11880
ttgcgacggg tacgtcgtta aaagaatagc tatcagtcca ggcctgtatg ggaagccttc  11940
aggctatgct gctacgatgc accgcgaggg attcttgtgc tgcaaagtga cagacacatt  12000
gaacggggag agggtctctt ttcccgtgtg cacgtatgtg ccagctacat tgtgtgacca  12060
aatgactggc atactggcaa cagatgtcag tgcggacgac gcgcaaaaac tgctggttgg  12120
gctcaaccag cgtatagtcg tcaacggtcg cacccagaga aacaccaata ccatgaaaaa  12180
ttaccttttg cccgtagtgg cccaggcatt tgctaggtgg gcaaaggaat ataaggaaga  12240
tcaagaagat gaaaggccac taggactacg agatagacag ttagtcatgg ggtgttgttg  12300
ggcttttaga aggcacaaga taacatctat ttataagcgc ccggataccc aaaccatcat  12360
caaagtgaac agcgatttcc actcattcgt gctgcccagg ataggcagta acacattgga  12420
gatcgggctg agaacaagaa tcaggaaaat gttagaggag cacaaggagc cgtcacctct  12480
cattaccgcc gaggacgtac aagaagctaa gtgcgcagcc gatgaggcta aggaggtgcg  12540
tgaagccgag gagttgcgcg cagctctacc acctttggca gctgatgttg aggagcccac  12600
tctggaggca gacgtcgact tgatgttaca agaggctggg gccggctcag tggagacacc  12660
tcgtggcttg ataaaggtta ccagctacga tggcgaggac aagatcggct cttacgctgt  12720
gctttctccg caggctgtac tcaagagtga aaaattatct tgcatccacc ctctcgctga  12780
acaagtcata gtgataacac actctggccg aaaagggcgt tatgccgtgg aaccatacca  12840
tggtaaagta gtggtgccag agggacatgc aatacccgtc caggactttc aagctctgag  12900
tgaaagtgcc accattgtgt acaacgaacg tgagttcgta aacaggtacc tgcaccatat  12960
tgccacacat ggaggagcgc tgaacactga tgaagaatat tacaaaactg tcaagcccag  13020
cgagcacgac ggcgaatacc tgtacgacat cgacaggaaa cagtgcgtca agaaagaact  13080
agtcactggg ctagggctca caggcgagct ggtggatcct ccccttccatg aattcgccta  13140
cgagagtctg agaacacgac cagccgctcc ttaccaagta ccaaccatag ggggtgtatgg  13200
cgtgccagga tcaggcaagt ctggcatcat taaaagcgca gtcaccaaaa aagatctagt  13260
ggtgagcgcc aagaaagaaa actgtgcaga aattataagg gacgtcaaga aaatgaaagg  13320
gctggacgtc aatgccagaa ctgtggactc agtgctcttg aatggatgca aacaccccgt  13380
agagaccctg tatattgacg aagcttttgc ttgtcatgca ggtactctca gagcgctcat  13440
agccattata agacctaaaa aggcagtgct ctgcggggat cccaaacagt gcggtttttt  13500
taacatgatg tgcctgaaag tgcattttaa ccacgagatt tgcacacaag tcttccacaa  13560
aagcatctct cgccgttgca ctaaatctgt gacttcggtc gtctcaacct tgttttacga  13620
caaaaaaatg agaacgacga atccgaaaga gactaagatt gtgattgaca ctaccggcag  13680
taccaaacct aagcaggacg atctcattct cacttgtttc agagggtggg tgaagcagtt  13740
gcaaatagat tacaaaggca acgaaataat gacggcagct gcctctcaag ggctgacccg  13800
taaaggtgtg tatgccgttc ggtacaaggt gaatgaaa                          13838
```

<210> SEQ ID NO 77
<211> LENGTH: 39
<212> TYPE: PRT
<213> ORGANISM: SARS-CoV-2

<400> SEQUENCE: 77

-continued

```
Cys Cys Met Thr Ser Cys Cys Ser Cys Leu Lys Gly Cys Cys Ser Cys
1               5                   10                  15

Gly Ser Cys Cys Lys Phe Asp Glu Asp Asp Ser Glu Pro Val Leu Lys
            20                  25                  30

Gly Val Lys Leu His Tyr Thr
        35


<210> SEQ ID NO 78
<211> LENGTH: 1234
<212> TYPE: PRT
<213> ORGANISM: SARS-CoV-2

<400> SEQUENCE: 78

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335
```

-continued

```
Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750
```

```
Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
```

```
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu


<210> SEQ ID NO 79
<211> LENGTH: 3702
<212> TYPE: DNA
<213> ORGANISM: Artificial Sequence
<220> FEATURE:
<223> OTHER INFORMATION: Synthetised Sequence

<400> SEQUENCE: 79

atgttcgtgt ttctggtgct gctgcctctg gtgtccagcc agtgtgtgaa cctgaccacc     60

agaacacagc tgcctccagc ctacaccaac agctttacca gaggcgtgta ctaccccgac    120

aaggtgttca gatccagcgt gctgcactct acccaggacc tgttcctgcc tttcttcagc    180

aacgtgacct ggttccacgc catccacgtg tccggcacca atggcaccaa gagattcgac    240

aaccccgtgc tgcccttcaa cgacggggtg tactttgcca gcaccgagaa gtccaacatc    300

atcagaggct ggatcttcgg caccacactg gacagcaaga cccagagcct gctgatcgtg    360

aacaacgcca ccaacgtggt catcaaagtg tgcgagttcc agttctgcaa cgaccccttc    420

ctgggcgtct actaccacaa gaacaacaag agctggatgg aaagcgagtt ccgggtgtac    480

agcagcgcca acaactgcac cttcgagtac gtgtcccagc ctttcctgat ggacctggaa    540

ggcaagcagg gcaacttcaa gaacctgcgc gagttcgtgt tcaagaacat cgacggctac    600

ttcaagatct acagcaagca cacccctatc aacctcgtgc gggatctgcc tcagggcttc    660

tctgctctgg aacccctggt ggatctgccc atcggcatca acatcacccg gtttcagaca    720

ctgctggccc tgcacagaag ctacctgaca cctggcgata gcagcagcgg atggacagct    780

ggtgccgccg cttactatgt gggctacctg cagcctagaa ccttcctgct gaagtacaac    840

gagaacggca ccatcaccga cgccgtggat tgtgcccttg atcctctgag cgagacaaag    900

tgcaccctga agtccttcac cgtggaaaag ggcatctacc agaccagcaa cttccgggtg    960

cagcccaccg aatccatcgt gcggttcccc aatatcacca atctgtgccc cttcggcgag   1020

gtgttcaatg ccaccagatt cgcctctgtg tacgcctgga accggaagcg gatcagcaat   1080

tgcgtggccg actactccgt gctgtacaac tccgccagct tcagcacctt caagtgctac   1140

ggcgtgtccc ctaccaagct gaacgacctg tgcttcacaa acgtgtacgc cgacagcttc   1200

gtgatccggg gagatgaagt gcggcagatt gcccctggac agacaggcaa gatcgccgac   1260

tacaactaca agctgcccga cgacttcacc ggctgtgtga ttgcctggaa cagcaacaac   1320

ctggactcca aagtcggcgg caactacaat tacctgtacc ggctgttccg gaagtccaat   1380

ctgaagccct tcgagcggga catctccacc gagatctatc aggccggcag cacccccttgt   1440

aacggcgtgg aaggcttcaa ctgctacttc ccactgcagt cctacggctt tcagcccaca   1500

aatggcgtgg gctatcagcc ctacagagtg gtggtgctga gcttcgaact gctgcatgcc   1560

cctgccacag tgtgcggccc taagaaaagc accaatctcg tgaagaacaa atgcgtgaac   1620
```

-continued ttcaacttca acggcctgac cggcacaggc gtgctgacag agagcaacaa gaagttcctg 1680
ccattccagc agtttggccg ggatatcgcc gataccacag acgccgttag agatccccag 1740
acactggaaa tcctggacat cacccttgc agcttcggcg gagtgtctgt gatcacccct 1800
ggcaccaaca ccagcaatca ggtggcagtg ctgtaccagg acgtgaactg taccgaagtg 1860
cccgtggcca ttcacgccga tcagctgaca cctacatggc gggtgtactc caccggcagc 1920
aatgtgtttc agaccagagc cggctgtctg atcggagccg agcacgtgaa caatagctac 1980
gagtgcgaca tccccatcgg cgctggcatc tgtgccagct accagacaca gacaaacagc 2040
cccagacggg ccagatctgt ggccagccag agcatcattg cctacacaat gtctctgggc 2100
gccgagaaca gcgtggccta ctccaacaac tctatcgcta tccccaccaa cttcaccatc 2160
agcgtgacca cagagatcct gcctgtgtcc atgaccaaga ccagcgtgga ctgcaccatg 2220
tacatctgcg gcgattccac cgagtgctcc aacctgctgc tgcagtacgg cagcttctgc 2280
acccagctga atagagccct gacagggatc gccgtggaac aggacaagaa cacccaagag 2340
gtgttcgccc aagtgaagca gatctacaag accccctccta tcaaggactt cggcggcttc 2400
aatttcagcc agattctgcc cgatcctagc aagcccagca agcggagctt catcgaggac 2460
ctgctgttca acaaagtgac actggccgac gccggcttca tcaagcagta tggcgattgt 2520
ctgggcgaca ttgccgccag ggatctgatt tgcgcccaga agtttaacgg actgacagtg 2580
ctgcctcctc tgctgaccga tgagatgatc gcccagtaca catctgccct gctggccggc 2640
acaatcacaa gcggctggac atttggagct ggcgccgctc tgcagatccc ctttgctatg 2700
cagatggcct acagattcaa cggcatcgga gtgacccaga atgtgctgta cgagaaccag 2760
aagctgatcg ccaaccagtt caacagcgcc atcggcaaga tccaggacag cctgagcagc 2820
acagcaagcg ccctgggaaa gctgcaggac gtggtcaacc agaatgccca ggcactgaac 2880
accctggtca agcagctgtc ctccaacttc ggcgccatca gctctgtgct gaacgatatc 2940
ctgagcagac tggaccctcc tgaggccgag gtgcagatcg acagactgat cacaggcaga 3000
ctgcagagcc tccagacata cgtgacccag cagctgatca gagccgccga gattagagcc 3060
tctgccaatc tggccgccac caagatgtct gagtgtgtgc tgggccagag caagagagtg 3120
gacttttgcg gcaagggcta ccacctgatg agcttccctc agtctgcccc tcacggcgtg 3180
gtgtttctgc acgtgacata cgttcccgct caagagaaga atttcaccac cgctccagcc 3240
atctgccacg acggcaaagc ccactttcct agagaaggcg tgttcgtgtc caacggcacc 3300
cattggttcg tgacacagcg gaacttctac gagccccaga tcatcaccac cgacaacacc 3360
ttcgtgtctg gcaactgcga cgtcgtgatc ggcattgtga acaataccgt gtacgaccct 3420
ctgcagcccg agctggacag cttcaaagag gaactggaca agtactttaa gaaccacaca 3480
agccccgacg tggacctggg cgatatcagc ggaatcaatg ccagcgtcgt gaacatccag 3540
aaagagatcg accggctgaa cgaggtggcc aagaatctga acgagagcct gatcgacctg 3600
caagaactgg ggaagtacga gcagtacatc aagtggccct ggtacatctg gctgggcttt 3660
atcgccggac tgattgccat cgtgatggtc acaatcatgc tg 3702

<210> SEQ ID NO 80
<211> LENGTH: 3702
<212> TYPE: RNA
<213> ORGANISM: Artificial Sequence
<220> FEATURE:
<223> OTHER INFORMATION: Synthetised Sequence

<400> SEQUENCE: 80
auguucgugu uucuggugcu gcugccucug guguccagcc agugugugaa ccugaccacc 60
agaacacagc ugccuccagc cuacaccaac agcuuuacca gaggcgugua cuaccccgac 120
aagguguuca gauccagcgu gcugcacucu acccaggacc uguuccugcc uuucuucagc 180
aacgugaccu gguuccacgc cauccacgug uccggcacca auggcaccaa gagauucgac 240
aaccccgugc ugcccuucaa cgacggggug uacuuugcca gcaccgagaa guccaacauc 300
aucagaggcu ggaucuucgg caccacacug gacagcaaga cccagagccu gcugaucgug 360
aacaacgcca ccaacguggu caucaaagug ugcgaguucc aguucugcaa cgaccccuuc 420
cugggcgucu acuaccacaa gaacaacaag agcuggaugg aaagcgaguu ccggguguac 480
agcagcgcca acaacugcac cuucgaguac gugucccagc cuuuccugau ggaccuggaa 540
ggcaagcagg gcaacuucaa gaaccugcgc gaguucgugu ucaagaacau cgacggcuac 600
uucaagaucu acagcaagca caccccuauc aaccucgugc gggaucugcc ucagggcuuc 660
ucugcucugg aaccccuggu ggaucugccc aucggcauca acaucacccg guuucagaca 720
cugcuggccc ugcacagaag cuaccugaca ccuggcgaua gcagcagcgg auggacagcu 780
ggugccgccg cuuacuaugu gggcuaccug cagccuagaa ccuuccugcu gaaguacaac 840
gagaacggca ccaucaccga cgccguggau ugugcccuug auccucugag cgagacaaag 900
ugcacccuga aguccuucac cguggaaaag ggcaucuacc agaccagcaa cuuccgggug 960
cagcccaccg aauccaucgu gcgguucccc aauaucacca aucugugccc cuucggcgag 1020
guguucaaug ccaccagauu cgccucugug uacgccugga accggaagcg gaucagcaau 1080
ugcguggccg acuacuccgu gcuguacaac uccgccagcu ucagcaccuu caagugcuac 1140 ggcgpuguccc cuaccaagcu gaacgaccug ugcuucacaa acguguacgc cgacagcuuc 1200
gugauccggg gagaugaagu gcggcagauu gccccuggac agacaggcaa gaucgccgac 1260
uacaacuaca agcugcccga cgacuucacc ggcuguguga uugccuggaa cagcaacaac 1320
cuggacucca aagucggcgg caacuacaau uaccuguacc ggcuguuccg gaaguccaau 1380
cugaagcccu ucgagcggga caucuccacc gagaucuauc aggccggcag caccccuugu 1440
aacggcgugg aaggcuucaa cugcuacuuc ccacugcagu ccuacggcuu ucagcccaca 1500
aauggcgugg gcuaucagcc cuacagagug guggugcuga gcuucgaacu gcugcaugcc 1560
ccugccacag ugugcggccc uaagaaaagc accaaucucg ugaagaacaa augcgugaac 1620
uucaacuuca acggccugac cggcacaggc gugcugacag agagcaacaa gaaguuccug 1680
ccauuccagc aguuuggccg ggauaucgcc gauaccacag acgccguuag agaucccag 1740 acacuggaaa uccuggacau caccccuugc agcuucggcg gagugucugu gaucaccccu 1800
ggcaccaaca ccagcaauca gguggcagug cuguaccagg acgugaacug uaccgaagug 1860
cccguggcca uucacgccga ucagcugaca ccuacauggc ggguguacuc caccggcagc 1920
aauguguuuc agaccagagc cggcugucug aucggagccg agcacgugaa caauagcuac 1980
gagugcgaca uccccaucgg cgcuggcauc ugugccagcu accagacaca gacaaacagc 2040
cccagacggg ccagaucugu ggccagccag agcaucauug ccuacacaau gucucugggc 2100
gccgagaaca gcguggccua cuccaacaac ucuaucgcua uccccaccaa cuucaccauc 2160
agcgugacca cagagauccu gccugugucc augaccaaga ccagcgugga cugcaccaug 2220
uacaucugcg gcgauuccac cgagugcucc aaccugcugc ugcaguacgg cagcuucugc 2280
acccagcuga auagagcccu gacagggauc gccguggaac aggacaagaa cacccaagag 2340

-continued guguucgccc aagugaagca gaucuacaag accccuccua ucaaggacuu cggcggcuuc 2400
aauuucagcc agauucugcc cgauccuagc aagcccagca agcggagcuu caucgaggac 2460
cugcuguuca acaaagugac acuggccgac gccggcuuca ucaagcagua uggcgauugu 2520
cugggcgaca uugccgccag ggaucugauu ugcgcccaga aguuuaacgg acugacagug 2580
cugccuccuc ugcugaccga ugagaugauc gcccaguaca caucugcccu gcuggccggc 2640
acaaucacaa gcggcuggac auuuggagcu ggcgccgcuc ugcagauccc cuuugcuaug 2700
cagauggccu acagauucaa cggcaucgga gugacccaga augugcugua cgagaaccag 2760
aagcugaucg ccaaccaguu caacagcgcc aucggcaaga uccaggacag ccugagcagc 2820
acagcaagcg cccugggaaa gcugcaggac guggucaacc agaaugccca ggcacugaac 2880
acccugguca agcagcuguc cuccaacuuc ggcgccauca gcucugugcu gaacgauauc 2940
cugagcagac uggacccucc ugaggccgag gugcagaucg acagacugau cacaggcaga 3000
cugcagagcc uccagacaua cgugacccag cagcugauca gagccgccga gauuagagcc 3060
ucugccaauc uggccgccac caagaugucu gagugugugc ugggccagag caagagagug 3120
gacuuuugcg gcaagggcua ccaccugaug agcuucccuc agucugcccc ucacggcgug 3180
guguuucugc acgugacaua cguucccgcu caagagaaga auuucaccac cgcuccagcc 3240
aucugccacg acggcaaagc ccacuuuccu agagaaggcg uguucguguc caacggcacc 3300
cauugguucg ugacacagcg gaacuucuac gagccccaga ucaucaccac cgacaacacc 3360
uucgugucug gcaacugcga cgucgugauc ggcauuguga acaauaccgu guacgacccu 3420
cugcagcccg agcuggacag cuucaaagag gaacuggaca aguacuuuaa gaaccacaca 3480
agccccgacg uggaccuggg cgauaucagc ggaaucaaug ccagcgucgu gaacauccag 3540
aaagagaucg accggcugaa cgagguggcc aagaaucuga acgagagccu gaucgaccug 3600
caagaacugg ggaaguacga gcaguacauc aaguggcccu gguacaucug gcugggcuuu 3660
aucgccggac ugauugccau cgugauggugc acaaucaugc ug 3702

<210> SEQ ID NO 81
<211> LENGTH: 1254
<212> TYPE: PRT
<213> ORGANISM: SARS-CoV-2

<400> SEQUENCE: 81

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

-continued

```
Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
```

-continued

```
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975
```

-continued

```
Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
            995                 1000                1005

Thr Gln  Gln Leu Ile Arg Ala  Ala Glu Ile Arg Ala  Ser Ala Asn
         1010                1015                1020

Leu Ala  Ala Thr Lys Met Ser  Glu Cys Val Leu Gly  Gln Ser Lys
         1025                1030                1035

Arg Val  Asp Phe Cys Gly Lys  Gly Tyr His Leu Met  Ser Phe Pro
         1040                1045                1050

Gln Ser  Ala Pro His Gly Val  Val Phe Leu His Val  Thr Tyr Val
         1055                1060                1065

Pro Ala  Gln Glu Lys Asn Phe  Thr Thr Ala Pro Ala  Ile Cys His
         1070                1075                1080

Asp Gly  Lys Ala His Phe Pro  Arg Glu Gly Val Phe  Val Ser Asn
         1085                1090                1095

Gly Thr  His Trp Phe Val Thr  Gln Arg Asn Phe Tyr  Glu Pro Gln
         1100                1105                1110

Ile Ile  Thr Thr Asp Asn Thr  Phe Val Ser Gly Asn  Cys Asp Val
         1115                1120                1125

Val Ile  Gly Ile Val Asn Asn  Thr Val Tyr Asp Pro  Leu Gln Pro
         1130                1135                1140

Glu Leu  Asp Ser Phe Lys Glu  Glu Leu Asp Lys Tyr  Phe Lys Asn
         1145                1150                1155

His Thr  Ser Pro Asp Val Asp  Leu Gly Asp Ile Ser  Gly Ile Asn
         1160                1165                1170

Ala Ser  Val Val Asn Ile Gln  Lys Glu Ile Asp Arg  Leu Asn Glu
         1175                1180                1185

Val Ala  Lys Asn Leu Asn Glu  Ser Leu Ile Asp Leu  Gln Glu Leu
         1190                1195                1200

Gly Lys  Tyr Glu Gln Tyr Ile  Lys Trp Pro Trp Tyr  Ile Trp Leu
         1205                1210                1215

Gly Phe  Ile Ala Gly Leu Ile  Ala Ile Val Met Val  Thr Ile Met
         1220                1225                1230

Leu Cys  Cys Met Thr Ser Cys  Cys Ser Cys Leu Lys  Gly Cys Cys
         1235                1240                1245

Ser Cys  Gly Ser Cys Cys
         1250
```

```
<210> SEQ ID NO 82
<211> LENGTH: 3762
<212> TYPE: DNA
<213> ORGANISM: Artificial Sequence
<220> FEATURE:
<223> OTHER INFORMATION: Synthetised Sequence

<400> SEQUENCE: 82

atgttcgtgt ttctggtgct gctgcctctg gtgtccagcc agtgtgtgaa cctgaccacc      60

agaacacagc tgcctccagc ctacaccaac agctttacca gaggcgtgta ctaccccgac     120

aaggtgttca gatccagcgt gctgcactct acccaggacc tgttcctgcc tttcttcagc     180

aacgtgacct ggttccacgc catccacgtg tccggcacca atggcaccaa gagattcgac     240

aaccccgtgc tgcccttcaa cgacggggtg tactttgcca gcaccgagaa gtccaacatc     300

atcagaggct ggatcttcgg caccacactg gacagcaaga cccagagcct gctgatcgtg     360
```

-continued

```
aacaacgcca ccaacgtggt catcaaagtg tgcgagttcc agttctgcaa cgaccccttc    420
ctgggcgtct actaccacaa gaacaacaag agctggatgg aaagcgagtt ccgggtgtac    480
agcagcgcca acaactgcac cttcgagtac gtgtcccagc ctttcctgat ggacctggaa    540
ggcaagcagg gcaacttcaa gaacctgcgc gagttcgtgt tcaagaacat cgacggctac    600
ttcaagatct acagcaagca cacccctatc aacctcgtgc gggatctgcc tcagggcttc    660
tctgctctgg aacccctggt ggatctgccc atcggcatca acatcacccg gtttcagaca    720
ctgctggccc tgcacagaag ctacctgaca cctggcgata gcagcagcgg atggacagct    780
ggtgccgccg cttactatgt gggctacctg cagcctagaa ccttcctgct gaagtacaac    840
gagaacggca ccatcaccga cgccgtggat tgtgcccttg atcctctgag cgagacaaag    900
tgcaccctga agtccttcac cgtggaaaag ggcatctacc agaccagcaa cttccgggtg    960
cagcccaccg aatccatcgt gcggttcccc aatatcacca atctgtgccc cttcggcgag   1020
gtgttcaatg ccaccagatt cgcctctgtg tacgcctgga accggaagcg gatcagcaat   1080
tgcgtggccg actactccgt gctgtacaac tccgccagct tcagcacctt caagtgctac   1140
ggcgtgtccc ctaccaagct gaacgacctg tgcttcacaa acgtgtacgc cgacagcttc   1200
gtgatccggg gagatgaagt gcggcagatt gcccctggac agacaggcaa gatcgccgac   1260
tacaactaca agctgcccga cgacttcacc ggctgtgtga ttgcctggaa cagcaacaac   1320
ctggactcca aagtcggcgg caactacaat tacctgtacc ggctgttccg gaagtccaat   1380
ctgaagccct tcgagcggga catctccacc gagatctatc aggccggcag caccccttgt   1440
aacggcgtgg aaggcttcaa ctgctacttc ccactgcagt cctacggctt tcagcccaca   1500
aatggcgtgg gctatcagcc ctacagagtg gtggtgctga gcttcgaact gctgcatgcc   1560
cctgccacag tgtgcggccc taagaaaagc accaatctcg tgaagaacaa atgcgtgaac   1620
ttcaacttca acggcctgac cggcacaggc gtgctgacag agagcaacaa gaagttcctg   1680
ccattccagc agtttggccg ggatatcgcc gataccacag acgccgttag agatccccag   1740
acactggaaa tcctggacat caccccttgc agcttcggcg gagtgtctgt gatcacccct   1800
ggcaccaaca ccagcaatca ggtggcagtg ctgtaccagg acgtgaactg taccgaagtg   1860
cccgtggcca ttcacgccga tcagctgaca cctacatggc gggtgtactc caccggcagc   1920
aatgtgtttc agaccagagc cggctgtctg atcggagccg agcacgtgaa caatagctac   1980
gagtgcgaca tccccatcgg cgctggcatc tgtgccagct accagacaca gacaaacagc   2040
cccagacggg ccagatctgt ggccagccag agcatcattg cctacacaat gtctctgggc   2100
gccgagaaca gcgtggccta ctccaacaac tctatcgcta tccccaccaa cttcaccatc   2160
agcgtgacca cagagatcct gcctgtgtcc atgaccaaga ccagcgtgga ctgcaccatg   2220
tacatctgcg gcgattccac cgagtgctcc aacctgctgc tgcagtacgg cagcttctgc   2280
acccagctga atagagccct gacagggatc gccgtggaac aggacaagaa cacccaagag   2340
gtgttcgccc aagtgaagca gatctacaag acccctccta tcaaggactt cggcggcttc   2400
aatttcagcc agattctgcc cgatcctagc aagcccagca agcggagctt catcgaggac   2460
ctgctgttca acaaagtgac actggccgac gccggcttca tcaagcagta tggcgattgt   2520
ctgggcgaca ttgccgccag ggatctgatt tgcgcccaga agtttaacgg actgacagtg   2580
ctgcctcctc tgctgaccga tgagatgatc gcccagtaca catctgccct gctggccggc   2640
acaatcacaa gcggctggac atttggagct ggcgccgctc tgcagatccc ctttgctatg   2700
```

-continued

```
cagatggcct acagattcaa cggcatcgga gtgacccaga atgtgctgta cgagaaccag   2760
aagctgatcg ccaaccagtt caacagcgcc atcggcaaga tccaggacag cctgagcagc   2820
acagcaagcg ccctgggaaa gctgcaggac gtggtcaacc agaatgccca ggcactgaac   2880
accctggtca agcagctgtc ctccaacttc ggcgccatca gctctgtgct gaacgatatc   2940
ctgagcagac tggaccctcc tgaggccgag gtgcagatcg acagactgat cacaggcaga   3000
ctgcagagcc tccagacata cgtgacccag cagctgatca gagccgccga gattagagcc   3060
tctgccaatc tggccgccac caagatgtct gagtgtgtgc tgggccagag caagagagtg   3120
gacttttgcg gcaagggcta ccacctgatg agcttccctc agtctgcccc tcacggcgtg   3180
gtgtttctgc acgtgacata cgttcccgct caagagaaga atttcaccac cgctccagcc   3240
atctgccacg acggcaaagc ccactttcct agagaaggcg tgttcgtgtc caacggcacc   3300
cattggttcg tgacacagcg gaacttctac gagccccaga tcatcaccac cgacaacacc   3360
ttcgtgtctg gcaactgcga cgtcgtgatc ggcattgtga acaataccgt gtacgaccct   3420
ctgcagcccg agctggacag cttcaaagag gaactggaca agtactttaa gaaccacaca   3480
agccccgacg tggacctggg cgatatcagc ggaatcaatg ccagcgtcgt gaacatccag   3540
aaagagatcg accggctgaa cgaggtggcc aagaatctga acgagagcct gatcgacctg   3600
caagaactgg ggaagtacga gcagtacatc aagtggccct ggtacatctg gctgggcttt   3660
atcgccggac tgattgccat cgtgatggtc acaatcatgc tgtgttgcat gaccagctgc   3720
tgtagctgcc tgaagggctg ttgtagctgt ggcagctgct gc                       3762
```

```
<210> SEQ ID NO 83
<211> LENGTH: 3762
<212> TYPE: RNA
<213> ORGANISM: Artificial Sequence
<220> FEATURE:
<223> OTHER INFORMATION: Synthetised Sequence

<400> SEQUENCE: 83
```

```
auguucgugu uucuggugcu gcugccucug guguccagcc agugugugaa ccugaccacc     60
agaacacagc ugccuccagc cuacaccaac agcuuuacca gaggcgugua cuaccccgac    120
aagguguuca gauccagcgu gcugcacucu acccaggacc uguuccugcc uuucuucagc    180
aacgugaccu gguuccacgc cauccacgug uccggcacca auggcaccaa gagauucgac    240
aaccccgugc ugcccuucaa cgacggggug uacuuugcca gcaccgagaa guccaacauc    300
aucagaggcu ggaucuucgg caccacacug gacagcaaga cccagagccu gcugaucgug    360
aacaacgcca ccaacguggu caucaaagug ugcgaguucc aguucugcaa cgaccccuuc    420
cugggcgucu acuaccacaa gaacaacaag agcuggaugg aaagcgaguu ccggguguac    480
agcagcgcca acaacugcac cuucgaguac gugucccagc cuuuccugau ggaccuggaa    540
ggcaagcagg gcaacuucaa gaaccugcgc gaguucgugu ucaagaacau cgacggcuac    600
uucaagaucu acagcaagca caccccuauc aaccucgugc gggaucugcc ucagggcuuc    660
ucugcucugg aaccccuggu ggaucugccc aucggcauca acaucacccg guuucagaca    720
cugcuggccc ugcacagaag cuaccugaca ccuggcgaua gcagcagcgg auggacagcu    780
ggugccgccg cuuacuaugu gggcuaccug cagccuagaa ccuuccugcu gaaguacaac    840
gagaacggca ccaucaccga cgccguggau ugugcccuug auccucugag cgagacaaag    900
ugcacccuga aguccuucac cguggaaaag ggcaucuacc agaccagcaa cuuccgggug    960
cagcccaccg aauccaucgu gcgguucccc aauaucacca aucugugccc cuucggcgag   1020
```

-continued

```
guguucaaug ccaccagauu cgccucugug uacgccugga accggaagcg gaucagcaau   1080
ugcguggccg acuacuccgu gcuguacaac uccgccagcu ucagcaccuu caagugcuac   1140
ggcgCguccc cuaccaagcu gaacgaccug ugcuucacaa acguguacgc cgacagcuuc   1200
gugauccggg gagaugaagu gcggcagauu gccccuggac agacaggcaa gaucgccgac   1260
uacaacuaca agcugcccga cgacuucacc ggcuguguga uugccuggaa cagcaacaac   1320
cuggacucca aagucggcgg caacuacaau uaccuguacc ggcuguuccg gaaguccaau   1380
cugaagcccu ucgagcggga caucuccacc gagaucuauc aggccggcag caccccuugu   1440
aacggcgugg aaggcuucaa cugcuacuuc ccacugcagu ccuacggcuu ucagcccaca   1500
aauggcgugg gcuaucagcc cuacagagug guggugcuga gcuucgaacu gcugcaugcc   1560
ccugccacag ugugcggccc uaagaaaagc accaaucucg ugaagaacaa augcgugaac   1620
uucaacuuca acggccugac cggcacaggc gugcugacag agagcaacaa gaaguuccug   1680
ccauuccagc aguuuggccg ggauaucgcc gauaccacag acgccguuag agauccccag   1740
acacuggaaa uccuggacau caccccuugc agcuucggcg gagugucugu gaucaccccu   1800
ggcaccaaca ccagcaauca gguggcagug cuguaccagg acgugaacug uaccgaagug   1860
cccguggcca uucacgccga ucagcugaca ccuacauggc ggguguacuc caccggcagc   1920
aauguguuuc agaccagagc cggcugucug aucggagccg agcacgugaa caauagcuac   1980
gagugcgaca uccccaucgg cgcuggcauc ugugccagcu accagacaca gacaaacagc   2040
cccagacggg ccagaucugu ggccagccag agcaucauug ccuacacaau gucucugggc   2100
gccgagaaca gcguggccua cuccaacaac ucuaucgcua uccccaccaa cuucaccauc   2160
agcgugacca cagagauccu gccugugucc augaccaaga ccagcgugga cugcaccaug   2220
uacaucugcg gcgauuccac cgagugcucc aaccugcugc ugcaguacgg cagcuucugc   2280
acccagcuga auagagcccu gacagggauc gccguggaac aggacaagaa cacccaagag   2340
guguucgccc aagugaagca gaucuacaag accccuccua ucaaggacuu cggcggcuuc   2400
aauuucagcc agauucugcc cgauccuagc aagcccagca agcggagcuu caucgaggac   2460
cugcuguuca acaaagugac acuggccgac gccggcuuca ucaagcagua uggcgauugu   2520
cugggcgaca uugccgccag ggaucugauu ugcgcccaga aguuuaacgg acugacagug   2580
cugccuccuc ugcugaccga ugagaugauc gcccaguaca caucugcccu gcuggccggc   2640
acaaucacaa gcggcuggac auuuggagcu ggcgccgcuc ugcagauccc cuuugcuaug   2700
cagauggccu acagauucaa cggcaucgga gugacccaga augugcugua cgagaaccag   2760
aagcugaucg ccaaccaguu caacagcgcc aucggcaaga uccaggacag ccugagcagc   2820
acagcaagcg cccugggaaa gcugcaggac guggucaacc agaaugccca ggcacugaac   2880
acccugguca agcagcuguc cuccaacuuc ggcgccauca gcucugugcu gaacgauauc   2940
cugagcagac uggacccucc ugaggccgag gugcagaucg acagacugau cacaggcaga   3000
cugcagagcc uccagacaua cgugacccag cagcugauca gagccgccga gauuagagcc   3060
ucugccaauc uggccgccac caagaugucu gagugugugc ugggccagag caagagagug   3120
gacuuuugcg gcaagggcua ccaccugaug agcuucccuc agucugcccc ucacggcgug   3180
guguuucugc acgugacaua cguucccgcu caagagaaga auuucaccac cgcuccagcc   3240
aucugccacg acggcaaagc ccacuuuccu agagaaggcg uguucguguc caacggcacc   3300
cauugguucg ugacacagcg gaacuucuac gagccccaga ucaucaccac cgacaacacc   3360
```

-continued

```
uucgugucug gcaacugcga cgucgugauc ggcauuguga acaauaccgu guacgacccu   3420

cugcagcccg agcuggacag cuucaaagag gaacuggaca aguacuuuaa gaaccacaca   3480

agccccgacg uggaccuggg cgauaucagc ggaaucaaug ccagcgucgu gaacauccag   3540

aaagagaucg accggcugaa cgagguggcc aagaaucuga acgagagccu gaucgaccug   3600

caagaacugg ggaaguacga gcaguacauc aaguggcccu gguacaucug gcugggcuuu   3660

aucgccggac ugauugccau cgugaugguc acaaucaugc uguguugcau gaccagcugc   3720

uguagcugcc ugaagggcug uuguagcugu ggcagcugcu gc                       3762


<210> SEQ ID NO 84
<211> LENGTH: 1252
<212> TYPE: PRT
<213> ORGANISM: SARS-CoV-2

<400> SEQUENCE: 84

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300
```

-continued

```
Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
```

-continued

```
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140
```

```
Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser
    1250
```

<210> SEQ ID NO 85
<211> LENGTH: 3756
<212> TYPE: DNA
<213> ORGANISM: Artificial Sequence
<220> FEATURE:
<223> OTHER INFORMATION: Synthetised Sequence

<400> SEQUENCE: 85

```
atgttcgtgt ttctggtgct gctgcctctg gtgtccagcc agtgtgtgaa cctgaccacc     60

agaacacagc tgcctccagc ctacaccaac agctttacca gaggcgtgta ctaccccgac    120

aaggtgttca gatccagcgt gctgcactct acccaggacc tgttcctgcc tttcttcagc    180

aacgtgacct ggttccacgc catccacgtg tccggcacca atggcaccaa gagattcgac    240

aaccccgtgc tgcccttcaa cgacggggtg tactttgcca gcaccgagaa gtccaacatc    300

atcagaggct ggatcttcgg caccacactg gacagcaaga cccagagcct gctgatcgtg    360

aacaacgcca ccaacgtggt catcaaagtg tgcgagttcc agttctgcaa cgaccccttc    420

ctgggcgtct actaccacaa gaacaacaag agctggatgg aaagcgagtt ccgggtgtac    480

agcagcgcca acaactgcac cttcgagtac gtgtcccagc ctttcctgat ggacctggaa    540

ggcaagcagg gcaacttcaa gaacctgcgc gagttcgtgt tcaagaacat cgacggctac    600

ttcaagatct acagcaagca cacccctatc aacctcgtgc gggatctgcc tcagggcttc    660

tctgctctgg aacccctggt ggatctgccc atcggcatca acatcacccg gtttcagaca    720

ctgctggccc tgcacagaag ctacctgaca cctggcgata gcagcagcgg atggacagct    780

ggtgccgccg cttactatgt gggctacctg cagcctagaa ccttcctgct gaagtacaac    840

gagaacggca ccatcaccga cgccgtggat tgtgcccttg atcctctgag cgagacaaag    900

tgcaccctga agtccttcac cgtggaaaag ggcatctacc agaccagcaa cttccgggtg    960

cagcccaccg aatccatcgt gcggttcccc aatatcacca atctgtgccc cttcggcgag   1020

gtgttcaatg ccaccagatt cgcctctgtg tacgcctgga accggaagcg gatcagcaat   1080

tgcgtggccg actactccgt gctgtacaac tccgccagct tcagcacctt caagtgctac   1140

ggcgtgtccc ctaccaagct gaacgacctg tgcttcacaa acgtgtacgc cgacagcttc   1200

gtgatccggg gagatgaagt gcggcagatt gcccctggac agacaggcaa gatcgccgac   1260

tacaactaca agctgcccga cgacttcacc ggctgtgtga ttgcctggaa cagcaacaac   1320
```

-continued ctggactcca aagtcggcgg caactacaat tacctgtacc ggctgttccg gaagtccaat 1380
ctgaagccct tcgagcggga catctccacc gagatctatc aggccggcag cacccccttgt 1440 aacggcgtgg aaggcttcaa ctgctacttc ccactgcagt cctacggctt tcagcccaca 1500
aatggcgtgg gctatcagcc ctacagagtg gtggtgctga gcttcgaact gctgcatgcc 1560
cctgccacag tgtgcggccc taagaaaagc accaatctcg tgaagaacaa atgcgtgaac 1620
ttcaacttca acggcctgac cggcacaggc gtgctgacag agagcaacaa gaagttcctg 1680
ccattccagc agtttggccg ggatatcgcc gataccacag acgccgttag agatccccag 1740
acactggaaa tcctggacat caccccttgc agcttcggcg gagtgtctgt gatcacccct 1800
ggcaccaaca ccagcaatca ggtggcagtg ctgtaccagg acgtgaactg taccgaagtg 1860
cccgtggcca ttcacgccga tcagctgaca cctacatggc gggtgtactc caccggcagc 1920
aatgtgtttc agaccagagc cggctgtctg atcggagccg agcacgtgaa caatagctac 1980
gagtgcgaca tccccatcgg cgctggcatc tgtgccagct accagacaca gacaaacagc 2040
cccagacggg ccagatctgt ggccagccag agcatcattg cctacacaat gtctctgggc 2100
gccgagaaca gcgtggccta ctccaacaac tctatcgcta tccccaccaa cttcaccatc 2160
agcgtgacca cagagatcct gcctgtgtcc atgaccaaga ccagcgtgga ctgcaccatg 2220
tacatctgcg gcgattccac cgagtgctcc aacctgctgc tgcagtacgg cagcttctgc 2280
acccagctga atagagccct gacagggatc gccgtggaac aggacaagaa cacccaagag 2340
gtgttcgccc aagtgaagca gatctacaag acccctccta tcaaggactt cggcggcttc 2400
aatttcagcc agattctgcc cgatcctagc aagcccagca agcggagctt catcgaggac 2460
ctgctgttca acaaagtgac actggccgac gccggcttca tcaagcagta tggcgattgt 2520
ctgggcgaca ttgccgccag ggatctgatt tgcgcccaga agtttaacgg actgacagtg 2580
ctgcctcctc tgctgaccga tgagatgatc gcccagtaca catctgccct gctggccggc 2640
acaatcacaa gcggctggac atttggagct ggcgccgctc tgcagatccc ctttgctatg 2700
cagatggcct acagattcaa cggcatcgga gtgacccaga atgtgctgta cgagaaccag 2760
aagctgatcg ccaaccagtt caacagcgcc atcggcaaga tccaggacag cctgagcagc 2820
acagcaagcg ccctgggaaa gctgcaggac gtggtcaacc agaatgccca ggcactgaac 2880
accctggtca agcagctgtc ctccaacttc ggcgccatca gctctgtgct gaacgatatc 2940
ctgagcagac tggaccctcc tgaggccgag gtgcagatcg acagactgat cacaggcaga 3000
ctgcagagcc tccagacata cgtgacccag cagctgatca gagccgccga gattagagcc 3060
tctgccaatc tggccgccac caagatgtct gagtgtgtgc tgggccagag caagagagtg 3120
gacttttgcg gcaagggcta ccacctgatg agcttccctc agtctgcccc tcacggcgtg 3180
gtgtttctgc acgtgacata cgttcccgct caagagaaga atttcaccac cgctccagcc 3240
atctgccacg acggcaaagc ccactttcct agagaaggcg tgttcgtgtc caacggcacc 3300
cattggttcg tgacacagcg gaacttctac gagccccaga tcatcaccac cgacaacacc 3360
ttcgtgtctg gcaactgcga cgtcgtgatc ggcattgtga acaataccgt gtacgaccct 3420
ctgcagcccg agctggacag cttcaaagag gaactggaca agtactttaa gaaccacaca 3480
agccccgacg tggacctggg cgatatcagc ggaatcaatg ccagcgtcgt gaacatccag 3540
aaagagatcg accggctgaa cgaggtggcc aagaatctga acgagagcct gatcgacctg 3600
caagaactgg ggaagtacga gcagtacatc aagtggccct ggtacatctg gctgggcttt 3660
atcgccggac tgattgccat cgtgatggtc acaatcatgc tgtgttgcat gaccagctgc 3720

```
tgtagctgcc tgaagggctg ttgtagctgt ggcagc                              3756


<210> SEQ ID NO 86
<211> LENGTH: 3756
<212> TYPE: RNA
<213> ORGANISM: Artificial Sequence
<220> FEATURE:
<223> OTHER INFORMATION: Synthetised Sequence

<400> SEQUENCE: 86

auguucgugu uucuggugcu gcugccucug guguccagcc agugugugaa ccugaccacc      60

agaacacagc ugccuccagc cuacaccaac agcuuuacca gaggcgugua cuaccccgac     120

aagguguuca gauccagcgu gcugcacucu acccaggacc uguuccugcc uuucuucagc     180

aacgugaccu gguuccacgc cauccacgug uccggcacca auggcaccaa gagauucgac     240

aaccccgugc ugcccuucaa cgacggggug uacuuugcca gcaccgagaa guccaacauc     300

aucagaggcu ggaucuucgg caccacacug gacagcaaga cccagagccu gcugaucgug     360

aacaacgcca ccaacguggu caucaaagug ugcgaguucc aguucugcaa cgaccccuuc     420

cugggcgucu acuaccacaa gaacaacaag agcuggaugg aaagcgaguu ccgggugcac     480

agcagcgcca acaacugcac cuucgaguac guguccccagc cuuuccugau ggaccuggaa     540

ggcaagcagg gcaacuucaa gaaccugcgc gaguucgugu ucaagaacau cgacggcuac     600

uucaagaucu acagcaagca caccccuauc aaccucgugc gggaucugcc ucagggcuuc     660

ucugcucugg aaccccuggu ggaucugccc aucggcauca acaucacccg guuucagaca     720

cugcuggccc ugcacagaag cuaccugaca ccuggcgaua gcagcagcgg auggacagcu     780

ggugccgccg cuuacuaugu gggcuaccug cagccuagaa ccuuccugcu gaaguacaac     840

gagaacggca ccaucaccga cgccguggau ugugcccuug auccucugag cgagacaaag     900

ugcacccuga aguccuucac cguggaaaag ggcaucuacc agaccagcaa cuuccgggug     960

cagcccaccg aauccaucgu gcgguucccc aauaucacca aucugugccc cuucggcgag    1020

guguucaaug ccaccagauu cgccucugug uacgccugga accggaagcg gaucagcaau    1080

ugcguggccg acuacuccgu gcuguacaac uccgccagcu ucagcaccuu caagugcuac    1140

ggcgugucccc cuaccaagcu gaacgaccug ugcuucacaa acguguacgc cgacagcuuc    1200

gugauccggg gagaugaagu gcggcagauu gccccuggac agacaggcaa gaucgccgac    1260

uacaacuaca agcugcccga cgacuucacc ggcuguguga uugccuggaa cagcaacaac    1320

cuggacucca aagucggcgg caacuacaau uaccuguacc ggcuguuccg gaaguccaau    1380

cugaagcccu ucgagcggga caucuccacc gagaucuauc aggccggcag caccccuugu    1440

aacggcgugg aaggcuucaa cugcuacuuc ccacugcagu ccuacggcuu ucagcccaca    1500

aauggcgugg gcuaucagcc cuacagagug guggugcuga gcuucgaacu gcugcaugcc    1560

ccugccacag ugugcggccc uaagaaaagc accaaucucg ugaagaacaa augcgugaac    1620

uucaacuuca acggccugac cggcacaggc gugcugacag agagcaacaa gaaguuccug    1680

ccauuccagc aguuuggccg ggauaucgcc gauaccacag acgccguuag agaucccccag    1740

acacuggaaa uccuggacau caccccuugc agcuucggcg gagugucugu gaucaccccu    1800

ggcaccaaca ccagcaauca gguggcagug cuguaccagg acgugaacug uaccgaagug    1860

cccguggcca uucacgccga ucagcugaca ccuacauggc ggguguacuc caccggcagc    1920

aauguguuuc agaccagagc cggcugucug aucggagccg agcacgugaa caauagcuac    1980
```

-continued

| | |
|---|---|
| gagugcgaca uccccaucgg cgcuggcauc ugugccagcu accagacaca gacaaacagc | 2040 |
| cccagacggg ccagaucugu ggccagccag agcaucauug ccuacacaau gucucugggc | 2100 |
| gccgagaaca gcguggccua cuccaacaac ucuaucgcua uccccaccaa cuucaccauc | 2160 |
| agcgugacca cagagauccu gccugugucc augaccaaga ccagcgugga cugcaccaug | 2220 |
| uacaucugcg gcgauuccac cgagugcucc aaccugcugc ugcaguacgg cagcuucugc | 2280 |
| acccagcuga auagagcccu gacagggauc gccguggaac aggacaagaa cacccaagag | 2340 |
| guguucgccc aagugaagca gaucuacaag accccuccua ucaaggacuu cggcggcuuc | 2400 |
| aauuucagcc agauucugcc cgauccuagc aagcccagca agcggagcuu caucgaggac | 2460 |
| cugcuguuca acaaagugac acuggccgac gccggcuuca ucaagcagua uggcgauugu | 2520 |
| cugggcgaca uugccgccag ggaucugauu ugcgcccaga aguuuaacgg acugacagug | 2580 |
| cugccuccuc ugcugaccga ugagaugauc gcccaguaca caucugcccu gcuggccggc | 2640 |
| acaaucacaa gcggcuggac auuuggagcu ggcgccgcuc ugcagauccc cuuugcuaug | 2700 |
| cagauggccu acagauucaa cggcaucgga gugacccaga augugcugua cgagaaccag | 2760 |
| aagcugaucg ccaaccaguu caacagcgcc aucggcaaga uccaggacag ccugagcagc | 2820 |
| acagcaagcg cccugggaaa gcugcaggac guggucaacc agaaugccca ggcacugaac | 2880 |
| acccugguca agcagcuguc cuccaacuuc ggcgccauca gcucugugcu gaacgauauc | 2940 |
| cugagcagac uggacccucc ugaggccgag gugcagaucg acagacugau cacaggcaga | 3000 |
| cugcagagcc uccagacaua cgugacccag cagcugauca gagccgccga gauuagagcc | 3060 |
| ucugccaauc uggccgccac caagaugucu gagugugugc ugggccagag caagagagug | 3120 |
| gacuuuugcg gcaagggcua ccaccugaug agcuucccuc agucugcccc ucacggcgug | 3180 |
| guguuucugc acgugacaua cguucccgcu caagagaaga auuucaccac cgcuccagcc | 3240 |
| aucugccacg acggcaaagc ccacuuuccu agagaaggcg uguucguguc caacggcacc | 3300 |
| cauugguucg ugacacagcg gaacuucuac gagccccaga ucaucaccac cgacaacacc | 3360 |
| uucgugucug gcaacugcga cgucgugauc ggcauuguga acaauaccgu guacgacccu | 3420 |
| cugcagcccg agcuggacag cuucaaagag gaacuggaca aguacuuuaa gaaccacaca | 3480 |
| agccccgacg uggaccuggg cgauaucagc ggaaucaaug ccagcgucgu gaacauccag | 3540 |
| aaagagaucg accggcugaa cgagguggcc aagaaucuga acgagagccu gaucgaccug | 3600 |
| caagaacugg ggaaguacga gcaguacauc aaguggcccu gguacaucug gcugggcuuu | 3660 |
| aucgccggac ugauugccau cgugaugguc acaaucaugc uguguugcau gaccagcugc | 3720 |
| uguagcugcc ugaagggcug uuguagcugu ggcagc | 3756 |